US008518639B2

(12) United States Patent
Rihet et al.

(10) Patent No.: US 8,518,639 B2
(45) Date of Patent: Aug. 27, 2013

(54) HPV DETECTION AND QUANTIFICATION BY REAL-TIME MULTIPLEX AMPLIFICATION

(75) Inventors: Stéphane Rihet, Gargenville (FR); Fatima Zeryouh, Choisy le Roi (FR)

(73) Assignee: Bio-Rad Innovations, Marnes-la-Coquette (FR)

( * ) Notice: Subject to any disclaimer, the term of this patent is extended or adjusted under 35 U.S.C. 154(b) by 749 days.

(21) Appl. No.: 12/226,283

(22) PCT Filed: Apr. 11, 2006

(86) PCT No.: PCT/EP2006/004314
§ 371 (c)(1),
(2), (4) Date: Oct. 14, 2008

(87) PCT Pub. No.: WO2007/115582
PCT Pub. Date: Oct. 18, 2007

(65) Prior Publication Data

US 2009/0275025 A1 Nov. 5, 2009

(51) Int. Cl.
*C12Q 1/68* (2006.01)
*C07H 21/04* (2006.01)

(52) U.S. Cl.
USPC ........................................ 435/6.1; 536/24.33

(58) Field of Classification Search
None
See application file for complete search history.

(56) References Cited

U.S. PATENT DOCUMENTS

| | | | | |
|---|---|---|---|---|
| 5,667,965 A | 9/1997 | Androphy et al. | |
| 2001/0053519 A1 * | 12/2001 | Fodor et al. | 435/6 |
| 2006/0051809 A1 | 3/2006 | Nazarenko et al. | |
| 2006/0160069 A1 * | 7/2006 | Chau et al. | 435/5 |

FOREIGN PATENT DOCUMENTS

| | | |
|---|---|---|
| EP | 0 524 807 | 1/1993 |
| JP | 2001-502546 | 2/2001 |
| JP | 2001-321168 | 11/2001 |
| JP | 2004-121240 | 4/2004 |
| JP | 2004-532022 A | 10/2004 |
| JP | 2005-500856 | 1/2005 |
| JP | 2005-514038 | 5/2005 |
| KR | 1019970005651 A | 10/1998 |
| WO | WO 98/17829 | 4/1998 |
| WO | WO 01/40489 A1 | 6/2001 |
| WO | WO 02/068637 A2 | 9/2002 |
| WO | 02/103050 | 12/2002 |
| WO | WO 03/019143 | 3/2003 |
| WO | 03/057927 | 7/2003 |
| WO | WO 03/057914 | 7/2003 |
| WO | WO 2004/092360 A2 | 10/2004 |
| WO | WO 2005/030041 | 4/2005 |

OTHER PUBLICATIONS de Villiers et al., Classification of papillomaviruses, Virology 324 (2004) 17-27.*
Zhao et al., Identification of an hnRNP A1-Dependent Splicing Silencer in theHuman Papillomavirus Type 16 L1 Coding Region That Prevents Premature Expression of the Late L1 Gene, Journal of Virology, Oct. 2004, p. 10888-10905, vol. 78, No. 20.*
Buck et al., Design Strategies and Performance of Custom DNA Sequencing Primers BioTechniques 27:528-536 (Sep. 1999).*
Molden et al., Comparison of Human Papillomavirus Messenger RNA and DNA Detection: A Cross-sectional Study of 4,136 Women >30 Years of Age with a 2-Year Follow-up of High-Grade Squamous Intraepithelial Lesion, Cancer Epidemiol Biomarkers Prev 2005;14:367-372. Published online Feb. 25, 2005.*
Richtsteiger et al., Quantitative multiplex real-time PCR for the sensitive detection of interferon b gene induction and viral suppression of interferon b expression, Cytokine 24 (2003) pp. 190-200.*
Walboomers et al., Human Papillomavirus is a necessary cause of invasive cervical cancer worldwide, Journal of Pathology, J. Pathol. 189: 12-19 (1999).*
Szuhai et al. (Am J Pathol. Nov. 2001;159(5):1651-60).*
Vernon et al. (Int J Cancer. Feb. 20, 1997;74(1):50-6).*
Teshima et al. (Arch Gynecol Obstet. 1997;259(4):169-77).*
NCBI Accession No. X74481 (Sep. 3, 1993).*
NCBI Accession No. M74117 (May 10, 2002).*
NCBI Accession No. X04773 (Sep. 12, 1993).*
NCBI Accession No. M73258 (Nov. 30, 1999).*
NCBI Accession No. X74479 (Sep. 3, 1993).*
NCBI Accession No. K02718 (Mar. 18, 1994).*
Van Ham et al, "Comparison of Two Commercial Assays for Detection of Human Papillomavirus (HPV) in Cervical Scrape Specimens: Validation of the Roche AMPLICOR HPV Test as a Means to Screen for HPV Genotypes Associated with a Higher Risk of Cervical Disorders", Journal of Clinical Microbiology, vol. 43, No. 6, Jun. 2005, pp. 2662-2667.
Tieben et al, "Detection of cutaneous and genital HPV types in clinical samples by PCR using consensus primers", Journal of Virological Methods, 42 (1993) 265-280.
Kleter et al, "Development and Clinical Evaluation of a Highly Sensitive PCR-Reverse Hybridization Line Probe Assay for Detection and Identification of Anogenital Human Papillomavirus", Journal of Clinical Microbiology, vol. 37, No. 8, Aug. 1999, pp. 2508-2517.
Kleter et al, "Novel Short-Fragment PCR Assay for Highly Sensitive Broad-Spectrum Detection of Anogenital Human Papillomaviruses", American Journal of Pathology, vol. 153, No. 6, Dec. 1998, pp. 1731-1739.

(Continued)

*Primary Examiner* — Christopher M. Babic
(74) *Attorney, Agent, or Firm* — Nixon & Vanderhye P.C.

(57) ABSTRACT

The present invention relates to amplification primers and detection probes, which are useful for the detection of human papillomaviruses (HPV), and more particularly of HPV, which can be oncogenic for the mucosal epithelia. The amplification and detection systems provided by the present invention are group-targeted systems, namely A5-, A6- A7-, and A9-targeted systems. The amplification and detection systems of the invention allow for an amplification of HPV in multiplex as well as for a real-time detection, whereby at least the thirteen HR HPV can be detected in a single-tube assay. The invention further allows for a reliable quantitation of HPV viral loads in real-time multiplex amplification.

200 Claims, 26 Drawing Sheets

(56) References Cited

OTHER PUBLICATIONS

Poljak et al, "Retrospective and prospective evaluation of the Amplicor HPV test for detection of 13 high-risk human papillomavirus genotypes on 862 clinical samples", Acta Dermatoven APA, vol. 14, No. 4, 2005, pp. 147-152.
Hesselink et al, "Comparison of Three Different PCR Methods for Quantifying Human Papillomavirus Type 16 DNA in Cervical Scrape Specimens", Journal of Clinical Microbiology, vol. 43, No. 9, Sep. 2005, pp. 4868-4871.
Gravitt et al, "A Comparison between Real-Time Polymerase Chain Reaction and Hybrid Capture 2 for Human Papillomavirus DNA Quantitation", Cancer Epidemiology, Biomarkers & Prevention, vol. 12, Jun. 2003, pp. 477-484.
van Duin et al, "Human Papillomavirus 16 Load in Normal and Abnormal Cervical Scrapes: an Indicator of CIN II/III and Viral Clearance", Int. J. Cancer: 98, pp. 590-595 (2002).
Szuhai et al, "A Novel Strategy for Human Papillomavirus Detection and Genotyping with SybrGreen and Molecular Beacon Polymerase Chain Reaction", American Journal of Pathology, vol. 159, No. 5, Nov. 2001, pp. 1651-1660.
International Search Report for PCT/EP2006/004314, mailed Apr. 25, 2007.
Written Opinion of the International Searching Authority for PCT/EP2006/004314, mailed Apr. 25, 2007.
Prado, J. C. et al., "Worldwide Genomic Diversity of the Human Papillomaviruses-53, 56, and 66, a Group of High-Risk HPVs Unrelated to HPV-16 and HPV-18", Virology, vol. 340, No. 1, pp. 95-104, (Sep. 15, 2005).
De Villiers, E-M et al., "Classification of Papillomaviruses", Virology, vol. 324, No. 1, pp. 17-27, (Jun. 20, 2004).
Moberg, M. et al., "Real-Time PCR-Based System for Simultaneous Quantification of Human Papillomavirus Types Associated With High Risk of Cervical Cancer", Journal of Clinical Microbiology, vol. 41, No. 7, pp. 3221-3228, (Jul. 2003).
Yuko, I. et al., "Detection and Typing of Genital High-Risk HPV DNAS in Cervical Scrapes Using the E6E7-Specific Consensus PCR", Tumor Research, vol. 30, pp. 1-19, (1995).
Vernon, S.D. et al., "Association of Human Papillomavirus Type 16 Integration in the E2 Gene with Poor Disease-Free Survival from Cervical Cancer", International Journal of Cancer, vol. 74, No. 1, pp. 50-56, (Feb. 20, 1997).
Database EMBL, "Human Papillomavirus Type 56 Genomic DNA", Accession No. X74483, (Apr. 18, 2005).
Database EMBL, "Human Papillomavirus Type 51 Genomic DNA, partial sequence", Accession No. M62877, (Jul. 10, 1991).
Database EMBL, "Human Papillomavirus Type 16 (HPV16), Complete Genome", Accession No. K02718, (Jan. 28, 1986).
Database EMBL, "Human Papillomavirus Type 18 E6, E7, E1, E2, E4, E5, L1 & L2 Genes", Accession No. X05015, (Sep. 19, 1987).
Calleja-Macias, I. E. et al., Worldwide Genomic Diversity of the High-Risk Human Papillomavirus Types 31, 35, 52, and 58, Four Close Relatives of Human Papillomavirus Type 16, Journal of Virology, vol. 79, No. 21, (Nov. 2005).
Australian Office Action dated Jan. 11, 2013, issued in connection with Australian Patent Application No. 2006341730.
Tucker et al, "Real-time PCR-based Fluorescent Assay for Quantitation of Human Papillomovirus Types 6, 11, 16, and 18", Molecular Diagnosis, vol. 6, No. 1, pp. 39-47, 2001.
Notice of Acceptance & accepted claims dated Mar. 28, 2013, issued in connection with Australian Patent Application No. 2006341730.

* cited by examiner

```
LOCUS       NC_001594               7844 bp    DNA     linear   VRL 25-JAN-2005
DEFINITION  Human papillomavirus type 56, complete genome.
ACCESSION   NC_001594
VERSION     NC_001594.1  GI:9627383
KEYWORDS    E1 gene; E2 gene; E4 gene; E6 gene; E7 gene; early protein; L1
            gene; L2 gene; late protein.
SOURCE      Human papillomavirus type 56
  ORGANISM  Human papillomavirus type 56
            Viruses; dsDNA viruses, no RNA stage; Papillomaviridae;
            Alphapapillomavirus.
REFERENCE   1  (bases 1 to 7844)
  AUTHORS   Delius,H. and Hofmann,B.
  TITLE     Primer-directed sequencing of human papillomavirus types
  JOURNAL   Curr. Top. Microbiol. Immunol. 186, 13-31 (1994)
   PUBMED   8205838
REFERENCE   2  (bases 1 to 7844)
  AUTHORS   Delius,H.
  TITLE     Direct Submission
  JOURNAL   Submitted (06-AUG-1993) H. Delius, Deutsches
            Krebsforschungszentrum, Abteilung ATV, Im Neuenheimer Feld 506, W
            6900 Heidelberg, FRG
COMMENT     REVIEWED REFSEQ: This record has been curated by NCBI staff. The
            reference sequence was derived from X74483.
            The HPV56 E1 open reading frame is fragmented.
FEATURES             Location/Qualifiers
     source          1..7844
                     /organism="Human papillomavirus type 56"
                     /mol_type="genomic DNA"
                     /db_xref="taxon:10596"
                     /clone="insert in BamHI site of pT713"
     gene            102..566
                     /gene="E6"
                     /locus_tag="HpV56gp1"
                     /db_xref="GeneID:1489330"
     CDS             102..>566
                     /gene="E6"
                     /locus_tag="HpV56gp1"
                     /codon_start=1
                     /product="envelope protein"
                     /protein_id="NP_041849.1"
                     /db_xref="GI:9627384"
                     /db_xref="UniProtKB/Swiss-Prot:P24836"
                     /db_xref="GeneID:1489330"
                     /translation="MEPQFNNPQERPRSLHHLSEVLEIPLIDLRLSCVYCKKELTRAE
                     VYNFACTELKLVYRDDFPYAVCRVCLLFYSKVRKYRYYDYSVYGATLESITKKQLCDL
                     LIRCYRCQSPLTPEEKQLHCDRKRRFHLIAHGWTGSCLGCWRQTSREPRESTV"
                                                             SEQ ID NO: 424
     gene            572..889
                     /gene="E7"
                     /locus_tag="HpV56gp2"
                     /db_xref="GeneID:1489331"
     CDS             572..889
                     /gene="E7"
                     /locus_tag="HpV56gp2"
                     /codon_start=1
                     /product="envelope protein"
                     /protein_id="NP_041850.1"
                     /db_xref="GI:9627385"
                     /db_xref="UniProtKB/Swiss-Prot:P36833"
                     /db_xref="GeneID:1489331"
```

FIGURE 3

```
                /translation="MHGKVPTLQDVVLELTPQTEIDLQCNEQLDSSEDEDEDEVDHLQ
                ERPQQARQAKQHTCYLIHVPCCECKFVVQLDIQSTKEDLRVVQQLLMGALTVTCPLCA
                SSN" SEO ID NO: 425
gene            895..2804
                /locus_tag="HpV56gp3"
                /db_xref="GeneID:1724546"
CDS             join(895..1089,1089..2804)
                /locus_tag="HpV56gp3"
                /exception="artificial frameshift"
                /note="Predicted by GeneMark"
                /codon_start=1
                /product="Replication protein E1"
                /protein_id="NP_597794.3"
                /db_xref="GI:22507279"
                /db_xref="GeneID:1724546"
                /translation="MASPEGTDGEGKGCCGWFEVEAIVEKKTGDKISDDESDEEDEID
                TDLDGFIDDSYIQNIQADAETSQQLLQVQTAHADKQTLQKLKRKYIASPLRDISNQQT
                VCREGVKRRLILSDLQDSGYGNTLETLETPEQVDEEVQGRGCGNTQNGGSQNSTYSNN
                SEDSVIHMDIDRNNETPTQQLQDLFKSSNLQGKLYYKFKEVYGIPFSELVRTFKSDST
                CCNDWICAIFGVNETLAEALKTIIKPHCMYYHMQCLTCTWGVIVMMLIRYTCGKNRKT
                IAKALSSILNVPQEQMLIQPPKIRSPAVALYFYKTAMSNISDVYGDTPEWIQRQTQLQ
                HSLQDSQFELSKMVQWAFDNEVTDDSQIAFQYAQLADVDSNAQAFLKSNMQAKYVKDC
                GIMCRHYKRAQQQQMNMCQWIKHICSKTDEGGDWKPIVQFLRYQGVDFISFLSYFKLF
                LQGTPKHNCLVLCGPPNTGKSCFAMSLIKFFQGSVISFVNSQSHFWLQPLDNAKLGLL
                DDATEICWKYIDDYLRNLVDGNPISLDRKHKQLVQIKCPPLLITTNINPMLDAKLRYL
                HSRMLVFQFQNPFPLDNNGNPVYELSNVNWKCFFTRTWSRLNLDNDEDKENNGDAFPT
                FKCVPEQNTRLF" SEQ ID NO: 426
gene            2918..3850
                /gene="E2"
                /locus_tag="HpV56gp4"
                /db_xref="GeneID:1489332"
CDS             2918..3850
                /gene="E2"
                /locus_tag="HpV56gp4"
                /codon_start=1
                /product="envelope protein"
                /protein_id="NP_041851.1"
                /db_xref="GI:9627386"
                /db_xref="UniProtKB/Swiss-Prot:P36798"
                /db_xref="GeneID:1489332"
                /translation="MVPCLQVCKAKACSAIEVQIALESLSTTIYNNEEWTLRDTCEEL
                WLTEPKKCFKKEGQHIEVWFDGSKNNCMQYVAWKYIYYNGDCGWQKVCSGVDYRGIYY
                VHDGHKTYYTDFEQEAKKFGCKNIWEVHMENESIYCPDSVSSTCRYNVSPVETVNEYN
                THKTTTTTSTSVGNQDAAVSHRPGKRPRLRESEFDSSRESHAKCVTTHTHISDTDNTD
                SRSRSINNNNHPGDKTTPVVHLKGEPNRLKCCRYRFQKYKTLFVDVTSTYHWTSTDNK
                NYSIITIIYKDETQRNSFLSHVKIPVVYRLVWDK" SEQ ID NO: 427
gene            4222..5616
                /gene="L2"
                /locus_tag="HpV56gp5"
                /db_xref="GeneID:1489333"
CDS             4222..5616
                /gene="L2"
                /locus_tag="HpV56gp5"
                /codon_start=1
                /product="late protein"
                /protein_id="NP_041852.1"
```

FIGURE 3 (cont'd)

```
                     /db_xref="GI:9627387"
                     /db_xref="UniProtKB/Swiss-Prot:P36765"
                     /db_xref="GeneID:1489333"
                     /translation="MVAHRATRRKRASATQLYKTCKLSGTCPEDVVNKIEQKTWADKI
                     LQWGSLFTYFGGLGIGTGTGSGGRAGYVPLGSRPSTIVDVTPARPPIVVESVGPTDPS
                     IVTLVEESSVIESGAGIPNFTGSGGFEITSSSTTTPAVLDITPTSSTVHVSSTHITNP
                     LFIDPPVIEAPQTGEVSGNILISTPTSGIHSYEEIPMQTFAVHGSGTEPISSTPIPGF
                     RRIAAPRLYRKAFQQVKVTDPAFLDRPATLVSADNPLFEGTDTSLAFSPSGVAPDPDF
                     MNIVALHRPAFTTRRGGVRFSRLGRKATIQTRRGTQIGARVHYYYDISPIAQAEEIEM
                     QPLLSANNSFDGLYDIYANIDDEAPGLSSQSVATPSAHLPIKPSTLSFASNTTNVTAP
                     LGNVWETPFYSGPDIVLPTGPSTWPFVPQSPYDVTHDVYIQGSSFALWPVYFFRRRRR
                     KRIPYFFADGDVAA" SEQ ID NO: 428
     gene            5492..7096
                     /gene="L1"
                     /locus_tag="HpV56gp6"
                     /db_xref="GeneID:1489334"
     CDS             5492..7096
                     /gene="L1"
                     /locus_tag="HpV56gp6"
                     /codon_start=1
                     /product="late protein"
                     /protein_id="NP_041853.1"
                     /db_xref="GI:9627388"
                     /db_xref="UniProtKB/Swiss-Prot:P36743"
                     /db_xref="GeneID:1489334"
                     /translation="MMLPMMYIYRDPPLHYGLCIFLDVGAVNVFPIFLQMATWRPSEN
                     KVYLPPTPVSKVVATDSYVKRTSIFYHAGSSRLLAVGHPYYSVTKDNTKTNIPKVSAY
                     QYRVFRVRLPDPNKFGLPDTNIYNPDQERLVWACVGLEVGRGQPLGAGLSGHPLFNRL
                     DDTESSNLANNNVIEDSRDNISVDGKQTQLCIVGCTPAMGEHWTKGAVCKSTQVTTGD
                     CPPLALINTPIEDGDMIDTGFGAMDFKVLQESKAEVPLDIVQSTCKYPDYLKMSADAY
                     GDSMWFYLRREQLFARHYFNRAGKVGETIPAELYLKGSNGREPPPSSVYVATPSGSMI
                     TSEAQLFNKPYWLQRAQGHNNGICWGNQLFVTVVDTTRSTNMTISTATEQLSKYDARK
                     INQYLRHVEEYELQFVFQLCKITLSAEVMAYLHNMNANLLEDWNIGLSPPVATSLEDK
                     YRYVRSTAITCQREQPPTEKQDPLAKYKFWDVNLQDSFSTDLDQFPLGRKFLMQLGTR
                     SKPAVATSKKRSAPTSTSTPAKRKRR" SEQ ID NO: 429
ORIGIN      SEQ ID NO:420:
        1 gaaagtttca atcatacttt tatatattgg gagtgaccga aaagggttta agaccgaaaa
       61 cggtacatat aaaaggcagc ttattctgtg tggacatatc catggagcca caattcaaca
      121 atccacagga acgtccacga agcctgcacc acttgagtga ggtattagaa ataccttttaa
      181 ttgatcttag attatcatgt gtatattgca aaaaagaact aacacgtgct gaggtatata
      241 attttgcatg cactgaatta aaattagtgt atagggatga ttttccttat gcagtgtgca
      301 gagtatgttt attgttttat agtaaagtta gaaaatatag gtattatgac tattcagtgt
      361 atggagctac actagaaagt ataactaaaa aacagttatg tgatttatta ataaggtgct
      421 acagatgtca aagtccgtta actccggagg aaaagcaatt gcattgtgac agaaaaagac
      481 gatttcatct aatagcacat ggttggaccg ggtcatgttt ggggtgctgg agacaaacat
      541 ctagagaacc tagagaatct acagtataat catgcatggt aaagtaccaa cgctgcaaga
      601 cgttgtatta gaactaacac ctcaaacaga aattgaccta cagtgcaatg agcaattgga
      661 cagctcagag gatgaggatg aggatgaagt agaccatttg caggagcggc cacagcaagc
      721 tagacaagct aaacaacata cgtgttacct aatacacgta ccttgttgtg agtgtaagtt
      781 tgtggtgcag ttggacattc agagtaccaa agaggacctg cgtgttgtac aacagctgct
      841 tatgggtgcg ttaacagtaa cgtgcccact ctgcgcatca agtaactaac tgcaatggcg
      901 tcacctgaag gtacagatgg ggaggggaag ggatgttgtg gatggtttga agtagaggca
      961 attgtagaaa aaaaaacagg agataaaata tcagatgatg aaagtgacga ggaggatgaa
     1021 atagatacag atttagatgg atttatagac gattcatata tacaaaatat acaggcagac
     1081 gcagaaacag tcaacaattg ttgcaagtac aaacagcaca tgcagataaa cagacgttgc
     1141 aaaaactaaa acgaaagtat atagctagtc cattaaggga tattagtaat cagcaaactg
     1201 tgtgccggga aggagtaaaa cggaggctta ttttatcaga cctacaagac agcgggtatg
     1261 gcaatacatt ggaaactctg gaaacaccag aacaggtaga tgaagaggta cagggacgtg
     1321 ggtgcgggaa tacacaaaat ggaggctcac aaaacagtac ctatagtaac aatagtgagg
     1381 actctgtaat acatatggat attgatagaa acaatgaaac gccaacacaa caattgcagg
     1441 acttgtttaa aagtagcaat ttacaaggta aattatatta taaatttaaa gaagtgtatg
```

FIGURE 3 (cont'd)

```
1501 gtattccatt ttcagaattg gtgcgtacgt ttaaaagtga tagtacatgt tgcaatgatt
1561 ggatatgtgc tatatttggt gttaatgaaa cattagccga ggcactaaaa actataataa
1621 aaccacactg tatgtattat catatgcaat gtttaacatg tacatggggg gttatagtaa
1681 tgatgctaat tagatataca tgtggcaaaa acagaaaaac aattgcaaaa gcattaagct
1741 caatattaaa tgtaccacag gagcaaatgt taattcaacc accaaaaata cgaagtcctg
1801 ctgtagcttt atatttttat aaaacagcaa tgtcaaatat tagtgatgtg tatggagaca
1861 caccagaatg gatacaaaga caaacacaat tgcaacacag tttacaggat agtcaatttg
1921 aattatctaa aatggtgcag tgggcatttg ataatgaagt aacagatgat agccaaattg
1981 cgtttcaata tgcacaatta gcagatgtag acagcaatgc acaagccttt ttaaaaagca
2041 atatgcaggc aaaatatgta aaggattgtg gaataatgtg tagacattat aaaagggcac
2101 aacagcaaca aatgaatatg tgccagtgga taaagcacat atgtagtaaa acagatgaag
2161 ggggtgattg gaaacccatt gtacaatttt taagatatca aggggtcgat ttcatttcat
2221 ttctaagtta ctttaaatta tttctacaag gaacacctaa acataactgt ttggtacttt
2281 gtggaccgcc aaatacaggt aaatcatgct ttgctatgag tcttataaag tttttttcaag
2341 ggtctgtcat ttcatttgtg aattcacaaa gccacttttg gttgcagcca ttagacaatg
2401 ctaaacttgg gttgttggat gatgcaacag aaatatgttg gaaatatata gacgattatt
2461 taaggaattt ggtagatgga aatcctataa gtttagatag aaaacataaa caattagtac
2521 aaataaaatg tccaccatta ctaattacaa ccaatataaa tcctatgcta gatgctaaat
2581 tacgatattt acacagtaga atgttagtgt ttcagtttca aaatccattt ccattagata
2641 ataatggtaa tcctgtatat gaattaagta atgtaaactg gaaatgtttc tttacaagga
2701 cgtggtccag attaaatttg gataacgacg aggacaaaga aaacaatgga gacgctttcc
2761 caacgtttaa atgcgtgcca gaacaaaata ctagactgtt ttgaaaaaag atagtagatg
2821 tattgcagat catatagaat attggaaagc tgtgcgacat gaaaatgtgc tatactataa
2881 agcaagagaa aatgacatta ctgtactaaa ccaccagatg gtgccttgtt tacaagtatg
2941 taaagcaaaa gcatgtagtg caatagaagt gcaaatagca ctggaatcat taagtacaac
3001 aatatataac aatgaagagt ggacattaag agacacatgc gaggaactat ggcttactga
3061 acctaaaaaa tgctttaaaa aagaaggaca acatatagaa gtatggtttg atggtagtaa
3121 aaacaattgt atgcaatatg tagcctggaa atatatatat tacaatggag attgtgggtg
3181 gcaaaaagtg tgttctgggg tagactatag aggtatatat tatgtacatg atggccacaa
3241 aacatactac acagactttg aacaagaggc caaaaaattt gggtgtaaaa acatatggga
3301 agtacatatg gaaaatgaga gtatttattg tcctgactct gtgtctagta cctgtagata
3361 caacgtatcc cctgttgaaa ctgttaacga atacaacacc cacaagacca ccaccaccac
3421 ctccacgtcc gtgggcaacc aagacgccgc agtatcccac agaccaggaa aacgacccag
3481 actacgggaa tcagaatttg actcctccag agagtcccac gcaaagtgtg tcacaacaca
3541 cacacacatc agcgacacag acaataccga cagtagaagt agaagtatca acaacaacaa
3601 ccacccctggt gataagacta cgcctgtagt acatttaaaa ggtgaaccta acagattaaa
3661 atgttgtaga tatcgatttc aaaaatataa aacattgttt gtggatgtaa catcaacata
3721 tcattggaca agtacagaca ataaaaatta tagcataatt acaattatat ataaggatga
3781 aacacaacga aacagctttt taagtcatgt aaaaattcca gtagtgtaca ggttagtttg
3841 ggacaaatga gttttccata aagtgctgta tatattgtat atacatttgt gttattgtaa
3901 cacacaaata cgtgaagtgt acctgccata cattgctgct acgcatatat attgcaacca
3961 ttgatttttg tgttattggt gtgtttgcgc tttgcttttg tgtttgtttg cttgtgtgtc
4021 atgttgtccc gcttttgcta tctgcctctg tgttttccag ttgtatatta ttaataatat
4081 tgttttggtt tgttatagcc acatcctttt ttaatacatt tataatattt ttgatatttt
4141 tttactgtcc tgtgctgtgt atatatttac atgctttgtg gataataaat aatatgtaaa
4201 tgtagtagta ctgttactac tatggttgcc caccgtgcca cacgacgcaa acgcgcatct
4261 gcaacacaac tatataaaac atgtaagttg tctggtacat gtccagagga tgttgttaat
4321 aaaatagagc aaaaaacatg ggctgataaa atattgcaat ggggaagttt atttacatat
4381 tttggaggcc ttggcattgg tacaggaact gggtctgggg gtcgtgcagg ctatgttcca
4441 ttggggtcta ggccttccac aatagttgat gtaactccgg cgcgaccacc tattgttgtg
4501 gaatccgtag ggcctacaga cccttccatt gttacattag ttgaggagtc cagtgttata
4561 gaatctggtg cagggattcc taattttact gggtctgggg gatttgaaat tacatcctca
4621 tcaacaacta cacctgccgt gttggatatt acaccaacct ctagtactgt acatgtcagt
4681 agtacccata taaccaatcc gttatttatt gatccccctg ttattgaggc ccccacaaaca
4741 ggcgaggtgt ctggcaatat tttaattagc acacccacat ctggtataca tagctatgaa
4801 gaaataccta tgcaaacatt tgctgttcac ggttctggta cagaacctat tagtagtact
4861 cctattccag gctttaggcg tattgcagct cctagattat atagaaaagc atttcagcag
4921 gttaaggtaa ctgaccctgc atttcttgat agacctgcaa cattagtatc tgctgataat
4981 ccactttttg aaggtactga cacatcttta gctttttctc cgtcgggtgt ggctcctgac
5041 cctgatttta tgaatatagt agcattacat aggcctgcat ttactacacg taggggtggt
```

FIGURE 3 (cont'd)

```
5101 gtacgtttta gtaggcttgg cagaaaggct actatacaaa cacgtagagg cacacaaata
5161 ggtgcccgtg tgcattatta ttatgatata agtcctattg cacaggctga ggaaattgaa
5221 atgcagccat tattgtctgc aaataattca tttgatggcc tatatgatat ttatgcaaat
5281 atagatgatg aagcacctgg tttgtctagc cagtcagttg ctacaccttc tgcacactta
5341 cctataaagc cttccacatt gtcttttgct agtaacacca ctaatgtaac tgcccccttta
5401 ggtaatgtgt gggaaacacc attttattca ggtcctgaca tagtgttgcc tacaggcccc
5461 agtacgtggc cctttgttcc tcagtctcct tatgatgtta cccatgatgt atatatacag
5521 ggatcctcct ttgcattatg gcctgtgtat ttttttagac gtaggcgccg taaacgtatt
5581 ccctattttt ttgcagatgg cgacgtggcg gcctagtgaa aataaggtgt atctacctcc
5641 aacacctgtt tcaaaggttg tggcaacgga ttcctatgta aaacgcacta gtatatttta
5701 tcatgcaggc agttcacgat tgcttgccgt aggacatccc tattactctg tgactaagga
5761 caataccaaa acaaacattc ccaaagttag tgcatatcaa tatagggtat ttagggtacg
5821 gttgcccgac cctaataagt ttgggcttcc agatactaat atttataatc cggaccagga
5881 acggttagtg tgggcatgtg taggtttgga ggtaggccgc ggacagcctt taggtgctgg
5941 gctaagtggc catccattgt ttaataggct ggatgatact gaaagttcca atttagcaaa
6001 taataatgtt atagaagata gtagggacaa tatatcagtt gatggcaagc aaacacagtt
6061 gtgtattgtt ggatgtactc ccgctatggg tgaacattgg actaaaggtg ctgtgtgtaa
6121 gtccacacaa gttaccacag ggactgccc gcctcttgca ttaattaata cacctataga
6181 ggatggggac atgatagaca caggatttgg cgctatggac tttaaggtgt tgcaggaatc
6241 taaggctgag gtacctttag acattgtaca atccacctgt aaatatcctg actatttaaa
6301 aatgtctgca gatgcctatg gtgattctat gtggttttac ttacgcaggg aacaattatt
6361 tgccagacat tattttaata gggctggtaa agttggggaa acaatacctg cagagttata
6421 tttaaagggt agcaatggta gagaaccccc tccgagttct gtatatgttg ctacgcctag
6481 tgggtctatg attacgtctg aggcacagtt atttaataaa ccttattggt tgcaacgtgc
6541 ccaaggccat aataatggca tttgctgggg taatcaatta tttgttactg tagtagatac
6601 tactagaagt actaacatga ctattagtac tgctacagaa cagttaagta aatatgatgc
6661 acgaaaaatt aatcagtacc ttagacatgt ggaggaatat gaattacaat ttgtttttca
6721 attatgcaaa attactttgt ctgcagaggt tatggcatat ttacataata tgaatgctaa
6781 cctactggag gactggaata ttgggttatc ccgccagtg gccaccagcc tagaagataa
6841 atatagatat gttagaagca cagctataac atgtcaacgg gaacagccac caacagaaaa
6901 acaggaccca ttagctaaat ataaattttg ggatgttaac ttacaggaca gtttttctac
6961 agacctggat caatttccac tgggtagaaa atttttaatg caactgggca ctaggtcaaa
7021 gcctgctgta gctacctcta aaaagcgatc tgctcctacc tccacctcta caccagcaaa
7081 acgtaaaagg cggtagtgtg ttgttgtgtg tttgtgtaac tgtgtttgtg tgttgtatat
7141 atggtatgtt tgtgtatgtg ctttatttta tactttgtat gtgtatgttg tgtttgtgta
7201 aatgtttgtg tgaaatgttt gtgtgtgtat tcattgtatg tatgactgta tatatgtgta
7261 atgtttgtgt gtctgtaata aacatgaatg agtgctttta cgcgtggttg cataaactaa
7321 ggtgtgtcat tattgtggct tttgttttgt aagttattgt gtacagtgta ctatgtgtat
7381 tgtgcataca tatatatacc ataacatact ccattttgtt gtttttccgc cattttgtac
7441 atgcaaccga attcggttgc atggcctagt gccattattt aaactaaaag gaattcggtt
7501 gcatggccta gtgccattat ttaaaccaaa aggccctttt cagcagaaca gttaatcctt
7561 tggcatattg ccgtttcctg tgttttatac ttgaattatg tacagtaccg caccctgtat
7621 tactcacagg tactatgact gccaactatg cttttatctg catactttag tgctgttggg
7681 cacacatttt tatacatgtg tctgcaactt tggtgttttg gcttgcagaa tacactatgt
7741 aggccaagta tctgtcagta tctgttttgc aaacatgtaa catacaatta ctcatttttt
7801 aaaaccgttt acggtcgtgc aaaaacaggt ttcttttaat tgtt
// end of SEQ ID NO:420
```

reprinted from NCBI website (http://www.ncbi.nlm.nih.gov)

FIGURE 3 (end)

```
LOCUS       NC_001533               7808 bp    DNA     linear   VRL 25-JAN-2005
DEFINITION  Human papillomavirus type 51, complete genome.
ACCESSION   NC_001533
VERSION     NC_001533.1  GI:9627155
KEYWORDS
SOURCE      Human papillomavirus - 51
  ORGANISM  Human papillomavirus - 51
            Viruses; dsDNA viruses, no RNA stage; Papillomaviridae;
            Alphapapillomavirus.
REFERENCE   1  (bases 1 to 7808)
  AUTHORS   Lungu,O., Crum,C.P. and Silverstein,S.
  TITLE     Biologic properties and nucleotide sequence analysis of human
            papillomavirus type 51
  JOURNAL   J. Virol. 65 (8), 4216-4225 (1991)
   PUBMED   1649326
COMMENT     REVIEWED REFSEQ: This record has been curated by NCBI staff. The
            reference sequence was derived from M62877.
FEATURES             Location/Qualifiers
     source          1..7808
                     /organism="Human papillomavirus - 51"
                     /mol_type="genomic DNA"
                     /db_xref="taxon:10595"
     gene            97..552
                     /gene="E6"
                     /locus_tag="HpV51gp1"
                     /db_xref="GeneID:1489322"
     CDS             97..552
                     /gene="E6"
                     /locus_tag="HpV51gp1"
                     /codon_start=1
                     /product="E6 protein"
                     /protein_id="NP_068496.1"
                     /db_xref="GI:11119520"
                     /db_xref="UniProtKB/Swiss-Prot:P2655"
                     /db_xref="GeneID:1489322"
                     /translation="MFEDKRERPRTLHELCEALNVSMHNIQVVCVYCKKELCRADVYN
VAFTEIKIVYRDNNPYAVCKQCLLFYSKIREYRRYSRSVYGTTLEAITKKSLYDLSIR
CHRCQRPLGPEEKQKLVDEKKRFHEIAGRWTGQCANCWQRTRQRNETQV" SEQ ID NO: 430
     gene            560..865
                     /gene="E7"
                     /locus_tag="HpV51gp2"
                     /db_xref="GeneID:1489323"
     CDS             560..865
                     /gene="E7"
                     /locus_tag="HpV51gp2"
                     /codon_start=1
                     /product="E7 protein"
                     /protein_id="NP_068497.1"
                     /db_xref="GI:11119522"
                     /db_xref="UniProtKB/Swiss-Prot:P26558"
                     /db_xref="GeneID:1489323"
                     /translation="MRGNVPQLKDVVLHLTPQTEIDLQCYEQFDSSEEEDEVDNMRDQ
 LPERRAGQATCYRIEAPCCRCSSVVQLAVESSGDTLRVVQQMLMGELSLVCPCCANN" SEQ ID NO: 431
```

FIGURE 4

```
     gene            874..2778
                     /gene="E1"
                     /locus_tag="HpV51gp3"
                     /db_xref="GeneID:1489324"
     CDS             874..2778
                     /gene="E1"
                     /locus_tag="HpV51gp3"
                     /codon_start=1
                     /product="replication protein E1"
                     /protein_id="NP_068498.1"
                     /db_xref="GI:11119519"
                     /db_xref="UniProtKB/Swiss-Prot:P26544"
                     /db_xref="GeneID:1489324"
                     /translation="MDCEGTEDEGAGCNGWFFVEAIVEKKTGDNVSDDEDENADDTGS
DLINFIDSETSICSQAEQETARALFQAQELQANKEAVHQLKRKFLVSPRSSPLGDITN
QNNTHSHSQANESQVKRRLLDSYPDSGYGNTQVETVEATLQVDGQHGGSQNSVCSSGG
GSVMDVETTESCANVELNSICEVLKSSNAKATLMAKFKELYGISYNELVRVFKSDKTC
CIDWVCALFGVSPMVAENLKTLIKPFCMYYHIQCLSCDWGTIVLMLIRFSCAKNRTTI
AKCLSTLVNIPQSQMFIEPPKLRSTPVALYFYRTGISNISNTYGETPEWITRQTQLQH
SFEDSTFELSQMVQWAFDHEVLDDSEIAFHYAQLADIDSNAAAFLKSNCQAKYVKDCG
TMARHYKRAQRKSLSMSAWIRYRCDRAKDGGNWREIAKFLRYQGVNFMSFIQMFKQFL
KGTPKHNCIVIYGPPNTGKSLFAMSLMKFMQGSIISYVNSGSHFWLQPLEDAKIALLD
DATYGCWTYIDQYLRNFLDGNPCSIDRKHRSLIQLVCPPLLITSNINPQEDANLMYLH
TRVTVLKFLNTFPFDNNGNAVYTLNDENWKNFFSTTWSRLDLEEEEDKENGDPMPPFK
CVPGENTRLL" SEQ ID NO: 432
     gene            2720..3796
                     /gene="E2"
                     /locus_tag="HpV51gp4"
                     /db_xref="GeneID:1489325"
     CDS             2720..3796
                     /gene="E2"
                     /locus_tag="HpV51gp4"
                     /codon_start=1
                     /product="regulatory protein E2"
                     /protein_id="NP_068499.1"
                     /db_xref="GI:11119523"
                     /db_xref="UniProtKB/Swiss-Prot:P26547"
                     /db_xref="GeneID:1489325"
/translation="METLCHRLNVCQEKILDCYELDSDKLVDQINYWTLLRYEAAMFY
AARERNLRTINHQVVPATTVSKQKACQAIEMHMALQSLNKSDYNMEPWTMRETCYELW
CVAPKQCFKKGGITVTVIFDGNKDNAMDYTSWKFIYIYDNDKWVKTNGNVDYTGIYYT
VNSKKEYYVQFKDEAKIYGAQQWEVYMYGTVITCPEYVSSTCSDALSTTTTVEQLSNT
PTTNPLTTCVGAKEAQTQQRKRQRLTEPDSSTISPLSVDNTNNQIHCGSGSTNTGGHQ
SATQTAFIVHLKGDTNCLKCFRYRFTKHKGLYKNVSSTWHWTSNTKTGIVTIVFDSAH
                     QRETFIKTIKVPPSVTLSLGIMTL" SEQ ID NO: 433
     gene            3309..3572
                     /gene="E4"
                     /locus_tag="HpV51gp5"
                     /db_xref="GeneID:1489327"
     CDS             3309..3572
                     /gene="E4"
                     /locus_tag="HpV51gp5"
                     /codon_start=1
                     /product="probable E4 protein"
                     /protein_id="NP_068500.1"
                     /db_xref="GI:11119525"
                     /db_xref="UniProtKB/Swiss-Prot:P26548"
                     /db_xref="GeneID:1489327"
                     /translation="MYLVPAATRYPLLQLLNNYQTPQRPIPLPPAWAPKKPRHNSEND
                     SDLLSPTPPQSPHCPWTIQTTKYTVEVEALTLEGTKVQLRLRL"
                                                         SEQ ID NO: 434
```

FIGURE 4 (cont'd)

```
     gene            4134..5540
                     /gene="L2"
                     /locus_tag="HpV51gp6"
                     /db_xref="GeneID:1489326"
     CDS             4134..5540
                     /gene="L2"
                     /locus_tag="HpV51gp6"
                     /codon_start=1
                     /product="minor capsid protein L2"
                     /protein_id="NP_068501.1"
                     /db_xref="GI:11119524"
                     /db_xref="UniProtKB/Swiss-Prot:P26539"
                     /db_xref="GeneID:1489326"
                     /translation="MVATRARRRKRASVTQLYSTCKAAGTCPPDVVNKVEGTTLADKI
LQWSGLGIFLGGLGIGTGSGSGGRTGYIPLGGGGRPGVVDIAPARPPIIIDLWHHTEP
SIVNLVEDSSIIQSGSPIPTFTGTDGFEITSSSTTTPAVLDITPSAGTVHVSSTNIEN
PLYIEPPSIEAPQSGEVSDIYLLVHYSGTHGYEEIPMEVFASNVSTGTEPISSTPTPG
VSRIAAPRLYSKSYTQVKVTNPDFISKPSTFVTFNNPAFEPIDTSITFEEPDAVAPDP
DFLDIITLHRPALTSRRGTVRFSRLGQKATMRTRSGKQIGARVHYYHDISRIAPADEL
EMQPLLSPSNNYSYDIYADLDEAETGFIQPTHTTPMSHSSLSRQLPSLSSSMSSSYAN
VTIPFSTTYSVPIHTGPDVVLPTSPTVWPYVPHTSIDTKHSIVILGGDYYLWPYTHLL
                     RKRRKRIPYFFTDGIVAH" SEQ ID NO: 435
     gene            5521..7035
                     /gene="L1"
                     /locus_tag="HpV51gp7"
                     /db_xref="GeneID:1489328"
     CDS             5521..7035
                     /gene="L1"
                     /locus_tag="HpV51gp7"
                     /codon_start=1
                     /product="major capsid protein L1"
                     /protein_id="NP_068502.1"
                     /db_xref="GI:11119521"
                     /db_xref="UniProtKB/Swiss-Prot:P26536"
                     /db_xref="GeneID:1489328"
                     /translation="MALWRTNDSKVYLPPAPVSRIVNTEEYITRTGIYYYAGSSRLIT
LGHPYFPIPKTSTRAAIPKVSAFQYRVFRVQLPDPNKFGLPDPNLYNPDTDRLVWGCV
GVEVGRGQPLGVGLSGHPLFNKYDDTENSRIANGNAQQDVRDNTSVDNKQTQLCIIGC
APPIGEHWGIGTTCKNTPVPPGDCPPLELVSSVIQDGDMIDTGFGAMDFAALQATKSD
VPLDISQSVCKYPDYLKMSADTYGNSMFFHLRREQIFARHYYNKLVGVGEDIPNDYYI
KGSGNGRDPIESYIYSATPSGSMITSDSQIFNKPYWLHRAQGHNNGICWNNQLFITCV
DTTRSTNLTISTATAAVSPTFTPSNFKQYIRHGEEYELQFIFQLCKITLTTEVMAYLH
TMDPTILEQWNFGLTLPPSASLEDAYRFVRNAATSCQKDTPPQAKPDPLAKYKFWDVD
LKERFSLDLDQFALGRKFLLQVGVQRKPRPGLKRPASSASSSSSSSAKRKRVKK" SEQ ID NO: 436
ORIGIN      SEQ ID NO:421:
        1 aacaattatc ttgtaaaaac tagggtgtaa ccgaaaaggg ttatgaccga aaacggtgca
       61 tataaaagtg cagtggtaaa agtatagaag aacaccatgt tcgaagacaa gagggaaaga
      121 ccacgaacgc tgcatgaatt atgtgaagct ttgaacgttt ctatgcacaa tatacaggta
      181 gtgtgtgtgt attgtaaaaa ggaattatgt agagcagatg tatataatgt agcatttact
      241 gaaattaaga ttgtatatag ggataataat ccatatgcag tatgcaaaca atgtttactg
      301 ttttattcaa aaattagaga gtatagacgt tatagcaggt ctgtgtatgg tactacatta
      361 gaggcaatta ctaaaaaaag cttatatgat ttatcgataa ggtgtcatag atgtcaaaga
      421 ccacttgggc ctgaagaaaa gcaaaaattg gtggacgaaa aaaaaaggtt ccatgaaata
      481 gcgggacgtt ggacggggca atgcgctaat tgctggcaac gtacacgaca acgtaacgaa
      541 acccaagtgt aataaagcca tgcgtggtaa tgtaccacaa ttaaaagatg tagtattgca
      601 tttaacacca cagactgaaa ttgacttgca atgctacgag caatttgaca gctcagagga
      661 ggaggatgaa gtagataata tgcgtgacca gctaccagaa agacgggctg gacaggctac
      721 gtgttacaga attgaagctc cgtgttgcag gtgttcaagt gtagtacaac tggcagtgga
      781 aagcagtgga gacacccttc gcgttgtaca gcagatgtta atgggcgaac taagcctggt
      841 ttgcccgtgt tgtgcgaaca actagcaacg gcgatggact gtgaaggtac agaggatgag
      901 ggggcggggt gtaatgggtg gtttttttgtt gaagcaatag tagaaaaaaa aacaggagat
```

FIGURE 4 (cont'd)

```
 961 aatgtttcgg atgatgagga tgaaaatgca gatgatacag gatctgattt aataaacttt
1021 atagatagtg aaactagtat ttgcagtcag gcggaacagg agacagcacg ggcgttgttt
1081 caggcccaag aattacaggc aaacaaagag gctgtgcatc agttaaaacg aaagtttcta
1141 gtcagcccgc gaagcagccc attaggagac attacaaatc aaaacaacac acacagccat
1201 agtcaggcaa acgagtcaca agttaaaagg agattactgg acagttatcc ggacagcgga
1261 tatggcaata cacaagtgga aactgtggaa gcaacgttgc aggtagatgg gcaacatggc
1321 ggttcacaga acagtgtgtg tagtagcggg gggggcagtg ttatggatgt ggaaacaaca
1381 gaaagctgtg caaatgtaga actaaacagt atatgtgaag tattaaaaag cagtaatgca
1441 aaagcaacgt taatggcaaa atttaaagag ttgtatggta ttagttataa tgagttggta
1501 cgggtgttta aaagtgataa aacatgttgt atagattggg tttgtgcatt gtttggcgtt
1561 tccccaatgg tagcagaaaa tttaaaaaca ctaattaagc cattttgcat gtactaccat
1621 atacaatgtt tatcatgtga ttggggcacc attgtattaa tgctaattag gttttcatgt
1681 gcaaaaaaca gaacaacaat tgctaagtgt ttaagtacat tagtaaatat cccacaatca
1741 caaatgttta tagaaccacc aaaattacgt agtacacctg tggcattata tttttataga
1801 acaggcatat caaacattag caatacatat ggagagacac ctgaatggat tacacgacaa
1861 acgcaactac aacatagttt tgaggatagt acctttgaat tatcacaaat ggtgcaatgg
1921 gcatttgacc atgaagtatt agatgatagt gaaatagcat ttcattatgc acaattagca
1981 gatatagata gtaatgctgc agcgttttta aagagtaatt gccaagcaaa atatgtaaaa
2041 gattgtggga ccatggcacg gcattacaaa cgagcacaaa gaaaatcatt atctatgtca
2101 gcctggataa ggtatagatg tgatagagca aaggatggag gcaactggag agaaattgct
2161 aaatttttaa gatatcaagg tgtaaacttt atgtccttta ttcaaatgtt taaacagttt
2221 ttaaaaggaa caccaaaaca caattgcata gtcatatatg gcccaccaaa cacaggcaag
2281 tcattatttg caatgagcct aatgaagttt atgcaagggt ccattatttc atatgtaaac
2341 tctggtagtc atttttggtt acagccacta gaggatgcta aaatagcatt gttagatgat
2401 gctacgtatg ggtgttggac atatattgat cagtatttaa gaaacttttt agatggtaat
2461 ccatgtagta tagatagaaa acataggagt ttaatacaat tagtatgtcc accattacta
2521 ataacgtcaa acataaatcc acaagaggat gcaaacctaa tgtatttaca tacaagggta
2581 acagtattaa agtttttaaa tacatttcca tttgataaca atgggaatgc tgtgtataca
2641 ttgaatgatg aaaattggaa aaattttttt tccaccacat ggtccagatt agatttggag
2701 gaggaagagg acaaagaaaa tggagacccc atgccaccgt ttaaatgtgt gccaggagaa
2761 aatactagac tgttatgaac tggacagtga taaattagta gatcaaatta actattggac
2821 attgttacga tatgaagctg ctatgtttta tgcagcacgg gaaagaaact tacgaacaat
2881 caatcaccag gtagtaccag caacaacagt atcaaaacaa aaggcctgtc aagcaattga
2941 aatgcacatg gccttacaat cgcttaacaa atcagactat aacatggaac catggacaat
3001 gcgggagaca tgttatgaac tatggtgtgt ggctcccaag caatgtttca aaaagggggg
3061 cataactgta acagttatat ttgatggaaa taaggacaat gcaatggact atacaagctg
3121 gaaatttata tatatatatg ataatgataa gtgggtaaag acaaatggaa atgtggacta
3181 tacgggtata tattacactg taaattcaaa aaaagaatat tatgtacagt ttaaagatga
3241 agccaaaata tatggggcac aacagtggga ggtctatatg tatggtactg taataacatg
3301 tcctgaatat gtatctagta cctgcagcga cgcgttatcc actactacaa ctgttgaaca
3361 actatcaaac accccaacga ccaatcccct taccacctgc gtgggcgcca aagaagccca
3421 gacacaacag cgaaaacgac agcgacttac tgagcccgac tcctccacaa tctccccact
3481 gtccgtggac aatacaaaca accaaataca ctgtggaagt ggaagcacta acactggagg
3541 gcaccaaagt gcaactcaga ctgcgtttat agtgcattta aaaggtgata caaattgttt
3601 aaaatgtttt agatacagat ttacaaaaca caaagggtta tataaaaacg tatcctcaac
3661 ctggcattgg accagtaata ctaaaacagg cattgttacc attgtgtttg acagtgcaca
3721 tcaacgggaa acatttataa aaaccattaa agtaccccca agtgtaacac tgtcattggg
3781 aattatgaca ctgtaactag tgtaatatat gtattgtaca tatatactgt cacaagccaa
3841 tatgtgctgc taattgtata gacatattgt aaccattgca gtgtttatta ttttgctatt
3901 tgtgctttgc ttgtgtgtgt gtcttgtgtt gtgttgtttg ttgccgctac tgctgtccca
3961 atacgtgttt gcagctgcct tattattaat tttatgtttt tggtttgttg ttgcaacatc
4021 ccaattaact acatttttg tatatttgat tttttttac ttaccttgtt tacttttaca
4081 tctatataca tttttacttt tgcaataaac ttgttatatt tttgtgatta aatatggtgg
4141 ctacacgtgc acggcgtcgg aagcgagcat ctgtaacaca attatattct acatgcaaag
4201 ctgctggtac atgtcctcct gatgttgtga ataaggttga aggtactaca ttggccgata
4261 aaatattaca gtggagtggg ttgggtatat ttttgggtgg cctaggtatt ggtactgggt
4321 ctggatctgg ggggcgtact ggatatatcc ctttaggtgg tgggggtcgc ccaggcgtgg
4381 tggatattgc tcctgcaagg ccacctatta taattgacct atggcaccat actgaacctt
4441 ctatagtaaa tttggttgag gactctagta ttattcagtc tgggtctcct atacctacct
4501 ttactggtac cgatggcttt gaaattactt catcttccac aacaacccct gctgtgttgg
4561 acatcacccc atctgctggt actgtacatg tttctagtac taacattgaa aatcctttat
```

FIGURE 4 (cont'd)

```
4621 atattgaacc tccatccatt gaggctccac aatctggaga agtgtcagat atatatttac
4681 tagtacacta ctctggtact catgggtatg aagaaatacc tatggaagtg tttgcatcca
4741 atgtcagtac tggtactgaa cctattagca gcacacctac tccaggggtt agtcgcatag
4801 ctgctccccg cttgtatagt aagtcctaca cacaggttaa agttacaaat cctgatttta
4861 ttagtaagcc atccacattt gttacattta ataatcctgc ttttgagcct attgacacat
4921 ccataacttt tgaggaacct gatgctgttg cacctgatcc tgattttctg gatattatta
4981 cactgcaccg ccctgccctt acatctcgta gaggcacagt acgctttagt aggttaggtc
5041 aaaaggccac catgcgcact cgtagtggca aacaaattgg tgctcgtgta cattattatc
5101 atgatattag tagaattgca ccagctgatg aacttgaaat gcagccttta ctttcacctt
5161 ctaataatta tagttatgac atttatgctg atttagatga agctgaaaca ggttttatac
5221 agcccacaca caccacacct atgtcacact cctctttgtc taggcagttg ccctccttat
5281 cttcatctat gtcttcatct tatgcaaatg ttactattcc attttcaact acatattctg
5341 ttcctattca tacagggcct gatgtggtat tgcccacatc tcctacagta tggccttatg
5401 ttccccacac ttccattgac accaagcatt ctattgttat actaggtggg gattactatt
5461 tgtggcccta tacacattta ctacgcaaac gccgtaaacg tataccctat ttttttacag
5521 atggcattgt ggcgcactaa tgacagcaag gtgtatttgc cacctgcacc tgtgtctcga
5581 attgtgaata cagaagaata tatcacacgc accggcatat attactatgc aggcagttcc
5641 agactaataa cattaggaca tccctatttt ccaataccta aaacctcaac gcgtgctgct
5701 attcctaaag tatctgcatt tcaatacagg gtatttaggg tacagttacc agatcctaac
5761 aagtttggac tcccggatcc aaatttatat aatccagaca cagataggtt ggtgtggggt
5821 tgtgtgggcg ttgaggtggg cagaggacag ccccttggtg ttggccttag tggtcatccc
5881 ttatttaata aatatgatga cacagaaaat tcacgcatag caaatggcaa tgcacaacaa
5941 gatgttagag ataacacatc tgttgacaac aaacagactc agttatgtat aataggctgt
6001 gctccaccta ttggggaaca ctggggtatt ggcactacat gcaaaaacac acctgtacct
6061 ccaggagact gcccccccct ggaacttgta tcctctgtca ttcaggatgg cgatatgatt
6121 gatacagggt ttggagctat ggatttcgct gccctacagg ccaccaaatc agacgtccct
6181 ttggatattt cacagtctgt ttgtaaatat cctgattatt taaaaatgtc tgcagacaca
6241 tatggtaatt ccatgttttt tcatttacgc agggagcaaa tctttgctag gcactattat
6301 aataaacttg taggtgttgg ggaagacatt cctaacgatt attatattaa gggtagtggt
6361 aatggccgtg accctataga aagttatata tactctgcta ctcccagtgg gtctatgata
6421 acatctgatt ctcaaatttt taataagcct tattggctcc accgtgcgca gggtcacaat
6481 aatggcattt gctggaacaa tcagcttttt attacctgtg ttgatactac cagaagtaca
6541 aatttaacta ttagcactgc cactgctgcg gtttccccaa catttactcc aagtaacttt
6601 aagcaatata ttaggcatgg ggaagagtat gaattgcaat ttattttca attatgtaaa
6661 attactttaa ctacagaggt aatggcttat ttacacacaa tggatcctac cattcttgaa
6721 cagtggaatt ttggattaac attacctccg tctgctagtt tggaggatgc atataggttt
6781 gttagaaatg cagctactag ctgtcaaaag gacacccctc cacaggctaa gccagatcct
6841 ttggccaaat ataaattttg ggatgttgat ttaaaggaac gattttcttt agatttagac
6901 caatttgcat tgggtcgcaa gtttttgttg caggttggcg tacaacgcaa gcccagacca
6961 ggccttaaac gcccggcctc atcggcatcc tcttcctctt cctcttcagc caaacgtaaa
7021 cgtgttaaaa agtaatgtat gttagttttt gtatgcttgt gcacactgtt gtatgcctgt
7081 atgtatatgt ttgtgtatgt actgtatgtg tttttgtgtg tgtgtgtgtt gttgttcctg
7141 tatgtatgag ttatgtatgt ttattattaa taaactatgt ggtgtgtgtg tgtgtgtttt
7201 tgcatgactg catttgtatg acatgtacgg gtgtatgtgg gtattacatt atccccgtag
7261 gtcaagggtg gtgtttcggt ggcgtcccta ttgccctacc catttttgc agcacaacag
7321 tttatatttg tgctatttag ttatactttg tagcttccat tttgttacag ctgcagccat
7381 tttgagtgca accgatttcg gttcgtgtac ttttagtata tttgccaagt tttaaaccac
7441 aactgccagt tgtttttggc ataaaccatc attttttat gacatagtgc atacatccgc
7501 ccgcccacgc cttgtacttg gcgcgcctta ccggcgctag tcatacaacc tattagtcat
7561 ttgtacttta acaattgttg gcacactgtt ttccgcccta taataattta actgcttata
7621 ggcatgtatt ttttggcata ttttatctta ctaattgcat agttggcagg tcaaatacta
7681 tgtttttagt gccaagtttc tatcctactt ataaaccatc ttactcatat gcaggtgtgc
7741 tacacaaatg tgttacctaa ccgatttgtg ttctgcctat gcttgcaaca tttttttctta
7801 taacattt
//      end of SEQ ID NO:421
```

reprinted from NCBI website (http://www.ncbi.nlm.nih.gov)

FIGURE 4 (end)

```
LOCUS       NC_001526               7904 bp    DNA     circular VRL 22-JUL-2005
DEFINITION  Human papillomavirus - 16, complete genome.
ACCESSION   NC_001526
VERSION     NC_001526.1  GI:9627100
KEYWORDS
SOURCE      Human papillomavirus type 16
  ORGANISM  Human papillomavirus type 16
            Viruses; dsDNA viruses, no RNA stage; Papillomaviridae;
            Alphapapillomavirus.
REFERENCE   1  (sites)
  AUTHORS   Kennedy,I.M., Haddow,J.K. and Clements,J.B.
  TITLE     A negative regulatory element in the human papillomavirus type 16
            genome acts at the level of late mRNA stability
  JOURNAL   J. Virol. 65 (4), 2093-2097 (1991)
   PUBMED   1848319
REFERENCE   2  (bases 1 to 7904)
  AUTHORS   Seedorf,K., Krammer,G., Durst,M., Suhai,S. and Rowekamp,W.G.
  TITLE     Human papillomavirus type 16 DNA sequence
  JOURNAL   Virology 145 (1), 181-185 (1985)
   PUBMED   2990099
REFERENCE   3  (bases 1 to 7904)
  AUTHORS
  CONSRTM   NCBI Genome Project
  TITLE     Direct Submission
  JOURNAL   Submitted (31-AUG-2004) National Center for Biotechnology
            Information, NIH, Bethesda, MD 20894, USA
(...)
FEATURES             Location/Qualifiers
     source          1..7904
                     /organism="Human papillomavirus type 16"
                     /mol_type="genomic DNA"
                     /db_xref="taxon:333760"
     TATA_signal     17..23
     TATA_signal     65..71
     gene            83..559
                     /gene="E6"
                     /locus_tag="HpV16gp1"
                     /db_xref="GeneID:1489078"
     CDS             83..559
                     /gene="E6"
                     /locus_tag="HpV16gp1"
                     /note="E6 ORF from 65 to 559; putative"
                     /codon_start=1
                     /product="transforming protein"
                     /protein_id="NP_041325.1"
                     /db_xref="GI:9627104"
                     /db_xref="GeneID:1489078"
                     /translation="MHQKRTAMFQDPQERPRKLPQLCTELQTTIHDIILECVYCKQQL
LRREVYDFAFRDLCIVYRDGNPYAVCDKCLKFYSKISEYRHYCYSLYGTTLEQQYNKP
LCDLLIRCINCQKPLCPEEKQRHLDKKQRFHNIRGRWTGRCMSCCRSSRTRRETQL" SEQ ID NO: 437
     gene            562..858
                     /gene="E7"
                     /locus_tag="HpV16gp2"
                     /db_xref="GeneID:1489079"
```

FIGURE 5

```
     CDS             562..858
                     /gene="E7"
                     /locus_tag="HpV16gp2"
                     /note="E7 ORF from 544 to 858; putative"
                     /codon_start=1
                     /product="transforming protein"
                     /protein_id="NP_041326.1"
                     /db_xref="GI:9627105"
                     /db_xref="GeneID:1489079"
                     /translation="MHGDTPTLHEYMLDLQPETTDLYCYEQLNDSSEEEDEIDGPAGQ
AEPDRAHYNIVTFCCKCDSTLRLCVQSTHVDIRTLEDLLMGTLGIVCPICSQKP" SEQ ID NO: 438
     gene            865..2813
                     /gene="E1"
                     /locus_tag="HpV16gp3"
                     /db_xref="GeneID:1489075"
     CDS             join(865..1140,1140..2813)
                     /gene="E1"
                     /locus_tag="HpV16gp3"
                     /note="E1 interrupted ORF from 859 to 2813; putative"
                     /codon_start=1
                     /product="replication protein"
                     /protein_id="NP_041327.1"
                     /db_xref="GI:9627101"
                     /db_xref="GeneID:1489075"
                     /translation="MADPAGTNGEEGTGCNGWFYVEAVVEKKTGDAISDDENENDSDT
GEDLVDFIVNDNDYLTQAETETAHALFTAQEAKQHRDAVQVLKRKYLVSPLSDISGCV
DNNISPRLKAICIEKQSRAAKRRLFESEDSGYGNTEVETQQMLQVEGRHETETPCSQY
SGGSGGGCSQYSSGSGGEGVSERHTICQTPLTNILNVLKTSNAKAAMLAKFKELYGVS
FSELVRPFKSNKSTCCDWCIAAFGLTPSIADSIKTLLQQYCLYLHIQSLACSWGMVVL
LLVRYKCGKNRETIEKLLSKLLCVSPMCMMIEPPKLRSTAAALYWYKTGISNISEVYG
DTPEWIQRQTVLQHSFNDCTFELSQMVQWAYDNDIVDDSEIAYKYAQLADTNSNASAF
LKSNSQAKIVKDCATMCRHYKRAEKKQMSMSQWIKYRCDRVDDGGDWKQIVMFLRYQG
VEFMSFLTALKRFLQGIPKKNCILLYGAANTGKSLFGMSLMKFLQGSVICFVNSKSHF
WLQPLADAKIGMLDDATVPCWNYIDDNLRNALDGNLVSMDVKHRPLVQLKCPPLLITS
NINAGTDSRWPYLHNRLVVFTFPNEFPFDENGNPVYELNDKNWKSFFSRTWSRLSLHE
                     DEDKENDGDSLPTFKCVSGQNTNTL" SEQ ID NO: 439
     gene            2755..3852
                     /gene="E2"
                     /locus_tag="HpV16gp4"
                     /db_xref="GeneID:1489080"
     CDS             2755..3852
                     /gene="E2"
                     /locus_tag="HpV16gp4"
                     /note="E2 ORF from 2725 to 3852; putative"
                     /codon_start=1
                     /product="regulatory protein"
                     /protein_id="NP_041328.1"
                     /db_xref="GI:9627106"
                     /db_xref="GeneID:1489080"
                     /translation="METLCQRLNVCQDKILTHYENDSTDLRDHIDYWKHMRLECAIYY
KAREMGFKHINHQVVPTLAVSKNKALQAIELQLTLETIYNSQYSNEKWTLQDVSLEVY
LTAPTGCIKKHGYTVEVQFDGDICNTMHYTNWTHIYICEEASVTVVEGQVDYYGLYYV
HEGIRTYFVQFKDDAEKYSKNKVWEVHAGGQVILCPTSVFSSNEVSSPEIIRQHLANH
PAATHTKAVALGTEETQTTIQRPRSEPDTGNPCHTTKLLHRDSVDSAPILTAFNSSHK
GRINCNSNTTPIVHLKGDANTLKCLRYRFKKHCTLYTAVSSTWHWTGHNVKHKSAIVT
                     LTYDSEWQRDQFLSQVKIPKTITVSTGFMSI" SEQ ID NO: 440
```

FIGURE 5 (cont'd)

```
gene            3332..3619
                /gene="E4"
                /locus_tag="HpV16gp5"
                /db_xref="GeneID:1489076"
CDS             <3332..3619
                /gene="E4"
                /locus_tag="HpV16gp5"
                /note="E4 ORF from 3332 to 3619; putative"
                /codon_start=1
                /protein_id="NP_041329.1"
                /db_xref="GI:9627102"
                /db_xref="GeneID:1489076"
                /translation="YYVLHLCLAATKYPLLKLLGSTWPTTPPRPIPKPSPWAPKKHRR
                LSSDQDQSQTPETPATPLSCCTETQWTVLQSSLHLTAHTKDGLTVIVTLHP"
                                                        SEQ ID NO: 441
gene            3863..4099
                /gene="E5"
                /locus_tag="HpV16gp6"
                /db_xref="GeneID:1489077"
CDS             <3863..4099
                /gene="E5"
                /locus_tag="HpV16gp6"
                /note="E5 ORF from 3863 to 4099; putative"
                /codon_start=1
                /protein_id="NP_041330.1"
                /db_xref="GI:9627103"
                /db_xref="GeneID:1489077"
                /translation="YCIHNITGVLFALLCVLLCVCLLIRPLLLSVSTYTSLIILVLLL
                WITAASAFRCFIVYIIFVYIPLFLIHTHARFLIT" SEQ ID NO: 442
polyA_signal    4213..4218
                /note="putative"
gene            4235..5656
                /gene="L2"
                /locus_tag="HpV16gp7"
                /db_xref="GeneID:1489081"
CDS             4235..5656
                /gene="L2"
                /locus_tag="HpV16gp7"
                /note="L2 ORF from 4133 to 5656; putative"
                /codon_start=1
                /product="minor capsid protein"
                /protein_id="NP_041331.1"
                /db_xref="GI:9627107"
                /db_xref="GeneID:1489081"
                /translation="MRHKRSAKRTKRASATQLYKTCKQAGTCPPDIIPKVEGKTIAEQ
ILQYGSMGVFFGGLGIGTGSGTGGRTGYIPLGTRPPTATDTLAPVRPPLTVDPVGPSD
PSIVSLVEETSFIDAGAPTSVPSIPPDVSGFSITTSTDTTPAILDINNTVTTVTTHNN
PTFTDPSVLQPPTPAETGGHFTLSSSTISTHNYEEIPMDTFIVSTNPNTVTSSTPIPG
SRPVARLGLYSRTTQQVKVVDPAFVTTPTKLITYDNPAYEGIDVDNTLYFSSNDNSIN
IAPDPDFLDIVALHRPALTSRRTGIRYSRIGNKQTLRTRSGKSIGAKVHYYYDLSTID
PAEEIELQTITPSTYTTTSHAASPTSINNGLYDIYADDFITDTSTTPVPSVPSTSLSG
YIPANTTIPFGGAYNIPLVSGPDIPINITDQAPSLIPIVPGSPQYTIIADAGDFYLHP
                SYYMLRKRRKRLPYFFSDVSLAA" SEQ ID NO: 443
TATA_signal     4289..4295
                /gene="L2"
                /locus_tag="HpV16gp7"
```

FIGURE 5 (cont'd)

```
     gene            5559..7154
                     /gene="L1"
                     /locus_tag="HpV16gp8"
                     /db_xref="GeneID:1489082"
     CDS             5559..7154
                     /gene="L1"
                     /locus_tag="HpV16gp8"
                     /note="L1 ORF from 5526 to 7154; putative"
                     /codon_start=1
                     /product="major capsid protein"
                     /protein_id="NP_041332.1"
                     /db_xref="GI:9627108"
                     /db_xref="GeneID:1489082"
                     /translation="MQVTFIYILVITCYENDVNVYHIFFQMSLWLPSEATVYLPPVPV
SKVVSTDEYVARTNIYYHAGTSRLLAVGHPYFPIKKPNNNKILVPKVSGLQYRVFRIH
LPDPNKFGFPDTSFYNPDTQRLVWACVGVEVGRGQPLGVGISGHPLLNKLDDTENASA
YAANAGVDNRECISMDYKQTQLCLIGCKPPIGEHWGKGSPCTNVAVNPGDCPPLELIN
TVIQDGDMVHTGFGAMDFTTLQANKSEVPLDICTSICKYPDYIKMVSEPYGDSLFFYL
RREQMFVRHLFNRAGTVGENVPDDLYIKGSGSTANLASSNYFPTPSGSMVTSDAQIFN
KPYWLQRAQGHNNGICWGNQLFVTVVDTTRSTNMSLCAAISTSETTYKNTNFKEYLRH
GEEYDLQFIFQLCKITLTADVMTYIHSMNSTILEDWNFGLQPPPGGTLEDTYRFVTQA
IACQKHTPPAPKEDDPLKKYTFWEVNLKEKFSADLDQFPLGRKFLLQAGLKAKPKFTL
                     GKRKATPTTSSTSTTAKRKKRKL" SEQ ID NO: 444
     polyA signal    7260..7265
ORIGIN   SEQ ID NO:422:
        1 actacaataa ttcatgtata aaactaaggg cgtaaccgaa atcggttgaa ccgaaaccgg
       61 ttagtataaa agcagacatt ttatgcacca aaagagaact gcaatgtttc aggacccaca
      121 ggagcgaccc agaaagttac cacagttatg cacagagctg caaacaacta tacatgatat
      181 aatattagaa tgtgtgtact gcaagcaaca gttactgcga cgtgaggtat atgactttgc
      241 ttttcgggat ttatgcatag tatatagaga tgggaatcca tatgctgtat gtgataaatg
      301 tttaaagttt tattctaaaa ttagtgagta tagacattat tgttatagtt tgtatggaac
      361 aacattagaa cagcaataca acaaaccgtt gtgtgatttg ttaattaggt gtattaactg
      421 tcaaaagcca ctgtgtcctg aagaaaagca aagacatctg gacaaaaagc aaagattcca
      481 taatataagg ggtcggtgga ccggtcgatg tatgtcttgt tgcagatcat caagaacacg
      541 tagagaaacc cagctgtaat catgcatgga gatacaccta cattgcatga atatatgtta
      601 gatttgcaac cagagacaac tgatctctac tgttatgagc aattaaatga cagctcagag
      661 gaggaggatg aaatagatgg tccagctgga caagcagaac cggacagagc ccattacaat
      721 attgtaacct tttgttgcaa gtgtgactct acgcttcggt tgtgcgtaca aagcacacac
      781 gtagacattc gtactttgga agacctgtta atgggcacac taggaattgt gtgccccatc
      841 tgttctcaga aaccataatc taccatggct gatcctgcag gtaccaatgg ggaagagggt
      901 acgggatgta atggatggtt ttatgtagag gctgtagtgg aaaaaaaaac aggggatgct
      961 atatcagatg acgagaacga aaatgacagt gatacaggtg aagatttggt agattttata
     1021 gtaaatgata atgattattt aacacaggca gaaacagaga cagcacatgc gttgtttact
     1081 gcacaggaag caaaacaaca tagagatgca gtacaggttc taaaacgaaa gtatttggta
     1141 gtccacttag tgatattagt ggatgtgtag acaataatat tagtcctaga ttaaaagcta
     1201 tatgtataga aaaacaaagt agagctgcaa aaaggagatt atttgaaagc gaagacagcg
     1261 ggtatggcaa tactgaagtg gaaactcagc agatgttaca ggtagaaggg cgccatgaga
     1321 ctgaaacacc atgtagtcag tatagtggtg gaagtggggg tggttgcagt cagtacagta
     1381 gtggaagtgg gggagagggt gttagtgaaa gacacactat atgccaaaca ccacttacaa
     1441 atattttaaa tgtactaaaa actagtaatg caaaggcagc aatgttagca aaatttaaag
     1501 agttatacgg ggtgagtttt tcagaattag taagaccatt taaaagtaat aaatcaacgt
     1561 gttgcgattg gtgtattgct gcatttggac ttacacccag tatagctgac agtataaaaa
     1621 cactattaca acaatattgt ttatatttac acattcaaag tttagcatgt tcatggggaa
     1681 tggttgtgtt actattagta agatataaat gtggaaaaaa tagagaaaca attgaaaaat
     1741 tgctgtctaa actattatgt gtgtctccaa tgtgtatgat gatagagcct ccaaaattgc
     1801 gtagtacagc agcagcatta tattggtata aaacaggtat atcaaatatt agtgaagtgt
     1861 atggagacac gccagaatgg atacaaagac aaacagtatt acaacatagt tttaatgatt
```

FIGURE 5 (cont'd)

```
1921 gtacatttga attatcacag atggtacaat gggcctacga taatgacata gtagacgata
1981 gtgaaattgc atataaatat gcacaattgg cagacactaa tagtaatgca agtgcctttc
2041 taaaaagtaa ttcacaggca aaaattgtaa aggattgtgc aacaatgtgt agacattata
2101 aacgagcaga aaaaaaacaa atgagtatga gtcaatggat aaaatataga tgtgataggg
2161 tagatgatgg aggtgattgg aagcaaattg ttatgttttt aaggtatcaa ggtgtagagt
2221 ttatgtcatt tttaactgca ttaaaaagat ttttgcaagg catacctaaa aaaaattgca
2281 tattactata tggtgcagct aacacaggta aatcattatt tggtatgagt ttaatgaaat
2341 ttctgcaagg gtctgtaata tgttttgtaa attctaaaag ccatttttgg ttacaaccat
2401 tagcagatgc caaaataggt atgttagatg atgctacagt gccctgttgg aactacatag
2461 atgacaattt aagaaatgca ttggatggaa atttagtttc tatggatgta aagcatagac
2521 cattggtaca actaaaatgc cctccattat taattacatc taacattaat gctggtacag
2581 attctaggtg gccttattta cataatagat tggtggtgtt tacatttcct aatgagtttc
2641 catttgacga aaacggaaat ccagtgtatg agcttaatga taagaactgg aaatcctttt
2701 tctcaaggac gtggtccaga ttaagtttgc acgaggacga ggacaaggaa aacgatggag
2761 actctttgcc aacgtttaaa tgtgtgtcag gacaaaatac taacacatta tgaaaatgat
2821 agtacagacc tacgtgacca tatagactat tggaaacaca tgcgcctaga atgtgctatt
2881 tattacaagg ccagagaaat gggatttaaa catattaacc accaagtggt gccaacactg
2941 gctgtatcaa agaataaagc attacaagca attgaactgc aactaacgtt agaaacaata
3001 tataactcac aatatagtaa tgaaaagtgg acattacaag acgttagcct tgaagtgtat
3061 ttaactgcac caacaggatg tataaaaaaa catggatata cagtggaagt gcagtttgat
3121 ggagacatat gcaatacaat gcattataca aactggacac atatatatat ttgtgaagaa
3181 gcatcagtaa ctgtggtaga gggtcaagtt gactattatg gtttatatta tgttcatgaa
3241 ggaatacgaa catattttgt gcagtttaaa gatgatgcag aaaaatatag taaaaataaa
3301 gtatgggaag ttcatgcggg tggtcaggta atattatgtc ctacatctgt gtttagcagc
3361 aacgaagtat cctctcctga aattattagg cagcacttgg ccaaccaccc cgccgcgacc
3421 cataccaaag ccgtcgcctt gggcaccgaa gaaacacaga cgactatcca gcgaccaaga
3481 tcagagccag acaccggaaa cccctgccac accactaagt tgttgcacag agactcagtg
3541 gacagtgctc caatcctcac tgcatttaac agctcacaca aaggacggat taactgtaat
3601 agtaacacta cacccatagt acatttaaaa ggtgatgcta atactttaaa atgtttaaga
3661 tatagattta aaaagcattg tacattgtat actgcagtgt cgtctacatg gcattggaca
3721 ggacataatg taaaacataa aagtgcaatt gttacactta catatgatag tgaatggcaa
3781 cgtgaccaat ttttgtctca agttaaaata ccaaaaacta ttacagtgtc tactggattt
3841 atgtctatat gacaaatctt gatactgcat ccacaacatt actggcgtgc tttttgcttt
3901 gctttgtgtg cttttgtgtg tctgcctatt aatacgtccg ctgcttttgt ctgtgtctac
3961 atacacatca ttaataatat tggtattact attgtggata acagcagcct ctgcgtttag
4021 gtgttttatt gtatatatta tatttgttta tataccatta tttttaatac atacacatgc
4081 acgcttttta attacataat gtatatgtac ataatgtaat tgttacatat aattgttgta
4141 taccataact tactattttt tctttttat tttcatatat aattttttt tttgtttgtt
4201 tgtttgtttt ttaataaact gttattactt aacaatgcga cacaaacgtt ctgcaaaacg
4261 cacaaaacgt gcatcggcta cccaacttta taaaacatgc aaacaggcag gtacatgtcc
4321 acctgacatt atacctaagg ttgaaggcaa aactattgct gaacaaatat tacaatatgg
4381 aagtatgggt gtattttttg gtgggttagg aattggaaca gggtcgggta caggcggacg
4441 cactgggtat attccattgg gaacaaggcc tcccacagct acagatacac ttgctcctgt
4501 aagacccct ttaacagtag atcctgtggg cccttctgat ccttctatag tttctttagt
4561 ggaagaaact agttttattg atgctggtgc accaacatct gtaccttcca ttcccccaga
4621 tgtatcagga tttagtatta ctacttcaac tgataccaca cctgctatat tagatattaa
4681 taatactgtt actactgtta ctacacataa taatcccact ttcactgacc catctgtatt
4741 gcagcctcca acacctgcag aaactggagg gcattttaca ctttcatcat ccactattag
4801 tacacataat tatgaagaaa ttcctatgga tacatttatt gttagcacaa accctaacac
4861 agtaactagt agcacaccca taccagggtc tcgcccagtg gcacgcctag gattatatag
4921 tcgcacaaca caacaggtta aagttgtaga ccctgctttt gtaaccactc ccactaaact
4981 tattacatat gataatcctg catatgaagg tatagatgtg gataatacat tatatttttc
5041 tagtaatgat aatagtatta atatagctcc agatcctgac tttttggata tagttgcttt
5101 acataggcca gcattaacct ctaggcgtac tggcattagg tacagtagaa ttggtaataa
5161 acaaacacta cgtactcgta gtggaaaatc tataggtgct aaggtacatt attattatga
5221 tttaagtact attgatcctg cagaagaaat agaattacaa actataacac cttctacata
5281 tactaccact tcacatgcag cctcacctac ttctattaat aatggattat atgatattta
5341 tgcagatgac tttattacag atacttctac aacccggta ccatctgtac cctctacatc
```

FIGURE 5 (cont'd)

```
5401 tttatcaggt tatattcctg caaatacaac aattcctttt ggtggtgcat acaatattcc
5461 tttagtatca ggtcctgata tacccattaa tataactgac caagctcctt cattaattcc
5521 tatagttcca gggtctccac aatatacaat tattgctgat gcaggtgact tttatttaca
5581 tcctagttat tacatgttac gaaaacgacg taaacgttta ccatattttt tttcagatgt
5641 ctctttggct gcctagtgag gccactgtct acttgcctcc tgtcccagta tctaaggttg
5701 taagcacgga tgaatatgtt gcacgcacaa acatatatta tcatgcagga acatccagac
5761 tacttgcagt tggacatccc tattttccta ttaaaaaacc taacaataac aaaatattag
5821 ttcctaaagt atcaggatta caatacaggg tatttagaat acatttacct gaccccaata
5881 agtttggttt tcctgacacc tcattttata atccagatac acagcggctg gtttgggcct
5941 gtgtaggtgt tgaggtaggt cgtggtcagc cattaggtgt gggcattagt ggccatcctt
6001 tattaaataa attggatgac acagaaaatg ctagtgctta tgcagcaaat gcaggtgtgg
6061 ataatagaga atgtatatct atggattaca aacaaacaca attgtgttta attggttgca
6121 aaccacctat aggggaacac tggggcaaag gatccccatg taccaatgtt gcagtaaatc
6181 caggtgattg tccaccatta gagttaataa acacagttat tcaggatggt gatatggttc
6241 atactggctt tggtgctatg gactttacta cattacaggc taacaaaagt gaagttccac
6301 tggatatttg tacatctatt tgcaaatatc cagattatat taaaatggtg tcagaaccat
6361 atggcgacag cttatttttt tatttacgaa gggaacaaat gtttgttaga catttattta
6421 atagggctgg tactgttggt gaaaatgtac cagacgattt atacattaaa ggctctgggt
6481 ctactgcaaa tttagccagt tcaaattatt ttcctacacc tagtggttct atggttacct
6541 ctgatgccca aatattcaat aaaccttatt ggttacaacg agcacagggc cacaataatg
6601 gcatttgttg gggtaaccaa ctatttgtta ctgttgttga tactacacgc agtacaaata
6661 tgtcattatg tgctgccata tctacttcag aaactacata taaaaatact aactttaagg
6721 agtacctacg acatggggag gaatatgatt tacagtttat ttttcaactg tgcaaaataa
6781 ccttaactgc agacgttatg acatacatac attctatgaa ttccactatt ttggaggact
6841 ggaattttgg tctacaacct cccccaggag gcacactaga agatacttat aggtttgtaa
6901 cccaggcaat tgcttgtcaa aaacatacac ctccagcacc taaagaagat gatcccctta
6961 aaaaatacac tttttgggaa gtaaatttaa aggaaaagtt ttctgcagac ctagatcagt
7021 ttcctttagg acgcaaattt ttactacaag caggattgaa ggccaaacca aaatttacat
7081 taggaaaacg aaaagctaca cccaccacct catctacctc tacaactgct aaacgcaaaa
7141 aacgtaagct gtaagtattg tatgtatgtt gaattagtgt tgtttgttgt gtatatgttt
7201 gtatgtgctt gtatgtgctt gtaaatatta agttgtatgt gtgtttgtat gtatggtata
7261 ataaacacgt gtgtatgtgt ttttaaatgc ttgtgtaact attgtgtcat gcaacataaa
7321 taaacttatt gtttcaacac ctactaattg tgttgtggtt attcattgta tataaactat
7381 atttgctaca tcctgttttt gttttatata tactatattt tgtagcgcca ggcccatttt
7441 gtagcttcaa ccgaattcgg ttgcatgctt tttggcacaa aatgtgtttt tttaaatagt
7501 tctatgtcag caactatggt ttaaacttgt acgtttcctg cttgccatgc gtgccaaatc
7561 cctgttttcc tgacctgcac tgcttgccaa ccattccatt gtttttttaca ctgcactatg
7621 tgcaactact gaatcactat gtacattgtg tcatataaaa taaatcacta tgcgccaacg
7681 ccttacatac cgctgttagg cacatatttt tggcttgttt taactaacct aattgcatat
7741 ttggcataag gtttaaactt ctaaggccaa ctaaatgtca ccctagttca tacatgaact
7801 gtgtaaaggt tagtcataca ttgttcattt gtaaaactgc acatgggtgt gtgcaaaccg
7861 attttgggtt acacatttac aagcaactta tataataata ctaa
//      end of SEQ ID NO :422
```

reprinted from NCBI website (http://www.ncbi.nlm.nih.gov)

FIGURE 5 (end)

```
LOCUS       NC_001357               7857 bp    DNA     linear   VRL 17-DEC-2005
DEFINITION  Human papillomavirus - 18, complete genome.
ACCESSION   NC_001357
VERSION     NC_001357.1  GI:9626069
PROJECT     GenomeProject:15506
KEYWORDS    E1 gene; E2 gene; E5 gene; E6 gene; E7 gene; L1 gene; L2 gene.
SOURCE      Human papillomavirus type 18
  ORGANISM  Human papillomavirus type 18
            Viruses; dsDNA viruses, no RNA stage; Papillomaviridae;
            Alphapapillomavirus.
REFERENCE   1
  AUTHORS   Cole,S.T. and Danos,O.
  TITLE     Nucleotide sequence and comparative analysis of the human
            papillomavirus type 18 genome. Phylogeny of papillomaviruses and
            repeated structure of the E6 and E7 gene products
  JOURNAL   J. Mol. Biol. 193 (4), 599-608 (1987)
   PUBMED   3039146
REFERENCE   2  (bases 1 to 7857)
  AUTHORS
  CONSRTM   NCBI Genome Project
  TITLE     Direct Submission
  JOURNAL   Submitted (01-AUG-2000) National Center for Biotechnology
            Information, NIH, Bethesda, MD 20894, USA
COMMENT     PROVISIONAL REFSEQ: This record has not yet been subject to final
            NCBI review. The reference sequence was derived from X05015.
            Data kindly reviewed (14-AUG-1987) by Danos O.
FEATURES             Location/Qualifiers
     source          1..7857
                     /organism="Human papillomavirus type 18"
                     /mol_type="genomic DNA"
                     /db_xref="taxon:333761"
     gene            105..581
                     /gene="E6"
                     /locus_tag="HpV18gp1"
                     /db_xref="GeneID:1489088"
     CDS             105..581
                     /gene="E6"
                     /locus_tag="HpV18gp1"
                     /codon_start=1
                     /product="E6 protein"
                     /protein_id="NP_040310.1"
                     /db_xref="GI:9626070"
                     /db_xref="GOA:P06463"
                     /db_xref="InterPro:IPR001334"
                     /db_xref="UniProtKB/Swiss-Prot:P06463"
                     /db_xref="GeneID:1489088"
                     /translation="MARFEDPTRRPYKLPDLCTELNTSLQDIEITCVYCKTVLELTEV
                     FEFAFKDLFVVYRDSIPHAACHKCIDFYSRIRELRHYSDSVYGDTLEKLTNTGLYNLL
                     IRCLRCQKPLNPAEKLRHLNEKRRFHNIAGHYRGQCHSCCNRARQERLQRRRETQV"
                                                            SEQ ID NO: 445
     gene            590..907
                     /gene="E7"
                     /locus_tag="HpV18gp2"
                     /db_xref="GeneID:1489089"
     CDS             590..907
                     /gene="E7"
                     /locus_tag="HpV18gp2"
                     /codon_start=1
                     /product="E7 protein"
                     /protein_id="NP_040311.1"
                     /db_xref="GI:9626071"
                     /db_xref="GOA:P06788"
```

FIGURE 6

/db_xref="UniProtKB/Swiss-Prot:P06788"
/db_xref="GeneID:1489089"
/translation="MHGPKATLQDIVLHLEPQNEIPVDLLCHEQLSDSEEENDEIDGV
NHQHLPARRAEPQRHTMLCMCCKCEARIELVVESSADDLRAFQQLFLNTLSFVCPWCA
SQQ" SEQ ID NO: 446 gene 914..2887
/gene="E1"
/locus_tag="HpV18gp3"
/db_xref="GeneID:1489084"

CDS 914..2887
/gene="E1"
/locus_tag="HpV18gp3"
/codon_start=1
/product="E1 protein"
/protein_id="NP_040312.1"
/db_xref="GI:9626072"
/db_xref="GOA:P06789"
/db_xref="InterPro:IPR001177"
/db_xref="UniProtKB/Swiss-Prot:P06789"
/db_xref="GeneID:1489084"
/translation="MADPEGTDGEGTGCNGWFYVQAIVDKKTGDVISDDEDENATDTG
SDMVDFIDTQGTFCEQAELETAQALFHAQEVHNDAQVLHVLKRKFAGGSTENSPLGER
LEVDTELSPRLQEISLNSGQKKAKRRLFTISDSGYGCSEVEATQIQVTTNGEHGGNVC
SGGSTEAIDNGGTEGNNSSVDGTSDNSNIENVNPQCTIAQLKDLLKVNNKQGAMLAVF
KDTYGLSFTDLVRNFKSDKTTCTDWVTAIFGVNPTIAEGFKTLIQPFILYAHIQCLDC
KWGVLILALLRYKCGKSRLTVAKGLSTLLHVPETCMLIQPPKLRSSVAALYWYRTGIS
NISEVMGDTPEWIQRLTIIQHGIDDSNFDLSEMVQWAFDNELTDESDMAFEYALLADS
NSNAAAFLKSNCQAKYLKDCATMCKHYRRAQKRQMNMSQWIRFRCSKIDEGGDWRPIV
QFLRYQQIEFITFLGALKSFLKGTPKKNCLVFCGPANTGKSYFGMSFIHFIQGAVISF
VNSTSHFWLEPLTDTKVAMLDDATTTCWTYFDTYMRNALDGNPISIDRKHKPLIQLKC
PPILLTTNIHPAKDNRWPYLESRITVFEFPNAFPFDKNGNPVYEINDKNWKCFFERTW
SRLDLHEEEEDADTEGNPFGTFKLRAGQNHRPL" SEQ ID NO: 447 gene 2817..3914
/gene="E2"
/locus_tag="HpV18gp4"
/db_xref="GeneID:1489085"

CDS 2817..3914
/gene="E2"
/locus_tag="HpV18gp4"
/codon_start=1
/product="E2 protein"
/protein_id="NP_040313.1"
/db_xref="GI:9626073"
/db_xref="GOA:P06790"
/db_xref="UniProtKB/Swiss-Prot:P06790"
/db_xref="GeneID:1489085"
/translation="MQTPKETLSERLSCVQDKIIDHYENDSKDIDSQIQYWQLIRWEN
AIFFAAREHGIQTLNHQVVPAYNISKSKAHKAIELQMALQGLAQSRYKTEDWTLQDTC
EELWNTEPTHCFKKGGQTVQVYFDGNKDNCMTYVAWDSVYYMTDAGTWDKTATCVSHR
GLYYVKEGYNTFYIEFKSECEKYGNTGTWEVHFGNNVIDCNDSMCSTSDDTVSATQLV
KQLQHTPSPYSSTVSVGTAKTYGQTSAATRPGHCGLAEKQHCGPVNPLLGAATPTGNN
KRRKLCSGNTTPIIHLKGDRNSLKCLRYRLRKHSDHYRDISSTWHWTGAGNEKTGILT
VTYHSETQRTKFLNTVAIPDSVQILVGYMTM" SEQ ID NO: 448 gene 3418..3684
/gene="E4"
/locus_tag="HpV18gp5"
/db_xref="GeneID:1489086"

CDS 3418..3684
/gene="E4"
/locus_tag="HpV18gp5"
/codon_start=1

FIGURE 6 (cont'd)

```
                     /product="E4 protein"
                     /protein_id="NP_040314.1"
                     /db_xref="GI:9626074"
                     /db_xref="InterPro:IPR003861"
                     /db_xref="UniProtKB/Swiss-Prot:P06791"
                     /db_xref="GeneID:1489086"
                     /translation="MTLCAVPVTTRYPLLSLLNSYSTPPHRIPAPCPWAPQRPTARRR
                     LLHDLDTVDSRRSSIVDLSTHFSVQLHLQATTKDGNSVVVTLRL"
                                                          SEQ ID NO: 449
gene                 3936..4157
                     /gene="E5"
                     /locus_tag="HpV18gp6"
                     /db_xref="GeneID:1489087"
CDS                  3936..4157
                     /gene="E5"
                     /locus_tag="HpV18gp6"
                     /codon_start=1
                     /product="E5 protein"
                     /protein_id="NP_040315.1"
                     /db_xref="GI:9626075"
                     /db_xref="InterPro:IPR004270"
                     /db_xref="UniProtKB/Swiss-Prot:P06792"
                     /db_xref="GeneID:1489087"
                     /translation="MLSLIFLFCFCVCMYVCCHVPLLPSVCMCAYAWVLVFVYIVVIT
                     SPATAFTVYVFCFLLPMLLLHIHAILSLQ" SEQ ID NO: 450
gene                 4244..5632
                     /gene="L2"
                     /locus_tag="HpV18gp7"
                     /db_xref="GeneID:1489091"
CDS                  4244..5632
                     /gene="L2"
                     /locus_tag="HpV18gp7"
                     /codon_start=1
                     /product="L2 protein"
                     /protein_id="NP_040316.1"
                     /db_xref="GI:9626076"
                     /db_xref="GOA:P06793"
                     /db_xref="InterPro:IPR000784"
                     /db_xref="UniProtKB/Swiss-Prot:P06793"
                     /db_xref="GeneID:1489091"
                     /translation="MVSHRAARRKRASVTDLYKTCKQSGTCPPDVVPKVEGTTLADKI
                     LQWSSLGIFLGGLGIGTGSGTGGRTGYIPLGGRSNTVVDVGPTRPPVVIEPVGPTDPS
                     IVTLIEDSSVVTSGAPRPTFTGTSGFDITSAGTTTPAVLDITPSSTSVSISTTNFTNP
                     AFSDPSIIEVPQTGEVAGNVFVGTPTSGTHGYEEIPLQTFASSGTGEEPISSTPLPTV
                     RRVAGPRLYSRAYQQVSVANPEFLTRPSSLITYDNPAFEPVDTTLTFDPRSDVPDSDF
                     MDIIRLHRPALTSRRGTVRFSRLGQRATMFTRSGTQIGARVHFYHDISPIAPSPEYIE
                     LQPLVSATEDNDLFDIYADDMDPAVPVPSRSTTSFAFFKYSPTISSASSYSNVTVPLT
                     SSWDVPVYTGPDITLPSTTSVWPIVSPTAPASTQYIGIHGTHYYLWPLYYFIPKKRKR
                     VPYFFADGFVAA" SEQ ID NO: 451
gene                 5430..7136
                     /gene="L1"
                     /locus_tag="HpV18gp8"
                     /db_xref="GeneID:1489090"
CDS                  5430..7136
                     /gene="L1"
                     /locus_tag="HpV18gp8"
                     /codon_start=1
                     /product="L1 protein"
                     /protein_id="NP_040317.1"
                     /db_xref="GI:9626077"
                     /db_xref="GOA:P06794"
                     /db_xref="InterPro:IPR002210"
```

FIGURE 6 (cont'd)

/db_xref="InterPro:IPR008975"
/db_xref="UniProtKB/Swiss-Prot:P06794"
/db_xref="GeneID:1489090"
/translation="MCLYTRVLILHYHLLPLYGPLYHPRPLPLHSILVYMVHIIICGH
YIILFLRNVNVFPIFLQMALWRPSDNTVYLPPPSVARVVNTDDYVTPTSIFYHAGSSR
LLTVGNPYFRVPAGGGNKQDIPKVSAYQYRVFRVQLPDPNKFGLPDTSIYNPETQRLV
WACAGVEIGRGQPLGVGLSGHPFYNKLDDTESSHAATSNVSEDVRDNVSVDYKQTQLC
ILGCAPAIGEHWAKGTACKSRPLSQGDCPPLELKNTVLEDGDMVDTGYGAMDFSTLQD
TKCEVPLDICQSICKYPDYLQMSADPYGDSMFFCLRREQLFARHFWNRAGTMGDTVPQ
SLYIKGTGMPASPGSCVYSPSPSGSIVTSDSQLFNKPYWLHKAQGHNNGVCWHNQLFV
TVVDTTPSTNLTICASTQSPVPGQYDATKFKQYSRHVEEYDLQFIFQLCTITLTADVM
SYIHSMNSSILEDWNFGVPPPPTTSLVDTYRFVQSVAITCQKDAAPAENKDPYDKLKF
WNVDLKEKFSLDLDQYPLGRKFLVQAGLRRKPTIGPRKRSAPSATTSSKPAKRVRVRA
RK" SEQ ID NO: 452

ORIGIN SEQ ID NO:423

```
   1 attaatactt ttaacaattg tagtatataa aaaagggagt aaccgaaaac ggtcgggacc
  61 gaaaacggtg tatataaaag atgtgagaaa cacaccacaa tactatggcg cgctttgagg
 121 atccaacacg gcgaccctac aagctacctg atctgtgcac ggaactgaac acttcactgc
 181 aagacataga aataacctgt gtatattgca agacagtatt ggaacttaca gaggtatttg
 241 aatttgcatt taaagattta tttgtggtgt atagagacag tataccccat gctgcatgcc
 301 ataaatgtat agatttttat tctagaatta gagaattaag acattattca gactctgtgt
 361 atggagacac attggaaaaa ctaactaaca ctgggttata caatttatta ataaggtgcc
 421 tgcggtgcca gaaaccgttg aatccagcag aaaaacttag acaccttaat gaaaaacgac
 481 gatttcacaa catagctggg cactatagag gccagtgcca ttcgtgctgc aaccgagcac
 541 gacaggaacg actccaacga cgcagagaaa cacaagtata atattaagta tgcatggacc
 601 taaggcaaca ttgcaagaca ttgtattgca tttagagccc caaaatgaaa ttccggttga
 661 ccttctatgt cacgagcaat taagcgactc agaggaagaa aacgatgaaa tagatggagt
 721 taatcatcaa catttaccag cccgacgagc cgaaccacaa cgtcacacaa tgttgtgtat
 781 gtgttgtaag tgtgaagcca gaattgagct agtagtagaa agctcagcag acgaccttcg
 841 agcattccag cagctgtttc tgaacaccct gtccttgtg tgtccgtggt gtgcatccca
 901 gcagtaagca acaatggctg atccagaagg tacagacggg gagggcacgg gttgtaacgg
 961 ctggttttat gtacaagcta ttgtagacaa aaaaacagga gatgtaatat cagatgacga
1021 ggacgaaaat gcaacagaca cagggtcgga tatggtagat tttattgata cacaaggaac
1081 attttgtgaa caggcagagc tagagacagc acaggcattg ttccatgcgc aggaggtcca
1141 caatgatgca caagtgttgc atgttttaaa acgaaagttt gcaggaggca gcacagaaaa
1201 cagtccatta ggggagcggc tggaggtgga tacagagtta agtccacggt tacaagaaat
1261 atctttaaat agtgggcaga aaaaggcaaa aaggcggctg tttacaatat cagatagtgg
1321 ctatggctgt tctgaagtgg aagcaacaca gattcaggta actacaaatg gcgaacatgg
1381 cggcaatgta tgtagtggcg gcagtacgga ggctatagac aacgggggca cagagggcaa
1441 caacagcagt gtagacggta caagtgacaa tagcaatata gaaaatgtaa atccacaatg
1501 taccatagca caattaaaag acttgttaaa agtaaacaat aaacaaggag ctatgttagc
1561 agtatttaaa gacacatatg ggctatcatt tacagattta gttagaaatt ttaaaagtga
1621 taaaaccacg tgtacagatt gggttacagc tatatttgga gtaaacccaa caatagcaga
1681 aggatttaaa acactaatac agccatttat attatatgcc catattcaat gtctagactg
1741 taaatgggga gtattaatat tagccctgtt gcgttacaaa tgtggtaaga gtagactaac
1801 agttgctaaa ggtttaagta cgttgttaca cgtacctgaa acttgtatgt taattcaacc
1861 accaaaattg cgaagtagtg ttgcagcact atattggtat agaacaggaa tatcaaatat
1921 tagtgaagta atgggagaca cacctgagtg gatacaaaga cttactatta tacaacatgg
1981 aatagatgat agcaattttg atttgtcaga aatggtacaa tgggcatttg ataatgagct
2041 gacagatgaa agcgatatgg catttgaata tgccttatta gcagacagca acagcaatgc
2101 agctgccttt ttaaaaagca attgccaagc taaatattta aaagattgtg ccacaatgtg
2161 caaacattat aggcgagccc aaaaacgaca aatgaatatg tcacagtgga tacgatttag
2221 atgttcaaaa atagatgaag ggggagattg gagaccaata gtgcaattcc tgcgatacca
2281 acaaatagag tttataacat ttttaggagc cttaaaatca tttttaaaag gaacccccaa
2341 aaaaaattgt ttagtatttt gtggaccagc aaatacagga aaatcatatt ttggaatgag
2401 ttttatacac tttatacaag gagcagtaat atcatttgtg aattccacta gtcatttttg
2461 gttggaaccg ttaacagata ctaaggtggc catgttagat gatgcaacga ccacgtgttg
2521 gacatacttt gatacctata tgagaaatgc gttagatggc aatccaataa gtattgatag
2581 aaagcacaaa ccattaatac aactaaaatg tcctccaata ctactaacca caaatataca
2641 tccagcaaag gataatagat ggccatattt agaaagtaga ataacagtat ttgaatttcc
2701 aaatgcattt ccatttgata aaaatggcaa tccagtatat gaaataaatg acaaaaattg
```

FIGURE 6 (cont'd)

2761 gaaatgtttt tttgaaagga catggtccag attagatttg cacgaggaag aggaagatgc
2821 agacaccgaa ggaaaccctt tcggaacgtt taagttgcgt gcaggacaaa atcatagacc
2881 actatgaaaa tgacagtaaa gacatagaca gccaaataca gtattggcaa ctaatacgtt
2941 gggaaaatgc aatattcttt gcagcaaggg aacatggcat acagacatta aaccaccagg
3001 tggtgccagc ctataacatt tcaaaaagta aagcacataa agctattgaa ctgcaaatgg
3061 ccctacaagg ccttgcacaa agtcgataca aaaccgagga ttggacactg caagacacat
3121 gcgaggaact atggaataca gaacctactc actgctttaa aaaaggtggc caaacagtac
3181 aagtatattt tgatggcaac aaagacaatt gtatgaccta tgtagcatgg gacagtgtgt
3241 attatatgac tgatgcagga acatgggaca aaaccgctac ctgtgtaagt cacaggggat
3301 tgtattatgt aaaggaaggg tacaacacgt tttatataga atttaaaagt gaatgtgaaa
3361 aatatgggaa cacaggtacg tgggaagtac attttgggaa taatgtaatt gattgtaatg
3421 actctatgtg cagtaccagt gacgacacgg tatccgctac tcagcttgtt aaacagctac
3481 agcacacccc ctcaccgtat tccagcaccg tgtccgtggg caccgcaaag acctacggcc
3541 agacgtcggc tgctacacga cctggacact gtggactcgc ggagaagcag cattgtggac
3601 ctgtcaaccc acttctcggt gcagctacac ctacaggcaa caacaaaaga cggaaactct
3661 gtagtggtaa cactacgcct ataatacatt taaaaggtga cagaaacagt ttaaaatgtt
3721 tacggtacag attgcgaaaa catagcgacc actatagaga tatatcatcc acctggcatt
3781 ggacaggtgc aggcaatgaa aaaacaggaa tactgactgt aacataccat agtgaaacac
3841 aaagaacaaa atttttaaat actgttgcaa ttccagatag tgtacaaata ttggtgggat
3901 acatgacaat gtaatacata tgctgtagta ccaatatgtt atcacttatt tttttatttt
3961 gcttttgtgt atgcatgtat gtgtgctgcc atgtcccgct tttgccatct gtctgtatgt
4021 gtgcgtatgc atgggtattg gtatttgtgt atattgtggt aataacgtcc cctgccacag
4081 cattcacagt atatgtattt tgttttttat tgcccatgtt actattgcat atacatgcta
4141 tattgtcttt acagtaattg tataggttgt tttatacagt gtattgtaca ttgtatattt
4201 tgttttatac cttttatgct ttttgtattt ttgtaataaa agtatggtat ccccaccgtgc
4261 cgcacgacgc aaacgggctt cggtaactga cttatataaa acatgtaaac aatctggtac
4321 atgtccacct gatgttgttc ctaaggtgga gggcaccacg ttagcagata aaatattgca
4381 atggtcaagc cttggtatat ttttgggtgg acttggcata ggtactggca gtggtacagg
4441 gggtcgtaca gggtacattc cattgggtgg gcgttccaat acagtggtgg atgttggtcc
4501 tacacgtccc ccagtggtta ttgaacctgt gggccccaca gacccatcta ttgttacatt
4561 aatagaggac tccagtgtgg ttacatcagg tgcacctagg cctacgttta ctggcacgtc
4621 tgggtttgat ataacatctg cgggtacaac tacacctgcg gttttggata tcacaccttc
4681 gtctacctct gtgtctattt ccacaaccaa ttttaccaat cctgcatttt ctgatccgtc
4741 cattattgaa gttccacaaa ctggggaggt ggcaggtaat gtatttgttg gtacccctac
4801 atctggaaca catgggtatg aggaaatacc tttacaaaca tttgcttctt ctggtacggg
4861 ggaggaaccc attagtagta ccccattgcc tactgtgcgg cgtgtagcag gtccccgcct
4921 ttacagtagg gcctaccaac aagtgtcagt ggctaaccct gagtttctta cacgtccatc
4981 ctctttaatt acatatgaca acccggcctt tgagcctgtg gacactacat taacatttga
5041 tcctcgtagt gatgttcctg attcagattt tatggatatt atccgtctac ataggcctgc
5101 tttaacatcc aggcgtggga ctgttcgctt tagtagatta ggtcaacggg caactatgtt
5161 taccccgcagc ggtacacaaa taggtgctag ggttcacttt tatcatgata taagtcctat
5221 tgcaccttcc ccagaatata ttgaactgca gcctttagta tctgccacgg aggacaatga
5281 cttgtttgat atatatgcag atgacatgga ccctgcagtg cctgtaccat cgcgttctac
5341 tacctccttt gcatttttta aatattcgcc cactatatct tctgcctctt cctatagtaa
5401 tgtaacggtc cctttaacct cctcttggga tgtgcctgta tacacgggtc ctgatattac
5461 attaccatct actacctctg tatggcccat tgtatcaccc acggcccctg cctctacaca
5521 gtatattggt atacatggta cacattatta tttgtggcca ttatattatt ttattcctaa
5581 gaaacgtaaa cgtgttccct attttttttgc agatggcttt gtggcggcct agtgacaata
5641 ccgtatatct tccacctcct tctgtggcaa gagttgtaaa taccgatgat tatgtgactc
5701 ccacaagcat attttatcat gctggcagct ctagattatt aactgttggt aatccatatt
5761 ttagggttcc tgcaggtggt ggcaataagc aggatattcc taaggtttct gcataccaat
5821 atagagtatt tagggtgcag ttacctgacc caaataaatt tggtttacct gatactagta
5881 tttataatcc tgaaacacaa cgtttagtgt gggcctgtgc tggagtggaa attggccgtg
5941 gtcagccttt aggtgttggc cttagtgggc atccatttta taataaatta gatgacactg
6001 aaagttccca tgccgccacg tctaatgttt ctgaggacgt tagggacaat gtgtctgtag
6061 attataagca gacacagtta tgtattttgg gctgtgcccc tgctattggg gaacactggg
6121 ctaaaggcac tgcttgtaaa tcgcgtcctt tatcacaggg cgattgcccc cctttagaac
6181 ttaaaaacac agttttggaa gatggtgata tggtagatac tggatatggt gccatggact
6241 ttagtacatt gcaagatact aaatgtgagg taccattgga tatttgtcag tctatttgta
6301 aatatcctga ttatttacaa atgtctgcag atccttatgg ggattccatg ttttttgct
6361 tacggcgtga gcagcttttt gctaggcatt tttggaatag agcaggtact atgggtgaca FIGURE 6 (cont'd)

```
6421 ctgtgcctca atccttatat attaaaggca caggtatgcc tgcttcacct ggcagctgtg
6481 tgtattctcc ctctccaagt ggctctattg ttacctctga ctcccagttg tttaataaac
6541 catattggtt acataaggca cagggtcata acaatggtgt ttgctggcat aatcaattat
6601 ttgttactgt ggtagatacc actcccagta ccaatttaac aatatgtgct tctacacagt
6661 ctcctgtacc tgggcaatat gatgctacca aatttaagca gtatagcaga catgttgagg
6721 aatatgattt gcagtttatt tttcagttgt gtactattac tttaactgca gatgttatgt
6781 cctatattca tagtatgaat agcagtattt tagaggattg gaactttggt gttccccccc
6841 ccccaactac tagtttggtg gatacatatc gttttgtaca atctgttgct attacctgtc
6901 aaaaggatgc tgcaccggct gaaaataagg atccctatga taagttaaag ttttggaatg
6961 tggatttaaa ggaaaagttt tctttagact tagatcaata tccccttgga cgtaaatttt
7021 tggttcaggc tggattgcgt cgcaagccca ccataggccc tcgcaaacgt tctgctccat
7081 ctgccactac gtcttctaaa cctgccaagc gtgtgcgtgt acgtgccagg aagtaatatg
7141 tgtgtgtgta tatatatata catctattgt tgtgtttgta tgtcctgtgt ttgtgtttgt
7201 tgtatgattg cattgtatgg tatgtatggt tgttgttgta tgttgtatgt tactatattt
7261 gttggtatgt ggcattaaat aaaatatgtt ttgtggttct gtgtgttatg tggttgcgcc
7321 ctagtgagta acaactgtat ttgtgtttgt ggtatgggtg ttgcttgttg ggctatatat
7381 tgtcctgtat ttcaagttat aaaactgcac accttacagc atccatttta tcctacaatc
7441 ctccattttg ctgtgcaacc gatttcggtt gcctttggct tatgtctgtg gttttctgca
7501 caatacagta cgctggcact attgcaaact ttaatctttt gggcactgct cctacatatt
7561 ttgaacaatt ggcgcgcctc tttggcgcat ataaggcgca cctggtatta gtcattttcc
7621 tgtccaggtg cgctacaaca attgcttgca taactatatc cactccctaa gtaataaaac
7681 tgcttttagg cacatatttt agtttgtttt tacttaagct aattgcatac ttggcttgta
7741 caactacttt catgtccaac attctgtcta cccttaacat gaactataat atgactaagc
7801 tgtgcataca tagtttatgc aaccgaaata ggttgggcag cacatactat acttttc
//     end of SEQ ID NO:423
```

reprinted from NCBI website (http://www.ncbi.nlm.nih.gov)

FIGURE 6 (end)

HPV DETECTION AND QUANTIFICATION BY REAL-TIME MULTIPLEX AMPLIFICATION

This application is the U.S. nation phase of International Application No. PCT/EP2006/004314, filed Apr. 11, 2006, which designated the U.S. and the entire contents of which is hereby incorporated by reference.

FIELD

The present invention relates to the detection of human papillomaviruses (HPV), more particularly of HPV, which have a tropism for the mucosal epithelia (mucosal-type HPV), still more particularly of HPV, which can be oncogenic for the mucosal epithelia. The present invention provides amplification primers and detection probes, which are useful therefor, as well as reference template sequences suitable for designing and building such primers and probes.

BACKGROUND OF THE INVENTION

Human papillomavirus (HPV) contains a circular double-stranded DNA genome of about 7,900 bp, which is organized into three main regions, i.e.:

- an early coding region containing genes E1, E2, E4, E5, E6 and E7, which are involved in viral replication and in neoplastic transformation,
- a late coding region, containing genes L1 and L2, which code for viral capside proteins,
- a non-coding regulatory region, which is referred to as LRC (Long Control Region), which is located between the E genes and the L genes.

HPV constitute a group of viruses, which are associated with benign and malignant lesions of cutaneous or mucosal epithelia. To date, more than 100 different HPV types have been identified.

More than 40 HPV types belonging to the mucosal group have been detected in the anogenital mucosa.

HPV is the major risk factor in the development of squamous intraepithelial lesions (SILs), which are classified as low grade (LSIL) or high grade (HSIL) in severity.

HPV may induce cervical intraepithelial neoplasia (CIN), ranging from benign lesions (CIN1), such as condylomata acuminata, through pre-cancerous lesions (CIN2 to CIN3), up to in situ carcinoma and invasive cancer.

It is now established that HPV is directly involved in cervical carcinogenesis. Detecting HPV is essential to the prognosis of CIN and cervical cancer.

Early and precise detection of HPV is the key factor for recovery from cervical cancer.

It has also been shown that an increased HPV viral load within a cervical smear to specimen is associated with an increased risk of CIN3 and of cervical carcinomas.

A number of oncogenic HPV genotypes that infect the anogenital tract have been classified as potentially high risk HPV genotypes (HR HPV), based on their occurrence or prevalence in cervical carcinomas. The presence, persistence and/or re-occurrence of HR HPV is a bad prognostic indicator. So far, thirteen HPV types are said to be HR HPV, namely HPV 56, 51, 58, 33, 52, 35, 31, 16, 68, 39, 59, 45 and 18. Those HR HPV, which have the highest prevalence, are HPV types 33, 31, 16, 45 and 18.

Other oncogenic HPV are considered to be Low Risk HPV (LR HPV), e.g., HPV2, HPV3, HPV6, HPV11, HPV13, HPV32, HPV40, HPV42, HPV43, HPV44, HPV57.

The clinical classification of HPV types into either the HR or the LR group might evolve, or slightly diverge from one author to another, as the classification of a given HPV into the LR group only stands for as long as this HPV type is not found to be associated with a cervical carcinoma.

For example, it is now contemplated that HPV53 and HPV66 probably are HR HPV (van Ham et al. 2005, J. Clin. Microbiol. Vol. 43, n°6, p. 2662-2667). Hence, the initial group of thirteen HR HPV might further increase to a number of at least 15 HPV types.

Other HPV have been described as oncogenic HPV, but without any definitive settlement on the issue of their HR or LR status, such as is the case for HPV67, HPV82, HPV85. Appropriate detection means are required to analyze their oncogenicity.

New, or yet unidentified, mucosal oncogenic HPV types may further arise.

Furthermore, HPV multi-infection, involving several types of HPV, is a common situation: multi-infection is thought to account for about 20% of the HPV infection cases. An HPV multi-infection case may involve HPV types, which all are oncogenic HPV, or which comprise at least one oncogenic HPV and at least one non-oncogenic HPV. An HPV multi-infection case may involve HPV types, which all are mucosal HPV types, or may involve at least one mucosal type and at least one cutaneous type.

Also, co-infection may also occur, which involves at least one HPV and at least one virus other than HPV, e.g., a co-infection with at least one HPV, and at least one HIV.

Such multi- and/or co-infection situations render accurate HPV detection much more difficult.

HPV primers and probes, which are suitable for the detection of mucosal oncogenic HPV, have been disclosed in prior art.

The first techniques that were developed involved type-specific probes, which were designed to detect oncogenic HPV by direct hybridization of a type-specific probe to a non-amplified HPV genome, e.g., by Southern blotting or dot blotting.

Signal-amplified tests have then been developed, such as the Hybrid Capture test (HC2®) of Digene Corporation, Gaithersburg, Md., USA. The HC2® test has been approved by the FDA, and is at present time the reference test for clinical diagnosis.

The HC2® system is a liquid phase microplate system using DNA/RNA hybridization assay, which does not comprise any target amplification: viral DNA hybridizes in liquid phase to a RNA probe which targets the 13 HR HPV, the hybrids thus formed being detected by anti-DNA/RNA antibodies and visualized by chemoluminescence.

The HC2® test is a sensitive assay. It however is only of qualitative value. Viral loads assessed by the HC2® test does not increase with increasing grade of SIL, and are not sufficiently reliable in case of multiple HPV infections. Hence, the HC2® test is not a quantitative assay.

As the HC2® test does not reflect the viral load initially contained in the analyzed sample, it is recommended to combine it with classic cytology, to distinguish the cases with high grade lesions from those without high grade lesions.

Amplification methods have then been developed, wherein HPV target(s) is(are) amplified by at least one primer pair, the amplicon thus produced being detected either by this (labelled) primer pair or by a probe.

Such prior art primers have first been designed as general consensus primers, which are intended for amplifying several HPV, usually several of the thirteen HR HPV, as well as other HPV (oncogenic LR, and sometimes also non-oncogenic HPV).

Such consensus primers are also referred to as "universal" primers. These consensus primers target conserved regions in the HPV L1 gene (e.g., the MY09/MY11/HMB01 primers, the GP5+/GP6+ primers, the PGMY09/PGMY11 primers, and the SPF1/SPF2 or SPF10 primers), or the E1 ORF region (e.g., the CPIIG/CPI primers described in Tieben et al. 1993, J. Virol. Methods 42:265-279).

To render consensus PCR applicable to clinical diagnosis, HPV probes have been developed to detect and type HPV amplicons generated by consensus primer sets. Detection of the HPV amplicons generated by consensus primers is usually performed by a reverse hybridization line blot assay, or by calorimetric microtiter plate-based enzyme immunoassay.

Illustrative of such consensus PCR methods are the INNO-LiPA HPV test (Innogenetics, Gent, Belgium), and the Amplicor HPV test (Roche Molecular Systems, Branchburg, N.J., USA).

The INNO-LiPA HPV test is a reverse hybridization line probe assay, the prototype research version of which has been described in Kleter et al., 1999 (Journal of Clinical Microbiology, vol. 37, n°8, p. 2508-2517), and Kleter et al. 1998 (American Journal of Pathology, vol. 153, n°6, p. 1731-1739), Briefly, a PCR primer set is used to generate a short PCR fragment (SPF PCR) of 65-bp from the L1 open reading frame. The prototype research INNO-LiPA primer set consists of 10 biotinylated primers (referred to as the SPF10 primer set), namely the six primers of the SPF1/2 system (described in Kleter et al. 1998), and four additional primers (MY09/11 and GP5+/6+).

The SPF10 amplimers are denatured, and incubated under hybridization conditions with poly(dT)-tailed type-specific oligonucleotide probes, which are immobilized as parallel lines on nitrocellulose membrane strips. The probe strips are then washed out for detection of the retained hybrids.

The INNO-LiPA HPV test allows the detection of at least 25 HPV genotypes (the 13 HR HPV, i.e., HPV 56, 51, 58, 33, 52, 35, 31, 16, 68, 39, 59, 45, 18, as well as other HPV, e.g., HPV 6, 11, 34, 40, 42, 43, 44, 53, 66, 70, and 74). It is a genotyping line probe assay, and is of qualitative value. The INNO-LiPA HPV test is not a quantitative assay.

The Amplicor HPV test uses amplification of target HPV DNA by PCR followed by nucleic acid hybridization for the detection of the thirteen HR HPV. The Amplicor HPV test amplifies a sequence of about 165 bp within the L1 region. The primer sets consist of 12 primers, which have been designed as general consensus primers, to amplify the initial group of 13 HR HPV. After amplification and denaturation, the amplified HPV sequences are distributed in a microwell plate, and incubated with L1 capture probes, the hybrids being detected and visualized by colorimetric enzyme immunoassay (avidin-horseradish peroxidase conjugate).

The Amplicor HPV test has been reported as being of higher analytical specificity, compared to the HC2® test (less false negative results, see Poljak et al. 2005, Acta Dermatoven APA, vol. 14, n°4, p. 147-152).

The Amplicor HPV test is sensitive, but its HPV spectrum is restricted to those 13 HPV, which have been initially considered as being the HR HPV. For example, the Amplicor HPV test does not detect HPV66 and HPV53, which are now thought to be HR HPV. In other words, the Amplicor test is not designed to be adaptive to any change or evolution in HPV classification or knowledge.

Furthermore, the Amplicor HPV test is not a quantitative assay.

These line blot or microwell-based prior art techniques use consensus HPV primers, i.e., primers which result from sequence alignment of a pre-determined set of selected oncogenic HPV, and from the determination of those consensus sequences, which have a sufficient similarity or identity score with all of the selected HPV, to hybridize to all of them. Consensus primers are thus designed to amplify a predetermined sub-set of oncogenic HPV, and may not succeed in amplifying other oncogenic HPV (such as HR new corners, or non-HR oncogenic HPV).

Such a consensus approach is restricted by the possibility of determining primer sequences, which would still sufficiently hybridize to the ever increasing and ever evolving desired targets.

If one or several new oncogenic HPV strain(s) appear, such prior art consensus primers might give false negative results.

Also, none of the prior art line blot or microwell-based techniques is of a quantitative nature, whereas recent findings show that the HPV copy number accounts for the phase and/or severity of the disease, and/or have a diagnostic and/or prognostic value in the field of oncogeny.

Absence of quantitative performance limits the spectrum of clinical applicability, as such tests cannot give information on the actual cancer risk level, or on the actual cancer grade.

Moreover, according to these prior art consensus line blot or microwell-based techniques, the detection step is an additional and tedious step, which has to be performed as a separated step after amplification has occurred.

Real-time PCR amplification techniques have recently been developed for the detection of HPV16 or HPV18 (Hesselink et al. 2005, Journal of Clinical Microbiology, vol. 43, n°9, p. 4868-4871; Gravitt et al. 2003, Cancer Epidemiology, Biomarkers & Prevention, vol. 12, p. 477-484).

These real-time PCR either are based on FRET (LightCycler), or use TaqMan probes (Applied Biosystems).

Compared to prior art line blot or microwell-based techniques, such real-time PCR have the advantage of combining amplification and detection in one single step, and of opening the way to quantification.

For example, van Duin et al. 2002 (Int. J. Cancer, vol. 98, n°4, p. 590-595) describes a quantitative real-time PCR assay for the detection of HPV16.

Prior art real-time PCR protocols however are type-specific PCR protocols, which are limited to the detection of only one HPV per amplification run, and more particularly to the sole detection of HPV16 or HPV18. They thus represent valuable research tool, but have a very limited clinical applicability.

Attempts have been made to develop multiplex real-time PCR amplification of HPV. These attempts are however limited to duplex or triplex real-time PCR for the detection of HPV16, HPV18, HPV45. For example, Szuhai et al. 2001 (American Journal of Pathology, 159(5): 1651-1660) disclose seven type-specific to molecular beacons, which are said to be type-specific molecular beacons, namely five HR HPV molecular beacons (HPV16, 18, 31, 33, 45) and two LR HPV molecular beacons (HPV6, 11); see table 1 of Szuhai et al. These molecular beacons are described as being useful for the detection of amplicons generated by the CPI/CPIIG "universal" primers. Multiplex attempts are disclosed in Szuhai et al., but are limited to duplex or triplex assays (HPV16, HPV18, HPV45). The authors explicitly indicate that "although the multiplexing capacity of molecular beacon PCR is higher than three, it is unlikely that it will approach the number of different HPV genotypes" (see page 1656, righthand column, second paragraph). For this reason, the authors came to the conclusion that type-specific molecular beacons cannot by their own solve the problem of HPV clinical diagnosis, and that they shall be used in combination with a general pre-screening HPV detection method, to arrive at a two-step HPV detection and genotyping strategy (see e.g., FIG. 6 of Szuhai et al.), wherein type-specific HPV molecular beacon PCR is disclosed to be used in combination with a SybrGreen general primer PCR pre-screening.

Hence, to the best of the inventors' knowledge, prior art does neither describe nor suggest any real-time amplification technique that could be worked in multiplex, whilst retaining the required HPV detection specificity, which would allow to cover at least the 13 HR HPV in a single step (amplification+detection) run. Furthermore, to the best of the inventors' knowledge, prior art does not describe any quantitative real-time HPV amplification technique, which would allow to cover at least the five most common HR HPV (namely, HPV16, 18, 45, 31 and 33), preferably at least the 13 HR HPV, more preferably at least the 13 HR HPV as well as five other oncogenic HPV, in a single step (amplification+detection) run, and which would be quantitative, even when implemented in multiplex.

ABSTRACT OF THE INVENTION

The present invention relates to the detection of HPV by amplification, more particularly of mucosal-type HPV, still more particularly of HPV, which can be oncogenic for the mucosal epithelia.

The present invention allows the detection of at least the five most common HR HPV (HPV16, 18, 45, 31, 33), preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV (HPV 56, 51, 58, 33, 52, 35, 31, 16, 68, 39, 59, 45, 18), most preferably at least the 13 HR HPV and five other oncogenic HPV (HPV66, 53, 82, 67, 85).

The present invention relates to amplification primer systems, and to detection probe systems, as well as to the amplification-detection systems (i.e. real-time amplification systems), which result from the combination of at least one amplification primer system of the invention and at least one detection probe system of the invention.

The present invention also relates to reference template HPV sequences, which are suitable for the production of amplification primers and detection probes of the invention, as well as to amplicons obtainable by amplification of an HPV nucleic acid with at least one amplification primer system of the invention, and optionally by detection with at least one detection probe system of the invention.

The present invention further relates to the biological and pharmaceutical applications thereof, more particularly to the diagnostic and prognostic applications thereof, notably in the field of CIN and cervical cancer.

The HPV amplification method of the invention is based on an approach of HPV tropism and oncogenicity, which is completely different from, and completely innovative compared to prior art approaches: contrary to the global consensus approaches, or to the type-specific approaches, which prior art methods have up to now followed, the present inventors have designed and built an approach, which is an HPV group-based approach (see the phylogenetic tree shown in FIG. 1, which has been built by the present inventors). According to the inventors' HPV group-based approach, amplification primer systems and detection probe systems are provided for each HPV group that comprises at least one HPV type capable of being oncogenic for the mucosal epithelia, namely at least for each of groups A6, A5, A9 and A7.

Indeed, the present inventors have selected appropriate targets within each of said HPV groups, which are suitable for the production of primers and probes covering at least the five most common HR HPV (namely, HPV16, 18, 45, 31 and 33), preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and five other oncogenic HPV (HPV66, 53, 82, 67, 85), in a single step (amplification+detection) run.

The selected targets of the present invention are reference template sequences, which allow designing and building primers (hybridizing to one end of said selected targets, or to the complementary sequence thereof), as well as amplicon-annealing probes, which allow to cover said HPV in a single step (amplification+detection) run.

The amplification primer systems of the present invention are targeted to the HPV of group A6 or A5 or A9 or A7, and are intended to amplify as many HPV types belonging to one of these groups as possible.

The detection probe systems of the present invention allow the detection of one or several of the amplicon(s) obtainable by amplification of a given HPV by an amplification system of the present invention. They are targeted to group(s) A6 and/or A5 and/or A9 and/or A7, and are especially adapted to implementation in real-time with said amplification primer systems.

The detection probe systems of the invention comprise probes, which allow for the general detection of at least one HPV that belongs to the HPV set formed by groups A6 and A5 and A9 and A7, as well as more precise detections, such as:

- the detection of at least one HPV that belongs to group A6 or A5 or A9 or A7, or
- the detection of at least one HPV that belongs to a sub-set of group A6 HPV, or of group A5 HPV, or of group A9 HPV, or of group A7 HPV, or
- the detection of at least one particular HPV type.

The present invention thereby provides a great flexibility of precision levels for the detection of HPV. Such flexibility has, to the best of the inventors' knowledge, never has been previously attained.

The present invention further provides A6- and/or A5- and/or A9- and/or A7-targeted systems, resulting from the combination of at least one amplification primer system of the invention and at least one detection probe system of the invention.

The present invention more particularly provides A6- or A5- or A9- or A7-targeted systems, which comprise at least one amplification primer system of the invention and at least one detection probe system of the invention, wherein said at least one amplification primer system and said at least one detection probe system are targeted to the same group, i.e., A6 or A5 or A9 or A7.

Most of the amplification primer and/or detection probe systems of the present invention comprise more than two primers and/or more than one probe. Hence, most of the amplification primer and/or detection probe systems of the invention, and notably the A9-targeted systems, and the A7-targeted systems, already are by themselves multiplex systems.

According to a very advantageous feature of the present invention, the group-targeted systems of the present invention are suitable for use together in a single-tube amplification, i.e., the present invention allows for implementation of at least one A6-targeted system, and at least one A5-targeted system, and at least one A9-targeted system, and at least one A7-targeted system, together in a single-tube assay, thereby resulting in what could be called a multi-multiplex, i.e., a "megaplex" amplification and/or detection: see e.g., in the examples below, illustrative "megaplex" involving 17 primers and 12 probes, which are capable of amplifying and detecting seventeen oncogenic mucosal-type HPV in a single-tube assay, without any significant loss in specificity, and without any significant loss in sensitivity.

Hence, the amplification primer systems and detection probe systems are specifically adapted to real-time multiplex amplification.

To the best of the inventors' knowledge, there is no prior art method, which would allow for a real-time multiplex amplification of at least the five most common HR HPV, preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV.

Advantageously, the present invention allows for the detection of at least 18 oncogenic mucosal-type HPV in a single-tube assay, namely the 13 HR HPV, as well as five other oncogenic HPV (HPV66, 53, 82, 67, 85).

A further advantageous aspect of the present invention is that it is especially adapted to HPV viral load quantification. The HPV method of the invention is able to remain specific and quantitative, even when implemented in a single-tube multiplex.

The amplification primer systems and detection probe systems are specifically adapted to real-time quantitative multiplex amplification, and retain this capacity even when implemented in a "megaplex" mode comprising at least one A6-targeted system, and at least one A5-targeted system, and at least one A9-targeted system, and at least one A7-targeted system, together in a single-tube assay.

To the best of the inventors' knowledge, there is no prior art method, which would allow for a real-time quantitative multiplex amplification of said at least five most common HR HPV, preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, more preferably at least the 13 HR HPV and five other oncogenic HPV (HPV66, 53, 82, 67, 85).

The amplification primer systems and the detection probe systems of the invention all share the special technical feature of being designed and built according to a group-based approach of HPV oncogenicity, and of being suitable for implementation together in a the same assay tube.

More particularly, they enable a real-time "megaplex" implementation covering at least the five most common HR HPV types, preferably at least 7 HR HPV (e.g., HPV 56, 51, 33, 31, 16, 45, 18), still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, more preferably at least 18 oncogenic mucosal-type HPV (i.e., at least the 13 HR HPV, and five other oncogenic HPV, e.g., HPV66, 53, 82, 67, 85), in a single-tube assay, without any significant loss in the qualitative accuracy of the HPV detection.

The amplification primer systems and the detection probe systems of the invention further show levels of specificity, Ct and sensitivity, which are sufficiently homogeneous to allow for a real-time "megaplex" amplification, which is of quantitative value.

The group-based approach of the present invention further provides flexibility to the amplification and/or detection systems, as their intrinsic design is likely to make them suitable for detection of any oncogenic HPV "new corner" that may arise by mutagenesis.

The group-based approach of the present invention also confers flexibility in the use for clinical diagnosis: depending on the choice of probe system(s) that is made by the user, the precision level in HPV detection can range from a general response indicating the detection of at least one HPV belonging to the set formed by groups A6 and A5 and A9 and A7, to the very precise response indicating the detection of at least one particular HPV type. To the best of the inventors' knowledge, such flexibility has up to now never been attained.

The group-based approach of the present invention further is suitable for providing accuracy in case of multi- and/or co-infections.

It is believed that such an achievement represents a technological breakthrough, compared to prior art HPV detection systems.

BRIEF DESCRIPTION OF THE FIGURES

FIG. 3: reprint of NCBI_001594.1, sequence of HPV56 (reference HPV for group A6); SEQ ID NO:420;

FIG. 4: reprint of NCBI_001533.1, sequence of HPV51 (reference HPV for group A5); SEQ ID NO:421;

FIG. 5: reprint of NCBI_001526.1, sequence of HPV16 (reference HPV for group A9); SEQ ID NO:422;

FIG. 6: reprint of NCBI_001357.1, sequence of HPV18 (reference HPV for group A7); SEQ ID NO:423;

All sequences, including reverse primers, are listed in their 5' to 3' orientation. Start and stop positions on a reference HPV sequences are given in increasing value order. Hence:

- concerning primers: start and stop positions are either the start and stop positions of the reference HPV fragment, to which the sequence of the primer corresponds (case of forward primer), or the start and stop positions of the reference HPV target fragment, to which the primer anneals (case of the reverse primers);
- with regards to the probes: as a probe and its complementary sequence are, at least in simplex amplification, products, which have equivalent functions, the start and stop positions are either those of the reference HPV fragment, to which the sequence of the probe corresponds, or those of the reference HPV target fragment, to which the probe anneals.

DETAILED DESCRIPTION

The present invention is based on an approach, which is completely different from, and truly innovative, compared to prior art techniques. The invention overcomes the drawbacks of prior art techniques, and has numerous advantages, notably in terms of clinical applicability, performance, reliance and flexibility.

As mentioned in "the above background" section, prior art primers are designed either as type-specific primers, or as general consensus primers by classic alignment of as many mucosal HPV sequence as required, or desired, or as possible (e.g., by direct alignment of the 13 HR HPV).

On the contrary, the primers of the invention have been designed by HPV groups (=HPV genera).

Figure 1:
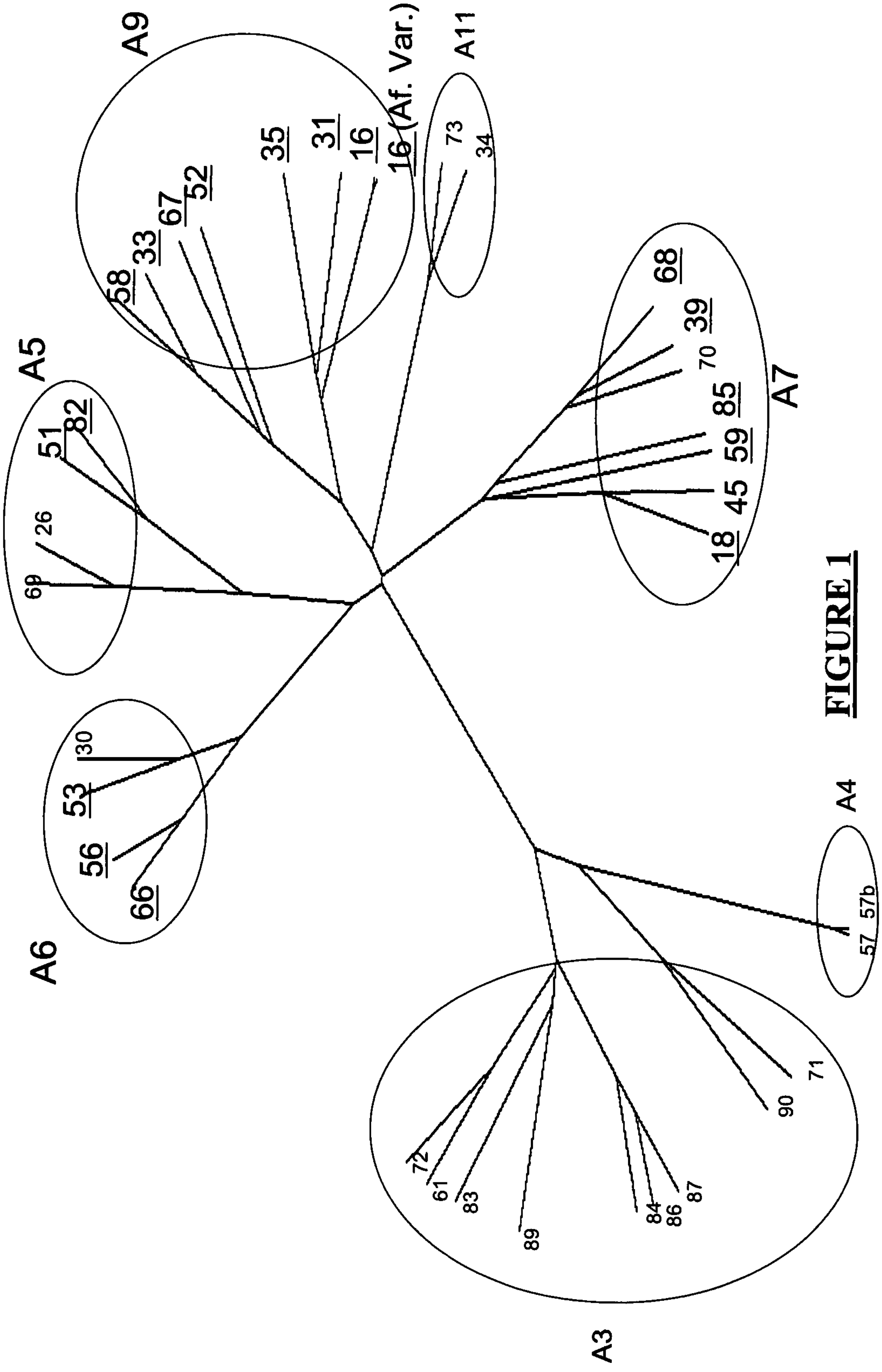
FIG. 1: phylogenic tree of the present invention.

Indeed, the present inventors analyzed the phylogeny of HPV, and have constructed the resulting phylogenic tree, which is shown in FIG. 1.

The present inventors selected one HPV sub-family, which is involved in carcinogenesis of the mucosal epithelia, namely sub-family A. They further selected a set of HPV types, which is representative of HPV sub-family A. This representative set consists in 35 different HPV types, among which 18 types are mucosal HPV, which are at least potentially oncogenic HPV (i.e., the 13 HPV known as the 13 HR; two potentially HR HPV -HPV53 and HPV66-; and three other HPV, which are believed to have an oncogenic potential -HPV82, HPV67 and HPV85-), the remaining 17 other HPV types being up to now known as being non-oncogenic HPV (see FIG. 1).

The inventors thus came to the conclusion that those HPV, which have a tropism for the mucosal epithelia, and which are at least potentially oncogenic HPV, are distributed among groups A6, A5, A9 and A7 (see FIG. 1). More precisely, said mucosal oncogenic HPV are distributed among:

- group A6, for HPV66, HPV56, HPV53;
- group A5, for HPV51, HPV82;
- group A9, for HPV58, HPV33, HPV67, HPV52, HPV35, HPV31, HPV16;
- group A7, for HPV68, HPV39, HPV85, HPV59, HPV45, HPV18.

By "HPV, which is at least potentially oncogenic", it is meant that said HPV is either known to be oncogenic (such as those 13 HPV, which are usually referred to as the 13 HR HPV, as well as other oncogenic HPV, such as HPV66, HPV53, and HPV82), or which have been described at least by some authors as potentially oncogenic (such as HPV85), or which would be in the future described as associated to a tumorous mucosa.

The design by group is a special feature shared by all the products of the invention.

In addition to covering at least the five most common HR HPV types, preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the thirteen HR HPV types, in a single-tube experiment, the means offered by the present invention is likely to detect any particular variant that a patient may have. Hence, the method of the invention is much safer than any prior art method.

In case of multiple HPV infections, several HPV types are present in the collected sample. A competitive effect may then be observed, wherein one HPV type takes prevalence over another one for the same consensus primer. Detection of the competed HPV may then be hampered, although the primer has initially been designed to hybridize to both HPV.

The present invention further has the advantage of enabling the analysis of multi- and/or co-infection cases, without any loss in specificity and sensitivity.

The present invention thus relates to amplification primer systems, to detection probes system, and to pharmaceutical compositions, biological compositions, and detection kits comprising at least one of said amplification and detection systems.

The present invention also relates to a method of HPV detection, which comprises the amplification of at least one HPV nucleic acid fragment, by at least one amplification primer system of the invention, and which optionally comprises the detection of the amplicon(s) thereby produced, by at least one detection probe system of the invention.

The HPV detection method of the invention is notably useful for the diagnosis of an HPV-related disease or condition, for the prognosis or risk assessment of such an HPV-related disease or condition, for monitoring of the evolution of an HPV-related disease or condition, for monitoring the efficiency of an anti-HPV drug or treatment, such as e.g., an anti-HPV vaccine or an anti-HPV vaccine candidate (e.g., an anti-HPV16 and/or anti-HPV18 and/or anti-HPV45 vaccine, or vaccine candidate).

Said HPV-related disease or condition is any disease or condition involving HPV, and more particularly an HPV-related neoplasia (e.g., cervical intraepithelial neoplasia) or cancer, such as a cervical cancer.

The present invention thus provides amplification primer systems and detection probe systems, which are targeted to the oncogenic HPV of group A6, and/or to the oncogenic HPV of A5, and/or to the oncogenic HPV of A9, and/or to the oncogenic HPV of A7.

Most of the amplification and/or detection systems of the present invention are multiplex systems, which comprises more than two primers and/or more than one probe. It is notably the case of the A9-targeted systems and of the A7-targeted systems.

Each amplification primer system can be implemented with an amplification primer system of another group in a single-tube amplification assay, without any significant loss in specificity. Hence, at least one A6-targeted amplification primer system of the present invention and at least one A5-targeted amplification primer system of the present invention and at least one A9-targeted amplification primer system of the present invention and at least one A7-targeted amplification primer system of the present invention, can be used together in a single-tube amplification assay, without any significant loss in specificity.

For each amplification primer system, the invention provides at least one detection probe system, thereby forming an amplification and detection system (i.e., a real-time amplification system).

Each detection probe system of the present invention can be implemented with its corresponding amplification primer system in a single-tube assay, without any significant loss in specificity, thereby allowing for a real-time HPV amplification and detection.

The present invention thus provides with group-targeted amplification and detection systems, namely:

- several A6-targeted amplification and detection systems,
- several A5-targeted amplification and detection systems,
- several A9-targeted amplification and detection systems,
- several A7-targeted amplification and detection systems.

Each amplification and detection system can be implemented with an amplification and detection system of another group in a single-tube amplification assay, without any significant loss in specificity, thereby allowing for a single-tube multi-multiplex (or "megaplex") real-time amplification and detection of those HPV, which have a tropism for the mucosal epithelia, and which are at least potentially oncogenic HPV.

Hence, at least one A6-targeted amplification and detection system of the present invention, and at least one A5-targeted amplification and detection system of the present invention, and at least one A9-targeted amplification and detection system of the present invention, and at least one A7-targeted amplification and detection system of the present invention, can be used together in a single-tube amplification assay, without any significant loss in specificity.

Whilst the invention provides systems, which are especially adapted to multiplex or multi-multiplex implementation, the implementation of a system of the invention in simplex mode is of course also encompassed by the present invention.

The amplification and detection systems of the present invention further have levels of Ct and sensitivity, which are sufficiently homogeneous to allow for a quantitative HPV amplification and detection. The present invention thereby allows for the identification of the presence of one or several mucosal HPV in a single-tube assay, as well as for the determination of the viral HPV load(s). The quantitative property of the present invention is retained, even when it is implemented in a “megaplex” mode.

The invention thus relates to group-targeted amplification and/or detection systems, and to their use for the detection of mucosal HPV, said group-targeted amplification and/or detection systems sharing the special technical feature of being suitable for multiplex (in fact, multi-multiplex, i.e., “megaplex”) amplification and for real-time detection thereof, whereby these systems allow for the detection in a single-tube assay of at least the five most common HR HPV (i.e., HPV16, 18, 45, 31, 33), preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), even still preferably at least the thirteen HPV known as HR HPV (HPV types 56, 51, 58, 33, 52, 35, 31, 16, 68, 39, 59, 45 and 18), more preferably, at least the thirteen HPV as well as at least one among HPV types 66, 82, 67, 85, and 53 still more preferably, at least the thirteen HPV as well as at least two among HPV types 66, 82, 67, 85, and 53 even still more preferably, at least the thirteen HPV as well as at least three among HPV types 66, 82, 67, 85, and 53 most preferably, at least the thirteen. HPV as well as at least four among HPV types 66, 82, 67, 85, and 53, notably of least the seventeen mucosal HPV, consisting of said 13 HR HPV and HPV types 66, 82, 67, 85, still most preferably, at least the thirteen HPV as well as at least the five HPV types 66, 82, 67, 85, and 53.

The group-targeted amplification and/or detection systems of the present invention further share the special technical feature of allowing such a real-time “megaplex” amplification to be quantitative.

As above-mentioned, the amplification and detection systems of the present invention are based on a truly innovative group-based approach.

Indeed, according to prior art general consensus techniques, the design of the primers (also referred to as “universal” primers) is made by alignment of all HPV sequences to be amplified, e.g., the 13 HR HPV, and determination of consensus sequences, which targets as many of the 13 HPV as possible. Hence, such consensus sequences are found in a conserved gene or region, such as a gene of late coding region (e.g., gene L1), and the same conserved gene or region is selected for the whole set of HPV to be amplified.

On the contrary, the present inventors made a design per HPV group, i.e., they selected appropriate targets for each HPV group. More particularly, they selected to genes of the early coding region, more particularly genes E1, E2, E6, E7. The present inventors have designed particular targets for each the desired HPV groups.

Figure 2A:
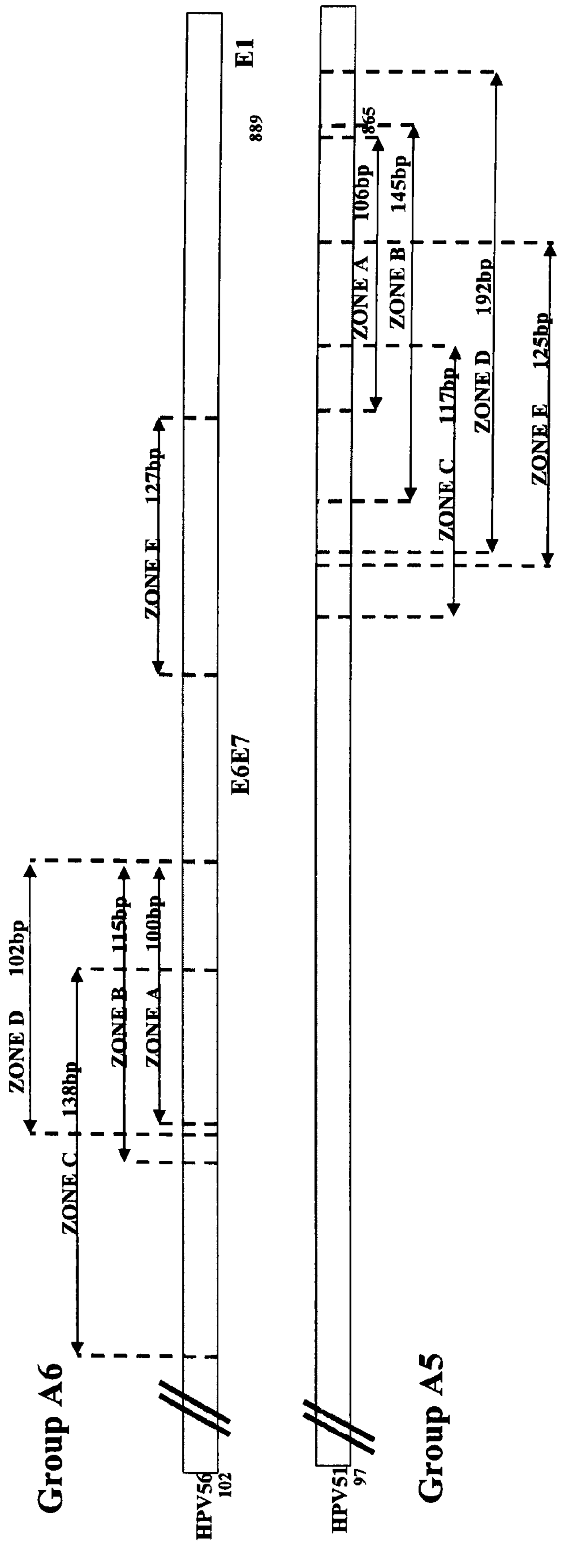
FIGS. 2A and 2B: schematic presentation of the amplification targets for HPV groups A6 (HPV56) and A5 (HPV51) (FIG. 2A), and for groups A9 (HPV16) and A7 (HPV18) (FIG. 2B)
Figure 2B:
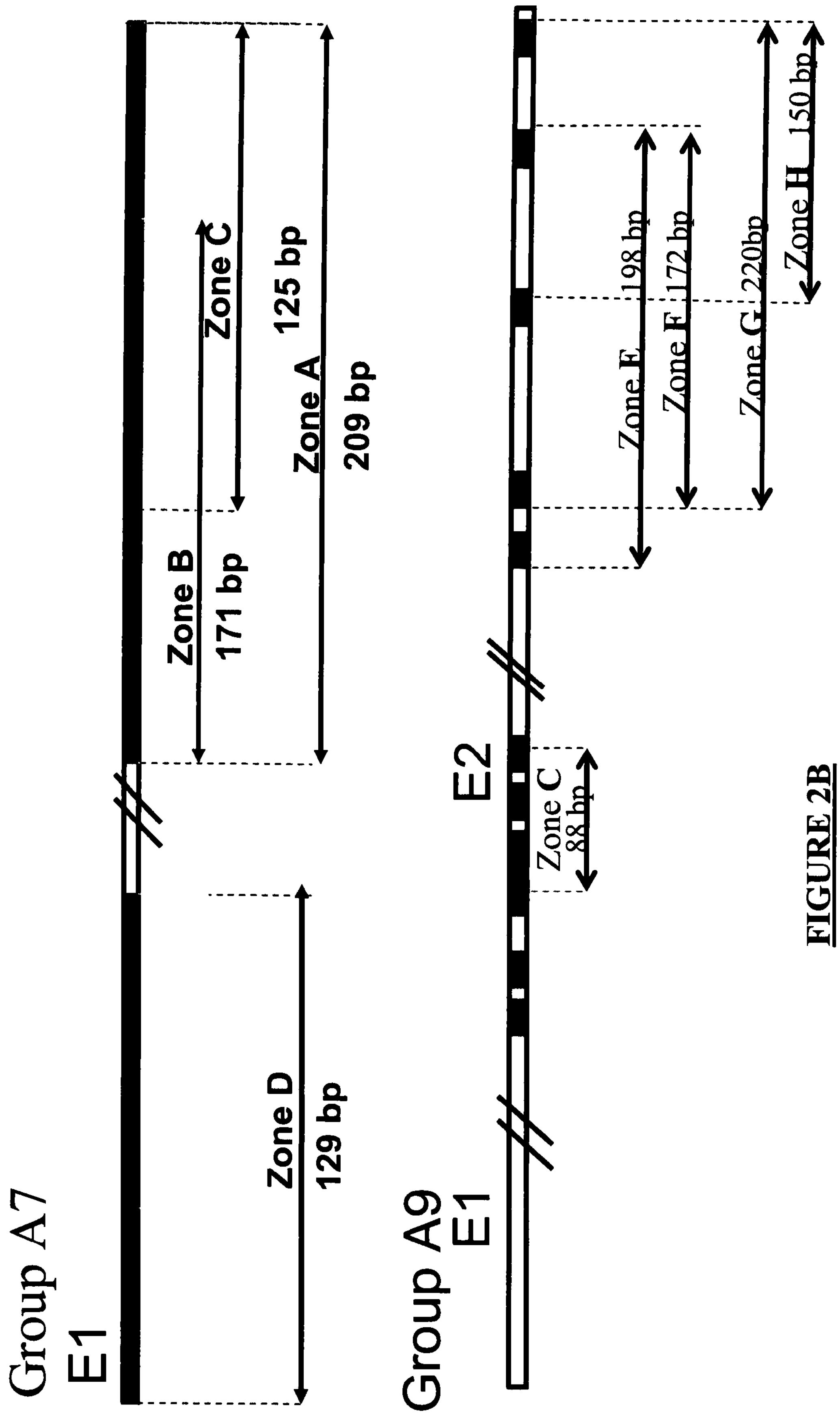
Figure 7:
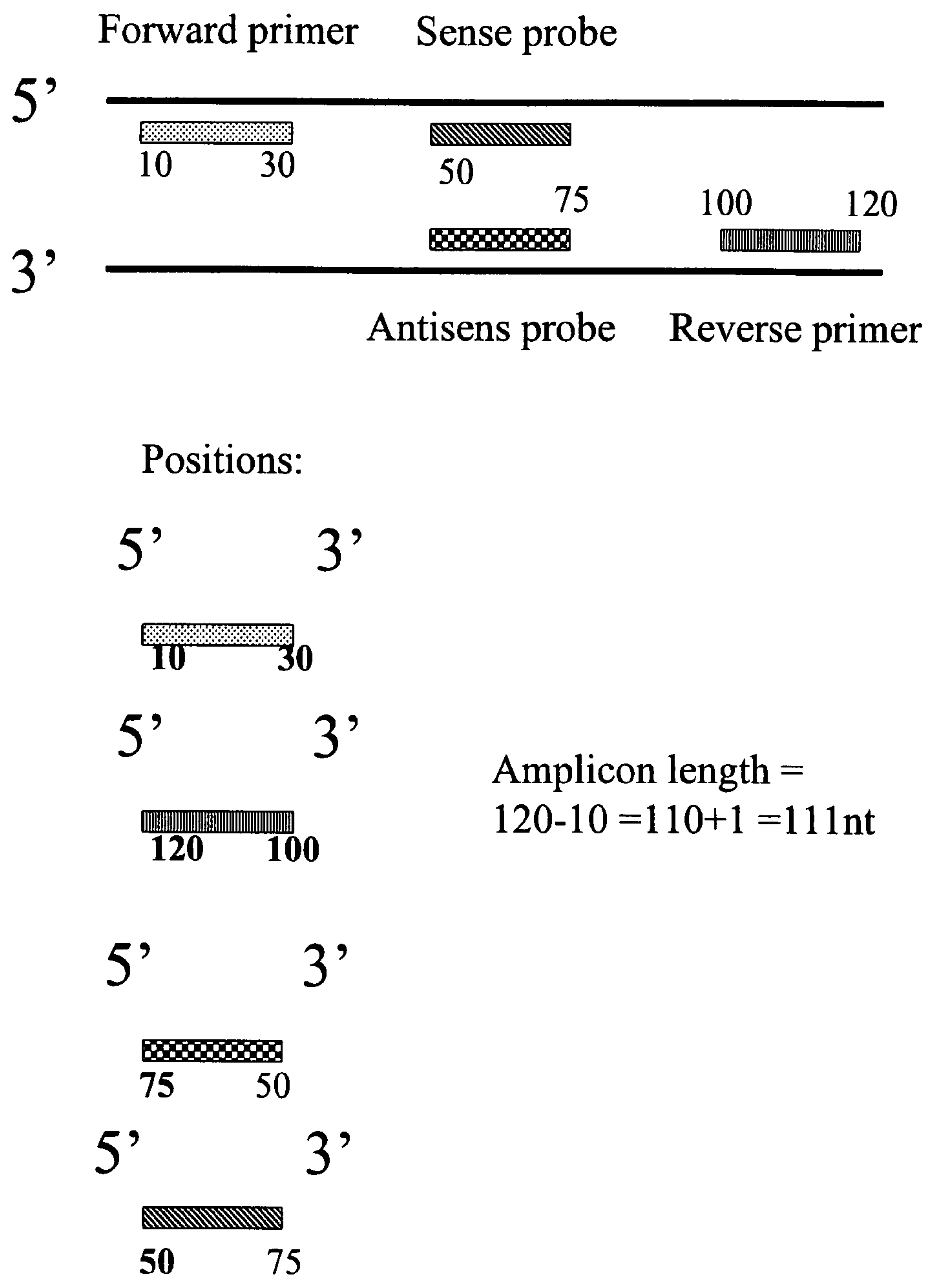
FIG. 7: convention for positions, which is followed in present application.

For example, the primers, which have been designed for group A5, have their target within genes E7, E1; the primers, which have been designed for group A6, have their target within genes E6, E7; the primers, which have been designed for group A7, have their target within gene E1; and the primers, which have been designed for group A9, have their target within genes E1, E2. Illustrative targets of the invention are shown in FIGS. 2A (groups A5 and A6) and 2B (groups A7 and A9).

Hence, the present inventors selected reference template sequences for each of groups A5, A6, A7 and A9, wherein the A5 reference template sequences are within the region consisting of genes E7 and E1, the A6 reference template sequences are within the region consisting of genes E6 and E7, the A7 reference template sequences are within gene E1, and the A9 reference template sequences are within the region consisting of genes E1 and E2.

The primers are designed and built to hybridize to one end of said targets (or to the complementary sequence thereof), whereby a primer pair anneals to each end of said target (or to the complementary sequence thereof).

The probes are designed and built to anneal to one of said reference template sequences, whereby each probe anneals to at least one of the amplicons generated by a primer system of the invention.

An amplification primer system of the invention comprises at least two primers.

A detection probe system of the invention comprises at least one probe.

The amplification primer systems of the invention preferentially amplify HPV that belong to group A6 or A5 or A9 or A7, i.e., oncogenic HPV.

The present inventors further succeeded in producing amplification primer systems, which are specific of the HPV set formed by groups A5 and A6 and A7 and A9. These amplification primer systems of the invention do not amplify any HPV that would belong to a group other than A5, A6, A7, A9. Indeed, most primer systems of the invention are specific of the HPV set formed by groups A6 and A5 and A9 and A7.

Moreover, most of amplification primer systems of the invention are specific of the group to which they are targeted, i.e., most primer systems of the invention are specific of group A6 or A5 or A9 or A7: most primers of a given amplification system amplify one or several HPV of the same HPV group, without amplifying any HPV that would belong to another HPV group.

Those primer systems of the invention, which are not specific of the HPV set formed by groups A5 and A6 and A7 and A9, may amplify nucleic acids that are not from an HPV of said groups, e.g., a non-oncogenic HPV. In such a case, these primer systems of the invention do however show a much lower amplification efficiency for these non-target amplicons (e.g., they lead to a PCR efficiency that is much lower than the one obtained for HPV of groups A5 and/or A6 and/or A9 and/or A7, and are therefore not quantitative).

When a group-targeted primer system of the invention is combined with a probe system of the invention that is targeted to the same group, the group-targeted real-time amplification system that results therefrom is specific of the HPV set formed by groups A5 and A6 and A9 and A7: none of such real-time amplification systems detects an HPV that would not belong to group A5 or A6 or A9 or A7. Furthermore, most of these real-time amplification systems are specific of the group to which they targeted.

Only one real-time amplification system of the invention has a cross-group reactivity: the real-time amplification primer system designed for group A9, which is referred to in the examples below as system C, detects the seven HPV types of group A9, and also HPV53, which is an oncogenic HPV belonging to group A6 (HPV53 being a potentially HR HPV); this group A9 system C does however not detect any other HPV among the 42 HPV tested (no group A6 HPV other than HPV53; no group A5 HPV; no group A11 HPV; no group A7 HPV, no group A4 HPV; no group A3 HPV).

In any case, does a real-time amplification system of the present invention detect a nucleic acid that would be a human nucleic acid.

When it is desired to amplify any HPV, which belongs to group A6, A5, A9, or A7, most of the amplification primer systems of the present invention will in fact comprise more than two primers, i.e., at least three primers.

For example, the amplification primer systems, which are targeted to group A6 or A5, only require a primer pair to amplify HPV56 and optionally HPV66 (for group A6), or HPV51 and optionally HPV82 (for group A5). But, those amplification primer systems, which are targeted to group A9 or A7, have to amplify six or seven HPV types of group A9, or five or six HPV types of group A7, if a complete coverage of the HPV spectrum of the group is desired. Under such instances, an A9- or A7-targeted amplification system of the invention may comprise e.g., at least three or four forward primers, and two, three, four, five or more reverse primers. Such A9- or A7-targeted amplification primer systems therefore are already multiplex systems by themselves.

Of course, the skilled person, who would like to restrict the spectrum of amplified HPV, might select fewer forward and/or reverse primers, depending on which HPV types or strain he/she would like to amplify.

Similarly, when it is desired to detect any HPV, which belongs to group A6, A5, A9, or A7, most of the detection probe systems of the present invention will in fact comprise more than one probe, i.e. at least two probes.

For example, the detection probe systems, which are targeted to group A6 or A5, only require probe to detect HPV56 and optionally HPV66 (for group A6), or HPV51 and optionally HPV82 (for group A5). But, those detection probe systems, which are targeted to group A9 or A7, may comprise one probe per HPV type or strain to be detected, notably when a both a complete coverage of the HPV group spectrum, and a simultaneous HPV group or type discrimination are desired. An A9- or A7-targeted detection probe system may thus comprise at least four probes, for example four, five or six probes.

As above-mentioned, all detection probe systems of the present invention are adapted to real-time detection, and can thus be implemented with their corresponding amplification primer systems in the very same tube.

In the examples below, are described several A6-, A5-, A9 and A7-targeted amplification and/or detection systems of the invention.

In these examples, are shown table 12 to table 88:

- tables 12-35: these tables gives the SEQ ID NO: and positions of the reference amplicons (the sequences of these reference template amplicons are also listed after the last table, i.e., before the "claims" section), the forward primers, the reverse primers, the probes, the beacons probes of illustrative group-targeted systems of the invention;
- tables 35-50: these tables show the number of nucleotide mismatches shown by primers and probes of the invention (alignment of the sequences of 50 HPV types); an empty box indicates there is no coherent sequence alignment;
- tables 51-68: specificity of the detection systems of the invention;
- tables 69-82: system sensitivity;
- tables 83-88: "megaplex" specificity and sensitivity,
- table 89: list of HPV genome sequences.

A reference genome has been elected for each HPV group, namely:

- for group A5: the reference genome is the genome sequence of HPV51 available under accession number NC_001533.1,
- for group A6: the reference genome is the genome sequence of HPV56 available under accession number NC_001594.1,
- for group A7: the reference genome is the genome sequence of HPV18 available under accession number NC_001357.1,
- for group A9: the reference genome is the genome sequence of HPV16 available under accession number NC_001526.1, In the following tables, the term <<address>> means a nucleotide position in the reference genome. More precisely:

- a forward primer having an address X is an isolated oligonucleotide, which has a sequence which is the sequence of a fragment of the reference genome starting at position X in said reference genome, or a variant of such a fragment sequence (see the mismatch count tables below),
- a reverse primer having an address X is an isolated oligonucleotide, which has a sequence which is complementary to the sequence of a fragment of the reference genome ending at position X in said reference genome, or a variant of such a fragment sequence (see the mismatch count tables below),
- a probe having an address X is an isolated oligonucleotide, the sequence of which is the sequence of a fragment of the reference genome starting at position X in said reference genome, or which is the complementary sequence of such a fragment sequence (over the entire length of this fragment sequence), or a variant of such a fragment sequence or of such a complementary fragment sequence (see the mismatch count tables below).

As a consequence, when a primer pair, which is selected from a given system, to consist of a forward primer having the address Xf, and of a reverse primer having the address Xr, is implemented on its reference HPV genome under conditions favorable to nucleic acid amplification, this primer pair then amplifies from said HPV reference genome an amplicon, which consists of the sequence that extends from position Xf to position Xr in said reference HPV genome (start and stop positions included).

When this primer pair is, under conditions favorable to nucleic acid amplification, implemented on a given HPV genome, which is not its reference HPV genome, but which belongs to the same group as this reference HPV genome, this primer pair then amplifies from said given HPV genome an amplicon, which consists in the sequence of the fragment of said given HPV genome, which corresponds by sequence alignment to the fragment that extends from position Xf to position Xr in said reference HPV genome.

A fragment. A, which is a fragment of a given HPV genome and, which corresponds by sequence alignment to a fragment B of a HPV reference genome, means that said fragment A has the same length as said fragment B, and that the start and stop positions of said fragment A within said given HPV genome are such that, among those fragments of said given HPV genome, which have the same length as said fragment B, said fragment A is the fragment, which gives the best identity score when compared to the nucleotide sequence of said fragment B, as determined by global alignment to the nucleotide sequence of fragment B.

It will also be understood that:

a forward primer having an address Xf and a length Lf is an isolated oligonucleotide, which has a sequence which is the sequence of a fragment of the reference genome starting at position Xf in said reference genome, and ending at position Xf+Lf−1 in said reference genome, or a variant of such a fragment sequence (see the alignments shown below), a reverse primer having an address Xr and a length Lr is an isolated oligonucleotide, which has a sequence which is complementary to the sequence of a fragment of the reference genome starting at position Xr−Lr−1, and ending at position Xr in said reference genome, or a variant of such a fragment sequence (see the alignments shown below), a probe having an address Xp and a length Lp is an isolated oligonucleotide, the sequence of which is the sequence of a fragment of the reference genome starting at position Xp and ending at position Xp+Lp−1 in said reference genome, or which is complementary to such a fragment sequence, or a variant of such a fragment sequence or of such a complementary fragment sequence (see the alignments shown below).

The present invention thus relates to a process for the nucleic acid amplification of at least one HPV target, wherein said HPV is an HPV, which has a tropism for the mucosal epithelia, and which is at least potentially oncogenic, preferably at least one oncogenic anogenital HPV target, most preferably at least one oncogenic cervical HPV. The amplification process of the invention comprises the step of producing from said at least one HPV target at least one amplicon by means of at least two primers.

According to an advantageous embodiment of the present invention, the amplification process of the present invention can be a real-time multiplex amplification process, involving at least one probe that can anneal to the amplicon(s) generated by said t least two primers.

The present invention relates to a process for the detection of at least one HPV, which has a tropism for the mucosal epithelia, and which is an at least potentially oncogenic HPV, preferably at least one oncogenic anogenital HPV, most preferably at least one oncogenic cervical HPV, in a sample. The detection process of the present invention comprises the detection of at least one nucleic acid HPV target which has been amplified by the process of nucleic acid amplification of the invention.

The present invention relates to a process for the detection of at least one HPV, which has a tropism for the mucosal epithelia, and which is an at least potentially oncogenic HPV, preferably at least one oncogenic anogenital HPV, most preferably at least one oncogenic cervical HPV, in a sample, by determination of whether at least one amplicon has been, or is produced from said sample, or from nucleic acid material thereof, by amplification by means of at least two amplification primers of the invention, and/or at least one amplification primer system of the invention.

The production of at least one amplicon indicates that at least one HPV, which has a tropism for the mucosal epithelia, and which is at least potentially oncogenic, preferably at least one oncogenic anogenital HPV, most preferably at least one oncogenic cervical HPV, is present in said sample.

According to an advantageous embodiment of the present invention, the determination of whether at least one amplicon is produced can be carried out in real-time multiplex amplification, preferably with at least one probe of the invention and/or at least one probe system of the invention.

The present invention thus relates to a process for the detection of at least one HPV, which has a tropism for the mucosal epithelia, and which is at least potentially oncogenic, preferably at least one oncogenic anogenital HPV, most preferably at least one oncogenic cervical HPV, in a sample, which comprises:

contacting said sample, or nucleic acid material thereof, with at least two amplification primers of the invention and/or at least one primer system of the invention, under conditions suitable to the production of at least one amplicon by said primers (i.e., under conditions, which would be suitable to the production by said primers of at least one amplicon from said at least one HPV to be detected, if this HPV were present in said sample), determining whether at least one amplicon has been produced, or is produced by said primers (e.g., by means of at least one detection probe, preferably in real-time amplification involving at least one probe of the invention and/or at least one detection probe system of the invention).

The production of at least one amplicon indicates that at least one HPV, which has a tropism for the mucosal epithelia, and which is an at least potentially oncogenic HPV, preferably at least one oncogenic anogenital HPV, most preferably at least one oncogenic cervical HPV, is present in said sample.

By "sample containing nucleic acid material", it is meant any sample, which contains at least one nucleic acid, e.g., a biological sample, such as a sample which has been collected from a cell culture, or from an animal or a human being, e.g., from a female human being, preferably a sample which has been collected from a uterine cervix.

Said sample may optionally have been further treated and/or purified according to any technique known by the skilled person, to improve the amplification efficiency and/or qualitative accuracy and/or quantitative accuracy. The sample may thus exclusively, or essentially, consist of nucleic acid(s), whether obtained by purification, isolation, or by chemical synthesis. Means are available to the skilled person, who would like to isolate or purify nucleic acids, such as DNA, from a biological sample, for example to isolate or purify DNA from cervical scrapes (e.g., QIAamp-DNA Mini-Kit; Qiagen, Hilden, Germany).

Hence, the detection method of the present invention enables the real-time multiplex detection, preferably the real-time quantitative multiplex detection of: at least the five most common HR HPV (i.e., HPV16, 18, 45, 31, 33), preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), even still preferably at least the thirteen HPV known as HR HPV (HPV types 56, 51, 58, 33, 52, 35, 31, 16, 68, 39, 59, 45 and 18), more preferably, at least the thirteen HPV as well as at least one among HPV types 66, 82, 67, 85, and 53 still more preferably, at least the thirteen HPV as well as at least two among HPV types 66, 82, 67, 85, and 53 even still more preferably, at least the thirteen HPV as well as at least three among HPV types 66, 82, 67, 85, and 53 most preferably, at least the thirteen HPV as well as at least four among HPV types 66, 82, 67, 85, and 53, notably of least the seventeen mucosal HPV, consisting of said 13 HR HPV and HPV types 66, 82, 67, 85, still most preferably, at least the thirteen HPV as well as at least the five HPV types 66, 82, 67, 85, and 53, in a single-tube assay.

The present invention also relates to all the medical, biological, pharmaceutical applications of the detection method of the invention, and/or of the primers and/or probes of the invention.

The present invention thus relates to a process for the diagnosis or prognosis of cervical neoplasia or cancer, which comprises determining the presence, re-occurrence, persistence, or cellular spread of at least one HPV by the detection method of the invention, e.g., by implementing it on a sample, which may have been collected from a patient, whereby a positive determination indicates that there is a cervical neoplasia or cancer, or that there is a prevalent risk of such a condition or disease.

The present invention also relates to a process for monitoring the efficiency of an anti-HPV treatment or drug, or an anti-HPV candidate treatment or drug, such as an anti-HPV16 and/or 18 and/or 45 treatment, drug, candidate treatment or candidate drug, which comprises determining said treatment, drug, candidate treatment or candidate drug induces the non-reoccurrence, non-persistence, disappearance, or a decrease in cellular spread of at least one HPV by the detection method of the invention, whereby a positive determination indicates that said treatment, drug, candidate treatment or candidate drug is an efficient anti-HPV drug.

The present invention also relates to a method to produce an anti-HPV drug, which comprises:

- providing at least one anti-HPV candidate drug,
- administering said at least one candidate anti-HPV drug to a cell culture or to a non-human animal, wherein said cell culture or animal is or comprises at least one cervical neoplasia or cancer, and
- determining by the HPV detection method of the invention whether said candidate anti-HPV drug induces the regression or disappearance of said at least one neoplasia or cancer, whereby a positive determination indicates that said candidate drug is an efficient anti-HPV drug.

As above-mentioned, the present invention thus provides HPV amplification and detection means, which can be implemented in real-time and in multiplex, i.e., which combine target amplification and detection in one single operative step, and which enables the detection of mucosal HPV in one single operative step, without any significant loss in specificity.

Furthermore, the amplification and detection systems of the invention have Ct and sensitivity levels, which are sufficiently homogeneous to allow for a real-time quantitative multiplex HPV detection.

According to the present invention, said amplification primers may comprise:

- at least two primers, which are intended for targeting oncogenic HPV of group A6, wherein said at least two A6-targeted primers are oligonucleotides, which consist of 14-30 nucleotides, preferably of 15-29, more preferably of 16-28, most preferably of 17-25 nucleotides, the sequences of which are suitable for use as forward and reverse primers, respectively, in the amplification of at least one nucleic acid of 90-390 nucleotides, preferably of 95-385 nucleotides, more preferably of 100-379 nucleotides, from the A6-target region consisting of the E6 and E7 genes of HPV56, and/or
- at least two primers, which are intended for targeting oncogenic HPV of group A5, wherein said at least two A5-targeted primers are oligonucleotides, which consist of 14-30 nucleotides, preferably of 15-29, more preferably of 16-28, most preferably of 17-25 nucleotides, the sequences of which are suitable for use as forward and reverse primers, respectively, in the amplification of at least one nucleic acid of at least 90-240 nucleotides, preferably of 100-230 nucleotides, more preferably of 106-225 nucleotides, from the A5-target region consisting of the E7 and E1 genes of HPV51, and/or
- at least two primers, which are intended for targeting oncogenic HPV of group A9, wherein said at least two A9-targeted primers are oligonucleotides, which consist of 14-30 nucleotides, preferably of 15-29, more preferably of 16-28, most preferably of 17-25 nucleotides, the sequences of which are suitable for use as forward and reverse primers, respectively, in the amplification of at least one nucleic acid of at least 80-260 nucleotides, preferably of 85-250 nucleotides, more preferably of 88-241 nucleotides, from the A9-target region consisting of the E1 and E2 genes of each of the following group A9 HPV: HPV58, HPV33, HPV52, HPV35, HPV31 and HPV16, preferably from the E2 gene of each of said group A9 HPV, and/or
- at least two primers, which are intended for targeting oncogenic HPV of group A7, wherein said at least two A7-targeted primers are oligonucleotides, which consist of 14-30 nucleotides, preferably of 15-29, more preferably of 16-28, most preferably of 17-25 nucleotides, the sequences of which are suitable for use as forward and reverse primers, respectively, in the amplification of at least one nucleic acid of at least 100-220 nucleotides, preferably of 120-215 nucleotides, more preferably of 125-209 nucleotides, from the A7-target region consisting of the E1 gene of each of the following group A7 HPV: HPV68, HPV39, HPV59, HPV45, and HPV18.

The nucleic acid which is amplified from said A6 or A5 or A9 or A7 target region corresponds in said HPV to the nucleic acid sequence of the A6 or A5 or A9 or A7 reference template, respectively. Hence, these amplified nucleic acids usually have a high degree of identity with their respective reference template sequences, e.g., an identity of at least 80%, preferably of at least 85%, more preferably of at least 90%, most preferably of at least 95%, over the entire length of said respective reference template sequence.

By nucleic acid, it herein preferably meant DNA.

Preferably, the at least two primers, which are intended for targeting one HPV group, are different from the at least two primers, which are intended for targeting the three other groups.

Said at least two A6-targeted primers may target a sequence, which is entirely within the E6 gene of each of said group A6 HPV (namely, HPV56), or which is entirely within the E7 gene of each of said group A6 HPV, or which overlap the E6 and E7 genes, for example with a forward primer targeting E6 and the reverse primer targeting E7, or conversely. Preferably, said at least two A6-targeted primers target a sequence, which overlap the E6 and E7 genes, for example with a forward primer targeting E6 and the reverse primer targeting E7, or conversely.

Said at least two A5-targeted primers may target a sequence, which is entirely within the E7 gene of each of said group A5 HPV (namely, HPV51), or which is entirely within the E1 gene of each of said group A5 HPV, or which overlap the E7 and E1 genes, for example with a forward primer targeting E7 and the reverse primer targeting E1, or conversely.

Said at least two A9-targeted primers may target a sequence, which is entirely within the E1 gene of each of said group A9 HPV (namely, of at least each of HPV58, HPV33, HPV52, HPV35, HPV31 and HPV16), or which is entirely within the E2 gene of each of said group A9 HPV, or which overlap the E1 and E2 genes, for example with a forward primer targeting E1 and the reverse primer targeting E2, or conversely. In the examples given below, all A9 amplification systems target the E2 gene, except system C, which has a target that overlaps the E1 and E2 genes.

Said at least two A7-targeted primers may target a sequence, which is entirely within the E1 gene of each of said group A7 HPV (namely, within the E1 gene of at least each of HPV68, HPV39, HPV59, HPV45, HPV18).

In accordance with the present invention, said at least two A6-, A5-, A9- and A7-targeted primers notably share the specific technical feature of being suitable for use in a real-time (quantitative) multiplex detection of HPV, which can be oncogenic for the mucosal epithelia.

By “consisting of 14-30 nucleotides”, it is meant “consisting of 14, 15, 16, 17, 18, 19, 20, 21, 22, 23, 24, 25, 26, 27, 28, 29 or 30 nucleotides”.

The same applies mutatis mutandis to any range, which is recited in the present application.

The nucleotide lengths of the primers can be chosen independently from each other.

By oligonucleotide or primer, “the sequence of which is suitable for use in the amplification of” at least one HPV, or nucleic acid or sequence, it is meant that the sequence of the oligonucleotide or primer is such that they can hybridize to this HPV or nucleic acid or sequence, under conditions of moderate, but preferably high or very high stringency.

A primer of the invention may consist of a 1430 nt oligonucleotide (preferably a 17-25 nt oligonucleotide), the sequence of which has an identity of at least 80%, preferably of at least 85%, more preferably of at least 90%, most preferably of at least 92%, with a sequence of the same length contained in its group reference template sequence, most preferably with a sequence of the same length contained at the very 3' end or at the very 5' end of said group reference template sequence.

According to an advantageous embodiment of the present invention, said determination of whether at least one amplicon is produced can be carried out by using in real-time amplification at least one probe, preferably at least one A6-targeted probe and/or at least one at least one A5-targeted probe and/or at least one A9-targeted probe and/or at least one A7-targeted probe.

Preferably, said at least two A6-targeted primers are suitable for use in the amplification of more than one oncogenic HPV of group A6, namely at least HPV56 and at least one other oncogenic HPV of group A6 (e.g., HPV66, HPV53). According to the present invention, said at least two A6-targeted primers anneal to each of the group A6 HPV they target, in their E6 and/or E7 genes. Hence, according to an advantageous embodiment of the present invention, said at least two A6-targeted primers are oligonucleotides, the respective sequences of which are suitable for use as forward and reverse primers in the amplification of at least one nucleic acid from the region consisting of the E6 and E7 genes of each of the following group A6 HPV: HPV56 and HPV66. HPV66 is at present time not listed within the 13 HR HPV; some authors however consider that HPV66 could be a HR HPV.

Preferably, said at least two A5-targeted primers are suitable for use in the amplification of more than one oncogenic HPV of group A5, namely at least HPV51 and at least one other oncogenic HPV of group A5 (e.g., HPV82). According to the present invention, said at least two A5-targeted primers anneal to each of the group A5 HPV they target, in their E7 and/or E1 genes. Hence, according to an advantageous embodiment of the present invention, said at least two A5-targeted primers are oligonucleotides, the respective sequences of which are suitable for use as forward and reverse primers in the amplification of at least one nucleic acid from the region consisting of the E7 and E1 genes of each of the following group A5 HPV: HPV51 and HPV82.

Preferably, said at least two A9-targeted primers are suitable for use in the amplification of more than the six above-mentioned oncogenic HPV of group A9, namely at least HPV58, HPV33, HPV52, HPV35, HPV31 and HPV16, and at least one other oncogenic HPV of group A9 (e.g., HPV67). According to the present invention, said at least two A9-targeted primers anneal to each of the group A9 HPV they target, in their E1 and/or E2 genes. Hence, according to an advantageous embodiment of the present invention, said at least two A9-targeted primers are oligonucleotides, the respective sequences of which are suitable for use as forward and reverse primers in the amplification of at least one nucleic acid from the region consisting of the E1 and the E2 genes of each of the following group A9 HPV: HPV58, HPV33, HPV67, HPV52, HPV35, HPV31 and HPV16.

A group-targeted primer of the present invention may further target a HPV, which does not belong to the same group (as long as it does not target any group other than A6, A5, A7 or A9), i.e., an A9-targeted primer pair may target an HPV belonging to group A6 (such as HPV53), in addition to targeting the above-mentioned HPV of group A9. Hence, the respective sequences of said at least two A9-targeted primers may further be suitable for use as forward and reverse primers in the amplification of at least one nucleic acid of HPV53.

Preferably, said at least two A7-targeted primers are suitable for use in the amplification of more than the five above-mentioned oncogenic HPV of group A7, namely at least HPV68, HPV39, HPV59, HPV45, and HPV18, and at least one other oncogenic HPV of group A7 (e.g., HPV85). According to the present invention, said at least two A7-targeted primers anneal to each of the group A7 HPV they target, in their E1 gene. Hence, according to an advantageous embodiment of the present invention, said at least two A7-targeted primers are oligonucleotides, the respective sequences of which are suitable for use as forward and reverse primers in the amplification of at least one nucleic acid from the E1 gene of each of the following group A7 HPV: HPV68, HPV39, HPV85, HPV59, HPV45, and HPV18.

To the best of the inventors' knowledge, there is no prior art multiplex process, which would allow the detection of a mucosal oncogenic HPV other than HPV56, HPV51, HPV58, HPV33, HPV52, HPV35, HPV31 and HPV16, HPV68, HPV39, HPV59, HPV45, and HPV18. Until recently, these thirteen HPV were considered to be the 13 HR HPV (i.e., the 13 high risk HPV, i.e., the HPV which have the highest tumor prevalence). However, other HPV are now thought to belong to the HR HPV group, e.g., HPV66 and HPV53 (group A6). As prior art techniques, such as the HPV Amplicor test, are based on a global consensus design, additional HPV cannot be encompassed. On the contrary, the present invention is based on a design by group, and cover more than the 13 basic HR HPV, which is much safer for the patient, and which has the special advantage of being evolutive, in the sense that any oncogenic A6, A5, A9 and A7 new corner are likely to be taken into account.

Hence, to the best of the inventors' knowledge, the present invention has a mucosal oncogenic HPV spectrum, which is broadest than any other prior art technique, and has a bigger potential of adaptability to any evolution of HPV spectrum to be detected. The present invention therefore is safer than any other prior art technique.

The amplification primer systems of the invention preferentially amplify HPV that belong to group A6 or A5 or A9 or A7, i.e., oncogenic HPV.

As above-mentioned, most of amplification primer systems of the invention are specific of the HPV set formed by groups A5 and A6 and A7 and A9, and more particularly are specific of the group to which they are targeted, i.e., most primer systems of the invention are specific of group A6 or A5 or A9 or A7 (and do not amplify any HPV of groups A11 or A4 or A3).

Hence, said at least two primers can advantageously be specific of the HPV set formed by groups A5 and A6 and A7 and A9, and more particularly of group A6, or group A5, or group A9, or group A7, preferably of the oncogenic HPV of group A6, or group A5, or group A9, or group A7.

Hence, according to a preferred embodiment of the present invention, said at least two primers can have such sequences that they are not suitable for use as forward and reverse primers in the amplification of any nucleic acid from an HPV, which would not belong to group A6, A5, A9 or A7. According to a more preferred embodiment of the present invention, the respective sequences of said at least two primers therefore are not suitable for use as forward and reverse primers in the amplification of a nucleic acid from an HPV, which is not oncogenic, preferably which is not oncogenic for the mucosal epithelia, more preferably which is not an anogenital HPV, most preferably which is not a cervical HPV.

In other words, said at least two primers preferably are specific of oncogenic HPV, compared to non-oncogenic HPV.

The present invention can be implemented in simplex, multi-tube simplex, in multiplex, as well as in multi-multiplex ("megaplex"). According to an advantageous embodiment of the present invention, said amplification can be a single-tube multiplex amplification, or a single-tube multi-multiplex amplification ("megaplex").

By "single-tube multiplex amplification" or "multiplex amplification", it is herein meant any amplification reaction aiming at the amplification, and optionally the detection, of more than one target in the same tube. For instance, multiplex amplification include duplex amplification (two targets), triplex amplification (three targets), as well as higher multiplex amplification. Multiplex amplification includes amplification reactions with more than one primer pair, for instance two primer pairs. In this case, there might be four different primers, but it is also possible for the two primer pairs to have one primer in common, e.g., the forward primer, and to have two distinct reverse primers. Multiplex amplification and detection also includes amplification reactions with a unique primer pair, but with more than one probe.

Hence, according to the multiplex embodiment of the present invention, more than one primer pair is present in the amplification reaction mixture. As a very advantageous embodiment of the present invention, at least four, preferably at least six, more preferably at least eight primer pairs can be present in the amplification reaction mixture. Indeed, the primers of the invention allow for a multiplex amplification, without any significant specificity loss. Hence, all reagents can be placed in the same tube to carry out the amplification assay on the sample to be tested, whereby whatever mucosal oncogenic HPV is present in this sample, it will be detected in a single-step procedure.

Preferably, said amplification primers comprise said at least two A6-targeted primers, and at least two primers selected from:

said at least two A5-targeted primers,
said at least two A9-targeted primers, and
said at least two A7-targeted primers.

Preferably, said amplification primers comprise said at least two A5-targeted primers, and at least two primers selected from:

said at least two A6-targeted primers, and/or
said at least two A9-targeted primers, and/or
said at least two A7-targeted primers.

Preferably, said amplification primers comprise said at least two A9-targeted primers, and at least two primers selected from:

said at least two A5-targeted primers, and/or
said at least two A6-targeted primers, and/or
said at least two A7-targeted primers.

Preferably, said amplification primers comprise said at least two A7-targeted primers, and at least two primers selected from:

said at least two A5-targeted primers, and/or
said at least two A9-targeted primers, and/or
said at least two A6-targeted primers.

Most preferably, said amplification primers comprise:

said at least two A6-targeted primers, and
said at least two A5-targeted primers, and
said at least two A9-targeted primers, and
said at least two A7-targeted primers.

According to an advantageous embodiment of the present invention, said determination of whether at least one amplicon is produced, is carried out by means of at least one probe, which is intended to anneal to said at least one amplicon, i.e., the sequence of the probe is sufficiently complementary to said at least one amplicon (or to the complementary sequence thereof) that the probe can anneal to said at least one amplicon, preferably under conditions of moderate, high or very high stringency.

The probe(s) of the invention can be implemented in any appropriate format.

Preferably, the probe(s) of the invention is(are) not immobilized onto a solid support.

Most preferably, the probe(s) of the invention is(are) used in real-time amplification.

Hence, according to an advantageous embodiment of the present invention, said amplification can be a real-time amplification.

According to an advantageous embodiment of the present invention, said at least one probe is used in real-time amplification, i.e., said at least two primers and said at least two probes can be both present in the amplification reaction mixture, whereby said at least one probe anneal to the amplicon(s) produced by said at least two primers in real-time. In other words, the amplification and the detection can be carried out in a single step, namely in real-time amplification.

By real-time amplification, we hereby understand any amplification-based process allowing for monitoring of fluorescence emitted during the reaction as an indicator of amplicon production during each amplification cycle as opposed to the endpoint detection by conventional amplification process.

The present invention provides probes, which are intended to target the amplicon(s) obtainable by amplification of a mucosal oncogenic HPV nucleic acid by at least two A6- and/or A5- and/or A9- and/or A7-targeted primers.

These probes share the specific technical features of being suitable for use in a real-time multiplex amplification.

Some probes of the present invention allow to detect all the HPV of one group (i.e., they anneal to every amplicon that is obtainable by means of a group-targeted primer pair of the invention). Other probes of the present invention detect one or only some HPV of one group. Hence, the present invention further provides different levels of detection: the response can be a global detection of the presence or absence of at least one mucosal oncogenic HPV, or a more precise response, such as presence or absence of at least one mucosal oncogenic HPV of group A6 and/or A5 and/or A9 and/or A7, or an even more precise response such as presence or absence of at least one mucosal oncogenic HPV type(s).

Preferably, said determination of whether at least one amplicon is produced, is carried out by using in real-time amplification at least one A6- and/or A5- and/or A9- and/or A7-targeted probe, the sequence of which is suitable for use as a probe for the detection of at least one amplicon produced by said at least two A6- and/or A5- and/or A9- and/or A7-targeted primers, respectively.

According to an advantageous embodiment of the present invention, said amplification can be a real-time multiplex amplification.

According to a very advantageous embodiment of the present invention, said amplification can be carried out as a real-time multiplex amplification. Hence, the amplification reaction mixture can comprise more than two primers, and also at least one probe, without any significant loss of specificity in the detection of HPV. To the best of the inventors' knowledge, the present technique is the first to allow a real-time multiplex amplification. It is very advantageous, in the sense that any mucosal oncogenic HPV can be screened in a single tube assay, wherein all reactants (primers and probe(s)) have been poured. More particularly, the present invention provides A6-, A5, A9- and A7-targeted primers and probes, which can all be placed in the same reaction mixture, without any significant loss in specificity.

The present invention therefore is much easier-to-handle and much quicker than any prior art technique. It further limits the possibility of any experimental error or contamination in the sample analysis.

To the best of the inventors' knowledge, the present technique is the first to enable a real-time multiplex amplification, which allows to cover at least the five most common HR HP V (HPV16, 18, 45, 31, 33), preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, and as above-mentioned, most preferably at least 18 oncogenic HPV (namely, at least the 13 HR and five other oncogenic HPV, i.e., HPV 66, 53, 82, 67, 85).

According to an advantageous embodiment of the present invention, said amplification can be a quantitative real-time multiplex amplification.

According to an even more advantageous embodiment of the present invention, said amplification can be carried out as a quantitative real-time multiplex amplification. Indeed, the primers and probes of the present invention have such a sequence that there is no loss in specificity and no loss in quantitative accuracy, even when they are implemented in real-time multiplex amplification.

To the best of the inventors' knowledge, the present technique is the first to enable a quantitative real-time multiplex amplification, which allows to cover at least the five most common HR HPV (HPV16, 18, 45, 31, 33), preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, and as above-mentioned, most preferably at least 18 oncogenic HPV (namely, at least the 13 HR and five other oncogenic HPV, i.e., HPV 66, 53, 82, 67, 85).

The invention thereby finds applications not only in the field of diagnostic, but also in the field of therapy evaluation, such as to monitor the efficiency of an anti-HPV treatment, or to evaluate the efficiency of an anti-HPV drug. To the best of the inventors' knowledge, such therapy-related applications were previously unattainable by any of the prior art process.

The present invention thus represents a technological breakthrough in the field of HPV monitoring.

Hence, said amplification can be a quantitative real-time multiplex amplification, which allows for the detection of one or several of HPV, which can be oncogenic for the mucosal epithelia, in a single-tube amplification run.

The present invention thereby allows for the real-time multiplex detection, preferably the real-time quantitative multiplex detection of: at least the five most common HPV (HPV16, 18, 45, 31, 33)

preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), even still preferably at least the thirteen HPV known as HR HPV (HPV types 56, 51, 58, 33, 52, 35, 31, 16, 68, 39, 59, 45 and 18), more preferably, at least the thirteen HPV as well as at least one among HPV types 66, 82, 67, 85, and 53 still more preferably, at least the thirteen HPV as well as at least two among HPV types 66, 82, 67, 85, and 53 even still more preferably, at least the thirteen HPV as well as at least three among HPV types 66, 82, 67, 85, and 53 most preferably, at least the thirteen HPV as well as at least four among HPV types 66, 82, 67, 85, and 53, notably of least the seventeen mucosal HPV, consisting of said 13 HR HPV and HPV types 66, 82, 67, 85, still most preferably, at least the thirteen HPV as well as at least the five HPV types 66, 82, 67, 85, and 53, in a single-tube assay.

Preferably, the respective sequences of said at least two A6-targeted primers are suitable for use in the amplification of at least one reference template sequence, wherein said at least one reference template sequence is a fragment consisting of positions 413-791 (SEQ ID NO:337) of the HPV56 sequence of SEQ ID NO:420 (accession NC_001594.1); or a conservative sub-fragment thereof, which has retained the property of being a suitable reference template sequence, to construct and produce A6-targeted primers, which allow for a real-time multiplex detection of those HPV, which can be oncogenic for the mucosal epithelia, preferably of at least the five most common HPV (HPV16, 18, 45, 31, 33), still preferably at least 7 HR HPV, even still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and at least one, at least two, at least three, at least four, or the five of HPV66, 53, 82, 67, 85; or a sequence which is fully complementary to said fragment or sub-fragment over the entire length of said fragment or sub-fragment.

More preferably, the respective sequences of said at least two A6-targeted primers are suitable for use in the specific amplification of at least one reference template sequence, which consists of one of SEQ ID NO:25-29 and NO:334-338, as shown in Table 18 (A6 reference templates); or a sequence which is fully complementary thereto over the entire length of said SEQ ID NO sequence.

Said reference template sequences notably share the specific technical feature of being suitable references to construct and produce A6-targeted primers, which allow for a real-time multiplex detection of HPV, which can be oncogenic for the mucosal epithelia, preferably of at least the five most common HPV (HPV16, 18, 45, 31, 33), still preferably at least 7 HR HPV, even still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and at least one, at least two, at least three, at least four, or the five of HPV66, 53, 82, 67, 85, and preferably for a real-time quantitative multiplex detection of such HPV.

As the reference template sequence is defined as consisting of one of the above-mentioned SEQ ID NOs (and not as comprising one of the above-mentioned SEQ ID NOs), the primers do not flank these reference template sequences, but fall within the reference template sequence, in such a way that the amplicon consists of one of the listed SEQ ID NOs. Unless otherwise stated, it applies to any reference template sequence that is herein defined as consisting of a SEQ ID NO. Said at least two A6-targeted primers can, for example, be at least one of SEQ ID NO: 30-34 (forward primer) and at least one of SEQ ID NO: 35-37 (reverse primer).

As illustrated by the examples below (see e.g., Table 23), preferred combinations of forward and reverse primers are as follows:

TABLE 1

(A6 primer systems):

| SEQ ID NO: | 35 | 36 | 37 |
|---|---|---|---|
| 30 | X | | X |
| 31 | X | | X |
| 32 | X | X | X |
| 33 | X | | X |
| 34 | | | X |

wherein X indicates that the primers can be combined with each other as a pair.

According to an advantageous embodiment of the present invention, said determination of whether at least one amplicon is produced by said at least one A6-targeted primer system, can be carried out by using in real-time amplification at least one probe, preferably at least one A6-targeted probe.

Advantageously, said determination of whether at least one amplicon is produced is carried out by using in real-time amplification at least one A6-targeted probe, which consists of one of SEQ ID NO:38-40, or of one of the complementary sequences thereof (i.e., sequences of the same length, which are fully complementary over the entire length of the sequence), and optionally at least one 5' and/or 3' detection label and/or at least one HPV-unrelated arm intended to carry a quencher or a reporter (e.g., a fluorophore), such as at least one beacon arm, or Scorpion™ arm, preferably at least one of such arms in 5' and/or 3', most preferably two of such arms, in 5' and in 3', respectively.

As illustrated by the examples below (see e.g., table 23), preferred combinations of primer pair and probe are as follows:

TABLE 2

(A6 primer and probe systems):

| A6 amplification system | Primer pair SEQ ID NO: | At least one probe of SEQ ID NO: |
|---|---|---|
| A | 30; 35 | 38 |
| AE | 30; 37 | 38 and/or 40 |
| B | 31; 35 | 38 |
| BE | 31; 37 | 38 and/or 40 |
| C | 32; 36 | 39 |
| CA | 32; 35 | 38 and/or 39 |
| CE | 32; 37 | 38 and/or 39 and/or 40 |
| D | 33; 35 | 38 |
| DE | 33; 37 | 38 and/or 40 |
| E | 34; 37 | 40 |

Advantageously, said at least one A6-targeted probe is a beacon probe, the sequence of which is one of SEQ ID NO:41-45, or of one of the complementary sequences thereof (i.e., sequences of the same length, which are fully complementary over the entire length of the sequence).

As illustrated by the examples below (see e.g., Table 23), most preferred combinations of primer pair and beacon probes are as follows:

TABLE 3

(A6 primer and beacon probe systems):

| A6 amplification system | Primer pair SEQ ID NO: | At least one beacon probe of SEQ ID NO: |
|---|---|---|
| A | 30; 35 | 41 |
| AE | 30; 37 | 41 and/or 44 and/or 45 |
| B | 31; 35 | 41 |
| BE | 31; 37 | 41 and/or 44 and/or 45 |
| C | 32; 36 | 42 and/or 43 |
| CA | 32; 35 | 41 and/or 42 and/or 43 |
| CE | 32; 37 | 41 and/or 42 and/or 43 and/or 44 and/or 45 |
| D | 33; 35 | 41 |
| DE | 33; 37 | 41 and/or 44 and/or 45 |
| E | 34; 37 | 44 and/or 45 |

Preferably, the respective sequences of said at least two A5-targeted primers are suitable for use in the amplification of at least one reference template sequence, which is a fragment consisting of positions 678-902 (SEQ ID NO:326) of the HPV51 sequence of SEQ ID NO:421 (accession NC_001533.1), or a conservative sub-fragment thereof, which has retained the property of being a suitable reference template sequence, to construct and produce A5-targeted primers, which allow for a real-time multiplex detection of those HPV, which can be oncogenic for the mucosal epithelia, preferably of at least the five most common HPV (HPV16, 18, 45, 31, 33), still preferably at least 7 HR HPV, even still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and at least one, at least two, at least three, at least four, or the five of HPV66, 53, 82, 67, 85; or a sequence which is fully complementary to said fragment or sub-fragment over the entire length of said fragment or sub-fragment.

More preferably, the respective sequences of said at least two A5-targeted primers are suitable for use in the specific amplification of at least one reference template sequence, wherein said at least one reference template sequence consists of one of SEQ ID NO: 1-5 and NO: 320-333, as shown in Table 12; or a sequence which is fully complementary thereto over the entire length of said SEQ ID sequence.

Said reference template sequences share the specific technical feature of being suitable references to construct and produce A5-targeted primers, which allow for a real-time multiplex detection of HPV, which can be oncogenic for the mucosal epithelia, preferably of at least the five most common HPV (HPV16, 18, 45, 31, 33), still preferably at least 7 HR HPV, even still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and at least one, at least two, at least three, at least four, or the five of HPV66, 53, 82, 67, 85, and preferably for a real-time quantitative multiplex detection of such HPV.

Said at least two A5-targeted primers may, for example, be at least one of SEQ ID NO: 6-10 (forward primer) and at least one of SEQ ID NO: 11-15 (reverse primer).

As illustrated by the examples below (see e.g., Table 17), preferred combinations of forward and reverse primers are as follows:

TABLE 4

(A5 primer systems):

| SEQ ID NO: | 6 | 7 | 8 | 9 | 10 |
|---|---|---|---|---|---|
| 11 | X | X | X | X | X |
| 12 | X | X | X | X | X |
| 13 | | | X | | |
| 14 | X | X | X | X | X |
| 15 | | | X | X | X |

wherein X indicates that the primers can be combined with each other as a pair.

Advantageously, said determination of whether at least one amplicon is produced is carried out by using in real-time amplification at least one A5-targeted probe, which consists of one of SEQ ID NO:16-19, or of one of the complementary sequences thereof (i.e., sequences of the same length, which are fully complementary over the entire length of the sequence), and optionally at least one detection label and/or at least one HPV-unrelated arm intended to carry a quencher or a reporter (e.g., a fluorophore), such as at least one beacon arm, or Scorpion™ arm, preferably at least one of such arms in 5' and/or 3', most preferably two of such arms, in 5' and in 3', respectively.

As illustrated by the examples below (see e.g., Table 17), preferred combinations of primer pair and probe are as follows:

TABLE 5

(A5 primer and probe systems):

| A5 amplification system | Primer pair SEQ ID NO: | At least one probe of SEQ ID NO: |
|---|---|---|
| A | 6; 11 | 16 |
| AB | 6; 12 | 16 |
| AD | 6; 14 | 16 |
| B | 7; 12 | 16; 17 |
| BA | 7; 11 | 16; 17 |
| BD | 7; 14 | 16; 17 |
| C | 8; 13 | 18 |

TABLE 5-continued (A5 primer and probe systems):

| A5 amplification system | Primer pair SEQ ID NO: | At least one probe of SEQ ID NO: |
|---|---|---|
| CA | 8; 11 | 16; 17; 18; 19 |
| CB | 8; 12 | 16; 17; 18; 19 |
| CD | 8; 14 | 16; 17; 18; 19 |
| CE | 8; 15 | 18; 19 |
| D | 9; 14 | 16; 17; 19 |
| DA | 9; 11 | 16; 17; 19 |
| DB | 9; 12 | 16; 17; 19 |
| DE | 9; 15 | 19 |
| E | 10; 15 | 19 |
| EA | 10; 11 | 16; 17; 19 |
| EB | 10; 12 | 16; 17; 19 |
| ED | 10; 14 | 16; 17; 19 |

Advantageously, said at least one A5-targeted probe is a beacon probe, the sequence of which is one of SEQ ID NO: 20-24, or of one of the complementary sequences thereof (i.e., sequences of the same length, which are fully complementary over the entire length of the sequence).

As illustrated by the examples below (see e.g., Table 17), most preferred combinations of primer pair and probe are as follows:

TABLE 6

(A5 primer and beacon probe systems):

| A5 amplification system | Primer pair SEQ ID NO: | At least one beacon probe of SEQ ID NO: |
|---|---|---|
| A | 6; 11 | 20; 21 |
| AB | 6; 12 | 20; 21 |
| AD | 6; 14 | 20; 21 |
| B | 7; 12 | 20; 21; 22 |
| BA | 7; 11 | 20; 21; 22 |
| BD | 7; 14 | 20; 21; 22 |
| C | 8; 13 | 23 |
| CA | 8; 11 | 20; 21; 22; 23; 24 |
| CB | 8; 12 | 20; 21; 22; 23; 24 |
| CD | 8; 14 | 20; 21; 22; 23; 24 |
| CE | 8; 15 | 23; 24 |
| D | 9; 14 | 20; 21; 22; 24 |
| DA | 9; 11 | 20; 21; 22; 24 |
| DB | 9; 12 | 20; 21; 22; 24 |
| DE | 9; 15 | 24 |
| E | 10; 15 | 24 |
| EA | 10; 11 | 20; 21; 22; 24 |
| EB | 10; 12 | 20; 21; 22; 24 |
| ED | 10; 14 | 20; 21; 22; 24 |

Preferably, the respective sequences of said at least two A9-targeted primers are suitable for use in the amplification of at least one reference template sequence, which is:

a fragment consisting of positions 2707-2794 (SEQ ID NO:122) of the HPV16 sequence of SEQ ID NO:422 (accession NC_001526.1); or a conservative sub-fragment thereof, which has retained the property of being a suitable reference template sequence, to construct and produce A9-targeted primers, which allow for a real-time multiplex detection of those HPV, which can be oncogenic for the mucosal epithelia, preferably of at least the five most common HPV (HPV16, 18, 45, 31, 33), still preferably at least 7 HR HPV, even still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and at least one, at least two, at least three, at least four, or the five of HPV66, 53, 82, 67, 85; or a sequence which is fully complementary to said fragment or sub-fragment over the entire length of said fragment or sub-fragment or a fragment consisting of positions 3600-3840 (SEQ ID NO:377) of the HPV16 sequence of SEQ ID NO:422 (accession NC_001526.1); or a conservative sub-fragment thereof, which has retained the property of being a suitable reference template sequence, to construct and produce A9-targeted primers, which allow for a real-time multiplex detection of those HPV, which can be oncogenic for the mucosal epithelia, preferably of at least the five most common HPV (HPV16, 18, 45, 31, 33), still preferably at least 7 HR HPV, even still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and at least one, at least two, at least three, at least four, or the five of HPV66, 53, 82, 67, 85; or a sequence which is fully complementary to said fragment or sub-fragment over the entire length of said fragment or sub-fragment.

More preferably, the respective sequences of said at least two A9-targeted primers are suitable for use in the specific amplification of at least one reference template sequence, which consists of any one of SEQ ID NO: 122-210 and 359-419, as shown in Table 30; or a sequence which is fully complementary thereto over the entire length of said SEQ ID NO sequence.

Said reference template sequences notably share the specific technical feature of being suitable references to construct and produce A9-targeted primers, which allow for a real-time multiplex detection of HPV, which can be oncogenic for the mucosal epithelia, preferably of at least the five most common HPV (HPV16, 18, 45, 31, 33), still preferably at least 7 HR HPV, even still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and at least one, at least two, at least three, at least four, or the five of HPV66, 53, 82, 67, 85, and preferably for a real-time quantitative multiplex detection of such HPV.

Said at least two A9-targeted primers can, for example, be at least one of SEQ ID NO: 211-239 (forward primers) and at least one of SEQ ID NO: 240-265 (reverse primers).

As illustrated by the examples below (see e.g., Table 35), preferred combinations of forward and reverse primers are as follows:

A9 amplification system C: at least one of SEQ ID NO:211-217 and at least one of SEQ ID NO:240-241; preferably, when amplification of all oncogenic HPV of group A9 is desired, at least three of SEQ ID NO: 211-217, e.g., 212, 214 and 216, and both of SEQ ID NO:240-241;

A9 amplification system E1: at least one of SEQ ID NO:218-220 and at least one of SEQ ID NO:242-247; preferably, when amplification of all oncogenic HPV of group A9 is desired, at least the three of SEQ ID NO:218-220 and at least five of SEQ ID NO:242-247 (e.g., SEQ ID NO:242-243, 245-247);

A9 amplification system E2: at least one of SEQ ID NO:221-223 and at least one of SEQ ID NO:242-247; preferably, when amplification of all oncogenic HPV of group A9 is desired, at least the three of SEQ ID NO:221-223 and at least five of SEQ ID NO:242-247 (e.g., SEQ ID NO:242-243, 245-247);

A9 amplification system E3: at least one of SEQ ID NO:221-223 and at least one of SEQ ID NO:248-255; preferably, when amplification of all oncogenic HPV of group A9 is desired, at least the three of SEQ ID NO:221-223 and at least five of SEQ ID NO:248-255 (e.g., SEQ ID NO:248-252);

A9 amplification system E4: at least one of SEQ ID NO:224-226 and at least one of SEQ ID NO:248-255; preferably, when amplification of all oncogenic HPV of group A9 is desired, at least the three: of SEQ ID NO:224-226 and at least five of SEQ ID NO:248-255 (e.g., SEQ ID NO:248-252);

A9 amplification system E5: at least one of SEQ ID NO:224-226 and at least one of SEQ ID NO:242-247; preferably, when amplification of all oncogenic HPV of group A9 is desired, at least the three of SEQ ID NO:224-226 and at least five of SEQ ID NO:242-247 (e.g., SEQ ID NO:242-243, 245-247);

A9 amplification system E6: at least one of SEQ ID NO:218-220 and at least one of SEQ ID NO:248-255; preferably, when amplification of all oncogenic HPV of group A9 is desired, at least the three of SEQ ID NO:218-220 and at least five of SEQ ID NO:248-255 (e.g., SEQ ID NO:248-252);

A9 amplification system E1H Z7: at least one of SEQ ID NO:218-220 and at least one of SEQ ID NO:256-259; 261-265; preferably, when amplification of all oncogenic HPV of group A9 is desired, at least the three of SEQ ID NO:218-220 and at least four of SEQ ID NO: 256-259; 261-265 (e.g., SEQ ID NO:258; 261; 264; 265);

A9 amplification system E1H Z8: at least one of SEQ ID NO: 218-220 and at least one of SEQ ID NO:256-259; 261-265; preferably, when amplification of all oncogenic HPV of group A9 is desired, at least the three of SEQ ID NO:218-220 and at least four of SEQ ID NO:256-259; 261-265 (e.g., SEQ ID NO:258; 261; 264; 265);

A9 amplification system E2H Z7: at least one of SEQ ID NO:221-223 and at least one of SEQ ID NO:256-259; 261-265; preferably, when amplification of all oncogenic HPV of group A9 is desired, at least the three of SEQ ID NO:221-223 and at least four of SEQ ID NO:256-259; 261-265 (e.g., SEQ ID NO: 258; 261; 264; 265);

A9 amplification system E2H Z8: identical to A9 amplification system E2H Z7, i.e., at least one of SEQ ID NO:221-223 and at least one of SEQ ID NO: 256-259; 261-265; preferably, when amplification of all oncogenic HPV of group A9 is desired, at least the three of SEQ ID NO:221-223 and at least four of SEQ ID NO:256-259; 261-265 (e.g., SEQ ID NO:258; 261; 264; 265);

A9 amplification system E4H Z7: at least one of SEQ ID NO:224-226 and at least one of SEQ ID NO: 256-259; 261-265; preferably, when amplification of all oncogenic HPV of group A9 is desired, at least the three of SEQ ID NO:224-226 and at least four of SEQ ID NO:256-259; 261-265 (e.g., SEQ ID NO:258; 261; 264; 265);

A9 amplification system E4H Z8: at least one of SEQ ID NO:224-226 and at least one of SEQ ID NO: 256-259; 261-265; preferably, when amplification of all oncogenic HPV of group A9 is desired, at least the three of SEQ ID NO:224-226 and at least four of SEQ ID NO:256-259; 261-265 (e.g., SEQ ID NO: 258; 261; 264; 265);

A9 amplification system F: at least one of SEQ ID NO:227-230 and at least one of SEQ ID NO:248-255; preferably, when amplification of all oncogenic HPV of group A9 is desired, at least the four of SEQ ID NO:227-230 and at least five of SEQ ID NO:248-255 (e.g., SEQ ID NO:248-252);

A9 amplification system FE: at least one of SEQ ID NO:227-230 and at least one of SEQ ID NO:242-247; preferably, when amplification of all oncogenic HPV of group A9 is desired, at least the four of SEQ ID NO:227-230 and at least five of SEQ ID NO:242-247 (e.g., SEQ ID NO:242-243; 245-247);

A9 amplification system FH Z7: at least one of SEQ ID NO:227-230 and at least one of SEQ ID NO:256-259; 261-265; preferably, when amplification of all oncogenic HPV of group A9 is desired, at least the four of SEQ ID NO:227-230 and at least four of SEQ ID NO:256-259; 261-265 (e.g., SEQ ID NO:258; 261; 264; 265);

A9 amplification system FHZ8: identical to A9 amplification system FH Z7, i.e., at least one of SEQ ID NO:227-230 and at least one of SEQ ID NO:256-259; 261-265; preferably, when amplification of all oncogenic HPV of group A9 is desired, at least the three of SEQ ID NO:227-230 and at least four of SEQ ID NO:256-259; 261-265 (e.g., SEQ ID NO:258; 261; 264; 265);

A9 amplification system G Z7: at least one of SEQ ID NO:227-230 and at least one of SEQ ID NO:256-261; preferably, when amplification of all oncogenic HPV of group A9 is desired, at least the three of SEQ ID NO:227-230 and at least five of SEQ ID NO:256-261 (e.g., SEQ ID NO:257-261);

A9 amplification system G Z8: identical to A9 amplification system G Z7, i.e., at least one of SEQ ID NO:227-230 and at least one of SEQ ID NO:256-261; preferably, when amplification of all oncogenic HPV of group A9 is desired, at least the three of SEQ ID NO:227-230 and at least five of SEQ ID NO:256-261 (e.g., SEQ ID NO:257-261);

A9 amplification system H: at least one of SEQ ID NO:231-239 and at least one of SEQ ID NO: 256-259; 261-265; preferably, when amplification of all oncogenic HPV of group A9 is desired, at least three of SEQ ID NO:231-239 (e.g., SEQ ID NO:232; 234; 235) and at least four of SEQ ID NO: 256-259; 261-265 (e.g., SEQ ID NO:258; 261; 264; 265).

Advantageously, said determination of whether at least one amplicon is produced is carried out by using in real-time amplification at least one A9-targeted probe, which consists of one of SEQ ID NO: 266-282, or of one of the complementary sequences thereof (i.e., sequences of the same length, which are fully complementary over the entire length of the sequence), and optionally at least one detection label and/or at least one HPV-unrelated arm intended to carry a quencher or a reporter (e.g., a fluorophore), such as at least one beacon arm, or Scorpion™ arm, preferably at least one of such arms in 5' and/or 3', most preferably two of such arms, in 5' and in 3', respectively.

As illustrated by the examples below (see e.g., Table 35), preferred combinations of primer pair and probe are as follows:

TABLE 7

(A9 primer and probe systems):

| A9 amplification system | At least one probe of SEQ ID NO: |
|---|---|
| C | 266-271 |
| E1 | 272-276 |
| E2 | 272-276 |
| E3 | 272-276 |
| E4 | 272-276 |
| E5 | 272-276 |
| E6 | 272-276 |
| E1H Z7 | 272-276 |
| E1H Z8 | 277-282 |
| E2H Z7 | 272-276 |
| E2H Z8 | 277-282 |
| E4H Z7 | 272-276 |
| E4H Z8 | 277-282 |
| F | 272-276 |
| FE | 272-276 |
| FH Z7 | 272-276 |
| FH Z8 | 277-282 |
| G Z7 | 272-276 |
| G Z8 | 277-282 |
| H | 277-282 |

Advantageously, said at least one A9-targeted probe is a beacon probe, the sequence of which is one of SEQ ID NO: 283-319, or of one of the complementary sequences thereof (i.e., sequences of the same length, which are fully complementary over the entire length of the sequence).

As illustrated by the examples below (see e.g., Table 35), most preferred combinations of primer pair and probe are as follows:

TABLE 8

(A9 primer and beacon probe systems):

| A9 amplification system | At least one beacon probe of SEQ ID NO: |
|---|---|
| C | 283-295 |
| E1 | 296-303 |
| E2 | 296-303 |
| E3 | 296-303 |
| E4 | 296-303 |
| E5 | 296-303 |
| E6 | 296-303 |
| E1H Z7 | 296-303 |
| E1H Z8 | 304-319 |
| E2H Z7 | 296-303 |
| E2H Z8 | 304-319 |
| E4H Z7 | 296-303 |
| E4H Z8 | 304-319 |
| F | 296-303 |
| FE | 296-303 |
| FH Z7 | 296-303 |
| FH Z8 | 304-319 |
| G Z7 | 296-303 |
| G Z8 | 304-319 |
| H | 304-319 |

Some of the specificity results of the above-mentioned probes are shown in Tables 60-68 (Specificity A9).

In all tables, when the name of a probe differs from the name of another probe by only the last letter (e.g., A9E1S10 and A9E1S10a), these probes have the same hybridizing segment, and only differ in their beacon arms.

Gray boxes indicate that the tested probe detects the amplicon.

For example, probe A9E1S11 of SEQ ID NO: 285 detects HPV31 and HPV35, without detecting the other HPV.

For example, probe A9E1S10a of SEQ ID NO: 284 detects all oncogenic HPV of group A9 (HPV16, 31, 33, 35, 52, 58, 67) and one HPV of group A6 (HPV53), and probe A9E1S12a of SEQ ID NO: 288 detects HPV31 and HPV35, without detecting HPV53 ("ND"). Hence, a combination of A9E1S10a and of A9E1S12a allows the specific detection of HPV16, 31, 33, 35, 52, 58, 67, 53.

Any combination that the skilled person may find appropriate is herein specifically encompassed.

Preferably, the respective sequences of said at least two A7-targeted primers are suitable for use in the amplification of at least one reference template sequence, wherein said at least one reference template sequence is:

a fragment consisting of positions 1895-2103 (SEQ ID NO:48) of the HPV18 sequence of SEQ ID NO:423 (accession NC_001357.1); or a conservative sub-fragment thereof, which has retained the property of being a suitable reference template sequence, to construct and produce A7-targeted primers, which allow for a real-time multiplex detection of those HPV, which can be oncogenic for the mucosal epithelia, preferably of at least the five most common HPV (HPV16, 18, 45, 31, 33), still preferably at least 7 HR HPV, even still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and at least one, at least two, at least three, at least four, or the five of HPV66, 53, 82, 67, 85; or a sequence which is fully complementary to said fragment or sub-fragment over the entire length of said fragment or sub-fragment, or a fragment consisting of positions 916-1044 (SEQ ID NO: 65) of the HPV18 sequence of SEQ ID NO:423 (accession NC_001357.1); or a conservative sub-fragment thereof, which has retained the property of being a suitable reference template sequence, to construct and produce A7-targeted primers, which allow for a real-time multiplex detection of those HPV, which can be oncogenic for the mucosal epithelia, preferably of at least the five most common HPV (HPV16, 18, 45, 31, 33), still preferably at least 7 HR HPV, even still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and at least one, at least two, at least three, at least four, or the five of HPV66, 53, 82, 67, 85; or a sequence which is fully complementary to said fragment or sub-fragment over the entire length of said fragment or sub-fragment.

More preferably, the respective sequences of said at least two A7-targeted primers are suitable for use in the specific amplification of at least one reference template sequence, which consists of one of SEQ ID NO:46-67; 339-358, as shown in Table 24; or a sequence which is fully complementary thereto over the entire length of said SEQ ID NO sequence.

Said reference template sequences notably share the specific technical feature of being suitable references to construct and produce A7-targeted primers, which allow for a real-time multiplex detection of HPV, which can be oncogenic for the mucosal epithelia, preferably of at least the five most common HPV (HPV16, 18, 45, 31, 33), still preferably at least 7 HR HPV, even still preferably the five most common HR HPV as well as at least two other HR HPV, advantageously at least two other HR HPV belonging to groups A6 and/or A5 (e.g., HPV 56, 51, 33, 31, 16, 45, 18), more preferably at least the 13 HR HPV, most preferably at least the 13 HR HPV and at least one, at least two, at least three, at least four, or the five of HPV66, 53, 82, 67, 85, and preferably for a real-time quantitative multiplex detection of such HPV.

Said at least two A7-targeted primers can, for example, be at least one of SEQ ID NO: 68-78 (forward primer) and at least one of SEQ ID NO: 79-87 (reverse primer).

As illustrated by the examples below (see e.g., Table 29), preferred combinations of forward and reverse primers are as follows:

A7 amplification system A: at least one of SEQ ID NO:68-70 and at least one of SEQ ID NO:79-81; preferably, when amplification of all oncogenic HPV of group A7 is desired, all of them;

A7 amplification system A1: identical to A7 amplification system A, i.e., at least one of SEQ ID NO:68-70 and at least one of SEQ ID NO:79-81; preferably, when amplification of all oncogenic HPV of group A7 is desired, all of them;

A7 amplification system A2: identical to A7 amplification system A or A1, i.e., at least one of SEQ ID NO:68-70 and at least one of SEQ ID NO:79-81; preferably, when amplification of all oncogenic HPV of group A7 is desired, all of them;

A7 amplification system AB: at least one of SEQ ID NO:68-70 and at least one of SEQ ID NO:82-83; preferably, when amplification of all oncogenic HPV of group A7 is desired, all of them;

A7 amplification system AC1: at least one of SEQ ID NO:68-70 and at least one of SEQ ID NO:84-85; preferably, when amplification of all oncogenic HPV of group A7 is desired, all of them;

A7 amplification system AC2: identical to A7 amplification system AC1, i.e., at least one of SEQ ID NO:68-70 and at least one of SEQ ID NO:84-85; preferably, when amplification of all oncogenic HPV of group A7 is desired, all of them;

A7 amplification system AC3: identical to A7 amplification system AC1 or AC2, i.e., at least one of SEQ ID NO:68-70 and at least one of SEQ ID NO:84-85; preferably, when amplification of all oncogenic HPV of group A7 is desired, all of them;

A7 amplification system B: at least one of SEQ ID NO:71-73 and at least one of SEQ ID NO:82-83; preferably, when amplification of all oncogenic HPV of group A7 is desired, all of them;

A7 amplification system BA1: at least one of SEQ ID NO:71-73 and at least one of SEQ ID NO:79-81; preferably, when amplification of all oncogenic HPV of group A7 is desired, all of them;

A7 amplification system BA2: identical to A7 amplification system BA1, i.e., at least one of SEQ ID NO:71-73 and at least one of SEQ ID NO:79-81; preferably, when amplification of all oncogenic HPV of group A7 is desired, all of them;

A7 amplification system BA3: identical to A7 amplification system BA1 or BA2, i.e., at least one of SEQ ID NO:71-73 and at least one of SEQ ID NO:79-81; preferably, when amplification of all oncogenic HPV of group A7 is desired, all of them;

A7 amplification system BC1: at least one of SEQ ID NO:71-73 and at least one of SEQ ID NO:84-85; preferably, when amplification of all oncogenic HPV of group A7 is desired, all of them;

A7 amplification system BC2: identical to A7 amplification system BC1, i.e., at least one of SEQ ID NO:71-73 and at least one of SEQ ID NO:84-85; preferably, when amplification of all oncogenic HPV of group A7 is desired, all of them;

A7 amplification system BC3: identical to A7 amplification system BC1 or BC2, i.e., at least one of SEQ ID NO:71-73 and at least one of SEQ ID NO:84-85; preferably, when amplification of all oncogenic HPV of group A7 is desired, all of them;

A7 amplification system C: at least one of SEQ ID NO:74-76 and at least one of SEQ ID NO:84-85; preferably, when amplification of all oncogenic HPV of group A7 is desired, all of them;

A7 amplification system C1: identical to A7 amplification system C, i.e., at least one of SEQ ID NO:74-76 and at least one of SEQ ID NO:84-85; preferably, when amplification of all oncogenic HPV of group A7 is desired, all of them;

A7 amplification system CA1: identical to A7 amplification system C1, i.e., at least one of SEQ ID NO:74-76 and at least one of SEQ ID NO:79-81; preferably, when amplification of all oncogenic HPV of group A7 is desired, all of them;

A7 amplification system CA2: identical to A7 amplification system C1 or CA1, i.e., at least one of SEQ ID NO:7476 and at least one of SEQ ID NO:79-81; preferably, when amplification of all oncogenic HPV of group A7 is desired, all of them;

A7 amplification system D: at least one of SEQ ID NO:77-78 and at least one of SEQ ID NO:86-87; preferably, when amplification of all oncogenic HPV of group A7 is desired, all of them.

Advantageously, said determination of whether at least one amplicon is produced is carried out by using in real-time amplification at least one A7-targeted probe, which consists of one of SEQ ID NO:88-101, or of one of the complementary sequences thereof (i.e., sequences of the same length, which are fully complementary over the entire length of the sequence), and optionally at least one detection label and/or at least one HPV-unrelated arm intended to carry a quencher or a reporter (e.g., a fluorophore), such as at least one beacon arm, or Scorpion™ arm, preferably at least one of such arms in 5' and/or 3', most preferably two of such arms, in 5' and in 3', respectively.

As illustrated by the examples below (see e.g., Table 29), preferred combinations of primer pair and probe are as follows:

TABLE 10

(A7 primer and probe systems):

| A7 amplification system | At least one probe of SEQ ID NO: |
|---|---|
| A | 88-92 |
| A1 | 92-95 |
| A2 | 89-91; 96 |
| AB | 92-95 |
| AC1 | 88-92 |
| AC2 | 92-95 |
| AC3 | 89-91; 96 |
| B | 92-95 |
| BA1 | 88-92 |
| BA2 | 92-95 |
| BA3 | 89-91; 96 |
| BC1 | 88-92 |
| BC2 | 92-95 |
| BC3 | 89-91; 96 |
| C | 89-91; 96 |
| C1 | 88-91; 96 |

TABLE 10-continued (A7 primer and probe systems):

| A7 amplification system | At least one probe of SEQ ID NO: |
|---|---|
| CA1 | 89-91; 96 |
| CA2 | 88-91; 96 |
| D | 97-101 |

Advantageously, said at least one A7-targeted probe is a beacon probe, the sequence of which is one of SEQ ID NO:102-121, or of one of the complementary sequences thereof (i.e., sequences of the same length, which are fully complementary over the entire length of the sequence).

As illustrated by the examples below (see e.g., Table 29), most preferred combinations of primer pair and probe are as follows:

TABLE 11

(A7 primer and beacon probe systems):

| A7 amplification system | At least one beacon probe of SEQ ID NO: |
|---|---|
| A | 102-106 |
| A1 | 106-110 |
| A2 | 105; 111-114 |
| AB | 106-110 |
| AC1 | 102-106 |
| AC2 | 106-110 |
| AC3 | 105; 111-114 |
| B | 106-110 |
| BA1 | 102-106 |
| BA2 | 106-110 |
| BA3 | 105; 111-114 |
| BC1 | 102-106 |
| BC2 | 106-110 |
| BC3 | 105; 111-114 |
| C | 105; 111-114 |
| C1 | 102-105; 114 |
| CA1 | 105; 111-114 |
| CA2 | 102-105; 114 |
| D | 115-121 |

Said amplification can be any nucleic acid amplification, which is found appropriate to the skilled person, for example a PCR (Polymerase Chain Reaction), or an isothermal amplification technique, e.g., TMA (transcription mediated amplification), NASBA (nucleic acid sequence based amplification), 3SR (self sustained sequence replication) or strand displacement amplification. Said amplification preferably is a PCR.

In a preferred embodiment, the primers according to the invention are used in a final concentration range 100-200 nM. Typically, said primers can be used at a final concentration range 200-1500 nM, preferably 250-1000 nM, more preferably 500-1000 nM, even more preferably 600-1000 nM.

Probe concentration in a PCR reaction can be optimized, typically by varying the final concentration from 50 nM to 1000 nM. In a preferred embodiment, the probes according to the invention are used at a final concentration range 50-1000 nM, preferably 100-800 nM, more preferably 100-600 nM, even more preferably 200-600 nM.

Appropriate amplification conditions are known to those skilled in the art. They include temperature conditions, in particular thermal cycling conditions, e.g. temperature, duration, number, heating rate of the cycles. In a preferred embodiment, said temperature conditions include conditions suitable for a PCR. In another preferred embodiment, said conditions include conditions suitable for a Q-PCR.

Any megaplex, i.e., multi-multiplex comprising at least A6-targeted one real-time amplification system of the invention and at least one A5-targeted one real-time amplification system of the invention and at least one A9-targeted one real-time amplification system of the invention and at least one A7-targeted one real-time amplification system of the invention, which would be contemplated by the person of ordinary skill in the art is encompassed by the present application.

For example, the A5-targeted system E, and the A6-targeted system A, and the A7-targeted system A, and the A9-targeted system H, can be used together in a single-tube assay, thereby forming a megaplex ("megaplex EAAH").

For example, the A5-targeted system E, and the A6-targeted system B, and the A7-targeted system A, and the A9-targeted system C, can be used together in a single-tube assay, thereby forming a megaplex ("megaplex EBAC").

Illustrative specificity and sensitivity results of such megaplex are shown in tables 83-88 below.

From tables 84 and 87 ("megaplex EAAH"), it can be seen that such a megaplex enable to efficiently detect the oncogenic HPV, namely the 13 HR HPV and five other oncogenic HPV (HPV66, 53, 82, 67, 85), and that this megaplex has sufficiently homogeneous sensitivity and specificity (Ct) results to be quantitative for at least the 13 HR HPV and four other oncogenic HPV (HPV66, 53, 82, 85).

From tables 86 and 88 ("megaplex EBAC"), it can be seen that such a megaplex enable to efficiently detect the oncogenic HPV, namely at least the 13 HR HPV, and that this megaplex has sufficiently homogeneous sensitivity and specificity (Ct) results to be quantitative for at least the five most common HR HPV (HPV16, 18, 45, 31, 33).

Preferred megaplex notably comprise the above-mentioned EAAH and EBAC megaplex, as well as the following megaplex systems:

- the combination of A5-targeted system E, and the A6-targeted system B, and the A7-targeted system C, and the A9-targeted system C, can be used together in a single-tube assay, thereby forming a megaplex ("megaplex EBCC");
- the combination of A5-targeted system E, and the A6-targeted system B, and the A7-targeted system B, and the A9-targeted system C, can be used together in a single-tube assay, thereby forming a megaplex ("megaplex EBBC");
- the combination of A5-targeted system E, and the A6-targeted system B, and the A7-targeted system D, and the A9-targeted system C, can be used together in a single-tube assay, thereby forming a megaplex ("megaplex EBDC");
- the combination of A5-targeted system E, and the A6-targeted system B, and the A7-targeted system A, and the A9-targeted system H, can be used together in a single-tube assay, thereby forming a megaplex ("megaplex EBAH").

The present application also relates to any amplicon obtainable by implementation of the process according to any one claims 1-45 on a HPV-containing sample, which contains at least one HPV of group A6, A5, A9 or A7, for example, a sample which contains HPV66 and/or HPV53 and/or HPV82 and/or HPV58 and/or HPV33 and/or HPV67 and/or HPV52 and/or HPV35 and/or HPV31 and/or HPV68 and/or HPV39 and/or HPV85 and/or HPV59 and/or HPV45.

The invention is also directed to a polynucleotide suitable for use as a reference template sequence in the design of primers that can be used in multiplex to cover at least the five most common HR HPV (HPV16, 18, 45, 31, 33), preferably at least 7 HR HPV, still preferably the five most common HR HPV as well as at least two other HR HPV, advantageously at least two other HR HPV belonging to groups A6 and/or A5 (e.g., HPV 56, 51, 33, 31, 16, 45, 18), even still preferably at least the thirteen HPV known as HR HPV (HPV types 56, 51, 58, 33, 52, 35, 31, 16, 68, 39, 59, 45 and 18), more preferably, at least the thirteen HPV as well as at least one among HPV types 66, 82, 67, 85, and 53 still more preferably, at least the thirteen HPV as well as at least two among HPV types 66, 82, 67, 85, and 53 even still more preferably, at least the thirteen HPV as well as at least three among HPV types 66, 82, 67, 85, and 53 most preferably, at least the thirteen HPV as well as at least four among HPV types 66, 82, 67, 85, and 53, notably of least the seventeen mucosal HPV, consisting of said 13 HR HPV and HPV types 66, 82, 67, 85, still most preferably, at least the thirteen HPV as well as at least the five HPV types 66, 82, 67, 85, and 53, in a single amplification run while still offering a real time quantitative amplification thereof.

Of course, the polynucleotides according to the present invention are also suitable for further protocols, including simplex protocols, multiplex protocols, end-point protocols, qualitative protocols, quantitative protocols, combinations thereof, and the like.

By polynucleotide, we hereby understand any polymer of nucleotides, wherein nucleotides can be ribonucleotides, deoxyribonucleotides, dideoxyribonucleotides, degenerated nucleotides, and the like. Said nucleotides are preferably single-stranded, but can also be double stranded. The length of said polynucleotides can vary, and is usually under 500 nucleotides (nt), preferably in the range of 50-400 nt, more preferably 100-300 nt, even more preferably 80-260 nt.

The present application also relates to any polynucleotide suitable for use as a reference template sequence in the design of primers that can be used in a single-tube multiplex to amplify those HPV of groups A6, A5, A9 and A7, and in the design of probes that can be used in said single-tube multiplex for real-time detection of said amplified HPV, said reference template polynucleotide being selected from:

- for group A6: a fragment consisting of positions 413-791 of the HPV56 sequence of SEQ ID NO:420 (accession NC_001594.1), or a conservative sub-fragment thereof, or a sequence which is fully complementary to said fragment or sub-fragment over the entire length of said fragment or sub-fragment;
- for group A5: a fragment consisting of positions 678-902 of the HPV51 sequence of SEQ ID NO:421 (accession NC_001533.1), or a conservative sub-fragment thereof, or a sequence which is fully complementary to said fragment or sub-fragment over the entire length of said fragment or sub-fragment;
- for group A9: a fragment consisting of positions 2707-2794 of the HPV16 sequence of SEQ ID NO:422 (accession NC_001526.1), or a conservative sub-fragment thereof, or a sequence which is fully complementary to said fragment or sub-fragment over the entire length of said fragment or sub-fragment; or a fragment consisting of positions 3600-3840 of the HPV16 sequence of SEQ ID NO:422 (accession NC_001526.1), or a conservative sub-fragment thereof, or a sequence which is fully complementary to said fragment or sub-fragment over the entire length of said fragment or sub-fragment;
- for group A7: a fragment consisting of positions 1895-2103 of the HPV18 sequence of SEQ ID NO:423 (accession NC_001357.1), or a conservative sub-fragment thereof, or a sequence which is fully complementary to said fragment or sub-fragment over the entire length of said fragment or sub-fragment; or a fragment consisting of positions 916-1044 of the HPV18 sequence of SEQ ID NO:423 (accession NC_001357.1), or a conservative sub-fragment thereof, or a sequence which is fully complementary to said fragment or sub-fragment over the entire length of said fragment or sub-fragment, wherein said conservative fragment thereof have retained the property of being a suitable reference template sequence, to construct and produce group-targeted primers, which allow for a real-time multiplex detection of those HPV, which can be oncogenic for the mucosal epithelia.

The present application more particularly relates to any reference template polynucleotide, which consists of one of SEQ ID NO:25-29 and NO:334-338 (group A6-targeted reference template polynucleotides), or a sequence which is fully complementary thereto over the entire length of said SEQ ID NO sequence.

The present application more particularly relates to any reference template polynucleotide, which consists of one of SEQ ID NO: 1-5 and NO:320-333 (group A5-targeted reference template sequences), or a sequence which is fully complementary thereto over the entire length of said SEQ ID NO sequence.

The present application more particularly relates to any reference template polynucleotide, which consists of one of SEQ ID NO: SEQ ID NO:122-210 and 359-419 (group A9-targeted reference template sequences), or a sequence which is fully complementary thereto over the entire length of said SEQ ID NO sequence.

The present application more particularly relates to any reference template polynucleotide, which consists of one of SEQ ID NO: 46-67; 339-358 (group A7-targeted reference template sequences), or a sequence which is fully complementary thereto over the entire length of said SEQ ID NO sequence.

Conservative variants of the reference template polynucleotide of the invention are also encompassed by the present application. Conservative variants of a given parent reference template polynucleotide notably include any polynucleotide, which derives from said parent reference template polynucleotide, or the sequence which is fully complementary thereto, by deletion and/or substitution and/or addition of at least one nucleotide, but which has retained the capacity of being a reference template polynucleotide for designing and building an A5- and/or A6- and/or A7- and/or A9-targeted primer pair enabling the amplification of at least one HPV, which can be oncogenic for the mucosal epithelia. Illustrative conservative variants usually comprise those polynucleotides, which have a sequence identity of at least 80%, preferably of at least 85%, more preferably of at least 90%, most preferably of at least 95%, with said parent reference template polynucleotide or with the sequence which is fully complementary thereto (said identity score being computed over the entire length of said parent reference template polynucleotide, or fully complementary sequence). Illustrative conservative variants comprise those which do not differ from plus or minus 5 nucleotides in length from the parent sequence.

The present application also relates to the primers and probes of the present invention, as such, i.e., as individual oligonucleotide products.

Conservative variants of the primers of the invention are also encompassed by the present application. Conservative variants of a given parent primer notably include any oligonucleotide, which derives from said parent primer by deletion and/or substitution and/or addition of at least one nucleotide, but which has retained the capacity of being a forward or reverse A5- and/or A6- and/or A7- and/or A9-targeted primer for the amplification of at least one HPV, which can be oncogenic for the mucosal epithelia. Illustrative conservative variants usually comprise those oligonucleotides, which have a sequence identity of at least 80%, preferably of at least 81%, more preferably of at least 83%, most preferably of least 85%, with said parent primer (said identity score being computed over the entire length of said parent primer). Illustrative conservative variants comprise those which do not differ from plus or minus 5 nucleotides in length from the parent sequence.

Conservative variants of the probes of the invention are also encompassed by the present application. Conservative variants of a given parent probe notably include any oligonucleotide, which derives from said parent probe, or the sequence which is fully complementary thereto, by deletion and/or substitution and/or addition of at least one nucleotide, but which has retained the capacity of being an A5- and/or A6- and/or A7- and/or A9-targeted probe for the detection of at least one HPV, which can be oncogenic for the mucosal epithelia. Illustrative conservative variants usually comprise those oligonucleotides, which have a sequence identity of at least 90%, preferably of at least 91%, more preferably of at least 93%, most preferably of at least 95%, with said parent probe or with the sequence which is fully complementary thereto (said identity score being computed over the entire length of said parent probe). Illustrative conservative variants comprise those which do not differ from plus or minus 5 nucleotides in length from the parent sequence.

The present application more particularly relates to primers, which are suitable for HPV amplification, and which are especially adapted to the real-time multiplex amplification of HPV groups A6 and A5 and A9 and A7.

Said primer can e.g., be:

an A6-targeted primer, consisting of any one of SEQ ID NO: 30-34 and SEQ ID NO: 35-37; or an A5-targeted primer, consisting of any one of SEQ ID NO: 6-10 and SEQ ID NO: 11-15; or an A9-targeted primer, consisting of any one of SEQ ID NO: 211-239 and SEQ ID NO: 240-265; or an A7-targeted primer, consisting of any one of SEQ ID NO: 68-78 and SEQ ID NO: 79-87.

The present application more particularly relates to primer systems suitable for HPV amplification, which are especially adapted to the real-time multiplex amplification of HPV groups A6 and A5 and A9 and A7.

Said primer system may e.g., be:

at least one A6-targeted primer consisting of one of SEQ ID NO: 30-34, and at least one A6-targeted primer consisting of one of SEQ ID NO: 35-37; and/or at least one A5-targeted primer consisting of one of SEQ ID NO: 6-10, and at least one A5-targeted primer consisting of one of SEQ ID NO: 11-15; and/or at least one A9-targeted primer consisting of one of SEQ ID NO: 211-239, and at least one A9-targeted primer consisting of one of SEQ ID NO: 240-265; and/or at least one A7-targeted primer consisting of one of SEQ ID NO: 68-78, and at least one A7-targeted primer consisting of one of SEQ ID NO: 79-87.

The present application more particularly relates to probes, which are suitable for HPV detection, and which are especially adapted to the real-time multiplex amplification of HPV groups A6 and A5 and A9 and A7.

Said probe may e.g., be:

an A6-targeted probe, consisting of any one of SEQ ID NO:38-40, or a sequence which is fully complementary thereto over the entire length of said SEQ ID NO sequence; or an A5-targeted probe, consisting of any one of SEQ ID NO:16-19, or a sequence which is fully complementary thereto over the entire length of said SEQ ID NO sequence; or an A9-targeted probe, consisting of any one of SEQ ID NO: 266-282, or a sequence which is fully complementary thereto over the entire length of said SEQ ID NO sequence; or an A7-targeted probe, consisting of any one of SEQ ID NO:88-101, or a sequence which is fully complementary thereto over the entire length of said SEQ ID NO sequence.

Said probes can be produced in various format, e.g., including Taqman™ probes (hydrolysis probes), molecular Beacons™ (beacon probes or molecular beacon probes), and Scorpion™ probes. One of preferred formats is the beacon format.

Hence, the present application more particularly relates to beacon probes, which are suitable for HPV detection, and which are especially adapted to the real-time multiplex amplification of HPV groups A6 and A5 and A9 and A7.

Said beacon probe may e.g., be:

an A6-targeted probe, consisting of any one of SEQ ID NO:41-45, or a sequence which is fully complementary thereto over the entire length of said SEQ ID NO sequence; or an A5-targeted probe, consisting of any one of SEQ ID NO:20-24, or a sequence which is fully complementary thereto over the entire length of said SEQ ID NO sequence; or an A9-targeted probe, consisting of any one of SEQ ID NO: 283-319, or a sequence which is fully complementary thereto over the entire length of said SEQ ID NO sequence; or an A7-targeted probe, consisting of any one of SEQ ID NO:102-121, or a sequence which is fully complementary thereto over the entire length of said SEQ ID NO sequence.

Beacon probe may further comprise a quencher and a reporter (e.g., a fluorophore).

Preferably, each probe has its own reporter, whereby each probe has a reporter that is different from the ones displayed by the other probes, whereby each probe can be easily distinguished from the other probes.

The present application more particularly relates to primer and probe systems, which are suitable for HPV amplification, and which are especially adapted to the real-time multiplex amplification of HPV groups A6 and A5 and A9 and A7.

Said primer and probe system comprises at least one primer system according to the invention, and at least one probe according to the invention.

The present application further relates to any amplicon obtainable by amplification of at least one nucleic acid from an HPV of group A6, A5, A9 or A7, by means of at least one primer system according to claim 53, for example, HPV66 and/or HPV53 and/or HPV82 and/or HPV58 and/or HPV33 and/or HPV67 and/or HPV52 and/or HPV35 and/or HPV31 and/or HPV68 and/or HPV39 and/or HPV85 and/or HPV59 and/or HPV45.

An amplification composition comprising such an amplicon is also encompassed by the present invention.

The present invention also relates to an amplification composition, a pharmaceutical composition, a biological composition, comprising at least one primer or probe of the invention.

The present invention also relates to a kit for the diagnostic or prognostic of a cervical neoplasia or cancer, comprising:

at least one primer system according to the invention, and/or at least one probe according to the invention, optionally, instructions for the use thereof and/or nucleotides.

Preferably, said kit comprises at least two primer systems according to the invention, more preferably at least three primer systems according to the invention, most preferably at least four primer systems according to the invention.

Said kit comprises more than one probe, e.g. at least two, at least three, at least four, at least five different probes, notably when the kit is intended to discriminate between different HPV types.

In the kit according to the invention, the oligonucleotides (primers, probes) can be either kept separately, or partially mixed, or totally mixed.

Said oligonucleotides can be provided under dry form, or solubilized in a suitable solvent, as judged by the skilled person. Suitable solvents include TE, PCR-grade water, and the like.

In a preferred embodiment, the kit according to the invention can also contain further reagents suitable for a PCR step.

Such reagents are known to those skilled in the art, and include water, like nuclease-free water, RNase free water, DNAse-free water, PCR-grade water; salts, like magnesium, potassium; buffers such as Tris; enzymes, including polymerases, such as Taq, Vent, Pfu (all of them Trade-Marks), activable polymerase, and the like; nucleotides like deoxynucleotides, dideoxynucleotides, dNTPs, dATP, dTTP, dCTP, dGTP, dUTP; other reagents, like DTT and/or RNase inhibitors; and polynucleotides like polyT, polydT, and other oligonucleotides, e.g., primers.

In another preferred embodiment, the kit according to the invention comprises PCR controls. Such controls are known in the art, and include qualitative controls, positive controls, negative controls, internal controls, quantitative controls, internal quantitative controls, as well as calibration ranges. The internal control for said PCR step can be a template which is unrelated to the target template in the PCR step. Such controls also may comprise control primers and/or control probes. For example, in the case of HPV detection, it is possible to use as an internal control, a polynucleotide chosen within a gene whose presence is excluded in a sample originating from a human body (for example, from a plant gene), and whose size and GC content is equivalent to those from the target sequence.

In a preferred embodiment, the kit according to the invention contains means for extracting and/or purifying nucleic acid from a biological sample, e.g. from blood, serum, plasma. Such means are well known to those skilled in the art.

In a preferred embodiment, the kit according to the invention contains instructions for the use thereof. Said instructions can advantageously be a leaflet, a card, or the like. Said instructions can also be present under two forms: a detailed one, gathering exhaustive information about the kit and the use thereof, possibly also including literature data; and a quick-guide form or a memo, e.g., in the shape of a card, gathering the essential information needed for the use thereof.

In a preferred embodiment, said kit is a diagnostics kit, especially an in vitro diagnostics kit, i.e., an HPV diagnostics kit.

The present invention also relates to the field of diagnostics, prognosis and drug/treatment efficiency monitoring, as above-described.

The oligonucleotides according to the present invention can be used for the diagnostic of HPV group, types, subtypes or strains. In particular, the primers and probes according to the invention can be used for in vitro typing, sub-typing, and quantification of HPV nucleic acids present in an in vitro sample, for instance, in a patient's cervical sample, or in a cell culture supernatant.

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited. The term essentially consisting of is a partially open terms which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

In the present application, the term "at least x" relating to a set or group of n elements (wherein x is different from zero, and n is a number that is higher than x), explicitly encompasses each value, which is comprises between x and n. For example, the term "at least one" relating to a group or set of six elements explicitly encompasses one, two, three, four, five and six of said elements, as well as at least two, at least three, at least four, at least five of said elements.

Each of the relevant disclosures of all references cited herein is specifically incorporated by reference. The following examples are offered by way of illustration, and not by way of limitation.

DEFINITIONS

The terms and names used in the present application have their ordinary meaning in the field of HPV detection in general, and of molecular biology in particular.

By <<amplification>>, it is meant any technique of nucleic acid amplification, such as the PCR (Polymerase Chain Reaction), or the isothermal amplification techniques, e.g., TMA (transcription mediated amplification), NASBA (nucleic acid sequence based amplification), 3SR (self sustained sequence replication) or strand displacement amplification.

Amplification methods, especially PCR-based methods, are known in the art (*Molecular Cloning: A Laboratory Manual*, Maniatis, Fritsch, and Sambrook, CSHL Press; *Molecular Biology of the Cell*, Alberts et al.; *PCR Primer: A Laboratory Manual*, Dieffenbach and Dveksler, CSHL Press; *The Polymerase Chain Reaction*, Mullis, Ferré, and Gibbs, Birkhauser Boston Press; Gene quantification, Ferré, Birkhauser Boston Press).

By PCR or PCR reaction, we hereby understand any PCR-based method. This includes standard PCR, qualitative, quantitative and semi-quantitative PCR, real-time PCR, reverse-transcriptase PCR (RT-PCR), simplex and multiplex PCR, and the like.

By real-time PCR, we hereby understand any PCR-based method allowing for monitoring of a signal, such as fluorescence, emitted during the reaction as an indicator of amplicon production during each PCR cycle as opposed to the endpoint detection by conventional PCR methods.

By quantitative PCR, we hereby understand any PCR-based method allowing for the estimation of the initial amount of a given PCR target in a given sample.

By multiplex PCR, we hereby understand any PCR reaction aiming at the amplification of more than one target. For instance, multiplex PCR include duplex PCR (two targets), triplex PCR (three targets), and higher multiplex PCR. Multiplex PCR includes PCR reactions with more than one primer pair, for instance two primer pairs. In this case, there might be four different primers, but it is also possible for the two primer pairs to have one primer in common, e.g. the forward primer, and to have two distinct reverse primers. Multiplex PCR also includes PCR reactions with a unique primer pair, but with more than one probe.

The term "megaplex" is herein sometimes used: it basically has the same meaning as "multiplex", but is used to distinguish multi-multiplex, which involves at least two different group-targeted systems (e.g., an A5- and an A6- and an A7- and an A9-targeted systems), from the "multiplex", which involve one group-targeted system (e.g., an A7- or an A9-targeted system).

By nucleic acid, we hereby understand any nucleic acid: it can be synthetic or not, recombinant or naturally occurring, linear or circular. This includes DNA and RNA. The nucleic acid can be either single stranded or double stranded or even triple stranded. It can stem from various biological sources, such as micro organisms (bacteria, yeasts, and the like), or higher organisms, like mammal cells. Said nucleic acid can also be of viral nature, e.g., the HPV nucleic acids. The nucleic acid can also comprise total DNA, total RNA, genomic DNA, mitochondrial DNA, plasmidic DNA, BAC DNA, and mixtures thereof. Moreover, the nucleic acid can assume various states of purity.

By oligonucleotide, we hereby understand any short polymer of nucleotides, wherein nucleotides can be ribonucleotides, deoxyribonucleotides, dideoxyribonucleotides, degenerated nucleotides, and the like. Said oligonucleotides are preferably single-stranded. The length of said oligonucleotides can vary, and is usually under 150 nucleotides (nt), preferably in the range of 10-100 nt, more preferably 13-60 nt, even more preferably 13-50 nt. Said oligonucleotides can bear chemical modifications, such as tagging or marking, for instance radioactive, fluorescent, biotinylated, dig labelling. An oligonucleotide according to the invention can be either forward (sense) or reverse (antisense). In addition, it should be stressed, that although preferred functions may be mentioned in relation to some oligonucleotides according to the present invention, it is obvious that a given oligonucleotide may assume several functions, and may be used in different ways according to the present invention. For example, an oligonucleotide can be used either as a primer, or as a probe. Also, when an oligonucleotide is described as being useful as an amplicon-targeting probe, the skilled person understands that the complementary sequence of this oligonucleotide is equally useful as a probe to target the same amplicon. Moreover, it is also obvious, that any primer suitable for a multiplex assay, can also, within the meaning of the present invention, be used in a simplex protocol. The same applies to a primer suitable for a real-time protocol, which can also be used in the framework of an end-point assay within the meaning of the present invention.

Oligonucleotides according to the invention especially include PCR primers and probes. Unless otherwise stated, nucleic acid sequences are given in the 5' to 3' direction. Said oligonucleotides can be under many forms, e.g. under dry state, in solution/suspension with the desired solvent and the desired concentration. The skilled person would know, which solvents, concentrations, storage conditions are suitable for the oligonucleotides of the invention. In particular, the skilled person would know how to prepare said oligonucleotides as stock solutions. The oligonucleotides according to the invention can also assume various degrees of purity, as can be judged by those skilled in the art, e.g., by HPLC chromatography.

By set or systems of oligonucleotides, we hereby understand any combination comprising at least one oligonucleotide, preferably at least two, e.g. 2-10 oligonucleotides. Said set can thus comprise one PCR primer, or a pair of PCR primers, or a probe, or a probe and a pair of primers. Said oligonucleotides can be separately kept, or partially mixed, or entirely mixed.

The notion of primer or PCR primer is known to those skilled in the art. For example, it includes any oligonucleotide able to anneal to a target template under suitable stringency conditions, and allowing for polymerase strand elongation. The typical length of said primer is 13-30 nt, preferably 14, 15, 16, 17, 18, 19, 20, 21, 22, 23, 24, 25, 26 or 27 nt.

The terms "primer", "amplification primer" or "nucleic acid primer" are used interchangeably herein. A "primer" refers to a short polynucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a polymerase and at a suitable temperature and pH. The primer must be sufficiently long to prime the synthesis of the desired extension product. The exact length of the primer will depend upon experimental factors, and notably upon temperature, source of primer and use of the process.

A primer pair consists of a forward primer and a reverse primer, wherein the forward primer is sufficiently complementary to one HPV strand to hybridize thereto, and the reverse primer is sufficiently complementary to the other HPV strand to hybridize thereto.

Stringency refers to hybridization conditions chosen to optimize binding of polynucleotide sequences with different degrees of complementarity. Stringency is affected by factors such as temperature, salt conditions, the presence of organic solvents in the hybridization mixtures, and the lengths and base compositions of the sequences to be hybridized and the extent of base mismatching, and the combination of parameters is more important than the absolute measure of any one factor.

Very High Stringency: Very high stringency conditions refers to hybridization to filter-bound DNA in. 5×SSC, 2% sodium dodecyl sulfate (SDS), 100 microgrammes/ml single stranded DNA at 55-65° C. for 8 hours, and washing in 0.1×SSC and 0.1% SDS at 60-65° C. for thirty minutes.

High Stringency High stringency conditions refers to hybridization to filter-bound DNA in 5×SSC, 2% sodium dodecyl sulfate (SDS), 100 microgrammes/ml single stranded DNA at 55-65° C. for 8 hours, and washing in 0.2×SSC and 0.2% SDS at 60-65° C. for thirty minutes.

Moderate Stringency Moderate stringency conditions refers to hybridization to filter-bound DNA in 5×SSC, 2% sodium dodecyl sulfate (SDS), 100 microgrammes/ml single stranded DNA at 55-65° C. for 8 hours, and washing in 0.2×SSC and 0.2% SDS at 50-55° C. for thirty minutes.

The notion of probe is also known to those skilled in the art. For example, it includes any oligonucleotide able to anneal to a target template under the desired hybridization conditions. The typical length of said probe is 15-60 nt, preferably 16-50 nt, more preferably 17-40 nt, more preferably 17-35 nt, more preferably 20-30 nt. Preferably, said probe is fluorescently labelled. However, it is clear to those skilled in the art that under certain conditions, one may use a primer as a probe and vice-versa. Moreover, it is herein stressed that the products according to the present invention, especially, inter alia, oligonucleotides, are not limited to the intended use herein mentioned, but rather are to be broadly construed, irrespective of the indicated destination. For instance, a claim to a product (oligonucleotide) for a particular use should be construed as meaning a product (oligonucleotide) which is in fact suitable for the stated use. Thus, an oligonucleotide suitable for use as a primer in a multiplex protocol is also clearly adapted to a simplex protocol within the meaning of the present invention.

A probe may entirely consist of a hybridizing segment. By "hybridizing segment" or "annealing segment" of a probe, it is meant the nucleotide sequence, which is intended to anneal to the HPV target(s).

Alternatively, a probe may comprise at least one detection component, e.g. at least one detection label (such as a radioactive element, or a fluorophore). This detection label can be linked to the hybridizing segment of the probe via short HPV-unrelated oligonucleotide arms, which are known to the skilled person as beacon arm, or Scorpion™ arm. A probe, which comprises at least one 5' and/or 3' detection label, or at least one 5' and/or 3' beacon arm, consists of a hybridizing segment and of at least one 5' and/or 3' label or beacon arm.

Various formats (types) of probes, including Taqman™ probes (hydrolysis probes), molecular Beacons™ (beacon probes or molecular beacon probes), and Scorpion™ probes are known in the art.

In a preferred embodiment, the probes according to the invention can all be synthesized and used in the molecular beacon format.

The structure of molecular beacons is as follows. A short nucleotide sequence (so-called beacon arm) which is unrelated to the target sequence is thus covalently linked to both ends of the probe. A short unrelated arm is thus linked in 5' of the probe, and is labelled with a fluorescent moiety (i.e. fluorescent dye or fluorescent marker). Another but still unrelated arm is linked to the 3' end of probe and is labelled with a fluorescence quenching moiety. Thus, molecular beacons have a fluorophore and a quencher at opposite ends. The 5' short arm is totally complementary to the one in 3' so that they can anneal together, and thus can assume a hairpin structure when unhybridized to the target in solution. In this hairpin conformation, the quencher and the fluorescent dye are close enough to each other to allow efficient quenching of the fluorophore. However, when the probe encounters a target molecule, annealing is favoured with respect to the hairpin conformation when values of beacon arm Tm and probe Tm are suitably chosen (theoretically: probe Tm>beacon arm Tm>primer Tm, wherein Tm is the melting temperature of interest). The fluorophore and quencher move away from each other and the fluorophore can then fluoresce when illuminated by suitable light excitation. As PCR proceeds, amplification product accumulates, and the amount of fluorescence at any given cycle depends on the amount of amplification product present at that time. (See e.g., Sanjay Tyagi and Fred Russell Kramer, *Nature Biotechnology* 1996, volume 14, pages 303-308; *Nature Biotechnology* 1998, volume 16, pages 49-53).

(Remark: It is also possible to link the fluorophore at the 3' end, while attaching the quencher at the 5' end.)

Schematically, said probe can have the following formulae (molecular beacon format):

5'Fluorophore-(arm1)-probe-(arm2)-Quencher 3'

5' Quencher-(arm1)-probe-(arm2)-Fluorophore 3' wherein arm1 and arm2 can be any short nucleotide sequences, e.g. in the range of 3-10 nucleotides, preferably 5, 6, 7 nucleotides, allowing for the hair pin structure formation under suitable stringency conditions, i.e. arm1 and arm2 are totally complementary to anneal under the desired stringency conditions (standard PCR stringency conditions include, for example, an annealing temperature of 55 to 65° C. and an Mg concentration of 4 to 8 mM). However, arm1 and arm2 are unrelated to the target sequence of the probe, i.e. the hairpin conformation resulting from the annealing between arm1 and arm2 is essentially the only possible secondary structure for the probe when unhybridized. The skilled person would know how to choose such arms for a given probe.

Illustrative beacon formats include:

```
TGCGC-(probe sequence)-GCGCA

GCGCA-(probe sequence)-TGCGC

AGCGC-(probe sequence)-GCGCT

GCGCT-(probe sequence)-AGCGC

CGCGA-(probe sequence)-TCGCG

CGCGC-(probe sequence)-GCGCG.
```

By fluorophore, it is herein understood any fluorescent marker/dye known in the art. Examples of such suitable fluorescent markers include Fam, Hex, Tet, Joe, Rox, Tamra, Max, Edans, Cy dyes such as Cy5, Fluorescein, Coumarin, Eosine, Rhodamine, Bodipy, Alexa, Cascade Blue, Yakima Yellow, Lucifer Yellow and Texas Red (all of them are Trade-Marks), the family of ATTO dyes.

By quencher, we herein understand any quencher known in the art. Examples of such quenchers include Dabcyl, Dark Quencher, Eclipse Dark Quencher, ElleQuencher, Tamra, BHQ and QSY (all of them are Trade-Marks).

The skilled person would know which combinations of dye/quencher are suitable when designing a probe.

In a preferred embodiment according to the invention, spectral properties of said probes can be chosen as to not interfere with each other. In particular, when probes are used in multiplex, each single probe can have its own fluorophore being spectrally significantly different from each other, i.e. the absorption/emission spectra are essentially non-overlapping. This advantageously allows for low-noise multiplex detection for all single probes, making sure that individual signals do not interfere with each other in detection. Examples of dyes which can be used together in multiplex include Fam with Tamra, Fam with Tamra with Texas Red.

The choice of appropriate dyes to be used together may also be dependent of the filter contained in the amplification apparatus.

According to the invention, all the provided oligonucleotides can be either kept separately, or partially mixed, or totally mixed.

Said oligonucleotides can be provided under dry form, or solubilized in a suitable solvent, as judged by the skilled person. Suitable solvents include TE, PCR-grade water, and the like.

The term “significantly” is herein used in its usual meaning in the field of statistics (e.g., t test, z test, chi squared value, or F ratio, etc.), i.e., for comparing a value to another one, and determining whether these values differ from each other. The term “significantly” hence encompasses the fact that the skilled person may take into account the standard deviation (if any), which measures the amount of spread of data in a frequency distribution. The desired p value is usually set at an alpha level of 5%, or at the more stringent alpha level of 1%.

In the examples below, are described several A6-, A5-, A9 and A7-targeted amplification and/or detection systems of the invention.

Tables 12-35:

these tables give the SEQ ID NO: and positions of the reference amplicons, the forward primers, the reverse primers, the probes, the beacons probes of illustrative group-targeted systems of the invention.

Table 12: Reference amplicons of A5-targeted systems (from HPV51 genome)

Table 13: Forward primers of A5-targeted systems

Table 14: Reverse primers of A5-targeted systems

Table 15: Probes of A5-targeted systems

Table 16: Beacon probes of A5-targeted systems

Table 17: A5-targeted systems

Table 18: Reference amplicons of A6-targeted systems (from HPV56 genome)

Table 19: Forward primers of A6-targeted systems

Table 20: Reverse primers of A6-targeted systems

Table 21: Probes of A6-targeted systems

Table 22: Beacon probes of A6-targeted systems

Table 23: A6-targeted systems

Table 24: Reference amplicons of A7-targeted systems (from HPV18 genome)

Table 25: Forward primers of A7-targeted systems

Table 26: Reverse primers of A7-targeted systems

Table 27: Probes of A7-targeted systems

Table 28: Beacon probes of A7-targeted systems

Table 29: A7-targeted systems

Table 30: Reference amplicons of A9-targeted systems (from HPV16 genome)

Table 31: Forward primers of A9-targeted systems

Table 32: Reverse primers of A9-targeted systems

Table 33: Probes of A9-targeted systems

Table 34: Beacon probes of A9-targeted systems

Table 35: A9-targeted systems

Tables 36-50:

these tables show the number of nucleotide mismatches shown by primers and probes of the invention (alignment of the sequences of 50 HPV types); an empty box indicates there is no coherent sequence alignment; a gray box indicates that the number of mismatch(es) is of 0, 1, 2 or 3.

Table 36: mismatch numbers shown by primers and probes of A5-targeted systems of the invention (systems A to C)

Table 37: mismatch numbers shown by primers and probes of A5-targeted systems of the invention (systems D to E)

Table 38: mismatch numbers shown by primers and probes of A6-targeted systems of the invention (systems A to C)

Table 39: mismatch numbers shown by primers and probes of A6-targeted systems of the invention (systems D to E)

Table 40: mismatch numbers shown by primers and probes of A7-targeted systems of the invention (systems A to B)

Table 41: mismatch numbers shown by primers and probes of A7-targeted systems of the invention (systems C to D)

Table 42: mismatch numbers shown by primers and probes of A9-targeted systems of the invention (system C)

Table 43: mismatch numbers shown by primers and probes of A9-targeted systems of the invention (system E1)

Table 44: mismatch numbers shown by primers and probes of A9-targeted systems of the invention (system E2)

Table 45: mismatch numbers shown by primers and probes of A9-targeted systems of the invention (system E3)

Table 46: mismatch numbers shown by primers and probes of A9-targeted systems of the invention (system E4)

Table 47: mismatch numbers shown by primers and probes of A9-targeted systems of the invention (system F)

Table 48: mismatch numbers shown by primers and probes of A9-targeted systems of the invention (system GZ7)

Table 49: mismatch numbers shown by primers and probes of A9-targeted systems of the invention (system GZ8)

Table 50: mismatch numbers shown by primers and probes of A9-targeted systems of the invention (system H)

Tables 51-68: Specificity of the Detection Systems of the Invention

The amplification systems described in tables 36-50 have been used to test the specificity of the probes of the invention.

Table 51: illustrative list of HPV plasmids, which can be used to test the HPV specificity of the detection systems of the invention; the whole list of plasmids have been used for the specificity results, which are herein described Table 52: illustrative PCR material and method conditions, which can be used to test the specificity of the A5- and A6-targeted detection systems of the invention Table 53: specificity results of A5-targeted probes (box "other HPV"=all the other HPV of the list given in Table 51)

Table 54: specificity results of A6-targeted probes (box "other HPV"=all the other HPV of the list given in Table 51)

Table 55: illustrative PCR material and method conditions, which can be used to test the specificity of the A7-targeted detection systems of the invention Tables 56-59: specificity results of A7-targeted probes (box "other HPV"=all the other HPV of the list given in Table 51)

Table 56: A7-targeted amplification system A, and probes of A7-targeted amplification system A (one probe per PCR)

Table 57: A7-targeted amplification system B, and probes of A7-targeted amplification system B (one probe per PCR)

Table 58: A7-targeted amplification system C, and probes of A7-targeted amplification system C (one probe per PCR)

Table 59: A7-targeted amplification system D, and probes of A7-targeted amplification system D (one probe per PCR)

Table 60: illustrative PCR material and method conditions, which can be used to test the specificity of the A9-targeted detection systems of the invention Tables 61-68: specificity results of A9-targeted probes (box "other HPV"=all the other HPV of the list given in Table 51)

Table 61: A9-targeted amplification system C, and probes of A9-targeted amplification system C (one probe per PCR)

Table 62: A9-targeted amplification system E2, and probes of A9-targeted amplification system E2 (one probe per PCR)

Table 63: A9-targeted amplification system E3, and probes of A9-targeted amplification system E3 (one probe per PCR)

Table 64: A9-targeted amplification system E4, and probes of A9-targeted amplification system E4 (one probe per PCR)

Table 65: A9-targeted amplification system F, and probes of A9-targeted amplification system F (one probe per PCR)

Table 66: A9-targeted amplification system GZ7, and probes of A9-targeted amplification system GZ7 (one probe per PCR)

Table 67: A9-targeted amplification system GZ8, and probes of A9-targeted amplification system GZ8 (one probe per PCR)

Table 68: A9-targeted amplification system H, and probes of A9-targeted amplification system H (one probe per PCR)

The amplification and detection systems, which were used for the specificity tests, are those shown in Table 17 (A5-targeted systems); Table 23 (A6-targeted systems); Table 29 (A7-targeted systems); Table 35 (A9-targeted systems).

For the A9-targeted systems, those primers, which are shown between brackets in Table 35 were not used, as they would have been redundant: indeed, those primers, which are not between brackets, are sufficient to amplify all group A9 HPV. Hence, in table 35, those A9-targeted primers which are shown between brackets are optional and/or equivalent and/or alternative primers, if it is wished to amplify all group A9 HPV.

Tables 69-82: System Sensitivity

The sensitivity of systems of the invention has been tested under the same experimental conditions, as for the specificity tests (see Tables 52, 55, 60).

Table 69: sensitivity of A5-targeted systems (systems A, B, C, D and E)

Table 70: sensitivity of A6-targeted systems (systems A, B, C, D and E)

Tables 71-74: Sensitivity of A7-Targeted Systems

Table 71: sensitivity of A7-targeted system A

Table 72: sensitivity of A7-targeted system B

Table 73: sensitivity of A7-targeted system C

Table 74: sensitivity of A7-targeted system D

Tables 75-82: Sensitivity of A9-Targeted Systems

Table 75: sensitivity of A9-targeted system C

Table 76: sensitivity of A9-targeted system E2

Table 77: sensitivity of A9-targeted system E3

Table 78: sensitivity of A9-targeted system E4

Table 79: sensitivity of A9-targeted system F

Table 80: sensitivity of A9-targeted system GZ7

Table 81: sensitivity of A9-targeted system GZ8

Table 82: sensitivity of A9-targeted system H

Tables 83-88: "Megaplex" Specificity and Sensitivity

PCR runs have been conducted with one A5-targeted system, one A6-targeted system, one A7-targeted system, one A9-targeted system, in a single-tube amplification.

As the A7- and A9-targeted systems already are multiplex systems (i.e., they each have more than two primers), the mix of the four group-targeted systems is herein referred to as a "megaplex".

The megaplex PCR have been tested with the plasmids listed in Table 51, in specificity (Ct; RFU) and in sensitivity (Ct; RFU).

Tables 83-86: Specificity Results for Megaplex EAAH and EBAC

Tables 83-84: Specificity of the Megaplex EAAH

Table 83: illustrative megaplex material and method conditions, which can be used for a mix of A5-targeted system E, A6-targeted system A, A7-targeted system A and A9-targeted system H (i.e., megaplex EAAH); these experimental conditions have been used for the results depicted in table 84

Table 84: specificity results of the EAAH megaplex

Tables 85-86: Specificity of the Megaplex EBAC

Table 85: illustrative megaplex material and method conditions, which can be used for a mix of A5-targeted system E, A6-targeted system B, A7-targeted system A and A9-targeted system C (i.e., megaplex EBAC); these experimental conditions have been used for the results depicted in table 86;

Table 86: specificity results of the EBAC megaplex

Tables 87-88: Sensitivity Results of the Megaplex EAAH and EBAC

Table 87: sensitivity results of the megaplex EAAH

Table 88: sensitivity results of the megaplex EBAC

Table 89: list of HPV genome sequences.

These tables are followed by a listing of sequences of reference templates.

A5 Group=HPV51; HPV26; HPV69; HPV82

A5 HR HPV=HPV51

A5 Reference Genome=HPV51 (NC_001533.1; Human HPV, Complete Genome)

TABLE 12

A5 REFERENCE AMPLICON SEQUENCES (from reference genome) =

| Systems | Size (bp) | Start and stop positions within reference genome | SEQ ID NO: |
|---|---|---|---|
| System A | 106 | 772-877 | 1 |
| System AB | 109 | 772-880 | 320 |
| System AD | 131 | 772-902 | 321 |
| System B | 145 | 736-880 | 2 |
| System BA | 142 | 736-877 | 322 |
| System BD | 167 | 736-902 | 323 |
| System C | 117 | 678-794 | 3 |
| System CA | 200 | 678-877 | 324 |
| System CB | 203 | 678-880 | 325 |
| System CD | 225 | 678-902 | 326 |
| System CE | 151 | 678-828 | 327 |
| System D | 192 | 711-902 | 4 |
| System DA | 167 | 711-877 | 328 |
| System DB | 170 | 711-880 | 329 |
| System DE | 118 | 711-828 | 330 |
| System E | 125 | 704-828 | 5 |
| System EA | 174 | 704-877 | 331 |

TABLE 12-continued

A5 REFERENCE AMPLICON SEQUENCES (from reference genome) =

| Systems | Size (bp) | Start and stop positions within reference genome | SEQ ID NO: |
|---|---|---|---|
| System EB | 177 | 704-880 | 332 |
| System ED | 199 | 704-902 | 333 |

TABLE 13

A5 FORWARD PRIMERS

| Name | Sequence | Address | Size (bp) | SEQ ID NO: |
|---|---|---|---|---|
| A5E6f1 | GGCAGTGGAAAGCAGTGGAGAC | 772 | 22 | 6 |
| A5E6f2 | AGCTCCGTGTTGCAGGTGTTC | 736 | 21 | 7 |
| A5E6f3 | ATATGCGTGACCAGCTACCAG | 678 | 21 | 8 |
| A5E6f4 | GACAGGCTACGTGTTACAGAA | 711 | 21 | 9 |
| A5E6f5 | CGGGCTGGACAGGCTACG | 704 | 18 | 10 |

TABLE 14

A5 REVERSE PRIMERS

| Name | Sequence | Address | Size bp | SEQ ID NO: |
|---|---|---|---|---|
| A5E6r1 | CCATCGCCGTTGCTAGTTGTTC | 877 | 22 | 11 |
| A5E6r2 | AGTCCATCGCCGTTGCTAGTTG | 880 | 22 | 12 |
| A5E6r3 | TGTCTCCACTGCTTTCCACTG | 794 | 21 | 13 |
| A5E6r4 | CCCTCATCCTCTGTACCTTC | 902 | 20 | 14 |
| A5E6r5 | TCGCCCATTAACATCTGCTGT | 828 | 21 | 15 |

TABLE 15

A5 PROBES

| Corresponding beacon probes | Sequence | Address | Size (bp) | SEQ ID NO: |
|---|---|---|---|---|
| A5E6s1, A5E6s1b | GCTTAGTTCGCCCATTAACATCTGCTG | 835 | 27 | 16 |
| A5E6s2 | CGAAGGGTGTCTCCACTGCTTTCCA | 801 | 25 | 17 |
| A5E6s3 | ACACGGAGCTTCAATTCTGTAACACG | 745 | 26 | 18 |
| A5E6s4 | TAGTACAACTGGCAGTGGAAAGCAGT | 762 | 26 | 19 |

TABLE 16

A5 BEACON PROBES

| Name | Sequence (underlined are shown the beacon arms) | Address | SEQ ID NO: |
|---|---|---|---|
| A5E6s1 | CCCCCTCGCTTAGTTCGCCCATTAACATCTGCTGGAGGGGG | 835 | 20 |
| A5E6s1b | CGCTGCGCTTAGTTCGCCCATTAACATCTGCTGGCAGCG | 835 | 21 |
| A5E6s2 | CGCGATCCGAAGGGTGTCTCCACTGCTTTCCAGATCGCG | 801 | 22 |
| A5E6s3 | CGCGATCACACGGAGCTTCAATTCTGTAACACGGATCGCG | 745 | 23 |

TABLE 16-continued

| A5 BEACON PROBES | | | |
|---|---|---|---|
| Name | Sequence (underlined are shown the beacon arms) | Address | SEQ ID NO: |
| A5E6s4 | CGCGATCTAGTACAACTGGCAGTGGAAAGCAGTGATCGCG | 762 | 24 |
| A5E6s4 | CGCGATCTAGTACAACTGGCAGTGGAAAGCAGTGATCGCG | 762 | 24 |

TABLE 17

A5 systems; minimal set = one forward primer, one reverse primer, and one probe

| A5 | HPV51 reference amplicon SEQ ID NO: | Forward primer Name | Forward primer SEQ ID NO: | Reverse primer Name | Reverse primer SEQ ID NO: | Probe SEQ ID NO: | Beacon ® Probe Name | Beacon ® Probe SEQ ID NO: |
|---|---|---|---|---|---|---|---|---|
| System A | 1 | A5E6f1 | 6 | A5E6r1 | 11 | 16 | A5E6s1 | 20 |
| | | | | | | 16 | A5E6s1b | 21 |
| System AB | 320 | A5E6f1 | 6 | A5E6r2 | 12 | 16 | A5E6s1 | 20 |
| | | | | | | 16 | A5E6s1b | 21 |
| System AD | 321 | A5E6f1 | 6 | A5E6r4 | 14 | 16 | A5E6s1 | 20 |
| | | | | | | 16 | A5E6s1b | 21 |
| System B | 2 | A5E6f2 | 7 | A5E6r2 | 12 | 17 | A5E6s2 | 22 |
| | | | | | | 16 | A5E6s1 | 20 |
| | | | | | | 16 | A5E6s1b | 21 |
| System BA | 322 | A5E6f2 | 7 | A5E6r1 | 11 | 16 | A5E6s1 | 20 |
| | | | | | | 16 | A5E6s1b | 21 |
| | | | | | | 17 | A5E6s2 | 22 |
| System BD | 323 | A5E6f2 | 7 | A5E6r4 | 14 | 16 | A5E6s1 | 20 |
| | | | | | | 16 | A5E6s1b | 21 |
| | | | | | | 17 | A5E6s2 | 22 |
| System C | 3 | A5E6f3 | 8 | A5E6r3 | 13 | 18 | A5E6s3 | 23 |
| System CA | 324 | A5E6f3 | 8 | A5E6r1 | 11 | 16 | A5E6s1 | 20 |
| | | | | | | 16 | A5E6s1b | 21 |
| | | | | | | 17 | A5E6s2 | 22 |
| | | | | | | 18 | A5E6s3 | 23 |
| | | | | | | 19 | A5E6s4 | 24 |
| System CB | 325 | A5E6f3 | 8 | A5E6r2 | 12 | 16 | A5E6s1 | 20 |
| | | | | | | 16 | A5E6s1b | 21 |
| | | | | | | 17 | A5E6s2 | 22 |
| | | | | | | 18 | A5E6s3 | 23 |
| | | | | | | 19 | A5E6s4 | 24 |
| System CD | 326 | A5E6f3 | 8 | A5E6r4 | 14 | 16 | A5E6s1 | 20 |
| | | | | | | 16 | A5E6s1b | 21 |
| | | | | | | 17 | A5E6s2 | 22 |
| | | | | | | 18 | A5E6s3 | 23 |
| | | | | | | 19 | A5E6s4 | 24 |
| System CE | 327 | A5E6f3 | 8 | A5E6r5 | 15 | 18 | A5E6s3 | 23 |
| | | | | | | 19 | A5E6s4 | 24 |
| System D | 4 | A5E6f4 | 9 | A5E6r4 | 14 | 19 | A5E6s4 | 24 |
| | | | | | | 16 | A5E6s1 | 20 |
| | | | | | | 16 | A5E6s1b | 21 |
| | | | | | | 17 | A5E6s2 | 22 |
| System DA | 328 | A5E6f4 | 9 | A5E6r1 | 11 | 16 | A5E6s1 | 20 |
| | | | | | | 16 | A5E6s1b | 21 |
| | | | | | | 17 | A5E6s2 | 22 |
| | | | | | | 19 | A5E6s4 | 24 |
| System DB | 329 | A5E6f4 | 9 | A5E6r2 | 12 | 16 | A5E6s1 | 20 |
| | | | | | | 16 | A5E6s1b | 21 |
| | | | | | | 17 | A5E6s2 | 22 |
| | | | | | | 19 | A5E6s4 | 24 |
| System DE | 330 | A5E6f4 | 9 | A5E6r5 | 15 | 19 | A5E6s4 | 24 |
| System D | 4 | A5E6f4 | 9 | A5E6r4 | 14 | 19 | A5E6s4 | 24 |
| | | | | | | 16 | A5E6s1 | 20 |
| | | | | | | 16 | A5E6s1b | 21 |
| | | | | | | 17 | A5E6s2 | 22 |
| System DA | 328 | A5E6f4 | 9 | A5E6r1 | 11 | 16 | A5E6s1 | 20 |
| | | | | | | 16 | A5E6s1b | 21 |
| | | | | | | 17 | A5E6s2 | 22 |
| | | | | | | 19 | A5E6s4 | 24 |

TABLE 17-continued

| A5 systems; minimal set = one forward primer, one reverse primer, and one probe | | | | | | | | |
|---|---|---|---|---|---|---|---|---|
| | HPV51 reference amplicon | Forward primer | | Reverse primer | | Probe | Beacon ® Probe | |
| A5 | SEQ ID NO: | Name | SEQ ID NO: | Name | SEQ ID NO: | SEQ ID NO: | Name | SEQ ID NO: |
| System DB | 329 | A5E6f4 | 9 | A5E6r2 | 12 | 16 | A5E6s1 | 20 |
| | | | | | | 16 | A5E6s1b | 21 |
| | | | | | | 17 | A5E6s2 | 22 |
| | | | | | | 19 | A5E6s4 | 24 |
| System DE | 330 | A5E6f4 | 9 | A5E6r5 | 15 | 19 | A5E6s4 | 24 |

A6 Group=HPV30; HPV53; HPV56; HPV66
A6 HR HPV=HPV56
A6 Reference Genome=HPV56 (NC__001594.1; Human HPV56, Complete Genome)

TABLE 18

| A6 REFERENCE AMPLICON SEQUENCES (from reference genome) = | | | |
|---|---|---|---|
| Systems | Size (bp) | Start and stop positions within reference genome | SEQ ID NO: |
| System A | 100 | 504-603 | 25 |
| System AE | 288 | 504-791 | 334 |
| System B | 115 | 489-603 | 26 |
| System BE | 303 | 489-791 | 335 |
| System C | 138 | 413-550 | 27 |
| System CA | 191 | 413-603 | 336 |
| System CE | 379 | 413-791 | 337 |
| System D | 102 | 502-603 | 28 |
| System DE | 290 | 502-791 | 338 |
| System E | 127 | 665-791 | 29 |

TABLE 19

| A6 FORWARD PRIMERS | | | | |
|---|---|---|---|---|
| Name | Sequence | Address | Size (bp) | SEQ ID NO: |
| A6E6f1 | TGGACCGGGTCATGTTTGGG | 504 | 20 | 30 |
| A6E6f2 | CTAATAGCACATGGTTGGACCG | 489 | 22 | 31 |

TABLE 19-continued

| A6 FORWARD PRIMERS | | | | |
|---|---|---|---|---|
| Name | Sequence | Address | Size (bp) | SEQ ID NO: |
| A6E6f3 | AAGGTGCTACAGATGTCAAAG | 413 | 21 | 32 |
| A6E6f4 | GTTGGACCGGGTCATGTTTGG | 502 | 21 | 33 |
| A6E6f5 | TCAGAGGATGAGGATGAGGATG | 665 | 22 | 34 |

TABLE 20

| A6 REVERSE PRIMERS | | | | |
|---|---|---|---|---|
| Name | Sequence | Address | Size bp | SEQ ID NO: |
| A6E6r1 | ACGTCTTGCAGCGTTGGTAC | 603 | 20 | 35 |
| A6E6r1 | ACGTCTTGCAGCGTTGGTAC | 603 | 20 | 35 |
| A6E6r2 | GGTTCTCTAGATGTTTGTCTCC | 550 | 22 | 36 |
| A6E6r1 | ACGTCTTGCAGCGTTGGTAC | 603 | 20 | 35 |
| A6E6r3 | ACTGCACCACAAACTTACACTC | 791 | 22 | 37 |

TABLE 21

| A6 PROBES | | | | |
|---|---|---|---|---|
| Corresponding beacon probes | Sequence | Address | Size (bp) | SEQ ID NO: |
| A6E6s1 | ACATCTAGAGAACCTAGAGAATCTACAGTA | 537 | 30 | 38 |
| A6E6s2, A6E6s2b | GGTCCAACCATGTGCTATTAGATGAA | 509 | 26 | 39 |
| A6E6s3, A6E6s3b | CGGCCACAGCAAGCTAGACA | 707 | 20 | 40 |

TABLE 22

| A6 BEACON PROBES | | | |
|---|---|---|---|
| Name | Sequence (underlined are shown the beacon arms) | Address | SEQ ID NO: |
| A6E6s1 | CGCGATCACATCTAGAGAACCTAGAGAATCTACAGTAGATCGCG | 537 | 41 |
| A6E6s1 | CGCGATCACATCTAGAGAACCTAGAGAATCTACAGTAGATCGCG | 537 | 41 |
| A6E6s2 | CGCGATCGGTCCAACCATGTGCTATTAGATGAAGATCGCG | 509 | 42 |

TABLE 22-continued

| A6 BEACON PROBES | | | |
|---|---|---|---|
| Name | Sequence (underlined are shown the beacon arms) | Address | SEQ ID NO: |
| A6E6s2b | CGCCTCGGTCCAACCATGTGCTATTAGATGAAGAGGCG | 509 | 43 |
| A6E6s1 | CGCGATCACATCTAGAGAACCTAGAGAATCTACAGTAGATCGCG | 537 | 41 |
| A6E6s3 | CGCGACGGCCACAGCAAGCTAGACATCGCG | 707 | 44 |
| A6E6s3b | CGCCTCCGGCCACAGCAAGCTAGACAGAGGCG | 707 | 45 |

TABLE 23

A6 SYSTEMS; minimal set = one forward primer, one reverse primer, and one probe

| A6 | HPV56 reference amplicon SEQ ID NO: | Forward primer Name | Forward primer SEQ ID NO: | Reverse Primer Name | Reverse Primer SEQ ID NO: | Probe SEQ ID NO: | Beacon ® Probe Name | Beacon ® Probe SEQ ID NO: |
|---|---|---|---|---|---|---|---|---|
| System A | 25 | A6E6f1 | 30 | A6E6r1 | 35 | 38 | A6E6s1 | 41 |
| System AE | 334 | A6E6f1 | 30 | A6E6r3 | 37 | 38 | A6E6s1 | 41 |
| | | | | | | 40 | A6E6s3 | 44 |
| | | | | | | 40 | A6E6s3b | 45 |
| System B | 26 | A6E6f2 | 31 | A6E6r1 | 35 | 38 | A6E6s1 | 41 |
| System BE | 335 | A6E6f2 | 31 | A6E6r3 | 37 | 38 | A6E6s1 | 41 |
| | | | | | | 40 | A6E6s3 | 44 |
| | | | | | | 40 | A6E6s3b | 45 |
| System C | 27 | A6E6f3 | 32 | A6E6r2 | 36 | 39 | A6E6s2 | 42 |
| | | | | | | 39 | A6E6s2b | 43 |
| System CA | 336 | A6E6f3 | 32 | A6E6r1 | 35 | 38 | A6E6s1 | 41 |
| | | | | | | 39 | A6E6s2 | 42 |
| | | | | | | 39 | A6E6s2b | 43 |
| System CE | 337 | A6E6f3 | 32 | A6E6r3 | 37 | 38 | A6E6s1 | 41 |
| | | | | | | 39 | A6E6s2 | 42 |
| | | | | | | 39 | A6E6s2b | 43 |
| | | | | | | 40 | A6E6s3 | 44 |
| | | | | | | 40 | A6E6s3b | 45 |
| System D | 28 | A6E6f4 | 33 | A6E6r1 | 35 | 38 | A6E6s1 | 41 |
| System DE | 338 | A6E6f4 | 33 | A6E6r3 | 37 | 38 | A6E6s1 | 41 |
| | | | | | | 40 | A6E6s3 | 44 |
| | | | | | | 40 | A6E6s3b | 45 |
| System E | 29 | A6E6f5 | 34 | A6E6r3 | 37 | 40 | A6E6s3 | 44 |
| | | | | | | 40 | A6E6s3b | 45 |

A7 Group=HPV18; HPV39; HPV45; HPV59; HPV68; HPV70; HPV85

A7 HR HPV=HPV18; HPV39; HPV45; HPV59; HPV68

A7 Reference Genome=HPV18 (NC_001357.1; Human HPV, Complete Genome)

TABLE 24

A7 REFERENCE AMPLICON SEQUENCES (from reference genome) =

| Systems | Size (bp) | Start and stop positions within reference genome | SEQ ID NO: |
|---|---|---|---|
| Systems A, A1, A2 | 198 à 209 | 1895-2099 | 46 |
| | | 1895-2102 | 47 |
| | | 1895-2103 | 48 |
| | | 1902-2099 | 49 |
| | | 1902-2102 | 50 |
| | | 1902-2103 | 51 |
| System AB | 161 à 171 | 1895-2062 | 52 |
| | | 1895-2065 | 53 |
| | | 1902-2062 | 339 |
| | | 1902-2065 | 340 |

TABLE 24-continued

A7 REFERENCE AMPLICON SEQUENCES (from reference genome) =

| Systems | Size (bp) | Start and stop positions within reference genome | SEQ ID NO: |
|---|---|---|---|
| Systems AC1, AC2, AC3 | 199 à 209 | 1895-2100 | 341 |
| | | 1895-2103 | 48 |
| | | 1902-2100 | 342 |
| | | 1902-2103 | 51 |
| System B | 166 à 171 | 1895-2062 | 52 |
| | | 1895-2065 | 53 |
| | | 1896-2062 | 54 |
| | | 1896-2065 | 55 |
| | | 1897-2062 | 56 |
| | | 1897-2065 | 57 |
| Systems BA1, BA2, BA3 | 203 à 209 | 1895-2099 | 46 |
| | | 1895-2102 | 47 |
| | | 1895-2103 | 48 |
| | | 1896-2099 | 343 |
| | | 1896-2102 | 344 |
| | | 1896-2103 | 345 |
| | | 1897-2099 | 346 |
| | | 1897-2102 | 347 |
| | | 1897-2103 | 348 |

TABLE 24-continued

| A7 REFERENCE AMPLICON SEQUENCES (from reference genome) = | | | |
|---|---|---|---|
| Systems | Size (bp) | Start and stop positions within reference genome | SEQ ID NO: |
| Systems BC1, BC2, BC3 | 204 à 209 | 1895-2100 | 349 |
| | | 1895-2103 | 48 |
| | | 1896-2100 | 350 |
| | | 1896-2103 | 345 |
| | | 1897-2100 | 351 |
| | | 1897-2103 | 352 |
| Systems C, C1 | 113 à 125 | 1987-2100 | 58 |
| | | 1987-2103 | 59 |
| | | 1988-2100 | 60 |
| | | 1988-2103 | 61 |
| | | 1979-2100 | 62 |
| | | 1979-2103 | 63 |

TABLE 24-continued

| A7 REFERENCE AMPLICON SEQUENCES (from reference genome) = | | | |
|---|---|---|---|
| Systems | Size (bp) | Start and stop positions within reference genome | SEQ ID NO: |
| Systems CA1, CA2 | 112 à 125 | 1979-2099 | 353 |
| | | 1979-2102 | 354 |
| | | 1979-2103 | 63 |
| | | 1987-2099 | 355 |
| | | 1987-2102 | 356 |
| | | 1987-2103 | 59 |
| | | 1988-2099 | 357 |
| | | 1988-2102 | 358 |
| | | 1988-2103 | 61 |
| System D | 113 à 129 | 916-1032 | 64 |
| | | 916-1044 | 65 |
| | | 920-1032 | 66 |
| | | 920-1044 | 67 |

TABLE 25

| A7 FORWARD PRIMERS | | | | |
|---|---|---|---|---|
| Name | Sequence | Address | Size (bp) | SEQ ID NO: |
| A7E16f1a | TGGTATAGAACAGGAATATCAAAT | 1895 | 24 | 68 |
| A7E16f2a | GAACAGGTATATCCAATATTAGTG | 1902 | 24 | 69 |
| A7E16f3a | GAACAGGAATGTCCAATATTAG | 1902 | 22 | 70 |
| A7E115f1a | TGGTATAGAACAGGAATATCAAATAT | 1895 | 26 | 71 |
| A7E115f2a | GTACAGAACAGGAATGTCCAA | 1897 | 21 | 72 |
| A7E115f3d | GGTATCGCACAGGTATATCC | 1896 | 20 | 73 |
| A7E17f1 | TGATAGCAATTTTGATTTGTCAG | 1987 | 23 | 74 |
| A7E17f2 | GATAGCGTATTTGACCTATCAG | 1988 | 22 | 75 |
| A7E17f3 | GGAATAGATGATAGTGTATTTGATC | 1979 | 25 | 76 |
| A7E12f1 | GGCCGATCCAGAAGGTACAGAC | 916 | 22 | 77 |
| A7E12f2 | CAATCGTGAAGGTACAGATGG | 920 | 21 | 78 |

TABLE 26

| A7 REVERSE PRIMERS | | | | |
|---|---|---|---|---|
| Name | Sequence | Address | Size bp | SEQ ID NO: |
| A7E16r1b | CATTGCTGTTGCAGTCTG | 2099 | 18 | 79 |
| A7E16r2b | GCAGCATTACTGTTACAATC | 2103 | 20 | 80 |
| A7E16r3b | CGGCGTTACTATTACTATCTG | 2102 | 21 | 81 |
| A7E115r1a | TGCCATATCGCTTTCATCTG | 2062 | 20 | 82 |
| A7E115r2b | AAATGCTATATCACTTTCATCTG | 2065 | 23 | 83 |
| A7E17r1 | GCATTACTGTTGCTGTCTG | 2100 | 19 | 84 |
| A7E17r2 | GCGGCATTACTATTACAATCTG | 2103 | 22 | 85 |
| A7E12r2 | GCATTTTCATCCTCATCCTCTG | 1032 | 22 | 86 |
| A7E12r3 | CCTGTGTCTGTTGCATTTTC | 1044 | 20 | 87 |

TABLE 27

| A7 PROBES | | | | |
|---|---|---|---|---|
| Sequence | Address | Size (bp) | SEQ ID NO: | Corresponding beacon probes |
| CAGATGAAAGCGATATGGCATT | 2043 | 22 | 88 | A7E1ZAS61f |
| CAGATGAAAGTGATATTGCATAT | 2043 | 23 | 89 | A7E1ZAS63f |
| CTGATGAAAGTGACATAGCATTT | 2043 | 23 | 90 | A7E1ZAS64f |
| CAGATGAAAGTGATATGGCATTT | 2043 | 23 | 91 | A7E1ZCS40f |
| TGGAATAGATGATAGTGTATTTGAT | 1978 | 25 | 92 | A7E1ZBS74f |
| GATAGCAATTTTGATTTGTCAGA | 1988 | 23 | 93 | A7E1ZBS26f |
| TGGAATAGATGATAGTGTATTTGAT | 1978 | 25 | 92 | A7E1ZBS74f |
| AGTTGATGATAGCGTGTTTGAC | 1981 | 22 | 94 | A7E1ZBS79f |
| AGTTGATGATAGCGTGTTTGAC | 1981 | 22 | 94 | A7E1ZBS80f |
| CGATAGTAATTTTGATTTGTCAGA | 1987 | 24 | 95 | A7E1ZBS27f |
| CAGATGAAAGTGATATGGCATTT | 2043 | 23 | 91 | A7E1ZCS11f |
| CAGATGAAAGTGATATGGCATTT | 2043 | 23 | 91 | A7E1ZCS40f |
| CTGATGAAAGTGACATAGCATTT | 2043 | 23 | 90 | A7E1ZCS45f |
| CAGATGAAAGTGATATTGCATAT | 2043 | 23 | 89 | A7E1ZCS63f |
| AATGAGTTAACAGATGAAAGTGA | 2032 | 23 | 96 | A7E1ZCS90f |
| GTAATGGCTGGTTCTTTGTAGAAACAA | 954 | 27 | 97 | A7E1ZDS36f |
| GTAACGGCTGGTTTTATGTACAAGCTA | 954 | 27 | 98 | A7E1ZDS37f |
| GTAATGGATGGTTTTTTGTACAGGCAAT | 954 | 28 | 99 | A7E1ZDS38f |
| GTAACGGATGGTTTTTTGTACAAGCAAT | 954 | 28 | 100 | A7E1ZDS2f |
| GGTGTAATGGCTGGTTCTTTGTAGA | 951 | 25 | 101 | A7E1ZDS3f |
| GGTGTAATGGCTGGTTCTTTGTAGA | 951 | 25 | 101 | A7E1ZDS4f |
| GGTGTAATGGCTGGTTCTTTGTAGA | 951 | 25 | 101 | A7E1ZDS11f |

TABLE 28

| A7 BEACON PROBES | | | |
|---|---|---|---|
| Name | Sequence (underlined are shown the beacon arms) | Address | SEQ ID NO: |
| A7E1ZAS61f | CGACGTCAGATGAAAGCGATATGGCATTACGTCG | 2043 | 102 |
| A7E1ZAS63f | CGACGTCAGATGAAAGTGATATTGCATATACGTCG | 2043 | 103 |
| A7E1ZAS64f | CGACGTCTGATGAAAGTGACATAGCATTTACGTCG | 2043 | 104 |
| A7E1ZCS40f | CCGAGTCAGATGAAAGTGATATGGCATTTACTCGG | 2043 | 105 |
| A7E1ZBS74f | ACGTCGTGGAATAGATGATAGTGTATTTGATCGACGT | 1978 | 106 |
| A7E1ZBS26f | CGCAGTGATAGCAATTTTGATTTGTCAGAACTGCG | 1988 | 107 |
| A7E1ZBS74f | ACGTCGTGGAATAGATGATAGTGTATTTGATCGACGT | 1978 | 106 |
| A7E1ZBS79f | ACGTCGAGTTGATGATAGCGTGTTTGACCGACGT | 1981 | 108 |
| A7E1ZBS80f | CCGGCTAGTTGATGATAGCGTGTTTGACAGCCGG | 1981 | 109 |
| A7E1ZBS27f | CGCAGTCGATAGTAATTTTGATTTGTCAGAACTGCG | 1987 | 110 |
| A7E1ZCS11f | CGCAGTCAGATGAAAGTGATATGGCATTTACTGCG | 2043 | 111 |

TABLE 28-continued

| A7 BEACON PROBES | | | |
|---|---|---|---|
| Name | Sequence (underlined are shown the beacon arms) | Address | SEQ ID NO: |
| A7E1ZCS40f | CCGAGTCAGATGAAAGTGATATGGCATTTACTCGG | 2043 | 105 |
| A7E1ZCS45f | CGTCGTCTGATGAAAGTGACATAGCATTTACGACG | 2043 | 112 |
| A7E1ZCS63f | CGAGGTCAGATGAAAGTGATATTGCATATACCTCG | 2043 | 113 |
| A7E1ZCS90f | CCACGTAATGAGTTAACAGATGAAAGTGAACGTGG | 2032 | 114 |
| A7E1ZDS36f | CGCGACGTAATGGCTGGTTCTTTGTAGAAACAAGTCGCG | 954 | 115 |
| A7E1ZDS37f | CGCGATCGTAACGGCTGGTTTTATGTACAAGCTAGATCGCG | 954 | 116 |
| A7E1ZDS38f | CGCGATCGTAATGGATGGTTTTTTGTACAGGCAATGATCGCG | 954 | 117 |
| A7E1ZDS2f | CGCGCTGTAACGGATGGTTTTTTGTACAAGCAATAGCGCG | 954 | 118 |
| A7E1ZDS3f | CGCGATGGTGTAATGGCTGGTTCTTTGTAGAATCGCG | 951 | 119 |
| A7E1ZDS4f | CGCGATGGTGTAATGGCTGGTTCTTTGTAGAGATCGCG | 951 | 120 |
| A7E1ZDS11f | CTCGCTCGGTGTAATGGCTGGTTCTTTGTAGAGAGCGAG | 951 | 121 |

TABLE 29

| A7 SYSTEMS | | | | | | | | |
|---|---|---|---|---|---|---|---|---|
| | HPV18 reference amplicon | Forward Primers | | Reverse Primers | | Probes | Beacon ® Probes | |
| A7 | SEQ ID NO: | Name | SEQ ID NO: | Name | SEQ ID NO: | SEQ ID NO: | Name | SEQ ID NO: |
| System A | 46 to 51 | A7E16f1a | 68 | A7E16r1b | 79 | 88 | A7E1ZAS61f | 102 |
| | | A7E16f2a | 69 | A7E16r2b | 80 | 89 | A7E1ZAS63f | 103 |
| | | A7E16f3a | 70 | A7E16r3b | 81 | 90 | A7E1ZAS64f | 104 |
| | | | | | | 91 | A7E1ZCS40f | 105 |
| | | | | | | 92 | A7E1ZBS74f | 106 |
| System A1 | 46 to 51 | A7E16f1a | 68 | A7E16r1b | 79 | 93 | A7E1ZBS26f | 107 |
| | | A7E16f2a | 69 | A7E16r2b | 80 | 92 | A7E1ZBS74f | 106 |
| | | A7E16f3a | 70 | A7E16r3b | 81 | 94 | A7E1ZBS79f | 108 |
| | | | | | | 94 | A7E1ZBS80f | 109 |
| | | | | | | 95 | A7E1ZBS27f | 110 |
| System A2 | 46 to 51 | A7E16f1a | 68 | A7E16r1b | 79 | 91 | A7E1ZCS11f | 111 |
| | | A7E16f2a | 69 | A7E16r2b | 80 | 91 | A7E1ZCS40f | 105 |
| | | A7E16f3a | 70 | A7E16r3b | 81 | 90 | A7E1ZCS45f | 112 |
| | | | | | | 89 | A7E1ZCS63f | 113 |
| | | | | | | 96 | A7E1ZCS90f | 114 |
| System AB | 52-53-339-340 | A7E16f1a | 68 | A7E115r1a | 82 | 93 | A7E1ZBS26f | 107 |
| | | A7E16f2a | 69 | A7E115r2b | 83 | 92 | A7E1ZBS74f | 106 |
| | | A7E16f3a | 70 | | | 94 | A7E1ZBS79f | 108 |
| | | | | | | 94 | A7E1ZBS80f | 109 |
| | | | | | | 95 | A7E1ZBS27f | 110 |
| System AC1 | 48-51-341-342 | A7E16f1a | 68 | A7E17r1 | 84 | 88 | A7E1ZAS61f | 102 |
| | | A7E16f2a | 69 | A7E17r2 | 85 | 89 | A7E1ZAS63f | 103 |
| | | A7E16f3a | 70 | | | 90 | A7E1ZAS64f | 104 |
| | | | | | | 91 | A7E1ZCS40f | 105 |
| | | | | | | 92 | A7E1ZBS74f | 106 |
| System AC2 | 48-51-341-342 | A7E16f1a | 68 | A7E17r1 | 84 | 93 | A7E1ZBS26f | 107 |
| | | A7E16f2a | 69 | A7E17r2 | 85 | 92 | A7E1ZBS74f | 106 |
| | | A7E16f3a | 70 | | | 94 | A7E1ZBS79f | 108 |
| | | | | | | 94 | A7E1ZBS80f | 109 |
| | | | | | | 96 | A7E1ZBS27f | 110 |
| System AC3 | 48-51-341-342 | A7E16f1a | 68 | A7E17r1 | 84 | 91 | A7E1ZCS11f | 111 |
| | | A7E16f2a | 69 | A7E17r2 | 85 | 91 | A7E1ZCS40f | 105 |
| | | A7E16f3a | 70 | | | 90 | A7E1ZCS45f | 112 |
| | | | | | | 89 | A7E1ZCS63f | 113 |
| | | | | | | 96 | A7E1ZCS90f | 114 |
| System B | 52 to −57 | A7E115f1a | 71 | A7E115r1a | 82 | 93 | A7E1ZBS26f | 107 |
| | | A7E115f2a | 72 | A7E115r2b | 83 | 92 | A7E1ZBS74f | 106 |
| | | A7E115f3d | 73 | | | 94 | A7E1ZBS79f | 108 |
| | | | | | | 94 | A7E1ZBS80f | 109 |
| | | | | | | 95 | A7E1ZBS27f | 110 |

TABLE 29-continued

| A7 SYSTEMS | | | | | | | | |
|---|---|---|---|---|---|---|---|---|
| | HPV18 reference amplicon | Forward Primers | | Reverse Primers | | Probes | Beacon ® Probes | |
| A7 | SEQ ID NO: | Name | SEQ ID NO: | Name | SEQ ID NO: | SEQ ID NO: | Name | SEQ ID NO: |
| System BA1 | 46-47-48- | A7E115f1a | 71 | A7E16r1b | 79 | 88 | A7E1ZAS61f | 102 |
| | 343 to | A7E115f2a | 72 | A7E16r2b | 80 | 89 | A7E1ZAS63f | 103 |
| | 348 | A7E115f3d | 73 | A7E16r3b | 81 | 90 | A7E1ZAS64f | 104 |
| | | | | | | 91 | A7E1ZCS40f | 105 |
| | | | | | | 92 | A7E1ZBS74f | 106 |
| System BA2 | 46-47-48- | A7E115f1a | 71 | A7E16r1b | 79 | 93 | A7E1ZBS26f | 107 |
| | 343 to | A7E115f2a | 72 | A7E16r2b | 80 | 92 | A7E1ZBS74f | 106 |
| | 348 | A7E115f3d | 73 | A7E16r3b | 81 | 94 | A7E1ZBS79f | 108 |
| | | | | | | 94 | A7E1ZBS80f | 109 |
| | | | | | | 95 | A7E1ZBS27f | 110 |
| System BA3 | 46-47-48- | A7E115f1a | 71 | A7E16r1b | 79 | 91 | A7E1ZCS11f | 111 |
| | 343 to | A7E115f2a | 72 | A7E16r2b | 80 | 91 | A7E1ZCS40f | 105 |
| | 348 | A7E115f3d | 73 | A7E16r3b | 81 | 90 | A7E1ZCS45f | 112 |
| | | | | | | 89 | A7E1ZCS63f | 113 |
| | | | | | | 96 | A7E1ZCS90f | 114 |
| System BC1 | 48-345- | A7E115f1a | 71 | A7E17r1 | 84 | 88 | A7E1ZAS61f | 102 |
| | 349 to | A7E115f2a | 72 | A7E17r2 | 85 | 89 | A7E1ZAS63f | 103 |
| | 352 | A7E115f3d | 73 | | | 90 | A7E1ZAS64f | 104 |
| | | | | | | 91 | A7E1ZCS40f | 105 |
| | | | | | | 92 | A7E1ZBS74f | 106 |
| System BC2 | 48-345- | A7E115f1a | 71 | A7E17r1 | 84 | 93 | A7E1ZBS26f | 107 |
| | 349 to | A7E115f2a | 72 | A7E17r2 | 85 | 92 | A7E1ZBS74f | 106 |
| | 352 | A7E115f3d | 73 | | | 94 | A7E1ZBS79f | 108 |
| | | | | | | 94 | A7E1ZBS80f | 109 |
| | | | | | | 95 | A7E1ZBS27f | 110 |
| System BC3 | 48-345- | A7E115f1a | 71 | A7E17r1 | 84 | 91 | A7E1ZCS11f | 111 |
| | 349 to | A7E115f2a | 72 | A7E17r2 | 85 | 91 | A7E1ZCS40f | 105 |
| | 352 | A7E115f3d | 73 | | | 90 | A7E1ZCS45f | 112 |
| | | | | | | 89 | A7E1ZCS63f | 113 |
| | | | | | | 96 | A7E1ZCS90f | 114 |
| System C | 58 to 63 | A7E17f1 | 74 | A7E17r1 | 84 | 91 | A7E1ZCS11f | 111 |
| | | A7E17f2 | 75 | A7E17r2 | 85 | 91 | A7E1ZCS40f | 105 |
| | | A7E17f3 | 76 | | | 90 | A7E1ZCS45f | 112 |
| | | | | | | 89 | A7E1ZCS63f | 113 |
| | | | | | | 96 | A7E1ZCS90f | 114 |
| System C1 | 58 to 63 | A7E17f1 | 74 | A7E17r1 | 84 | 88 | A7E1ZAS61f | 102 |
| | | A7E17f2 | 75 | A7E17r2 | 85 | 89 | A7E1ZAS63f | 103 |
| | | A7E17f3 | 76 | | | 90 | A7E1ZAS64f | 104 |
| | | | | | | 91 | A7E1ZCS40f | 105 |
| | | | | | | 96 | A7E1ZCS90f | 114 |
| System CA1 | 59-61-63- | A7E17f1 | 74 | A7E16r1b | 79 | 91 | A7E1ZCS11f | 111 |
| | 353 to | A7E17f2 | 75 | A7E16r2b | 80 | 91 | A7E1ZCS40f | 105 |
| | 358 | A7E17f3 | 76 | A7E16r3b | 81 | 90 | A7E1ZCS45f | 112 |
| | | | | | | 89 | A7E1ZCS63f | 113 |
| | | | | | | 96 | A7E1ZCS90f | 114 |
| System CA2 | 59-61-63- | A7E17f1 | 74 | A7E16r1b | 79 | 88 | A7E1ZAS61f | 102 |
| | 353 to | A7E17f2 | 75 | A7E16r2b | 80 | 89 | A7E1ZAS63f | 103 |
| | 358 | A7E17f3 | 76 | A7E16r3b | 81 | 90 | A7E1ZAS64f | 104 |
| | | | | | | 91 | A7E1ZCS40f | 105 |
| | | | | | | 96 | A7E1ZCS90f | 114 |
| System D | 64 to 67 | A7E12f1 | 77 | A7E12r2 | 86 | 97 | A7E1ZDS36f | 115 |
| | | A7E12f2 | 78 | A7E12r3 | 87 | 98 | A7E1ZDS37f | 116 |
| | | | | | | 99 | A7E1ZDS38f | 117 |
| | | | | | | 100 | A7E1ZDS2f | 118 |
| | | | | | | 101 | A7E1ZDS3f | 119 |
| | | | | | | 101 | A7E1ZDS4f | 120 |
| | | | | | | 101 | A7E1ZDS11f | 121 |

A9 Group=HPV16; HPV31; HPV33; HPV35; HPV52; HPV58; HPV67

A9 HR HPV=HPV16; HPV31; HPV33; HPV35; HPV52; HPV58

A9 Reference Genome=HPV16 (NC_001526.1; Human HPV16, Complete Genome)

TABLE 30

A9 REFERENCE AMPLICON SEQUENCES (from reference genome) =

| Systems | Amplicons size bp | Forward address | Reverse address | Start-stop positions | SEQ ID NO: |
|---|---|---|---|---|---|
| System C | 88 | 2707 | 2794 | 2707-2794 | 122 |
| | | 2707 | 2794 | | |
| | | 2707 | | | |
| | | 2707 | | | |
| | | 2707 | | | |
| | | 2707 | | | |
| | | 2707 | | | |
| System E1 | 191 à 198 | 3600 | 3790 | 3600-3790 | 123 |
| | | 3600 | 3793 | 3600-3793 | 124 |
| | | 3600 | 3791 | 3600-3791 | 125 |
| | | | 3790 | 3600-3797 | 126 |
| | | | 3797 | 3600-3795 | 127 |
| | | | 3795 | | |
| System E2 | 190 à 198 | 3600 | 3790 | 3600-3790 | 123 |
| | | 3601 | 3793 | 3600-3793 | 124 |
| | | 3600 | 3791 | 3600-3791 | 125 |
| | | | 3790 | 3600-3797 | 126 |
| | | | 3797 | 3600-3795 | 127 |
| | | | 3795 | 3601-3790 | 128 |
| | | | | 3601-3793 | 129 |
| | | | | 3601-3791 | 130 |
| | | | | 3601-3797 | 131 |
| | | | | 3601-3795 | 132 |

| Systems | Amplicons size pb | address forw | address rev | Start-stop position | SEQ ID NO: |
|---|---|---|---|---|---|
| System E3 | 188 à 193 | 3600 | 3788 | 3600-3788 | 133 |
| | | 3601 | 3792 | 3600-3792 | 134 |
| | | 3600 | 3792 | 3600-3790 | 135 |
| | | | 3790 | 3601-3788 | 136 |
| | | | 3792 | 3601-3792 | 137 |
| | | | 3792 | 3601-3790 | 138 |
| | | | 3792 | | |
| | | | 3790 | | |
| System E4 | 179 à 186 | 3607 | 3788 | 3607-3788 | 139 |
| | | 3610 | 3792 | 3607-3792 | 140 |
| | | 3609 | 3792 | 3607-3790 | 141 |
| | | | 3790 | 3610-3788 | 142 |
| | | | 3792 | 3610-3792 | 143 |
| | | | 3792 | 3610-3790 | 144 |
| | | | 3792 | 3609-3788 | 145 |
| | | | 3790 | 3609-3792 | 146 |
| | | | | 3609-3790 | 147 |
| System E5 | 181à 191 | 3607 | 3790 | 3607-3790 | 141 |
| | | 3610 | 3793 | 3607-3791 | 359 |
| | | 3609 | 3791 | 3607-3793 | 360 |
| | | | 3790 | 3607-3795 | 361 |
| | | | 3797 | 3607-3797 | 362 |
| | | | 3795 | 3609-3790 | 363 |
| | | | | 3609-3791 | 364 |
| | | | | 3609-3793 | 365 |
| | | | | 3609-3795 | 366 |
| | | | | 3609-3797 | 367 |
| | | | | 3610-3790 | 144 |
| | | | | 3610-3791 | 368 |
| | | | | 3610-3793 | 369 |
| | | | | 3610-3795 | 370 |
| | | | | 3610-3797 | 371 |

TABLE 30-continued

A9 REFERENCE AMPLICON SEQUENCES (from reference genome) =

| | | | | | |
|---|---|---|---|---|---|
| System E6 | 189 à 193 | 3600 | 3788 | 3600-3788 | 133 |
| | | 3600 | 3792 | 3600-3790 | 135 |
| | | 3600 | 3792 | 3600-3792 | 134 |
| | | | 3790 | | |
| | | | 3792 | | |
| | | | 3792 | | |
| | | | 3792 | | |
| | | | 3790 | | |
| System E1 H Z7, Z8 | 231 à 241 | 3600 | 3838 | 3600-3830 | 372 |
| | | 3600 | 3831 | 3600-3831 | 373 |
| | | 3600 | 3830 | 3600-3837 | 374 |
| | | | 3830 | 3600-3838 | 375 |
| | | | 3838 | 3600-3839 | 376 |
| | | | 3840 | 3600-3840 | 377 |
| | | | 3839 | | |
| | | | 3838 | | |
| | | | 3837 | | |
| System E2H Z7, Z8 | 230 à 241 | 3600 | 3838 | 3600-3830 | 372 |
| | | 3601 | 3831 | 3600-3831 | 373 |
| | | 3600 | 3830 | 3600-3837 | 374 |
| | | | 3830 | 3600-3838 | 375 |
| | | | 3838 | 3600-3839 | 376 |
| | | | 3840 | 3600-3840 | 377 |
| | | | 3839 | 3601-3830 | 378 |
| | | | 3838 | 3601-3831 | 379 |
| | | | 3837 | 3601-3837 | 380 |
| | | | | 3601-3838 | 381 |
| | | | | 3601-3839 | 382 |
| | | | | 3601-3840 | 383 |
| System E4H Z7, Z8 | 224 à 234 | 3607 | 3838 | 3607-3830 | 384 |
| | | 3610 | 3831 | 3607-3831 | 385 |
| | | 3609 | 3830 | 3607-3837 | 386 |
| | | | 3830 | 3607-3838 | 387 |
| | | | 3838 | 3607-3839 | 388 |
| | | | 3840 | 3607-3840 | 389 |
| | | | 3839 | 3609-3830 | 390 |
| | | | 3838 | 3609-3831 | 391 |
| | | | 3837 | 3609-3837 | 392 |
| | | | | 3609-3838 | 393 |
| | | | | 3609-3839 | 394 |
| | | | | 3609-3840 | 395 |
| | | | | 3610-3830 | 396 |
| | | | | 3610-3831 | 397 |
| | | | | 3610-3837 | 398 |
| | | | | 3610-3838 | 399 |
| | | | | 3610-3839 | 400 |
| | | | | 3610-3840 | 401 |
| System F | 163 à 172 | 3626 | 3788 | 3626-3788 | 148 |
| | | 3626 | 3792 | 3626-3792 | 149 |
| | | 3621 | 3792 | 3626-3790 | 150 |
| | | 3625 | 3790 | 3621-3788 | 151 |
| | | | 3792 | 3621-3792 | 152 |
| | | | 3792 | 3621-3790 | 153 |
| | | | 3792 | 3625-3788 | 154 |
| | | | 3790 | 3625-3792 | 155 |
| | | | | 3625-3790 | 156 |
| System FE | 165 à 177 | 3626 | 3790 | 3621-3790 | 153 |
| | | 3626 | 3793 | 3621-3791 | 402 |
| | | 3621 | 3791 | 3621-3793 | 403 |
| | | 3625 | 3790 | 3621-3795 | 404 |
| | | | 3797 | 3621-3797 | 405 |
| | | | 3795 | 3625-3790 | 156 |
| | | | | 3625-3791 | 406 |
| | | | | 3625-3793 | 407 |
| | | | | 3625-3795 | 408 |
| | | | | 3625-3797 | 409 |
| | | | | 3626-3790 | 150 |
| | | | | 3626-3791 | 410 |
| | | | | 3626-3793 | 411 |
| | | | | 3626-3795 | 412 |
| | | | | 3626-3797 | 413 |
| System FH Z7, Z8 | 205 à 220 | 3626 | 3838 | 3621-3830 | 163 |
| | | 3626 | 3831 | 3621-3831 | 162 |
| | | 3621 | 3830 | 3621-3837 | 164 |
| | | 3625 | 3830 | 3621-3838 | 414 |
| | | | 3838 | 3621-3839 | 415 |
| | | | 3840 | 3621-3840 | 161 |

TABLE 30-continued

A9 REFERENCE AMPLICON SEQUENCES (from reference genome) =

| | | | | | |
|---|---|---|---|---|---|
| | | | 3839 | 3625-3830 | 167 |
| | | | 3838 | 3625-3831 | 166 |
| | | | 3837 | 3625-3837 | 168 |
| | | | | 3625-3838 | 416 |
| | | | | 3625-3839 | 417 |
| | | | | 3625-3840 | 165 |
| | | | | 3626-3830 | 159 |
| | | | | 3626-3831 | 158 |
| | | | | 3626-3837 | 160 |
| | | | | 3626-3838 | 418 |
| | | | | 3626-3839 | 419 |
| | | | | 3626-3840 | 157 |
| System G Z7, Z8 | 205 à 220 | 3626 | 3840 | 3626-3840 | 157 |
| | | 3626 | 3831 | 3626-3831 | 158 |
| | | 3621 | 3830 | 3626-3830 | 159 |
| | | 3625 | 3837 | 3626-3837 | 160 |
| | | | 3840 | 3621-3840 | 161 |
| | | | 3840 | 3621-3831 | 162 |
| | | | | 3621-3830 | 163 |
| | | | | 3621-3837 | 164 |
| | | | | 3625-3840 | 165 |
| | | | | 3625-3831 | 166 |
| | | | | 3625-3830 | 167 |
| | | | | 3625-3837 | 168 |
| System H | 132 à 150 | 3699 | 3838 | 3699-3838 | 169 |
| | | 3691 | 3831 | 3699-3831 | 170 |
| | | 3693 | 3830 | 3699-3830 | 171 |
| | | 3696 | 3830 | 3699-3840 | 172 |
| | | 3695 | 3838 | 3699-3839 | 173 |
| | | 3698 | 3840 | 3699-3837 | 174 |
| | | 3697 | 3839 | 3691-3838 | 175 |
| | | 3699 | 3838 | 3691-3831 | 176 |
| | | 3698 | 3837 | 3691-3830 | 177 |
| | | | | 3691-3840 | 178 |
| | | | | 3691-3839 | 179 |
| | | | | 3691-3837 | 180 |
| | | | | 3693-3838 | 181 |
| | | | | 3693-3831 | 182 |
| | | | | 3693-3830 | 183 |
| | | | | 3693-3840 | 184 |
| | | | | 3693-3839 | 185 |
| | | | | 3693-3837 | 186 |
| System H | 132 à 150 | 3696 | 3838 | 3696-3838 | 187 |
| | | 3695 | 3831 | 3696-3831 | 188 |
| | | 3698 | 3830 | 3696-3830 | 189 |
| | | 3697 | 3840 | 3696-3840 | 190 |
| | | | 3839 | 3696-3839 | 191 |
| | | | 3837 | 3696-3837 | 192 |
| | | | | 3695-3838 | 193 |
| | | | | 3695-3831 | 194 |
| | | | | 3695-3830 | 195 |
| | | | | 3695-3840 | 196 |
| | | | | 3695-3839 | 197 |
| | | | | 3695-3837 | 198 |
| | | | | 3698-3838 | 199 |
| | | | | 3698-3831 | 200 |
| | | | | 3698-3830 | 201 |
| | | | | 3698-3840 | 202 |
| | | | | 3698-3839 | 203 |
| | | | | 3698-3837 | 204 |
| | | | | 3697-3838 | 205 |
| | | | | 3697-3831 | 206 |
| | | | | 3697-3830 | 207 |
| | | | | 3697-3840 | 208 |
| | | | | 3697-3839 | 209 |
| | | | | 3697-3837 | 210 |

TABLE 31

A9 FORWARD PRIMERS

| Forward Primer | | | | |
|---|---|---|---|---|
| Name | 5' Sequence 3' | address | size bp | SEQ ID NO: |
| A9E1f7 | AGGACGTGGTCCAGATTAAGTTT | 2707 | 23 | 211 |
| A9E1f8 | AGGACGTGGTGCAGATTAAG | 2707 | 20 | 212 |
| A9E1f9 | AGGACGTGGTGCAAATTAAGTTT | 2707 | 23 | 213 |
| A9E1f10 | AGGACGTGGTGCAGATTAAATTT | 2707 | 23 | 214 |
| A9E1f11 | AGGACGTGGTGCAGATTAGGTTT | 2707 | 23 | 215 |
| A9E1f12 | AGGACGTGGTGCAAATTAAATTT | 2707 | 23 | 216 |
| A9E1f13 | AGGACGTGGTGCAAATTAGGTTT | 2707 | 23 | 217 |
| A9E2f1 | TAGTAACACTACACCCATAGTACAT | 3600 | 25 | 218 |
| A9E2f2 | TCTAACGTTGCACCTATCGTG | 3600 | 21 | 219 |
| A9E2f4 | TCCTTCTACTGCACCTATAATACA | 3600 | 24 | 220 |
| A9E2f1a | TAGTACCACTACACCCATAGTACAT | 3600 | 25 | 221 |
| A9E2f2a | TCTAACGTTGCACCTATCGTGCAT | 3601 | 24 | 222 |
| A9E2f4a | TCCTTCTACTGCACCTATAATACAC | 3600 | 25 | 223 |
| A9E2Z5Z6f1c | ACTACACCTATAGTACATTTAAAAGG | 3607 | 26 | 224 |
| A9E2Z5Z6f2c | GCACCTATAGTGCATTTAAAAG | 3610 | 22 | 225 |
| A9E2Z5Z6f3b | TGCACCTATAATACACCTAAAAG | 3609 | 23 | 226 |

TABLE 31-continued

A9 FORWARD PRIMERS

| Name | Forward Primer 5' Sequence 3' | address | size bp | SEQ ID NO: |
|---|---|---|---|---|
| A9E21f1az | TAAAAGGTGATGCTAATACTTTAAA | 3626 | 25 | 227 |
| A9E21f2bz | TAAAAGGTGATGCAAATACATTAAA | 3626 | 25 | 228 |
| A9E21f3dz | GCATTTAAAAGGTGAATCAAATAG | 3621 | 24 | 229 |
| A9E21f4cz | CTAAAAGGTGATCCTAATAGTTTAAA | 3625 | 26 | 230 |
| A9E2f5 | GTCGTCTACATGGCATTGGA | 3699 | 20 | 231 |
| A9E2f6 | CAAGATGCTTCATCTACATGGAG | 3691 | 23 | 232 |
| A9E2f7 | AGAAGCGTCATCTACATGGAG | 3693 | 21 | 233 |
| A9E2f8 | AGTGTCGTCTACATGGCATTG | 3696 | 21 | 234 |
| A9E2f9 | ATATGTCATCTACATGGCATTGG | 3695 | 23 | 235 |
| A9E2f10 | TGTCATCCACATGGCATTGG | 3698 | 20 | 236 |
| A9E2f10b | ATGTCATCCACATGGCATTG | 3697 | 20 | 237 |
| A9E2f11 | TTCATCTACCTGGAGTTGGAC | 3699 | 21 | 238 |
| A9E2f12 | TTTCATCTACATGGAGTTGGAC | 3698 | 22 | 239 |

TABLE 32

A9 REVERSE PRIMERS

| Name | Reverse Primer 5' Sequence 3' | address | size bp | SEQ ID NO: |
|---|---|---|---|---|
| A9E1r5 | TGTCCTGACACACATTTAAACG | 2794 | 22 | 240 |
| A9E1r6 | TGTCCTGCACTGCATTTAAAC | 2794 | 21 | 241 |
| A9E2r1 | ATTGGTCACGTTGCCATTC | 3790 | 19 | 242 |
| A9E2r2 | AAAATTGTTGACGTTGTGTTTC | 3793 | 22 | 243 |
| A9E2r3 | AACTGTTGACGTTGTGTTTC | 3791 | 20 | 244 |
| A9E2r4 | ACATTTGTCGTTGCGGTTC | 3790 | 19 | 245 |
| A9E2r13 | GTCTCTTTGTGATGTACTTATATATG | 3797 | 26 | 246 |
| A9E2r14 | CCCTTTGATATTCTGTTGTGTAAG | 3795 | 24 | 247 |
| A9E21r1cz | TGGTCACGTTGCCATTC | 3788 | 17 | 248 |
| A9E21r2az | AAAATCGTCTCTTTGTGATGT | 3792 | 21 | 249 |
| A9E21r3az | AAACATTTGTTGTTGCTGTTC | 3792 | 21 | 250 |
| A9E21r4fz | ATTTATCCCTTTGATATTCTGTTG | 3790 | 24 | 251 |
| A9E21r5az | AAACAGTTGACGTTGTGTTTC | 3792 | 21 | 252 |
| A9E21r6az | AAACTGTTGACGTTGTGTTTC | 3792 | 21 | 253 |
| A9E21r7az | AAATTGTTGACGTTGTGTTTC | 3792 | 21 | 254 |
| A9E21r8az | ACAGTTGTCGTTGTGTTTC | 3790 | 19 | 255 |
| A9E2r7C | AAATCCTGTAGACACTGTAACAGT | 3840 | 24 | 256 |
| A9E2r8 | ACTTATTTGCACAGTAGGTGGT | 3831 | 22 | 257 |
| A9E2r10 | CTTACTTGCACAGTAGTTGGTA | 3830 | 22 | 258 |

TABLE 32-continued

| A9 REVERSE PRIMERS | | | | |
|---|---|---|---|---|
| Reverse Primer | | | | |
| Name | 5' Sequence 3' | address | size bp | SEQ ID NO: |
| A9E2r12 | ATCCTGTTGACACTGATACTGT | 3837 | 22 | 259 |
| A9E2r12B | TATCCTGTAGACACTGAAACTGTG | 3840 | 24 | 260 |
| A9E2r15 | AAATCCAGTAGACACTGTAATAGTT | 3840 | 25 | 261 |
| A9E2r7B | ATCCTGTAGACACTGTAACAGTT | 3838 | 23 | 262 |
| A9E2r8 | ACTTATTTGCACAGTAGGTGGT | 3831 | 22 | 257 |
| A9E2r9 | CTTACTTGCACAGTAGGTGGTA | 3830 | 22 | 263 |
| A9E2r10 | CTTACTTGCACAGTAGTTGGTA | 3830 | 22 | 258 |
| A9E2r12 | ATCCTGTTGACACTGATACTGT | 3838 | 22 | 259 |
| A9E2r7C | AAATCCTGTAGACACTGTAACAGT | 3840 | 24 | 256 |
| A9E2r12B | TATCCTGTAGACACTGAAACTGTG | 3839 | 24 | 264 |
| A9E2r15 | AAATCCAGTAGACACTGTAATAGTTT | 3838 | 26 | 261 |
| A9E2r16 | ACCGTACTTATTTGCACAGTG | 3837 | 21 | 265 |

TABLE 33

| A9 PROBES | | | | |
|---|---|---|---|---|
| 5' Sequence 3' | address | size pb | SEQ ID NO: | Corresponding beacon probes |
| TCCATCGTTTTCCTTGTCCTCT | 2738 | 22 | 266 | A9E1S10 and S10a |
| TCCATCGTTTTCTTTGACCTCT | 2738 | 22 | 267 | A9E1S11 and S11a |
| TCCATCATTTTCTTTGACCTCT | 2738 | 22 | 268 | A9E1S12, S12a and S12b |
| TCTCCATCATTTTCTTTGTCCTCT | 2738 | 24 | 269 | A9E1S13a, S13b and S13c |
| CTCCATCGTTTTCTTTGTCCTC | 2739 | 22 | 270 | A9E1S14a |
| CTCCATCATTTTCTTTGACCTCTC | 2737 | 24 | 271 | A9E1S15a and 15b |
| AGTGTCGTCTACATGGCATTGGAC | 3696 | 24 | 272 | A9E2Z7S1 |
| ATATGTCATCCACCTGGCATTGGAC | 3695 | 25 | 273 | A9E2Z7S2 and S2a |
| ATATGTCATCCACCTGGCATTGGA | 3695 | 24 | 274 | A9E2Z7S2b |
| ATGCTTCATCTACATGGAGATGGAC | 3695 | 25 | 275 | A9E2Z7S3 and S3a |
| CAAGTTTCATCTACATGGCATTGGAC | 3694 | 26 | 276 | A9E2Z7S4 and S4a |
| GATAGTGAATGGCAACGTGA | 3766 | 20 | 277 | A9E2Z8S2f, S21f and S28f |
| ATAAGTACATCACAAAGAGACGA | 3766 | 23 | 278 | A9E2Z8S56f, S58f and S61f |
| TAACTGAACAGCAACAACAAATG | 3767 | 23 | 279 | A9E2Z8S101f, 105f and 127f |
| CACAACAGAATATCAAAGGGATAAATT | 3765 | 27 | 280 | A9E2Z8S146f, 155f and 156f |
| CGTACAGTGATGAAACACAAC | 3761 | 21 | 281 | A9E2Z8S210f |
| AACGGAAACACAACGACAAC | 3768 | 20 | 282 | A9E2Z8S231f, 236f and 250f |

TABLE 34

A9 BEACON PROBES

| Name | Beacon probe 5' Sequence 3' | address | size bp | SEQ ID NO: |
|---|---|---|---|---|
| A9E1S10 | CGCGATTCCATCGTTTTCCTTGTCCTCTATCGCG | 2738 | 22 | 283 |
| A9E1S10a | CGCGATCCATCGTTTTCCTTGTCCTCTTCGCG | 2738 | 22 | 284 |
| A9E1S11 | CGCGATTCCATCGTTTTCTTTGACCTCTATCGCG | 2738 | 22 | 285 |
| A9E1S11a | CGCGATCCATCGTTTTCTTTGACCTCTTCGCG | 2738 | 22 | 286 |
| A9E1S12 | CGCGATTCCATCATTTTCTTTGACCTCTATCGCG | 2738 | 22 | 287 |
| A9E1S12a | CGCGATCCATCATTTTCTTTGACCTCTTCGCG | 2738 | 22 | 288 |
| A9E1S12b | CGCTGTCCATCATTTTCTTTGACCTCTCAGCG | 2738 | 22 | 289 |
| A9E1S13a | CGCGTTCTCCATCATTTTCTTTGTCCTCTACGCG | 2738 | 24 | 290 |
| A9E1S13b | CGCCGTCTCCATCATTTTCTTTGTCCTCTCGGCG | 2738 | 24 | 291 |
| A9E1S13c | CGCGATTCTCCATCATTTTCTTTGTCCTCTATCGCG | 2738 | 24 | 292 |
| A9E1S14a | CGCGATCTCCATCGTTTTCTTTGTCCTCATCGCG | 2739 | 22 | 293 |
| A9E1S15a | CGCCGCTCCATCATTTTCTTTGACCTCTCCGGCG | 2737 | 24 | 294 |
| A9E1S15b | CGCGATCTCCATCATTTTCTTTGACCTCTCATCGCG | 2737 | 24 | 295 |
| A9E2Z7S1 | CGCGAAGTGTCGTCTACATGGCATTGGACTCGCG | 3696 | 24 | 296 |
| A9E2Z7S2 | CGCTCGATATGTCATCCACCTGGCATTGGACCGAGCG | 3695 | 25 | 297 |
| A9E2Z7S2a | CGCATGATATGTCATCCACCTGGCATTGGACCATGCG | 3695 | 25 | 298 |
| A9E2Z7S2b | CGCATGATATGTCATCCACCTGGCATTGGACATGCG | 3695 | 24 | 299 |
| A9E2Z7S3 | CGCACTATGCTTCATCTACATGGAGATGGACAGTGCG | 3695 | 25 | 300 |
| A9E2Z7S3a | CCGACGATGCTTCATCTACATGGAGATGGACCGTCGG | 3695 | 25 | 301 |
| A9E2Z7S4 | CGCGATCAAGTTTCATCTACATGGCATTGGACATCGCG | 3694 | 26 | 302 |
| A9E2Z7S4a | CGCGAGCAAGTTTCATCTACATGGCATTGGACCTCGCG | 3694 | 26 | 303 |
| A9E2Z8S2f | CAGCGTGATAGTGAATGGCAACGTGAACGCTG | 3766 | 20 | 304 |
| A9E2Z8S21f | CGGACTGATAGTGAATGGCAACGTGAAGTCCG | 3766 | 20 | 305 |
| A9E2Z8S28f | CTCGCTGATAGTGAATGGCAACGTGAAGCGAG | 3766 | 20 | 306 |
| A9E2Z8S56f | CGAGCTATAAGTACATCACAAAGAGACGAAGCTCG | 3766 | 23 | 307 |
| A9E2Z8S58f | CGCAGTATAAGTACATCACAAAGAGACGAACTGCG | 3766 | 23 | 308 |
| A9E2Z8S61f | CGCGTTATAAGTACATCACAAAGAGACGAAACGCG | 3766 | 23 | 309 |
| A9E2Z8S101f | CGAGGTTAACTGAACAGCAACAACAAATGACCTCG | 3767 | 23 | 310 |
| A9E2Z8S105f | CGCGATTAACTGAACAGCAACAACAAATGATCGCG | 3767 | 23 | 311 |
| A9E2Z8S127f | CCGGCTTAACTGAACAGCAACAACAAATGAGCCGG | 3767 | 23 | 312 |
| A9E2Z8S146f | CGCGATCACAACAGAATATCAAAGGGATAAATTATCGCG | 3765 | 27 | 313 |
| A9E2Z8S155f | CGCACGCACAACAGAATATCAAAGGGATAAATTCGTGCG | 3765 | 27 | 314 |
| A9E2Z8S156f | CCGGCTCACAACAGAATATCAAAGGGATAAATTAGCCGG | 3765 | 27 | 315 |
| A9E2Z8S210f | CCGGCTCGTACAGTGATGAAACACAACAGCCGG | 3761 | 21 | 316 |
| A9E2Z8S231f | CGAGGTAACGGAAACACAACGACAACACCTCG | 3768 | 20 | 317 |
| A9E2Z8S236f | CGCGTTAACGGAAACACAACGACAACAACGCG | 3768 | 20 | 318 |
| A9E2Z8S250f | CGATGCAACGGAAACACAACGACAACGCATCG | 3768 | 20 | 319 |

TABLE 35

A9 SYSTEMS

| | HPV16 reference amplicon | Forward Primer | | Reverse Primer | | Probe | Beacon Probe | |
|---|---|---|---|---|---|---|---|---|
| A9 | SEQ ID NO: | Name | SEQ ID NO: | Name | SEQ ID NO: | SEQ ID NO: | Name | SEQ ID NO: |
| System C | 122 | A9E1f8<br>A9E1f10<br>A9E1f12<br>(A9E1f7)<br>(A9E1f9)<br>(A9E1f11)<br>(A9E1f13) | 212; 214;<br>216<br>(211; 213;<br>215; 217) | A9E1r5<br>A9E1r6 | 240-241 | 266-271 | A9E1S10<br>A9E1S10a<br>—<br>A9E1S11<br>A9E1S11a<br>—<br>A9E1S12<br>A9E1S12a<br>A9E1S12b<br>—<br>A9E1S13a<br>A9E1S13b<br>A9E1S13c<br>—<br>A9E1S14a<br>—<br>A9E1S15a<br>A9E1S15b | 283-295 |
| System E1 | 123 to 127 | A9E2f1<br>A9E2f2<br>A9E2f4 | 218-220 | A9E2r1<br>A9E2r2<br>A9E2r4<br>A9E2r13<br>A9E2r14<br>(A9E2r3) | 242-243;<br>245-247<br>(244) | 272-276 | A9E2Z7S1<br>—<br>A9E2Z7S2<br>A9E2Z7S2a<br>A9E2Z7S2b<br>—<br>A9E2Z7S3<br>A9E2Z7S3a<br>—<br>A9E2Z7S4<br>A9E2Z7S4a | 296-303 |
| System E2 | 123 to 132 | A9E2f1a<br>A9E2f2a<br>A9E2f4a | 221-223 | A9E2r1<br>A9E2r2<br>A9E2r4<br>A9E2r13<br>A9E2r14<br>(A9E2r3) | 242-243;<br>246-247<br>(244) | 272-276 | A9E2Z7S1<br>—<br>A9E2Z7S2<br>A9E2Z7S2a<br>A9E2Z7S2b<br>—<br>A9E2Z7S3<br>A9E2Z7S3a<br>—<br>A9E2Z7S4<br>A9E2Z7S4a | 296-303 |
| System E3 | 133 to 138 | A9E2f1a<br>A9E2f2a<br>A9E2f4a | 221-223 | A9E21r1cz<br>A9E21r2az<br>A9E21r3az<br>A9E21r4fz<br>A9E21r5az<br>(A9E21r6az)<br>(A9E21r7az)<br>(A9E21r8az) | 248-252<br>(253-255) | 272-276 | A9E2Z7S1<br>—<br>A9E2Z7S2<br>A9E2Z7S2a<br>A9E2Z7S2b<br>—<br>A9E2Z7S3<br>A9E2Z7S3a<br>—<br>A9E2Z7S4<br>A9E2Z7S4a | 296-303 |
| System E4 | 139 to 147 | A9E2Z5Z6f1c<br>A9E2Z5Z6f2c<br>A9E2Z5Z6f3b | 224-226 | A9E21r1cz<br>A9E21r2az<br>A9E21r3az<br>A9E21r4fz<br>A9E21r5az<br>(A9E21r6az<br>A9E21r7az<br>A9E21r8az) | 248-252<br>(253-255) | 272-276 | A9E2Z7S1<br>—<br>A9E2Z7S2<br>A9E2Z7S2a<br>A9E2Z7S2b<br>—<br>A9E2Z7S3<br>A9E2Z7S3a<br>—<br>A9E2Z7S4<br>A9E2Z7S4a | 296-303 |

TABLE 35-continued

A9 SYSTEMS

| A9 | HPV16 reference amplicon SEQ ID NO: | Forward Primer Name | Forward Primer SEQ ID NO: | Reverse Primer Name | Reverse Primer SEQ ID NO: | Probe SEQ ID NO: | Beacon Probe Name | Beacon Probe SEQ ID NO: |
|---|---|---|---|---|---|---|---|---|
| System E5 | 141; 144 and 359 to 371 | A9E2Z5Z6f1c<br>A9E2Z5Z6f2c<br>A9E2Z5Z6f3b | 224-226 | A9E2r1<br>A9E2r2<br>A9E2r4<br>A9E2r13<br>A9E2r14<br>(A9E2r3) | 242-243;<br>245-247;<br>(244) | 272-276 | A9E2Z7S1<br>—<br>A9E2Z7S2<br>A9E2Z7S2a<br>A9E2Z7S2b<br>—<br>A9E2Z7S3<br>A9E2Z7S3a<br>—<br>A9E2Z7S4<br>A9E2Z7S4a | 296-303 |
| System E6 | 133 to 135 | A9E2f1<br>A9E2f2<br>A9E2f4 | 218-220 | A9E21r1cz<br>A9E21r2az<br>A9E21r3az<br>A9E21r4az<br>A9E21r5az<br>(A9E21r6az)<br>(A9E21r7az)<br>(A9E21r8az) | 248-252;<br>(253-255) | 272-276 | A9E2Z7S1<br>—<br>A9E2Z7S2<br>A9E2Z7S2a<br>A9E2Z7S2b<br>—<br>A9E2Z7S3<br>A9E2Z7S3a<br>—<br>A9E2Z7S4<br>A9E2Z7S4a | 296-303 |
| System E1H Z7 | 372 to 377 | A9E2f1<br>A9E2f2<br>A9E2f4 | 218-220 | (A9E2r7B)<br>(A9E2r8)<br>(A9E2r9)<br>A9E2r10<br>(A9E2r12)<br>(A9E2r7C)<br>A9E2r12B<br>A9E2r15<br>A9E2r16 | (256; 257; 259; 262; 263);<br>258; 261; 264; 265 | 272-276 | A9E2Z7S1<br>—<br>A9E2Z7S2<br>A9E2Z7S2a<br>A9E2Z7S2b<br>—<br>A9E2Z7S3<br>A9E2Z7S3a<br>—<br>A9E2Z7S4<br>A9E2Z7S4a | 296-303 |
| System E1H Z8 | 372 to 377 | A9E2f1<br>A9E2f2<br>A9E2f4 | 218-220 | (A9E2r7B)<br>(A9E2r8)<br>(A9E2r9)<br>A9E2r10<br>(A9E2r12)<br>(A9E2r7C)<br>A9E2r12B<br>A9E2r15<br>A9E2r16 | (256; 257; 259,<br>262; 263);<br>258; 261; 264;<br>265 | 277-282 | A9E2Z8S2f<br>A9E2Z8S21f<br>A9E2Z8S28f<br>—<br>A9E2Z8S56f<br>A9E2Z8S58f<br>A9E2Z8S61f<br>—<br>A9E2Z8S101f<br>A9E2Z8S105f<br>A9E2Z8S127f<br>—<br>A9E2Z8S146f<br>A9E2Z8S155f<br>A9E2Z8S156f<br>—<br>A9E2Z8S210f<br>—<br>A9E2Z8S231f<br>A9E2Z8S236f<br>A9E2Z8S250f | 304-319 |
| System E2H Z7 | 372 to 383 | A9E2f1a<br>A9E2f2a<br>A9E2f4a | 221-223 | (A9E2r7B)<br>(A9E2r8)<br>(A9E2r9)<br>A9E2r10<br>(A9E2r12)<br>(A9E2r7C)<br>A9E2r12B<br>A9E2r15<br>A9E2r16 | (256; 257; 259; 262; 263);<br>258; 261; 264; 265 | 272-276 | A9E2Z7S1<br>—<br>A9E2Z7S2<br>A9E2Z7S2a<br>A9E2Z7S2b<br>—<br>A9E2Z7S3<br>A9E2Z7S3a<br>—<br>A9E2Z7S4<br>A9E2Z7S4a | 296-303 |

TABLE 35-continued

A9 SYSTEMS

| A9 | HPV16 reference amplicon SEQ ID NO: | Forward Primer Name | Forward Primer SEQ ID NO: | Reverse Primer Name | Reverse Primer SEQ ID NO: | Probe SEQ ID NO: | Beacon Probe Name | Beacon Probe SEQ ID NO: |
|---|---|---|---|---|---|---|---|---|
| System E2H Z8 | 372 to 383 | A9E2f1a<br>A9E2f2a<br>A9E2f4a | 221-223 | (A9E2r7B)<br>(A9E2r8)<br>(A9E2r9)<br>A9E2r10<br>(A9E2r12)<br>(A9E2r7C)<br>A9E2r12B<br>A9E2r15<br>A9E2r16 | (256; 257; 259; 262; 263); 258; 261; 264; 265 | 277-282 | A9E2Z82f<br>A9E2Z8S21f<br>A9E2Z8S28f<br>—<br>A9E2Z8S56f<br>A9E2Z8S58f<br>A9E2Z8S61f<br>—<br>A9E2Z8S101f<br>A9E2Z8S105f<br>A9E2Z8S127f<br>—<br>A9E2Z8S146f<br>A9E2Z8S155f<br>A9E2Z8S156f<br>—<br>A9E2Z8S210f<br>—<br>A9E2Z8S231f<br>A9E2Z8S236f<br>A9E2Z8S250f | 304-319 |
| System E7H Z7 | 384 to 401 | A9E2Z5Z6f1c<br>A9E2Z5Z6f2c<br>A9E2Z5Z6f3b | 224-226 | (A9E2r7B)<br>(A9E2r8)<br>(A9E2r9)<br>A9E2r10<br>(A9E2r12)<br>(A9E2r7C)<br>A9E2r12B<br>A9E2r15<br>A9E2r16 | (256; 257; 259; 262; 263); 258; 261; 264; 265 | 272-276 | A9E2Z7S1<br>—<br>A9E2Z7S2<br>A9E2Z7S2a<br>A9E2Z7S2b<br>—<br>A9E2Z7S3<br>A9E2Z7S3a<br>—<br>A9E2Z7S4<br>A9E2Z7S4a | 296-303 |
| System E4H Z8 | 384 to 401 | A9E2Z5Z6f1c<br>A9E2Z5Z6f2c<br>A9E2Z5Z6f3b | 224-226 | (A9E2r7B)<br>(A9E2r8)<br>(A9E2r9)<br>A9E2r10<br>(A9E2r12)<br>(A9E2r7C)<br>A9E2r12B<br>A9E2r15<br>A9E2r16 | (256; 257; 259; 262; 263); 258; 261; 264; 265 | 277-282 | A9E2Z8S2f<br>A9E2Z8S21f<br>A9E2Z8S28f<br>—<br>A9E2Z8S56f<br>A9E2Z8S58f<br>A9E2Z8S61f<br>—<br>A9E2Z8S101f<br>A9E2Z8S105f<br>A9E2Z8S127f<br>—<br>A9E2Z8S146f<br>A9E2Z8S155f<br>A9E2Z8S156f<br>—<br>A9E2Z8S210f<br>—<br>A9E2Z8S231f<br>A9E2Z8S236f<br>A9E2Z8S250f | 304-319 |
| System F | 148 to 156 | A9E21f1az<br>A9E21f2bz<br>A9E21f3dz<br>A9E21f4cz | 227-230 | A9E21r1cz<br>A9E21r2az<br>A9E21r3az<br>A9E21r4fz<br>A9E21r5az<br>(A9E21r6az)<br>(A9E21r7az)<br>(A9E21r8az) | 248-252; (2530255) | 272-276 | A9E2Z7S1<br>—<br>A9E2Z7S2<br>A9E2Z7S2a<br>A9E2Z7S2b<br>—<br>A9E2Z7S3<br>A9E2Z7S3a<br>—<br>A9E2Z7S4<br>A9E2Z7S4a | 296-303 |

TABLE 35-continued

| A9 SYSTEMS | | | | | | | | |
|---|---|---|---|---|---|---|---|---|
| | HPV16 reference amplicon | Forward Primer | | Reverse Primer | | Probe | Beacon Probe | |
| A9 | SEQ ID NO: | Name | SEQ ID NO: | Name | SEQ ID NO: | SEQ ID NO: | Name | SEQ ID NO: |
| System FE | 153; 153; 156; 402 to 413 | A9E21f1az | 227-230 | A9E2r1 | 242-243; | 272-276 | A9E2Z7S1 | 296-303 |
| | | A9E21f2bz | | A9E2r2 | (244); | | — | |
| | | A9E21f3dz | | (A9E2r3) | 245-247 | | A9E2Z7S2 | |
| | | A9E21f4cz | | A9E2r4 | | | A9E2Z7S2a | |
| | | | | A9E2r13 | | | A9E2Z7S2b | |
| | | | | A9E2r14 | | | — | |
| | | | | | | | A9E2Z7S3 | |
| | | | | | | | A9E2Z7S3a | |
| | | | | | | | — | |
| | | | | | | | A9E2Z7S4 | |
| | | | | | | | A9E2Z7S4a | |
| System FH Z7 | 157 to 168 and 414 to 419 | A9E21f1az | 227-230 | (A9E2r7B) | (262); | 272-276 | A9E2Z7S1 | 296-303 |
| | | A9E21f2bz | | (A9E2r8) | (257); | | — | |
| | | A9E21f3dz | | (A9E2r9) | (263); | | A9E2Z7S2 | |
| | | A9E21f4cz | | (A9E2r12) | (259); | | A9E2Z7S2a | |
| | | | | (A9E2r7C) | (256); | | A9E2Z7S2b | |
| | | | | A9E2r10 | 258; | | — | |
| | | | | A9E2r12B | 264 | | A9E2Z7S3 | |
| | | | | A9E2r15 | 261 | | A9E2Z7S3a | |
| | | | | A9E2r16 | 265 | | — | |
| | | | | | | | A9E2Z7S4 | |
| | | | | | | | A9E2Z7S4a | |
| System FH Z8 | 157 to 168 and 414 to 419 | A9E21f1az | 227-230 | (A9E2r7B) | (262); | 277-282 | A9E2Z8S2f | 304-319 |
| | | A9E21f2bz | | (A9E2r8) | (257); | | A9E2Z8S21f | |
| | | A9E21f3dz | | (A9E2r9) | (263); | | A9E2Z8S28f | |
| | | A9E21f4cz | | (A9E2r12) | (259); | | — | |
| | | | | (A9E2r7C) | (256); | | A9E2Z8S56f | |
| | | | | A9E2r10 | 258; | | A9E2Z8S58f | |
| | | | | A9E2r12B | 264 | | A9E2Z8S61f | |
| | | | | A9E2r15 | 261 | | — | |
| | | | | A9E2r16 | 265 | | A9E2Z8S101f | |
| | | | | | | | A9E2Z8S105f | |
| | | | | | | | A9E2Z8S127f | |
| | | | | | | | — | |
| | | | | | | | A9E2Z8S146f | |
| | | | | | | | A9E2Z8S155f | |
| | | | | | | | A9E2Z8S156f | |
| | | | | | | | — | |
| | | | | | | | A9E2Z8S210f | |
| | | | | | | | — | |
| | | | | | | | A9E2Z8S231f | |
| | | | | | | | A9E2Z8S236f | |
| | | | | | | | A9E2Z8S250f | |
| System G Z7 | 157 to 168 | A9E21f1az | 227-230 | (A9E2r7C) | (256); | 272-276 | A9E2Z7S1 | 296-303 |
| | | A9E21f2bz | | A9E2r8 | 257-261 | | — | |
| | | A9E21f3dz | | A9E2r10 | | | A9E2Z7S2 | |
| | | A9E21f4cz | | A9E2r12 | | | A9E2Z7S2a | |
| | | | | A9E2r12B | | | A9E2Z7S2b | |
| | | | | A9E2r15 | | | — | |
| | | | | | | | A9E2Z7S3 | |
| | | | | | | | A9E2Z7S3a | |
| | | | | | | | — | |
| | | | | | | | A9E2Z7S4 | |
| | | | | | | | A9E2Z7S4a | |
| System G Z8 | 157 to 168 | A9E21f1az | 227-230 | (A9E2r7C) | (256); | 277-282 | A9E2Z8S2f | 304-319 |
| | | A9E21f2bz | | A9E2r8 | 257-261 | | A9E2Z8S21f | |
| | | A9E21f3dz | | A9E2r10 | | | A9E2Z8S28f | |
| | | A9E21f4cz | | A9E2r12 | | | — | |
| | | | | A9E2r12B | | | A9E2Z8S56f | |
| | | | | A9E2r15 | | | A9E2Z8S58f | |
| | | | | | | | A9E2Z8S61f | |
| | | | | | | | — | |
| | | | | | | | A9E2Z8S101f | |
| | | | | | | | A9E2Z8S105f | |
| | | | | | | | A9E2Z8S127f | |
| | | | | | | | — | |
| | | | | | | | A9E2Z8S146f | |
| | | | | | | | A9E2Z8S155f | |
| | | | | | | | A9E2Z8S156f | |
| | | | | | | | — | |
| | | | | | | | A9E2Z8S210f | |
| | | | | | | | — | |

TABLE 35-continued

| A9 SYSTEMS | | | | | | | | |
|---|---|---|---|---|---|---|---|---|
| | HPV16 reference amplicon | Forward Primer | | Reverse Primer | | Probe | Beacon Probe | |
| A9 | SEQ ID NO: | Name | SEQ ID NO: | Name | SEQ ID NO: | SEQ ID NO: | Name | SEQ ID NO: |
| | | | | | | | A9E2Z8S231f | |
| | | | | | | | A9E2Z8S236f | |
| | | | | | | | A9E2Z8S250f | |
| System H | 169 to 210 | (A9E2f5) | (231); | (A9E2r7B) | (262); | 277-282 | A9E2Z8S2f | 304-319 |
| | | A9E2f6 | 232; | (A9E2r8) | (257); | | A9E2Z8S21f | |
| | | (A9E2f7) | (233); | (A9E2r9) | (263); | | A9E2Z8S28f | |
| | | A9E2f8 | 234; | (A9E2r12) | (259); | | — | |
| | | A9E2f9 | 235; | (A9E2r7C) | (256); | | A9E2Z8S56f | |
| | | (A9E2f10) | (236); | A9E2r10 | 258; | | A9E2Z8S58f | |
| | | (A9E2f10b) | (237); | A9E2r12B | 264; | | A9E2Z8S61f | |
| | | (A9E2f11) | (238); | A9E2r15 | 261; | | — | |
| | | (A9E2f12) | (239) | A9E2r16 | 265 | | A9E2Z8S101f | |
| | | | | | | | A9E2Z8S105f | |
| | | | | | | | A9E2Z8S127f | |
| | | | | | | | — | |
| | | | | | | | A9E2Z8S146f | |
| | | | | | | | A9E2Z8S155f | |
| | | | | | | | A9E2Z8S156f | |
| | | | | | | | — | |
| | | | | | | | A9E2Z8S210f | |
| | | | | | | | — | |
| | | | | | | | A9E2Z8S231f | |
| | | | | | | | A9E2Z8S236f | |
| | | | | | | | A9E2Z8S250f | |

Those primers which are between brackets are optional and/or equivalent and/or alternative primers.

TABLE 36

| A5 Systems A to C: sequence aligment mismach evaluation<br>Reference of sequence: HPV 56->ref\|NC_001594.1\| | | | | | | | | | | |
|---|---|---|---|---|---|---|---|---|---|---|
| | | System A | | | System B | | | System C | | |
| N°HPV | Group | forward primer SEQ ID NO: 6 A5E6f1 | reverse primer SEQ ID NO: 11 A5E6r1 | probe SEQ ID NO: 20 A5E6s1 | forward primer SEQ ID NO: 7 A5E6f2 | reverse primer SEQ ID NO: 12 A5E6r2 | probe SEQ ID NO: 22 A5E6s2 | forward primer SEQ ID NO: 8 A5E6f3 | reverse primer SEQ ID NO: 13 A5E6r3 | probe SEQ ID NO: 23 A5E6s3 |
| 51 | A5 | 0 | 0 | 0 | 0 | 0 | 0 | 0 | 0 | 0 |
| 26 | A5 | 7 | 11 | 8 | 7 | 8 | 7 | 5 | 6 | 4 |
| 69 | A5 | 8 | 9 | 8 | 10 | 7 | 9 | 6 | 7 | 6 |
| 82 | A5 | 1 | 4 | 3 | 4 | 4 | 1 | 3 | 0 | 5 |
| 56 | A6 | 12 | 13 | 10 | 9 | 12 | 12 | 10 | 13 | 8 |
| 30 | A6 | 12 | 10 | 8 | 6 | 10 | 15 | 11 | 13 | 8 |
| 53 | A6 | 12 | 11 | 11 | 6 | 11 | 15 | 9 | 13 | 6 |
| 66 | A6 | 12 | 14 | 10 | 8 | 13 | 13 | 10 | 13 | 8 |
| 18 | A7 | 7 | 18 | 11 | 9 | 18 | 7 | 18 | 7 | 13 |
| 39 | A7 | 10 | 16 | 7 | 8 | 16 | 11 | 18 | 10 | 11 |
| 45 | A7 | 9 | 16 | 11 | 10 | 17 | 10 | 19 | 8 | 13 |
| 59 | A7 | 9 | 17 | 7 | 9 | 16 | 12 | 18 | 9 | 12 |
| 68 | A7 | 12 | 16 | 10 | 8 | 16 | 12 | 16 | 11 | 10 |
| 85 | A7 | 9 | 17 | 9 | 11 | 16 | 10 | 17 | 9 | 14 |
| 70 | A7 | 11 | 17 | 11 | 9 | 16 | 11 | 16 | 10 | 12 |
| 16 | A9 | 12 | 13 | 9 | 8 | 14 | 12 | 16 | 12 | 12 |
| 16 | A9 | 12 | 13 | 9 | 8 | 14 | 13 | 16 | 12 | 12 |
| 31 | A9 | 12 | 13 | 9 | 11 | 14 | 13 | 16 | 12 | 14 |
| 33 | A9 | 14 | 15 | 11 | 11 | 15 | 13 | 17 | 13 | 13 |
| 35 | A9 | 14 | 14 | 12 | 9 | 15 | 15 | 16 | 14 | 12 |
| 52 | A9 | 14 | 16 | 10 | 11 | 15 | 11 | 17 | 13 | 13 |
| 58 | A9 | 14 | 14 | 9 | 9 | 14 | 14 | 17 | 14 | 12 |
| 67 | A9 | 13 | 15 | 8 | 10 | 15 | 13 | 17 | 13 | 12 |
| 54 | A | 14 | 12 | 14 | 12 | 12 | 15 | 21 | 13 | |
| 42 | A1 | 13 | 10 | 10 | 11 | 10 | 15 | 19 | 13 | 13 |
| 32 | A1 | 13 | 11 | 9 | 13 | 11 | 15 | 18 | 13 | 13 |
| 61 | A3 | 11 | 19 | 13 | 9 | 20 | 14 | 18 | 12 | 13 |
| 72 | A3 | 9 | 20 | 14 | 7 | 20 | 13 | 21 | 10 | 14 |
| 89 | A3 | 16 | 18 | 12 | 8 | 18 | 19 | 21 | 16 | 13 |
| 86 | A3 | 12 | 18 | 11 | 11 | 19 | 14 | 21 | 13 | 16 |

TABLE 36-continued

A5 Systems A to C: sequence aligment mismach evaluation
Reference of sequence: HPV 56->ref|NC_001594.1|

| | | System A | | | System B | | | System C | | |
|---|---|---|---|---|---|---|---|---|---|---|
| N°HPV | Group | forward primer SEQ ID NO: 6 A5E6f1 | reverse primer SEQ ID NO: 11 A5E6r1 | probe SEQ ID NO: 20 A5E6s1 | forward primer SEQ ID NO: 7 A5E6f2 | reverse primer SEQ ID NO: 12 A5E6r2 | probe SEQ ID NO: 22 A5E6s2 | forward primer SEQ ID NO: 8 A5E6f3 | reverse primer SEQ ID NO: 13 A5E6r3 | probe SEQ ID NO: 23 A5E6s3 |
| 87 | A3 | 13 | 18 | 12 | 11 | 19 | 15 | 21 | 14 | 16 |
| 84 | A3 | 11 | 18 | 11 | 10 | 19 | 14 | 21 | 12 | 14 |
| 83 | A3 | 13 | 18 | 15 | 9 | 19 | 17 | 21 | 13 | 15 |
| 71 | A3 | 9 | 18 | 8 | 10 | 20 | 11 | 16 | 9 | 16 |
| 90 | A3 | 11 | 18 | 11 | 7 | 19 | 15 | 17 | 12 | 15 |
| 57 | A4 | 11 | 18 | 13 | 9 | 19 | 14 | 20 | 12 | 14 |
| 57 | A4 | 12 | 18 | 13 | 8 | 19 | 14 | 20 | 12 | 14 |
| 7 | A8 | 13 | 13 | 8 | 12 | 13 | 17 | 21 | 13 | 13 |
| 40 | A8 | 14 | 12 | 9 | 10 | 12 | 20 | 21 | 14 | 12 |
| 91 | A8 | 14 | 12 | 13 | 11 | 13 | | 15 | 14 | 11 |
| 6 | A10 | 12 | 11 | 10 | 12 | 11 | 15 | 19 | 13 | 16 |
| 6 | A10 | 12 | 11 | 11 | 12 | 11 | 15 | 19 | 13 | 17 |
| 6 | A10 | 12 | 11 | 10 | 12 | 11 | 15 | 19 | 13 | 17 |
| 11 | A10 | 10 | 12 | 11 | 12 | 12 | 13 | 20 | 11 | 17 |
| 44 | A10 | 10 | 9 | 15 | 10 | 10 | 13 | 16 | 11 | 13 |
| 55 | A10 | 10 | 8 | 15 | 10 | 9 | 13 | 16 | 11 | 13 |
| 74 | A10 | 12 | 8 | 11 | 10 | 9 | 15 | 16 | 12 | 14 |
| 13 | A10 | 10 | 11 | 14 | 9 | 11 | 12 | 16 | 11 | 12 |
| 34 | A11 | 13 | | 11 | 10 | | 14 | 18 | 12 | 10 |
| 73 | A11 | 10 | | 11 | 12 | | 13 | 18 | 10 | 9 |

TABLE 37

A5 Systems D & E: sequence aligment mismach evaluation
Reference of sequence: HPV 56->ref|NC_001594.1|

| | | System D | | | System E | | |
|---|---|---|---|---|---|---|---|
| N°HPV | Group | forward primer SEQ ID NO: 9 A5E6f4 | reverse primer SEQ ID NO: 14 A5E6r4 | probe SEQ ID NO: 24 A5E6s4 | forward primer SEQ ID NO: 10 A5E6f5 | reverse primer SEQ ID NO: 15 A5E6r5 | probe SEQ ID NO: 24 A5E6s4 |
| 51 | A5 | 0 | 0 | 0 | 0 | 0 | 0 |
| 26 | A5 | 5 | 3 | 6 | 7 | 4 | 6 |
| 69 | A5 | 6 | 3 | 7 | 7 | 5 | 7 |
| 82 | A5 | 1 | 0 | 3 | 3 | 3 | 3 |
| 56 | A6 | 6 | 5 | 13 | 7 | 6 | 13 |
| 30 | A6 | 8 | 1 | 13 | 10 | 4 | 13 |
| 53 | A6 | 8 | 3 | 12 | 8 | 6 | 12 |
| 66 | A6 | 7 | 5 | 13 | 7 | 6 | 13 |
| 18 | A7 | 15 | 3 | 11 | 13 | 8 | 11 |
| 39 | A7 | 14 | 4 | 11 | 12 | 5 | 11 |
| 45 | A7 | 15 | 4 | 12 | 13 | 6 | 12 |
| 59 | A7 | 16 | 4 | 11 | 12 | 5 | 11 |
| 68 | A7 | 15 | 4 | 11 | 13 | 8 | 11 |
| 85 | A7 | 17 | 4 | 13 | 14 | 6 | 13 |
| 70 | A7 | 14 | 4 | 13 | 12 | 7 | 13 |
| 16 | A9 | 13 | 9 | 14 | 9 | 8 | 14 |
| 16 | A9 | 13 | 9 | 14 | 9 | 8 | 14 |
| 31 | A9 | 12 | 4 | 14 | 8 | 6 | 14 |
| 33 | A9 | 13 | 6 | 15 | 9 | 7 | 15 |
| 35 | A9 | 14 | 6 | 12 | 10 | 9 | 12 |
| 52 | A9 | 12 | 4 | 13 | 7 | 6 | 13 |
| 58 | A9 | 12 | 6 | 16 | 8 | 5 | 16 |
| 67 | A9 | 13 | 6 | 17 | 9 | 7 | 17 |
| 54 | A | 18 | 2 | 11 | | 14 | 11 |
| 42 | A1 | 42 | 6 | 13 | | 7 | 13 |
| 32 | A1 | 12 | 6 | 13 | | 8 | 13 |
| 61 | A3 | 15 | 10 | 12 | | 8 | 12 |
| 72 | A3 | 16 | 12 | 10 | | 9 | 10 |
| 89 | A3 | 18 | 13 | 18 | 11 | 8 | 18 |
| 86 | A3 | 17 | 10 | 14 | | 7 | 14 |
| 87 | A3 | 18 | 11 | 14 | | 7 | 14 |
| 84 | A3 | 17 | 13 | 13 | | 8 | 13 |

TABLE 37-continued

A5 Systems D & E: sequence aligment mismach evaluation
Reference of sequence: HPV 56->ref|NC_001594.1|

| | | System D | | | System E | | |
|---|---|---|---|---|---|---|---|
| N°HPV | Group | forward primer SEQ ID NO: 9 A5E6f4 | reverse primer SEQ ID NO: 14 A5E6r4 | probe SEQ ID NO: 24 A5E6s4 | forward primer SEQ ID NO: 10 A5E6f5 | reverse primer SEQ ID NO: 15 A5E6r5 | probe SEQ ID NO: 24 A5E6s4 |
| 83 | A3 | 17 | 11 | 14 | 11 | 10 | 14 |
| 71 | A3 | 17 | 15 | 11 | | 6 | 11 |
| 90 | A3 | 17 | 13 | 10 | | 8 | 10 |
| 57 | A4 | 17 | 14 | 11 | | 10 | 11 |
| 57 | A4 | 17 | 14 | 12 | | 10 | 12 |
| 7 | A8 | 24 | 3 | 11 | | 7 | 11 |
| 40 | A8 | 24 | 4 | 13 | | 6 | 13 |
| 91 | A8 | 18 | 1 | 14 | | 10 | 14 |
| 6 | A10 | 19 | 4 | 12 | | 10 | 12 |
| 6 | A10 | 20 | 4 | 12 | | 10 | 12 |
| 6 | A10 | 20 | 4 | 12 | | 10 | 12 |
| 11 | A10 | 19 | 4 | 10 | | 9 | 10 |
| 44 | A10 | 21 | 9 | 12 | | 11 | 12 |
| 55 | A10 | 21 | 9 | 12 | | 11 | 12 |
| 74 | A10 | 18 | 9 | 15 | | 10 | 15 |
| 13 | A10 | 32 | 6 | 12 | | 10 | 12 |
| 34 | A11 | 42 | 15 | 13 | 15 | 9 | 13 |
| 73 | A11 | 42 | 15 | 10 | 14 | 9 | 10 |

TABLE 38

A6 Systems A to C: sequence aligment mismach evaluation
Reference of sequence: HPV 56->ref|NC_001594.1|

| | | System A | | | System B | | | System C | | |
|---|---|---|---|---|---|---|---|---|---|---|
| N°HPV | Group | forward primer SEQ ID NO: 30 A6E6f1 | reverse primer SEQ ID NO: 35 A6E6r1 | probe SEQ ID NO: 41 A6E6s1 | forward primer SEQ ID NO: 31 A6E6f2 | reverse primer SEQ ID NO: 35 A6E6r1 | probe SEQ ID NO: 41 A6E6s1 | forward primer SEQ ID NO: 32 A6E6f3 | reverse primer SEQ ID NO: 36 A6E6r2 | probe SEQ ID NO: 42 A6E6s2 |
| 51 | A5 | 9 | 7 | 17 | 8 | 7 | 17 | 3 | 14 | 9 |
| 26 | A5 | 9 | 10 | 19 | 10 | 10 | 19 | 4 | 13 | 11 |
| 69 | A5 | 10 | 11 | 16 | 10 | 11 | 16 | 5 | 11 | 11 |
| 82 | A5 | 10 | 8 | 18 | 9 | 8 | 18 | 4 | 14 | 9 |
| 56 | A6 | 0 | 0 | 0 | 0 | 0 | 0 | 0 | 0 | 0 |
| 30 | A6 | 4 | 8 | 16 | 7 | 8 | 16 | 2 | 10 | 8 |
| 53 | A6 | 5 | 7 | 14 | 7 | 7 | 14 | 2 | 10 | 8 |
| 66 | A6 | 2 | 2 | 6 | 6 | 2 | 6 | 2 | 6 | 6 |
| 18 | A7 | 14 | 7 | 21 | 14 | 7 | 21 | 8 | 22 | 15 |
| 39 | A7 | 11 | 9 | 23 | 10 | 9 | 23 | 8 | 22 | 10 |
| 45 | A7 | 13 | 8 | 22 | 15 | 8 | 22 | 8 | 22 | 16 |
| 59 | A7 | 10 | 9 | 20 | 13 | 9 | 20 | 7 | 22 | 14 |
| 68 | A7 | 12 | 9 | 25 | 11 | 9 | 25 | 9 | 22 | 11 |
| 85 | A7 | 12 | 8 | 22 | 12 | 8 | 22 | 6 | 22 | 13 |
| 70 | A7 | 13 | 8 | 23 | 9 | 8 | 23 | 8 | 22 | 10 |
| 16 | A9 | 6 | 9 | 17 | 10 | 9 | 17 | 8 | 13 | 11 |
| 16 | A9 | 6 | 9 | 17 | 10 | 9 | 17 | 8 | 13 | 11 |
| 31 | A9 | 9 | 6 | 21 | 10 | 6 | 21 | 7 | 16 | 12 |
| 33 | A9 | 8 | 10 | 16 | 11 | 10 | 16 | 6 | 16 | 11 |
| 35 | A9 | 8 | 7 | 18 | 12 | 7 | 18 | 7 | 14 | 13 |
| 52 | A9 | 7 | 10 | 23 | 11 | 10 | 23 | 9 | 14 | 11 |
| 58 | A9 | 8 | 9 | 18 | 10 | 9 | 18 | 8 | 14 | 10 |
| 67 | A9 | 8 | 9 | 23 | 9 | 9 | 23 | 7 | 15 | 9 |
| 54 | A | 10 | 10 | 30 | 14 | 10 | 30 | 8 | 18 | 16 |
| 42 | A1 | 9 | 9 | | 11 | 9 | | 9 | 20 | 12 |
| 32 | A1 | 10 | 5 | | 9 | 5 | | 9 | 20 | 11 |
| 61 | A3 | 9 | 8 | | 11 | 8 | | 10 | 21 | 13 |
| 72 | A3 | 10 | 8 | | 13 | 8 | | 9 | 21 | 15 |
| 89 | A3 | 9 | 10 | | 10 | 10 | | 9 | 18 | 10 |
| 86 | A3 | 11 | 10 | | 9 | 10 | | 10 | 18 | 9 |
| 87 | A3 | 11 | 10 | | 10 | 10 | | 9 | 17 | 12 |
| 84 | A3 | 9 | 9 | | 10 | 9 | | 9 | 18 | 12 |
| 83 | A3 | 10 | 10 | | 10 | 10 | | 10 | 18 | 10 |
| 71 | A3 | 10 | 12 | | 9 | 12 | | 6 | 18 | 9 |
| 90 | A3 | 10 | 8 | | 11 | 8 | | 8 | 18 | 12 |
| 57 | A4 | 8 | 10 | | 10 | 10 | | 8 | 18 | 12 |
| 57 | A4 | 8 | 9 | | 9 | 9 | | 8 | 18 | 11 |
| 7 | A8 | 6 | 7 | | 11 | 7 | | 6 | 18 | 13 |
| 40 | A8 | 7 | 7 | | 10 | 7 | | 8 | 18 | 13 |
| 91 | A8 | 10 | 8 | | 12 | 8 | | 11 | 19 | 14 |
| 6 | A10 | 11 | 12 | | 14 | 12 | | 7 | 16 | 18 |
| 6 | A10 | 11 | 12 | | 14 | 12 | | 7 | 16 | 17 |
| 6 | A10 | 11 | 12 | | 14 | 12 | | 7 | 16 | 18 |
| 11 | A10 | 10 | 11 | | 13 | 11 | | 9 | 16 | 17 |
| 44 | A10 | 10 | 12 | | 11 | 12 | | 9 | 17 | 14 |
| 55 | A10 | 10 | 10 | | 12 | 10 | | 10 | 17 | 14 |
| 74 | A14 | 9 | 11 | | 12 | 11 | | 8 | 16 | 14 |
| 13 | A10 | 9 | 9 | | 12 | 9 | | 9 | 18 | 14 |
| 34 | A11 | 9 | 7 | 25 | 6 | 7 | 25 | 6 | 15 | 7 |
| 73 | A11 | 8 | 7 | 24 | 6 | 7 | 24 | 6 | 15 | 6 |

TABLE 39

A6 Systems D & E: sequence aligment mismach evaluation
Reference of sequence: HPV 56->ref|NC_001594.1|

| | | System D | | | System E | | |
|---|---|---|---|---|---|---|---|
| N°HPV | Group | forward primer SEQ ID NO: 33 A6E6f4 | reverse primer SEQ ID NO: 35 A6E6r1 | probe SEQ ID NO: 41 A6E6s1 | forward primer SEQ ID NO: 34 A6E6f5 | reverse primer SEQ ID NO: 37 A6E6r3 | probe SEQ ID NO: 44 A6E6s3 |
| 51 | A5 | 8 | 7 | 17 | | 11 | 9 |
| 26 | A5 | 10 | 10 | 19 | | 8 | 9 |

TABLE 39-continued

A6 Systems D & E: sequence aligment mismach evaluation
Reference of sequence: HPV 56->ref|NC_001594.1|

| | | System D | | | System E | | |
|---|---|---|---|---|---|---|---|
| N°HPV | Group | forward primer SEQ ID NO: 33 A6E6f4 | reverse primer SEQ ID NO: 35 A6E6r1 | probe SEQ ID NO: 41 A6E6s1 | forward primer SEQ ID NO: 34 A6E6f5 | reverse primer SEQ ID NO: 37 A6E6r3 | probe SEQ ID NO: 44 A6E6s3 |
| 69 | A5 | 11 | 11 | 16 | | 8 | 8 |
| 82 | A5 | 10 | 8 | 18 | | 9 | 9 |

TABLE 39-continued

A6 Systems D & E: sequence aligment mismach evaluation
Reference of sequence: HPV 56->ref|NC_001594.1|

| | | System D | | | System E | | |
|---|---|---|---|---|---|---|---|
| N°HPV | Group | forward primer SEQ ID NO: 33 A6E6f4 | reverse primer SEQ ID NO: 35 A6E6r1 | probe SEQ ID NO: 41 A6E6s1 | forward primer SEQ ID NO: 34 A6E6f5 | reverse primer SEQ ID NO: 37 A6E6r3 | probe SEQ ID NO: 44 A6E6s3 |
| 56 | A6 | 0 | 0 | 0 | | 0 | 0 |
| 30 | A6 | 5 | 8 | 16 | | 6 | 1 |
| 53 | A6 | 6 | 7 | 14 | | 6 | 2 |
| 66 | A6 | 3 | 2 | 6 | | 3 | 0 |
| 18 | A7 | 15 | 7 | 21 | | 13 | 12 |
| 39 | A7 | 12 | 9 | 23 | | 10 | 13 |
| 45 | A7 | 14 | 8 | 22 | | 13 | 15 |
| 59 | A7 | 12 | 9 | 20 | | 10 | 15 |
| 68 | A7 | 13 | 9 | 25 | | 10 | 12 |
| 85 | A7 | 14 | 8 | 22 | | 10 | 12 |
| 70 | A7 | 13 | 8 | 23 | | 9 | 12 |
| 16 | A9 | 6 | 9 | 17 | | 9 | |
| 16 | A9 | 6 | 9 | 17 | | 9 | |
| 31 | A9 | 9 | 6 | 21 | | 9 | |
| 33 | A9 | 7 | 10 | 16 | | 13 | |
| 35 | A9 | 8 | 7 | 18 | | 14 | |
| 52 | A9 | 6 | 10 | 23 | | 15 | |
| 58 | A9 | 7 | 9 | 18 | | 14 | |
| 67 | A9 | 7 | 9 | 23 | | 12 | |
| 54 | A | 10 | 10 | 30 | | 13 | |
| 42 | A1 | 10 | 9 | | | 13 | |
| 32 | A1 | 10 | 5 | | | 14 | |
| 61 | A3 | 10 | 8 | | | 11 | 13 |
| 72 | A3 | 11 | 8 | | | 14 | 14 |
| 89 | A3 | 10 | 10 | | | 11 | 12 |
| 86 | A3 | 12 | 10 | | | 13 | 15 |
| 87 | A3 | 12 | 10 | | | 14 | 13 |
| 84 | A3 | 10 | 9 | | | 13 | 13 |
| 83 | A3 | 11 | 10 | | | 16 | 14 |
| 71 | A3 | 10 | 12 | | | 14 | 16 |
| 90 | A3 | 10 | 8 | | | 13 | 13 |
| 57 | A4 | 9 | 10 | | | 12 | |
| 57 | A4 | 9 | 9 | | | 12 | |
| 7 | A8 | 7 | 7 | | | 12 | 14 |
| 40 | A8 | 8 | 7 | | | 8 | 14 |
| 91 | A8 | 11 | 8 | | | 14 | 14 |
| 6 | A10 | 12 | 12 | | | 14 | |
| 6 | A10 | 12 | 12 | | | 14 | |
| 6 | A10 | 12 | 12 | | | 14 | |
| 11 | A10 | 11 | 11 | | | 14 | |
| 44 | A10 | 11 | 12 | | | 13 | |
| 55 | A10 | 11 | 10 | | | 13 | |
| 74 | A10 | 10 | 11 | | | 12 | |
| 13 | A10 | 8 | 9 | | | 14 | |
| 34 | A11 | 10 | 7 | 25 | | 13 | |
| 73 | A11 | 10 | 7 | 24 | | 12 | |

TABLE 40

A7 Systems A & B: sequence aligment mismach evaluation
Reference of sequence: HPV 18 ->gi|9626069|ref|NC_001357.1|

| | | System A | | | | | | | | | | |
|---|---|---|---|---|---|---|---|---|---|---|---|---|
| | | forward primer | | | reverse primer | | | probes | | | | |
| | | SEQ ID NO: | | | | | | | | | | |
| N°HPV | Group | 68 6f1a | 69 6f2a | 70 6f3a | 79 6r1b | 80 6r2b | 81 6r3b | 102 A7E1ZAS61f | 103 A7E1ZAS63f | 104 A7E1ZAS64f | 105 A7E1ZCS40f | 106 A7E1ZBS74f |
| 51 | A5 | 4 | 5 | 4 | 7 | 5 | 5 | 5 | 5 | 4 | 4 | 9 |
| 26 | A5 | 7 | 5 | 4 | 7 | 7 | 7 | 4 | 3 | 4 | 3 | 8 |
| 69 | A5 | 5 | 6 | 6 | 7 | 7 | 6 | 4 | 3 | 4 | 3 | 8 |
| 82 | A5 | 3 | 4 | 3 | 7 | 7 | 7 | 6 | 6 | 5 | 5 | 10 |
| 56 | A6 | 5 | 5 | 3 | 5 | 8 | 9 | 5 | 6 | 7 | 6 | 9 |
| 30 | A6 | 8 | 6 | 4 | 7 | 8 | 7 | 4 | 3 | 3 | 3 | 13 |
| 53 | A6 | 8 | 4 | 6 | 6 | 7 | 8 | 6 | 6 | 4 | 5 | 10 |
| 66 | A6 | 5 | 5 | 3 | 5 | 10 | 8 | 5 | 6 | 7 | 6 | 11 |
| 18 | A7 | 0 | 2 | 2 | 1 | 5 | 6 | 0 | 3 | 4 | 1 | 4 |
| 39 | A7 | 4 | 1 | 3 | 3 | 0 | 4 | 4 | 4 | 0 | 3 | 1 |
| 45 | A7 | 2 | 0 | 2 | 1 | 3 | 6 | 1 | 2 | 3 | 0 | 6 |
| 59 | A7 | 3 | 2 | 0 | 6 | 4 | 0 | 3 | 0 | 4 | 2 | 5 |
| 68 | A7 | 1 | 2 | 2 | 4 | 1 | 3 | 2 | 2 | 2 | 1 | 0 |
| 85 | A7 | 1 | 3 | 3 | 5 | 2 | 4 | 5 | 3 | 3 | 4 | 3 |
| 70 | A7 | 3 | 5 | 3 | 5 | 2 | 2 | 6 | 4 | 4 | 5 | 2 |
| 16 | A9 | 2 | 2 | 4 | 5 | 7 | 5 | 7 | 4 | 7 | 6 | 9 |
| 16 | A9 | 3 | 3 | 3 | 5 | 7 | 5 | 7 | 4 | 7 | 6 | 9 |
| 31 | A9 | 3 | 5 | 2 | 6 | 7 | 6 | 8 | 5 | 7 | 7 | 10 |
| 33 | A9 | 4 | 5 | 3 | 5 | 3 | 5 | 7 | 4 | 5 | 6 | 7 |
| 35 | A9 | 4 | 5 | 3 | 6 | 7 | 5 | 5 | 3 | 5 | 4 | 10 |
| 52 | A9 | 4 | 3 | 3 | 5 | 5 | 6 | 5 | 3 | 3 | 4 | 9 |
| 58 | A9 | 3 | 5 | 3 | 6 | 4 | 4 | 5 | 2 | 4 | 4 | 8 |
| 67 | A9 | 2 | 4 | 2 | 5 | 4 | 5 | 5 | 3 | 4 | 4 | 6 |
| 54 | A | 7 | 9 | 8 | 10 | 9 | 9 | 9 | 9 | 9 | 9 | 10 |
| 42 | A1 | 3 | 7 | 5 | 4 | 6 | 6 | 7 | 4 | 4 | 6 | 12 |
| 32 | A1 | 4 | 6 | 6 | 7 | 7 | 7 | 7 | 4 | 5 | 6 | 12 |
| 61 | A3 | 6 | 11 | 9 | 10 | 9 | 12 | 6 | 5 | 7 | 5 | 13 |
| 72 | A3 | 4 | 10 | 7 | 11 | 9 | 13 | 5 | 5 | 6 | 6 | 13 |

TABLE 40-continued

A7 Systems A & B: sequence aligment mismach evaluation
Reference of sequence: HPV 18 ->gi|9626069|ref|NC_001357.1|

| | | | | | | | | | | | | |
|---|---|---|---|---|---|---|---|---|---|---|---|---|
| 89 | A3 | 4 | 10 | 7 | 9 | 10 | 13 | 6 | 4 | 5 | 5 | 13 |
| 86 | A3 | 9 | 9 | 9 | 10 | 9 | 12 | 6 | 6 | 7 | 7 | 12 |
| 87 | A3 | 8 | 9 | 8 | 11 | 9 | 11 | 8 | 6 | 5 | 7 | 12 |
| 84 | A3 | 5 | 9 | 7 | 12 | 12 | 14 | 5 | 4 | 6 | 4 | 12 |
| 83 | A3 | 6 | 11 | 10 | 10 | 10 | 10 | 7 | 8 | 7 | 9 | 12 |
| 71 | A3 | 10 | 13 | 12 | 8 | 6 | 7 | 6 | 5 | 7 | 5 | 13 |
| 90 | A3 | 7 | 8 | 7 | 8 | 7 | 7 | 7 | 6 | 8 | 6 | 13 |
| 57 | A4 | 10 | 12 | 11 | 7 | 9 | 12 | 6 | 9 | 8 | 7 | 14 |
| 57 | A4 | 10 | 12 | 11 | 18 | 20 | 21 | 6 | 9 | 8 | 7 | 14 |
| 7 | A8 | 6 | 9 | 7 | 9 | 9 | 8 | 5 | 3 | 4 | 4 | 14 |
| 40 | A8 | 6 | 10 | 7 | 8 | 10 | 10 | 6 | 5 | 6 | 6 | 15 |
| 91 | A8 | 7 | 8 | 8 | 9 | 10 | 9 | 7 | 5 | 5 | 6 | 15 |
| 6 | A10 | 4 | 6 | 7 | 9 | 8 | 9 | 7 | 6 | 6 | 6 | 11 |
| 6 | A10 | 4 | 6 | 7 | 9 | 8 | 9 | 7 | 6 | 6 | 6 | 11 |
| 6 | A10 | 4 | 6 | 7 | 9 | 8 | 9 | 7 | 6 | 6 | 6 | 12 |
| 11 | A10 | 4 | 8 | 7 | 6 | 9 | 12 | 6 | 6 | 3 | 5 | 10 |
| 44 | A10 | 5 | 6 | 7 | 8 | 11 | 8 | 6 | 5 | 4 | 5 | 12 |
| 55 | A10 | 6 | 7 | 8 | 9 | 11 | 9 | 6 | 5 | 4 | 5 | 12 |
| 74 | A10 | 8 | 10 | 11 | 8 | 12 | 10 | 6 | 5 | 4 | 5 | 10 |
| 13 | A10 | 4 | 5 | 5 | 9 | 9 | 9 | 4 | 6 | 3 | 5 | 9 |
| 34 | A11 | 6 | 6 | 7 | 8 | 8 | 9 | 7 | 5 | 6 | 6 | 10 |
| 73 | A11 | 4 | 4 | 6 | 9 | 6 | 10 | 7 | 5 | 6 | 6 | 6 |

| | | System B | | | | | | | | | |
|---|---|---|---|---|---|---|---|---|---|---|---|
| | | forward primer | | | reverse primer | | probes | | | | |
| | | SEQ ID NO: | | | | | | | | | |
| N°HPV | Group | 71<br>15f1a | 72<br>15f2a | 73<br>15f3d | 82<br>15r1a | 83<br>15r2b | 107<br>A7E1ZBS26f | 106<br>A7E1ZBS74f | 108<br>A7E1ZBS79f | 109<br>A7E1ZBS80f | 110<br>A7E1ZBS27f |
| 51 | A5 | 4 | 5 | 6 | 5 | 3 | 6 | 9 | 8 | 8 | 6 |
| 26 | A5 | 7 | 5 | 8 | 4 | 3 | 7 | 8 | 9 | 9 | 7 |
| 69 | A5 | 5 | 6 | 8 | 4 | 3 | 6 | 8 | 8 | 8 | 7 |
| 82 | A5 | 3 | 4 | 6 | 6 | 4 | 7 | 10 | 5 | 5 | 9 |
| 56 | A6 | 5 | 5 | 9 | 5 | 6 | 7 | 9 | 10 | 10 | 7 |
| 30 | A6 | 8 | 5 | 11 | 4 | 3 | 8 | 13 | 10 | 10 | 10 |
| 53 | A6 | 8 | 7 | 7 | 6 | 4 | 10 | 10 | 10 | 10 | 10 |
| 66 | A6 | 5 | 5 | 9 | 5 | 6 | 8 | 11 | 12 | 12 | 8 |
| 18 | A7 | 0 | 3 | 4 | 0 | 2 | 0 | 4 | 6 | 6 | 2 |
| 39 | A7 | 4 | 5 | 0 | 4 | 2 | 8 | 1 | 4 | 4 | 8 |
| 45 | A7 | 2 | 3 | 2 | 1 | 1 | 1 | 6 | 8 | 8 | 0 |
| 59 | A7 | 3 | 0 | 5 | 2 | 2 | 5 | 5 | 0 | 0 | 7 |
| 68 | A7 | 1 | 3 | 4 | 2 | 0 | 6 | 0 | 5 | 5 | 6 |
| 85 | A7 | 1 | 4 | 4 | 4 | 3 | 7 | 3 | 6 | 6 | 7 |
| 70 | A7 | 3 | 3 | 6 | 5 | 4 | 8 | 2 | 5 | 5 | 8 |
| 16 | A9 | 2 | 5 | 4 | 6 | 6 | 7 | 9 | 9 | 9 | 7 |
| 16 | A9 | 3 | 4 | 5 | 6 | 6 | 7 | 9 | 9 | 9 | 7 |
| 31 | A9 | 3 | 1 | 6 | 7 | 7 | 7 | 10 | 10 | 10 | 8 |
| 33 | A9 | 4 | 4 | 7 | 6 | 6 | 8 | 7 | 8 | 8 | 8 |
| 35 | A9 | 4 | 5 | 8 | 4 | 3 | 9 | 10 | 8 | 8 | 10 |
| 52 | A9 | 4 | 4 | 5 | 4 | 3 | 7 | 9 | 8 | 8 | 8 |
| 58 | A9 | 3 | 4 | 7 | 4 | 4 | 9 | 8 | 9 | 9 | 9 |
| 67 | A9 | 2 | 3 | 6 | 4 | 3 | 7 | 6 | 7 | 7 | 7 |
| 54 | A | 9 | 6 | 8 | 8 | 9 | 6 | 10 | 9 | 9 | 8 |
| 42 | A1 | 5 | 5 | 6 | 6 | 6 | 7 | 12 | 11 | 11 | 9 |
| 32 | A1 | 6 | 6 | 5 | 6 | 6 | 7 | 12 | 10 | 10 | 8 |
| 61 | A3 | 8 | 6 | 8 | 5 | 6 | 11 | 13 | 13 | 13 | 12 |
| 72 | A3 | 6 | 5 | 8 | 4 | 5 | 13 | 13 | 11 | 11 | 14 |
| 89 | A3 | 6 | 5 | 8 | 5 | 4 | 10 | 13 | 11 | 11 | 12 |
| 86 | A3 | 11 | 6 | 8 | 5 | 6 | 12 | 12 | 12 | 12 | 13 |
| 87 | A3 | 10 | 5 | 9 | 7 | 6 | 10 | 12 | 12 | 12 | 11 |
| 84 | A3 | 7 | 4 | 7 | 4 | 5 | 9 | 12 | 12 | 12 | 10 |
| 83 | A4 | 8 | 6 | 7 | 6 | 8 | 10 | 12 | 13 | 13 | 12 |
| 71 | A3 | 12 | 10 | 11 | 5 | 6 | 8 | 13 | 10 | 10 | 10 |
| 90 | A3 | 9 | 6 | 8 | 6 | 7 | 8 | 13 | 10 | 10 | 10 |
| 57 | A4 | 12 | 8 | 11 | 6 | 8 | 11 | 14 | 12 | 12 | 12 |
| 57 | A4 | 12 | 8 | 11 | 6 | 8 | 11 | 14 | 12 | 12 | 12 |
| 7 | A8 | 8 | 6 | 9 | 4 | 3 | 12 | 14 | 12 | 12 | 13 |
| 40 | A8 | 8 | 6 | 9 | 5 | 5 | 11 | 15 | 10 | 10 | 12 |
| 91 | A8 | 9 | 8 | 9 | 6 | 5 | 10 | 15 | 12 | 12 | 11 |
| 6 | A10 | 6 | 7 | 3 | 7 | 6 | 8 | 11 | 11 | 11 | 8 |
| 6 | A10 | 6 | 7 | 3 | 7 | 6 | 8 | 11 | 11 | 11 | 8 |
| 6 | A10 | 6 | 7 | 3 | 7 | 6 | 8 | 12 | 11 | 11 | 8 |
| 11 | A10 | 6 | 6 | 6 | 6 | 4 | 9 | 10 | 11 | 11 | 9 |
| 44 | A10 | 7 | 6 | 5 | 6 | 5 | 8 | 12 | 11 | 11 | 10 |

TABLE 40-continued

A7 Systems A & B: sequence aligment mismach evaluation
Reference of sequence: HPV 18 ->gi|9626069|ref|NC_001357.1|

| | | | | | | | | | | | |
|---|---|---|---|---|---|---|---|---|---|---|---|
| 55 | A10 | 8 | 7 | 6 | 6 | 5 | 9 | 12 | 11 | 11 | 11 |
| 74 | A10 | 10 | 10 | 8 | 6 | 5 | 9 | 10 | 12 | 12 | 9 |
| 13 | A10 | 6 | 5 | 5 | 4 | 4 | 9 | 9 | 10 | 10 | 9 |
| 34 | A11 | 6 | 6 | 8 | 6 | 5 | 10 | 10 | 10 | 10 | 10 |
| 73 | A11 | 4 | 7 | 6 | 6 | 5 | 8 | 6 | 7 | 7 | 8 |

TABLE 41

A7 Systems C & D: sequence aligment mismach evaluation
Reference of sequence: HPV 18 ->gi|9626069|ref|NC_001357.1|

| | | System C | | | | | | | | | |
|---|---|---|---|---|---|---|---|---|---|---|---|
| | | forward primer | | | reverse primer | | probes | | | | |
| | | SEQ ID NO: | | | | | | | | | |
| N°HPV | Group | 74 A7E17f1 | 75 A7E17f2 | 76 A7E17f3 | 84 A7E17r1 | 85 A7E17r2 | 111 A7E1ZCS11f | 105 A7E1ZCS40f | 112 A7E1ZCS45f | 113 A7E1ZCS63f | 114 A7E1ZCS90f |
| 51 | A5 | 7 | 7 | 10 | 5 | 5 | 4 | 4 | 4 | 5 | 6 |
| 26 | A5 | 7 | 8 | 9 | 5 | 7 | 3 | 3 | 4 | 3 | 4 |
| 69 | A5 | 7 | 6 | 9 | 5 | 8 | 3 | 3 | 4 | 3 | 4 |
| 82 | A5 | 7 | 6 | 9 | 7 | 7 | 5 | 5 | 5 | 6 | 7 |
| 56 | A6 | 8 | 7 | 9 | 6 | 9 | 6 | 6 | 7 | 6 | 5 |
| 30 | A6 | 9 | 8 | 12 | 6 | 7 | 3 | 3 | 3 | 3 | 3 |
| 53 | A6 | 11 | 8 | 10 | 5 | 8 | 5 | 5 | 4 | 6 | 5 |
| 66 | A6 | 9 | 10 | 11 | 5 | 9 | 6 | 6 | 7 | 6 | 5 |
| 18 | A7 | 0 | 6 | 5 | 1 | 6 | 1 | 1 | 4 | 3 | 3 |
| 39 | A7 | 8 | 2 | 1 | 3 | 2 | 3 | 3 | 0 | 4 | 4 |
| 45 | A7 | 2 | 7 | 7 | 1 | 4 | 0 | 0 | 3 | 2 | 3 |
| 59 | A7 | 5 | 2 | 5 | 4 | 2 | 2 | 2 | 4 | 0 | 2 |
| 68 | A7 | 6 | 2 | 0 | 4 | 1 | 1 | 1 | 2 | 2 | 0 |
| 85 | A7 | 7 | 3 | 3 | 5 | 2 | 4 | 4 | 3 | 3 | 4 |
| 70 | A7 | 8 | 4 | 2 | 3 | 2 | 5 | 5 | 4 | 4 | 4 |
| 16 | A9 | 7 | 7 | 10 | 3 | 6 | 6 | 6 | 7 | 4 | 6 |
| 16 | A9 | 7 | 7 | 10 | 3 | 6 | 6 | 6 | 7 | 4 | 6 |
| 31 | A9 | 7 | 10 | 11 | 4 | 7 | 7 | 7 | 7 | 5 | 6 |
| 33 | A9 | 8 | 8 | 8 | 5 | 3 | 6 | 6 | 5 | 4 | 4 |
| 35 | A9 | 9 | 5 | 10 | 4 | 6 | 4 | 4 | 5 | 3 | 4 |
| 52 | A9 | 8 | 8 | 10 | 6 | 5 | 4 | 4 | 3 | 3 | 4 |
| 58 | A9 | 9 | 9 | 9 | 5 | 3 | 4 | 4 | 4 | 2 | 4 |
| 67 | A9 | 7 | 7 | 7 | 4 | 4 | 4 | 4 | 4 | 3 | 3 |
| 54 | A | 7 | 8 | 11 | 9 | 9 | 9 | 9 | 9 | 9 | 10 |
| 42 | A1 | 8 | 8 | 13 | 4 | 6 | 6 | 6 | 4 | 4 | 6 |
| 32 | A1 | 8 | 9 | 13 | 5 | 7 | 6 | 6 | 5 | 4 | 4 |
| 61 | A3 | 11 | 14 | 14 | 10 | 11 | 5 | 5 | 7 | 5 | 3 |
| 72 | A3 | 13 | 11 | 13 | 11 | 12 | 6 | 6 | 6 | 5 | 4 |
| 89 | A3 | 10 | 9 | 12 | 9 | 12 | 5 | 5 | 5 | 4 | 4 |
| 86 | A3 | 12 | 8 | 12 | 10 | 11 | 7 | 7 | 7 | 6 | 4 |
| 87 | A3 | 10 | 8 | 13 | 11 | 10 | 7 | 7 | 5 | 6 | 4 |
| 84 | A3 | 10 | 11 | 13 | 12 | 13 | 4 | 4 | 6 | 4 | 3 |
| 83 | A3 | 10 | 10 | 13 | 10 | 10 | 9 | 9 | 7 | 8 | 9 |
| 71 | A3 | 8 | 8 | 13 | 7 | 6 | 5 | 5 | 7 | 5 | 5 |
| 90 | A3 | 8 | 8 | 13 | 7 | 6 | 6 | 6 | 8 | 6 | 6 |
| 57 | A4 | 11 | 11 | 14 | 8 | 11 | 7 | 7 | 8 | 9 | 8 |
| 57 | A4 | 11 | 11 | 14 | 8 | 11 | 7 | 7 | 8 | 9 | 8 |
| 7 | A8 | 12 | 14 | 15 | 8 | 8 | 4 | 4 | 4 | 3 | 5 |
| 40 | A8 | 11 | 9 | 14 | 8 | 9 | 6 | 6 | 6 | 5 | 7 |

TABLE 41-continued

A7 Systems C & D: sequence aligment mismach evaluation
Reference of sequence: HPV 18 ->gi|9626069|ref|NC_001357.1|

| | | | | | | | | | | | | |
|---|---|---|---|---|---|---|---|---|---|---|---|---|
| 91 | A8 | 11 | 12 | 15 | 8 | 9 | 6 | 6 | 5 | 5 | 6 |
| 6 | A10 | 9 | 9 | 12 | 9 | 8 | 6 | 6 | 6 | 6 | 7 |
| 6 | A10 | 9 | 9 | 12 | 9 | 8 | 6 | 6 | 6 | 6 | 7 |
| 6 | A10 | 9 | 9 | 12 | 9 | 8 | 6 | 6 | 6 | 6 | 7 |
| 11 | A10 | 9 | 9 | 11 | 8 | 11 | 5 | 5 | 3 | 6 | 7 |
| 44 | A10 | 9 | 8 | 13 | 8 | 9 | 5 | 5 | 4 | 5 | 6 |
| 55 | A10 | 9 | 9 | 13 | 8 | 10 | 5 | 5 | 4 | 5 | 6 |
| 74 | A10 | 10 | 9 | 11 | 7 | 11 | 5 | 5 | 4 | 5 | 6 |
| 13 | A10 | 10 | 9 | 10 | 10 | 8 | 5 | 5 | 3 | 6 | 6 |
| 34 | A11 | 11 | 7 | 9 | 9 | 8 | 6 | 6 | 6 | 5 | 5 |
| 73 | A11 | 8 | 5 | 6 | 8 | 9 | 6 | 6 | 6 | 5 | 5 |

| | | System D | | | | | | | | | | |
|---|---|---|---|---|---|---|---|---|---|---|---|---|
| | | forward primer | | reverse primer | | probe | | | | | | |
| | | SEQ ID NO: | | | | | | | | | | |
| N°HPV | Group | 77 A7E12f1 | 78 A7E12f2 | 86 A7E12r2 | 87 A7E12r3 | 115 A7E1ZDS36f | 116 A7E1ZDS37f | 117 A7E1ZDS38f | 118 A7E1ZDS2f | 119 A7E1ZDS3f | 120 A7E1ZDS4f | 121 A7E1ZDS11f |
| 51 | A5 | 8 | 7 | 2 | 4 | 4 | 6 | 4 | 4 | 3 | 3 | 3 |
| 26 | A5 | 9 | 7 | 8 | 7 | 8 | 6 | 8 | 7 | 6 | 6 | 6 |
| 69 | A5 | 8 | 6 | 9 | 8 | 7 | 7 | 7 | 6 | 6 | 6 | 6 |
| 82 | A5 | 8 | 6 | 4 | 5 | 9 | 7 | 7 | 7 | 6 | 6 | 6 |
| 56 | A6 | 6 | 5 | 8 | 11 | 9 | 9 | 6 | 6 | 8 | 8 | 8 |
| 30 | A6 | 6 | 6 | 8 | 9 | 12 | 9 | 9 | 10 | 8 | 8 | 8 |
| 53 | A6 | 6 | 6 | 11 | 12 | 12 | 11 | 9 | 10 | 11 | 11 | 11 |
| 66 | A6 | 6 | 5 | 9 | 9 | 8 | 8 | 7 | 7 | 8 | 8 | 8 |
| 18 | A7 | 1 | 5 | 3 | 0 | 6 | 0 | 5 | 3 | 5 | 5 | 5 |
| 39 | A7 | 3 | 1 | 1 | 1 | 8 | 6 | 3 | 3 | 7 | 7 | 7 |
| 45 | A7 | 2 | 6 | 2 | 2 | 0 | 6 | 5 | 5 | 0 | 0 | 0 |
| 59 | A7 | 3 | 4 | 2 | 1 | 7 | 7 | 2 | 4 | 5 | 5 | 5 |
| 68 | A7 | 5 | 1 | 1 | 3 | 5 | 3 | 2 | 0 | 4 | 4 | 4 |
| 85 | A7 | 3 | 3 | 5 | 6 | 6 | 6 | 2 | 4 | 5 | 5 | 5 |
| 70 | A7 | 5 | 1 | 2 | 1 | 7 | 7 | 4 | 4 | 6 | 6 | 6 |
| 16 | A9 | 6 | 10 | 5 | 5 | 7 | 5 | 4 | 6 | 4 | 4 | 4 |
| 16 | A9 | 6 | 10 | 5 | 5 | 6 | 6 | 5 | 7 | 3 | 3 | 3 |
| 31 | A9 | 3 | 5 | 7 | 9 | 6 | 6 | 6 | 6 | 5 | 5 | 5 |
| 33 | A9 | 3 | 3 | 3 | 7 | 8 | 8 | 8 | 8 | 6 | 6 | 6 |
| 35 | A9 | 4 | 7 | | | 4 | 6 | 3 | 3 | 3 | 3 | 3 |
| 52 | A9 | 5 | 5 | 1 | 6 | 8 | 7 | 7 | 8 | 7 | 7 | 7 |
| 58 | A9 | 5 | 6 | 4 | 8 | 8 | 7 | 9 | 9 | 6 | 6 | 6 |
| 67 | A9 | 4 | 6 | 2 | 5 | 7 | 7 | 6 | 5 | 6 | 6 | 6 |
| 54 | A | 6 | 8 | 6 | 9 | 4 | 6 | 3 | 3 | 3 | 3 | 3 |
| 42 | A1 | 8 | 10 | 4 | 7 | 7 | 6 | 6 | 6 | 5 | 5 | 5 |
| 32 | A1 | 8 | 10 | 2 | 6 | 6 | 7 | 6 | 6 | 5 | 5 | 5 |
| 61 | A3 | 16 | 13 | 9 | 7 | 12 | 12 | 12 | 11 | 11 | 11 | 11 |
| 72 | A3 | 16 | 13 | 9 | 10 | 12 | 11 | 9 | 9 | 11 | 11 | 11 |
| 89 | A3 | 16 | 14 | 13 | 14 | 12 | 11 | 10 | 10 | 10 | 10 | 10 |

TABLE 41-continued

A7 Systems C & D: sequence aligment mismach evaluation
Reference of sequence: HPV 18 ->gi|9626069|ref|NC_001357.1|

| | | | | | | | | | | | | |
|---|---|---|---|---|---|---|---|---|---|---|---|---|
| 86 | A3 | 17 | 18 | 9 | 7 | 11 | 11 | 11 | 10 | 10 | 10 | 10 |
| 87 | A3 | 18 | 19 | 11 | 11 | 13 | 13 | 13 | 12 | 12 | 12 | 12 |
| 84 | A3 | 15 | 17 | 10 | 8 | 11 | 11 | 10 | 9 | 10 | 10 | 10 |
| 83 | A3 | 17 | 18 | 11 | 10 | 11 | 12 | 11 | 10 | 11 | 11 | 11 |
| 71 | A3 | 16 | 16 | 9 | 10 | 9 | 8 | 9 | 8 | 9 | 9 | 9 |
| 90 | A3 | 17 | 16 | 11 | 12 | 12 | 10 | 13 | 11 | 12 | 12 | 12 |
| 57 | A4 | 15 | 16 | 10 | 7 | 11 | 11 | 13 | 12 | 10 | 10 | 10 |
| 57 | A4 | 15 | 16 | 11 | 8 | 11 | 11 | 13 | 12 | 10 | 10 | 10 |
| 7 | A8 | 8 | 9 | 8 | 11 | 11 | 10 | 8 | 9 | 7 | 7 | 7 |
| 40 | A8 | 7 | 9 | 9 | 13 | 11 | 10 | 10 | 9 | 8 | 8 | 8 |
| 91 | A8 | 5 | 8 | 10 | 12 | 9 | 9 | 9 | 10 | 7 | 7 | 7 |
| 6 | A10 | 8 | 10 | 5 | 10 | 8 | 7 | 7 | 6 | 6 | 6 | 6 |
| 6 | A10 | 8 | 10 | 5 | 10 | 8 | 7 | 7 | 6 | 6 | 6 | 6 |
| 6 | A10 | 8 | 10 | 5 | 10 | 8 | 7 | 7 | 6 | 6 | 6 | 6 |
| 11 | A10 | 8 | 10 | 6 | 10 | 8 | 8 | 7 | 6 | 6 | 6 | 6 |
| 44 | A10 | 11 | 13 | 5 | 12 | 11 | 10 | 8 | 9 | 9 | 9 | 9 |
| 55 | A10 | 11 | 13 | 6 | 12 | 9 | 10 | 8 | 9 | 6 | 6 | 6 |
| 74 | A10 | 11 | 13 | 3 | 9 | 8 | 9 | 8 | 7 | 7 | 7 | 7 |
| 13 | A10 | 10 | 11 | 4 | 9 | 11 | 10 | 8 | 9 | 8 | 8 | 8 |
| 34 | A11 | 12 | 16 | 8 | 10 | 9 | 7 | 8 | 7 | 7 | 7 | 7 |
| 73 | A11 | 12 | 16 | 6 | 9 | 8 | 6 | 7 | 6 | 6 | 6 | 6 |

TABLE 42

A9 System C: sequence aligment mismach evaluation
Reference of sequence: HPV 16 ->gi|9627100|ref|NC_001526.1|

| | | forward primer | | | | | | | reverse primer | |
|---|---|---|---|---|---|---|---|---|---|---|
| N°HPV | Group | 211 A9E1f7 | 212 A9E1f8 | 213 A9E1f9 | 214 A9E1f10 | 215 A9E1f11 | 216 A9E1f12 | 217 A9E1f13 | 240 A9E1r5 | 241 A9E1r6 |
| 51 | A5 | 5 | 6 | 7 | 5 | 5 | 6 | 6 | 2 | 6 |
| 26 | A5 | 5 | 6 | 7 | 5 | 5 | 6 | 6 | 3 | 5 |
| 69 | A5 | 5 | 6 | 7 | 5 | 5 | 6 | 6 | 3 | 5 |
| 82 | A5 | 5 | 6 | 7 | 5 | 5 | 6 | 6 | 2 | 6 |
| 56 | A6 | 1 | 2 | 3 | 1 | 3 | 2 | 4 | 3 | 5 |
| 30 | A6 | 3 | 4 | 5 | 3 | 3 | 4 | 4 | 4 | 6 |
| 53 | A6 | 3 | 4 | 5 | 3 | 3 | 4 | 4 | 4 | 6 |
| 66 | A6 | 2 | 3 | 4 | 2 | 4 | 3 | 5 | 4 | 6 |
| 18 | A7 | 3 | 4 | 5 | 3 | 3 | 4 | 4 | 7 | 4 |
| 39 | A7 | 6 | 5 | 6 | 5 | 4 | 5 | 5 | 2 | 4 |
| 45 | A7 | 3 | 4 | 5 | 3 | 3 | 4 | 4 | 4 | 4 |
| 59 | A7 | 3 | 2 | 3 | 1 | 1 | 2 | 2 | 5 | 7 |
| 68 | A7 | 13 | 12 | 13 | 11 | 13 | 12 | 14 | 16 | 17 |
| 85 | A7 | 2 | 3 | 4 | 2 | 2 | 3 | 3 | 3 | 5 |
| 70 | A7 | 7 | 6 | 5 | 5 | 5 | 4 | 4 | 4 | 4 |
| 16 | A9 | 0 | 1 | 2 | 2 | 2 | 3 | 3 | 0 | 5 |
| 16 | A9 | 0 | 1 | 2 | 2 | 2 | 3 | 3 | 0 | 5 |
| 31 | A9 | 2 | 1 | 2 | 0 | 1 | 1 | 3 | 0 | 5 |
| 33 | A9 | 4 | 3 | 2 | 2 | 3 | 1 | 1 | 6 | 1 |
| 35 | A9 | 2 | 1 | 2 | 0 | 2 | 1 | 3 | 1 | 6 |
| 52 | A9 | 4 | 3 | 2 | 2 | 2 | 1 | 1 | 6 | 1 |
| 58 | A9 | 4 | 3 | 2 | 4 | 2 | 3 | 1 | 6 | 1 |
| 67 | A9 | 5 | 4 | 3 | 3 | 3 | 2 | 2 | 6 | 1 |
| 54 | A | 9 | 10 | 11 | 10 | 9 | 11 | 10 | 3 | 7 |
| 42 | A1 | 6 | 7 | 8 | 6 | 6 | 7 | 7 | 5 | 7 |
| 32 | A1 | 6 | 7 | 8 | 6 | 6 | 7 | 7 | 5 | 7 |
| 61 | A3 | 12 | 13 | 14 | 12 | 12 | 13 | 13 | 4 | 6 |
| 72 | A3 | 12 | 13 | 14 | 12 | 12 | 13 | 13 | 4 | 6 |
| 89 | A3 | 9 | 10 | 11 | 9 | 9 | 10 | 10 | 4 | 6 |
| 86 | A3 | 7 | 8 | 9 | 7 | 7 | 8 | 8 | 3 | 5 |
| 87 | A3 | 7 | 8 | 9 | 7 | 7 | 8 | 8 | 3 | 5 |
| 84 | A3 | 8 | 9 | 10 | 8 | 8 | 9 | 9 | 4 | 6 |
| 83 | A3 | 9 | 10 | 11 | 9 | 9 | 10 | 10 | 4 | 6 |
| 71 | A3 | 9 | 10 | 11 | 9 | 9 | 10 | 10 | 4 | 6 |
| 90 | A3 | 9 | 10 | 11 | 9 | 9 | 10 | 10 | 4 | 6 |
| 57 | A4 | 8 | 9 | 10 | 8 | 8 | 9 | 9 | 4 | 6 |
| 57 | A4 | 8 | 9 | 10 | 8 | 8 | 9 | 9 | 4 | 6 |
| 7 | A8 | 9 | 10 | 11 | 9 | 9 | 10 | 10 | 7 | 11 |
| 40 | A8 | 10 | 11 | 12 | 10 | 10 | 11 | 11 | 7 | 11 |
| 91 | A8 | 12 | 13 | 14 | 12 | 12 | 13 | 13 | 6 | 10 |
| 6 | A10 | 11 | 12 | 13 | 11 | 11 | 12 | 12 | 5 | 7 |
| 6 | A10 | 11 | 12 | 13 | 11 | 11 | 12 | 12 | 5 | 7 |
| 6 | A10 | 11 | 12 | 13 | 11 | 11 | 12 | 12 | 5 | 7 |

TABLE 42-continued

A9 System C: sequence aligment mismach evaluation
Reference of sequence: HPV 16 ->gi|9627100|ref|NC_001526.1|

| | | | | | | | | | | |
|---|---|---|---|---|---|---|---|---|---|---|
| 11 | A10 | 10 | 11 | 12 | 10 | 10 | 11 | 11 | 5 | 7 |
| 44 | A10 | 12 | 13 | 14 | 12 | 12 | 13 | 13 | 5 | 9 |
| 55 | A10 | 13 | 14 | 15 | 13 | 13 | 14 | 14 | 5 | 9 |
| 74 | A10 | 13 | 14 | 15 | 13 | 13 | 14 | 14 | 5 | 9 |
| 13 | A10 | 12 | 13 | 14 | 12 | 12 | 13 | 13 | 6 | 8 |
| 34 | A11 | 6 | 7 | 6 | 6 | 6 | 7 | 5 | 3 | 6 |
| 73 | A11 | 7 | 8 | 7 | 7 | 7 | 8 | 6 | 3 | 6 |

| | | probes | | | | | | | | | | | | |
|---|---|---|---|---|---|---|---|---|---|---|---|---|---|---|
| N°HPV | Group | 283 A9E1S10 | 284 A9E1S10a | 285 A9E1S11 | 286 A9E1S11a | 287 A9E1S12 | 288 A9E1S12a | 289 A9E1S12b | 290 A9E1S13a | 291 A9E1S13b | 292 A9E1S13c | 293 A9E1S14a | 294 A9E1S15a | 295 A9E1S15b |
| 51 | A5 | 4 | 4 | 4 | 4 | 4 | 4 | 4 | 3 | 3 | 3 | 3 | 4 | 4 |
| 26 | A5 | 6 | 6 | 6 | 6 | 6 | 6 | 6 | 5 | 5 | 5 | 4 | 6 | 6 |
| 69 | A5 | 6 | 6 | 6 | 6 | 6 | 6 | 6 | 5 | 5 | 5 | 4 | 6 | 6 |
| 82 | A5 | 4 | 4 | 4 | 4 | 4 | 4 | 4 | 3 | 3 | 3 | 3 | 4 | 4 |
| 56 | A6 | 3 | 3 | 3 | 3 | 4 | 4 | 4 | 3 | 3 | 3 | 1 | 4 | 4 |
| 30 | A6 | 3 | 3 | 5 | 5 | 6 | 6 | 6 | 5 | 5 | 5 | 3 | 6 | 6 |
| 53 | A6 | 2 | 2 | 4 | 4 | 5 | 5 | 5 | 4 | 4 | 4 | 2 | 5 | 5 |
| 66 | A6 | 3 | 3 | 3 | 3 | 4 | 4 | 4 | 3 | 3 | 3 | 1 | 4 | 4 |
| 18 | A7 | 9 | 9 | 9 | 9 | 10 | 10 | 10 | 10 | 10 | 10 | 9 | 11 | 11 |
| 39 | A7 | 9 | 9 | 9 | 9 | 10 | 10 | 10 | 9 | 9 | 9 | 9 | 10 | 10 |
| 45 | A7 | 9 | 9 | 9 | 9 | 10 | 10 | 10 | 13 | 13 | 13 | 11 | 13 | 13 |
| 59 | A7 | 9 | 9 | 9 | 9 | 8 | 8 | 8 | 8 | 8 | 8 | 9 | 9 | 9 |
| 68 | A7 | 17 | 17 | 17 | 17 | 17 | 17 | 17 | 20 | 20 | 20 | 18 | 22 | 22 |
| 85 | A7 | 5 | 5 | 5 | 5 | 4 | 4 | 4 | 7 | 7 | 7 | 8 | 7 | 7 |
| 70 | A7 | 9 | 9 | 9 | 9 | 10 | 10 | 10 | 8 | 8 | 8 | 8 | 9 | 9 |
| 16 | A9 | 1 | 1 | 3 | 3 | 4 | 4 | 4 | 3 | 3 | 3 | 1 | 4 | 4 |
| 16 | A9 | 1 | 1 | 3 | 3 | 4 | 4 | 4 | 3 | 3 | 3 | 1 | 4 | 4 |
| 31 | A9 | 1 | 1 | 1 | 1 | 2 | 2 | 2 | 1 | 1 | 1 | 0 | 2 | 2 |
| 33 | A9 | 1 | 1 | 3 | 3 | 4 | 4 | 4 | 4 | 4 | 4 | 3 | 4 | 4 |
| 35 | A9 | 3 | 3 | 1 | 1 | 0 | 0 | 0 | 1 | 1 | 1 | 2 | 0 | 0 |
| 52 | A9 | 0 | 0 | 2 | 2 | 3 | 3 | 3 | 3 | 3 | 3 | 2 | 3 | 3 |
| 58 | A9 | 0 | 0 | 2 | 2 | 3 | 3 | 3 | 3 | 3 | 3 | 2 | 3 | 3 |
| 67 | A9 | 1 | 1 | 3 | 3 | 4 | 4 | 4 | 4 | 4 | 4 | 3 | 4 | 4 |
| 54 | A | 9 | 9 | 11 | 11 | 11 | 11 | 11 | 12 | 12 | 12 | 11 | 13 | 13 |
| 42 | A1 | 3 | 3 | 5 | 5 | 6 | 6 | 6 | 5 | 5 | 5 | 4 | 7 | 7 |
| 32 | A1 | 4 | 4 | 6 | 6 | 6 | 6 | 6 | 5 | 5 | 5 | 5 | 7 | 7 |
| 61 | A3 | 9 | 9 | 11 | 11 | 11 | 11 | 11 | 20 | 20 | 20 | 20 | 20 | 20 |
| 72 | A3 | 9 | 9 | 11 | 11 | 10 | 10 | 10 | 19 | 19 | 19 | 19 | 19 | 19 |
| 89 | A3 | 8 | 8 | 10 | 10 | 10 | 10 | 10 | 20 | 20 | 20 | 19 | 20 | 20 |
| 86 | A3 | 9 | 9 | 11 | 11 | 11 | 11 | 11 | 21 | 21 | 21 | 19 | 22 | 22 |
| 87 | A3 | 11 | 11 | 13 | 13 | 13 | 13 | 13 | 18 | 18 | 18 | 16 | 18 | 18 |
| 84 | A3 | 11 | 11 | 13 | 13 | 13 | 13 | 13 | 18 | 18 | 18 | 17 | 19 | 19 |
| 83 | A3 | 9 | 9 | 11 | 11 | 11 | 11 | 11 | 19 | 19 | 19 | 18 | 19 | 19 |
| 71 | A3 | 7 | 7 | 9 | 9 | 10 | 10 | 10 | 13 | 13 | 13 | 11 | 14 | 14 |
| 90 | A3 | 6 | 6 | 8 | 8 | 9 | 9 | 9 | 12 | 12 | 12 | 10 | 13 | 13 |
| 57 | A4 | 4 | 4 | 6 | 6 | 7 | 7 | 7 | 11 | 11 | 11 | 10 | 13 | 13 |
| 57 | A4 | 4 | 4 | 6 | 6 | 7 | 7 | 7 | 11 | 11 | 11 | 10 | 13 | 13 |

TABLE 42-continued

A9 System C: sequence aligment mismach evaluation
Reference of sequence: HPV 16 ->gi|9627100|ref|NC_001526.1|

| | | | | | | | | | | | | | | |
|---|---|---|---|---|---|---|---|---|---|---|---|---|---|---|
| 7 | A8 | 7 | 7 | 9 | 9 | 9 | 9 | 9 | 8 | 8 | 8 | 8 | 10 | 10 |
| 40 | A8 | 9 | 9 | 11 | 11 | 11 | 11 | 11 | 10 | 10 | 10 | 9 | 12 | 12 |
| 91 | A8 | 9 | 9 | 9 | 9 | 9 | 9 | 9 | 8 | 8 | 8 | 8 | 10 | 10 |
| 6 | A10 | 5 | 5 | 7 | 7 | 7 | 7 | 7 | 8 | 8 | 8 | 8 | 9 | 9 |
| 6 | A10 | 5 | 5 | 7 | 7 | 7 | 7 | 7 | 8 | 8 | 8 | 8 | 9 | 9 |
| 6 | A10 | 6 | 6 | 8 | 8 | 8 | 8 | 8 | 9 | 9 | 9 | 8 | 10 | 10 |
| 11 | A10 | 5 | 5 | 7 | 7 | 7 | 7 | 7 | 8 | 8 | 8 | 8 | 9 | 9 |
| 44 | A10 | 6 | 6 | 8 | 8 | 8 | 8 | 8 | 7 | 7 | 7 | 7 | 9 | 9 |
| 55 | A10 | 7 | 7 | 9 | 9 | 9 | 9 | 9 | 8 | 8 | 8 | 7 | 10 | 10 |
| 74 | A10 | 6 | 6 | 8 | 8 | 8 | 8 | 8 | 7 | 7 | 7 | 7 | 9 | 9 |
| 13 | A10 | 7 | 7 | 9 | 9 | 9 | 9 | 9 | 8 | 8 | 8 | 7 | 10 | 10 |
| 34 | A11 | 3 | 3 | 5 | 5 | 4 | 4 | 4 | 3 | 3 | 3 | 3 | 4 | 4 |
| 73 | A11 | 3 | 3 | 5 | 5 | 4 | 4 | 4 | 3 | 3 | 3 | 3 | 4 | 4 |

TABLE 43

A9 System E1: sequence aligment mismach evaluation
Reference of sequemce: HPV 16 ->gi||ref|NC_001526.1|

| | | forward primer | | | reverse primer | | | | | | probes | | | | | | | |
|---|---|---|---|---|---|---|---|---|---|---|---|---|---|---|---|---|---|---|
| | | SEQ ID NO: | | | | | | | | | | | | | | | | |
| | | 218 | 219 | 220 | 242 | 243 | 244 | 245 | 246 | 247 | 296 | 297 | 298 | 299 | 300 | 301 | 302 | 303 |
| N°HPV | Group | A9E2f1 | A9E2f2 | A9E2f4 | A9E2r1 | A9E2r2 | A9E2r3 | A9E2r4 | A9E2r13 | A9E2r14 | A9E2Z7S1 | A9E2Z7S2 | A9E2Z7S2a | A9E2Z7S2b | A9E2Z7S3 | A9E2Z7S3a | A9E2Z7S4 | A9E2Z7S4a |
| 51 | A5 | 10 | 9 | 10 | 8 | 9 | 9 | 7 | 13 | 12 | 6 | 5 | 5 | 5 | 9 | 9 | 6 | 6 |
| 26 | A5 | 11 | 13 | 11 | 9 | 6 | 6 | 9 | 10 | 15 | 5 | 3 | 3 | 3 | 6 | 6 | 4 | 4 |
| 69 | A5 | 11 | 13 | 11 | 8 | 7 | 6 | 8 | 11 | 13 | 3 | 3 | 3 | 3 | 7 | 7 | 3 | 3 |
| 82 | A5 | 9 | 9 | 10 | 8 | 7 | 5 | 5 | 12 | 14 | 3 | 3 | 3 | 3 | 7 | 7 | 3 | 3 |
| 56 | A6 | 6 | 10 | 9 | 8 | 6 | 6 | 6 | 10 | 14 | 8 | 7 | 7 | 7 | 9 | 9 | 7 | 7 |
| 30 | A6 | 6 | 7 | 9 | 8 | 8 | 8 | 10 | 13 | 14 | 6 | 6 | 6 | 6 | 9 | 9 | 7 | 7 |
| 53 | A6 | 6 | 7 | 7 | 7 | 3 | 4 | 5 | 12 | 13 | 7 | 5 | 5 | 5 | 10 | 10 | 8 | 8 |
| 66 | A6 | 8 | 11 | 9 | 7 | 6 | 6 | 7 | 9 | 11 | 9 | 8 | 8 | 8 | 10 | 10 | 8 | 8 |
| 18 | A7 | 4 | 9 | 7 | 9 | 5 | 6 | 7 | 10 | 11 | 7 | 1 | 1 | 1 | 8 | 8 | 6 | 6 |
| 39 | A7 | 4 | 9 | 7 | 7 | 4 | 5 | 6 | 12 | 10 | 8 | 4 | 4 | 4 | 8 | 8 | 6 | 6 |
| 45 | A7 | 4 | 9 | 7 | 11 | 10 | 10 | 9 | 9 | 12 | 6 | 3 | 3 | 3 | 10 | 10 | 6 | 6 |
| 59 | A7 | 4 | 9 | 8 | 7 | 4 | 5 | 8 | 9 | 10 | 6 | 3 | 3 | 3 | 7 | 7 | 5 | 5 |
| 68 | A7 | 4 | 9 | 7 | 7 | 4 | 5 | 6 | 12 | 10 | 8 | 4 | 4 | 4 | 8 | 8 | 6 | 6 |
| 85 | A7 | 5 | 8 | 9 | 8 | 4 | 5 | 5 | 9 | 10 | 7 | 6 | 6 | 6 | 10 | 10 | 5 | 5 |
| 70 | A7 | 4 | 7 | 8 | 7 | 3 | 4 | 5 | 10 | 10 | 8 | 5 | 5 | 5 | 8 | 8 | 6 | 6 |
| 16 | A9 | 0 | 8 | 8 | 0 | 5 | 6 | 8 | 9 | 11 | 0 | 6 | 6 | 6 | 8 | 8 | 4 | 4 |
| 16 | A9 | 0 | 8 | 8 | 2 | 4 | 5 | 8 | 10 | 10 | 1 | 5 | 5 | 5 | 9 | 9 | 5 | 5 |
| 31 | A9 | 7 | 10 | 3 | 8 | 9 | 9 | 10 | 0 | 10 | 2 | 4 | 4 | 4 | 6 | 6 | 1 | 1 |
| 33 | A9 | 7 | 1 | 8 | 9 | 8 | 7 | 2 | 12 | 12 | 5 | 1 | 1 | 1 | 9 | 9 | 7 | 7 |
| 35 | A9 | 3 | 9 | 6 | 6 | 8 | 9 | 9 | 11 | 0 | 8 | 8 | 8 | 8 | 0 | 0 | 6 | 6 |
| 52 | A9 | 8 | 9 | 3 | 5 | 0 | 1 | 6 | 13 | 12 | 5 | 3 | 3 | 3 | 7 | 7 | 2 | 2 |
| 58 | A9 | 9 | 2 | 10 | 8 | 3 | 2 | 3 | 10 | 8 | 5 | 1 | 1 | 1 | 7 | 7 | 5 | 5 |
| 67 | A9 | 6 | 4 | 6 | 7 | 2 | 1 | 4 | 9 | 12 | 5 | 1 | 1 | 1 | 7 | 7 | 4 | 4 |
| 54 | A | 4 | 7 | 8 | 8 | 5 | 6 | 9 | 10 | 10 | 6 | 8 | 8 | 8 | 8 | 8 | 5 | 5 |
| 42 | A1 | 9 | 11 | 11 | 9 | 7 | 8 | 7 | 12 | 13 | 5 | 6 | 6 | 6 | 8 | 8 | 4 | 4 |
| 32 | A1 | 8 | 13 | 10 | 8 | 8 | 7 | 7 | 13 | 12 | 6 | 6 | 6 | 6 | 9 | 9 | 5 | 5 |
| 61 | A3 | 7 | 10 | 8 | 8 | 6 | 7 | 9 | 13 | 15 | 6 | 6 | 6 | 6 | 7 | 7 | 5 | 5 |
| 72 | A3 | 7 | 7 | 8 | 10 | 9 | 10 | 12 | 15 | 16 | 5 | 8 | 8 | 8 | 7 | 7 | 5 | 5 |
| 89 | A3 | 5 | 7 | 6 | 8 | 8 | 8 | 11 | 13 | 12 | 6 | 6 | 6 | 6 | 8 | 8 | 7 | 7 |
| 86 | A3 | 10 | 7 | 11 | 10 | 8 | 6 | 9 | 13 | 16 | 7 | 9 | 9 | 9 | 8 | 8 | 9 | 9 |
| 87 | A3 | 9 | 5 | 12 | 10 | 8 | 7 | 10 | 15 | 15 | 7 | 8 | 8 | 8 | 7 | 7 | 8 | 8 |
| 84 | A3 | 9 | 7 | 10 | 11 | 11 | 9 | 11 | 11 | 14 | 8 | 9 | 9 | 9 | 8 | 8 | 10 | 10 |
| 83 | A3 | 9 | 10 | 9 | 7 | 10 | 10 | 9 | 11 | 11 | 7 | 8 | 8 | 8 | 9 | 9 | 8 | 8 |
| 71 | A3 | 7 | 7 | 8 | 9 | 9 | 9 | 12 | 16 | 15 | 7 | 7 | 7 | 7 | 9 | 9 | 7 | 7 |
| 90 | A3 | 9 | 10 | 9 | 12 | 13 | 11 | 11 | 13 | 13 | 9 | 8 | 8 | 8 | 9 | 9 | 9 | 9 |
| 57 | A4 | 13 | 10 | 11 | 9 | 10 | 9 | 12 | 14 | 12 | 8 | 6 | 6 | 6 | 9 | 9 | 8 | 8 |
| 57 | A4 | 13 | 8 | 11 | 9 | 10 | 9 | 12 | 15 | 13 | 8 | 6 | 6 | 6 | 9 | 9 | 8 | 8 |
| 7 | A8 | 7 | 10 | 7 | 8 | 8 | 8 | 9 | 12 | 11 | 10 | 9 | 9 | 9 | 3 | 3 | 8 | 8 |
| 40 | A8 | 8 | 11 | 5 | 9 | 11 | 10 | 9 | 12 | 11 | 10 | 9 | 9 | 9 | 4 | 4 | 9 | 9 |
| 91 | A8 | 5 | 7 | 11 | 10 | 10 | 9 | 9 | 9 | 9 | 5 | 5 | 5 | 5 | 3 | 3 | 5 | 5 |
| 6 | A10 | 8 | 9 | 9 | 9 | 6 | 5 | 8 | 11 | 11 | 8 | 7 | 7 | 7 | 11 | 11 | 8 | 8 |

TABLE 43-continued

A9 System E1: sequence aligment mismach evaluation
Reference of sequemce: HPV 16 ->gi||ref|NC_001526.1|

| | | forward primer | | | reverse primer | | | | | | probes | | | | | | | |
|---|---|---|---|---|---|---|---|---|---|---|---|---|---|---|---|---|---|---|
| | | SEQ ID NO: | | | | | | | | | | | | | | | | |
| | | 218 | 219 | 220 | 242 | 243 | 244 | 245 | 246 | 247 | 296 | 297 | 298 | 299 | 300 | 301 | 302 | 303 |
| N°HPV | Group | A9E2f1 | A9E2f2 | A9E2f4 | A9E2r1 | A9E2r2 | A9E2r3 | A9E2r4 | A9E2r13 | A9E2r14 | A9E2Z7S1 | A9E2Z7S2 | A9E2Z7S2a | A9E2Z7S2b | A9E2Z7S3 | A9E2Z7S3a | A9E2Z7S4 | A9E2Z7S4a |
| 6 | A10 | 8 | 9 | 9 | 9 | 6 | 5 | 8 | 11 | 11 | 8 | 7 | 7 | 7 | 11 | 11 | 8 | 8 |
| 6 | A10 | 8 | 9 | 9 | 9 | 6 | 5 | 8 | 11 | 11 | 8 | 7 | 7 | 7 | 11 | 11 | 8 | 8 |
| 11 | A10 | 8 | 9 | 10 | 6 | 4 | 5 | 9 | 11 | 12 | 7 | 9 | 9 | 9 | 10 | 10 | 8 | 8 |
| 44 | A10 | 8 | 9 | 10 | 6 | 6 | 5 | 5 | 13 | 13 | 5 | 9 | 9 | 9 | 7 | 7 | 8 | 8 |
| 55 | A10 | 8 | 9 | 10 | 4 | 6 | 5 | 7 | 11 | 11 | 5 | 9 | 9 | 9 | 7 | 7 | 8 | 8 |
| 74 | A10 | 9 | 9 | 11 | 8 | 5 | 4 | 5 | 12 | 12 | 4 | 7 | 7 | 7 | 8 | 8 | 6 | 6 |
| 13 | A10 | 8 | 8 | 9 | 9 | 6 | 6 | 6 | 9 | 10 | 4 | 7 | 7 | 7 | 6 | 6 | 4 | 4 |
| 34 | A11 | 9 | 7 | 9 | 8 | 7 | 8 | 9 | 11 | 16 | 6 | 6 | 6 | 6 | 7 | 7 | 5 | 5 |
| 73 | A11 | 10 | 6 | 10 | 7 | 7 | 7 | 7 | 13 | 12 | 7 | 6 | 6 | 6 | 8 | 8 | 6 | 6 |

TABLE 44

E2: sequence aligment mismach evaluation
Reference of sequence: HPV 16 ->gi||ref|NC_001526.1|

| | | forward primer | | | reverse primer | | | | | | probes | | | | | | | |
|---|---|---|---|---|---|---|---|---|---|---|---|---|---|---|---|---|---|---|
| | | SEQ ID NO: | | | | | | | | | | | | | | | | |
| | | 221 | 222 | 223 | 242 | 243 | 244 | 245 | 246 | 247 | 296 | 297 | 298 | 299 | 300 | 301 | 302 | 303 |
| N°HPC | Group | A9E2f1a | A9E2f2a | A9E2f4a | A9E2r1 | A9E2r2 | A9E2r3 | A9E2r4 | A9E2r13 | A9E2r14 | A9E2Z7S1 | A9E2Z7S2 | A9E2Z7S2a | A9E2Z7S2b | A9E2Z7S3 | A9E2Z7S3a | A9E2Z7S4 | A9E2Z7S4a |
| 51 | A5 | 11 | 9 | 11 | 8 | 9 | 9 | 7 | 13 | 12 | 6 | 5 | 5 | 5 | 9 | 9 | 6 | 6 |
| 26 | A5 | 13 | 14 | 11 | 9 | 6 | 6 | 9 | 10 | 15 | 5 | 3 | 3 | 3 | 6 | 6 | 4 | 4 |
| 69 | A5 | 12 | 13 | 12 | 8 | 7 | 6 | 8 | 11 | 13 | 3 | 3 | 3 | 3 | 7 | 7 | 3 | 3 |
| 82 | A5 | 10 | 9 | 11 | 8 | 7 | 5 | 5 | 12 | 14 | 3 | 3 | 3 | 3 | 7 | 7 | 3 | 3 |
| 56 | A6 | 7 | 10 | 10 | 8 | 6 | 6 | 6 | 10 | 14 | 8 | 7 | 7 | 7 | 9 | 9 | 7 | 7 |
| 30 | A6 | 7 | 7 | 10 | 8 | 8 | 8 | 10 | 13 | 14 | 6 | 6 | 6 | 6 | 9 | 9 | 7 | 7 |
| 53 | A6 | 7 | 7 | 8 | 7 | 3 | 4 | 5 | 12 | 13 | 7 | 5 | 5 | 5 | 10 | 10 | 8 | 8 |
| 66 | A6 | 9 | 11 | 10 | 7 | 6 | 6 | 7 | 9 | 11 | 9 | 8 | 8 | 8 | 10 | 10 | 8 | 8 |
| 18 | A7 | 5 | 9 | 8 | 9 | 5 | 6 | 7 | 10 | 11 | 7 | 1 | 1 | 1 | 8 | 8 | 6 | 6 |
| 39 | A7 | 5 | 9 | 8 | 7 | 4 | 5 | 6 | 12 | 10 | 8 | 4 | 4 | 4 | 8 | 8 | 6 | 6 |
| 45 | A7 | 6 | 10 | 7 | 11 | 10 | 10 | 9 | 9 | 12 | 6 | 3 | 3 | 3 | 10 | 10 | 6 | 6 |
| 59 | A7 | 6 | 10 | 8 | 7 | 4 | 5 | 8 | 9 | 10 | 6 | 3 | 3 | 3 | 7 | 7 | 5 | 5 |
| 68 | A7 | | | | 7 | 4 | 5 | 6 | 12 | 10 | 8 | 4 | 4 | 4 | 8 | 8 | 6 | 6 |
| 85 | A7 | 7 | 9 | 9 | 8 | 4 | 5 | 5 | 9 | 10 | 7 | 6 | 6 | 6 | 10 | 10 | 5 | 5 |
| 70 | A7 | 5 | 7 | 9 | 7 | 3 | 4 | 5 | 10 | 10 | 8 | 5 | 5 | 5 | 8 | 8 | 6 | 6 |
| 16 | A9 | 1 | 8 | 9 | 0 | 5 | 6 | 8 | 9 | 11 | 0 | 6 | 6 | 6 | 8 | 8 | 4 | 4 |
| 16 | A9 | 1 | 8 | 9 | 2 | 4 | 5 | 8 | 10 | 10 | 1 | 5 | 5 | 5 | 9 | 9 | 5 | 5 |
| 31 | A9 | 7 | 11 | 3 | 8 | 9 | 9 | 10 | 0 | 10 | 2 | 4 | 4 | 4 | 6 | 6 | 1 | 1 |
| 33 | A9 | 8 | 1 | 9 | 9 | 8 | 7 | 2 | 12 | 12 | 5 | 1 | 1 | 1 | 9 | 9 | 7 | 7 |
| 35 | A9 | 2 | 9 | 7 | 6 | 8 | 9 | 9 | 11 | 0 | 8 | 8 | 8 | 8 | 0 | 0 | 6 | 6 |
| 52 | A9 | 9 | 10 | 3 | 5 | 0 | 1 | 6 | 13 | 12 | 5 | 3 | 3 | 3 | 7 | 7 | 2 | 2 |
| 58 | A9 | 10 | 2 | 11 | 8 | 3 | 2 | 3 | 10 | 8 | 5 | 1 | 1 | 1 | 7 | 7 | 5 | 5 |
| 67 | A9 | 7 | 4 | 7 | 7 | 2 | 1 | 4 | 9 | 12 | 5 | 1 | 1 | 1 | 7 | 7 | 4 | 4 |
| 54 | A | 6 | 8 | 8 | 8 | 5 | 6 | 9 | 10 | 10 | 6 | 8 | 8 | 8 | 8 | 8 | 5 | 5 |
| 42 | A1 | 10 | 11 | 12 | 9 | 7 | 8 | 7 | 12 | 13 | 5 | 6 | 6 | 6 | 8 | 8 | 4 | 4 |
| 32 | A1 | 10 | 14 | 10 | 8 | 8 | 7 | 7 | 13 | 12 | 6 | 6 | 6 | 6 | 9 | 9 | 5 | 5 |
| 61 | A3 | 9 | 11 | 8 | 8 | 6 | 7 | 9 | 13 | 15 | 6 | 6 | 6 | 6 | 7 | 7 | 5 | 5 |
| 72 | A3 | 8 | 7 | 9 | 10 | 9 | 10 | 12 | 15 | 16 | 5 | 8 | 8 | 8 | 7 | 7 | 5 | 5 |
| 89 | A3 | 7 | 8 | 6 | 8 | 8 | 8 | 11 | 13 | 12 | 6 | 6 | 6 | 6 | 8 | 8 | 7 | 7 |
| 86 | A3 | 12 | 8 | 11 | 10 | 8 | 8 | 9 | 13 | 16 | 7 | 9 | 9 | 9 | 8 | 8 | 9 | 9 |
| 87 | A3 | 11 | 6 | 12 | 10 | 8 | 7 | 10 | 15 | 15 | 7 | 8 | 8 | 8 | 7 | 7 | 8 | 8 |
| 84 | A3 | 11 | 8 | 10 | 11 | 11 | 9 | 11 | 11 | 14 | 8 | 9 | 9 | 9 | 8 | 8 | 10 | 10 |
| 83 | A3 | 11 | 11 | 9 | 7 | 10 | 10 | 9 | 11 | 11 | 7 | 8 | 8 | 8 | 9 | 9 | 8 | 8 |
| 71 | A3 | 9 | 8 | 8 | 9 | 9 | 9 | 12 | 16 | 15 | 7 | 7 | 7 | 7 | 9 | 9 | 7 | 7 |
| 90 | A3 | 11 | 11 | 9 | 12 | 13 | 11 | 11 | 13 | 13 | 9 | 8 | 8 | 8 | 9 | 9 | 9 | 9 |
| 57 | A4 | 15 | 11 | 11 | 9 | 10 | 9 | 12 | 14 | 12 | 8 | 6 | 6 | 6 | 9 | 9 | 8 | 8 |
| 57 | A4 | 15 | 9 | 11 | 9 | 10 | 9 | 12 | 15 | 13 | 8 | 6 | 6 | 6 | 9 | 9 | 8 | 8 |
| 7 | A8 | 9 | 11 | 8 | 8 | 8 | 8 | 9 | 12 | 11 | 10 | 9 | 9 | 9 | 3 | 3 | 8 | 8 |
| 40 | A8 | 8 | 12 | 6 | 9 | 11 | 10 | 9 | 12 | 11 | 10 | 9 | 9 | 9 | 4 | 4 | 9 | 9 |
| 91 | A8 | 7 | 8 | 12 | 10 | 10 | 9 | 9 | 9 | 9 | 5 | 5 | 5 | 5 | 3 | 3 | 5 | 5 |
| 6 | A10 | 8 | 10 | 10 | 9 | 6 | 5 | 8 | 11 | 11 | 8 | 7 | 7 | 7 | 11 | 11 | 8 | 8 |

TABLE 44-continued

E2: sequence aligment mismach evaluation
Reference of sequence: HPV 16 ->gi||ref|NC_001526.1|

| | | forward primer | | | reverse primer | | | | | | probes | | | | | | | |
|---|---|---|---|---|---|---|---|---|---|---|---|---|---|---|---|---|---|---|
| | | SEQ ID NO: | | | | | | | | | | | | | | | | |
| N°HPC | Group | 221 A9E2f1a | 222 A9E2f2a | 223 A9E2f4a | 242 A9E2r1 | 243 A9E2r2 | 244 A9E2r3 | 245 A9E2r4 | 246 A9E2r13 | 247 A9E2r14 | 296 A9E2Z7S1 | 297 A9E2Z7S2 | 298 A9E2Z7S2a | 299 A9E2Z7S2b | 300 A9E2Z7S3 | 301 A9E2Z7S3a | 302 A9E2Z7S4 | 303 A9E2Z7S4a |
| 6 | A10 | 8 | 10 | 10 | 9 | 6 | 5 | 8 | 11 | 11 | 8 | 7 | 7 | 7 | 11 | 11 | 8 | 8 |
| 6 | A10 | 8 | 10 | 10 | 9 | 6 | 5 | 8 | 11 | 11 | 8 | 7 | 7 | 7 | 11 | 11 | 8 | 8 |
| 11 | A10 | 8 | 10 | 11 | 6 | 4 | 5 | 9 | 11 | 12 | 7 | 9 | 9 | 9 | 10 | 10 | 8 | 8 |
| 44 | A10 | 8 | 10 | 11 | 6 | 6 | 5 | 5 | 13 | 13 | 5 | 9 | 9 | 9 | 7 | 7 | 8 | 8 |
| 55 | A10 | 8 | 10 | 11 | 4 | 6 | 5 | 7 | 11 | 11 | 5 | 9 | 9 | 9 | 7 | 7 | 8 | 8 |
| 74 | A10 | 10 | 10 | 12 | 8 | 5 | 4 | 5 | 12 | 12 | 4 | 7 | 7 | 7 | 8 | 8 | 6 | 6 |
| 13 | A10 | 8 | 9 | 10 | 9 | 6 | 6 | 6 | 9 | 10 | 4 | 7 | 7 | 7 | 6 | 6 | 4 | 4 |
| 34 | A11 | 10 | 7 | 10 | 8 | 7 | 8 | 9 | 11 | 16 | 6 | 6 | 6 | 6 | 7 | 7 | 5 | 5 |
| 73 | A11 | 11 | 6 | 11 | 7 | 7 | 7 | 7 | 13 | 12 | 7 | 6 | 6 | 6 | 8 | 8 | 6 | 6 |

TABLE 45

A9 System E3: sequence aligment mismach evaluation
Reference of sequence: HPV 16 ->gi||ref|NC_001526.1|

| | | forward primer | | | reverse primer | | | | | | | |
|---|---|---|---|---|---|---|---|---|---|---|---|---|
| | | SEQ ID NO: | | | | | | | | | | |
| N°HPV | Group | 221 A9E2f1a | 222 A9E2f2a | 223 A9E2f4a | 248 A9E21r1cz | 249 A9E21r2az | 250 A9E21r3az | 251 A9E21r4fz | 252 A9E21r5az | 253 A9E21r6az | 254 A9E21r7az | 255 A9E21r8az |
| 51 | A5 | 11 | 9 | 11 | 8 | 10 | 7 | 9 | 9 | 9 | 8 | 9 |
| 26 | A5 | 13 | 14 | 11 | 9 | 7 | 11 | 13 | 7 | 6 | 6 | 8 |
| 69 | A5 | 12 | 13 | 12 | 8 | 9 | 10 | 12 | 6 | 6 | 6 | 7 |
| 82 | A5 | 10 | 9 | 11 | 8 | 10 | 5 | 12 | 6 | 5 | 6 | 7 |
| 56 | A6 | 7 | 10 | 10 | 8 | 8 | 8 | 14 | 6 | 6 | 6 | 5 |
| 30 | A6 | 7 | 7 | 10 | 8 | 11 | 12 | 14 | 9 | 8 | 8 | 10 |
| 53 | A6 | 7 | 7 | 8 | 7 | 10 | 7 | 11 | 5 | 4 | 3 | 5 |
| 66 | A6 | 9 | 11 | 10 | 7 | 8 | 9 | 11 | 6 | 6 | 6 | 6 |
| 18 | A7 | 5 | 9 | 8 | 9 | 8 | 9 | 11 | 7 | 6 | 5 | 6 |
| 39 | A7 | 5 | 9 | 8 | 7 | 9 | 8 | 8 | 6 | 5 | 4 | 6 |
| 45 | A7 | 6 | 10 | 7 | 11 | 10 | 10 | 12 | 10 | 10 | 10 | 9 |
| 59 | A7 | 6 | 10 | 8 | 7 | 8 | 10 | 9 | 6 | 5 | 4 | 6 |
| 68 | A7 | | | | | | | | | | | |
| 85 | A7 | 7 | 9 | 9 | 8 | 8 | 7 | 8 | 6 | 5 | 4 | 5 |
| 70 | A7 | 5 | 7 | 9 | 7 | 9 | 7 | 9 | 5 | 4 | 3 | 5 |
| 16 | A9 | 1 | 8 | 9 | 0 | 8 | 9 | 10 | 7 | 6 | 5 | 8 |
| 16 | A9 | 1 | 8 | 9 | 2 | 9 | 9 | 9 | 6 | 5 | 4 | 7 |
| 31 | A9 | 7 | 11 | 3 | 8 | 0 | 12 | 11 | 10 | 9 | 9 | 9 |
| 33 | A9 | 8 | 1 | 9 | 9 | 12 | 0 | 11 | 6 | 7 | 8 | 5 |
| 35 | A9 | 2 | 9 | 7 | 6 | 8 | 9 | 0 | 10 | 9 | 8 | 10 |
| 52 | A9 | 9 | 10 | 3 | 5 | 9 | 8 | 13 | 2 | 1 | 0 | 3 |
| 58 | A9 | 10 | 2 | 11 | 8 | 9 | 5 | 11 | 1 | 2 | 3 | 0 |
| 67 | A9 | 7 | 4 | 7 | 7 | 8 | 6 | 12 | 2 | 1 | 2 | 1 |
| 54 | A | 6 | 8 | 8 | 8 | 9 | 9 | 10 | 7 | 6 | 5 | 7 |
| 42 | A1 | 10 | 11 | 12 | 9 | 8 | 9 | 12 | 7 | 8 | 7 | 6 |
| 32 | A1 | 10 | 14 | 10 | 8 | 9 | 7 | 10 | 8 | 7 | 8 | 7 |
| 61 | A3 | 9 | 11 | 8 | 8 | 10 | 9 | 13 | 8 | 7 | 6 | 7 |
| 72 | A3 | 8 | 7 | 9 | 10 | 11 | 12 | 15 | 11 | 10 | 9 | 11 |
| 89 | A3 | 7 | 8 | 6 | 8 | 10 | 11 | 11 | 9 | 8 | 7 | 9 |
| 86 | A3 | 12 | 8 | 11 | 10 | 9 | 9 | 16 | 7 | 6 | 7 | 7 |
| 87 | A3 | 11 | 6 | 12 | 10 | 9 | 10 | 16 | 8 | 7 | 8 | 8 |
| 84 | A3 | 11 | 8 | 10 | 10 | 12 | 12 | 15 | 11 | 10 | 11 | 10 |
| 83 | A3 | 11 | 11 | 9 | 7 | 10 | 9 | 10 | 9 | 10 | 9 | 9 |
| 71 | A3 | 9 | 8 | 8 | 9 | 12 | 12 | 13 | 10 | 9 | 8 | 10 |
| 90 | A3 | 11 | 11 | 9 | 12 | 11 | 12 | 12 | 12 | 12 | 12 | 11 |
| 57 | A4 | 15 | 11 | 11 | 9 | 12 | 13 | 13 | 11 | 10 | 9 | 11 |
| 57 | A4 | 15 | 9 | 11 | 9 | 12 | 13 | 14 | 11 | 10 | 9 | 11 |
| 7 | A8 | 9 | 11 | 8 | 8 | 12 | 9 | 12 | 9 | 8 | 7 | 9 |
| 40 | A8 | 8 | 12 | 6 | 9 | 12 | 10 | 12 | 12 | 11 | 11 | 11 |
| 91 | A8 | 7 | 8 | 12 | 10 | 8 | 9 | 10 | 9 | 9 | 10 | 9 |
| 6 | A10 | 8 | 10 | 10 | 9 | 10 | 8 | 11 | 6 | 5 | 6 | 6 |

TABLE 45-continued

A9 System E3: sequence aligment mismach evaluation
Reference of sequence: HPV 16 ->gi||ref|NC_001526.1|

| | | | | | | | | | | | | |
|---|---|---|---|---|---|---|---|---|---|---|---|---|
| 6 | A10 | 8 | 10 | 10 | 9 | 10 | 8 | 11 | 6 | 5 | 6 | 6 |
| 6 | A10 | 8 | 10 | 10 | 9 | 10 | 8 | 11 | 6 | 5 | 6 | 6 |
| 11 | A10 | 8 | 10 | 11 | 6 | 11 | 9 | 12 | 6 | 5 | 4 | 7 |
| 44 | A10 | 8 | 10 | 11 | 6 | 11 | 5 | 13 | 6 | 5 | 6 | 6 |
| 55 | A10 | 8 | 10 | 11 | 4 | 10 | 7 | 11 | 6 | 5 | 6 | 7 |
| 74 | A10 | 10 | 10 | 12 | 8 | 10 | 5 | 12 | 5 | 4 | 5 | 4 |
| 13 | A10 | 8 | 9 | 10 | 9 | 7 | 6 | 10 | 7 | 6 | 6 | 6 |
| 34 | A11 | 10 | 7 | 10 | 8 | 7 | 9 | 13 | 9 | 8 | 7 | 8 |
| 73 | A11 | 11 | 6 | 11 | 7 | 9 | 6 | 11 | 8 | 7 | 7 | 7 |

| | | probes SEQ ID NO: | | | | | | | |
|---|---|---|---|---|---|---|---|---|---|
| N°HPV | Group | 296 A9E2Z7S1 | 297 A9E2Z7S2 | 298 A9E2Z7S2a | 299 A9E2Z7S2b | 300 A9E2Z7S3 | 301 A9E2Z7S3a | 302 A9E2Z7S4 | 303 A9E2Z7S4a |
| 51 | A5 | 6 | 5 | 5 | 5 | 9 | 9 | 6 | 6 |
| 26 | A5 | 5 | 3 | 3 | 3 | 6 | 6 | 4 | 4 |
| 69 | A5 | 3 | 3 | 3 | 3 | 7 | 7 | 3 | 3 |
| 82 | A5 | 3 | 3 | 3 | 3 | 7 | 7 | 3 | 3 |
| 56 | A6 | 8 | 7 | 7 | 7 | 9 | 9 | 7 | 7 |
| 30 | A6 | 6 | 6 | 6 | 6 | 9 | 9 | 7 | 7 |
| 53 | A6 | 7 | 5 | 5 | 5 | 10 | 10 | 8 | 8 |
| 66 | A6 | 9 | 8 | 8 | 8 | 10 | 10 | 8 | 8 |
| 18 | A7 | 7 | 1 | 1 | 1 | 8 | 8 | 6 | 6 |
| 39 | A7 | 8 | 4 | 4 | 4 | 8 | 8 | 6 | 6 |
| 45 | A7 | 6 | 3 | 3 | 3 | 10 | 10 | 6 | 6 |
| 59 | A7 | 6 | 3 | 3 | 3 | 7 | 7 | 5 | 5 |
| 68 | A7 | 8 | 4 | 4 | 4 | 8 | 8 | 6 | 6 |
| 85 | A7 | 7 | 6 | 6 | 6 | 10 | 10 | 5 | 5 |
| 70 | A7 | 8 | 5 | 5 | 5 | 8 | 8 | 6 | 6 |
| 16 | A9 | 0 | 6 | 6 | 6 | 8 | 8 | 4 | 4 |
| 16 | A9 | 1 | 5 | 5 | 5 | 9 | 9 | 5 | 5 |
| 31 | A9 | 2 | 4 | 4 | 4 | 6 | 6 | 1 | 1 |
| 33 | A9 | 5 | 1 | 1 | 1 | 9 | 9 | 7 | 7 |
| 35 | A9 | 8 | 8 | 8 | 8 | 0 | 0 | 6 | 6 |
| 52 | A9 | 5 | 3 | 3 | 3 | 7 | 7 | 2 | 2 |
| 58 | A9 | 5 | 1 | 1 | 1 | 7 | 7 | 5 | 5 |
| 67 | A9 | 5 | 1 | 1 | 1 | 7 | 7 | 4 | 4 |
| 54 | A | 6 | 8 | 8 | 8 | 8 | 8 | 5 | 5 |
| 42 | A1 | 5 | 6 | 6 | 6 | 8 | 8 | 4 | 4 |
| 32 | A1 | 6 | 6 | 6 | 6 | 9 | 9 | 5 | 5 |
| 61 | A3 | 6 | 6 | 6 | 6 | 7 | 7 | 5 | 5 |
| 72 | A3 | 5 | 8 | 8 | 8 | 7 | 7 | 5 | 5 |
| 89 | A3 | 6 | 6 | 6 | 6 | 8 | 8 | 7 | 7 |
| 86 | A3 | 7 | 9 | 9 | 9 | 8 | 8 | 9 | 9 |
| 87 | A3 | 7 | 8 | 8 | 8 | 7 | 7 | 8 | 8 |
| 84 | A3 | 8 | 9 | 9 | 9 | 8 | 8 | 10 | 10 |
| 83 | A3 | 7 | 8 | 8 | 8 | 9 | 9 | 8 | 8 |
| 71 | A3 | 7 | 7 | 7 | 7 | 9 | 9 | 7 | 7 |

TABLE 45-continued

| A9 System E3: sequence aligment mismach evaluation Reference of sequence: HPV 16 ->gi\|\|ref\|NC_001526.1\| | | | | | | | | | |
|---|---|---|---|---|---|---|---|---|---|
| 90 | A3 | 9 | 8 | 8 | 8 | 9 | 9 | 9 | 9 |
| 57 | A4 | 8 | 6 | 6 | 6 | 9 | 9 | 8 | 8 |
| 57 | A4 | 8 | 6 | 6 | 6 | 9 | 9 | 8 | 8 |
| 7 | A8 | 10 | 9 | 9 | 9 | 3 | 3 | 8 | 8 |
| 40 | A8 | 10 | 9 | 9 | 9 | 4 | 4 | 9 | 9 |
| 91 | A8 | 5 | 5 | 5 | 5 | 3 | 3 | 5 | 5 |
| 6 | A10 | 8 | 7 | 7 | 7 | 11 | 11 | 8 | 8 |
| 6 | A10 | 8 | 7 | 7 | 7 | 11 | 11 | 8 | 8 |
| 6 | A10 | 8 | 7 | 7 | 7 | 11 | 11 | 8 | 8 |
| 11 | A10 | 7 | 9 | 9 | 9 | 10 | 10 | 8 | 8 |
| 44 | A10 | 5 | 9 | 9 | 9 | 7 | 7 | 8 | 8 |
| 55 | A10 | 5 | 9 | 9 | 9 | 7 | 7 | 8 | 8 |
| 74 | A10 | 4 | 7 | 7 | 7 | 8 | 8 | 6 | 6 |
| 13 | A10 | 4 | 7 | 7 | 7 | 6 | 6 | 4 | 4 |
| 34 | A11 | 6 | 6 | 6 | 6 | 7 | 7 | 5 | 5 |
| 73 | A11 | 7 | 6 | 6 | 6 | 8 | 8 | 6 | 6 |

TABLE 46

| | | | | | | | | | | | | |
|---|---|---|---|---|---|---|---|---|---|---|---|---|
| A9 System E4: sequence aligment mismach evaluation | | | | | | | | | | | | |
| | | forward primer | | | reverse primer | | | | | | | |
| | | SEQ ID NO: | | | | | | | | | | |
| N°HPV | Group | 224 A9E2Z5Z6f1c | 225 A9E2Z5Z6f2c | 226 A9E2Z5Z6f3b | 248 A9E21r1cz | 249 A9E21r2az | 250 A9E21r3az | 251 A9E21r4fz | 252 A9E21r5az | 253 A9E21r6az | 254 A9E21r7az | 255 A9E21r8az |
| 51 | A5 | 5 | 3 | 7 | 8 | 10 | 7 | 9 | 9 | 9 | 8 | 9 |
| 26 | A5 | 7 | 7 | 5 | 9 | 7 | 11 | 13 | 7 | 6 | 6 | 8 |
| 69 | A5 | 5 | 5 | 7 | 8 | 9 | 10 | 12 | 6 | 6 | 6 | 7 |
| 82 | A5 | 5 | 4 | 7 | 8 | 10 | 5 | 12 | 6 | 5 | 6 | 7 |
| 56 | A6 | 2 | 4 | 6 | 8 | 8 | 8 | 14 | 6 | 6 | 6 | 5 |
| 30 | A6 | 2 | 2 | 6 | 8 | 11 | 12 | 14 | 9 | 8 | 8 | 10 |
| 53 | A6 | 3 | 3 | 4 | 7 | 10 | 7 | 11 | 5 | 4 | 3 | 5 |
| 66 | A6 | 4 | 5 | 6 | 7 | 8 | 9 | 11 | 6 | 6 | 6 | 6 |
| 18 | A7 | 2 | 4 | 4 | 9 | 8 | 9 | 11 | 7 | 6 | 5 | 6 |
| 39 | A7 | 2 | 4 | 4 | 7 | 9 | 8 | 8 | 6 | 5 | 4 | 6 |
| 45 | A7 | 3 | 5 | 3 | 11 | 10 | 10 | 12 | 10 | 10 | 10 | 9 |
| 59 | A7 | 3 | 5 | 3 | 7 | 8 | 10 | 9 | 6 | 5 | 4 | 6 |
| 68 | A7 | | | | | | | | | | | |
| 85 | A7 | 4 | 4 | 4 | 8 | 8 | 7 | 8 | 6 | 5 | 4 | 5 |
| 70 | A7 | 1 | 1 | 5 | 7 | 9 | 7 | 9 | 5 | 4 | 3 | 5 |
| 16 | A9 | 1 | 3 | 5 | 0 | 8 | 9 | 10 | 7 | 6 | 5 | 8 |
| 16 | A9 | 1 | 3 | 5 | 2 | 9 | 9 | 9 | 6 | 5 | 4 | 7 |
| 31 | A9 | 2 | 4 | 2 | 8 | 0 | 12 | 11 | 10 | 9 | 9 | 9 |
| 33 | A9 | 4 | 0 | 4 | 9 | 12 | 0 | 11 | 6 | 7 | 8 | 5 |
| 35 | A9 | 0 | 2 | 4 | 6 | 8 | 9 | 0 | 10 | 9 | 8 | 10 |
| 52 | A9 | 4 | 4 | 0 | 5 | 9 | 8 | 13 | 2 | 1 | 0 | 3 |
| 58 | A9 | 5 | 2 | 6 | 8 | 9 | 5 | 11 | 1 | 2 | 3 | 0 |
| 67 | A9 | 2 | 0 | 4 | 7 | 8 | 6 | 12 | 2 | 1 | 2 | 1 |
| 54 | A | 3 | 3 | 5 | 8 | 9 | 9 | 10 | 7 | 6 | 5 | 7 |
| 42 | A1 | 6 | 6 | 7 | 9 | 8 | 9 | 12 | 7 | 8 | 7 | 6 |
| 32 | A1 | 6 | 8 | 6 | 8 | 9 | 7 | 10 | 8 | 7 | 8 | 7 |
| 61 | A3 | 6 | 6 | 2 | 8 | 10 | 9 | 13 | 8 | 7 | 6 | 7 |
| 72 | A3 | 4 | 2 | 2 | 10 | 11 | 12 | 15 | 11 | 10 | 9 | 11 |
| 89 | A3 | 6 | 6 | 2 | 8 | 10 | 11 | 11 | 9 | 8 | 7 | 9 |
| 86 | A3 | 8 | 5 | 4 | 10 | 9 | 9 | 16 | 7 | 6 | 7 | 7 |
| 87 | A3 | 9 | 5 | 4 | 10 | 9 | 10 | 16 | 8 | 7 | 8 | 8 |
| 84 | A3 | 7 | 6 | 3 | 10 | 12 | 12 | 15 | 11 | 10 | 11 | 10 |
| 83 | A3 | 8 | 7 | 4 | 7 | 10 | 9 | 10 | 9 | 10 | 9 | 9 |
| 71 | A3 | 8 | 7 | 3 | 9 | 12 | 12 | 13 | 10 | 9 | 8 | 10 |
| 90 | A3 | 10 | 9 | 5 | 12 | 11 | 12 | 12 | 12 | 12 | 12 | 11 |
| 57 | A4 | 12 | 10 | 7 | 9 | 12 | 13 | 13 | 11 | 10 | 9 | 11 |
| 57 | A4 | 12 | 10 | 7 | 9 | 12 | 13 | 14 | 11 | 10 | 9 | 11 |
| 7 | A8 | 6 | 7 | 4 | 8 | 12 | 9 | 12 | 9 | 8 | 7 | 9 |
| 40 | A8 | 4 | 5 | 4 | 9 | 12 | 10 | 12 | 12 | 11 | 11 | 11 |
| 91 | A8 | 5 | 5 | 7 | 10 | 8 | 9 | 10 | 9 | 9 | 10 | 9 |
| 6 | A10 | 6 | 5 | 8 | 9 | 10 | 8 | 11 | 6 | 5 | 6 | 6 |
| 6 | A10 | 6 | 5 | 8 | 9 | 10 | 8 | 11 | 6 | 5 | 6 | 6 |

TABLE 46-continued

A9 System E4: sequence aligment mismach evaluation

| | | | | | | | | | | | | |
|---|---|---|---|---|---|---|---|---|---|---|---|---|
| 6 | A10 | 6 | 5 | 8 | 9 | 10 | 8 | 11 | 6 | 5 | 6 | 6 |
| 11 | A10 | 7 | 6 | 7 | 6 | 11 | 9 | 12 | 6 | 5 | 4 | 7 |
| 44 | A10 | 6 | 6 | 8 | 6 | 11 | 5 | 13 | 6 | 5 | 6 | 6 |
| 55 | A10 | 6 | 6 | 8 | 4 | 10 | 7 | 11 | 6 | 5 | 6 | 7 |
| 74 | A10 | 5 | 5 | 7 | 8 | 10 | 5 | 12 | 5 | 4 | 5 | 4 |
| 13 | A10 | 4 | 4 | 6 | 9 | 7 | 6 | 10 | 7 | 6 | 6 | 6 |
| 34 | A11 | 5 | 3 | 5 | 8 | 7 | 9 | 13 | 9 | 8 | 7 | 8 |
| 73 | A11 | 6 | 2 | 6 | 7 | 9 | 6 | 11 | 8 | 7 | 7 | 7 |

| | | probes SEQ ID NO: | | | | | | | |
|---|---|---|---|---|---|---|---|---|---|
| N°HPV | Group | 296 A9E2Z7S1 | 297 A9E2Z7S2 | 298 A9E2Z7S2a | 299 A9E2Z7S2b | 300 A9E2Z7S3 | 301 A9E2Z7S3a | 302 A9E2Z7S4 | 303 A9E2Z7S4a |
| 51 | A5 | 6 | 5 | 5 | 5 | 9 | 9 | 6 | 6 |
| 26 | A5 | 5 | 3 | 3 | 3 | 6 | 6 | 4 | 4 |
| 69 | A5 | 3 | 3 | 3 | 3 | 7 | 7 | 3 | 3 |
| 82 | A5 | 3 | 3 | 3 | 3 | 7 | 7 | 3 | 3 |
| 56 | A6 | 8 | 7 | 7 | 7 | 9 | 9 | 7 | 7 |
| 30 | A6 | 6 | 6 | 6 | 6 | 9 | 9 | 7 | 7 |
| 53 | A6 | 7 | 5 | 5 | 5 | 10 | 10 | 8 | 8 |
| 66 | A6 | 9 | 8 | 8 | 8 | 10 | 10 | 8 | 8 |
| 18 | A7 | 7 | 1 | 1 | 1 | 8 | 8 | 6 | 6 |
| 39 | A7 | 8 | 4 | 4 | 4 | 8 | 8 | 6 | 6 |
| 45 | A7 | 6 | 3 | 3 | 3 | 10 | 10 | 6 | 6 |
| 59 | A7 | 6 | 3 | 3 | 3 | 7 | 7 | 5 | 5 |
| 68 | A7 | 8 | 4 | 4 | 4 | 8 | 8 | 6 | 6 |
| 85 | A7 | 7 | 6 | 6 | 6 | 10 | 10 | 5 | 5 |
| 70 | A7 | 8 | 5 | 5 | 5 | 8 | 8 | 6 | 6 |
| 16 | A9 | 0 | 6 | 6 | 6 | 8 | 8 | 4 | 4 |
| 16 | A9 | 1 | 5 | 5 | 5 | 9 | 9 | 5 | 5 |
| 31 | A9 | 2 | 4 | 4 | 4 | 6 | 6 | 1 | 1 |
| 33 | A9 | 5 | 1 | 1 | 1 | 9 | 9 | 7 | 7 |
| 35 | A9 | 8 | 8 | 8 | 8 | 0 | 0 | 6 | 6 |
| 52 | A9 | 5 | 3 | 3 | 3 | 7 | 7 | 2 | 2 |
| 58 | A9 | 5 | 1 | 1 | 1 | 7 | 7 | 5 | 5 |
| 67 | A9 | 5 | 1 | 1 | 1 | 7 | 7 | 4 | 4 |
| 54 | A | 6 | 8 | 8 | 8 | 8 | 8 | 5 | 5 |
| 42 | A1 | 5 | 6 | 6 | 6 | 8 | 8 | 4 | 4 |
| 32 | A1 | 6 | 6 | 6 | 6 | 9 | 9 | 5 | 5 |
| 61 | A3 | 6 | 6 | 6 | 6 | 7 | 7 | 5 | 5 |
| 72 | A3 | 5 | 8 | 8 | 8 | 7 | 7 | 5 | 5 |
| 89 | A3 | 6 | 6 | 6 | 6 | 8 | 8 | 7 | 7 |
| 86 | A3 | 7 | 9 | 9 | 9 | 8 | 8 | 9 | 9 |
| 87 | A3 | 7 | 8 | 8 | 8 | 7 | 7 | 8 | 8 |
| 84 | A3 | 8 | 9 | 9 | 9 | 8 | 8 | 10 | 10 |
| 83 | A3 | 7 | 8 | 8 | 8 | 9 | 9 | 8 | 8 |
| 71 | A3 | 7 | 7 | 7 | 7 | 9 | 9 | 7 | 7 |
| 90 | A3 | 9 | 8 | 8 | 8 | 9 | 9 | 9 | 9 |
| 57 | A4 | 8 | 6 | 6 | 6 | 9 | 9 | 8 | 8 |

TABLE 46-continued

| A9 System E4: sequence aligment mismach evaluation | | | | | | | | | |
|---|---|---|---|---|---|---|---|---|---|
| 57 | A4 | 8 | 6 | 6 | 6 | 9 | 9 | 8 | 8 |
| 7 | A8 | 10 | 9 | 9 | 9 | 3 | 3 | 8 | 8 |
| 40 | A8 | 10 | 9 | 9 | 9 | 4 | 4 | 9 | 9 |
| 91 | A8 | 5 | 5 | 5 | 5 | 3 | 3 | 5 | 5 |
| 6 | A10 | 8 | 7 | 7 | 7 | 11 | 11 | 8 | 8 |
| 6 | A10 | 8 | 7 | 7 | 7 | 11 | 11 | 8 | 8 |
| 6 | A10 | 8 | 7 | 7 | 7 | 11 | 11 | 8 | 8 |
| 11 | A10 | 7 | 9 | 9 | 9 | 10 | 10 | 8 | 8 |
| 44 | A10 | 5 | 9 | 9 | 9 | 7 | 7 | 8 | 8 |
| 55 | A10 | 5 | 9 | 9 | 9 | 7 | 7 | 8 | 8 |
| 74 | A10 | 4 | 7 | 7 | 7 | 8 | 8 | 6 | 6 |
| 13 | A10 | 4 | 7 | 7 | 7 | 6 | 6 | 4 | 4 |
| 34 | A11 | 6 | 6 | 6 | 6 | 7 | 7 | 5 | 5 |
| 73 | A11 | 7 | 6 | 6 | 6 | 8 | 8 | 6 | 6 |

TABLE 47

A9 System F: sequence aligment mismach evaluation

| | | forward primer | | | | reverse primer | | | | | | | |
|---|---|---|---|---|---|---|---|---|---|---|---|---|---|
| | | SEQ ID NO: | | | | | | | | | | | |
| N°HPV | Group | 227 A9E21f1az | 228 A9E21f2bz | 229 A9E21f3dz | 230 A9E21f4cz | 248 A9E21r1cz | 249 A9E21r2az | 250 A9E21r3az | 251 A9E21r4fz | 252 A9E21r5az | 253 A9E21r6az | 254 A9E21r7az | 255 A9E21r8az |
| 51 | A5 | 4 | 4 | 3 | 4 | 8 | 10 | 7 | 9 | 9 | 9 | 8 | 9 |
| 26 | A5 | 3 | 3 | 5 | 2 | 9 | 7 | 11 | 13 | 7 | 6 | 6 | 8 |
| 69 | A5 | 4 | 4 | 4 | 4 | 8 | 9 | 10 | 12 | 6 | 6 | 6 | 7 |
| 82 | A5 | 6 | 6 | 4 | 6 | 8 | 10 | 5 | 12 | 6 | 5 | 6 | 7 |
| 56 | A6 | 5 | 5 | 4 | 4 | 8 | 8 | 8 | 14 | 6 | 6 | 6 | 5 |
| 30 | A6 | 6 | 4 | 2 | 5 | 8 | 11 | 12 | 14 | 9 | 8 | 8 | 10 |
| 53 | A6 | 6 | 4 | 4 | 7 | 7 | 10 | 7 | 11 | 5 | 4 | 3 | 5 |
| 66 | A6 | 3 | 3 | 3 | 4 | 7 | 8 | 9 | 11 | 6 | 6 | 6 | 6 |
| 18 | A7 | 6 | 6 | 5 | 6 | 9 | 8 | 9 | 11 | 7 | 6 | 5 | 6 |
| 39 | A7 | 6 | 6 | 5 | 6 | 7 | 9 | 8 | 8 | 6 | 5 | 4 | 6 |
| 45 | A7 | 7 | 7 | 6 | 7 | 11 | 10 | 10 | 12 | 10 | 10 | 10 | 9 |
| 59 | A7 | 9 | 8 | 6 | 9 | 7 | 8 | 10 | 9 | 6 | 5 | 4 | 6 |
| 68 | A7 | | | | | | | | | | | | |
| 85 | A7 | 5 | 3 | 5 | 4 | 8 | 8 | 7 | 8 | 6 | 5 | 4 | 5 |
| 70 | A7 | 6 | 6 | 4 | 6 | 7 | 9 | 7 | 9 | 5 | 4 | 3 | 5 |
| 16 | A9 | 0 | 2 | 5 | 3 | 0 | 8 | 9 | 10 | 7 | 6 | 5 | 8 |
| 16 | A9 | 0 | 2 | 5 | 3 | 2 | 9 | 9 | 9 | 6 | 5 | 4 | 7 |
| 31 | A9 | 3 | 1 | 5 | 5 | 8 | 0 | 12 | 11 | 10 | 9 | 9 | 9 |
| 33 | A9 | 4 | 4 | 0 | 4 | 9 | 12 | 0 | 11 | 6 | 7 | 8 | 5 |
| 35 | A9 | 2 | 0 | 4 | 5 | 6 | 8 | 9 | 0 | 10 | 9 | 8 | 10 |
| 52 | A9 | 2 | 4 | 6 | 0 | 5 | 9 | 8 | 13 | 2 | 1 | 0 | 3 |
| 58 | A9 | 4 | 4 | 2 | 3 | 8 | 9 | 5 | 11 | 1 | 2 | 3 | 0 |
| 67 | A9 | 3 | 5 | 3 | 2 | 7 | 8 | 6 | 12 | 2 | 1 | 2 | 1 |
| 54 | A | 4 | 4 | 5 | 5 | 8 | 9 | 9 | 10 | 7 | 6 | 5 | 7 |
| 42 | A1 | 7 | 8 | 6 | 6 | 9 | 8 | 9 | 12 | 7 | 8 | 7 | 6 |
| 32 | A1 | 6 | 7 | 7 | 5 | 8 | 9 | 7 | 10 | 8 | 7 | 8 | 7 |
| 61 | A3 | 4 | 2 | 6 | 3 | 8 | 10 | 9 | 13 | 8 | 7 | 6 | 7 |
| 72 | A3 | 5 | 4 | 3 | 5 | 10 | 11 | 12 | 15 | 11 | 10 | 9 | 11 |
| 89 | A3 | 7 | 6 | 8 | 8 | 8 | 10 | 11 | 11 | 9 | 8 | 7 | 9 |
| 86 | A3 | 8 | 9 | 7 | 7 | 10 | 9 | 9 | 16 | 7 | 6 | 7 | 7 |
| 87 | A3 | 8 | 8 | 6 | 6 | 10 | 9 | 10 | 16 | 8 | 7 | 8 | 8 |
| 84 | A3 | 8 | 8 | 5 | 7 | 10 | 12 | 12 | 15 | 11 | 10 | 11 | 10 |
| 83 | A3 | 7 | 5 | 6 | 6 | 7 | 10 | 9 | 10 | 9 | 10 | 9 | 9 |
| 71 | A3 | 7 | 6 | 8 | 8 | 9 | 12 | 12 | 13 | 10 | 9 | 8 | 10 |
| 90 | A3 | 8 | 6 | 10 | 7 | 12 | 11 | 12 | 12 | 12 | 12 | 12 | 11 |
| 57 | A4 | 7 | 7 | 8 | 7 | 9 | 12 | 13 | 13 | 11 | 10 | 9 | 11 |
| 57 | A4 | 6 | 6 | 9 | 6 | 9 | 12 | 13 | 14 | 11 | 10 | 9 | 11 |
| 7 | A8 | 5 | 6 | 9 | 5 | 8 | 12 | 9 | 12 | 9 | 8 | 7 | 9 |
| 40 | A8 | 6 | 6 | 6 | 7 | 9 | 12 | 10 | 12 | 12 | 11 | 11 | 11 |
| 91 | A8 | 5 | 5 | 9 | 8 | 10 | 8 | 9 | 10 | 9 | 9 | 10 | 9 |
| 6 | A10 | 6 | 8 | 5 | 6 | 9 | 10 | 8 | 11 | 6 | 5 | 6 | 6 |
| 6 | A10 | 6 | 8 | 5 | 6 | 9 | 10 | 8 | 11 | 6 | 5 | 6 | 6 |

TABLE 47-continued

A9 System F: sequence aligment mismach evaluation

| | | | | | | | | | | | | | |
|---|---|---|---|---|---|---|---|---|---|---|---|---|---|
| 6 | A10 | 7 | 8 | 5 | 7 | 9 | 10 | 8 | 11 | 6 | 5 | 6 | 6 |
| 11 | A10 | 6 | 7 | 7 | 5 | 6 | 11 | 9 | 12 | 6 | 5 | 4 | 7 |
| 44 | A10 | 3 | 5 | 7 | 4 | 6 | 11 | 5 | 13 | 6 | 5 | 6 | 6 |
| 55 | A10 | 4 | 6 | 7 | 3 | 4 | 10 | 7 | 11 | 6 | 5 | 6 | 7 |
| 74 | A10 | 6 | 6 | 6 | 5 | 8 | 10 | 5 | 12 | 5 | 4 | 5 | 4 |
| 13 | A10 | 6 | 8 | 6 | 6 | 9 | 7 | 6 | 10 | 7 | 6 | 6 | 6 |
| 34 | A11 | 6 | 6 | 5 | 6 | 8 | 7 | 9 | 13 | 9 | 8 | 7 | 8 |
| 73 | A11 | 7 | 6 | 4 | 7 | 7 | 9 | 6 | 11 | 8 | 7 | 7 | 7 |

| | | probes SEQ ID NO: | | | | | | | |
|---|---|---|---|---|---|---|---|---|---|
| N°HPV | Group | 296 A9E2Z7S1 | 297 A9E2Z7S2 | 298 A9E2Z7S2a | 299 A9E2Z7S2b | 300 A9E2Z7S3 | 301 A9E2Z7S3a | 302 A9E2Z7S4 | 303 A9E2Z7S4a |
| 51 | A5 | 5 | 5 | 5 | 5 | 9 | 9 | 6 | 6 |
| 26 | A5 | 4 | 3 | 3 | 3 | 6 | 6 | 4 | 4 |
| 69 | A5 | 2 | 3 | 3 | 3 | 7 | 7 | 3 | 3 |
| 82 | A5 | 2 | 3 | 3 | 3 | 7 | 7 | 3 | 3 |
| 56 | A6 | 7 | 7 | 7 | 7 | 9 | 9 | 7 | 7 |
| 30 | A6 | 5 | 6 | 6 | 6 | 9 | 9 | 7 | 7 |
| 53 | A6 | 7 | 5 | 5 | 5 | 10 | 10 | 8 | 8 |
| 66 | A6 | 8 | 8 | 8 | 8 | 10 | 10 | 8 | 8 |
| 18 | A7 | 6 | 1 | 1 | 1 | 8 | 8 | 6 | 6 |
| 39 | A7 | 7 | 4 | 4 | 4 | 8 | 8 | 6 | 6 |
| 45 | A7 | 5 | 3 | 3 | 3 | 10 | 10 | 6 | 6 |
| 59 | A7 | 5 | 3 | 3 | 3 | 7 | 7 | 5 | 5 |
| 68 | A7 | | 4 | 4 | 4 | 8 | 8 | 6 | 6 |
| 85 | A7 | 6 | 6 | 6 | 6 | 10 | 10 | 5 | 5 |
| 70 | A7 | 7 | 5 | 5 | 5 | 8 | 8 | 6 | 6 |
| 16 | A9 | 0 | 6 | 6 | 6 | 8 | 8 | 4 | 4 |
| 16 | A9 | 1 | 5 | 5 | 5 | 9 | 9 | 5 | 5 |
| 31 | A9 | 1 | 4 | 4 | 4 | 6 | 6 | 1 | 1 |
| 33 | A9 | 5 | 1 | 1 | 1 | 9 | 9 | 7 | 7 |
| 35 | A9 | 7 | 8 | 8 | 8 | 0 | 0 | 6 | 6 |
| 52 | A9 | 4 | 3 | 3 | 3 | 7 | 7 | 2 | 2 |
| 58 | A9 | 4 | 1 | 1 | 1 | 7 | 7 | 5 | 5 |
| 67 | A9 | 4 | 1 | 1 | 1 | 7 | 7 | 4 | 4 |
| 54 | A | 5 | 8 | 8 | 8 | 8 | 8 | 5 | 5 |
| 42 | A1 | 4 | 6 | 6 | 6 | 8 | 8 | 4 | 4 |
| 32 | A1 | 5 | 6 | 6 | 6 | 9 | 9 | 5 | 5 |
| 61 | A3 | 5 | 6 | 6 | 6 | 7 | 7 | 5 | 5 |
| 72 | A3 | 4 | 8 | 8 | 8 | 7 | 7 | 5 | 5 |
| 89 | A3 | 5 | 6 | 6 | 6 | 8 | 8 | 7 | 7 |
| 86 | A3 | 6 | 9 | 9 | 9 | 8 | 8 | 9 | 9 |
| 87 | A3 | 6 | 8 | 8 | 8 | 7 | 7 | 8 | 8 |
| 84 | A3 | 7 | 9 | 9 | 9 | 8 | 8 | 10 | 10 |
| 83 | A3 | 6 | 8 | 8 | 8 | 9 | 9 | 8 | 8 |
| 71 | A3 | 6 | 7 | 7 | 7 | 9 | 9 | 7 | 7 |
| 90 | A3 | 8 | 8 | 8 | 8 | 9 | 9 | 9 | 9 |
| 57 | A4 | 7 | 6 | 6 | 6 | 9 | 9 | 8 | 8 |

TABLE 47-continued

A9 System F: sequence aligment mismach evaluation

| | | | | | | | | | |
|---|---|---|---|---|---|---|---|---|---|
| 57 | A4 | 7 | 6 | 6 | 6 | 9 | 9 | 8 | 8 |
| 7 | A8 | 9 | 9 | 9 | 9 | 3 | 3 | 8 | 8 |
| 40 | A8 | 9 | 9 | 9 | 9 | 4 | 4 | 9 | 9 |
| 91 | A8 | 4 | 5 | 5 | 5 | 3 | 3 | 5 | 5 |
| 6 | A10 | 7 | 7 | 7 | 7 | 11 | 11 | 8 | 8 |
| 6 | A10 | 7 | 7 | 7 | 7 | 11 | 11 | 8 | 8 |
| 6 | A10 | 7 | 7 | 7 | 7 | 11 | 11 | 8 | 8 |
| 11 | A10 | 6 | 9 | 9 | 9 | 10 | 10 | 8 | 8 |
| 44 | A10 | 5 | 9 | 9 | 9 | 7 | 7 | 8 | 8 |
| 55 | A10 | 5 | 9 | 9 | 9 | 7 | 7 | 8 | 8 |
| 74 | A10 | 4 | 7 | 7 | 7 | 8 | 8 | 6 | 6 |
| 13 | A10 | 3 | 7 | 7 | 7 | 6 | 6 | 4 | 4 |
| 34 | A11 | 5 | 6 | 6 | 6 | 7 | 7 | 5 | 5 |
| 73 | A11 | 6 | 6 | 6 | 6 | 8 | 8 | 6 | 6 |

TABLE 48

A9 System GZ7: sequence aligment mismach evaluation

| | | forward primer | | | | reverse primer | | | | | |
|---|---|---|---|---|---|---|---|---|---|---|---|
| | | SEQ ID NO: | | | | | | | | | |
| N° HPV | Group | 227 A9E21f1az | 228 A9E21f2bz | 229 A9E21f3dz | 230 A9E21f4cz | 256 A9E2r7C | 257 A9E2r8 | 258 A9E2r10 | 259 A9E2r12 | 260 A9E2r12B | 261 A9E2r15 |
| 51 | A5 | 4 | 4 | 3 | 4 | 8 | 11 | 11 | 8 | 12 | 9 |
| 26 | A5 | 3 | 3 | 5 | 2 | 14 | 12 | 12 | 13 | 17 | 13 |
| 69 | A5 | 4 | 4 | 4 | 4 | 14 | 11 | 11 | 13 | 17 | 14 |
| 82 | A5 | 6 | 6 | 4 | 6 | 8 | 10 | 8 | 9 | 12 | 9 |
| 56 | A6 | 5 | 5 | 4 | 4 | 14 | 8 | 7 | 13 | 14 | 16 |
| 30 | A6 | 6 | 4 | 2 | 5 | 13 | 9 | 10 | 12 | 14 | 13 |
| 53 | A6 | 6 | 4 | 4 | 7 | 12 | 10 | 10 | 9 | 12 | 14 |
| 66 | A6 | 3 | 3 | 3 | 4 | 14 | 6 | 6 | 13 | 14 | 16 |
| 18 | A7 | 6 | 6 | 5 | 6 | 13 | 8 | 8 | 11 | 13 | 15 |
| 39 | A7 | 6 | 6 | 5 | 6 | 13 | 10 | 8 | 10 | 13 | 15 |
| 45 | A7 | 7 | 7 | 6 | 7 | 12 | 11 | 10 | 10 | 11 | 14 |
| 59 | A7 | 9 | 8 | 6 | 9 | 13 | 8 | 8 | 13 | 14 | 14 |
| 68 | A7 | | | | | 13 | 10 | 8 | 10 | 13 | 15 |
| 85 | A7 | 5 | 3 | 5 | 4 | 9 | 10 | 7 | 11 | 11 | 10 |
| 70 | A7 | 6 | 6 | 4 | 6 | 10 | 7 | 7 | 10 | 11 | 12 |
| 16 | A9 | 0 | 2 | 5 | 3 | 2 | 11 | 9 | 6 | 6 | 0 |
| 16 | A9 | 0 | 2 | 5 | 3 | 2 | 11 | 9 | 6 | 6 | 0 |
| 31 | A9 | 3 | 1 | 5 | 5 | 5 | 13 | 10 | 0 | 2 | 8 |
| 33 | A9 | 4 | 4 | 0 | 4 | 8 | 0 | 2 | 10 | 11 | 9 |
| 35 | A9 | 2 | 0 | 4 | 5 | 3 | 12 | 10 | 4 | 2 | 6 |
| 52 | A9 | 2 | 4 | 6 | 0 | 12 | 6 | 3 | 11 | 14 | 15 |
| 58 | A9 | 4 | 4 | 2 | 3 | 10 | 1 | 3 | 12 | 12 | 11 |
| 67 | A9 | 3 | 5 | 3 | 2 | 13 | 5 | 7 | 14 | 14 | 14 |
| 54 | A | 4 | 4 | 5 | 5 | 12 | 11 | 12 | 9 | 13 | 13 |
| 42 | A1 | 7 | 8 | 6 | 6 | 13 | 12 | 12 | 13 | 14 | 12 |
| 32 | A1 | 6 | 7 | 7 | 5 | 14 | 12 | 12 | 15 | 15 | 13 |
| 61 | A3 | 4 | 2 | 6 | 3 | 12 | 12 | 10 | 12 | 13 | 13 |
| 72 | A3 | 5 | 4 | 3 | 5 | 14 | 13 | 11 | 13 | 14 | 13 |
| 89 | A3 | 7 | 6 | 8 | 8 | 17 | 13 | 10 | 16 | 18 | 18 |
| 86 | A3 | 8 | 9 | 7 | 7 | 14 | 15 | 12 | 13 | 15 | 14 |
| 87 | A3 | 8 | 8 | 6 | 6 | 16 | 17 | 14 | 15 | 16 | 15 |
| 84 | A3 | 8 | 8 | 5 | 7 | 16 | 15 | 12 | 15 | 17 | 14 |
| 83 | A3 | 7 | 5 | 6 | 6 | 14 | 14 | 11 | 14 | 16 | 15 |
| 71 | A3 | 7 | 6 | 8 | 8 | 14 | 18 | 15 | 11 | 14 | 15 |
| 90 | A3 | 8 | 6 | 10 | 7 | 17 | 15 | 12 | 15 | 16 | 16 |
| 57 | A4 | 7 | 7 | 8 | 7 | 14 | 14 | 11 | 14 | 15 | 16 |
| 57 | A4 | 6 | 6 | 9 | 6 | 14 | 14 | 11 | 14 | 15 | 16 |
| 7 | A8 | 5 | 6 | 9 | 5 | 12 | 10 | 9 | 15 | 15 | 12 |
| 40 | A8 | 6 | 6 | 6 | 7 | 16 | 11 | 9 | 14 | 17 | 15 |
| 91 | A8 | 5 | 5 | 9 | 8 | 9 | 12 | 11 | 11 | 11 | 9 |
| 6 | A10 | 6 | 8 | 5 | 6 | 12 | 10 | 10 | 14 | 16 | 12 |
| 6 | A10 | 6 | 8 | 5 | 6 | 13 | 10 | 10 | 15 | 17 | 13 |
| 6 | A10 | 7 | 8 | 5 | 7 | 13 | 12 | 12 | 14 | 16 | 13 |
| 11 | A10 | 6 | 7 | 7 | 5 | 14 | 12 | 12 | 16 | 16 | 14 |
| 44 | A10 | 3 | 5 | 7 | 4 | 12 | 11 | 11 | 11 | 12 | 12 |
| 55 | A10 | 4 | 6 | 7 | 3 | 11 | 11 | 11 | 10 | 11 | 11 |
| 74 | A10 | 6 | 6 | 6 | 5 | 14 | 14 | 12 | 14 | 14 | 13 |
| 13 | A10 | 6 | 8 | 6 | 6 | 12 | 12 | 12 | 11 | 15 | 12 |
| 34 | A11 | 6 | 6 | 5 | 6 | 7 | 10 | 9 | 4 | 7 | 7 |
| 73 | A11 | 7 | 6 | 4 | 7 | 9 | 10 | 9 | 8 | 9 | 9 |

| | | probes SEQ ID NO: | | | | | | | |
|---|---|---|---|---|---|---|---|---|---|
| N° HPV | Group | 296 A9E2Z7S1 | 297 A9E2Z7S2 | 298 A9E2Z7S2a | 299 A9E2Z7S2b | 300 A9E2Z7S3 | 301 A9E2Z7S3a | 302 A9E2Z7S4 | 303 A9E2Z7S4a |
| 51 | A5 | 5 | 5 | 5 | 5 | 9 | 9 | 6 | 6 |
| 26 | A5 | 4 | 3 | 3 | 3 | 6 | 6 | 4 | 4 |
| 69 | A5 | 2 | 3 | 3 | 3 | 7 | 7 | 3 | 3 |
| 82 | A5 | 2 | 3 | 3 | 3 | 7 | 7 | 3 | 3 |
| 56 | A6 | 7 | 7 | 7 | 7 | 9 | 9 | 7 | 7 |
| 30 | A6 | 5 | 6 | 6 | 6 | 9 | 9 | 7 | 7 |
| 53 | A6 | 7 | 5 | 5 | 5 | 10 | 10 | 8 | 8 |
| 66 | A6 | 8 | 8 | 8 | 8 | 10 | 10 | 8 | 8 |
| 18 | A7 | 6 | 1 | 1 | 1 | 8 | 8 | 6 | 6 |
| 39 | A7 | 7 | 4 | 4 | 3 | 8 | 8 | 6 | 6 |
| 45 | A7 | 5 | 3 | 3 | 3 | 10 | 10 | 6 | 6 |
| 59 | A7 | 5 | 3 | 3 | 3 | 7 | 7 | 5 | 5 |
| 68 | A7 | | | | | | | | |
| 85 | A7 | 6 | 6 | 6 | 5 | 10 | 10 | 5 | 5 |

TABLE 48-continued

| A9 System GZ7: sequence aligment mismach evaluation | | | | | | | | | |
|---|---|---|---|---|---|---|---|---|---|
| 70 | A7 | 7 | 5 | 5 | 4 | 8 | 8 | 6 | 6 |
| 16 | A9 | 0 | 6 | 6 | 6 | 8 | 8 | 4 | 4 |
| 16 | A9 | 1 | 5 | 5 | 5 | 9 | 9 | 5 | 5 |
| 31 | A9 | 1 | 4 | 4 | 4 | 6 | 6 | 1 | 1 |
| 33 | A9 | 5 | 1 | 1 | 1 | 9 | 9 | 7 | 7 |
| 35 | A9 | 7 | 8 | 8 | 8 | 0 | 0 | 6 | 6 |
| 52 | A9 | 4 | 3 | 3 | 3 | 7 | 7 | 2 | 2 |
| 58 | A9 | 4 | 1 | 1 | 1 | 7 | 7 | 5 | 5 |
| 67 | A9 | 4 | 1 | 1 | 1 | 7 | 7 | 4 | 4 |
| 54 | A | 5 | 8 | 8 | 8 | 8 | 8 | 5 | 5 |
| 42 | A1 | 4 | 6 | 6 | 6 | 8 | 8 | 4 | 4 |
| 32 | A1 | 5 | 6 | 6 | 6 | 9 | 9 | 5 | 5 |
| 61 | A3 | 5 | 6 | 6 | 6 | 7 | 7 | 5 | 5 |
| 72 | A3 | 4 | 8 | 8 | 8 | 7 | 7 | 5 | 5 |
| 89 | A3 | 5 | 6 | 6 | 6 | 8 | 8 | 7 | 7 |
| 86 | A3 | 6 | 9 | 9 | 9 | 8 | 8 | 9 | 9 |
| 87 | A3 | 6 | 8 | 8 | 8 | 7 | 7 | 8 | 8 |
| 84 | A3 | 7 | 9 | 9 | 9 | 8 | 8 | 10 | 10 |
| 83 | A3 | 6 | 8 | 8 | 8 | 9 | 9 | 8 | 8 |
| 71 | A3 | 6 | 7 | 7 | 7 | 9 | 9 | 7 | 7 |
| 90 | A3 | 8 | 8 | 8 | 8 | 9 | 9 | 9 | 9 |
| 57 | A4 | 7 | 6 | 6 | 6 | 9 | 9 | 8 | 8 |
| 57 | A4 | 7 | 6 | 6 | 6 | 9 | 9 | 8 | 8 |
| 7 | A8 | 9 | 9 | 9 | 9 | 3 | 3 | 8 | 8 |
| 40 | A8 | 9 | 9 | 9 | 9 | 4 | 4 | 9 | 9 |
| 91 | A8 | 4 | 5 | 5 | 5 | 3 | 3 | 5 | 5 |
| 6 | A10 | 7 | 7 | 7 | 7 | 11 | 11 | 8 | 8 |
| 6 | A10 | 7 | 7 | 7 | 7 | 11 | 11 | 8 | 8 |
| 6 | A10 | 7 | 7 | 7 | 7 | 11 | 11 | 8 | 8 |
| 11 | A10 | 6 | 9 | 9 | 9 | 10 | 10 | 8 | 8 |
| 44 | A10 | 5 | 9 | 9 | 9 | 7 | 7 | 8 | 8 |
| 55 | A10 | 5 | 9 | 9 | 9 | 7 | 7 | 8 | 8 |
| 74 | A10 | 4 | 7 | 7 | 7 | 8 | 8 | 6 | 6 |
| 13 | A10 | 3 | 7 | 7 | 7 | 6 | 6 | 4 | 4 |
| 34 | A11 | 5 | 6 | 6 | 6 | 7 | 7 | 5 | 5 |
| 73 | A11 | 6 | 6 | 6 | 6 | 8 | 8 | 6 | 6 |

TABLE 49

| A9 System GZ8: sequence aligment mismach evaluation | | | | | | | | | | | | | | |
|---|---|---|---|---|---|---|---|---|---|---|---|---|---|---|
| | | forward primer | | | | reverse primer | | | | | | probes | | |
| | | SEQ ID NO: | | | | | | | | | | | | |
| N°HPV | Group | 227 A9E21f1az | 228 A9E21f2bz | 229 A9E21f3dz | 230 A9E21f4cz | 256 A9E2r7C | 257 A9E2r8 | 258 A9E2r10 | 259 A9E2r12 | 264 A9E2r12B | 261 A9E2r15 | 304 A9E2Z8S2f | 305 A9E2Z8S21f | 306 A9E2Z8S28f |
| 51 | A5 | 4 | 4 | 3 | 4 | 8 | 11 | 11 | 8 | 12 | 9 | 6 | 6 | 6 |
| 26 | A5 | 3 | 3 | 5 | 2 | 14 | 12 | 12 | 13 | 17 | 13 | 8 | 8 | 8 |
| 69 | A5 | 4 | 4 | 4 | 4 | 14 | 11 | 11 | 13 | 17 | 14 | 4 | 4 | 4 |
| 82 | A5 | 6 | 6 | 4 | 6 | 8 | 10 | 8 | 9 | 12 | 9 | 6 | 6 | 6 |
| 56 | A6 | 5 | 5 | 4 | 4 | 14 | 8 | 7 | 13 | 14 | 16 | 9 | 9 | 9 |
| 30 | A6 | 6 | 4 | 2 | 5 | 13 | 9 | 10 | 12 | 14 | 13 | 10 | 10 | 10 |
| 53 | A6 | 6 | 4 | 4 | 7 | 12 | 10 | 10 | 9 | 12 | 14 | 9 | 9 | 9 |
| 66 | A6 | 3 | 3 | 3 | 4 | 14 | 6 | 6 | 13 | 14 | 16 | 8 | 8 | 8 |
| 18 | A7 | 6 | 6 | 5 | 6 | 13 | 8 | 8 | 11 | 13 | 15 | 8 | 8 | 8 |
| 39 | A7 | 6 | 6 | 5 | 6 | 13 | 10 | 8 | 10 | 13 | 15 | 9 | 9 | 9 |
| 45 | A7 | 7 | 7 | 6 | 7 | 12 | 11 | 10 | 10 | 11 | 14 | 8 | 8 | 8 |
| 59 | A7 | 9 | 8 | 6 | 9 | 13 | 8 | 8 | 13 | 14 | 14 | 9 | 9 | 9 |
| 68 | A7 | | | | | 13 | 10 | 8 | 10 | 13 | 15 | | | |
| 85 | A7 | 5 | 3 | 5 | 4 | 9 | 10 | 7 | 11 | 11 | 10 | 9 | 9 | 9 |
| 70 | A7 | 6 | 6 | 4 | 6 | 10 | 7 | 7 | 10 | 11 | 12 | 8 | 8 | 8 |
| 16 | A9 | 0 | 2 | 5 | 3 | 2 | 11 | 9 | 6 | 6 | 0 | 0 | 0 | 0 |
| 16 | A9 | 0 | 2 | 5 | 3 | 2 | 11 | 9 | 6 | 6 | 0 | 1 | 1 | 1 |
| 31 | A9 | 3 | 1 | 5 | 5 | 5 | 13 | 10 | 0 | 2 | 8 | 9 | 9 | 9 |
| 33 | A9 | 4 | 4 | 0 | 4 | 8 | 0 | 2 | 10 | 11 | 9 | 8 | 8 | 8 |
| 35 | A9 | 2 | 0 | 4 | 5 | 3 | 12 | 10 | 4 | 2 | 6 | 9 | 9 | 9 |
| 52 | A9 | 2 | 4 | 6 | 0 | 12 | 6 | 3 | 11 | 14 | 15 | 8 | 8 | 8 |
| 58 | A9 | 4 | 4 | 2 | 3 | 10 | 1 | 3 | 12 | 12 | 11 | 10 | 10 | 10 |
| 67 | A9 | 3 | 5 | 3 | 2 | 13 | 5 | 7 | 14 | 14 | 14 | 7 | 7 | 7 |
| 54 | A | 4 | 4 | 5 | 5 | 12 | 11 | 12 | 9 | 13 | 13 | 9 | 9 | 9 |
| 42 | A1 | 7 | 8 | 6 | 6 | 13 | 12 | 12 | 13 | 14 | 12 | 9 | 9 | 9 |
| 32 | A1 | 6 | 7 | 7 | 5 | 14 | 12 | 12 | 15 | 15 | 13 | 7 | 7 | 7 |
| 61 | A3 | 4 | 2 | 6 | 3 | 12 | 12 | 10 | 12 | 13 | 13 | 9 | 9 | 9 |
| 72 | A3 | 5 | 4 | 3 | 5 | 14 | 13 | 11 | 13 | 14 | 13 | 13 | 13 | 13 |
| 89 | A3 | 7 | 6 | 8 | 8 | 17 | 13 | 10 | 16 | 18 | 18 | 9 | 9 | 9 |
| 86 | A3 | 8 | 9 | 7 | 7 | 14 | 15 | 12 | 13 | 15 | 14 | 13 | 13 | 13 |
| 87 | A3 | 8 | 8 | 6 | 6 | 16 | 17 | 14 | 15 | 16 | 15 | 13 | 13 | 13 |
| 84 | A3 | 8 | 8 | 5 | 7 | 16 | 15 | 12 | 15 | 17 | 14 | 10 | 10 | 10 |
| 83 | A3 | 7 | 5 | 6 | 6 | 14 | 14 | 11 | 14 | 16 | 15 | 7 | 7 | 7 |
| 71 | A3 | 7 | 6 | 8 | 8 | 14 | 18 | 15 | 11 | 14 | 15 | 8 | 8 | 8 |
| 90 | A3 | 8 | 6 | 10 | 7 | 17 | 15 | 12 | 15 | 16 | 16 | 8 | 8 | 8 |
| 57 | A4 | 7 | 7 | 8 | 7 | 14 | 14 | 11 | 14 | 15 | 16 | 9 | 9 | 9 |
| 57 | A4 | 6 | 6 | 9 | 6 | 14 | 14 | 11 | 14 | 15 | 16 | 9 | 9 | 9 |
| 7 | A8 | 5 | 6 | 9 | 5 | 12 | 10 | 9 | 15 | 15 | 12 | 9 | 9 | 9 |
| 40 | A8 | 6 | 6 | 6 | 7 | 16 | 11 | 9 | 14 | 17 | 15 | 8 | 8 | 8 |
| 91 | A8 | 5 | 5 | 9 | 8 | 9 | 12 | 11 | 11 | 11 | 9 | 7 | 7 | 7 |
| 6 | A10 | 6 | 8 | 5 | 6 | 12 | 10 | 10 | 14 | 16 | 12 | 8 | 8 | 8 |
| 6 | A10 | 6 | 8 | 5 | 6 | 13 | 10 | 10 | 15 | 17 | 13 | 8 | 8 | 8 |

TABLE 49-continued

A9 System GZ8: sequence aligment mismach evaluation

| | | | | | | | | | | | | | | |
|---|---|---|---|---|---|---|---|---|---|---|---|---|---|---|
| 6 | A10 | 7 | 8 | 5 | 7 | 13 | 12 | 12 | 14 | 16 | 13 | 7 | 7 | 7 |
| 11 | A10 | 6 | 7 | 7 | 5 | 14 | 12 | 12 | 16 | 16 | 14 | 8 | 8 | 8 |
| 44 | A10 | 3 | 5 | 7 | 4 | 12 | 11 | 11 | 11 | 12 | 12 | 7 | 7 | 7 |
| 55 | A10 | 4 | 6 | 7 | 3 | 11 | 11 | 11 | 10 | 11 | 11 | 4 | 4 | 4 |
| 74 | A10 | 6 | 6 | 6 | 5 | 14 | 14 | 12 | 14 | 14 | 13 | 8 | 8 | 8 |
| 13 | A10 | 6 | 8 | 6 | 6 | 12 | 12 | 12 | 11 | 16 | 12 | 9 | 9 | 9 |
| 34 | A11 | 6 | 6 | 5 | 6 | 7 | 10 | 9 | 4 | 7 | 7 | 10 | 10 | 10 |
| 73 | A11 | 7 | 6 | 4 | 7 | 9 | 10 | 9 | 8 | 9 | 9 | 9 | 9 | 9 |
| | | probes SEQ ID NO: | | | | | | | | | | | | |
| | | 307 | 308 | 309 | 310 | 311 | 312 | 313 | 314 | 315 | 316 | 317 | 318 | 319 |
| N°HPV | Group | A9E2Z8S56f | A9E2Z8S58f | A9E2Z8S61f | A9E2Z8S101f | A9E2Z8S105f | A9E2Z8S127f | A9E2Z8S146f | A9E2Z8S155f | A9E2Z8S156f | A9E2Z8S210f | A9E2Z8S231f | A9E2Z8S236f | A9E2Z8S250f |
| 51 | A5 | 12 | 12 | 12 | 10 | 10 | 10 | 11 | 11 | 11 | 12 | 10 | 10 | 10 |
| 26 | A5 | 9 | 9 | 9 | 14 | 14 | 14 | 14 | 14 | 14 | 9 | 9 | 9 | 9 |
| 69 | A5 | 12 | 12 | 12 | 13 | 13 | 13 | 14 | 14 | 14 | 7 | 8 | 8 | 8 |
| 82 | A5 | 12 | 12 | 12 | 8 | 8 | 8 | 14 | 14 | 14 | 12 | 9 | 9 | 9 |
| 56 | A6 | 11 | 11 | 11 | 12 | 12 | 12 | 15 | 15 | 15 | 5 | 7 | 7 | 7 |
| 30 | A6 | 13 | 13 | 13 | 15 | 15 | 15 | 15 | 15 | 15 | 8 | 11 | 11 | 11 |
| 53 | A6 | 12 | 12 | 12 | 10 | 10 | 10 | 12 | 12 | 12 | 6 | 6 | 6 | 6 |
| 66 | A6 | 10 | 10 | 10 | 12 | 12 | 12 | 12 | 12 | 12 | 5 | 7 | 7 | 7 |
| 18 | A7 | 10 | 10 | 10 | 12 | 12 | 12 | 12 | 12 | 12 | 6 | 7 | 7 | 7 |
| 39 | A7 | 13 | 13 | 13 | 11 | 11 | 11 | 10 | 10 | 10 | 10 | 6 | 6 | 6 |
| 45 | A7 | 11 | 11 | 11 | 13 | 13 | 13 | 13 | 13 | 13 | 9 | 10 | 10 | 10 |
| 59 | A7 | 9 | 9 | 9 | 13 | 13 | 13 | 10 | 10 | 10 | 7 | 6 | 6 | 6 |
| 68 | A7 | | | | | | | | | | | | | |
| 85 | A7 | 10 | 10 | 10 | 9 | 9 | 9 | 10 | 10 | 10 | 8 | 5 | 5 | 5 |
| 70 | A7 | 11 | 11 | 11 | 9 | 9 | 9 | 10 | 10 | 10 | 6 | 5 | 5 | 5 |
| 16 | A9 | 10 | 10 | 10 | 12 | 12 | 12 | 12 | 12 | 12 | 9 | 9 | 9 | 9 |
| 16 | A9 | 11 | 11 | 11 | 12 | 12 | 12 | 11 | 11 | 11 | 9 | 8 | 8 | 8 |
| 31 | A9 | 0 | 0 | 0 | 13 | 13 | 13 | 12 | 12 | 12 | 10 | 9 | 9 | 9 |
| 33 | A9 | 13 | 13 | 13 | 0 | 0 | 0 | 13 | 13 | 13 | 11 | 6 | 6 | 6 |
| 35 | A9 | 10 | 10 | 10 | 11 | 11 | 11 | 0 | 0 | 0 | 10 | 9 | 9 | 9 |
| 52 | A9 | 12 | 12 | 12 | 12 | 12 | 12 | 13 | 13 | 13 | 0 | 5 | 5 | 5 |
| 58 | A9 | 11 | 11 | 11 | 7 | 7 | 7 | 11 | 11 | 11 | 6 | 0 | 0 | 0 |
| 67 | A9 | 10 | 10 | 10 | 9 | 9 | 9 | 14 | 14 | 14 | 7 | 3 | 3 | 3 |
| 54 | A | 10 | 10 | 10 | 12 | 12 | 12 | 11 | 11 | 11 | 8 | 8 | 8 | 8 |
| 42 | A1 | 12 | 12 | 12 | 13 | 13 | 13 | 14 | 14 | 14 | 7 | 9 | 9 | 9 |
| 32 | A1 | 12 | 12 | 12 | 10 | 10 | 10 | 12 | 12 | 12 | 9 | 9 | 9 | 9 |
| 61 | A3 | 12 | 12 | 12 | 11 | 11 | 11 | 15 | 15 | 15 | 9 | 8 | 8 | 8 |
| 72 | A3 | 14 | 14 | 14 | 15 | 15 | 15 | 17 | 17 | 17 | 11 | 13 | 13 | 13 |
| 89 | A3 | 12 | 12 | 12 | 14 | 14 | 14 | 13 | 13 | 13 | 10 | 10 | 10 | 10 |
| 86 | A3 | 12 | 12 | 12 | 13 | 13 | 13 | 17 | 17 | 17 | 8 | 10 | 10 | 10 |
| 87 | A3 | 13 | 13 | 13 | 15 | 15 | 15 | 16 | 16 | 16 | 9 | 11 | 11 | 11 |
| 84 | A3 | 10 | 10 | 10 | 12 | 12 | 12 | 16 | 16 | 16 | 12 | 10 | 10 | 10 |
| 83 | A3 | 11 | 11 | 11 | 11 | 11 | 11 | 12 | 12 | 12 | 13 | 10 | 10 | 10 |
| 71 | A3 | 14 | 14 | 14 | 15 | 15 | 15 | 15 | 15 | 15 | 12 | 11 | 11 | 11 |
| 90 | A3 | 12 | 12 | 12 | 14 | 14 | 14 | 14 | 14 | 14 | 12 | 12 | 12 | 12 |
| 57 | A4 | 11 | 11 | 11 | 14 | 14 | 14 | 13 | 13 | 13 | 10 | 11 | 11 | 11 |

TABLE 49-continued

| A9 System GZ8: sequence aligment mismach evaluation | | | | | | | | | | | | | | |
|---|---|---|---|---|---|---|---|---|---|---|---|---|---|---|
| 57 | A4 | 12 | 12 | 12 | 15 | 15 | 15 | 14 | 14 | 14 | 10 | 12 | 12 | 12 |
| 7 | A8 | 13 | 13 | 13 | 12 | 12 | 12 | 13 | 13 | 13 | 8 | 10 | 10 | 10 |
| 40 | A8 | 12 | 12 | 12 | 12 | 12 | 12 | 13 | 13 | 13 | 8 | 12 | 12 | 12 |
| 91 | A8 | 10 | 10 | 10 | 12 | 12 | 12 | 12 | 12 | 12 | 10 | 11 | 11 | 11 |
| 6 | A10 | 12 | 12 | 12 | 11 | 11 | 11 | 13 | 13 | 13 | 10 | 8 | 8 | 8 |
| 6 | A10 | 12 | 12 | 12 | 11 | 11 | 11 | 13 | 13 | 13 | 10 | 8 | 8 | 8 |
| 6 | A10 | 12 | 12 | 12 | 11 | 11 | 11 | 13 | 13 | 13 | 10 | 8 | 8 | 8 |
| 11 | A10 | 12 | 12 | 12 | 12 | 12 | 12 | 13 | 13 | 13 | 8 | 8 | 8 | 8 |
| 44 | A10 | 14 | 14 | 14 | 8 | 8 | 8 | 15 | 15 | 15 | 7 | 9 | 9 | 9 |
| 55 | A10 | 12 | 12 | 12 | 9 | 9 | 9 | 13 | 13 | 13 | 8 | 9 | 9 | 9 |
| 74 | A10 | 13 | 13 | 13 | 8 | 8 | 8 | 14 | 14 | 14 | 8 | 6 | 6 | 6 |
| 13 | A10 | 8 | 8 | 8 | 7 | 7 | 7 | 12 | 12 | 12 | 9 | 6 | 6 | 6 |
| 34 | A11 | 9 | 9 | 9 | 12 | 12 | 12 | 15 | 15 | 15 | 12 | 9 | 9 | 9 |
| 73 | A11 | 11 | 11 | 11 | 7 | 7 | 7 | 12 | 12 | 12 | 11 | 6 | 6 | 6 |

TABLE 50

| | | A9 System H | | | | | | | | | | |
|---|---|---|---|---|---|---|---|---|---|---|---|---|
| | | forward primer | | | | | | | | | reverse primer | |
| | | SEQ ID NO: | | | | | | | | | | |
| N°HPV | Group | 232 A9E2f5 | 232 A9E2f6 | 233 A9E2f7 | 234 A9E2f8 | 235 A9E2f9 | 236 A9E2f10 | 237 A9E2f10b | 238 A9E2f11 | 239 A9E2f12 | 262 A9E2r7B | 257 A9E2r8 |
| 51 | A5 | 4 | 8 | 8 | 5 | 6 | 4 | 5 | 5 | 6 | 8 | 11 |
| 26 | A5 | 3 | 7 | 8 | 4 | 3 | 3 | 4 | 3 | 4 | 13 | 12 |
| 69 | A5 | 2 | 8 | 6 | 2 | 3 | 2 | 3 | 3 | 4 | 14 | 11 |
| 82 | A5 | 2 | 6 | 4 | 2 | 3 | 2 | 3 | 3 | 4 | 8 | 10 |
| 56 | A6 | 6 | 10 | 11 | 7 | 6 | 5 | 6 | 8 | 7 | 13 | 8 |
| 30 | A6 | 3 | 10 | 11 | 5 | 4 | 5 | 5 | 7 | 6 | 13 | 9 |
| 53 | A6 | 6 | 12 | 13 | 7 | 7 | 4 | 5 | 6 | 7 | 12 | 10 |
| 66 | A6 | 7 | 10 | 11 | 8 | 7 | 6 | 7 | 9 | 8 | 13 | 6 |
| 18 | A7 | 4 | 7 | 8 | 6 | 3 | 2 | 2 | 4 | 5 | 12 | 8 |
| 39 | A7 | 5 | 7 | 9 | 6 | 3 | 4 | 4 | 4 | 5 | 12 | 10 |
| 45 | A7 | 4 | 10 | 9 | 5 | 5 | 3 | 3 | 5 | 6 | 11 | 11 |
| 59 | A7 | 3 | 7 | 9 | 5 | 3 | 4 | 4 | 3 | 4 | 13 | 8 |
| 68 | A7 | 5 | 7 | 9 | 6 | 3 | 4 | 4 | 4 | 5 | 12 | 10 |
| 85 | A7 | 5 | 9 | 8 | 6 | 4 | 4 | 4 | 6 | 6 | 9 | 10 |
| 70 | A7 | 5 | 6 | 8 | 6 | 3 | 4 | 4 | 5 | 5 | 10 | 7 |
| 16 | A9 | 0 | 8 | 6 | 0 | 4 | 2 | 3 | 5 | 4 | 2 | 11 |
| 16 | A9 | 1 | 8 | 6 | 1 | 5 | 1 | 2 | 6 | 5 | 2 | 11 |
| 31 | A9 | 1 | 5 | 3 | 1 | 2 | 1 | 2 | 4 | 3 | 5 | 13 |
| 33 | A9 | 3 | 10 | 10 | 5 | 3 | 1 | 1 | 4 | 5 | 9 | 0 |
| 35 | A9 | 5 | 0 | 2 | 7 | 6 | 6 | 7 | 2 | 2 | 3 | 12 |
| 52 | A9 | 3 | 8 | 8 | 4 | 3 | 3 | 3 | 2 | 3 | 12 | 6 |
| 58 | A9 | 2 | 9 | 9 | 4 | 1 | 0 | 0 | 5 | 4 | 11 | 1 |
| 67 | A9 | 2 | 8 | 8 | 4 | 1 | 0 | 0 | 5 | 4 | 13 | 5 |
| 54 | A | 4 | 7 | 6 | 4 | 6 | 4 | 5 | 7 | 7 | 12 | 11 |
| 42 | A1 | 3 | 7 | 6 | 3 | 4 | 3 | 3 | 6 | 5 | 13 | 12 |
| 32 | A1 | 5 | 9 | 7 | 5 | 6 | 3 | 4 | 8 | 7 | 13 | 12 |
| 61 | A3 | 4 | 7 | 6 | 4 | 5 | 2 | 3 | 6 | 6 | 12 | 12 |
| 72 | A3 | 3 | 7 | 6 | 3 | 5 | 4 | 5 | 6 | 6 | 14 | 13 |
| 89 | A3 | 3 | 7 | 7 | 4 | 5 | 2 | 3 | 7 | 7 | 17 | 13 |
| 86 | A3 | 5 | 9 | 8 | 6 | 10 | 6 | 7 | 6 | 7 | 14 | 15 |
| 87 | A3 | 5 | 9 | 8 | 6 | 9 | 6 | 7 | 6 | 7 | 15 | 17 |
| 84 | A3 | 5 | 9 | 9 | 7 | 10 | 6 | 7 | 6 | 7 | 15 | 15 |
| 83 | A3 | 4 | 10 | 10 | 6 | 8 | 4 | 5 | 7 | 7 | 14 | 14 |
| 71 | A3 | 5 | 10 | 9 | 5 | 7 | 4 | 5 | 7 | 8 | 14 | 18 |
| 90 | A3 | 8 | 12 | 11 | 7 | 9 | 6 | 7 | 7 | 8 | 15 | 15 |
| 57 | A4 | 5 | 10 | 10 | 6 | 7 | 4 | 5 | 6 | 8 | 13 | 14 |
| 57 | A4 | 5 | 10 | 10 | 6 | 7 | 4 | 5 | 6 | 8 | 13 | 14 |
| 7 | A8 | 6 | 5 | 7 | 9 | 7 | 7 | 8 | 3 | 3 | 11 | 10 |
| 40 | A8 | 6 | 8 | 9 | 9 | 7 | 7 | 8 | 4 | 4 | 15 | 11 |
| 91 | A8 | 3 | 5 | 5 | 4 | 3 | 3 | 4 | 4 | 3 | 9 | 12 |
| 6 | A10 | 6 | 11 | 10 | 6 | 6 | 4 | 4 | 7 | 7 | 13 | 10 |
| 6 | A10 | 6 | 11 | 10 | 6 | 6 | 4 | 4 | 7 | 7 | 14 | 10 |

TABLE 50-continued

| | | A9 System H | | | | | | | | | | |
|---|---|---|---|---|---|---|---|---|---|---|---|---|
| 6 | A10 | 6 | 11 | 10 | 6 | 6 | 4 | 4 | 7 | 7 | 14 | 12 |
| 11 | A10 | 5 | 9 | 8 | 5 | 8 | 5 | 6 | 7 | 8 | 15 | 12 |
| 44 | A10 | 4 | 8 | 7 | 5 | 9 | 6 | 6 | 6 | 6 | 11 | 11 |
| 55 | A10 | 4 | 8 | 7 | 5 | 9 | 5 | 6 | 6 | 6 | 10 | 11 |
| 74 | A10 | 3 | 10 | 9 | 4 | 7 | 3 | 4 | 6 | 6 | 13 | 14 |
| 13 | A10 | 2 | 8 | 7 | 3 | 5 | 3 | 4 | 4 | 4 | 12 | 12 |
| 34 | A11 | 4 | 8 | 9 | 5 | 4 | 4 | 5 | 6 | 5 | 6 | 10 |
| 73 | A11 | 5 | 8 | 9 | 6 | 5 | 4 | 5 | 7 | 6 | 7 | 10 |

| | | reverse primer | | | | | | | probes | | | |
|---|---|---|---|---|---|---|---|---|---|---|---|---|
| | | SEQ ID NO: | | | | | | | | | | |
| N°HPV | Group | 263 A9E2r9 | 258 A9E2r10 | 259 A9E2r12 | 256 A9E2r7C | 264 A9E2r12B | 261 A9E2r15 | 265 A9E2r16 | 304 A9E2Z8S2f | 305 A9E2Z8S21f | 306 A9E2Z8S28f | 307 A9E2Z8S56f |
| 51 | A5 | 10 | 11 | 8 | 8 | 12 | 9 | 14 | 6 | 6 | 6 | 12 |
| 26 | A5 | 11 | 12 | 13 | 14 | 17 | 13 | 15 | 8 | 8 | 8 | 9 |
| 69 | A5 | 10 | 11 | 13 | 14 | 17 | 14 | 13 | 4 | 4 | 4 | 12 |
| 82 | A5 | 8 | 8 | 9 | 8 | 12 | 9 | 12 | 6 | 6 | 6 | 12 |
| 56 | A6 | 7 | 7 | 13 | 14 | 14 | 16 | 10 | 9 | 9 | 9 | 11 |
| 30 | A6 | 9 | 10 | 12 | 13 | 14 | 13 | 11 | 10 | 10 | 10 | 13 |
| 53 | A6 | 9 | 10 | 9 | 12 | 12 | 14 | 14 | 9 | 9 | 9 | 12 |
| 66 | A6 | 5 | 6 | 13 | 14 | 14 | 16 | 11 | 8 | 8 | 8 | 10 |
| 18 | A7 | 8 | 8 | 11 | 13 | 13 | 15 | 10 | 8 | 8 | 8 | 10 |
| 39 | A7 | 8 | 8 | 10 | 13 | 13 | 15 | 12 | 9 | 9 | 9 | 13 |
| 45 | A7 | 11 | 10 | 10 | 12 | 11 | 14 | 10 | 8 | 8 | 8 | 11 |
| 59 | A7 | 9 | 8 | 13 | 13 | 14 | 14 | 8 | 9 | 9 | 9 | 9 |
| 68 | A7 | 8 | 8 | 10 | 13 | 13 | 15 | 12 | | | | |
| 85 | A7 | 8 | 7 | 11 | 9 | 11 | 10 | 10 | 9 | 9 | 9 | 10 |
| 70 | A7 | 6 | 7 | 10 | 10 | 11 | 12 | 11 | 8 | 8 | 8 | 11 |
| 16 | A9 | 10 | 9 | 6 | 2 | 6 | 0 | 10 | 0 | 0 | 0 | 10 |
| 16 | A9 | 10 | 9 | 6 | 2 | 6 | 0 | 10 | 1 | 1 | 1 | 11 |
| 31 | A9 | 11 | 10 | 0 | 5 | 2 | 8 | 11 | 9 | 9 | 9 | 0 |
| 33 | A9 | 1 | 2 | 10 | 8 | 11 | 9 | 2 | 8 | 8 | 8 | 13 |
| 35 | A9 | 11 | 10 | 4 | 3 | 2 | 6 | 11 | 9 | 9 | 9 | 10 |
| 52 | A9 | 4 | 3 | 11 | 12 | 14 | 15 | 8 | 8 | 8 | 8 | 12 |
| 58 | A9 | 2 | 3 | 12 | 10 | 12 | 11 | 0 | 10 | 10 | 10 | 11 |
| 67 | A9 | 6 | 7 | 14 | 13 | 14 | 14 | 5 | 7 | 7 | 7 | 10 |
| 54 | A | 11 | 12 | 9 | 12 | 13 | 13 | 15 | 9 | 9 | 9 | 10 |
| 42 | A1 | 12 | 12 | 13 | 13 | 14 | 12 | 13 | 9 | 9 | 9 | 12 |
| 32 | A1 | 11 | 12 | 15 | 14 | 15 | 13 | 13 | 7 | 7 | 7 | 12 |
| 61 | A3 | 11 | 10 | 12 | 12 | 13 | 13 | 12 | 9 | 9 | 9 | 12 |
| 72 | A3 | 12 | 11 | 13 | 14 | 14 | 13 | 12 | 13 | 13 | 13 | 14 |
| 89 | A3 | 11 | 10 | 16 | 17 | 18 | 18 | 14 | 9 | 9 | 9 | 12 |
| 86 | A3 | 13 | 12 | 13 | 14 | 15 | 14 | 16 | 13 | 13 | 13 | 12 |
| 87 | A3 | 15 | 14 | 15 | 16 | 16 | 15 | 18 | 13 | 13 | 13 | 13 |
| 84 | A3 | 13 | 12 | 15 | 16 | 17 | 14 | 15 | 10 | 10 | 10 | 10 |
| 83 | A3 | 12 | 11 | 14 | 14 | 16 | 15 | 15 | 7 | 7 | 7 | 11 |
| 71 | A3 | 16 | 15 | 11 | 14 | 14 | 15 | 17 | 8 | 8 | 8 | 14 |
| 90 | A3 | 13 | 12 | 15 | 17 | 16 | 16 | 16 | 8 | 8 | 8 | 12 |

TABLE 50-continued

A9 System H

| | | | | | | | | | | | | |
|---|---|---|---|---|---|---|---|---|---|---|---|---|
| 57 | A4 | 12 | 11 | 14 | 14 | 15 | 16 | 14 | 9 | 9 | 9 | 11 |
| 57 | A4 | 12 | 11 | 14 | 14 | 15 | 16 | 14 | 9 | 9 | 9 | 12 |
| 7 | A8 | 10 | 9 | 15 | 12 | 15 | 12 | 11 | 9 | 9 | 9 | 13 |
| 40 | A8 | 10 | 9 | 14 | 16 | 17 | 15 | 12 | 8 | 8 | 8 | 12 |
| 91 | A8 | 12 | 11 | 11 | 9 | 11 | 9 | 13 | 7 | 7 | 7 | 10 |
| 6 | A10 | 9 | 10 | 14 | 12 | 16 | 12 | 14 | 8 | 8 | 8 | 12 |
| 6 | A10 | 9 | 10 | 15 | 13 | 17 | 13 | 15 | 8 | 8 | 8 | 12 |
| 6 | A10 | 11 | 12 | 14 | 13 | 16 | 13 | 16 | 7 | 7 | 7 | 12 |
| 11 | A10 | 11 | 12 | 16 | 14 | 16 | 14 | 15 | 8 | 8 | 8 | 12 |
| 44 | A10 | 10 | 11 | 11 | 12 | 12 | 12 | 14 | 7 | 7 | 7 | 14 |
| 55 | A10 | 10 | 11 | 10 | 11 | 11 | 11 | 13 | 4 | 4 | 4 | 12 |
| 74 | A10 | 13 | 12 | 14 | 14 | 14 | 13 | 16 | 8 | 8 | 8 | 13 |
| 13 | A10 | 11 | 12 | 11 | 12 | 15 | 12 | 14 | 9 | 9 | 9 | 8 |
| 34 | A11 | 8 | 9 | 4 | 7 | 7 | 7 | 13 | 10 | 10 | 10 | 9 |
| 73 | A11 | 8 | 9 | 8 | 9 | 9 | 9 | 12 | 9 | 9 | 9 | 11 |

| | | probes SEQ ID NO: | | | | | | | | | | | |
|---|---|---|---|---|---|---|---|---|---|---|---|---|---|
| N°HPV | Group | 308 A9E2Z8S58f | 309 A9E2Z8S61f | 310 A9E2Z8S101f | 311 A9E2Z8S105f | 312 A9E2Z8S127f | 313 A9E2Z8S146f | 314 A9E2Z8S155f | 315 A9E2Z8S156f | 316 A9E2Z8S210f | 317 A9E2Z8S231f | 318 A9E2Z8S236f | 319 A9E2Z8S250f |
| 51 | A5 | 12 | 12 | 10 | 10 | 10 | 11 | 11 | 11 | 12 | 10 | 10 | 10 |
| 26 | A5 | 9 | 9 | 14 | 14 | 14 | 14 | 14 | 14 | 9 | 9 | 9 | 9 |
| 69 | A5 | 12 | 12 | 13 | 13 | 13 | 14 | 14 | 14 | 7 | 8 | 8 | 8 |
| 82 | A5 | 12 | 12 | 8 | 8 | 8 | 14 | 14 | 14 | 12 | 9 | 9 | 9 |
| 56 | A6 | 11 | 11 | 12 | 12 | 12 | 15 | 15 | 15 | 5 | 7 | 7 | 7 |
| 30 | A6 | 13 | 13 | 15 | 15 | 15 | 15 | 15 | 15 | 8 | 11 | 11 | 11 |
| 53 | A6 | 12 | 12 | 10 | 10 | 10 | 12 | 12 | 12 | 6 | 6 | 6 | 6 |
| 66 | A6 | 10 | 10 | 12 | 12 | 12 | 12 | 12 | 12 | 5 | 7 | 7 | 7 |
| 18 | A7 | 10 | 10 | 12 | 12 | 12 | 12 | 12 | 12 | 6 | 7 | 7 | 7 |
| 39 | A7 | 13 | 13 | 11 | 11 | 11 | 10 | 10 | 10 | 10 | 6 | 6 | 6 |
| 45 | A7 | 11 | 11 | 13 | 13 | 13 | 13 | 13 | 13 | 9 | 10 | 10 | 10 |
| 59 | A7 | 9 | 9 | 13 | 13 | 13 | 10 | 10 | 10 | 7 | 6 | 6 | 6 |
| 68 | A7 | | | | | | | | | | | | |
| 85 | A7 | 10 | 10 | 9 | 9 | 9 | 10 | 10 | 10 | 8 | 5 | 5 | 5 |
| 70 | A7 | 11 | 11 | 9 | 9 | 9 | 10 | 10 | 10 | 6 | 5 | 5 | 5 |
| 16 | A9 | 10 | 10 | 12 | 12 | 12 | 12 | 12 | 12 | 9 | 9 | 9 | 9 |
| 16 | A9 | 11 | 11 | 12 | 12 | 12 | 11 | 11 | 11 | 9 | 8 | 8 | 8 |
| 31 | A9 | 0 | 0 | 13 | 13 | 13 | 12 | 12 | 12 | 10 | 9 | 9 | 9 |
| 33 | A9 | 13 | 13 | 0 | 0 | 0 | 13 | 13 | 13 | 11 | 6 | 6 | 6 |
| 35 | A9 | 10 | 10 | 11 | 11 | 11 | 0 | 0 | 0 | 10 | 9 | 9 | 9 |
| 52 | A9 | 12 | 12 | 12 | 12 | 12 | 13 | 13 | 13 | 0 | 5 | 5 | 5 |
| 68 | A9 | 11 | 11 | 7 | 7 | 7 | 11 | 11 | 11 | 6 | 0 | 0 | 0 |
| 67 | A9 | 10 | 10 | 9 | 9 | 9 | 14 | 14 | 14 | 7 | 3 | 3 | 3 |
| 54 | A | 10 | 10 | 12 | 12 | 12 | 11 | 11 | 11 | 8 | 8 | 8 | 8 |
| 42 | A1 | 12 | 12 | 13 | 13 | 13 | 14 | 14 | 14 | 7 | 9 | 9 | 9 |
| 32 | A1 | 12 | 12 | 10 | 10 | 10 | 12 | 12 | 12 | 9 | 9 | 9 | 9 |
| 61 | A3 | 12 | 12 | 11 | 11 | 11 | 15 | 15 | 15 | 9 | 8 | 8 | 8 |
| 72 | A3 | 14 | 14 | 15 | 15 | 15 | 17 | 17 | 17 | 11 | 13 | 13 | 13 |
| 89 | A3 | 12 | 12 | 14 | 14 | 14 | 13 | 13 | 13 | 10 | 10 | 10 | 10 |

TABLE 50-continued

| A9 System H | | | | | | | | | | | | | |
|---|---|---|---|---|---|---|---|---|---|---|---|---|---|
| 86 | A3 | 12 | 12 | 13 | 13 | 13 | 17 | 17 | 17 | 8 | 10 | 10 | 10 |
| 87 | A3 | 13 | 13 | 15 | 15 | 15 | 16 | 16 | 16 | 9 | 11 | 11 | 11 |
| 84 | A3 | 10 | 10 | 12 | 12 | 12 | 16 | 16 | 16 | 12 | 10 | 10 | 10 |
| 83 | A3 | 11 | 11 | 11 | 11 | 11 | 12 | 12 | 12 | 13 | 10 | 10 | 10 |
| 71 | A3 | 14 | 14 | 15 | 15 | 15 | 15 | 15 | 15 | 12 | 11 | 11 | 11 |
| 90 | A3 | 12 | 12 | 14 | 14 | 14 | 14 | 14 | 14 | 12 | 12 | 12 | 12 |
| 57 | A4 | 11 | 11 | 14 | 14 | 14 | 13 | 13 | 13 | 10 | 11 | 11 | 11 |
| 57 | A4 | 12 | 12 | 15 | 15 | 15 | 14 | 14 | 14 | 10 | 12 | 12 | 12 |
| 7 | A8 | 13 | 13 | 12 | 12 | 12 | 13 | 13 | 13 | 8 | 10 | 10 | 10 |
| 40 | A8 | 12 | 12 | 12 | 12 | 12 | 13 | 13 | 13 | 8 | 12 | 12 | 12 |
| 91 | A8 | 10 | 10 | 12 | 12 | 12 | 12 | 12 | 12 | 10 | 11 | 11 | 11 |
| 6 | A10 | 12 | 12 | 11 | 11 | 11 | 13 | 13 | 13 | 10 | 8 | 8 | 8 |
| 6 | A10 | 12 | 12 | 11 | 11 | 11 | 13 | 13 | 13 | 10 | 8 | 8 | 8 |
| 6 | A10 | 12 | 12 | 11 | 11 | 11 | 13 | 13 | 13 | 10 | 8 | 8 | 8 |
| 11 | A10 | 12 | 12 | 12 | 12 | 12 | 13 | 13 | 13 | 8 | 8 | 8 | 8 |
| 44 | A10 | 14 | 14 | 8 | 8 | 8 | 15 | 15 | 15 | 7 | 9 | 9 | 9 |
| 55 | A10 | 12 | 12 | 9 | 9 | 9 | 13 | 13 | 13 | 8 | 9 | 9 | 9 |
| 74 | A10 | 13 | 13 | 8 | 8 | 8 | 14 | 14 | 14 | 8 | 6 | 6 | 6 |
| 13 | A10 | 8 | 8 | 7 | 7 | 7 | 12 | 12 | 12 | 9 | 6 | 6 | 6 |
| 34 | A11 | 9 | 9 | 12 | 12 | 12 | 15 | 15 | 15 | 12 | 9 | 9 | 9 |
| 73 | A11 | 11 | 11 | 7 | 7 | 7 | 12 | 12 | 12 | 11 | 6 | 6 | 6 |

TABLE 51 list of HPV plasmids

| Name | Group | Plasmid size kb | Insert size kb | Source | Publications |
|---|---|---|---|---|---|
| pHPV 16 | A9 | 2.961 | 7.904 | ATCC 45113 | |
| pHPV 6B | A10 | 2.686 | 7.900 | ATCC 45150 | The EMBO Journal vol2 n°12 p.2341-2348 (1983) |
| pHPV 18 | A7 | 4.363 | 7.857 | ATCC 45152 | J. Mol. Biol. (1987) 193 p.599-608 |
| pHPV 31 | A9 | 4.363 | 8.000 | ATCC 65446 | J Virol 58: 225-229, 1986 |
| pHPV 11 | A10 | 4.363 | 7.931 | ATCC 45151 | Virology 151 124-130 (1986) |
| pHPV 35 cl 2A | A9 | 4.363 | 3.750 | ATCC 40330 | U.S. Pat. 4,849,332 |
| pHPV 35 cl 2B | A9 | 4.363 | 4.100 | ATCC 40331 | U.S. Pat. 4,849,332 |
| pHPV 56 cl 2A | A6 | 2.818 | 5.100 | ATCC 40341 | U.S. Pat. 4,908,306 |
| pHPV 56 cl 2C | A6 | 2.818 | 7.900 | ATCC 40549 | U.S. Pat. 4,908,306 |
| pHPV 56 cl 2B | A6 | 2.818 | 3.100 | ATCC 40379 | U.S. Pat. 4,908,306 |
| pHPV 43 cl 2A | A8 | 2.812 | 6.300 | ATCC 40338 | U.S. Pat. 4,849,334 |
| pHPV 43 cl 2B | A8 | 2.812 | 2.850 | ATCC 40339 | U.S. Pat. 4,849,334 |
| pHPV 44 cl 2 | A10 | 2.818 | 7.800 | ATCC 40353 | U.S. Pat. 4,849,331 |
| pHPV 7cl 7/4 | A8 | 2.686 | 3.905 | DKFZ | |
| pHPV 7cl 7/5 | A8 | 2.686 | 4.131 | DKFZ | |
| pHPV 13 cl 13 | A10 | 2.686 | 7.241 | DKFZ | |
| pHPV 30 cl 30 | A6 | 4.36 | 7.157 | DKFZ | |
| pHPV 40 cl 40 | A8 | 2.686 | 7.296 | DKFZ | |
| pHPV 53 cl 53 | A8 | 3.939 | 7.154 | DKFZ | |
| pHPV 57 cl 57 | A4 | 2.686 | 7.235 | DKFZ | |
| pHPV 72 cl 72 | A3 | 2.961 | 7.307 | DKFZ | |
| pHPV 73 cl 73 | A11 | 2.961 | 7.005 | DKFZ | |
| pHPV 45 cl 45 | A7 | 2.871 | 7.149 | DKFZ | |
| pHPV 51 | A5 | 2.68 | 7.800 | DKFZ | J. of Virology 1998 p1452-1455/aug.1991 p.4216-4225 |
| pHPV 26 | A5 | 2.686 | 7.100 | DKFZ | |
| pHPV 52 | A9 | 2.686 | 7.940 | DKFZ | |
| pHPV 89 Frag 1 | A3 | 3.015 | 0.700 | DKFZ | The Journal of infectious diseases 2002 185: 1794-7 |
| pHPV 89 Frag 2 | A3 | 3.015 | 1.100 | DKFZ | The Journal of infectious diseases 2002 185: 1794-7 |
| pHPV 89 Frag 3 | A3 | 3.015 | 2000 | DKFZ | The Journal of infectious diseases 2002 185: 1794-7 |
| pHPV 89 Frag 4 | A3 | 3.015 | 5.100 | DKFZ | The Journal of infectious diseases 2002 185: 1794-7 |
| pHPV 62 Frag 1 | A3 | 3.015 | 3.325 | DKFZ | |
| pHPV 62 Frag 2 | A3 | 3.015 | 4.040 | DKFZ | |
| pHPV 62 Frag 3 | A3 | 3.015 | 1.268 | DKFZ | |
| pHPV 84 Frag 1 | A3 | 3.015 | 0.700 | DKFZ | Virology 279, 109-115, 2001 |
| pHPV 84 Frag 2 | A3 | 3.015 | 4.500 | DKFZ | Virology 279, 109-115, 2001 |
| pHPV 84 Frag 3 | A3 | 3.015 | 1000 | DKFZ | Virology 279, 109-115, 2001 |
| pHPV 84 Frag 4 | A3 | 3.015 | 1.800 | DKFZ | Virology 279, 109-115, 2001 |
| pHPV 84 Frag 5 | A3 | 3.015 | 0.600 | DKFZ | Virology 279, 109-115, 2001 |
| pHPV 90 Frag 1 | A3 | 3.015 | 4.200 | DKFZ | The Journal of infectious diseases 2002 185: 1794-7 |
| pHPV 90 Frag 2 | A3 | 3.015 | 1.700 | DKFZ | The Journal of infectious diseases 2002 185: 1794-7 |
| pHPV 90 Frag 3 | A3 | 3.015 | 2.500 | DKFZ | The Journal of infectious diseases 2002 185: 1794-7 |
| pHPV 86 Frag 1 | A3 | 3.015 | 3.900 | DKFZ | J Gen Virol 2001, 82, 2035-2040 |
| pHPV 86 Frag 2 | A3 | 3.015 | 5.800 | DKFZ | J Gen Virol 2001, 82, 2035-2040 |
| pHPV 86 Frag 3 | A3 | 3.015 | 0.140 | DKFZ | J Gen Virol 2001, 82, 2035-2040 |
| pHPV 91 Frag 1 | A8 | 3.015 | 3.200 | DKFZ | The Journal of infectious diseases 2002 185: 1794-7 |
| pHPV 91 Frag 2 | A8 | 3.015 | 1.500 | DKFZ | The Journal of infectious diseases 2002 185: 1794-7 |
| pHPV 91 Frag 3 | A8 | 3.015 | 1.400 | DKFZ | The Journal of infectious diseases 2002 185: 1794-7 |
| pHPV 91 Frag 4 | A8 | 3.015 | 2.500 | DKFZ | The Journal of infectious diseases 2002 185: 1794-7 |
| pHPV 33 | A9 | 4.363 | 7.093 | CNCM I-450 | |
| pHPV 39 | A7 | 3.005 | 7.160 | CNCM I-507 | JCM mar 1996, 738-744 |
| pHPV 42 | A1 | 3.030 | 7.107 | CNCM I-508 | |
| pHPV 54 | A4 | 3.030 | 7.107 | CNCM I-756 | |
| pHPV 23 | B1 | 4.363 | 7.324 | CNCM I-391 | J Virol, december 1984, 52, 1013-1018 |
| pHPV 68 | A7 | 4.363 | 6.042 | CNCM I-1540 | JCM march 1996, 738-744/U.S. Pat. 5,981,173 |
| pHPV 66 | A6 | 4.363 | 7.158 | CNCM I-951 | J virol, 1986, 57, 688-692 |
| pHPV 87 L1 E1 16 | A3 | 3.015 | 1.014 | DKFZ | Journal of Virology déc. 2001 p11913-11919 |
| pHPV 87 L1 f | A3 | 3.015 | 0.974 | DKFZ | Journal of Virology déc. 2001 p11913-11919 |
| pHPV 87 MY 16 | A3 | 3.015 | 0.448 | DKFZ | Journal of Virology déc. 2001 p11913-11919 |
| pHPV 87 E1 L1 11/2 | A3 | 3.015 | 2.794 | DKFZ | Journal of Virology déc. 2001 p11913-11919 |
| pHPV 87 L1 E1 37 | A3 | 3.015 | 1.227 | DKFZ | Journal of Virology déc. 2001 p11913-11919 |
| pHPV 87 E11 E2 as | A3 | 3.015 | 1.130 | DKFZ | Journal of Virology déc. 2001 p11913-11919 |
| pHPV 58 | A8 | 3.800 | 7.824 | DKFZ | Virology (1990) 177: 833-836 |
| pHPV 59 | A7 | 2.695 | 7.896 | DKFZ | Int. J. Cancer (1995) 61: 13-22 |
| pHPV 87 | A9 | 2.695 | 7.801 | DKFZ | Int. J. Cancer (1995) 61: 13-22 |
| pHPV 81 | A3 | 3.204 | 4.759 | DKFZ | Virology (2001) 283: 139-147 |
| pHPV 82 | A5 | 3.204 | 7.871 | DKFZ | Clin. Diagn. Lab. Immu. (2000) 7: 91-95 |
| pHPV 85 | A7 | 3.500 | 7.812 | DKFZ | Journal of General Virology (1999) 80, 2923-2929 |

DKFZ is Deusches Kresbsorschungszentrum; Tumorvirologie; ATV0660; Im Neuenheimer Feld 242; DE-Heidelberg; Germany;
CNCM is Collection Nationale de Cultures de Microorganisme; Institut Pasteur; 25, rue du Docteur Roux; F-75724 Paris Cedex 15; France;
ATCC is American Type Culture Collection; 10801 University Blvd.; Manassas, Virginia 20110-2209; U.S.A.
All HPV strains are available from DKFZ.

TABLE 52

| A5 and A6 Systems PCR simplex probe conditions | | | | | | | |
|---|---|---|---|---|---|---|---|
| Kit | Kit Quantitect probe PCR | | | | | | |
| $MgCl_2$ | 6 mM | | | | | | |
| Plasmid concentration | $10^8$ cop de plasmides/PCR | | | | | | |
| | | forward primer | | reverse primer | | probes | |
| | Thermoprofile | Name | μM | Name | μM | Name | μM |
| A5 System A. B. C. D. E: PCR simplex probe conditions | | | | | | | |
| System A | 55° C. | A5E6f1 | 0.4 | A5E6r1 | 0.4 | A5E6S1 | 0.3 |
| System A | 53° C. | A5E6f1 | 0.4 | A5E6r1 | 0.4 | A5E6S1b | 0.2 |
| System B | 55° C. | A5E6f2 | 0.3 | A5E6r2 | 0.3 | A5E6S2 | 0.4 |
| System C | 55° C. | A5E6f3 | 0.6 | A5E6r3 | 0.6 | A5E6S3 | 0.3 |
| System D | 56° C. | A5E6f4 | 0.3 | A5E6r4 | 0.3 | A5E6S4 | 0.3 |
| System E | 55° C. | A5E6f5 | 0.6 | A5E6r5 | 0.6 | A5E6S4 | 0.2 |
| A6 System A. B. C. D. E: PCR simplex probe conditions | | | | | | | |
| System A | 58° C. | A6E6f1 | 0.4 | A6E6r1 | 0.4 | A6E6S1 | 0.3 |
| System B | 57° C. | A6E6f2 | 0.6 | A6E6r1 | 0.6 | A6E6S1 | 0.4 |
| System C | 55° C. | A6E6f3 | 0.6 | A6E6r2 | 0.6 | A6E6S2 | 0.3 |
| System C | 57° C. | A6E6f3 | 0.6 | A6E6r2 | 0.6 | A6E6S2b | 0.2 |
| System D | 58° C. | A6E6f4 | 0.5 | A6E6r1 | 0.5 | A6E6S1 | 0.4 |
| System E | 57° C. | A6E6f5 | 0.4 | A6E6r3 | 0.4 | A6E6S3 | 0.3 |
| System E | 56° C. | A6E6f5 | 0.4 | A6E6r3 | 0.4 | A6E6S3b | 0.2 |

TABLE 53

A5 System A, B, C, D, E, specificity

| | | Syt A A5E6S1b | | Syt A A5E6S1 | | Syt B A5E6S2 | | Syt C A5E6S3 | | Syt D A5E6S4 | | Syt E A5E6S4 | |
|---|---|---|---|---|---|---|---|---|---|---|---|---|---|
| N° HPV | Group | CT | RFU | CT | RFU | CT | RFU | CT | RFU | CT | RFU | CT | RFU |
| 51 | A5 | 22.2* | 500 | 10.95 | 600 | 9.9 | 350 | 9.9 | 500 | 10.5 | 1200 | 9.6 | 1700 |
| 26 | A5 | ND | ND | ND | ND | ND | ND | ND | ND | ND | ND | ND | ND |
| 69 | A5 | NT | NT | NT | NT | NT | NT | NT | NT | NT | NT | NT | NT |
| 82 | A5 | ND | ND | ND | ND | 22.5 | 200 | ND | ND | ND | ND | ND | ND |
| Other HPV | | ND | ND | ND | ND | ND | ND | ND | ND | ND | ND | ND | ND |
| DNA sample | | ND | ND | ND | ND | ND | ND | ND | ND | ND | ND | ND | ND |
| H2O sample | | ND | ND | ND | ND | ND | ND | ND | ND | ND | ND | ND | ND |

*Plasmid concentration: $5 \cdot 10^5$ copies of plasmids/PCR
ND: no Detection
NT: no test

TABLE 54

A6 System A, B, C, D, E, specificity

| | | Syt A A6E6S1 | | Syt B A6E6S1 | | Syt C A6E6S2 | | Syt C A6E6S2b | | Syt D A6E6S1 | | Syt E A5E6S3 | | Syt E A5E6S3b | |
|---|---|---|---|---|---|---|---|---|---|---|---|---|---|---|---|
| N° HPV | Group | CT | RFU | CT | RFU | CT | RFU | CT | RFU | CT | RFU | CT | RFU | CT | RFU |
| 56 | A6 | 14.3 | 250 | 13.0 | 500 | 13.6 | 3200 | 19.9* | 700 | 14.3 | 550 | 12.3 | 350 | 18.5* | 900 |
| 30 | A6 | ND | ND | ND | ND | ND | ND | ND | ND | ND | ND | ND | ND | ND | ND |
| 53 | A6 | NT | NT | NT | NT | NT | NT | NT | NT | NT | NT | NT | NT | NT | NT |
| 66 | A6 | ND | ND | ND | ND | ND | ND | ND | ND | ND | ND | 22.6* | 450 | 24.9* | 820 |
| Other HPV | | ND | ND | ND | ND | ND | ND | ND | ND | ND | ND | ND | ND | ND | ND |
| DNA sample | | ND | ND | ND | ND | ND | ND | ND | ND | ND | ND | ND | ND | ND | ND |
| H2O sample | | ND | ND | ND | ND | ND | ND | ND | ND | ND | ND | ND | ND | ND | ND |

*Plasmid concentration: 5 $10^6$ copies of plasmids/PCR
ND: no Detection
NT: no test

TABLE 55

| A7 System A. B. C. D: PCR simplex probe and PCR multiplex probes conditions | | | | | | | |
|---|---|---|---|---|---|---|---|
| Kit | Kit Quantitect probe PCR | | | | | | |
| $MgCl_2$ | 6 mM | | | | | | |
| Plasmid concentration | $10^6$ cop de plasmides/PCR | | | | | | |
| | | forward primer | | reverse primer | | probes | |
| | Thermoprofile | Name | μM | Name | μM | Name | μM |
| System A | 53° C. | A7E16f1a | 0.3 | A7E16r1b | 0.2 | A7E1ZAS61f | 0.2 |
| | | A7E16f2a | 0.3 | A7E16r2b | 0.3 | A7E1S63f | 0.2 |
| | | A7E16f3a | 0.3 | A7E16r3b | 0.3 | A7E1S64f | 0.2 |
| | | | | | | A7E1S40f | 0.2 |
| | | | | | | A7E1ZBS74f | 0.2 |

TABLE 55-continued

| A7 System A. B. C. D: PCR simplex probe and PCR multiplex probes conditions | | | | | | | |
|---|---|---|---|---|---|---|---|
| System B | 52° C. | A7E115f1a | 0.3 | A7E115r1a | 0.2 | A7E1ZBS26f | 0.2 |
| | | A7E115f2a | 0.3 | A7E115r2b | 0.3 | A7E1ZBS74f | 0.2 |
| | | A7E115f3d | 0.3 | | | A7E1ZBS80f | 0.2 |
| System C | 51° C. | A7E17f1 | 0.4 | A7E17r1 | 0.3 | A7E1ZCS11f | 0.2 |
| | | A7E17f2 | 0.4 | A7E17r2 | 0.4 | A7E1ZCS45f | 0.2 |
| | | A7E17f3 | 0.4 | | | A7E1ZCS63f | 0.2 |
| | | | | | | A7E1ZCS90f | 0.2 |
| System D | 53° C. | A7E12f1 | 0.3 | A7E12r2 | 0.3 | A7E1S36f | 0.2 |
| | | A7E12f2 | 0.3 | A7E12r3 | 0.1 | A7E1S37f | 0.2 |
| | | | | | | A7E1S38f | 0.2 |
| | | | | | | A7E1ZDS2f | 0.2 |

TABLE 56

A7 System A. specificity

| | Probe | Simplex A7E1ZAS61f | | Simplex A7E1ZAS63f | | Simplex A7E1ZAS64f | | Simplex A7E1ZCS40f | | Simplex A7E1ZBS74f | | Multiplex A7E1ZAS61f A7E1ZAS63f A7E1ZCS40f A7E1ZBS74f | |
|---|---|---|---|---|---|---|---|---|---|---|---|---|---|
| N° HPV | Group | CT | RFU | CT | RFU | CT | RFU | CT | RFU | CT | RFU | CT | RFU |
| 18 | A7 | 22.5 | 175 | ND | ND | ND | ND | ND | ND | ND | ND | 22.5 | 168 |
| 39 | A7 | ND | ND | ND | ND | 22.1 | 145 | ND | ND | 22.8 | 248 | 21.0 | 263 |
| 45 | A7 | ND | ND | ND | ND | ND | ND | 25.5 | 115 | ND | ND | 20.3 | 160 |
| 59 | A7 | ND | ND | 20.5 | 62.5 | ND | ND | ND | ND | ND | ND | 20.2 | 188 |
| 68 | A7 | ND | ND | ND | ND | ND | ND | ND | ND | 26.2 | 125 | 25.9 | 31 |
| 85 | A7 | ND | ND | ND | ND | ND | ND | ND | ND | ND | ND | ND | ND |
| 70 | A7 | NT | NT | NT | NT | NT | NT | NT | NT | NT | NT | NT | NT |
| Other HPV | | ND | ND | ND | ND | ND | ND | ND | ND | ND | ND | NT | NT |
| DNA sample | | ND | ND | ND | ND | ND | ND | ND | ND | ND | ND | ND | ND |
| $H_2O$ sample | | ND | ND | ND | ND | ND | ND | ND | ND | ND | ND | ND | ND |

ND: no Detection
NT: no test

TABLE 57

A7 System B. specificity

| | Probe | Simplex A7E1ZBS74f | | Simplex A7E1ZBS79f | | Simplex A7E1ZBS80f | | Simplex A7E1ZBS26f | | Simplex A7E1ZBS27f | |
|---|---|---|---|---|---|---|---|---|---|---|---|
| N° HPV | Groupe | CT | RFU | CT | RFU | CT | RFU | CT | RFU | CT | RFU |
| 18 | A7 | ND | ND | ND | ND | ND | ND | 22.9 | 770 | 22.5 | 43 |
| 39 | A7 | 24.2 | 900 | ND | ND | ND | ND | ND | ND | ND | ND |
| 45 | A7 | ND | ND | ND | ND | ND | ND | 25.6 | 312 | 21.7 | 665 |
| 59 | A7 | ND | ND | 18.6 | 2525 | 21.2 | 845 | ND | ND | ND | ND |
| 68 | A7 | 25.7 | 77 | ND | ND | ND | ND | ND | ND | ND | ND |
| 85 | A7 | ND | ND | ND | ND | ND | ND | ND | ND | ND | ND |
| 70 | A7 | NT | NT | NT | NT | NT | NT | NT | NT | NT | NT |
| Other HPV | | ND | ND | ND | ND | ND | ND | ND | ND | ND | ND |
| DNA sample | | ND | ND | ND | ND | ND | ND | ND | ND | ND | ND |
| $H_2O$ sample | | ND | ND | ND | ND | ND | ND | ND | ND | ND | ND |

| | Probe | Multiplex A7E1ZBS26f A7E1ZBS74f A7E1ZBS79f | | Multiplex A7E1ZBS26f A7E1ZBS74f A7E1ZBS80f | | Multiplex A7E1ZBS26f A7E1ZBS74f A7E1ZBS80f A7E1ZBS27f | |
|---|---|---|---|---|---|---|---|
| N° HPV | Groupe | CT | RFU | CT | RFU | CT | RFU |
| 18 | A7 | 22.3 | 215 | 20.9 | 248 | 20.3 | 318 |
| 39 | A7 | 34.8 | 155 | 26.7 | 375 | 32.9 | 213 |
| 45 | A7 | 26 | 72 | 26.3 | 98 | 26.2 | 173 |
| 59 | A7 | 24 | 505 | 21.7 | 338 | 21.5 | 308 |
| 68 | A7 | 34.5 | 128 | 22.8 | 163 | 27.1 | 135 |

TABLE 57-continued

A7 System B. specificity

| | | | | | | | |
|---|---|---|---|---|---|---|---|
| 85 | A7 | ND | ND | ND | ND | ND | ND |
| 70 | A7 | NT | NT | NT | NT | NT | NT |
| DNA sample | | ND | ND | ND | ND | ND | ND |
| $H_2O$ sample | | ND | ND | ND | ND | ND | ND |

ND: no Detection
NT: no test

TABLE 58

A7 System C. specificity

| | Probe | Simplex A7E1ZCS11f | | Simplex A7E1ZCS40f | | Simplex A7E1ZCS45f | | Simplex A7E1ZCS63f | | Simplex A7E1ZCS90f | | Multiplex A7E1ZCS40f A7E1ZCS45f A7E1ZCS63f A7E1ZCS90f | | Multiplex A7E1ZCS11f A7E1ZCS45f A7E1ZCS63f A7E1ZCS90f | |
|---|---|---|---|---|---|---|---|---|---|---|---|---|---|---|---|
| N° HPV | Groupe | CT | RFU | CT | RFU | CT | RFU | CT | RFU | CT | RFU | CT | RFU | CT | RFU |
| 18 | A7 | 22.0 | 247 | 23.4 | 200 | ND | ND | ND | ND | ND | ND | 22.6 | 231 | 22.0 | 239 |
| 39 | A7 | ND | ND | ND | ND | 21.9 | 350 | ND | ND | ND | ND | 21.7 | 649 | 21.1 | 451 |
| 45 | A7 | 21.9 | 349 | 24.0 | 325 | ND | ND | ND | ND | ND | ND | 25.6 | 319 | 24.7 | 192 |
| 59 | A7 | ND | ND | 24.4 | 35 | ND | ND | 22.4 | 400 | ND | ND | 24.4 | 491 | 25.3 | 309 |
| 68 | A7 | ND | ND | ND | ND | ND | ND | ND | ND | 26.2 | 250 | 24.5 | 344 | 25.3 | 181 |
| 85 | A7 | ND | ND | ND | ND | ND | ND | ND | ND | ND | ND | ND | ND | ND | ND |
| 70 | A7 | NT | NT | NT | NT | NT | NT | NT | NT | NT | NT | NT | NT | NT | NT |
| Other HPV | | ND | ND | ND | ND | ND | ND | ND | ND | ND | ND | NT | NT | NT | NT |
| DNA sample | | ND | ND | ND | ND | ND | ND | ND | ND | ND | ND | ND | ND | ND | ND |
| $H_2O$ sample | | ND | ND | ND | ND | ND | ND | ND | ND | ND | ND | ND | ND | ND | ND |

ND: no Detection
NT: no test

TABLE 59

A7 System D. specificity

| | Probe | Simplex A7E1ZDS37f | | Simplex A7E1ZDS38f | | Simplex A7E1S36 f | | Simplex A7E1ZDS2f | | Simplex A7E1ZDS3f | | Multiplex A7E1S36f A7E1S37f A7E1S38f A7E1ZDS2f | | Multiplex A7E1S3f A7E1S37f A7E1S38f A7E1ZDS2f | |
|---|---|---|---|---|---|---|---|---|---|---|---|---|---|---|---|
| N° HPV | Groupe | CT | RFU | CT | RFU | CT | RFU | CT | RFU | CT | RFU | CT | RFU | CT | RFU |
| 18 | A7 | 23.0 | 230 | ND | ND | ND | ND | ND | ND | ND | ND | 21.1 | 357 | 21.8 | 420 |
| 39 | A7 | ND | ND | 23.9 | 269 | ND | ND | 25.1 | 323 | ND | ND | 22.5 | 233 | 22.3 | 310 |
| 45 | A7 | ND | ND | ND | ND | 27.2 | 426 | ND | ND | 23.0 | 1545 | 26.6 | 295 | 23.5 | 508 |
| 59 | A7 | ND | ND | 23.8 | 592 | ND | ND | ND | ND | ND | ND | 22.6 | 135 | 22.6 | 230 |
| 68 | A7 | ND | ND | ND | ND | ND | ND | 22.9 | 897 | ND | ND | 23.4 | 363 | 23.5 | 548 |
| 85 | A7 | ND | ND | 31.8 | 262 | ND | ND | ND | ND | ND | ND | 32.6 | 63 | 29.2 | 103 |
| 70 | A7 | NT | NT | NT | NT | NT | NT | NT | NT | NT | NT | NT | NT | NT | NT |
| Other HPV | | ND | ND | ND | ND | ND | ND | ND | ND | ND | ND | NT | NT | NT | NT |
| DNA sample | | ND | ND | ND | ND | ND | ND | ND | ND | ND | ND | ND | ND | ND | ND |
| $H_2O$ sample | | ND | ND | ND | ND | ND | ND | ND | ND | ND | ND | ND | ND | ND | ND |

ND: no Detection
NT: no test

TABLE 60

A9 Systems: PCR simplex and PCR multiplex probes conditions

| | |
|---|---|
| Kit | Kit Quantitect probe PCR |
| $MgCl_2$ | 5 mM |
| Plasmid concentration | $10^6$ cop/PCR |

| | | forward primer | | reverse primer | | probes | |
|---|---|---|---|---|---|---|---|
| | Thermoprofile | Name | μM | Name | μM | Name | μM |
| System C | 51° C. | A9E1f8 | 0.4 | A9E1r5 | 0.4 | A9E1S10a | 0.2 |
| | | A9E1f10 | 0.4 | A9E1r6 | 0.4 | A9E1S12a | 0.2 |
| | | A9E1f12 | 0.2 | | | | |

TABLE 60-continued

| A9 Systems: PCR simplex and PCR multiplex probes conditions | | | | | | | |
|---|---|---|---|---|---|---|---|
| System E2 | 52° C. | A9E2f1a | 0.4 | A9E2r1 | 0.4 | A9E2Z7S1 | 0.2 |
| | | A9E2f2a | 0.6 | A9E2r2 | 0.4 | A9E2Z7S2 | 0.2 |
| | | A9E2f4a | 0.4 | A9E2r4 | 0.6 | A9E2Z7S3a | 0.2 |
| | | | | A9E2r13 | 0.4 | A9E2Z7S4a | 0.2 |
| | | | | A9E2r14 | 0.4 | | |
| System E3 | 52° C. | A9E2f1a | 0.4 | A9E21r1cz | 0.4 | A9E2Z7S1 | 0.2 |
| | | A9E2f2a | 0.4 | A9E21r2az | 0.4 | A9E2Z7S2 | 0.2 |
| | | A9E2f4a | 0.4 | A9E21r3az | 0.4 | A9E2Z7S3a | 0.2 |
| | | | | A9E21r4fz | | A9E2Z7S4a | 0.2 |
| | | | | A9E21r5az | | | |
| System E4 | 52° C. | A9E2Z5Z6f1c | 0.4 | A9E21r1cz | 0.4 | A9E2Z7S1 | 0.2 |
| | | A9E2Z5Z6f2c | 0.4 | A9E21r2az | 0.4 | A9E2Z7S2 | 0.2 |
| | | A9E2Z5Z6f3b | 0.4 | A9E21r3az | 0.4 | A9E2Z7S3a | 0.2 |
| | | | | A9E21r4fz | | A9E2Z7S4a | 0.2 |
| | | | | A9E21r5az | | | |
| System F | 52° C. | A9E2-1f1az | 0.4 | A9E2-1r1cz | 0.4 | A9E2Z7S1 | 0.2 |
| | | A9E2-1f2bz | 0.5 | A9E2-1r2az | 0.4 | A9E2Z7S2 | 0.2 |
| | | A9E2-1f3dz | 0.4 | A9E2-1r3az | 0.4 | A9E2Z7S3a | 0.2 |
| | | A9E2-1f4cz | 0.4 | A9E2-1r4fz | 0.4 | A9E2Z7S4a | 0.2 |
| | | | | A9E2-1r5az | 0.4 | | |
| System G Z7 | 52° C. | A9E2-1f1az | 0.4 | A9E2r8 | 0.4 | A9E2Z7S1 | 0.2 |
| | | A9E2-1f2bz | 0.4 | A9E2r10 | 0.4 | A9E2Z7S2a | 0.2 |
| | | A9E2-1f3dz | 0.4 | A9E2r12 | 0.4 | A9E2Z7S3a | 0.2 |
| | | A9E2-1f4cz | 0.5 | A9E2r12B | 0.4 | A9E2Z7S4a | 0.2 |
| | | | | A9E2r15 | 0.4 | | |
| System G Z8 | 52° C. | A9E2-1f1az | 0.6 | A9E2r8 | 0.4 | A9E2Z8S2f | 0.2 |
| | | A9E2-1f2bz | 0.4 | A9E2r10 | 0.4 | A9E2Z8S61f | 0.2 |
| | | A9E2-1f3dz | 0.4 | A9E2r12 | 0.4 | A9E2Z8S127f | 0.2 |
| | | A9E2-1f4cz | 0.5 | A9E2r12B | 0.4 | A9E2Z8S156f | 0.2 |
| | | | | A9E2r15 | 0.6 | A9E2Z8S210f | 0.2 |
| | | | | | | A9E2Z8S250f | 0.2 |
| System H | 53° C. | A9E2f6 | 0.4 | A9E2r10 | 0.4 | A9E2Z8S2f | 0.2 |
| | | A9E2f8 | 0.4 | A9E2r12B | 0.4 | A9E2Z8S61f | 0.2 |
| | | A9E2f9 | 0.4 | A9E2r15 | 0.4 | A9E2Z8S127f | 0.2 |
| | | | | A9E2r16 | 0.4 | A9E2Z8S156f | 0.2 |
| | | | | | | A9E2Z8S210f | 0.2 |
| | | | | | | A9E2Z8S231f | 0.2 |
| | | | | | | A9E2Z8S250f | 0.2 |

TABLE 61

A9 System C specificity

| | Probes | Simplex A9E1S10* | | Simplex A9E1S10a | | Simplex A9E1S11* | | Simplex A9E1S11a* | | Simplex A9E1S12* | | Simplex A9E1S12a | | Simplex A9E1S12b* | | Multiplex A9E2S10a A9E2S12a | |
|---|---|---|---|---|---|---|---|---|---|---|---|---|---|---|---|---|---|
| N° HPV | Group | CT | RFU | CT | RFU | CT | RFU | CT | RFU | CT | RFU | CT | RFU | CT | RFU | CT | RFU |
| 16 | A9 | 22.3 | 1125 | 21.9 | 492 | NT | NT | NT | NT | NT | NT | ND | ND | NT | NT | 21.0 | 442 |
| 31 | A9 | 27.3 | 625 | 23.0 | 469 | 25.7 | 679 | 24.6 | 415 | 39.4 | 14.5 | 26.6 | 103 | ND | ND | 20.8 | 458 |
| 33 | A9 | 25.8 | 450 | 22.9 | 374 | NT | NT | NT | NT | NT | NT | ND | ND | NT | NT | 22.3 | 327 |
| 35 | A9 | 33.0 | 181 | 24.9 | 188 | 27.2 | 342 | 26.4 | 234 | 26.5 | 224 | 23.2 | 502 | 26.9 | 241 | 23.0 | 435 |
| 52 | A9 | 23.4 | 1059 | 22.7 | 599 | NT | NT | 23.8 | 215 | NT | NT | ND | ND | NT | NT | 21.7 | 581 |
| 58 | A9 | 23.5 | 1435 | 23.7 | 582 | NT | NT | 24.3 | 278 | NT | NT | ND | ND | NT | NT | 23.7 | 525 |
| 67 | A9 | 25.0 | 334 | 22.4 | 294 | NT | NT | NT | NT | NT | NT | ND | ND | NT | NT | 21.9 | 279 |
| 53 | A6 | NT | NT | 29.7 | 449 | NT | NT | NT | NT | NT | NT | ND | ND | NT | NT | 31.1 | 263 |
| Other HPV | | ND | ND | ND | ND | ND | ND | ND | ND | ND | ND | ND | ND | ND | ND | ND | ND |
| DNA sample | | ND | ND | ND | ND | ND | ND | ND | ND | ND | ND | ND | ND | ND | ND | ND | ND |
| $H_2O$ sample | | ND | ND | ND | ND | ND | ND | ND | ND | ND | ND | ND | ND | ND | ND | ND | ND |

*Probes tested only with some A9 plasmids (i.e.. those A9 plasmids. which are indicated in this table)
ND: not detected
NT: not tested

TABLE 62

| A9 System E2 specificity | | | | | | | | | | | |
|---|---|---|---|---|---|---|---|---|---|---|---|
| | Probes | Simplex A9E2Z7S1 | | Simplex A9E2Z7S2 | | Simplex A9E2Z7S3a | | Simplex A9E2Z7S4a | | Multiplex A9E2S1 A9E2S2 A9E2S3a A9E2S4a | |
| N° HPV | Group | CT | RFU | CT | RFU | CT | RFU | CT | RFU | CT | RFU |
| 16 | A9 | 21.35 | 806 | ND | ND | ND | ND | 22.85 | 113 | 20.55 | 333 |
| 31 | A9 | 23.8 | 485 | ND | ND | ND | ND | 23.5 | 295 | 25.3 | 238 |
| 33 | A9 | 32.1 | 73 | 27.7 | 1415 | ND | ND | 27.5 | 45 | 31.45 | 256 |
| 35 | A9 | ND | ND | ND | ND | 27.8 | 840 | ND | ND | 30.1 | 160 |
| 52 | A9 | 25.2 | 80 | 22.4 | 186 | ND | ND | 21.45 | 278 | 21.7 | 115 |
| 58 | A9 | 24.45 | 130 | 22.1 | 435 | ND | ND | 23.55 | 94 | 24.1 | 113 |
| 67 | A9 | 30.2 | 173 | 28.7 | 447 | ND | ND | 29.35 | 123 | 31.9 | 125 |
| Other HPV | | ND | ND | ND | ND | ND | ND | ND | ND | NT | NT |
| DNA sample | | ND | ND | ND | ND | ND | ND | ND | ND | ND | ND |
| $H_2O$ sample | | ND | ND | ND | ND | ND | ND | ND | ND | ND | ND |

ND: not detected
NT: not tested

TABLE 63

| A9 System E3 specificity | | | | | | | | | | | |
|---|---|---|---|---|---|---|---|---|---|---|---|
| | Probes | Simplex A9E2Z7S1 | | Simplex A9E2Z7S2 | | Simplex A9E2Z7S3a | | Simplex A9E2Z7S4a | | Multiplex A9E2S1 A9E2S2 A9E2S3a A9E2S4a | |
| N° HPV | Group | CT | RFU | CT | RFU | CT | RFU | CT | RFU | CT | RFU |
| 16 | A9 | 20.5 | 2000 | ND | ND | ND | ND | 21.85 | 520 | 21 | 546 |
| 31 | A9 | 22.35 | 1200 | ND | ND | ND | ND | 22.65 | 660 | 25.2 | 336 |
| 33 | A9 | 27.05 | 250 | 20.7 | 1600 | ND | ND | 24.8 | 135 | 22.2 | 496 |
| 35 | A9 | ND | ND | ND | ND | 26.95 | 750 | ND | ND | 31.5 | 79 |
| 52 | A9 | 25.35 | 300 | 21.7 | 370 | ND | ND | 21.65 | 220 | 21.7 | 169 |
| 58 | A9 | 32.6 | 100 | 22.05 | 200 | ND | ND | 23.6 | 180 | 22.7 | 189 |
| 67 | A9 | 30.05 | 150 | 28.95 | 420 | ND | ND | 29.95 | 120 | NT | NT |
| Other HPV | | ND | ND | ND | ND | ND | ND | ND | ND | NT | NT |
| DNA sample | | ND | ND | ND | ND | ND | ND | ND | ND | ND | ND |
| $H_2O$ sample | | ND | ND | ND | ND | ND | ND | ND | ND | ND | ND |

ND: not detected
NT: not tested

TABLE 64

| A9 System E4 specificity | | | | | | | | | | | |
|---|---|---|---|---|---|---|---|---|---|---|---|
| | Probes | Simplex A9E2Z7S1 | | Simplex A9E2Z7S2 | | Simplex A9E2Z7S3a | | Simplex A9E2Z7S4a | | Multiplex A9E2S1 A9E2S2 A9E2S3a A9E2S4a | |
| N° HPV | Group | CT | RFU | CT | RFU | CT | RFU | CT | RFU | CT | RFU |
| 16 | A9 | 21.05 | 600.24 | ND | ND | ND | ND | 23.25 | 139.94 | 23.55 | 473.54 |
| 31 | A9 | 22.0 | 461.14 | ND | ND | ND | ND | 22.5 | 447.6 | 23.65 | 524.07 |
| 33 | A9 | 25.95 | 68.73 | 21.65 | 3190.34 | ND | ND | 24.95 | 108.385 | 23.2 | 800.33 |
| 35 | A9 | ND | ND | ND | ND | 21.6 | 1355.5 | ND | ND | 23.4 | 348.45 |
| 52 | A9 | 26.9 | 26.58 | 22.85 | 314.81 | ND | ND | 21.5 | 320.785 | 22.4 | 207.195 |
| 58 | A9 | 26.25 | 104.23 | 24.1 | 899.37 | ND | ND | 24.8 | 158.91 | 24.9 | 357.445 |
| 67 | A9 | 24.6 | 134.345 | 22.9 | 1275.03 | ND | ND | 23.85 | 188.72 | NT | NT |
| Other HPV | | ND | ND | ND | ND | ND | ND | ND | ND | NT | NT |
| DNA sample | | ND | ND | ND | ND | ND | ND | ND | ND | ND | ND |
| $H_2O$ sample | | ND | ND | ND | ND | ND | ND | ND | ND | ND | ND |

ND: not detected
NT: not tested

TABLE 65

A9 System F specificity

| | Probes | Simplex A9E2Z7S1 | | Simplex A9E2Z7S2 | | Simplex A9E2Z7S3a | | Simplex A9E2Z7S4a | | Multiplex A9E2S1 A9E2S2 A9E2S3a A9E2S4a | |
|---|---|---|---|---|---|---|---|---|---|---|---|
| N° HPV | Group | CT | RFU | CT | RFU | CT | RFU | CT | RFU | CT | RFU |
| 16 | A9 | 21.75 | 765 | ND | ND | ND | ND | 23.95 | 77 | 21.1 | 335 |
| 31 | A9 | 22.4 | 510 | ND | ND | ND | ND | 22.05 | 287 | 22.7 | 235 |
| 33 | A9 | 27.0 | 117 | 21.1 | 1298.5 | ND | ND | 24.4 | 61.5 | 21.1 | 443 |
| 35 | A9 | ND | ND | ND | ND | 21.0 | 1542.5 | ND | ND | 22.8 | 164 |
| 52 | A9 | 30.95 | 78.5 | 25.3 | 180 | ND | ND | 22.45 | 399 | 22.3 | 199 |
| 58 | A9 | 26.05 | 187.5 | 23.1 | 538.5 | ND | ND | 23.05 | 178 | 22.2 | 280 |
| 67 | A9 | 25.15 | 190.5 | 23.0 | 569.5 | ND | ND | 23.1 | 185.5 | NT | NT |
| Other HPV | | ND | ND | ND | ND | ND | ND | ND | ND | NT | NT |
| DNA sample | | ND | ND | ND | ND | ND | ND | ND | ND | ND | ND |
| $H_2O$ sample | | ND | ND | ND | ND | ND | ND | ND | ND | ND | ND |

ND: not detected

NT: not tested

TABLE 66

A9 System G Z7 specificity

| | Probes | Simplex A9E2Z7S1 | | Simplex A9E2Z7S2a | | Simplex A9E2Z7S3a | | Simplex A9E2Z7S4a | | Multiplex A9E2S1 A9E2S2a A9E2S3a A9E2S4a | |
|---|---|---|---|---|---|---|---|---|---|---|---|
| N° HPV | Group | CT | RFU | CT | RFU | CT | RFU | CT | RFU | CT | RFU |
| 16 | A9 | 20.3 | 600 | ND | ND | ND | ND | 24.6 | 56 | 21 | 658 |
| 31 | A9 | 20.6 | 303.5 | ND | ND | ND | ND | 22.7 | 167 | 23.1 | 501 |
| 33 | A9 | 22.9 | 80 | ND | ND | ND | ND | 22.1 | 280 | 20.4 | 920 |
| 35 | A9 | ND | ND | ND | ND | 22.2 | 1330 | ND | ND | 23.9 | 254 |
| 52 | A9 | 24.1 | 53 | 23 | 371.5 | ND | ND | 23 | 284 | 22.9 | 519 |
| 58 | A9 | 23.1 | 150 | 21.6 | 739 | ND | ND | 23.8 | 124 | 21.9 | 779 |
| 67 | A9 | 21.9 | 191.5 | 21.7 | 692 | ND | ND | 23.6 | 156.5 | NT | NT |
| Other HPV | | ND | ND | ND | ND | ND | ND | ND | ND | NT | NT |
| DNA sample | | ND | ND | ND | ND | ND | ND | ND | ND | ND | ND |
| $H_2O$ sample | | ND | ND | ND | ND | ND | ND | ND | ND | ND | ND |

ND: not detected
NT: not tested

TABLE 67

A9 system G Z8 specificity

| | Probes | Simplex A9E2Z8S2f | | Simplex A9E2Z8S61f | | Simplex A9E2Z8S127f | | Simplex A9E2Z8S156f | | Simplex A9E2Z8S210f | | Simplex A9E2Z8S250f | |
|---|---|---|---|---|---|---|---|---|---|---|---|---|---|
| N° HPV | Group | CT | RFU | CT | RFU | CT | RFU | CT | RFU | CT | RFU | CT | RFU |
| 16 | A9 | 21.5 | 261 | ND | ND | ND | ND | ND | ND | ND | ND | ND | ND |
| 31 | A9 | ND | ND | 21.9 | 291 | ND | ND | ND | ND | ND | ND | ND | ND |
| 33 | A9 | ND | ND | ND | ND | 20.5 | 677 | ND | ND | ND | ND | ND | ND |
| 35 | A9 | ND | ND | ND | ND | ND | ND | 22.6 | 333.5 | ND | ND | ND | ND |
| 52 | A9 | ND | ND | ND | ND | ND | ND | ND | ND | 23.0 | 115 | ND | ND |
| 58 | A9 | ND | ND | ND | ND | ND | ND | ND | ND | ND | ND | 20.0 | 1348 |
| 67 | A9 | ND | ND | ND | ND | ND | ND | ND | ND | ND | ND | 22.1 | 351.5 |
| Other HPV | | ND | ND | ND | ND | ND | ND | ND | ND | ND | ND | ND | ND |
| DNA sample | | ND | ND | ND | ND | ND | ND | ND | ND | ND | ND | ND | ND |
| $H_2O$ sample | | ND | ND | ND | ND | ND | ND | ND | ND | ND | ND | ND | ND |

TABLE 67-continued

A9 system G Z8 specificity

| | Probes | Multiplex A9E2Z8S2f A9E2Z8S61f A9E2Z8S127f A9E2Z8S156f A9E2Z8S210f A9E2Z8S250f* | | Multiplex A9E2Z8S2f** A9E2Z8S61f A9E2Z8S127f A9E2Z8S156f A9E2Z8S210f** A9E2Z8S250f* | |
|---|---|---|---|---|---|
| N° HPV | Group | CT | RFU | CT | RFU |
| 16 | A9 | 22.4 | 27 | 22.4 | 22 |
| 31 | A9 | 23.6 | 73.5 | 24 | 42 |
| 33 | A9 | 21.8 | 83.5 | 20.9 | 110 |
| 35 | A9 | 22.7 | 42 | 23.6 | 45 |
| 52 | A9 | 25.8 | 25 | 24 | 30 |
| 58 | A9 | 19.3 | 169 | 19.6 | 201 |
| 67 | A9 | 21.6 | 57 | NT | NT |
| DNA sample | | ND | ND | ND | ND |
| $H_2O$ sample | | ND | ND | ND | ND |

*probe at 0.1 μM in these tests

**probes at 0.3 μM in this test

ND: not detected

NT: not tested

TABLE 68

A9 SystemH specificity

| | Probes | Simplex A9E2Z8S2f | | Simplex A9E2Z8S61f | | Simplex A9E2Z8S127f | | Simplex A9E2Z8S156f | | Simplex A9E2Z8S210f | | Simplex A9E2Z8S231f | | Simplex A9E2Z8S250f | |
|---|---|---|---|---|---|---|---|---|---|---|---|---|---|---|---|
| N° HPV | Group | CT | RFU | CT | RFU | CT | RFU | CT | RFU | CT | RFU | CT | RFU | CT | RFU |
| 16 | A9 | 21.7 | 665 | ND | ND | ND | ND | ND | ND | ND | ND | ND | ND | ND | ND |
| 31 | A9 | ND | ND | 22.1 | 307 | ND | ND | ND | ND | ND | ND | ND | ND | ND | ND |
| 33 | A9 | ND | ND | ND | ND | 21.4 | 889 | ND | ND | ND | ND | ND | ND | ND | ND |
| 35 | A9 | ND | ND | ND | ND | ND | ND | 22.2 | 155 | ND | ND | ND | ND | ND | ND |
| 52 | A9 | ND | ND | ND | ND | ND | ND | ND | ND | 23.9 | 270 | ND | ND | ND | ND |
| 58 | A9 | ND | ND | ND | ND | ND | ND | ND | ND | ND | ND | 21.3 | 345 | 19.8 | 2690 |
| 67 | A9 | ND | ND | ND | ND | ND | ND | ND | ND | ND | ND | 27.0 | 82.5 | 27.1 | 276 |
| Other HPV | | ND | ND | ND | ND | ND | ND | ND | ND | ND | ND | ND | ND | ND | ND |
| DNA sample | | ND | ND | ND | ND | ND | ND | ND | ND | ND | ND | ND | ND | ND | ND |
| $H_2O$ sample | | ND | ND | ND | ND | ND | ND | ND | ND | ND | ND | ND | ND | ND | ND |

| | Probes | Multiplex A9E2Z8S2f A9E2Z8S61f A9E2Z8S127f A9E2Z8S156f A9E2Z8S210f A9E2Z8S250f | | Multiplex A9E2Z8S2f A9E2Z8S61f A9E2Z8S127f A9E2Z8S156f A9E2Z8S210f A9E2Z8S231f | | Multiplex A9E2Z8S2f A9E2Z8S61f A9E2Z8S127f A9E2Z8S156f A9E2Z8S210f A9E2Z8S250f | | Multiplex A9E2Z8S2f A9E2Z8S61f A9E2Z8S127f A9E2Z8S156f A9E2Z8S210f A9E2Z8S231f | |
|---|---|---|---|---|---|---|---|---|---|
| N° HPV | Group | CT | RFU | CT | RFU | CT | RFU | CT | RFU |
| 16 | A9 | 21.9 | 143 | 21.9 | 167 | 21.7 | 106 | 22.9 | 98 |
| 31 | A9 | 21.5 | 81 | 21.9 | 101 | 21.6 | 50 | 22.5 | 62 |
| 33 | A9 | 22.7 | 114 | 22.5 | 155 | 22.2 | 93 | 22.2 | 158 |
| 35 | A9 | 22.5 | 63 | 22.4 | 70 | 22.4 | 46 | 22.9 | 48 |
| 52 | A9 | 23.7 | 44 | 25.4 | 50 | 24.6 | 15 | 25.0 | 39 |
| 58 | A9 | 19.7 | 403 | 19.9 | 280 | 19.1 | 398 | 19.7 | 255 |
| 67 | A9 | 29.0 | 29 | 29.1 | 26 | 27.6 | 16 | 27.0 | 38 |
| DNA sample | | ND | ND | ND | ND | ND | ND | ND | ND |
| $H_2O$ sample | | ND | ND | ND | ND | ND | ND | ND | ND |

ND: not detected
NT: not tested

TABLE 69

| A5 Systems A, B, C, D, E/sensitivity | | | | | | | | |
|---|---|---|---|---|---|---|---|---|
| | System A | | | | System B | | System C | |
| | A5E6S1/HPV51 | | A5E6S1b/HPV51 | | A5E6S2/HPV51 | | A5E6S3/HPV51 | |
| | Moy Ct | Moy RFUs | Moy Ct | Moy RFUs | Moy Ct | Moy RFUs | Moy Ct | Moy RFUs |
| $10^3$ cop/PCR | 27.95 | 2700 | 25.65 | 1100 | 27.3 | 180 | 24.3 | 430 |
| $10^2$ cop/PCR | 31.3 | 2500 | 29.75 | 1000 | 31.0 | 180 | 26.85 | 380 |
| 10 cop/PCR | 34.85 | 2200 | 34.3 | 700 | 35.7 | 160 | 30.0 | 280 |
| 1 cop/PCR | 36.95 | 1700 | 36.65 | 450 | 38.85 | 150 | 33.1 | 180 |
| H2O sample | ND | ND | ND | ND | ND | ND | ND | ND |
| ADN Sample | ND | ND | ND | ND | ND | ND | ND | ND |
| r2/slope/PCR efficiency | 0.997/−2.988/116.1% | | 0.997/−3.647/88% | | 0.990/−3.924/79.8% | | 0.997/−2.955/118% | |

| | System D | | System E | |
|---|---|---|---|---|
| Copy number HPV | A5E6S4/HPV51 | | A5E6S4/HPV51 | |
| plasmid/PCR | Moy Ct | Moy RFUs | Moy Ct | Moy RFUs |
| $10^3$ cop/PCR | 31.45 | 750 | 24.55 | 500 |
| $10^2$ cop/PCR | 35.1 | 700 | 27.45 | 450 |
| 10 cop/PCR | 39.7 | 500 | 31.15 | 450 |
| 1 cop/PCR | 43.2 | 250 | 33.75 | 500 |
| H2O sample | ND | ND | ND | ND |
| ADN Sample | ND | ND | ND | ND |
| r2/slope/PCR fficiency | 0.994/−3.990/78.1% | | 0.997/−3.128/108.8% | |

ND: No Detection

NT: Not tested

TABLE 70

| A6 Systems A, B, C, D, E/sensitivity | | | | | | | | |
|---|---|---|---|---|---|---|---|---|
| | System A | | System B | | System C | | | |
| Copy number HPV | A6E6S1/HPV56 | | A6E6S1/HPV56 | | A6E6S2/HPV56 | | A6E6S2b/HPV56 | |
| plasmid/PCR | Moy Ct | Moy RFUs | Moy Ct | Moy RFUs | Moy Ct | Moy RFUs | Moy Ct | Moy RFUs |
| $10^3$ cop/PCR | 27.25 | 400 | 27.1 | 600 | 33.955 | 1700 | 29.55 | 650 |
| $10^2$ cop/PCR | 27.8 | 450 | 27.9 | 700 | 35.78 | 1500 | 33.1 | 550 |
| 10 cop/PCR | 30.8 | 450 | 30.75 | 700 | 38.89 | 1200 | 38.25 | 300 |
| 1 cop/PCR | 34.25 | 350 | 34.15 | 450 | 43.09 | 600 | ND | ND |
| H2O sample | ND | ND | ND | ND | ND | ND | ND | ND |
| ADN Sample | ND | ND | ND | ND | ND | ND | ND | ND |
| r2/slope/PCR efficiency | 0.974/−3.228/104.1% | | 0.997/−3.16/107% | | 0.989/−3.270/102.2% | | 0.998/−3.699/86.4% | |

| | System D | | System E | | | |
|---|---|---|---|---|---|---|
| Copy number HPV | A6E6S1/HPV56 | | A6E6S3/HPV56 | | A6E6S3b/HPV56 | |
| plasmid/PCR | Moy Ct | Moy RFUs | Moy Ct | Moy RFUs | Moy Ct | Moy RFUs |
| $10^3$ cop/PCR | 28.95 | 750 | 26.1 | 600 | 27.5 | 750 |
| $10^2$ cop/PCR | 30.75 | 750 | 27.45 | 650 | 30.35 | 750 |
| 10 cop/PCR | 33.65 | 800 | 30.45 | 550 | 33.9 | 600 |
| 1 cop/PCR | 35.4 | 700 | 32.15 | 550 | ND | ND |
| H2O sample | ND | ND | ND | ND | ND | ND |
| ADN Sample | ND | ND | ND | ND | ND | ND |
| r2/slope/PCR efficiency | 0.987/−2.461/154.8% | | 0.986/−2.126/195.4% | | 0.990/−3.183/106.1% | |

ND: No detection
NT: Not tested

TABLE 71

A7 System A, sensitivity

| copy number HPV plasmid/ | A7E1ZAS61f HPV 18 | | A7E1S63f HPV 59 | | A7E1S64f HPV 39 | | A7E1S40f HPV 45 | |
|---|---|---|---|---|---|---|---|---|
| PCR | Moy Ct | Moy RFU | Moy Ct | Moy RFUs | Moy Ct | Moy RFUs | Ecart-type | Moy RFUs |
| $10^6$ cop/PCR | 22.7 | 165 | 21.7 | 125 | 22.1 | 240 | 24.6 | 305 |
| $10^5$ cop/PCR | 25.95 | 170 | 24.6 | 95 | 25.0 | 310 | 27.45 | 320 |
| $10^4$ cop/PCR | 29.15 | 180 | 27.1 | 125 | 28.3 | 320 | 30.6 | 310 |
| $10^3$ cop/PCR | 32.6 | 180 | 31.0 | 105 | 31.1 | 350 | 33.85 | 272.5 |
| $10^2$ cop/PCR | 35.2 | 170 | 33.95 | 70 | 34.15 | 290 | 36.9 | 282.5 |
| $H_2O$ sample | ND | ND | ND | ND | ND | ND | ND | ND |
| ADN sample | ND | ND | ND | ND | ND | ND | ND | ND |
| r2/slope/efficiency PCR | 0.997/−3.16/107% | | 0.993/−3.1/110% | | 0.996/−3.19/106% | | 0.995/−3.27/102% | |

| copy number HPV plasmid/ | A7E1ZBS74f HPV 68 | | A7E1ZBS74f HPV 39 | |
|---|---|---|---|---|
| PCR | Moy Ct | Moy RFUs | Moy Ct | Moy RFUs |
| $10^6$ cop/PCR | 24.2 | 597.585 | 22.5 | 1095.195 |
| $10^5$ cop/PCR | 26.85 | 611.52 | 25.25 | 1182.205 |
| $10^4$ cop/PCR | 31.15 | 557.525 | 28.05 | 1062.505 |
| $10^3$ cop/PCR | 35.35 | 496.425 | 32.45 | 1005.26 |
| $10^2$ cop/PCR | 39.5 | 473.395 | 40.6 | 804 |
| $H_2O$ sample | ND | ND | ND | ND |
| ADN sample | ND | ND | ND | ND |
| r2/slope/efficiency PCR | 0.995/−3.919/80% | | 0.972/−3.271/102.2% | |

ND: no Detection
NT: no test

TABLE 72

A7 System B. sensitivity

| copy number HPV plasmid/ | A7E1ZBS26f HPV 18 | | A7E1ZBS26f HPV 45 | | A7E1ZBS74f HPV 68 | | A7E1ZBS74f HPV 39 | |
|---|---|---|---|---|---|---|---|---|
| PCR | Moy Ct | Moy RFU | Moy Ct | Moy RFUs | Moy Ct | Moy RFUs | Ecart-type | Moy RFUs |
| $10^6$ cop/PCR | 21.35 | 222.5 | 22.1 | 115 | 21.2 | 705 | 24.85 | 892.5 |
| $10^5$ cop/PCR | 23.05 | 252.5 | 24.75 | 130 | 24.7 | 690 | 27.0 | 852.5 |
| $10^4$ cop/PCR | 26.5 | 225 | 28.05 | 115 | 28.15 | 645 | 31.2 | 632.5 |
| $10^3$ cop/PCR | 28.6 | 180 | 29.7 | 112.5 | 30.85 | 540 | 32.65 | 445 |
| $10^2$ cop/PCR | 31.35 | 155 | 30.85 | 112.5 | 33.25 | 390 | 31.85 | 660.5 |
| $H_2O$ sample | ND | ND | ND | ND | 42.5 | 64 | 42.5 | 64 |
| ADN sample | ND | ND | ND | ND | ND | 23 | ND | 23 |
| r2/slope/efficiency PCR | 0.987/−2.55/146% | | 0.970/−2.24/179% | | 0.995/−3.02/114% | | 0.887/−1.96/223% | |

| copy number HPV plasmid/ | A7E1ZBS80f HPV 59 | | A7E1ZBS79f HPV 59 | | A7E1ZBS27f HPV 45 | | A7E1ZBS27f HPV 18 | |
|---|---|---|---|---|---|---|---|---|
| PCR | Moy Ct | Moy RFUs | Moy Ct | Moy RFUs | Moy Ct | Moy RFUs | Moy Ct | Moy RFUs |
| $10^6$ cop/PCR | 19.65 | 952.5 | 18.85 | 387.5 | 20.3 | 675 | 20.9 | 112.5 |
| $10^5$ cop/PCR | 21.85 | 1025 | 21.5 | 427.5 | 23.25 | 595 | 24.35 | 117.5 |
| $10^4$ cop/PCR | 23.75 | 997.5 | 24.1 | 405 | 26.3 | 557.5 | 28 | 122.5 |
| $10^3$ cop/PCR | 27.1 | 952.5 | 26.25 | 412.5 | 27.8 | 502.5 | 31.7 | 137.5 |
| $10^2$ cop/PCR | 31.7 | 907.5 | 29.0 | 377.5 | 33.05 | 440 | 31.05 | 157.5 |
| $H_2O$ sample | ND | ND | ND | ND | ND | ND | ND | ND |
| ADN sample | ND | ND | ND | ND | ND | ND | ND | ND |
| r2/slope/efficiency PCR | 0.981/−2.94/119% | | 0.976/−2.51/150% | | 0.973/−3.01/115% | | 0.934/−2.718/133.3% | |

ND: no Detection
NT: no test

TABLE 73

A7 System C. sensitivity

| copy number HPV plasmid/ | A7E1ZCS11f/HPV 45 | | A7E1ZCS45f/HPV 39 | | A7E1ZCS63f/HPV 59 | | A7E1ZCS90f/HPV 68 | |
|---|---|---|---|---|---|---|---|---|
| PCR | Moy Ct | Moy RFU | Moy Ct | Moy RFUs | Moy Ct | Moy RFUs | Ecart-type | Moy RFUs |
| $10^6$ cop/PCR | 21.95 | 349.45 | 20.35 | 649.815 | 23.1 | 256.71 | 24.05 | 234.305 |
| $10^5$ cop/PCR | 24.7 | 344.81 | 23.4 | 623.445 | 26.4 | 224.625 | 27.0 | 200 |
| $10^4$ cop/PCR | 28.35 | 274.81 | 26.95 | 502.52 | 28.9 | 178.505 | 30.5 | 140.205 |
| $10^3$ cop/PCR | 31.6 | 154.565 | 30.35 | 364.095 | 33.0 | 107.145 | 33.4 | 92.505 |
| $10^2$ cop/PCR | 35.1 | 48.72 | 33.45 | 173.17 | 35.3 | 49.965 | 37.15 | 46.65 |

TABLE 73-continued

A7 System C. sensitivity

| | | | | | | | | |
|---|---|---|---|---|---|---|---|---|
| $H_2O$ sample | ND | ND | ND | ND | ND | ND | ND | ND |
| ADN sample | ND | ND | ND | ND | ND | ND | ND | ND |
| r2/slope/efficiency PCR | 0.997/−3.321/100% | | 0.998/−3.322/100% | | 0.993/−3.111/109.9% | | 0.998/−3.255/102.9% | |

| copy number HPV plasmid/ | A7E1ZCS11f/HPV 18 | | A7E1ZCS40f/HPV 18 | | A7E1ZCS40f/HPV 45 | | A7E1ZCS40f/HPV 59 | |
|---|---|---|---|---|---|---|---|---|
| PCR | Moy Ct | Moy RFUs | Moy Ct | Moy RFUs | Moy Ct | Moy RFUs | Moy Ct | Moy RFUs |
| $10^6$ cop/PCR | 22.05 | 247.645 | 23.6 | 65.31 | 23.65 | 161.135 | 22.25 | 9.985 |
| $10^5$ cop/PCR | 24.45 | 230.285 | 26.25 | 79.255 | 27.5 | 138.725 | 22.65 | 27.19 |
| $10^4$ cop/PCR | 27.1 | 197.085 | 29.95 | 56.015 | 29.85 | 107.025 | 28.7 | 11.595 |
| $10^3$ cop/PCR | 31.35 | 94.76 | 34.2 | 29.31 | 37.9 | 14 | N/A | ND |
| $10^2$ cop/PCR | 35.0 | 12.61 | N/A | ND | N/A | ND | N/A | ND |
| $H_2O$ sample | ND | ND | ND | ND | ND | ND | ND | ND |
| ADN sample | ND | ND | ND | ND | ND | ND | ND | ND |
| r2/slope/efficiency PCR | 0.993/−3.275/102% | | 0.986/−3.55/91.3% | | 0.988/−3.079/111.3% | | 0.922/−4.269/71.5% | |

ND: no Detection

NT: no test

TABLE 74

A7 System D. sensitivity

| copy number HPV plasmid/ | A7E1ZDS36f HPV 45 | | A7E1ZDS37f HPV 18 | | A7E1ZDS38f HPV 59 | | A7E1ZDS38f HPV 39 | |
|---|---|---|---|---|---|---|---|---|
| PCR | Moy Ct | Moy RFUs | Moy Ct | Moy RFUs | Moy Ct | Moy RFUs | Moy Ct | Moy RFUs |
| $10^6$ cop/PCR | 26.0 | 705 | 21.9 | 305 | 21.05 | 525 | 24.2 | 190 |
| $10^5$ cop/PCR | 29.5 | 645 | 25.55 | 302.5 | 25.35 | 487.5 | 27.8 | 192.5 |
| $10^4$ cop/PCR | 33.25 | 537.5 | 27.1 | 292.5 | 29.2 | 402.5 | 32.25 | 155 |
| $10^3$ cop/PCR | 36.95 | 440 | 30.95 | 265 | 32.5 | 335 | 35.95 | 147.5 |
| $10^2$ cop/PCR | 40.0 | 332.5 | 32.45 | 247.5 | 33.7 | 342.5 | 39.2 | 140 |
| $H_2O$ sample | ND | ND | ND | ND | ND | ND | ND | ND |
| ADN sample | ND | ND | ND | ND | ND | ND | ND | ND |
| r2/slope/efficiency PCR | 0.998/−3.622/88.8% | | 0.978/−2.652/138.3% | | 0.981/−3.253/103% | | 0.995/−3.805/83.2% | |

| copy number HPV plasmid/ | A7E1ZDS2f HPV 68 | | A7E1ZDS2f HPV 39 | | A7E1ZDS3f HPV 45 | |
|---|---|---|---|---|---|---|
| PCR | Moy Ct | Moy RFUs | Moy Ct | Moy RFUs | Moy Ct | Moy RFUs |
| $10^6$ cop/PCR | 23.1 | 942 | 21.15 | 113.5 | 21.85 | 2075 |
| $10^5$ cop/PCR | 26.8 | 898.5 | 25.55 | 97.5 | 24.9 | 1875 |
| $10^4$ cop/PCR | 30.5 | 842.5 | 28.8 | 87.5 | 27.75 | 1617.5 |
| $10^3$ cop/PCR | 33.15 | 677.5 | 32.25 | 79 | 31.05 | 1250 |
| $10^2$ cop/PCR | 36.65 | 635 | 31.75 | 80 | 34.2 | 1007.5 |
| $H_2O$ sample | ND | ND | ND | ND | ND | ND |
| ADN sample | ND | ND | 36.1 | ND | ND | ND |
| r2/slope/efficiency PCR | 0.995/−3.334/99.5% | | 0.941/−2.797/127.8% | | 0.999/−3.086/110.9% | |

ND: no Detection
NT: no test

TABLE 75

A9 System C, sensitivity

| copy number HPV plasmid/ | A9E1S10a/HPV 16 | | A9E1S10a/HPV 31 | | A9E1S10a/HPV 33 | | A9E1S10a/HPV 35 | |
|---|---|---|---|---|---|---|---|---|
| PCR | Moy Ct | Moy RFUs | Moy Ct | Moy RFUs | Moy Ct | Moy RFUs | Moy Ct | Moy RFUs |
| $10^6$ cop/PCR | 22.4 | 457.5 | 22.15 | 477 | 22.5 | 410 | 24.4 | 233.5 |
| $10^5$ cop/PCR | 27.2 | 402.5 | 26.45 | 360 | 28.2 | 344 | 29.0 | 202 |
| $10^4$ cop/PCR | 30.85 | 341 | 29.9 | 342 | 31.0 | 306.5 | 32.65 | 192 |
| $10^3$ cop/PCR | 34.3 | 322.5 | 33.2 | 316.5 | 34.35 | 272 | 36.25 | 167 |
| $10^2$ cop/PCR | 37.35 | 320 | 36.7 | 259.5 | 37.1 | 227.5 | 39.45 | 135.5 |
| $H_2O$ sample | ND | ND | ND | ND | ND | ND | ND | ND |
| ADN sample | ND | ND | ND | ND | ND | ND | ND | ND |
| r2/slope/efficiency PCR | 0.996/−3.705/86.2% | | 0.998/−3.586/90.0% | | 0.987/−3.536/91.8% | | 0.997/−3.735/85.2% | |

TABLE 75-continued

A9 System C, sensitivity

| copy number HPV plasmid/ | A9E1S10a/HPV 52 | | A9E1S10a/HPV 58 | | A9E1S10a/HPV 67 | |
|---|---|---|---|---|---|---|
| PCR | Moy Ct | Moy RFUs | Moy Ct | Moy RFUs | Moy Ct | Moy RFUs |
| $10^6$ cop/PCR | 21.85 | 650 | 23.65 | 620 | 22.0 | 351 |
| $10^5$ cop/PCR | 26.4 | 507 | 28.3 | 558.5 | 25.95 | 339 |
| $10^4$ cop/PCR | 29.9 | 474.5 | 32.3 | 484 | 29.75 | 304 |
| $10^3$ cop/PCR | 33.55 | 429.5 | 35.95 | 422.5 | 33.05 | 261.5 |
| $10^2$ cop/PCR | 36.7 | 350.5 | 39.35 | 271.5 | 36.45 | 222.5 |
| $H_2O$ sample | ND | ND | ND | ND | ND | ND |
| ADN sample | ND | ND | ND | ND | ND | ND |
| r2/slope/efficiency PCR | 0.997/−3.680/87.0% | | 0.997/−3.915/80.1% | | 0.999/−3.594/89.8% | |

| copy number HPV plasmid/ | A9E1S12a/HPV 31 | | A9E1S12a/HPV 35 | |
|---|---|---|---|---|
| PCR | Moy Ct | Moy RFUs | Moy Ct | Moy RFUs |
| $10^6$ cop/PCR | 26.45 | 61 | 22.45 | 504 |
| $10^5$ cop/PCR | 31.3 | 53.5 | 27.6 | 469.5 |
| $10^4$ cop/PCR | 32.2 | 67 | 31.3 | 452 |
| $10^3$ cop/PCR | 36.25 | 56 | 34.25 | 419.5 |
| $10^2$ cop/PCR | 39.45 | 51 | 37.7 | 356.5 |
| $H_2O$ sample | ND | ND | ND | ND |
| ADN sample | ND | ND | ND | ND |
| r2/slope/efficiency PCR | 0.971/−3.099/110.2% | | 0.994/−3.719/85.7% | |

ND: not detected

NT: not tested

TABLE 76

A9 System E2, sensitivity

| copy number HPV plasmid/ | A9E2Z7S1/HPV 16 | | A9E2Z7S1/HPV 31 | | A9E2Z7S1/HPV 33 | | A9E2Z7S1/HPV 52 | |
|---|---|---|---|---|---|---|---|---|
| PCR | Moy Ct | Moy RFUs | Moy Ct | Moy RFUs | Moy Ct | Moy RFUs | Moy Ct | Moy RFUs |
| $10^6$ cop/PCR | 19.8 | 795 | 23.05 | 485 | 31.35 | 88.5 | 24.25 | 86 |
| $10^5$ cop/PCR | 24.1 | 765 | 26.5 | 425 | 34.4 | 83.5 | 27.05 | 82.5 |
| $10^4$ cop/PCR | 27.3 | 705 | 29.8 | 385 | 38.1 | 65 | 30.8 | 78.5 |
| $10^3$ cop/PCR | 31.5 | 610 | 33.0 | 342.5 | 42.8 | 35 | 33.85 | 77.5 |
| $10^2$ cop/PCR | 34.95 | 287.5 | 37.25 | 177.5 | 38.9 | 41.5 | 36.2 | 82.5 |
| $H_2O$ sample | ND | ND | ND | ND | ND | ND | ND | ND |
| ADN sample | ND | ND | ND | ND | ND | ND | ND | ND |
| r2/slope/efficiency PCR | 0.996/−3.767/84.3% | | 0.998/−3.492/93.4% | | 0.869/−2.762/130.2% | | 0.996/−3.069/111.7% | |

| copy number HPV plasmid/ | A9E2Z7S1/HPV 58 | | A9E2Z7S1/HPV 67 | | A9E1Z7S2/HPV 33 | | A9E1Z7S2/HPV 58 | |
|---|---|---|---|---|---|---|---|---|
| PCR | Moy Ct | Moy RFUs | Moy Ct | Moy RFUs | Moy Ct | Moy RFUs | Moy Ct | Moy RFUs |
| $10^6$ cop/PCR | 23.4 | 145 | 29.35 | 120.5 | 26.4 | 1257.5 | 20.95 | 485 |
| $10^5$ cop/PCR | 26.4 | 140 | 32.85 | 105 | 30.0 | 1120 | 24.35 | 395 |
| $10^4$ cop/PCR | 30.45 | 125 | 36.9 | 77.5 | 33.6 | 877.5 | 28.15 | 340 |
| $10^3$ cop/PCR | 34.35 | 95 | 42.4 | 37.5 | 37.05 | 520 | 31.85 | 310 |
| $10^2$ cop/PCR | 37.05 | 91 | ND | ND | 40.0 | 107.5 | 34.7 | 257.5 |
| $H_2O$ sample | ND | ND | ND | ND | ND | ND | ND | ND |
| ADN sample | ND | ND | ND | ND | ND | ND | ND | ND |
| r2/slope/efficiency PCR | 0.99/−3.525/90.2% | | 0.991/−4.333/70.1% | | 0.993/−3.431/95.7% | | 0.999/−3.508/92.8% | |

| copy number HPV plasmid/ | A9E1Z7S2/HPV 52 | | A9E1Z7S2/HPV 67 | | A9E1Z7S3a/HPV 35 | |
|---|---|---|---|---|---|---|
| PCR | Moy Ct | Moy RFUs | Moy Ct | Moy RFUs | Moy Ct | Moy RFUs |
| $10^6$ cop/PCR | 21.1 | 182.5 | 26.6 | 473 | 27.25 | 825 |
| $10^5$ cop/PCR | 24.65 | 197.5 | 30.4 | 430 | 30.85 | 807.5 |
| $10^4$ cop/PCR | 28.15 | 192.5 | 33.2 | 390 | 34.5 | 505 |
| $10^3$ cop/PCR | 31.85 | 182.5 | 35.7 | 200 | 37.9 | 82.5 |
| $10^2$ cop/PCR | 34.95 | 162.5 | 40.3 | 115 | 40.4 | 47.5 |
| $H_2O$ sample | ND | ND | ND | ND | ND | ND |
| ADN sample | ND | ND | ND | ND | ND | ND |
| r2/slope/efficiency PCR | 0.999/−3.480/92.8% | | 0.989/−3.279/101.8% | | 0.990/−3.396/97% | |

TABLE 76-continued

A9 System E2, sensitivity

| copy number HPV plasmid/ PCR | A9E2Z7S4a/HPV 31 Moy Ct | A9E2Z7S4a/HPV 31 Moy RFUs | A9E2Z7S4a/HPV 52 Moy Ct | A9E2Z7S4a/HPV 52 Moy RFUs | A9E2Z7S4a/HPV 16 Moy Ct | A9E2Z7S4a/HPV 16 Moy RFUs |
|---|---|---|---|---|---|---|
| $10^6$ cop/PCR | 23.2 | 460 | 21.45 | 485 | 21.85 | 182.5 |
| $10^5$ cop/PCR | 26.5 | 452.5 | 24.5 | 425 | 25.6 | 177.5 |
| $10^4$ cop/PCR | 29.85 | 435 | 28.35 | 385 | 29.8 | 147.5 |
| $10^3$ cop/PCR | 34.05 | 322.5 | 31.65 | 340 | 33.75 | 135 |
| $10^2$ cop/PCR | 38.0 | 165 | 35.55 | 280 | 36.2 | 145 |
| $H_2O$ sample | ND | ND | ND | ND | ND | ND |
| ADN sample | ND | ND | ND | ND | ND | ND |
| r2/slope/efficiency PCR | 0.998/−3.720/85.7% | | 0.996/−3.517/92.5% | | 0.996/−3.687/86.7% | |

| copy number HPV plasmid/ PCR | A9E2Z7S4a/HPV 33 Moy Ct | A9E2Z7S4a/HPV 33 Moy RFUs | A9E2Z7S4a/HPV 58 Moy Ct | A9E2Z7S4a/HPV 58 Moy RFUs | A9E2Z7S4a/HPV 67 Moy Ct | A9E2Z7S4a/HPV 67 Moy RFUs |
|---|---|---|---|---|---|---|
| $10^6$ cop/PCR | 32.0 | 57.5 | 23.6 | 115 | 28.45 | 177.5 |
| $10^5$ cop/PCR | 35.0 | 57.5 | 27.2 | 122.5 | 32.0 | 140 |
| $10^4$ cop/PCR | 43.6 | 31 | 31.5 | 87.5 | 36.3 | 107.5 |
| $10^3$ cop/PCR | ND | ND | 34.1 | 90 | 42.8 | 42.5 |
| $10^2$ cop/PCR | ND | ND | 40.4 | 50 | 46.7 | 20 |
| $H_2O$ sample | ND | ND | ND | ND | ND | ND |
| ADN sample | ND | ND | ND | ND | ND | ND |
| r2/slope/efficiency PCR | 0.938/−5.797/48..8% | | 0.980/−4.047/76.6% | | 0.981/−4.736/62.6% | |

ND: not detected
NT: not tested

TABLE 77

A9 System E3, sensitivity

| copy number HPV plasmid/ PCR | A9E2Z7S1/HPV 16 Moy Ct | A9E2Z7S1/HPV 16 Moy RFUs | A9E2Z7S1/HPV 31 Moy Ct | A9E2Z7S1/HPV 31 Moy RFUs | A9E2Z7S1/HPV 33 Moy Ct | A9E2Z7S1/HPV 33 Moy RFUs | A9E2Z7S1/HPV 52 Moy Ct | A9E2Z7S1/HPV 52 Moy RFUs |
|---|---|---|---|---|---|---|---|---|
| $10^6$ cop/PCR | 18.0 | 725 | 19.7 | 457 | 22.8 | 69 | 20.3 | 59 |
| $10^5$ cop/PCR | 20.3 | 754 | 23.7 | 428 | 26.9 | 58 | 22.7 | 77 |
| $10^4$ cop/PCR | 23.3 | 692 | 25.5 | 390 | 30.2 | 55 | 24.7 | 97 |
| $10^3$ cop/PCR | 26.2 | 611 | 29.4 | 322 | 34.1 | 48 | 28.4 | 73 |
| $10^2$ cop/PCR | 30.0 | 476 | 32.6 | 208 | 37.2 | 29 | 32.2 | 65 |
| $H^2O$ sample | ND | ND | ND | ND | ND | ND | ND | ND |
| ADN sample | ND | ND | ND | ND | ND | ND | ND | ND |
| r2/slope/efficiency PCR | 0.994/−2.994/115.8% | | 0.994/−3.148/107.8% | | 0.988/−3.647/88% | | 0.987/−2.952/118.2% | |

| copy number HPV plasmid/ PCR | A9E2Z7S1/HPV 58 Moy Ct | A9E2Z7S1/HPV 58 Moy RFUs | A9E2Z7S1/HPV 67 Moy Ct | A9E2Z7S1/HPV 67 Moy RFUs | A9E1Z7S2/HPV 33 Moy Ct | A9E1Z7S2/HPV 33 Moy RFUs | A9E1Z7S2/HPV 58 Moy Ct | A9E1Z7S2/HPV 58 Moy RFUs |
|---|---|---|---|---|---|---|---|---|
| $10^6$ cop/PCR | 20.8 | 117 | 27.5 | 111 | 16.7 | 1741 | 20.8 | 636 |
| $10^5$ cop/PCR | 22.5 | 113 | 29.4 | 110 | 19.2 | 1767 | 22.5 | 537 |
| $10^4$ cop/PCR | 24.9 | 123 | 33.1 | 99 | 22.7 | 1574 | 24.9 | 693 |
| $10^3$ cop/PCR | 28.4 | 117 | 36.9 | 70 | 26.9 | 1473 | 28.4 | 465 |
| $10^2$ cop/PCR | 31.3 | 104 | 41.3 | 30 | 29.6 | 1172 | 31.3 | 357 |
| $H_2O$ sample | ND | ND | ND | ND | ND | ND | ND | ND |
| ADN sample | ND | ND | ND | ND | ND | ND | ND | ND |
| r2/slope/efficiency PCR | 0.987/−2.296/134.9% | | 0.990/−3.509/92.7% | | 0.995/−3.318/100.1% | | 0.772/−2.474/153.6% | |

| copy number HPV plasmid/ PCR | A9E1Z7S2/HPV 52 Moy Ct | A9E1Z7S2/HPV 52 Moy RFUs | A9E1Z7S2/HPV67 Moy Ct | A9E1Z7S2/HPV67 Moy RFUs | A9E1Z7S3a/HPV 35 Moy Ct | A9E1Z7S3a/HPV 35 Moy RFUs |
|---|---|---|---|---|---|---|
| $10^6$ cop/PCR | 18.6 | 393 | 25.3 | 433 | 25.3 | 869 |
| $10^5$ cop/PCR | 21.1 | 303 | 28.8 | 375 | 27.6 | 611 |
| $10^4$ cop/PCR | 25.1 | 274 | 31.8 | 299 | 31.6 | 509 |
| $10^3$ cop/PCR | 28.0 | 260 | 35.4 | 214 | 34.7 | 294 |
| $10^2$ cop/PCR | 32.4 | 152 | ND | ND | ND | ND |
| $H_2O$ sample | ND | ND | ND | ND | ND | ND |
| ADN sample | ND | ND | ND | ND | ND | ND |
| r2/slope/efficiency PCR | 0.994/−3.523/92.3% | | 0.997/−3.323/99.9% | | 0.993/−3.328/104.1% | |

TABLE 77-continued

A9 System E3, sensitivity

| copy number HPV plasmid/ | A9E2Z7S4a/HPV 31 | | A9E2Z7S4a/HPV 52 | | A9E2Z7S4a/HPV 16 | |
|---|---|---|---|---|---|---|
| PCR | Moy Ct | Moy RFUs | Moy Ct | Moy RFUs | Moy Ct | Moy RFUs |
| $10^6$ cop/PCR | 19.2 | 494 | 18.1 | 427 | 18.9 | 79 |
| $10^5$ cop/PCR | 22.8 | 451 | 20.2 | 473 | 21.0 | 199 |
| $10^4$ cop/PCR | 26.0 | 360 | 23.7 | 460 | 23.7 | 170 |
| $10^3$ cop/PCR | 29.5 | 283 | 27.5 | 419 | 27.2 | 166 |
| $10^2$ cop/PCR | 33.4 | 82 | 31.0 | 273 | 31.3 | 37 |
| $H_2O$ sample | ND | ND | ND | ND | ND | ND |
| ADN sample | ND | ND | ND | ND | ND | ND |
| r2/slope/efficiency PCR | 0.998/−3.510/92.7% | | 0.995/−3.312/100.4% | | 0.989/−3.006/115.1% | |

| copy number HPV plasmid/ | A9E2Z7S4a/HPV 33 | | A9E2Z7S4a/HPV 58 | | A9E2Z7S4a/HPV 67 | |
|---|---|---|---|---|---|---|
| PCR | Moy Ct | Moy RFUs | Moy Ct | Moy RFUs | Moy Ct | Moy RFUs |
| $10^6$ cop/PCR | 21.0 | 66 | 19.7 | 105 | 27.2 | 494 |
| $10^5$ cop/PCR | 24.2 | 62 | 22.8 | 108 | 30.5 | 451 |
| $10^4$ cop/PCR | 27.5 | 56 | 25.8 | 108 | 36.1 | 360 |
| $10^3$ cop/PCR | 30.8 | 53 | 30.3 | 78 | 45.4 | 283 |
| $10^2$ cop/PCR | ND | 22 | 35.6 | 57 | ND | ND |
| $H_2O$ sample | ND | ND | ND | ND | ND | ND |
| ADN sample | ND | ND | ND | ND | ND | ND |
| r2/slope/efficiency PCR | 0.994/−3.257/102.8% | | 0.976/−3.920/79.9% | | 0.959/−5.655/50.3% | |

ND: not detected

NT: not tested

TABLE 78

A9 System E4, sensitivity

| copy number HPV plasmid/ | A9E2Z7S1/HPV 16 | | A9E2Z7S1/HPV 31 | | A9E2Z7S1/HPV 52 | | A9E2Z7S1/HPV 33 | |
|---|---|---|---|---|---|---|---|---|
| PCR | Moy Ct | Moy RFUs | Moy Ct | Moy RFUs | Moy Ct | Moy RFUs | Moy Ct | Moy RFUs |
| $10^6$ cop/PCR | 19.8 | 915 | 21.45 | 795 | 24.25 | 65 | 24.35 | 105 |
| $10^5$ cop/PCR | 23.25 | 940 | 24.3 | 717.5 | 31.1 | 47.5 | 28.65 | 90 |
| $10^4$ cop/PCR | 26.75 | 840 | 28.25 | 540 | 37.8 | 27 | 37.8 | 83 |
| $10^3$ cop/PCR | 30.85 | 615 | 32.5 | 412.5 | 35.15 | 40 | 36.15 | 75 |
| $10^2$ cop/PCR | 34.95 | 507.5 | 35.0 | 272.5 | 37.3 | 37.5 | 38.95 | 47.5 |
| $H_2O$ sample | ND | ND | ND | ND | ND | ND | ND | ND |
| ADN sample | ND | ND | ND | ND | ND | ND | ND | ND |
| r2/slope/efficiency PCR | 0.993/−3.789/83.7% | | 0.996/−3.509/92.8% | | 0.889/−3.017/114.5% | | 0.996/−3.664/87.5% | |

| copy number HPV plasmid/ | A9E2Z7S1/HPV 58 | | A9E2Z7S1/HPV 67 | | A9E1Z7S2/HPV 33 | | A9E1Z7S2/HPV 58 | |
|---|---|---|---|---|---|---|---|---|
| PCR | Moy Ct | Moy RFUs | Moy Ct | Moy RFUs | Moy Ct | Moy RFUs | Moy Ct | Moy RFUs |
| $10^6$ cop/PCR | 23.8 | 157.5 | 22.9 | 207.5 | 22.0 | 2871.625 | 22.75 | 903.92 |
| $10^5$ cop/PCR | 27.6 | 167.5 | 26.45 | 190 | 25.7 | 2916.84 | 25.95 | 822.335 |
| $10^4$ cop/PCR | 37.8 | 128 | 37.8 | 160 | 29.95 | 2525.075 | 29.55 | 731.815 |
| $10^3$ cop/PCR | 36.0 | 90 | 34.25 | 122.5 | 33.55 | 1574.41 | 33.95 | 614.88 |
| $10^2$ cop/PCR | 39.8 | 45 | 39.8 | 52.5 | 37.45 | 1675.46 | 37.35 | 155.27 |
| $H^2O$ sample | ND | ND | ND | ND | ND | ND | ND | ND |
| ADN sample | ND | ND | ND | ND | ND | ND | ND | ND |
| r2/slope/efficiency PCR | 0.999/−4.075/75.9% | | 0.996/−4.075/75.9% | | 0.998/−3.866/81.4% | | 0.998/−3.725/85.5% | |

| copy number HPV plasmid/ | A9E1Z7S2/HPV 52 | | A9E1Z7S2/HPV67 | | A9E1Z7S3a/HPV 35 | |
|---|---|---|---|---|---|---|
| PCR | Moy Ct | Moy RFUs | Moy Ct | Moy RFUs | Moy Ct | Moy RFUs |
| $10^6$ cop/PCR | 20.4 | 372.5 | 21.3 | 1225 | 22.6 | 1085.81 |
| $10^5$ cop/PCR | 23.6 | 360 | 24.35 | 1157.5 | 26.1 | 1037.5 |
| $10^4$ cop/PCR | 27.2 | 345 | 27.9 | 1055 | 29.6 | 932.32 |
| $10^3$ cop/PCR | 30.85 | 347.5 | 31.75 | 935 | 33.75 | 730.08 |
| $10^2$ cop/PCR | 34.65 | 310 | 35.85 | 757.5 | 38.55 | 501.76 |
| $H_2O$ sample | ND | ND | ND | ND | ND | ND |
| ADN sample | ND | ND | ND | ND | ND | ND |
| r2/slope/efficiency PCR | 0.997/−3.586/90.1% | | 0.998/−3.641/88.2% | | 0.997/−3.960/78.9% | |

TABLE 78-continued

A9 System E4, sensitivity

| copy number HPV plasmid/ PCR | A9E2Z7S4a/HPV 31 Moy Ct | Moy RFUs | A9E2Z7S4a/HPV 52 Moy Ct | Moy RFUs | A9E2Z7S4a/HPV 16 Moy Ct | Moy RFUs |
|---|---|---|---|---|---|---|
| $10^6$ cop/PCR | 21.8 | 800 | 20.45 | 640 | 22.35 | 267.5 |
| $10^5$ cop/PCR | 25.2 | 747.5 | 24.0 | 600 | 25.0 | 260 |
| $10^4$ cop/PCR | 28.4 | 665 | 27.5 | 562.5 | 29.55 | 240 |
| $10^3$ cop/PCR | 33.3 | 505 | 30.95 | 532.5 | 32.75 | 210 |
| $10^2$ cop/PCR | 37.2 | 335 | 34.4 | 422.5 | 33.55 | 207.5 |
| $H_2O$ sample | ND | ND | ND | ND | ND | ND |
| ADN sample | ND | ND | ND | ND | ND | ND |
| r2/slope/efficiency PCR | 0.996/−3.872/81.2% | | 1/−3.476/94% | | 0.976/−3.010/114.9% | |
| **copy number HPV plasmid/ PCR** | **A9E2Z7S4a/HPV 33 Moy Ct** | **Moy RFUs** | **A9E2Z7S4a/HPV 58 Moy Ct** | **Moy RFUs** | **A9E2Z7S4a/HPV 67 Moy Ct** | **Moy RFUs** |
| $10^6$ cop/PCR | 24.45 | 212.5 | 24.2 | 340 | 23.25 | 415 |
| $10^5$ cop/PCR | 27.3 | 230 | 27.45 | 305 | 25.55 | 407.5 |
| $10^4$ cop/PCR | 31.1 | 205 | 31.2 | 250 | 30.5 | 312.5 |
| $10^3$ cop/PCR | 35.1 | 162.5 | 34.35 | 187.5 | 33.75 | 277.5 |
| $10^2$ cop/PCR | 36.8 | 127.5 | 38.9 | 117.5 | 38.2 | 145 |
| $H_2O$ sample | ND | ND | ND | ND | ND | ND |
| ADN sample | ND | ND | ND | ND | ND | ND |
| r2/slope/efficiency PCR | 0.991/−3.264/102.5% | | 0.998/−3.632/88.5% | | 0.989/−3.810/83% | |

ND: not detected

NT: not tested

TABLE 79

A9 System F, sensitivity

| copy number HPV plasmid/ PCR | A9E2Z7S1/HPV 16 Moy Ct | Moy RFUs | A9E2Z7S1/HPV 31 Moy Ct | Moy RFUs | A9E2Z7S1/HPV 33 Moy Ct | Moy RFUs | A9E2Z7S1/HPV 52 Moy Ct | Moy RFUs |
|---|---|---|---|---|---|---|---|---|
| $10^6$ cop/PCR | 19.45 | 1815 | 19.85 | 1227.5 | 23.85 | 63 | 25.25 | 40 |
| $10^5$ cop/PCR | 22.25 | 1727.5 | 22.95 | 1215 | 27.1 | 63 | 28.55 | 41.5 |
| $10^4$ cop/PCR | 26.1 | 1665 | 26.75 | 1150 | 30.55 | 62.5 | 31.6 | 37.5 |
| $10^3$ cop/PCR | 26.65 | 1535 | 29.6 | 1055 | 33.9 | 62 | 35.4 | 41 |
| $10^2$ cop/PCR | 33.15 | 1312.5 | 35.2 | 753.5 | 37.8 | 47.5 | 38.25 | 34 |
| $H_2O$ sample | ND | ND | ND | ND | ND | ND | ND | ND |
| ADN sample | ND | ND | ND | ND | ND | ND | ND | ND |
| r2/slope/efficiency PCR | 0.969/−3.202/105.2% | | 0.990/−3.739/85.1% | | 0.999/−3.487/93.5% | | 0.998/−3.651/87.9% | |
| **copy number HPV plasmid/ PCR** | **A9E2Z7S1/HPV 58 Moy Ct** | **Moy RFUs** | **A9E2Z7S1/HPV 67 Moy Ct** | **Moy RFUs** | **A9E1Z7S2/HPV 33 Moy Ct** | **Moy RFUs** | **A9E1Z7S2/HPV 58 Moy Ct** | **Moy RFUs** |
| $10^6$ cop/PCR | 22.8 | 132.5 | 22.85 | 138 | 20.2 | 3013.235 | 21.75 | 1330.945 |
| $10^5$ cop/PCR | 26.1 | 125 | 25.95 | 127.5 | 23.4 | 3085.8 | 24.85 | 1292.96 |
| $10^4$ cop/PCR | 29.55 | 120 | 29.6 | 120 | 26.7 | 2967.135 | 28.35 | 1266.585 |
| $10^3$ cop/PCR | 33.45 | 107 | 33.65 | 96 | 30.45 | 2499.875 | 32.25 | 973.095 |
| $10^2$ cop/PCR | 37.4 | 100 | 35.85 | 100 | 33.8 | 2129.57 | 35.55 | 841.57 |
| $H_2O$ sample | ND | ND | ND | ND | ND | ND | ND | ND |
| ADN sample | ND | ND | ND | ND | ND | ND | ND | ND |
| r2/slope/efficiency PCR | 0.998/−3.651/87.9% | | 0.993/−3.366/98.20% | | 0.999/−3.435/95.5% | | 0.999/−3.502/93% | |
| **copy number HPV plasmid/ PCR** | **A9E1Z7S3a/HPV 35 Moy Ct** | **Moy RFUs** | **A9E2Z7S4a/HPV 31 Moy Ct** | **Moy RFUs** | **A9E2Z7S4a/HPV 52 Moy Ct** | **Moy RFUs** | **A9E2Z7S4a/HPV 58 Moy Ct** | **Moy RFUs** |
| $10^6$ cop/PCR | 22.1 | 1337.995 | 21.85 | 705 | 21.75 | 1022.5 | 22.1 | 522.5 |
| $10^5$ cop/PCR | 25.05 | 1354.145 | 24.1 | 730 | 24.25 | 992.5 | 24.55 | 460 |
| $10^4$ cop/PCR | 29.4 | 1254.22 | 27.9 | 665 | 27.65 | 1002.5 | 28.9 | 455 |
| $10^3$ cop/PCR | 33.25 | 1018.5 | 30.5 | 560 | 31.05 | 957.5 | 31.5 | 465 |
| $10^2$ cop/PCR | 37.0 | 678.815 | 35.25 | 430 | 34.7 | 650 | 35.2 | 382.5 |
| $H_2O$ sample | ND | ND | ND | ND | ND | ND | ND | ND |
| ADN sample | ND | ND | ND | ND | ND | ND | ND | ND |
| r2/slope/efficiency PCR | 0.996/−3.799/83.3% | | 0.989/−3.332/99.6% | | 0.996/−3.273/102.1% | | 0.994/−3.317/100.2% | |

TABLE 79-continued

A9 System F, sensitivity

| copy number HPV plasmid/ PCR | A9E2Z7S4a/HPV 67 Moy Ct | Moy RFUs | A9E2Z7S4a/HPV 16 Moy Ct | Moy RFUs | A9E2Z7S4a/HPV 33 Moy Ct | Moy RFUs |
|---|---|---|---|---|---|---|
| $10^6$ cop/PCR | 22.15 | 570 | 21.95 | 195 | 22.45 | 240 |
| $10^5$ cop/PCR | 24.2 | 670 | 24.65 | 227.5 | 25.15 | 245 |
| $10^4$ cop/PCR | 28.75 | 555 | 29.2 | 196 | 29.7 | 255 |
| $10^3$ cop/PCR | 31.2 | 460 | 32.6 | 187.5 | 32.55 | 187.5 |
| $10^2$ cop/PCR | 32.7 | 447.5 | 35.7 | 185 | 36.45 | 165 |
| $H_2O$ sample | ND | ND | ND | ND | ND | ND |
| ADN sample | ND | ND | ND | ND | ND | ND |
| r2/slope/efficiency PCR | 0.964/−2.805/127.3% | | 0.994/−3.487/93.5% | | 0.995/−3.538/91.7% | |

ND: not detected
NT: not tested

TABLE 80

A9 System G Z7, sensitivity

| copy number HPV plasmid/ PCR | A9E2Z7S1/HPV 16 Moy Ct | Moy RFUs | A9E2Z7S1/HPV 31 Moy Ct | Moy RFUs | A9E2Z7S1/HPV 33 Moy Ct | Moy RFUs | A9E2Z7S1/HPV 52 Moy Ct | Moy RFUs |
|---|---|---|---|---|---|---|---|---|
| $10^6$ cop/PCR | 20.25 | 771 | 20.85 | 468 | 22.85 | 113 | 23.2 | 82 |
| $10^5$ cop/PCR | 23.55 | 713.5 | 24.5 | 419.5 | 26.4 | 119 | 26.45 | 75 |
| $10^4$ cop/PCR | 27.0 | 654 | 27.6 | 375.5 | 30.8 | 79.5 | 29.65 | 65 |
| $10^3$ cop/PCR | 30.75 | 527 | 31.15 | 289 | 33.6 | 71 | 33.35 | 48.5 |
| $10^2$ cop/PCR | 34.45 | 296.5 | 35.1 | 186 | 37.3 | 44.5 | 37.05 | 30.5 |
| $H_2O$ sample | ND | ND | ND | ND | ND | ND | ND | ND |
| ADN sample | ND | ND | ND | ND | ND | ND | ND | ND |
| r2/slope/efficiency PCR | 0.999/−3.557/91% | | 0.998/−3.520/92.3% | | 0.996/−3.612/89.2% | | 0.998/−3.452/94.9% | |
| **copy number HPV plasmid/ PCR** | **A9E2Z7S1/HPV 58 Moy Ct** | **Moy RFUs** | **A9E2Z7S1/HPV 67 Moy Ct** | **Moy RFUs** | **A9E1Z7S2a/HPV 33 Moy Ct** | **Moy RFUs** | **A9E1Z7S2a/HPV 58 Moy Ct** | **Moy RFUs** |
| $10^6$ cop/PCR | 22.15 | 187.5 | 21.8 | 207 | 19.8 | 1165 | 20.65 | 717 |
| $10^5$ cop/PCR | 25.75 | 165.5 | 24.9 | 199 | 23.1 | 1080.5 | 23.75 | 682 |
| $10^4$ cop/PCR | 28.8 | 147 | 27.35 | 182.5 | 26.3 | 1015.5 | 27.35 | 603.5 |
| $10^3$ cop/PCR | 32.45 | 100 | 32.05 | 128.5 | 30.05 | 844 | 30.9 | 426 |
| $10^2$ cop/PCR | 35.35 | 63 | 35.4 | 78.5 | 33.65 | 605.5 | 34.8 | 234 |
| $H_2O$ sample | ND | ND | ND | ND | ND | ND | ND | ND |
| ADN sample | ND | ND | ND | ND | ND | ND | ND | ND |
| r2/slope/efficiency PCR | 0.998/−3.313/100.4% | | 0.993/−3.425/95.9% | | 0.998/−3.469/94.2% | | 0.998/−3.558/91% | |
| **copy number HPV plasmid/ PCR** | **A9E1Z7S3a/HPV 35 Moy Ct** | **Moy RFUs** | **A9E2Z7S4a/HPV 31 Moy Ct** | **Moy RFUs** | **A9E2Z7S4a/HPV 52 Moy Ct** | **Moy RFUs** | **A9E2Z7S4a/HPV 58 Moy Ct** | **Moy RFUs** |
| $10^6$ cop/PCR | 22.15 | 883.5 | 21.7 | 187.5 | 21.65 | 257 | 22.35 | 145 |
| $10^5$ cop/PCR | 25.3 | 795 | 25.95 | 180.5 | 26.45 | 268 | 26.05 | 136.5 |
| $10^4$ cop/PCR | 29.0 | 674.5 | 29.7 | 157.5 | 29.8 | 220 | 29.3 | 116 |
| $10^3$ cop/PCR | 32.2 | 546 | 33.4 | 128.5 | 33.6 | 155 | 33.65 | 80 |
| $10^2$ cop/PCR | 35.2 | 300 | 36.65 | 71 | 37.9 | 69 | 37.3 | 40 |
| $H_2O$ sample | ND | ND | ND | ND | ND | ND | ND | ND |
| ADN sample | ND | ND | ND | ND | ND | ND | ND | ND |
| r2/slope/efficiency PCR | 0.999/−3.656/87.7% | | 0.999/−3.727/85.5% | | 0.997/−3.967/78.7% | | 0.998/−3.751/84.7% | |

| copy number HPV plasmid/ PCR | A9E2Z7S4a/HPV 67 Moy Ct | Moy RFUs | A9E2Z7S4a/HPV 16 Moy Ct | Moy RFUs | A9E2Z7S4a/HPV 33 Moy Ct | Moy RFUs |
|---|---|---|---|---|---|---|
| $10^6$ cop/PCR | 22.4 | 159 | 22.4 | 67 | 22.65 | 69.5 |
| $10^5$ cop/PCR | 26.5 | 155.5 | 27.7 | 63 | 27.0 | 60 |
| $10^4$ cop/PCR | 30.1 | 134 | 31.0 | 60 | 30.25 | 58.5 |
| $10^3$ cop/PCR | 34.35 | 90.5 | 34.6 | 46 | 33.4 | 51.5 |
| $10^2$ cop/PCR | 38.55 | 33 | 38.4 | 23.5 | 37.8 | 32.5 |
| $H_2O$ sample | ND | ND | ND | ND | ND | ND |
| ADN sample | ND | ND | ND | ND | ND | ND |
| r2/slope/efficiency PCR | 0.996/−4.035/76.9% | | 0.996/−3.894/80.6% | | 0.996/−3.670/87.3% | |

ND: not detected
NT: not tested

TABLE 81

A9 System G Z8, sensitivity

| copy number HPV plasmid/ PCR | A9E2Z8S2f/HPV16 Moy Ct | A9E2Z8S2f/HPV16 Moy RFUs | A9E2Z8S61f/HPV 31 Moy Ct | A9E2Z8S61f/HPV 31 Moy RFUs | A9E2Z8S127f/HPV 33 Moy Ct | A9E2Z8S127f/HPV 33 Moy RFUs | A9E2Z8S156f/HPV35 Moy Ct | A9E2Z8S156f/HPV35 Moy RFUs |
|---|---|---|---|---|---|---|---|---|
| $10^6$ cop/PCR | 20.9 | 275 | 20.8 | 439.5 | 20.4 | 357 | 21.85 | 347.5 |
| $10^5$ cop/PCR | 24.65 | 274.5 | 25.25 | 382 | 24.95 | 322 | 25.75 | 334.5 |
| $10^4$ cop/PCR | 27.85 | 270 | 29.1 | 328 | 28.75 | 300.5 | 29.25 | 331.5 |
| $10^3$ cop/PCR | 31.55 | 217 | 32.3 | 242 | 31.6 | 261.5 | 32.8 | 243 |
| $10^2$ cop/PCR | 35.3 | 107.5 | 36.3 | 86 | 37.0 | 98 | 36.45 | 121 |
| $H_2O$ sample | ND | ND | ND | ND | ND | ND | ND | ND |
| ADN sample | ND | ND | ND | ND | ND | ND | ND | ND |
| r2/slope/efficiency PCR | 0.995/−3.587/90% | | 0.995/−3.799/83.3% | | 0.995/−3.990/78.1% | | 0.997/−3.639/88.3% | |

| copy number HPV plasmid/ PCR | A9E2Z8S210f/HPV52 Moy Ct | A9E2Z8S210f/HPV52 Moy RFUs | A9E2AZ8S250f/HPV58 Moy Ct | A9E2AZ8S250f/HPV58 Moy RFUs | A9E2AZ8S250f/HPV67 Moy Ct | A9E2AZ8S250f/HPV67 Moy RFUs |
|---|---|---|---|---|---|---|
| $10^6$ cop/PCR | 22.05 | 32 | 19.3 | 728 | 21.2 | 173 |
| $10^5$ cop/PCR | 25.65 | 57 | 22.6 | 663 | 26.2 | 152 |
| $10^4$ cop/PCR | 27.45 | 54.5 | 26.0 | 728 | 29.6 | 157 |
| $10^3$ cop/PCR | 32.7 | 31 | 29.7 | 627 | 32.6 | 149 |
| $10^2$ cop/PCR | 37.75 | 14 | 32.9 | 457 | 36.6 | 98 |
| $H_2O$ sample | ND | ND | ND | ND | ND | ND |
| ADN sample | ND | ND | ND | ND | ND | ND |
| r2/slope/efficiency PCR | 0.976/−3.880/81% | | 0.999/−3.425/95.9% | | 0.994/−3.701/86.3% | |

ND: not detected
NT: not tested

TABLE 82

A9 System H, sensitivity

| copy number HPV plasmid/ PCR | A9E2Z8S2f/HPV16 Moy Ct | A9E2Z8S2f/HPV16 Moy RFUs | A9E2Z8S61f/HPV 31 Moy Ct | A9E2Z8S61f/HPV 31 Moy RFUs | A9E2Z8S127f/HPV 33 Moy Ct | A9E2Z8S127f/HPV 33 Moy RFUs | A9E2Z8S156f/HPV35 Moy Ct | A9E2Z8S156f/HPV35 Moy RFUs |
|---|---|---|---|---|---|---|---|---|
| $10^6$ cop/PCR | 20.55 | 567.5 | 20.55 | 570 | 20.25 | 550 | 21.2 | 435 |
| $10^5$ cop/PCR | 23.7 | 530 | 23.25 | 530 | 23.7 | 490 | 24.55 | 437.5 |
| $10^4$ cop/PCR | 27.2 | 465 | 27.05 | 507.5 | 27.4 | 482.5 | 28.1 | 375 |
| $10^3$ cop/PCR | 31.85 | 395 | 29.8 | 400 | 31.5 | 450 | 32.95 | 250 |
| $10^2$ cop/PCR | 34.3 | 220 | 34.05 | 247.5 | 35.35 | 212.5 | 37.05 | 172.5 |
| $H_2O$ sample | ND | ND | ND | ND | ND | ND | ND | ND |
| ADN sample | ND | ND | ND | ND | ND | ND | ND | ND |
| r2/slope/efficiency PCR | 0.99/−3.570/90.6% | | 0.995/−3.352/98.8% | | 0.988/−3.805/83.2% | | 0.995/−4.011/77.5% | |

| copy number HPV plasmid/ PCR | A9E2Z8S210f/HPV52 Moy Ct | A9E2Z8S210f/HPV52 Moy RFUs | A9E2AZ8S250f/HPV58 Moy Ct | A9E2AZ8S250f/HPV58 Moy RFUs | A9E2AZ8S250f/HPV67 Moy Ct | A9E2AZ8S250f/HPV67 Moy RFUs |
|---|---|---|---|---|---|---|
| $10^6$ cop/PCR | 21.65 | 240 | 20.15 | 2300 | 27.5 | 150 |
| $10^5$ cop/PCR | 25.95 | 225 | 23.0 | 2405 | 32.3 | 100 |
| $10^4$ cop/PCR | 30.2 | 170 | 26.6 | 2350 | 35.2 | 62.5 |
| $10^3$ cop/PCR | 34.3 | 100 | 30.55 | 1800 | 37.55 | 82.5 |
| $10^2$ cop/PCR | 36.65 | 75 | 33.45 | 1387.5 | 40.2 | 52.5 |
| $H_2O$ sample | ND | ND | ND | ND | ND | ND |
| ADN sample | ND | ND | ND | ND | ND | ND |
| r2/slope/efficiency PCR | 0.988/−3.837/82.2% | | 0.993/−3.425/95.9% | | 0.976/−3.131/108.6% | |

| copy number HPV plasmid/ PCR | A9E2AZ8S231f/HPV58 Moy Ct | A9E2AZ8S231f/HPV58 Moy RFUs | A9E2AZ8S231f/HPV67 Moy Ct | A9E2AZ8S231f/HPV67 Moy RFUs |
|---|---|---|---|---|
| $10^6$ cop/PCR | 19.75 | 295 | 25.45 | 47.5 |
| $10^5$ cop/PCR | 22.95 | 287.5 | 29.4 | 47.5 |
| $10^4$ cop/PCR | 26.4 | 272.5 | 33.1 | 38.5 |
| $10^3$ cop/PCR | 30.35 | 210 | 35.8 | 28.5 |
| $10^2$ cop/PCR | 33.65 | 147.5 | 36.15 | 28.5 |
| $H_2O$ sample | ND | ND | ND | ND |
| ADN sample | ND | ND | ND | ND |
| r2/slope/efficiency PCR | 0.996/−3.525/92.2% | | 0.945/−2.778/129.1% | |

ND: not detected
NT: not tested

TABLE 83

| Megaplex A5 E A6 A A7 A A9 H | |
|---|---|
| Kit | Kit Quantitect probe PCR |
| $MgCl_2$ | 5 mM |
| Plasmid concentration | $10^6$ cop/PCR |
| Thermoprofile | 52° C. |
| Taq | 7U/well |
| Cycling | 42x |

| | forward primer | | reverse primer | | probes | |
|---|---|---|---|---|---|---|
| | Name | μM | Name | μM | Name | μM |
| A5 System E | A5E6f5 | 0.4 | A5E6r5 | 0.4 | A5E6s4 | 0.2 |
| A6 System A | A6E6f1 | 0.4 | A6E6r1 | 0.4 | A6E6s1 | 0.2 |
| A7 | A7E1-6f1a | 0.3 | A7E1-6r1b | 0.3 | A7E1ZCS40f | 0.2 |
| System A | A7E1-6f2a | 0.3 | A7E1-6r2b | 0.3 | A7E1ZAS61f | 0.2 |
| | A7E1-6f3a | 0.3 | A7E1-6r3b | 0.3 | A7E1ZAS63f | 0.2 |
| | | | | | A7E1ZBS74f | 0.2 |
| A9 | A9E2f6 | 0.4 | A9E2r10 | 0.6 | A9E2Z8S2f | 0.2 |
| System H | A9E2f8 | 0.4 | A9E2r12B | 0.4 | A9E2Z8S61f | 0.2 |
| | A9E2f9 | 0.6 | A9E2r15 | 0.4 | A9E2Z8S127f | 0.2 |
| | | | A9E2r16 | 0.4 | A9E2Z8S156f | 0.2 |
| | | | | | A9E2Z8S210f | 0.2 |
| | | | | | A9E2Z8S250f | 0.1 |

TABLE 84 specificity of megaplex EAAH

| | | Megaplex | |
|---|---|---|---|
| N° HPV | Group | CT | RFU |
| 51 | A5 | 21.9 | 226 |
| 26 | | ND | ND |
| 69 | | NT | NT |
| 82 | | ND | ND |
| 56 | A6 | 24.4 | 220 |
| 30 | | ND | ND |
| 53 | | ND | ND |
| 66 | | ND | ND |
| 18 | A7 | 23.3 | 148 |
| 39 | | 22.1 | 182 |
| 45 | | 23.1 | 215 |
| 59 | | 24.8 | 194 |
| 68 | | 24.1 | 169 |
| 85 | | ND | ND |
| 70 | | NT | NT |
| 16 | A9 | 24.0 | 136 |
| 16 | | 24.0 | 136 |
| 31 | | 22.5 | 121 |
| 33 | | 22.6 | 173 |
| 35 | | 23.6 | 94 |
| 52 | | 24.1 | 102 |
| 58 | | 21.7 | 268 |
| 67 | | 32.7 | 25 |
| | DNA sample | ND | ND |
| | $H_2O$ sample | ND | ND |

ND: no detection
NT: not tested

TABLE 85

| Megaplex A5 E A6 B A7 A A9 C | |
|---|---|
| Kit | Kit Quantitect probe PCR |
| $MgCl_2$ | 5 mM |
| Plasmid concentration | $10^6$ cop/PCR |
| Thermoprofile | 52° C. |
| Taq | 7U/well |
| Cycling | 42x |

TABLE 85-continued

Megaplex A5 E A6 B A7 A A9 C

| | Name | μM | Name | μM | Name | μM |
|---|---|---|---|---|---|---|
| A5 System E | A5E6f5 | 0.4 | A5E6r5 | 0.4 | A5E6s4 | 0.2 |
| A6 System B | A6E6f1 | 0.6 | A6E6r1 | 0.6 | A6E6s1 | 0.4 |
| A7 | A7E1-6f1a | 0.5 | A7E1-6r1b | 0.3 | A7E1ZCS40f | 0.2 |
| System A | A7E1-6f2a | 0.3 | A7E1-6r2b | 0.5 | A7E1ZAS61f | 0.2 |
| | A7E1-6f3a | 0.3 | A7E1-6r3b | 0.3 | A7E1ZAS63f | 0.2 |
| | | | | | A7E1ZBS74f | 0.2 |
| A9 System C | A9E1-f8 | 0.6 | A9E1-r5 | 0.6 | A9E1s10a | 0.2 |
| | A9E1-f10 | 0.6 | A9E1-r6 | 0.6 | A9E1s12a | 0.2 |
| | A9E1-f12 | 0.2 | | | | |
| | A9E1-f13 | 0.4 | | | | |

TABLE 86 specificity of meqaplex EBAC

| | | Megaplex | |
|---|---|---|---|
| N° HPV | Group | CT | RFU |
| 51 | A5 | 23.3 | 229 |
| 26 | | ND | ND |
| 69 | | NT | NT |
| 82 | | ND | ND |
| 56 | A6 | 24 | 458 |
| 30 | | ND | ND |
| 53 | | 36 | 170 |
| 66 | | ND | ND |
| 18 | A7 | 23.7 | 110 |
| 39 | | 23.8 | 185 |
| 45 | | 23.8 | 205 |
| 59 | | 29 | 47 |
| 68 | | 28.3 | 107 |
| 85 | | ND | ND |
| 70 | | NT | NT |
| 16 | A9 | 24.0 | 333 |
| 16 | | 24.0 | 333 |
| 31 | | 24.1 | 321 |
| 33 | | 23.3 | 364 |
| 35 | | 24.6 | 347 |
| 52 | | 22.7 | 390 |
| 58 | | 22 | 395 |
| 67 | | 22.8 | 303 |
| | DNA sample | ND | ND |
| | $H_2O$ sample | ND | ND |

ND: no Detection
NT: not tested

TABLE 87

Megaplex A5 E/A6 A/A7 A/A9 H; HPV16 and 18 sensitivity

| copy number HPV plasmid/ | HPV 16 | | HPV 18 | |
|---|---|---|---|---|
| PCR | Moy Ct | Moy RFU | Moy Ct | Moy RFUs |
| $10^6$ cop/PCR | 25.5 | 50 | 25.2 | 33 |
| $10^5$ cop/PCR | 28.1 | 87 | 27.9 | 79 |
| $10^4$ cop/PCR | 31.3 | 106 | 31.1 | 72 |
| $10^3$ cop/PCR | 35.0 | 98 | 34.3 | 53 |
| $10^2$ cop/PCR | 37.9 | 51 | 37.9 | 27 |
| $H_2O$ sample | ND | ND | ND | ND |
| ADN sample | ND | ND | ND | ND |
| r2/slope/efficiency PCR | 0.989/−3.16/107% | | 0.989/−3.17/107% | |

ND: not detected
NT: not tested

TABLE 88

Megaplex A5 E/A6 B/A7 A/A9 C; HPV16 and 18 sensitivity

| copy number HPV plasmid/ | HPV 16 | | HPV 18 | |
|---|---|---|---|---|
| PCR | Moy Ct | Moy RFU | Moy Ct | Moy RFUs |
| $10^6$ cop/PCR | 24.3 | 278 | 24.3 | 55 |
| $10^5$ cop/PCR | 26.8 | 475 | 28.1 | 154 |
| $10^4$ cop/PCR | 29.9 | 410 | 31.5 | 190 |
| $10^3$ cop/PCR | 31.2 | 412 | 34.3 | 271 |
| $10^2$ cop/PCR | 35.8 | 277 | 38.0 | 148 |
| $H_2O$ sample | ND | ND | ND | ND |
| ADN sample | ND | ND | ND | ND |
| r2/slope/efficiency PCR | 0.984/−2.76/130% | | 0.995/−3.36/98.5% | |

ND: not detected

NT: not tested

TABLE 89 list of HPV sequences

| Organism | Type | Accession number |
|---|---|---|
| human | 1 a | NC_001356 |
| human | 2 a | NC_001352 |
| human | 3 | NC_001588 |
| human | 4 | NC_001457 |
| human | 5 | NC_001531 |
| human | 5 b | NC_001444 |
| human | 6 | NC_000904 |
| human | 6 a | NC_001668 |
| human | 6 b | NC_001355 |
| human | 7 | NC_001595 |
| human | 8 | NC_001532 |
| human | 9 | NC_001596 |
| human | 10 | NC_001576 |
| human | 11 | NC_001525 |
| human | 12 | NC_001577 |
| human | 13 | NC_001349 |
| human | 14 D | NC_001578 |
| human | 15 | NC_001579 |
| human | 16 | AF472509 |
| human | 16 | NC_001526 |
| human | 17 | NC_001580 |
| human | 18 | NC_001357 |
| human | 19 | NC_001581 |
| human | 20 | NC_001679 |
| human | 21 | NC_001680 |
| human | 22 | NC_001681 |
| human | 23 | NC_001682 |
| human | 24 | NC_001683 |
| human | 25 | NC_001582 |
| human | 26 | NC_001583 |
| human | 27 | NC_001584 |
| human | 28 | NC_001684 |
| human | 29 | NC_001685 |
| human | 30 | NC_001585 |
| human | 31 | NC_001527 |
| human | 32 | NC_001586 |
| human | 33 | NC_001528 |
| human | 34 | NC_001587 |
| human | 35 | NC_001529 |
| human | 36 | NC_001686 |
| human | 37 | NC_001687 |
| human | 38 | NC_001688 |
| human | 39 | NC_001535 |
| human | 40 | NC_001589 |
| human | 41 | NC_001354 |
| human | 42 | NC_001534 |
| human | 44 | NC_001689 |
| human | 45 | NC_001590 |
| human | 47 | NC_001530 |
| human | 48 | NC_001690 |
| human | 49 | NC_001591 |
| human | 50 | NC_001691 |
| human | 51 | NC_001533 |
| human | 52 | NC_001592 |

TABLE 89-continued list of HPV sequences

| Organism | Type | Accession number |
|---|---|---|
| human | 53 | NC_001593 |
| human | 54 | NC_001676 |
| human | 55 | NC_001692 |
| human | 56 | NC_001594 |
| human | 57 | NC_001353 |
| human | 57 b | HPU37537 |
| human | 58 | NC_001443 |
| human | 59 | NC_001635 |
| human | 60 | NC_001693 |
| human | 61 | NC_001694 |
| human | 63 | NC_001458 |
| human | 65 | NC_001459 |
| human | 66 | NC_001695 |
| human | 67 | D21208 |
| human | 68 | M73258 |
| human | 69 | NC_002171 |
| human | 70 | NC_001711 |
| human | 71 | NC_002644 |
| human | 72 | X94164 partial E6; 7; 1; 2; 4; L2; 1 |
| human | 73 | X94165 partial E6; 7; 1; 2; 4; L2; 1 |
| human | 74 | NC_004501 |
| human | 82 | NC_002172 |
| human | 83 | NC_000856 |
| human | 84 | NC_002676 |
| human | 85 | AF131950 |
| human | 86 | NC_003115 |
| human | 87 | NC_002627 |
| human | 89 | NC_004103 |
| human | 90 | NC_004104 |
| human | 91 | NC_004085 |
| human | 92 | NC_004500 |
| bovine | BPV | NC_001522 |
| bovine | BPV2 | NC_001521 |
| bovine | BPV3 | NC_004197 |
| bovine | BPV4 | X05817 D00146 X59063 |
| bovine | BPV5 | NC_004195 |
| canine | Canine oral papillomavirus | NC_001619 |
| chimpanzee | Common chimpanzee papillomavirus | NC_001838 |
| rabbit | Cottontail rabbit papillomavirus | NC_001541 |
| Deer | Deer papillomavirus | NC_001523 |
| Equinus | Equinus papillomavirus | NC_004194 |
| Equus | Equus caballus papillomavirus type 1 | NC_003748 |
| elk | European elk papillomavirus | NC_001524 |
| Felis | Felis domesticus papillomavirus type 1 | AF480454 |
| coelebs | Fringilla coelebs papillomavirus | NC_004068 |
| Hamster | Hamster papovavirus | NC_001663 |
| Monkey | Monkey B-lymphotropic papovavirus | NC_001536 |
| rat | Multimammate rat papillomavirus | NC_001605 |
| Ovine | Ovine papillomavirus 2 | NC_001790 |
| Ovine | Ovine papillomavirus 1 | NC_001789 |
| Phocoena | Phocoena spinipinnis papillomavirus | NC_003348 |
| Psittacus | Psittacus erithacus papillomavirus | NC_003973 |
| Chimpanzee | Pygmy Chimpanzee papilloma virus type 1 | X62844 S43934 |
| Rabbit | Rabbit oral papillomavirus | NC_002232 |
| Reindeer | Reindeer papillomavirus | NC_004196 |

Sequences of the Reference Template Sequences:

<SEQ25; DNA; Human papillomavirus>
tggaccgggtcatgttt ggggtgctgg agacaaacat ctagagaacc
tagagaatct acagtataat catgcatggt aaagtaccaa
cgctgcaaga cgt <SEQ334; DNA; Human papillomavirus>
tggaccgggtcatgttt ggggtgctgg agacaaacat ctagagaacc
tagagaatct acagtataat catgcatggt aaagtaccaa
cgctgcaaga cgttgtatta gaactaacac ctcaaacaga
aattgaccta cagtgcaatg agcaattgga cagctcagag
gatgaggatg aggatgaagt agaccatttg caggagcggc
cacagcaagc tagacaagct aaacaacata cgtgttacct
aatacacgta ccttgttgtg agtgtaagtt tgtggtgcag t <SEQ26; DNA; Human papillomavirus>
ctaatagcacat ggttggaccg ggtcatgttt ggggtgctgg
agacaaacat ctagagaacc tagagaatct acagtataat
catgcatggt aaagtaccaa cgctgcaaga cgt <SEQ335; DNA; Human papillomavirus>
ctaatagcacat ggttggaccg ggtcatgttt ggggtgctgg
agacaaacat ctagagaacc tagagaatct acagtataat
catgcatggt aaagtaccaa cgctgcaaga cgttgtatta
gaactaacac ctcaaacaga aattgaccta cagtgcaatg
agcaattgga cagctcagag gatgaggatg aggatgaagt
agaccatttg caggagcggc cacagcaagc tagacaagct
aaacaacata cgtgttacct aatacacgta ccttgttgtg
agtgtaagtt tgtggtgcag t <SEQ27;DNA; Human papillomavirus>
aaggtgctacagatgtca aagtccgtta actccggagg
aaaagcaatt gcattgtgac agaaaaagac gatttcatct
aatagcacat ggttggaccg ggtcatgttt ggggtgctgg
agacaaacat ctagagaacc <SEQ336; DNA; Human papillomavirus>
aaggtgctacagatgtca aagtccgtta actccggagg
aaaagcaatt gcattgtgac agaaaaagac gatttcatct
aatagcacat ggttggaccg ggtcatgttt ggggtgctgg
agacaaacat ctagagaacc tagagaatct acagtataat
catgcatggt aaagtaccaa cgctgcaaga cgt <SEQ337; DNA; Human papillomavirus>
aaggtgctacagatgtca aagtccgtta actccggagg
aaaagcaatt gcattgtgac agaaaaagac gatttcatct
aatagcacat ggttggaccg ggtcatgttt ggggtgctgg
agacaaacat ctagagaacc tagagaatct acagtataat
catgcatggt aaagtaccaa cgctgcaaga cgttgtatta
gaactaacac ctcaaacaga aattgaccta cagtgcaatg
agcaattgga cagctcagag gatgaggatg aggatgaagt
agaccatttg caggagcggc cacagcaagc tagacaagct
aaacaacata cgtgttacct aatacacgta ccttgttgtg
agtgtaagtt tgtggtgcag t <SEQ28; DNA; Human papillomavirus>
gttggaccgggtcatgttt ggggtgctgg agacaaacat
ctagagaacc tagagaatct acagtataat catgcatggt
aaagtaccaa cgctgcaaga cgt <SEQ338; DNA; Human papillomavirus>
gttggaccg ggtcatgttt ggggtgctgg agacaaacat
ctagagaacc tagagaatct acagtataat catgcatggt
aaagtaccaa cgctgcaaga cgttgtatta gaactaacac
ctcaaacaga aattgaccta cagtgcaatg agcaattgga
cagctcagag gatgaggatg aggatgaagt agaccatttg
caggagcggc cacagcaagc tagacaagct aaacaacata
cgtgttacct aatacacgta ccttgttgtg agtgtaagtt
tgtggtgcag t <SEQ29; DNA; Human papillomavirus>
tcagaggatgaggatg aggatgaagt agaccatttg caggagcggc
cacagcaagc tagacaagct aaacaacata cgtgttacct
aatacacgta ccttgttgtg agtgtaagtt tgtggtgcag t <SEQ1; DNA; Human papillomavirus>
ggcagtggaaagcagtgga gacacccttc gcgttgtaca
gcagatgtta atgggcgaac taagcctggt ttgcccgtgt
tgtgcgaaca actagcaacg gcgatgg -continued <SEQ320; DNA; Human papillomavirus>
ggcagtggaaagcagtgga gacacccttc gcgttgtaca
gcagatgtta atgggcgaac taagcctggt ttgcccgtgt
tgtgcgaaca actagcaacg gcgatggact <SEQ321; DNA; Human papillomavirus>
ggcagtggaaagcagtgga gacacccttc gcgttgtaca
gcagatgtta atgggcgaac taagcctggt ttgcccgtgt
tgtgcgaaca actagcaacg gcgatggact gtgaaggtac
agaggatgag gg <SEQ2; DNA; Human papillomavirus>
agctccgtgttgcag gtgttcaagt gtagtacaac tggcagtgga
aagcagtgga gacacccttc gcgttgtaca gcagatgtta
atgggcgaac taagcctggt ttgcccgtgt tgtgcgaaca
actagcaacg gcgatggact <SEQ322; DNA; Human papillomavirus>
agctccgtgttgcag gtgttcaagt gtagtacaac tggcagtgga
aagcagtgga gacacccttc gcgttgtaca gcagatgtta
atgggcgaac taagcctggt ttgcccgtgt tgtgcgaaca
actagcaacg gcgatgg <SEQ323; DNA; Human papillomavirus>
agctccgtgttgcag gtgttcaagt gtagtacaac tggcagtgga
aagcagtgga gacacccttc gcgttgtaca gcagatgtta
atgggcgaac taagcctggt ttgcccgtgt tgtgcgaaca
actagcaacg gcgatggact gtgaaggtac agaggatgag gg <SEQ3; DNA; Human papillomavirus>
atatgcgtgacca gctaccagaa ag/acgggctg gacaggctac
gtgttacaga attgaagctc cgtgttgcag gtgttcaagt
gtagtacaac tggcagtgga aagcagtgga gaca <SEQ324; DNA; Human papillomavirus>
atatgcgtgacca gctaccagaa agacgggctg gacaggctac
gtgttacaga attgaagctc cgtgttgcag gtgttcaagt
gtagtacaac tggcagtgga aagcagtgga gacacccttc
gcgttgtaca gcagatgtta atgggcgaac taagcctggt
ttgcccgtgt tgtgcgaaca actagcaacg gcgatgg <SEQ325; DNA; Human papillomavirus>
atatgcgtgacca gctaccagaa agacgggctg gacaggctac
gtgttacaga attgaagctc cgtgttgcag gtgttcaagt
gtagtacaac tggcagtgga aagcagtgga gacacccttc
gcgttgtaca gcagatgtta atgggcgaac taagcctggt
ttgcccgtgt tgtgcgaaca actagcaacg gcgatggact (SEQ326; DNA; Human papillomavirus>
atatgcgtgacca gctaccagaa agacgggctg gacaggctac
gtgttacaga attgaagctc cgtgttgcag gtgttcaagt
gtagtacaac tggcagtgga aagcagtgga gacacccttc
gcgttgtaca gcagatgtta atgggcgaac taagcctggt
ttgcccgtgt tgtgcgaaca actagcaacg gcgatggact
gtgaaggtac agaggatgag gg <SEQ327; DNA; Human papillomavirus>
atatgcgtgacca gctaccagaa .agacgggctg gacaggctac
gtgttacaga attgaagctc cgtgttgcag gtgttcaagt
gtagtacaac tggcagtgga aagcagtgga gacacccttc
gcgttgtaca gcagatgtta atgggcga <SEQ4; DNA; Human papillomavirus>
gacaggctacgtgttacaga attgaagctc cgtgttgcag
gtgttcaagt gtagtacaac tggcagtgga aagcagtgga
gacacccttc gcgttgtaca gcagatgtta atgggcgaac
taagcctggt ttgcccgtgt tgtgcgaaca actagcaacg
gcgatggact gtgaaggtac agaggatgag gg <SEQ328; DNA; Human papillomavirus>
gacaggctac gtgttacaga attgaagctc cgtgttgcag
gtgttcaagt gtagtacaac tggcagtgga aagcagtgga
gacacccttc gcgttgtaca gcagatgtta atgggcgaac
taagcctggt ttgcccgtgt tgtgcgaaca actagcaacg
gcgatgg -continued <SEQ329; DNA; Human papillomavirus>
gacaggctac gtgttacaga attgaagctc cgtgttgcag
gtgttcaagt gtagtacaac tggcagtgga aagcagtgga
gacacccttc gcgttgtaca gcagatgtta atgggcgaac
taagcctggt ttgcccgtgt tgtgcgaaca actagcaacg
gcgatggact <SEQ330; DNA; Human papillomavirus>
gacaggctac gtgttacaga attgaagctc cgtgttgcag
gtgttcaagt gtagtacaac tggcagtgga aagcagtgga
gacacccttc gcgttgtaca gcagatgtta atgggcga <SEQ5; DNA; Human papillomavirus>
cgggctggacaggctac gtgttacaga attgaagctc cgtgttgcag
gtgttcaagt gtagtacaac tggcagtgga aagcagtgga
gacacccttc gcgttgtaca gcagatgtta atgggcga <SEQ331; DNA; Human papillomavirus>
cgggctggacaggctac gtgttacaga attgaagctc cgtgttgcag
gtgttcaagt gtagtacaac tggcagtgga aagcagtgga
gacacccttc gcgttgtaca gcagatgtta atgggcgaac
taagcctggt ttgcccgtgt tgtgcgaaca actagcaacg
gcgatgg <SEQ332; DNA; Human papillomavirus>
cgggctggacaggctac gtgttacaga attgaagctc cgtgttgcag
gtgttcaagt gtagtacaac tggcagtgga aagcagtgga
gacacccttc gcgttgtaca gcagatgtta atgggcgaac
taagcctggt ttgcccgtgt tgtgcgaaca actagcaacg
gcgatggact <SEQ333; DNA; Human papillomavirus>
cgggctggacaggctac gtgttacaga attgaagctc cgtgttgcag
gtgttcaagt gtagtacaac tggcagtgga aagcagtgga
gacacccttc gcgttgtaca gcagatgtta atgggcgaac
taagcctggt ttgcccgtgt tgtgcgaaca actagcaacg
gcgatggact gtgaaggtac agaggatgag gg <SEQ122; DNA; Human papillomavirus>
ggacgtggtccaga ttaagtttgc acgaggacga ggacaaggaa
aacgatggag actctttgcc aacgtttaaa tgtgtgtcag gaca <SEQ123; DNA; Human papillomavirus>
tagtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat <SEQ124; DNA; Human papillomavirus>
tagtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttt <SEQ125; DNA; Human papillomavirus>
tagtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat t <SEQ126; DNA; Human papillomavirus>
tagtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtc <SEQ127; DNA; Human papillomavirus>
tagtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttg -continued <SEQ128; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat <SEQ129; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttt <SEQ130; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat t <SEQ131; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtc <SEQ132; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttg <SEQ133; DNA; Human papillomavirus>
tagtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgacca <SEQ134; DNA; Human papillomavirus>
tagtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat tt <SEQ135; DNA; Human papillomavirus>
tagtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat <SEQ136; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgacca <SEQ137; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat tt <SEQ138; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat -continued <SEQ139; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgacca <SEQ140; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat tt <SEQ141; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat <SEQ142; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgacca <SEQ143; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat tt <SEQ144; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat <SEQ145; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgacca <SEQ146; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat tt <SEQ147; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat <SEQ359; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat t <SEQ360; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttt <SEQ361; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttg <SEQ362; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtc <SEQ363; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat <SEQ364; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat t <SEQ365; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttt <SEQ366; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttg <SEQ367; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtc <SEQ144; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat <SEQ368; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat t <SEQ369; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttt <SEQ370; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttg -continued <SEQ371; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtc <SEQ372; DNA; Human papillomavirus>
t agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc <SEQ373; DNA; Human papillomavirus>
t agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc t <SEQ374; DNA; Human papillomavirus>
t agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc tactgga <SEQ375; DNA; Human papillomavirus>
t agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc tactggat <SEQ376; DNA; Human papillomavirus>
t agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc tactggatt <SEQ377; DNA; Human papillomavirus>
t agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc tactggattt <SEQ378; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc <SEQ379; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc t <SEQ380; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc tactgga -continued <SEQ381; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc tactggat <SEQ382; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc tactggatt <SEQ383; DNA; Human papillomavirus>
agtaacacta cacccatagt acatttaaaa ggtgatgcta
atactttaaa atgtttaaga tatagattta aaaagcattg
tacattgtat actgcagtgt cgtctacatg gcattggaca
ggacataatg taaaacataa aagtgcaatt gttacactta
catatgatag tgaatggcaa cgtgaccaat ttttgtctca
agttaaaata ccaaaaacta ttacagtgtc tactggattt <SEQ384; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc <SEQ385; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc t <SEQ386; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactgga <SEQ387; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggat <SEQ388; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggatt <SEQ389; DNA; Human papillomavirus>
actacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggattt <SEQ390; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc -continued <SEQ391; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc t <SEQ392; DNA; Human papillomavirus>
tacacccatagt acatttaaaa ggtgatgcta atactttaaa
atgtttaaga tatagactta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactgga <SEQ393; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggat <SEQ394; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggatt <SEQ395; DNA; Human papillomavirus>
tacacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggattt <SEQ396; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc <SEQ397; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc t <SEQ398; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactgga <SEQ399; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggat <SEQ400; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggatt -continued <SEQ401; DNA; Human papillomavirus>
acacccatagt acatttaaaa ggtgatgcta atactttaaa
atgtttaaga tatagattta aaaagcattg tacattgtat
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggattt <SEQ148; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgacca <SEQ149; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat tt <SEQ150; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat <SEQ151; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgacca <SEQ152; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat tt <SEQ153; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat <SEQ154; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgacca <SEQ155; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat tt <SEQ156; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat <SEQ402; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat t <SEQ403; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat ttt -continued <SEQ404; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat ttttg <SEQ405; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat ttttgtc <SEQ406; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat t <SEQ407; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat ttt <SEQ408; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat ttttg <SEQ409; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtc <SEQ410; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat t <SEQ411; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat ttt <SEQ412; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat ttttg <SEQ413; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtc <SEQ163; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc <SEQ162; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc t -continued <SEQ164; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactgga <SEQ414; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggat <SEQ415; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggatt <SEQ161; DNA; Human papillomavirus>
acatttaaaa ggtgatgcta atactttaaa atgtttaaga
tatagattta aaaagcattg tacattgtat actgcagtgt
cgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggattt <SEQ167; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc <SEQ165; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc t <SEQ168; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc
tactgga <SEQ416; DNA; Human papillomavirus>
ttaaaaggtgatgcta atactttaaa atgtttaaga tatagattta
aaaagcattg tacattgtat actgcagtgt cgtctacatg
gcattggaca ggacacaatg taaaacataa aagtgcaatt
gttacactta catatgatag tgaatggcaa cgtgaccaat
ttttgtctca agttaaaata ccaaaaacta ttacagtgtc
tactggat <SEQ417; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc
tactggatt <SEQ165; DNA; Human papillomavirus>
ttaaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc
tactggattt <SEQ159; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc <SEQ158; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc t <SEQ160; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc
tactgga <SEQ418; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc
tactggat <SEQ419; DNA; Human papillomavirus>
taaaaggtgatgcta atactttaaa atgtttaaga tatagattta
aaaagcattg tacattgtat 8ctgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc
tactggatt <SEQ157; DNA; Human papillomavirus>
taaaaggtgatgcta atactttaaa atgtttaaga tatagattta
aaaagcattg tacattgtat actgcagtgt cgtctacatg
gcattggaca ggacataatg taaaacataa aagtgcaatt
gttacactta catatgatag tgaatggcaa cgtgaccaat
ttttgtctca agttaaaata ccaaaaacta ttacagtgtc
tactggattt <SEQ169; DNA; Human papillomavirus>
gtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggat <SEQ170; DNA; Human papillomavirus>
gtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc t <SEQ171; DNA; Human papillomavirus>
gtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc <SEQ172; DNA; Human papillomavirus>
gtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggattt <SEQ173; DNA; Human papillomavirus>
gtcgtctacatg gcattggaca ggacataatg taaaacataa
aagtgcaatt gttacactta catatgatag tgaatggcaa
cgt9accaat ttttgtctca agttaaaata ccaaaaacta
ttacagtgtc tactggatt <SEQ174; DNA; Human papillomavirus>
gtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactgga <SEQ175; DNA; Human papillomavirus>
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggat <SEQ176; DNA; Human papillomavirus>
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc t <SEQ177; DNA; Human papillomavirus>
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc <SEQ178; DNA; Human papillomavirus>
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggattt <SEQ179; DNA; Human papillomavirus>
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggatt <SEQ180; DNA; Human papillomavirus>
actgcagtgt cgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactgga <SEQ181; DNA; Human papillomavirus>
tgcagtgtcgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggat <SEQ182; DNA; Human papillomavirus
tgcagtgtcgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc t <SEQ183; DNA; Human papillomavirus>
tgcagtgtcgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc <SEQ184; DNA; Human papillomavirus>
tgcagtgtcgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggattt <SEQ185; DNA; Human papillomavirus>
tgcagtgtcgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactggatt <SEQ186; DNA; Human papillomavirus>
tgcagtgtcgtctacatg gcattggaca ggacataatg
taaaacataa aagtgcaatt gttacactta catatgatag
tgaatggcaa cgtgaccaat ttttgtctca agttaaaata
ccaaaaacta ttacagtgtc tactgga <SEQ187; DNA; Human papillomavirus>
agtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggat -continued <SEQ188; DNA; Human papillomavirus>
agtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc t <SEQ189; DNA; Human papillomavirus>
agtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc <SEQ190; DNA; Human papillomavirus>
agtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggattt <SEQ191;DNA; Human papillomavirus>
agtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggatt <SEQ192; DNA; Human papillomavirus>
agtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactgga <SEQ193; DNA; Human papillomavirus>
cagtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggat <SEQ194; DNA; Human papillomavirus>
cagtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc t <SEQ195; DNA; Human papillomavirus>
cagtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc <SEQ196; DNA; Human papillomavirus>
cagtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggattt <SEQ197; DNA; Human papillomavirus>
cagtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggatt <SEQ198; DNA; Human papillomavirus>
cagtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactgga <SEQ199; DNA; Human papillomavirus>
tgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggat <SEQ200; DNA; Human papillomavirus>
tgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc t <SEQ201; DNA; Human papillomavirus>
tgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc <SEQ202; DNA; Human papillomavirus>
tgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggattt <SEQ203; DNA; Human papillomavirus>
tgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggatt <SEQ204; DNA; Human papillomavirus>
tgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactgga <SEQ205; DNA; Human papillomavirus>
gtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggat <SEQ206; DNA; Human papillomavirus>
gtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc t <SEQ207; DNA; Human papillomavirus>
gtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc <SEQ208; DNA; Human papillomavirus>
gtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggattt <SEQ209; DNA; Human papillomavirus>
gtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactggatt <SEQ210; DNA; Human papillomavirus>
gtgtcgtctacatg gcattggaca ggacataatg taaaacataa
aagtgcaatt gttacactta catatgatag tgaatggcaa
cgtgaccaat ttttgtctca agttaaaata ccaaaaacta
ttacagtgtc tactgga <SEQ46; DNA; Human papillomavirus>
tggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatg <SEQ47; DNA; Human papillomavirus>
tggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc ag <SEQ48; DNA; Human papillomavirus>
tggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca atagcaatgc agc -continued <SEQ49; DNA; Human papillomavirus>
gaacaggaatatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatg <SEQ50; DNA; Human papillomavirus>
gaacaggaatatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc ag <SEQ51; DNA; Human papillomavirus>
gaacaggaatatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc agc <SEQ52; DNA; Human papillomavirus>
tggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg ca <SEQ53; DNA; Human papillomavirus>
tggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg cattt <SEQ339; DNA; Human papillomavirus>
gaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg ca <SEQ340; DNA; Human papillomavirus>
gaacaggaatatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg cattt <SEQ341; DNA; Human papillomavirus>
tggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc <SEQ342; DNA; Human papillomavirus>
gaacaggaatatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc <SEQ54; DNA; Human papillomavirus>
ggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg ca <SEQ55; DNA; Human papillomavirus>
ggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg cattt <SEQ56; DNA; Human papillomavirus>
gtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg ca -continued <SEQ57; DNA; Human papillomavirus>
gtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg cattt <SEQ343; DNA; Human papillomavirus>
ggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct acagatgaa agcgatatgg
catttgaata tgccttatta gcagacagca acagcaatg <SEQ344; DNA; Human papillomavirus>
ggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc ag <SEQ345; DNA; Human papillomavirus>
ggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc agc <SE0346; DNA; Human papillomavirus>
gtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatg <SEQ347; DNA; Human papillomavirus>
gtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc ag <SEQ348; DNA; Human papillomavirus>
gtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc agc <SEQ349; DNA; Human papillomavirus>
tggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc <SEQ350; DNA; Human papillomavirus>
ggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc <SEQ345; DNA; Human papillomavirus>
ggtatagaacaggaa tatcaaatat tagtgaagta atgggagaca
cacctgagtg gatacaaaga cttactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc agc <SEQ351; DNA; Human papillomavirus>
gtatagaacaggaa tatcaaatat tagtgaagta atgggagaca
cacctgagtg gatacaaaga ettactatta tacaacatgg
aatagatgat agcaattttg atttgtcaga aatggtacaa
tgggcatttg ataatgagct gacagatgaa agcgatatgg
catttgaata tgccttatta gcagacagca acagcaatgc -continued <SEQ352; DNA; Human papillomavirus>
gtatagaacaggaa tatcaaatat tagtgaagta atgggagaca cacctgagtg gatacaaaga cttactatta tacaacatgg aatagatgat agcaattttg atttgtcaga aatggtacaa tgggcatttg ataatgagct gacagatgaa agcgatatgg catttgaata tgccttatta gcagacagca acagcaatgc agc <SEQ58; DNA; Human papillomavirus>
tgatagcaattttg atttgtcaga aatggtacaa tgggcatttg ataatgagct gacagatgaa agcgatatgg catttgaata tgccttatta gcagacagca acagcaatgc <SEQ59; DNA; Human papillomavirus>
tgatagcaattttg atttgtcaga aatggtacaa tgggcatttg ataatgagct gacagatgaa agcgatatgg catttgaata tgccttatta gcagacagca acagcaatgc agc <SEQ60; DNA; Human papillomavirus>
gatagcaattttg atttgtcaga aatggtacaa tgggcatttg ataatgagct gacagatgaa agcgatatgg catttgaata tgccttatta gcagacagca acagcaatgc <SEQ61; DNA; Human papillomavirus>
gatagcaattttg atttgtcaga aatggtacaa tgggcatttg ataatgagct gacagatgaa agcgatatgg catttgaata tgccttatta gcagacagca acagcaatgc agc <SEQ62; DNA; Human papillomavirus>
ggaatagatgat agcaattttg atttgtcaga aatggtacaa tgggcatttg ataatgagct gacagatgaa agcgatatgg catttgaata tgccttatta gcagacagca acagcaatgc <SEQ63; DNA; Human papillomavirus>
ggaatagatgat agcaattttg atttgtcaga aatggtacaa tgggcatttg ataatgagct gacagatgaa agcgatatgg catttgaata tgccttatta gcagacagca acagcaatgc agc <SEQ353; DNA; Human papillomavirus>
ggaatagatgat agcaattttg atttgtcaga aatggtacaa tgggcatttg taatgagct gacagatgaa agcgatatgg catttgaata tgccttatta gcagacagca acagcaatg <SEQ354; DNA; Human papillomavirus>
ggaatagatgat agcaattttg atttgtcaga aatggtacaa tgggcatttg ataatgagct gacagatgaa agcgatatgg catttgaata tgccttatta gcagacagca acagcaatgc ag -continued <SEQ355; DNA; Human papillomavirus>
tgatagcaattttg atttgtcaga aatggtacaa tgggcatttg ataatgagct gacagatgaa agcgatatgg catttgaata tgccttatta gcagacagca acagcaatg <SEQ356; DNA; Human papillomavirus>
tgatagcaattttg atttgtcaga aatggtacaa tgggcatttg ataatgagct gacagatgaa agcgatatgg catttgaata tgccttatta gcagacagca acagcaatgc ag <SEQ59; DNA; Human papillomavirus>
tgatagcaattttg atttgtcaga aatggtacaa tgggcatttg ataatgagct gacagatgaa agcgatatgg catttgaata tgccttatta gcagacagca acagcaatgc agc <SEQ357; DNA; Human papillomavirus>
gatagcaattttg atttgtcaga aatggtacaa tgggcatttg ataatgagct gacagatgaa agcgatatgg catttgaata tgccttatta gcagacagca acagcaatg <SEQ358; DNA; Human papillomavirus>
gatagcaattttg atttgtcaga aatggtacaa tgggcatttg ataatgagct gacagatgaa agcgatatgg catttgaata tgccttatta gcagacagca acagcaatgc ag <SEQ64; DNA; Human papillomavirus>
ggctgatccagaagg tacagacggg gagggcacgg gttgtaacgg ctggttttat gtacaagcta ttgtagacaa aaaaacagga gatgtaatat cagatgacga ggacgaaaat gc <SEQ65; DNA; Human papillomavirus>
ggctgatccagaagg tacagacggg gagggcacgg gttgtaacgg ctggttttat gtacaagcta ttgtagacaa aaaaacagga gatgtaatat cagatgacga ggacgaaaat gcaacagaca cagg <SEQ66; DNA; Human papillomavirus>
gatccagaagg tacagacggg gagggcacgg gttgtaacgg ctggttttat gtacaagcta ttgtagacaa aaaaacagga gatgtaatat cagatgacga ggacgaaaat gc <SEQ67; DNA; Human papillomavirus>
gatccagaagg tacagacggg gagggcacgg gttgtaacgg ctggttttat gtacaagcta ttgtagacaa aaaaacagga gatgtaatat cagatgacga ggacgaaaat gcaacagaca cagg

The invention claimed is:

1. A process for detecting in a sample at least one HPV, which can be oncogenic for the mucosal epithelia, wherein said detection comprises the determination of whether at least one amplicon has been, or is, produced from said sample, or from nucleic acid material thereof, by amplification by means of amplification primers, whereby the production of at least one amplicon indicates that at least one HPV, which can be oncogenic for the mucosal epithelia, is present in said sample, wherein said amplification primers comprise at least two primers of 14-30 nucleotides, the sequences of which are suitable for use as primers in the amplification of at least one target template sequence, wherein said at least one target template sequence is at least one of the HPV16 fragments, which comprise the sequence of SEQ ID NO: 122 or the complementary sequence thereof or a fragment of said sequence of SEQ ID NO: 122 or complementary sequence, wherein said HPV16 fragments differ by at most 5 nucleotides in length from said sequence of SEQ ID NO: 122 or complementary sequence, wherein said at least two primers of 14-30 nucleotides anneal to the 5' terminal end of said at least one target template sequence and to the 5' terminal end of the sequence that is complementary to said at least one target template sequence;

and wherein said amplification primers further comprise at least two primers of 14-30 nucleotides, the sequences of which are suitable for use as primers in the amplification of at least one target template sequence, wherein said at least one target template sequence is at least one of the following HPV18 fragments:

the HPV18 fragments, which comprise the sequence of SEQ ID NO: 64 or the complementary sequence thereof or a fragment of said sequence of SEQ ID NO: 64 or complementary sequence, wherein said HPV18 fragments differ by at most 5 nucleotides in length from said sequence of SEQ ID NO: 64 or complementary sequence, the HPV18 fragments, which comprise the sequence of SEQ ID NO: 65 or the complementary sequence thereof or a fragment of said sequence of SEQ ID NO: 65 or complementary sequence, wherein said HPV18 fragments differ by at most 5 nucleotides in length from said sequence of SEQ ID NO: 65 or complementary sequence, the HPV18 fragments, which comprise the sequence of SEQ ID NO: 66 or the complementary sequence thereof or a fragment of said sequence of SEQ ID NO: 66 or complementary sequence, wherein said HPV18 fragments differ by at most 5 nucleotides in length from said sequence of SEQ ID NO: 66 or complementary sequence, and the HPV18 fragments, which comprise the sequence of SEQ ID NO: 67 or the complementary sequence thereof or a fragment of said sequence of SEQ ID NO: 67 or complementary sequence, wherein said HPV18 fragments differ by at most 5 nucleotides in length from said sequence of SEQ ID NO: 67 or complementary sequence, wherein said at least two primers of 14-30 nucleotides anneal to the 5' terminal end of said at least one target template sequence and to the 5' terminal end of the sequence that is complementary to said at least one target template sequence.

2. The process of claim 1, wherein said amplification primers comprise primers of 14-30 nucleotides, the sequences of which are suitable for use as primers in the amplification of at least two target template sequences, which are HPV18 fragments selected from two different groups among the following four groups i. to iv.:

i. the HPV18 fragments, which comprise the sequence of SEQ ID NO: 64 or the complementary sequence thereof or a fragment of said sequence of SEQ ID NO: 64 or complementary sequence, wherein said HPV18 fragments differ by at most 5 nucleotides in length from said sequence of SEQ ID NO: 64 or complementary sequence, ii. the HPV18 fragments, which comprise the sequence of SEQ ID NO: 65 or the complementary sequence thereof or a fragment of said sequence of SEQ ID NO: 65 or complementary sequence, wherein said HPV18 fragments differ by at most 5 nucleotides in length from said sequence of SEQ ID NO: 65 or complementary sequence, iii. the HPV18 fragments, which comprise the sequence of SEQ ID NO: 66 or the complementary sequence thereof or a fragment of said sequence of SEQ ID NO: 66 or complementary sequence, wherein said HPV18 fragments differ by at most 5 nucleotides in length from said sequence of SEQ ID NO: 66 or complementary sequence, iv. the HPV18 fragments, which comprise the sequence of SEQ ID NO: 67 or the complementary sequence thereof or a fragment of said sequence of SEQ ID NO: 67 or complementary sequence, wherein said HPV18 fragments differ by at most 5 nucleotides in length from said sequence of SEQ ID NO: 67 or complementary sequence, wherein said primers of 14-30 nucleotides anneal to the 5' terminal end of at least one of said at least two target template sequences or to the 5' terminal end of at least one of the sequences that are complementary to said at least two target template sequences.

3. The process of claim 1, wherein said amplification primers comprise more than two primers of 14-30 nucleotides, the sequences of which are suitable for use as primers in the amplification of at least one target template sequence, wherein said at least one target template sequence is at least one of the HPV16 fragments, which comprise the sequence of SEQ ID NO: 122 or the complementary sequence thereof or a fragment of said sequence of SEQ ID NO: 122 or complementary sequence, wherein said HPV16 fragments differ by at most 5 nucleotides in length from said sequence of SEQ ID NO: 122 or complementary sequence, wherein said more than two primers of 14-30 nucleotides anneal to the 5' terminal end of said at least one target template sequence or to the 5' terminal end of the sequence that is complementary to said at least one target template sequence.

4. The process of claim 1, wherein said fragment differs by at most 4 nucleotides or at most 3 nucleotides or at most 2 nucleotides or at most 1 nucleotide in length from said SEQ ID or complementary sequence.

5. The HPV detection process of claim 1, wherein said amplification primers comprise at least two primers of 14-30 nucleotides, the sequences of which are suitable for use as primers in the amplification of at least one target template sequence, which is at least one of the sequences of SEQ ID NOs: 64-65 and the sequences complementary to SEQ ID NOs: 64-65, wherein said at least two primers of 14-30 nucleotides anneal to the 5' terminal end of said at least one target template sequence and to the 5' terminal end of the sequence that is complementary to said at least one target template sequence.

6. The HPV detection process of claim 1, wherein said at least two primers, the sequences of which are suitable for use as primers in the amplification of at least one target template sequence, which is a fragment of HPV16, are suitable for use as primers in the amplification of at least one nucleic acid of 80-260 nucleotides from the target region consisting of the E1 and E2 genes from each of the following HPV: HPV16, HPV33 and HPV31.

7. The HPV detection process of claim 1, wherein said at least two primers, the sequences of which are suitable for use as primers in the amplification of at least one target template sequence, which is a fragment of HPV16, are suitable for use as primers in the amplification of at least one nucleic acid of 80-260 nucleotides from the target region consisting of the E1 and E2 genes from each of the following HPV: HPV16, HPV58, HPV33, HPV52, HPV35 and HPV31.

8. The HPV detection process of claim 1, wherein said at least two primers, the sequences of which are suitable for use as primers in the amplification of at least one target template sequence, which is a fragment of HPV16, are suitable for use as primers in the amplification of at least one nucleic acid of 80-260 nucleotides from the target region consisting of the E1 and E2 genes of HPV16, HPV58, HPV33, HPV52, HPV35, HPV31 and HPV67.

9. The HPV detection process of claim 1, wherein said at least two primers, the sequences of which are suitable for use as primers in the amplification of at least one target template sequence, which is a fragment of HPV18, are suitable for use as primers in the amplification of at least one nucleic acid of 100-220 nucleotides from the target region consisting of the E1 gene from each of the following HPV: HPV45 and HPV18.

10. The HPV detection process of claim 1, wherein said at least two primers, the sequences of which are suitable for use as primers in the amplification of at least one target template sequence, which is a fragment of HPV18, are suitable for use as primers in the amplification of at least one nucleic acid of 100-220 nucleotides from the target region consisting of the E1 gene from each of the following HPV: HPV45, HPV18, HPV68, HPV39 and HPV59.

11. The HPV detection process of claim 1, wherein said at least two primers, the sequences of which are suitable for use as primers in the amplification of at least one target template sequence, which is a fragment of HPV18, are suitable for use as primers in the amplification of at least one nucleic acid of 100-220 nucleotides from the target region consisting of the E1 gene from each of the following HPV: HPV45, HPV18, HPV68, HPV39, HPV59 and HPV85.

12. The HPV detection of claim 1, wherein said amplification primers comprise:

at least two primers, the sequences of which are suitable for use as primers in the amplification of at least one nucleic acid of 80-260 nucleotides from the target region consisting of the E1 and E2 genes from each of the following HPV: HPV16, HPV33 and HPV31; and at least two primers, the sequences of which are suitable for use as primers in the amplification of at least one nucleic acid of 100-220 nucleotides from the target region consisting of the E1 gene from each of the following HPV: HPV45 and HPV18.

13. The HPV detection process of claim 1, wherein said amplification primers comprise:

at least two primers, the sequences of which are suitable for use as primers in the amplification of at least one nucleic acid of 80-260 nucleotides from the target region consisting of the E1 and E2 genes from each of the following HPV: HPV16, HPV33 and HPV31; and at least two primers, the sequences of which are suitable for use as primers in the amplification of at least one nucleic acid of 100-220 nucleotides from the target region consisting of the E1 gene from each of the following HPV: HPV45 and HPV18; and wherein said amplification primers further comprise:

at least two primers, the sequences of which are suitable for use as primers in the amplification of at least one nucleic acid of 90-390 nucleotides from the target region consisting of the E6 and E7 genes of HPV56.

14. The HPV detection process of claim 1, wherein said amplification primers comprise:

at least two primers, the sequences of which are suitable for use as primers in the amplification of at least one nucleic acid of 80-260 nucleotides from the target region consisting of the E1 and E2 genes from each of the following HPV: HPV16, HPV33, and HPV31; and wherein said amplification primers further comprise:

at least two primers, the sequences of which are suitable for use as primers in the amplification of at least one nucleic acid of 100-220 nucleotides from the target region consisting of the E1 gene from each of the following HPV: HPV45 and HPV18; and wherein said amplification primers further comprise:

at least two primers, the sequences of which are suitable for use as primers in the amplification of at least one nucleic acid of 90-240 nucleotides from the target region consisting of the E7 and E1 genes of each of HPV51 and HPV82.

15. The HPV detection process of claim 1, wherein said amplification primers comprise:

at least two primers, the sequences of which are suitable for use as primers in the amplification of at least one nucleic acid of 80-260 nucleotides from the target region consisting of the E1 and E2 genes from each of the following HPV: HPV16, HPV33 and HPV31; and at least two primers, the sequences of which are suitable for use as primers in the amplification of at least one nucleic acid of 100-220 nucleotides from the target region consisting of the E1 gene from each of the following HPV: HPV45 and HPV18; and wherein said amplification primers further comprise:

at least two primers, the sequences of which are suitable for use as primers in the amplification of at least one nucleic acid of 90-390 nucleotides from the target region consisting of the E6 and E7 genes of HPV56;

and at least two primers, the sequences of which are suitable for use as primers in the amplification of at least one nucleic acid of 90-240 nucleotides from the target region consisting of the E7 and E1 genes of HPV51.

16. The HPV detection process of claim 1, wherein:

the oligonucleotide sequence of one of said at least two primers is at least 80% identical to the sequence of the same length that is the 5' terminal end of said target template sequence, and the oligonucleotide sequence of the other of said at least two primers is at least 80% identical to the sequence of the same length that is the 5' terminal end of the sequence that is complementary to said target template sequence.

17. The HPV detection process of claim 1, wherein:

the oligonucleotide sequence of one of said at least two primers is at least 85% identical to the sequence of the same length that is the 5' terminal end of said target template sequence, and the oligonucleotide sequence of the other of said at least two primers is at least 85% identical to the sequence of the same length that is the 5' terminal end of the sequence that is complementary to said target template sequence.

18. The HPV detection process of claim 1, wherein:

the oligonucleotide sequence of one of said at least two primers is 100% identical to the sequence of the same length that is the 5' terminal end of said target template sequence, and the oligonucleotide sequence of the other of said at least two primers is 100% identical to the sequence of the same length that is the 5' terminal end of the sequence that is complementary to said target template sequence.

19. The HPV detection process of claim 1, wherein at least two primers are oligonucleotides of 17-25 nucleotides.

20. The HPV detection process of claim 1, wherein said at least two primers, the sequences of which are suitable for use as primers in the amplification of at least one target template sequence, which is a fragment of HPV16, comprise at least one oligonucleotide of SEQ ID NOs: 211-217 and 240-241.

21. The HPV detection process of claim 1, wherein said at least two primers, the sequences of which are suitable for use as primers in the amplification of at least one target template sequence, which is a fragment of HPV16, comprise at least one oligonucleotide of SEQ ID NOs: 240-241.

22. The HPV detection process of claim 1, wherein said at least two primers, the sequences of which are suitable for use as primers in the amplification of at least one target template sequence, which is a fragment of HPV18, comprise at least one oligonucleotide of SEQ ID NOs: 77, 78, 86 and 87.

23. The HPV detection process of claim 1, wherein said at least two primers, the sequences of which are suitable for use as primers in the amplification of at least one target template sequence, which is a fragment of HPV18, comprise at least one oligonucleotide of SEQ ID NOs: 86-87.

24. The HPV detection process of claim 1, wherein said amplification primers comprise at least one of SEQ ID NOs: 211-217 and at least one of SEQ ID NOs: 240-241; and at least one of SEQ ID NOs: 77-78 and at least one of SEQ ID NOs: 86-87.

25. The HPV detection process of claim 1, wherein said amplification primers comprises the primers of SEQ ID NOs: 211-217 and 240-241.

26. The HPV detection process of claim 1, wherein said amplification primers comprises the primers of SEQ ID NOs: 77-78 and 86-87.

27. The HPV detection process of claim 1, wherein said amplification primers comprises the primers of SEQ ID NOs: 211-217 and 240-241, and the primers of SEQ ID NOs: 77-78 and 86-87.

28. The process of claim 1, wherein said detecting comprises contacting a nucleic acid product of said amplification with at least one HPV-specific probe.

29. The HPV detection process of claim 1, wherein said determination of whether at least one amplicon is produced is carried out by using in real-time amplification at least one probe, the oligonucleotide sequence of which is one of SEQ ID NOs: 266-271, or one of the complementary sequences thereof, or a sequence, which differs by at most 5 nucleotides in length from said SEQ ID or complementary sequence and which is at least 90% identical to said SEQ ID or complementary sequence, said probe being optionally linked to at least one detection label and/or to two complementary nucleotide sequences of 3 to 10 nucleotides, one of said two complementary nucleotide sequences of 3 to 10 nucleotides being linked at the 5' end of said probe, the other of said two complementary nucleotide sequences of 3 to nucleotides being linked at the 3' end of said probe.

30. The HPV detection process of claim 1, wherein said determination of whether at least one amplicon is produced is carried out by using in real-time amplification at least one probe, the oligonucleotide sequence of which is one of SEQ ID NOs: 266 and 268, or one of the complementary sequences thereof, or a sequence, which differs by at most 5 nucleotides in length from said SEQ ID or complementary sequence and which is at least 90% identical to said SEQ ID or complementary sequence, said probe being optionally linked to at least one detection label and/or to two complementary nucleotide sequences of 3 to 10 nucleotides, one of said two complementary nucleotide sequences of 3 to 10 nucleotides being linked at the 5' end of said probe, the other of said two complementary nucleotide sequences of 3 to nucleotides being linked at the 3' end of said probe.

31. The HPV detection process of claim 30, wherein said determination of whether at least one amplicon is produced is carried out by using in real-time amplification at least one probe, the sequence of which is one of SEQ ID NOs: 283, 284, 287, 288 and 289, or one of the complementary sequences thereof.

32. The HPV detection of claim 1, wherein the determination of whether at least one amplicon is produced is carried out by using in real-time amplification at least one probe, which is one of SEQ ID NOs: 97-101 or one of the complementary sequences thereof, or a sequence, which differs by at most 5 nucleotides in length from said SEQ ID or complementary sequence and which is at least 90% identical to said SEQ ID sequence, said probe being optionally linked to at least one detection label and/or to two complementary nucleotide sequences of 3 to 10 nucleotides, one of said two complementary nucleotide sequences of 3 to 10 nucleotides being linked at the 5' end of said probe, the other of said two complementary nucleotide sequences of 3 to 10 nucleotides being linked at the 3' end of said probe.

33. The HPV detection of claim 1, wherein the determination of whether at least one amplicon is produced is carried out by using in real-time amplification at least one probe, which is one of SEQ ID NOs: 98, 100 and 101, or one of the complementary sequences thereof, or a sequence, which differs by at most 5 nucleotides in length from said SEQ ID or complementary sequence and which is at least 90% identical to said SEQ ID sequence, said probe being optionally linked to at least one detection label and/or to two complementary nucleotide sequences of 3 to nucleotides, one of said two complementary nucleotide sequences of 3 to 10 nucleotides being linked at the 5' end of said probe, the other of said two complementary nucleotide sequences of 3 to 10 nucleotides being linked at the 3' end of said probe.

34. The HPV detection process of claim 33, wherein the determination of whether at least one amplicon is produced is carried out by using in real-time amplification at least one probe, the sequence of which is one of SEQ ID NOs: 116, 118 and 119-121, or one of the complementary sequences thereof.

35. The HPV detection process of claim 1, wherein said amplification primers further comprise:

at least two primers, the sequences of which are suitable for use as primers in the amplification of at least one nucleic acid of 90-390 nucleotides from the target region consisting of the E6 and E7 genes of HPV56; and/or at least two primers, the sequences of which are suitable for use as primers in the amplification of at least one nucleic acid of 90-240 nucleotides from the target region consisting of the E7 and E1 genes of HPV51.

36. The HPV detection process of claim 1, wherein said amplification primers further comprise:

at least two primers of 14-30 nucleotides, the sequences of which are suitable for use as primers in the amplification of at least one target template sequence, which is a fragment of HPV56, wherein said fragment comprises one of the sequences of SEQ ID NOs: 25-29 and 334-338, or the complementary sequence thereof, or a fragment of said SEQ ID or complementary sequence, wherein said HPV56 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence;

and/or at least two primers of 14-30 nucleotides, the sequences of which are suitable for use as primers in the amplification of at least one target template sequence, which is a fragment of HPV51, wherein said fragment comprises one of the sequences of SEQ ID NOs: 1-5 and 320-333, or the complementary sequence thereof, or a fragment of said SEQ ID or complementary sequence, wherein said HPV51 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence.

37. The HPV detection process of claim 1, wherein said amplification primers further comprise at least one of SEQ ID NOs: 30-34 and at least one of SEQ ID NOs: 35-37.

38. The HPV detection process of claim 1, wherein said amplification primers further comprise at least one of SEQ ID NOs: 6-10 and at least one of SEQ ID NOs: 11-15.

39. The HPV detection process of claim 35, which further comprises the determination of whether at least one amplicon is produced is carried out by using in real-time amplification at least one probe, which is one of SEQ ID NOs: 38-40, or one of the complementary sequences thereof, or a sequence, which differs by at most 5 nucleotides in length from said SEQ ID or complementary sequence and which is at least 90% identical to said SEQ ID or complementary sequence, said probe being optionally linked to at least one detection label and/or to two complementary nucleotide sequences of 3 to 10 nucleotides, one of said two complementary nucleotide sequences of 3 to 10 nucleotides being linked at the 5' end of said probe, the other of said two complementary nucleotide sequences of 3 to 10 nucleotides being linked at the 3' end of said probe.

40. The HPV detection process of claim 35, which further comprises the determination of whether at least one amplicon is produced is carried out by using in real-time amplification at least one probe, the sequence of which is one of SEQ ID NOs: 41-45, or one of the complementary sequences thereof.

41. The HPV detection process of claim 35, which further comprises the determination of whether at least one amplicon is produced is carried out by using in real-time amplification at least one probe, which is one of SEQ ID NOs: 16-19, or one of the complementary sequences thereof, or a sequence, which differs by at most 5 nucleotides in length from said SEQ ID or complementary sequence and which is at least 90% identical to said SEQ ID or complementary sequence, said probe being optionally linked to at least one detection label and/or to two complementary nucleotide sequences of 3 to 10 nucleotides, one of said two complementary nucleotide sequences of 3 to 10 nucleotides being linked at the 5' end of said probe, the other of said two complementary nucleotide sequences of 3 to 10 nucleotides being linked at the 3' end of said probe.

42. The HPV detection process of claim 35, which further comprises the determination of whether at least one amplicon is produced is carried out by using in real-time amplification at least one probe, the sequence of which is one of SEQ ID NOs: 20-24, or one of the complementary sequences thereof.

43. The HPV detection process of claim 1, wherein said at least one HPV, which can be oncogenic for the mucosal epithelia is an oncogenic anogenital HPV or an oncogenic cervical HPV.

44. The HPV detection process of claim 1, wherein said at least one HPV, which can be oncogenic for the mucosal epithelia, is at least one of HPV16, HPV58, HPV33, HPV52, HPV35, HPV31 and HPV67 and/or at least one of HPV18, HPV45, HPV59, HPV85, HPV39 and HPV68.

45. The process of claim 1, wherein said at least one HPV, which can be oncogenic for the mucosal epithelia, is one or several of HPV18, HPV45, HPV16, HPV31 and HPV33.

46. The process of claim 1, wherein said at least one HPV, which can be oncogenic for the mucosal epithelia, is one or several of HPV18, HPV45, HPV59, HPV39, HPV68, HPV16, HPV31, HPV33, HPV35, HPV52 and HPV58.

47. The HPV detection process of claim 35, wherein said at least one HPV, which can be oncogenic for the mucosal epithelia, is:

at least one of HPV16, HPV58, HPV33, HPV52, HPV35, HPV31, HPV67, HPV68, HPV39, HPV85, HPV59, HPV45 and HPV18;

and at least one of HPV56, HPV66, HPV 51.

48. The HPV detection process of claim 35, wherein said at least one HPV, which can be oncogenic for the mucosal epithelia, is:

at least one of HPV16, HPV58, HPV33, HPV52, HPV35, HPV31 and HPV67, and at least one of HPV 68, HPV39, HPV85, HPV59, HPV45 and HPV18, and at least one of HPV51 and HPV82;

or at least one of HPV16, HPV58, HPV33, HPV52, HPV35, HPV31 and HPV67, and at least one of HPV 68, HPV39, HPV85, HPV59, HPV45 and HPV18, and at least one of HPV56 and HPV66;

or at least one of HPV16, HPV58, HPV33, HPV52, HPV35, HPV31 and HPV67, and at least one of HPV 68, HPV39, HPV85, HPV59, HPV45 and HPV18, and at least one of HPV56 and HPV66, and at least one of HPV51 and HPV82.

49. The HPV detection process of claim 1, wherein said amplification is a real-time amplification.

50. The HPV detection process of claim 1, wherein said amplification is a real-time multiplex amplification.

51. The HPV detection process of claim 1, wherein said amplification is a quantitative real-time multiplex amplification.

52. The HPV detection process of claim 1, wherein said amplification is a multiplex amplification.

53. The HPV detection process of claim 1, wherein said amplification is a PCR.

54. The HPV detection process of claim 1, wherein said primers are in the same amplification tube.

55. A set of oligonucleotides, which comprises at least one probe, which is one of SEQ ID NOs: 266 and 268 or the complementary sequence thereof, or a sequence, which differs by at most 5 nucleotides in length from said SEQ ID or complementary sequence and which is at least 90% identical to said SEQ ID or complementary sequence, said probe being optionally linked to least one detection label and/or each of the 5' and 3' ends of said probe being optionally directly linked to an oligonucleotide of 3-10 nucleotides, said 5' oligonucleotide and said 3' end oligonucleotide imparting a hairpin structure to said probe when said probe is unhybridized; and/or at least one probe, which is one of SEQ ID NOs: 98, 100 and 101 or the complementary sequence thereof, or a sequence, which differs by at most 5 nucleotides in length from said SEQ ID or complementary sequence and which is at least 90% identical to said SEQ ID or complementary sequence, said probe being optionally linked to least one detection label and/or each of the 5' and 3' ends of said probe being optionally directly linked to an oligonucleotide of 3-10 nucleotides, said 5' oligonucleotide and said 3' end oligonucleotide imparting a hairpin structure to said probe when said probe is unhybridized;

and which further comprises at least two primers of 14-30 nucleotides, the sequences of which are suitable for annealing to HPV16 at such positions that they target on HPV16 at least one HPV16 fragment, which comprises the sequence of SEQ ID NO: 122 or the complementary sequence thereof or a fragment of said sequence of SEQ ID NO: 122 or complementary sequence, wherein said HPV16 fragment differs by at most 5 nucleotides in length from said sequence of SEQ ID NO: 122 or complementary sequence, wherein said at least two primers of 14-30 nucleotides anneal to the 5' terminal end of said at least one HPV16 fragment and to the 5' terminal end of the sequence that is complementary to said at least one HPV16 fragment, and/or at least two primers of 14-30 nucleotides, the sequences of which are suitable for annealing to HPV18 at such positions that they target on HPV18 at least one HPV18 fragment, which comprises at least one of the sequences of SEQ ID NOs: 64-67 or at least one of the complementary sequences thereof or a fragment of said at least one SEQ ID or complementary sequence, wherein said HPV18 fragment differs by at most 5 nucleotides in length from said at least one SEQ ID or complementary sequence, wherein said at least two primers of 14-30 nucleotides anneal to the 5' terminal end of said at least one HPV18 fragment and to the 5' terminal end of the sequence that is complementary to said at least one HPV18 fragment.

56. A set of oligonucleotides, which comprises more than two primers of 14-30 nucleotides, the sequences of which are suitable for annealing to HPV16 at such positions that they target on HPV16 at least one HPV16 fragment, which comprises the sequence of SEQ ID NO: 122 or the complementary sequence thereof or a fragment of said sequence of SEQ ID NO: 122 or complementary sequence, wherein said HPV16 fragment differs by at most 5 nucleotides in length from said sequence of SEQ ID NO: 122 or complementary sequence, wherein said more than two primers of 14-30 nucleotides anneal to the 5' terminal end of said at least one HPV16 fragment and to the 5' terminal end of the sequence that is complementary to said at least one HPV16 fragment and wherein said more than two primers are suitable for use as primers in the amplification of at least one nucleic acid of 80-260 nucleotides from the target region consisting of the E1 and E2 genes from each of the following HPV: HPV16, HPV33 and HPV31.

57. The set of claim 56, wherein said more than two primers are suitable for use as primers in the amplification of at least one nucleic acid of 80-260 nucleotides from the target region consisting of the E1 and E2 genes from each of the following HPV: HPV16, HPV58, HPV33, HPV52, HPV35 and HPV31.

58. The set of claim 56, wherein said more than two primers are suitable for use as primers in the amplification of at least one nucleic acid of 80-260 nucleotides from the target region consisting of the E1 and E2 genes of HPV16, HPV58, HPV33, HPV52, HPV35, HPV31 and HPV67.

59. The set of claim 56, wherein said fragment differs by at most 4 nucleotides or at most 3 nucleotides or at most 2 nucleotides or at most 1 nucleotide in length from said SEQ ID or complementary sequence.

60. A set of oligonucleotides, which comprises more than two primers of 14-30 nucleotides, the sequences of which are suitable for annealing to HPV18 at such positions that they target on HPV18 at least one HPV18 fragment, which comprises at least one of the sequences of SEQ ID NOs: 64-67 or at least one of the complementary sequences thereof or at least one fragment of said SEQ ID or complementary sequence, wherein said HPV18 fragment differs by at most 5 nucleotides in length from said at least one SEQ ID or complementary sequence, wherein said more than two primers of 14-30 nucleotides anneal to the 5' terminal end of said at least one HPV18 fragment and to the 5' terminal end of the sequence that is complementary to said at least one HPV18 fragment and wherein said more than two primers are suitable for use as primers in the amplification of at least one nucleic acid of 100-220 nucleotides from the target region consisting of the E1 gene from each of the following HPV: HPV45 and HPV18.

61. The set of claim 60, wherein said more than two primers are suitable for use as primers in the amplification of at least one nucleic acid of 100-220 nucleotides from the target region consisting of the E1 gene from each of the following HPV: HPV68, HPV39, HPV59, HPV45 and HPV18.

62. The set of claim 60, wherein said more than two primers are suitable for use as primers in the amplification of at least one nucleic acid of 100-220 nucleotides from the target region consisting of the E1 gene from each of the following HPV: HPV68, HPV39, HPV59, HPV45, HPV18 and HPV85.

63. The set of claim 60, wherein said fragment differs by at most 4 nucleotides or at most 3 nucleotides or at most 2 nucleotides or at most 1 nucleotide in length from said SEQ ID or complementary sequence.

64. A set of oligonucleotides, which comprises primers of 14-30 nucleotides, the sequences of which are suitable for annealing to HPV18 at such positions that they target on HPV18 at least one HPV18 fragment from two different groups among the following four groups i. to iv.:

i. the group of the HPV18 fragments, which comprise the sequence of SEQ ID NO: 64 or the complementary sequence thereof or a fragment of said SEQ ID or complementary sequence, wherein said HPV18 fragments differ by at most 5 nucleotides in length from said SEQ ID or complementary sequence;

ii. the group of the HPV18 fragments, which comprise the sequence of SEQ ID NO: 65 or the complementary sequence thereof or a fragment of said SEQ ID or complementary sequence, wherein said HPV18 fragments differ by at most 5 nucleotides in length from said SEQ ID or complementary sequence;

iii. the group of the HPV18 fragments, which comprise the sequence of SEQ ID NO: 66 or the complementary sequence thereof or a fragment of said SEQ ID or complementary sequence, wherein said HPV18 fragments differ by at most 5 nucleotides in length from said SEQ ID or complementary sequence;

iv. the group of the HPV18 fragments, which comprise the sequence of SEQ ID NO: 67 or the complementary sequence thereof or a fragment of said SEQ ID or complementary sequence, wherein said HPV18 fragments differ by at most 5 nucleotides in length from said SEQ ID or complementary sequence, wherein said primers of 14-30 nucleotides anneal to the 5' terminal end of said at least one HPV18 fragment and to the 5' terminal end of the sequence that is complementary to said at least one HPV18 fragment.

65. The set of claim 64, wherein said fragment differs by at most 4 nucleotides or at most 3 nucleotides or at most 2 nucleotides or at most 1 nucleotide in length from said SEQ ID or complementary sequence.

66. A kit for the diagnosis or prognosis of a cervical neoplasia or cancer, comprising:

at least one oligonucleotide set of claim 55, and/or at least one oligonucleotide set of claim 56 or 60 or 64, optionally, instructions for the use thereof and/or nucleotides.

67. A set of polynucleotides, which comprises:

at least one polynucleotide, the sequence of which consists of the sequence of SEQ ID NO: 122 or the complementary sequence thereof, or of a sequence, which differs by at most 5 nucleotides in length from said SEQ ID or complementary sequence and which is at least 80% identical to said SEQ ID or complementary sequence; and/or at least one polynucleotide, the sequence of which consists of one the sequences of SEQ ID NOs: 64-67 or the complementary sequence thereof, or of a sequence, which differs by at most 5 nucleotides in length from said SEQ ID or complementary sequence and which is at least 80% identical to said SEQ ID or complementary sequence.

68. A set of polynucleotides, which comprises at least two, at least three or at least four polynucleotides, the respective sequences of which consist of one the sequences of SEQ ID NOs: 64-67 or the complementary sequence thereof, or of a sequence, which differs by at most 5 nucleotides in length from said SEQ ID or complementary sequence and which is at least 80% identical to said SEQ ID or complementary sequence.

69. A process of production of HPV primers, which comprises producing at least two oligonucleotides, the respective sequences of which consist of 14-30 nucleotides each and are suitable for use as primers in the amplification of at least one target template sequence, wherein said at least one reference template sequence is a HPV16 fragment comprising the sequence of SEQ ID NO: 122 or the complementary sequence thereof or a fragment of said sequence of SEQ ID NO: 122 or complementary sequence, wherein said HPV16 fragment differs by at most 5 nucleotides in length from said sequence of SEQ ID NO: 122 or complementary sequence, wherein said each of said at least two primers anneal to the 5' terminal end of said at least one target template sequence or to the 5' terminal end of the sequence that is complementary to said at least one target template sequence, wherein said at least two primers anneal to at least two HPVs selected from the group consisting of HPV16, HPV31, HPV33, HPV35, HPV52, HPV58 and HPV67.

70. The process of claim 69, wherein said at least two primers anneal to at least HPV16, HPV31 and HPV33.

71. A process of production of HPV primers, which comprises producing at least two oligonucleotides, the respective sequences of which consist of 14-30 nucleotides each and are suitable for use as primers in the amplification of at least one target template sequence, wherein said at least one reference template sequence is at least one HPV18 fragment comprising one of the sequences of SEQ ID NOs: 64-67 or the complementary sequence thereof or a fragment of said SEQ ID or complementary sequence, wherein said fragment differs by at most 5 nucleotides in length from said SEQ ID or complementary sequence, wherein said each of said at least two primers anneal to the 5' terminal end of said at least one target template sequence or to the 5' terminal end of the sequence that is complementary to said at least one target template sequence, wherein said at least two primers anneal to at least two HPVs selected from the group consisting of HPV18, HPV45, HPV59, HPV39, HPV68 and HPV85.

72. The process of claim 71, wherein said at least two primers anneal to at least HPV18 and HPV45.

73. The process of claim 1, wherein said amplification primers comprise primers of 14-30 nucleotides, the sequences of which are suitable for use as primers in the amplification of at least four target template sequences, which are HPV18 fragments selected from each one of the following four groups i. to iv.:

i. the HPV18 fragments, which comprise the sequence of SEQ ID NO: 64 or the complementary sequence thereof or a fragment of said sequence of SEQ ID NO: 64 or complementary sequence, wherein said HPV18 fragments differ by at most 5 nucleotides in length from said sequence of SEQ ID NO: 64 or complementary sequence, ii. the HPV18 fragments, which comprise the sequence of SEQ ID NO: 65 or the complementary sequence thereof or a fragment of said sequence of SEQ ID NO: 65 or complementary sequence, wherein said HPV18 fragments differ by at most 5 nucleotides in length from said sequence of SEQ ID NO: 65 or complementary sequence, iii. the HPV18 fragments, which comprise the sequence of SEQ ID NO: 66 or the complementary sequence thereof or a fragment of said sequence of SEQ ID NO: 66 or complementary sequence, wherein said HPV18 fragments differ by at most 5 nucleotides in length from said sequence of SEQ ID NO: 66 or complementary sequence, iv. the HPV18 fragments, which comprise the sequence of SEQ ID NO: 67 or the complementary sequence thereof or a fragment of said sequence of SEQ ID NO: 67 or complementary sequence, wherein said HPV18 fragments differ by at most 5 nucleotides in length from said sequence of SEQ ID NO: 67 or complementary sequence, wherein each one of said at least four target template sequences and of the sequences that are complementary to said at least four target template sequences is annealed at its 5' terminal end by the sequence of at least one of said primers of 14-30 nucleotides.

74. The HPV detection process of claim 1, wherein said amplification primers further comprise primers annealing to HPV56 and/or primers annealing to HPV51.

75. The HPV detection process of claim 1, wherein said amplification primers further comprise:

at least two primers of 14-30 nucleotides, the sequences of which are suitable for use as primers in the amplification of at least one target template sequence, which is a fragment of HPV56, wherein said fragment comprises the sequence of SEQ ID NO: 26, or the complementary sequence thereof, or a fragment of said SEQ ID or complementary sequence, wherein said HPV56 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence;

and/or at least two primers of 14-30 nucleotides, the sequences of which are suitable for use as primers in the amplification of at least one target template sequence, which is a fragment of HPV51, wherein said fragment comprises the sequence of SEQ ID NO: 5, or the complementary sequence thereof, or a fragment of said SEQ ID or complementary sequence, wherein said HPV51 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence.

76. The HPV detection process of claim 1, wherein said amplification primers further comprise at least one of SEQ ID NO: 31 and at least one of SEQ ID NO: 35, and/or further comprise at least one of SEQ ID NO: 10 and at least one of SEQ ID NO: 15.

77. The HPV detection process of claim 1, which further comprises the determination of whether at least one amplicon is produced is carried out by using in real-time amplification at least one probe, which is one of SEQ ID NOs: 19 and 38, or one of the complementary sequences thereof, or a sequence, which differs by at most 5 nucleotides in length from said SEQ ID or complementary sequence and which is at least 90% identical to said SEQ ID or complementary sequence, said probe being optionally linked to at least one detection label and/or to two complementary nucleotide sequences of 3 to 10 nucleotides, one of said two complementary nucleotide sequences of 3 to 10 nucleotides being linked at the 5' end of said probe, the other of said two complementary nucleotide sequences of 3 to 10 nucleotides being linked at the 3' end of said probe.

78. The set of claim 55, which comprises at least two primer pairs.

79. The set of claim 55, which comprises at least four primer pairs.

80. The set of claim 55, which comprises at least two probes.

81. The set of claim 55, wherein said HPV16 fragment differs by at most 4, or at most 3, or at most 2 nucleotides in length from said at least one SEQ ID or complementary sequence.

82. The set of claim 55, wherein said HPV18 fragment differs by at most 4, or at most 3, or at most 2 nucleotides in length from said at least one SEQ ID or complementary sequence.

83. The set of claim 55, wherein said HPV16 fragment differs by at most 1 nucleotide in length from said at least one SEQ ID or complementary sequence.

84. The set of claim 55, wherein said HPV18 fragment differs by at most 1 nucleotide in length from said at least one SEQ ID or complementary sequence.

85. The set of claim 55, wherein:

the oligonucleotide sequence of one of said at least two primers is at least 80% identical to the sequence of the same length that is the 5' terminal end of said at least one HPV16 fragment, and the oligonucleotide sequence of the other of said at least two primers is at least 80% identical to the sequence of the same length that is the 5' terminal end of the sequence that is complementary to said at least one HPV16 fragment.

86. The set of claim 55, wherein:

the oligonucleotide sequence of one of said at least two primers is at least 85% identical to the sequence of the same length that is the 5' terminal end of said at least one HPV16 fragment, and the oligonucleotide sequence of the other of said at least two primers is at least 85% identical to the sequence of the same length that is the 5' terminal end of the sequence that is complementary to said at least one HPV16 fragment.

87. The set of claim 55, wherein:

the oligonucleotide sequence of one of said at least two primers is at least 100% identical to the sequence of the same length that is the 5' terminal end of said at least one HPV16 fragment, and the oligonucleotide sequence of the other of said at least two primers is at least 100% identical to the sequence of the same length that is the 5' terminal end of the sequence that is complementary to said at least one HPV16 fragment.

88. The set of claim 55, wherein:

the oligonucleotide sequence of one of said at least two primers is at least 80% identical to the sequence of the same length that is the 5' terminal end of said at least one HPV18 fragment, and the oligonucleotide sequence of the other of said at least two primers is at least 80% identical to the sequence of the same length that is the 5' terminal end of the sequence that is complementary to said at least one HPV18 fragment.

89. The set of claim 55, wherein:

the oligonucleotide sequence of one of said at least two primers is at least 85% identical to the sequence of the same length that is the 5' terminal end of said at least one HPV18 fragment, and the oligonucleotide sequence of the other of said at least two primers is at least 85% identical to the sequence of the same length that is the 5' terminal end of the sequence that is complementary to said at least one HPV18 fragment.

90. The set of claim 55, wherein said at least two primers are oligonucleotides of 17-25 nucleotides.

91. The set of claim 55, wherein said at least two primers comprise at least one of SEQ ID NOs: 211-217 and at least one of SEQ ID NOs: 240-241.

92. The set of claim 55, wherein said at least two primers comprise the primers of SEQ ID NOs: 240 and 241, and at least three primers selected from the primers of SEQ ID NOs: 211-217.

93. The set of claim 55, wherein said at least two primers comprise at least one of SEQ ID NOs: 77 and 78 and at least one of SEQ ID NOs: 86 and 87.

94. The set of claim 55, wherein said at least two primers comprise the four primers of SEQ ID NOs: 77, 78, 86 and 87.

95. The set of claim 55, which comprises primers, the sequences of which are suitable for annealing to HPV18 and HPV45.

96. The set of claim 55, which comprises primers, the sequences of which are suitable for annealing to HPV16, HPV31 and HPV33.

97. The set of claim 55, which further comprises primers, the sequences of which are suitable for annealing to HPV56 and/or primers, the sequences of which are suitable for annealing to HPV51.

98. The set of claim 55, which further comprises:

at least two primers of 14-30 nucleotides, the sequences of which are suitable for use as primers in the amplification of at least one target template sequence, which is a fragment of HPV56, wherein said fragment comprises the sequence of SEQ ID NO: 26, or the complementary sequence thereof, or a fragment of said SEQ ID or complementary sequence, wherein said HPV56 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence;

and/or at least two primers of 14-30 nucleotides, the sequences of which are suitable for use as primers in the amplification of at least one target template sequence, which is a fragment of HPV51, wherein said fragment comprises the sequence of SEQ ID NO: 5, or the complementary sequence thereof, or a fragment of said SEQ ID or complementary sequence, wherein said HPV51 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence.

99. The set of claim 55, which further comprises primers of SEQ ID NOs: 31 and 35, and/or which further comprises primers of SEQ ID NOs: 10 and 15.

100. The set of claim 55, which further comprises at least one probe, which is one of SEQ ID NOs: 19 and 38, or one of the complementary sequences thereof, or a sequence, which differs by at most 5 nucleotides in length from said SEQ ID or complementary sequence and which is at least 90% identical to said SEQ ID or complementary sequence, said probe being optionally linked to at least one detection label and/or to two complementary nucleotide sequences of 3 to 10 nucleotides, one of said two complementary nucleotide sequences of 3 to 10 nucleotides being linked at the 5' end of said probe, the other of said two complementary nucleotide sequences of 3 to nucleotides being linked at the 3' end of said probe.

101. The set of claim 56, which comprises at least two primer pairs.

102. The set of claim 56, which comprises at least four primer pairs.

103. The set of claim 56, wherein said HPV16 fragment differs by at most 1 nucleotide in length from said at least one SEQ ID or complementary sequence.

104. The set of claim 56, wherein:

the oligonucleotide sequence of at least one of said more than two primers is at least 80% identical to the sequence of the same length that is the 5' terminal end of said at least one HPV16 fragment, and the oligonucleotide sequence of at least another one of said more than two primers is at least 80% identical to the sequence of the same length that is the 5' terminal end of the sequence that is complementary to said at least one HPV16 fragment.

105. The set of claim 56, wherein:

the oligonucleotide sequence of at least one of said more than two primers is at least 85% identical to the sequence of the same length that is the 5' terminal end of said at least one HPV16 fragment, and the oligonucleotide sequence of at least another one of said more than two primers is at least 85% identical to the sequence of the same length that is the 5' terminal end of the sequence that is complementary to said at least one HPV16 fragment.

106. The set of claim 56, wherein:

the oligonucleotide sequence of at least one of said more than two primers is at least 100% identical to the sequence of the same length that is the 5' terminal end of said at least one HPV16 fragment, and the oligonucleotide sequence of at least another one of said more than two primers is at least 100% identical to the sequence of the same length that is the 5' terminal end of the sequence that is complementary to said at least one HPV16 fragment.

107. The set of claim 56, wherein the oligonucleotide sequence of said more than two primers is at least 80% identical to the sequence of the same length that is the 5' terminal end of said at least one HPV16 fragment, or at least 80% identical to the sequence of the same length that is the 5' terminal end of the sequence that is complementary to said at least one HPV16 fragment.

108. The set of claim 56, wherein the oligonucleotide sequence of said more than two primers is at least 85% identical to the sequence of the same length that is the 5' terminal end of said at least one HPV16 fragment, or at least 85% identical to the sequence of the same length that is the 5' terminal end of the sequence that is complementary to said at least one HPV16 fragment.

109. The set of claim 56, wherein said more than two primers are oligonucleotides of 17-25 nucleotides.

110. The set of claim 56, wherein said more than two primers comprise the two primers of SEQ ID NOs: 240 and 241 and at least three primers selected from the primers of SEQ ID NOs: 211-217.

111. The set of claim 56, wherein said more than two primers comprise the primers of SEQ ID NOs: 212, 214, 216, 240 and 241.

112. The set of claim 56, wherein said more than two primers are suitable for annealing to HPV16, HPV31 and HPV33.

113. The set of claim 56, wherein said more than two primers are suitable for annealing to HPV16, HPV31, HPV35, HPV52, HPV33 and HPV58.

114. The set of claim 56, which further comprises primers, the sequences of which are suitable for annealing to HPV18.

115. The set of claim 56, which further comprises primers, the sequences of which are suitable for annealing to HPV18 and HPV45.

116. The set of claim 56, which further comprises at least two primers of 14-30 nucleotides, the sequences of which are suitable for annealing to HPV18 at such positions that they target on HPV18 at least one HPV18 fragment, which comprises at least one of the sequences of SEQ ID NOs: 64-67 or at least one of the complementary sequences thereof or at least one fragment of said SEQ ID or complementary sequence, wherein said HPV18 fragment differs by at most 5 nucleotides in length from said at least one SEQ ID or complementary sequence, wherein said at least two primers of 14-30 nucleotides anneal to the 5' terminal end of said at least one HPV18 fragment and to the 5' terminal end of the sequence that is complementary to said at least one HPV18 fragment.

117. The set of claim 56, which further comprises primers, the sequences of which are suitable for annealing to HPV56 and/or primers, the sequences of which are suitable for annealing to HPV51.

118. The set of claim 56, which further comprises:

at least two primers of 14-30 nucleotides, the sequences of which are suitable for use as primers in the amplification of at least one target template sequence, which is a fragment of HPV56, wherein said fragment comprises the sequence of SEQ ID NO: 26, or the complementary sequence thereof, or a fragment of said SEQ ID or complementary sequence, wherein said HPV56 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence;

and/or at least two primers of 14-30 nucleotides, the sequences of which are suitable for use as primers in the amplification of at least one target template sequence, which is a fragment of HPV51, wherein said fragment comprises the sequence of SEQ ID NO: 5, or the complementary sequence thereof, or a fragment of said SEQ ID or complementary sequence, wherein said HPV51 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence.

119. The set of claim 56, which further comprises primers of SEQ ID NOs: 31 and 35, and/or which further comprises primers of SEQ ID NOs: 10 and 15.

120. The set of claim 56, which further comprises at least one probe, which is one of SEQ ID NOs: 19 and 38, or one of the complementary sequences thereof, or a sequence, which differs by at most 5 nucleotides in length from said SEQ ID or complementary sequence and which is at least 90% identical to said SEQ ID or complementary sequence, said probe being optionally linked to at least one detection label and/or to two complementary nucleotide sequences of 3 to 10 nucleotides, one of said two complementary nucleotide sequences of 3 to 10 nucleotides being linked at the 5' end of said probe, the other of said two complementary nucleotide sequences of 3 to nucleotides being linked at the 3' end of said probe.

121. The set of claim 60, which comprises at least two primer pairs.

122. The set of claim 60, which comprises at least four primer pairs.

123. The set of claim 60, wherein said HPV18 fragment differs by at most 1 nucleotide in length from said at least one SEQ ID or complementary sequence.

124. The set of claim 60, wherein:

the oligonucleotide sequence of at least one of said more than two primers is at least 80% identical to the sequence of the same length that is the 5' terminal end of said at least one HPV18 fragment, and the oligonucleotide sequence of at least another one of said more than two primers is at least 80% identical to the sequence of the same length that is the 5' terminal end of the sequence that is complementary to said at least one HPV18 fragment.

125. The set of claim 60, wherein:

the oligonucleotide sequence of at least one of said more than two primers is at least 85% identical to the sequence of the same length that is the 5' terminal end of said at least one HPV18 fragment, and the oligonucleotide sequence of at least another one of said more than two primers is at least 85% identical to the sequence of the same length that is the 5' terminal end of the sequence that is complementary to said at least one HPV18 fragment.

126. The set of claim 60, wherein the oligonucleotide sequence of said more than two primers is at least 80% identical to the sequence of the same length that is the 5' terminal end of said at least one HPV18 fragment, or at least 80% identical to the sequence of the same length that is the 5' terminal end of the sequence that is complementary to said at least one HPV18 fragment.

127. The set of claim 60, wherein the oligonucleotide sequence of said more than two primers is at least 85% identical to the sequence of the same length that is the 5' terminal end of said at least one HPV18 fragment, or at least 85% identical to the sequence of the same length that is the 5' terminal end of the sequence that is complementary to said at least one HPV18 fragment.

128. The set of claim 60, wherein said more than two primers are oligonucleotides of 17-25 nucleotides.

129. The set of claim 60, wherein said more than two primers comprise the primers of SEQ ID NOs: 77, 78, 86 and 87.

130. The set of claim 60, wherein said more than two primers are suitable for annealing to HPV18 and HPV45.

131. The set of claim 60, wherein said more than two primers are suitable for annealing to HPV18, HPV45, HPV59, HPV39 and HPV68.

132. The set of claim 60, which further comprises primers, the sequences of which are suitable for annealing to HPV16.

133. The set of claim 60, which further comprises primers, the sequences of which are suitable for annealing to HPV16 and HPV31.

134. The set of claim 60, which further comprises primers, the sequences of which are suitable for annealing to HPV16 and HPV33.

135. The set of claim 60, which further comprises primers, the sequences of which are suitable for annealing to HPV16, HPV31 and HPV33.

136. The set of claim 60, which further comprises at least two primers of 14-30 nucleotides, the sequences of which are suitable for annealing to HPV16 at such positions that they target on HPV16 at least one HPV16 fragment, which comprises the sequence of SEQ ID NO: 122 or the complementary sequence thereof or a fragment of said sequence of SEQ ID NO: 122 or complementary sequence, wherein said HPV16 fragment differs by at most 5 nucleotides in length from said sequence of SEQ ID NO: 122 or complementary sequence, wherein said at least two primers of 14-30 nucleotides anneal to the 5' terminal end of said at least one HPV16 fragment and to the 5' terminal end of the sequence that is complementary to said at least one HPV16 fragment.

137. The set of claim 60, which further comprises primers, the sequences of which are suitable for annealing to HPV56 and/or primers, the sequences of which are suitable for annealing to HPV51.

138. The set of claim 60, which further comprises:

at least two primers of 14-30 nucleotides, the sequences of which are suitable for use as primers in the amplification of at least one target template sequence, which is a fragment of HPV56, wherein said fragment comprises the sequence of SEQ ID NO: 26, or the complementary sequence thereof, or a fragment of said SEQ ID or complementary sequence, wherein said HPV56 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence;

and/or at least two primers of 14-30 nucleotides, the sequences of which are suitable for use as primers in the amplification of at least one target template sequence, which is a fragment of HPV51, wherein said fragment comprises the sequence of SEQ ID NO: 5, or the complementary sequence thereof, or a fragment of said SEQ ID or complementary sequence, wherein said HPV51 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence.

139. The set of claim 60, which further comprises primers of SEQ ID NOs: 31 and 35, and/or which further comprises primers of SEQ ID NOs: 10 and 15.

140. The set of claim 60, which further comprises at least one probe, which is one of SEQ ID NOs: 19 and 38, or one of the complementary sequences thereof, or a sequence, which differs by at most 5 nucleotides in length from said SEQ ID or complementary sequence and which is at least 90% identical to said SEQ ID or complementary sequence, said probe being optionally linked to at least one detection label and/or to two complementary nucleotide sequences of 3 to 10 nucleotides, one of said two complementary nucleotide sequences of 3 to 10 nucleotides being linked at the 5' end of said probe, the other of said two complementary nucleotide sequences of 3 to nucleotides being linked at the 3' end of said probe.

141. The set of claim 64, which comprises at least two primer pairs.

142. The set of claim 64, which comprises at least four primer pairs.

143. The set of claim 64, wherein said HPV18 fragment differs by at most 1 nucleotide in length from said at least one SEQ ID or complementary sequence.

144. The set of claim 64, wherein:

the oligonucleotide sequence of at least one of said primers is at least 80% identical to the sequence of the same length that is the 5' terminal end of said at least one HPV18 fragment, and the oligonucleotide sequence of at least one other of said primers is at least 80% identical to the sequence of the same length that is the 5' terminal end of the sequence that is complementary to said at least one HPV18 fragment.

145. The set of claim 64, wherein:

the oligonucleotide sequence of at least one of said primers is at least 85% identical to the sequence of the same length that is the 5' terminal end of said at least one HPV18 fragment, and the oligonucleotide sequence of at least one other of said primers is at least 85% identical to the sequence of the same length that is the 5' terminal end of the sequence that is complementary to said at least one HPV18 fragment.

146. The set of claim 64, wherein said primers are oligonucleotides of 17-nucleotides.

147. The set of claim 64, wherein said primers comprise the primers of SEQ ID NOs: 77, 78, 86 and 87.

148. The set of claim 64, wherein said primers are suitable for annealing to HPV18 and HPV45.

149. The set of claim 64, wherein said primers are suitable for annealing to HPV18, HPV45, HPV59, HPV39 and HPV68.

150. The set of claim 64, which further comprises primers, the sequences of which are suitable for annealing to HPV16.

151. The set of claim 64, which further comprises primers, the sequences of which are suitable for annealing to HPV16 and HPV31.

152. The set of claim 64, which further comprises primers, the sequences of which are suitable for annealing to HPV16 and HPV33.

153. The set of claim 64, which further comprises primers, the sequences of which are suitable for annealing to HPV16, HPV31 and HPV33.

154. The set of claim 64, which further comprises at least two primers of 14-30 nucleotides, the sequences of which are suitable for annealing to HPV16 at such positions that they target on HPV16 at least one HPV16 fragment, which comprises the sequence of SEQ ID NO: 122 or the complementary sequence thereof or a fragment of said sequence of SEQ ID NO: 122 or complementary sequence, wherein said HPV16 fragment differs by at most 5 nucleotides in length from said sequence of SEQ ID NO: 122 or complementary sequence, wherein said at least two primers of 14-30 nucleotides anneal to the 5' terminal end of said at least one HPV16 fragment and to the 5' terminal end of the sequence that is complementary to said at least one HPV16 fragment.

155. The set of claim 64, which further comprises primers, the sequences of which are suitable for annealing to HPV56 and/or primers, the sequences of which are suitable for annealing to HPV51.

156. The set of claim 64, which further comprises:

at least two primers of 14-30 nucleotides, the sequences of which are suitable for use as primers in the amplification of at least one target template sequence, which is a fragment of HPV56, wherein said fragment comprises the sequence of SEQ ID NO: 26, or the complementary sequence thereof, or a fragment of said SEQ ID or complementary sequence, wherein said HPV56 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence;

and/or at least two primers of 14-30 nucleotides, the sequences of which are suitable for use as primers in the amplification of at least one target template sequence, which is a fragment of HPV51, wherein said fragment comprises the sequence of SEQ ID NO: 5, or the complementary sequence thereof, or a fragment of said SEQ ID or complementary sequence, wherein said HPV51 fragment differs by at most 5 nucleotides in length from said SEQ ID or complementary sequence, wherein the sequences of said at least two primers anneal to the 5' terminal end of said at least one target template sequence and to the 5' terminal end of the sequence that is complementary to said at least one target template sequence.

157. The set of claim 64, which further comprises primers of SEQ ID NOs: 31 and 35, and/or which further comprises primers of SEQ ID NOs: 10 and 15.

158. The set of claim 64, which further comprises at least one probe, which is one of SEQ ID NOs: 19 and 38, or one of the complementary sequences thereof, or a sequence, which differs by at most 5 nucleotides in length from said SEQ ID or complementary sequence and which is at least 90% identical to said SEQ ID or complementary sequence, said probe being optionally linked to at least one detection label and/or to two complementary nucleotide sequences of 3 to 10 nucleotides, one of said two complementary nucleotide sequences of 3 to 10 nucleotides being linked at the 5' end of said probe, the other of said two complementary nucleotide sequences of 3 to nucleotides being linked at the 3' end of said probe.

159. A kit for the diagnosis or prognosis of cervical neoplasia or cancer, comprising:

at least one oligonucleotide set of claim 103, optionally, instructions for the use thereof and/or nucleotides.

160. A kit for the diagnosis or prognosis of cervical neoplasia or cancer, comprising:

at least one oligonucleotide set of claim 104, optionally, instructions for the use thereof and/or nucleotides.

161. A kit for the diagnosis or prognosis of cervical neoplasia or cancer, comprising:

at least one oligonucleotide set of claim 110, optionally, instructions for the use thereof and/or nucleotides.

162. A kit for the diagnosis or prognosis of cervical neoplasia or cancer, comprising:

at least one oligonucleotide set of claim 111, optionally, instructions for the use thereof and/or nucleotides.

163. A kit for the diagnosis or prognosis of cervical neoplasia or cancer, comprising:

at least one oligonucleotide set of claim 112, optionally, instructions for the use thereof and/or nucleotides.

164. A kit for the diagnosis or prognosis of cervical neoplasia or cancer, comprising:

at least one oligonucleotide set of claim 113, optionally, instructions for the use thereof and/or nucleotides.

165. A kit for the diagnosis or prognosis of cervical neoplasia or cancer, comprising:

at least one oligonucleotide set of claim 114, optionally, instructions for the use thereof and/or nucleotides.

166. A kit for the diagnosis or prognosis of cervical neoplasia or cancer, comprising:

at least one oligonucleotide set of claim 117, optionally, instructions for the use thereof and/or nucleotides.

167. A kit for the diagnosis or prognosis of cervical neoplasia or cancer, comprising:

at least one oligonucleotide set of claim 123, optionally, instructions for the use thereof and/or nucleotides.

168. A kit for the diagnosis or prognosis of cervical neoplasia or cancer, comprising:

at least one oligonucleotide set of claim 124, optionally, instructions for the use thereof and/or nucleotides.

169. A kit for the diagnosis or prognosis of cervical neoplasia or cancer, comprising:

at least one oligonucleotide set of claim 129, optionally, instructions for the use thereof and/or nucleotides.

170. A kit for the diagnosis or prognosis of cervical neoplasia or cancer, comprising:

at least one oligonucleotide set of claim 130, optionally, instructions for the use thereof and/or nucleotides.

171. A kit for the diagnosis or prognosis of cervical neoplasia or cancer, comprising:

at least one oligonucleotide set of claim 131, optionally, instructions for the use thereof and/or nucleotides.

172. A kit for the diagnosis or prognosis of cervical neoplasia or cancer, comprising:

at least one oligonucleotide set of claim 132, optionally, instructions for the use thereof and/or nucleotides.

173. A kit for the diagnosis or prognosis of cervical neoplasia or cancer, comprising:

at least one oligonucleotide set of claim 137, optionally, instructions for the use thereof and/or nucleotides.

174. A kit for the diagnosis or prognosis of cervical neoplasia or cancer, comprising:

at least one oligonucleotide set of claim 143, optionally, instructions for the use thereof and/or nucleotides.

175. A kit for the diagnosis or prognosis of cervical neoplasia or cancer, comprising:

at least one oligonucleotide set of claim 144, optionally, instructions for the use thereof and/or nucleotides.

176. A kit for the diagnosis or prognosis of cervical neoplasia or cancer, comprising:

at least one oligonucleotide set of claim 148, optionally, instructions for the use thereof and/or nucleotides.

177. A kit for the diagnosis or prognosis of cervical neoplasia or cancer, comprising:

at least one oligonucleotide set of claim 149, optionally, instructions for the use thereof and/or nucleotides.

178. A set of polynucleotides, which comprises:

at least one polynucleotide, the sequence of which consists of the sequence of SEQ ID NO: 122 or the complementary sequence thereof, or of a sequence, which differs by at most 5 nucleotides in length from said SEQ ID or complementary sequence and which is at least 80% identical to said SEQ ID or complementary sequence; and at least one polynucleotide, the sequence of which consists of the sequence of SEQ ID NO: 64 or the complementary sequence thereof, or of a sequence, which differs by at most 5 nucleotides in length from said SEQ ID or complementary sequence and which is at least 80% identical to said SEQ ID or complementary sequence.

179. A set of polynucleotides, which comprises:

at least one polynucleotide, the sequence of which consists of the sequence of SEQ ID NO: 122 or the complementary sequence thereof, or of a sequence, which differs by at most 5 nucleotides in length from said SEQ ID or complementary sequence and which is at least 80% identical to said SEQ ID or complementary sequence; and at least one polynucleotide, the sequence of which consists of the sequence of SEQ ID NO: 65 or the complementary sequence thereof, or of a sequence, which differs by at most 5 nucleotides in length from said SEQ ID or complementary sequence and which is at least 80% identical to said SEQ ID or complementary sequence.

180. A set of polynucleotides, which comprises:

at least one polynucleotide, the sequence of which consists of the sequence of SEQ ID NO: 122 or the complementary sequence thereof, or of a sequence, which differs by at most 5 nucleotides in length from said SEQ ID or complementary sequence and which is at least 80% identical to said SEQ ID or complementary sequence; and at least one polynucleotide, the sequence of which consists of the sequence of SEQ ID NO: 66 or the complementary sequence thereof, or of a sequence, which differs by at most 5 nucleotides in length from said SEQ ID or complementary sequence and which is at least 80% identical to said SEQ ID or complementary sequence.

181. A set of polynucleotides, which comprises:

at least one polynucleotide, the sequence of which consists of the sequence of SEQ ID NO: 122 or the complementary sequence thereof, or of a sequence, which differs by at most 5 nucleotides in length from said SEQ ID or complementary sequence and which is at least 80% identical to said SEQ ID or complementary sequence; and at least one polynucleotide, the sequence of which consists of the sequence of SEQ ID NO: 67 or the complementary sequence thereof, or of a sequence, which differs by at most 5 nucleotides in length from said SEQ ID or complementary sequence and which is at least 80% identical to said SEQ ID or complementary sequence.

182. The process of claim 69, wherein said at least two primers anneal to HPV16, HPV31, HPV33, HPV35, HPV52 and HPV58.

183. The process of claim 69, wherein said at least two primers anneal to HPV16, HPV31, HPV33, HPV35, HPV52, HPV58 and HPV67.

184. The process of claim 69, which comprises producing at least two primer pairs.

185. The process of claim 69, which comprises producing at least four primer pairs.

186. The process of claim 69, wherein said HPV16 fragment differs by at most 4, or at most 3, or at most 2 nucleotides in length from said at least one SEQ ID or complementary sequence.

187. The process of claim 69, wherein said HPV16 fragment differs by at most 1 nucleotide in length from said at least one SEQ ID or complementary sequence.

188. The process of claim 69, wherein:

the oligonucleotide sequence of one of said at least two primers is at least 80% identical to the sequence of the same length that is the 5' terminal end of said at least one HPV16 fragment, and the oligonucleotide sequence of the other of said at least two primers is at least 80% identical to the sequence of the same length that is the 5' terminal end of the sequence that is complementary to said at least one HPV16 fragment.

189. The process of claim 69, wherein:

the oligonucleotide sequence of one of said at least two primers is at least 85% identical to the sequence of the same length that is the 5' terminal end of said at least one HPV16 fragment, and the oligonucleotide sequence of the other of said at least two primers is at least 85% identical to the sequence of the same length that is the 5' terminal end of the sequence that is complementary to said at least one HPV16 fragment.

190. The process of claim 69, wherein:

the oligonucleotide sequence of one of said at least two primers is at least 100% identical to the sequence of the same length that is the 5' terminal end of said at least one HPV16 fragment, and the oligonucleotide sequence of the other of said at least two primers is at least 100% identical to the sequence of the same length that is the 5' terminal end of the sequence that is complementary to said at least one HPV16 fragment.

191. The process of claim 69, wherein said at least two primers are oligonucleotides of 17-25 nucleotides.

192. The process of claim 71, wherein said at least two primers anneal to HPV18, HPV45, HPV59, HPV39 and HPV68.

193. The process of claim 71, wherein said at least two primers anneal to HPV18, HPV45, HPV59, HPV39, HPV68 and HPV85.

194. The process of claim 71, which comprises producing at least two primer pairs.

195. The process of claim 71, which comprises producing at least four primer pairs.

196. The process of claim 71, wherein said HPV16 fragment differs by at most 4, or at most 3, or at most 2 nucleotides in length from said at least one SEQ ID or complementary sequence.

197. The process of claim 71, wherein said HPV16 fragment differs by at most 1 nucleotide in length from said at least one SEQ ID or complementary sequence.

198. The process of claim 71, wherein:

the oligonucleotide sequence of one of said at least two primers is at least 80% identical to the sequence of the same length that is the 5' terminal end of said at least one HPV18 fragment, and the oligonucleotide sequence of the other of said at least two primers is at least 80% identical to the sequence of the same length that is the 5' terminal end of the sequence that is complementary to said at least one HPV18 fragment.

199. The process of claim 71, wherein:

the oligonucleotide sequence of one of said at least two primers is at least 85% identical to the sequence of the same length that is the 5' terminal end of said at least one HPV18 fragment, and the oligonucleotide sequence of the other of said at least two primers is at least 85% identical to the sequence of the same length that is the 5' terminal end of the sequence that is complementary to said at least one HPV18 fragment.

200. The process of claim 71, wherein said at least two primers are oligonucleotides of 17-25 nucleotides.

* * * * *

SEQUENCE LISTING

<160> NUMBER OF SEQ ID NOS: 452

<210> SEQ ID NO 1
<211> LENGTH: 106
<212> TYPE: DNA
<213> ORGANISM: Human papillomavirus

<400> SEQUENCE: 1
ggcagtggaa agcagtggag acacccttcg cgttgtacag cagatgttaa tgggcgaact 60
aagcctggtt tgcccgtgtt gtgcgaacaa ctagcaacgg cgatgg 106

<210> SEQ ID NO 2
<211> LENGTH: 145
<212> TYPE: DNA
<213> ORGANISM: Human papillomavirus

<400> SEQUENCE: 2
agctccgtgt tgcaggtgtt caagtgtagt acaactggca gtggaaagca gtggagacac 60
ccttcgcgtt gtacagcaga tgttaatggg cgaactaagc ctggtttgcc cgtgttgtgc 120
gaacaactag caacggcgat ggact 145

-continued

<210> SEQ ID NO 3
<211> LENGTH: 117
<212> TYPE: DNA
<213> ORGANISM: Human papillomavirus

<400> SEQUENCE: 3
atatgcgtga ccagctacca gaaagacggg ctggacaggc tacgtgttac agaattgaag 60
ctccgtgttg caggtgttca agtgtagtac aactggcagt ggaaagcagt ggagaca 117

<210> SEQ ID NO 4
<211> LENGTH: 192
<212> TYPE: DNA
<213> ORGANISM: Human papillomavirus

<400> SEQUENCE: 4
gacaggctac gtgttacaga attgaagctc cgtgttgcag gtgttcaagt gtagtacaac 60
tggcagtgga aagcagtgga gacacccttc gcgttgtaca gcagatgtta atgggcgaac 120
taagcctggt ttgcccgtgt tgtgcgaaca actagcaacg gcgatggact gtgaaggtac 180
agaggatgag gg 192

<210> SEQ ID NO 5
<211> LENGTH: 125
<212> TYPE: DNA
<213> ORGANISM: Human papillomavirus

<400> SEQUENCE: 5
cgggctggac aggctacgtg ttacagaatt gaagctccgt gttgcaggtg ttcaagtgta 60
gtacaactgg cagtggaaag cagtggagac acccttcgcg ttgtacagca gatgttaatg 120
ggcga 125

<210> SEQ ID NO 6
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 6
ggcagtggaa agcagtggag ac 22

<210> SEQ ID NO 7
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 7
agctccgtgt tgcaggtgtt c 21

<210> SEQ ID NO 8
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 8
atatgcgtga ccagctacca g 21

<210> SEQ ID NO 9

-continued

<211> LENGTH: 21
<212> TYPE: DNA
<213> ORGANISM: Artificial
<220> FEATURE:
<223> OTHER INFORMATION: group-targeted HPV primer or probe

<400> SEQUENCE: 9
gacaggctac gtgttacaga a 21

<210> SEQ ID NO 10
<211> LENGTH: 18
<212> TYPE: DNA
<213> ORGANISM: Artificial
<220> FEATURE:
<223> OTHER INFORMATION: group-targeted HPV primer or probe

<400> SEQUENCE: 10
cgggctggac aggctacg 18

<210> SEQ ID NO 11
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 11
ccatcgccgt tgctagttgt tc 22

<210> SEQ ID NO 12
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 12
agtccatcgc cgttgctagt tg 22

<210> SEQ ID NO 13
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 13
tgtctccact gctttccact g 21

<210> SEQ ID NO 14
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 14
ccctcatcct ctgtaccttc 20

<210> SEQ ID NO 15
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 15
tcgcccatta acatctgctg t 21

<210> SEQ ID NO 16
<211> LENGTH: 27
<212> TYPE: DNA
<213> ORGANISM: Artificial
<220> FEATURE:
<223> OTHER INFORMATION: group-targeted HPV primer or probe

<400> SEQUENCE: 16
gcttagttcg cccattaaca tctgctg 27

<210> SEQ ID NO 17
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 17
cgaagggtgt ctccactgct ttcca 25

<210> SEQ ID NO 18
<211> LENGTH: 26
<212> TYPE: DNA
<213> ORGANISM: Artificial
<220> FEATURE:
<223> OTHER INFORMATION: group-targeted HPV primer or probe

<400> SEQUENCE: 18
acacggagct tcaattctgt aacacg 26

<210> SEQ ID NO 19
<211> LENGTH: 26
<212> TYPE: DNA
<213> ORGANISM: Artificial
<220> FEATURE:
<223> OTHER INFORMATION: group-targeted HPV primer or probe

<400> SEQUENCE: 19
tagtacaact ggcagtggaa agcagt 26

<210> SEQ ID NO 20
<211> LENGTH: 41
<212> TYPE: DNA
<213> ORGANISM: Artificial
<220> FEATURE:
<223> OTHER INFORMATION: group-targeted HPV primer or probe

<400> SEQUENCE: 20
ccccctcgct tagttcgccc attaacatct gctggagggg g 41

<210> SEQ ID NO 21
<211> LENGTH: 39
<212> TYPE: DNA
<213> ORGANISM: Artificial
<220> FEATURE:
<223> OTHER INFORMATION: group-targeted HPV primer or probe

<400> SEQUENCE: 21
cgctgcgctt agttcgccca ttaacatctg ctggcagcg 39

<210> SEQ ID NO 22
<211> LENGTH: 39
<212> TYPE: DNA
<213> ORGANISM: Artificial
<220> FEATURE:

<223> OTHER INFORMATION: group-targeted HPV primer or probe

<400> SEQUENCE: 22
cgcgatccga agggtgtctc cactgctttc cagatcgcg 39

<210> SEQ ID NO 23
<211> LENGTH: 40
<212> TYPE: DNA
<213> ORGANISM: Artificial
<220> FEATURE:
<223> OTHER INFORMATION: group-targeted HPV primer or probe

<400> SEQUENCE: 23
cgcgatcaca cggagcttca attctgtaac acggatcgcg 40

<210> SEQ ID NO 24
<211> LENGTH: 40
<212> TYPE: DNA
<213> ORGANISM: Artificial
<220> FEATURE:
<223> OTHER INFORMATION: group-targeted HPV primer or probe

<400> SEQUENCE: 24
cgcgatctag tacaactggc agtggaaagc agtgatcgcg 40

<210> SEQ ID NO 25
<211> LENGTH: 100
<212> TYPE: DNA
<213> ORGANISM: Human papillomavirus

<400> SEQUENCE: 25
tggaccgggt catgtttggg gtgctggaga caaacatcta gagaacctag agaatctaca 60
gtataatcat gcatggtaaa gtaccaacgc tgcaagacgt 100

<210> SEQ ID NO 26
<211> LENGTH: 115
<212> TYPE: DNA
<213> ORGANISM: Human papillomavirus

<400> SEQUENCE: 26
ctaatagcac atggttggac cgggtcatgt ttggggtgct ggagacaaac atctagagaa 60
cctagagaat ctacagtata atcatgcatg gtaaagtacc aacgctgcaa gacgt 115

<210> SEQ ID NO 27
<211> LENGTH: 138
<212> TYPE: DNA
<213> ORGANISM: Human papillomavirus

<400> SEQUENCE: 27
aaggtgctac agatgtcaaa gtccgttaac tccggaggaa aagcaattgc attgtgacag 60
aaaaagacga tttcatctaa tagcacatgg ttggaccggg tcatgtttgg ggtgctggag 120
acaaacatct agagaacc 138

<210> SEQ ID NO 28
<211> LENGTH: 102
<212> TYPE: DNA
<213> ORGANISM: Human papillomavirus

<400> SEQUENCE: 28
gttggaccgg gtcatgtttg gggtgctgga gacaaacatc tagagaacct agagaatcta 60
cagtataatc atgcatggta aagtaccaac gctgcaagac gt 102

<210> SEQ ID NO 29
<211> LENGTH: 127
<212> TYPE: DNA
<213> ORGANISM: Human papillomavirus

<400> SEQUENCE: 29
tcagaggatg aggatgagga tgaagtagac catttgcagg agcggccaca gcaagctaga 60
caagctaaac aacatacgtg ttacctaata cacgtacctt gttgtgagtg taagtttgtg 120
gtgcagt 127

<210> SEQ ID NO 30
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 30
tggaccgggt catgtttggg 20

<210> SEQ ID NO 31
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 31
ctaatagcac atggttggac cg 22

<210> SEQ ID NO 32
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 32
aaggtgctac agatgtcaaa g 21

<210> SEQ ID NO 33
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 33
gttggaccgg gtcatgtttg g 21

<210> SEQ ID NO 34
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 34
tcagaggatg aggatgagga tg 22

<210> SEQ ID NO 35
<211> LENGTH: 20
<212> TYPE: DNA
<213> ORGANISM: Artificial
<220> FEATURE:

<223> OTHER INFORMATION: group-targeted HPV primer or probe

<400> SEQUENCE: 35
acgtcttgca gcgttggtac 20

<210> SEQ ID NO 36
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 36
ggttctctag atgtttgtct cc 22

<210> SEQ ID NO 37
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 37
actgcaccac aaacttacac tc 22

<210> SEQ ID NO 38
<211> LENGTH: 30
<212> TYPE: DNA
<213> ORGANISM: Artificial
<220> FEATURE:
<223> OTHER INFORMATION: group-targeted HPV primer or probe

<400> SEQUENCE: 38
acatctagag aacctagaga atctacagta 30

<210> SEQ ID NO 39
<211> LENGTH: 26
<212> TYPE: DNA
<213> ORGANISM: Artificial
<220> FEATURE:
<223> OTHER INFORMATION: group-targeted HPV primer or probe

<400> SEQUENCE: 39
ggtccaacca tgtgctatta gatgaa 26

<210> SEQ ID NO 40
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 40
cggccacagc aagctagaca 20

<210> SEQ ID NO 41
<211> LENGTH: 44
<212> TYPE: DNA
<213> ORGANISM: Artificial
<220> FEATURE:
<223> OTHER INFORMATION: group-targeted HPV primer or probe

<400> SEQUENCE: 41
cgcgatcaca tctagagaac ctagagaatc tacagtagat cgcg 44

<210> SEQ ID NO 42

<211> LENGTH: 40
<212> TYPE: DNA
<213> ORGANISM: Artificial
<220> FEATURE:
<223> OTHER INFORMATION: group-targeted HPV primer or probe

<400> SEQUENCE: 42
cgcgatcggt ccaaccatgt gctattagat gaagatcgcg 40

<210> SEQ ID NO 43
<211> LENGTH: 38
<212> TYPE: DNA
<213> ORGANISM: Artificial
<220> FEATURE:
<223> OTHER INFORMATION: group-targeted HPV primer or probe

<400> SEQUENCE: 43
cgcctcggtc caaccatgtg ctattagatg aagaggcg 38

<210> SEQ ID NO 44
<211> LENGTH: 30
<212> TYPE: DNA
<213> ORGANISM: Artificial
<220> FEATURE:
<223> OTHER INFORMATION: group-targeted HPV primer or probe

<400> SEQUENCE: 44
cgcgacggcc acagcaagct agacatcgcg 30

<210> SEQ ID NO 45
<211> LENGTH: 32
<212> TYPE: DNA
<213> ORGANISM: Artificial
<220> FEATURE:
<223> OTHER INFORMATION: group-targeted HPV primer or probe

<400> SEQUENCE: 45
cgcctccggc cacagcaagc tagacagagg cg 32

<210> SEQ ID NO 46
<211> LENGTH: 205
<212> TYPE: DNA
<213> ORGANISM: Human papillomavirus

<400> SEQUENCE: 46
tggtatagaa caggaatatc aaatattagt gaagtaatgg gagacacacc tgagtggata 60
caaagactta ctattataca acatggaata gatgatagca attttgattt gtcagaaatg 120
gtacaatggg catttgataa tgagctgaca gatgaaagcg atatggcatt tgaatatgcc 180
ttattagcag acagcaacag caatg 205

<210> SEQ ID NO 47
<211> LENGTH: 208
<212> TYPE: DNA
<213> ORGANISM: Human papillomavirus

<400> SEQUENCE: 47
tggtatagaa caggaatatc aaatattagt gaagtaatgg gagacacacc tgagtggata 60
caaagactta ctattataca acatggaata gatgatagca attttgattt gtcagaaatg 120
gtacaatggg catttgataa tgagctgaca gatgaaagcg atatggcatt tgaatatgcc 180
ttattagcag acagcaacag caatgcag 208

<210> SEQ ID NO 48

<211> LENGTH: 209
<212> TYPE: DNA
<213> ORGANISM: Human papillomavirus

<400> SEQUENCE: 48
tggtatagaa caggaatatc aaatattagt gaagtaatgg gagacacacc tgagtggata 60
caaagactta ctattataca acatggaata gatgatagca attttgattt gtcagaaatg 120
gtacaatggg catttgataa tgagctgaca gatgaaagcg atatggcatt tgaatatgcc 180
ttattagcag acagcaacag caatgcagc 209

<210> SEQ ID NO 49
<211> LENGTH: 198
<212> TYPE: DNA
<213> ORGANISM: Human papillomavirus

<400> SEQUENCE: 49
gaacaggaat atcaaatatt agtgaagtaa tgggagacac acctgagtgg atacaaagac 60
ttactattat acaacatgga atagatgata gcaattttga tttgtcagaa atggtacaat 120
gggcatttga taatgagctg acagatgaaa gcgatatggc atttgaatat gccttattag 180
cagacagcaa cagcaatg 198

<210> SEQ ID NO 50
<211> LENGTH: 201
<212> TYPE: DNA
<213> ORGANISM: Human papillomavirus

<400> SEQUENCE: 50
gaacaggaat atcaaatatt agtgaagtaa tgggagacac acctgagtgg atacaaagac 60
ttactattat acaacatgga atagatgata gcaattttga tttgtcagaa atggtacaat 120
gggcatttga taatgagctg acagatgaaa gcgatatggc atttgaatat gccttattag 180
cagacagcaa cagcaatgca g 201

<210> SEQ ID NO 51
<211> LENGTH: 202
<212> TYPE: DNA
<213> ORGANISM: Human papillomavirus

<400> SEQUENCE: 51
gaacaggaat atcaaatatt agtgaagtaa tgggagacac acctgagtgg atacaaagac 60
ttactattat acaacatgga atagatgata gcaattttga tttgtcagaa atggtacaat 120
gggcatttga taatgagctg acagatgaaa gcgatatggc atttgaatat gccttattag 180
cagacagcaa cagcaatgca gc 202

<210> SEQ ID NO 52
<211> LENGTH: 168
<212> TYPE: DNA
<213> ORGANISM: Human papillomavirus

<400> SEQUENCE: 52
tggtatagaa caggaatatc aaatattagt gaagtaatgg gagacacacc tgagtggata 60
caaagactta ctattataca acatggaata gatgatagca attttgattt gtcagaaatg 120
gtacaatggg catttgataa tgagctgaca gatgaaagcg atatggca 168

<210> SEQ ID NO 53
<211> LENGTH: 171
<212> TYPE: DNA

<213> ORGANISM: Human papillomavirus

<400> SEQUENCE: 53
tggtatagaa caggaatatc aaatattagt gaagtaatgg gagacacacc tgagtggata 60
caaagactta ctattataca acatggaata gatgatagca attttgattt gtcagaaatg 120
gtacaatggg catttgataa tgagctgaca gatgaaagcg atatggcatt t 171

<210> SEQ ID NO 54
<211> LENGTH: 167
<212> TYPE: DNA
<213> ORGANISM: Human papillomavirus

<400> SEQUENCE: 54
ggtatagaac aggaatatca aatattagtg aagtaatggg agacacacct gagtggatac 60
aaagacttac tattatacaa catggaatag atgatagcaa ttttgatttg tcagaaatgg 120
tacaatgggc atttgataat gagctgacag atgaaagcga tatggca 167

<210> SEQ ID NO 55
<211> LENGTH: 170
<212> TYPE: DNA
<213> ORGANISM: Human papillomavirus

<400> SEQUENCE: 55
ggtatagaac aggaatatca aatattagtg aagtaatggg agacacacct gagtggatac 60
aaagacttac tattatacaa catggaatag atgatagcaa ttttgatttg tcagaaatgg 120
tacaatgggc atttgataat gagctgacag atgaaagcga tatggcattt 170

<210> SEQ ID NO 56
<211> LENGTH: 166
<212> TYPE: DNA
<213> ORGANISM: Human papillomavirus

<400> SEQUENCE: 56
gtatagaaca ggaatatcaa atattagtga agtaatggga gacacacctg agtggataca 60
aagacttact attatacaac atggaataga tgatagcaat tttgatttgt cagaaatggt 120
acaatgggca tttgataatg agctgacaga tgaaagcgat atggca 166

<210> SEQ ID NO 57
<211> LENGTH: 169
<212> TYPE: DNA
<213> ORGANISM: Human papillomavirus

<400> SEQUENCE: 57
gtatagaaca ggaatatcaa atattagtga agtaatggga gacacacctg agtggataca 60
aagacttact attatacaac atggaataga tgatagcaat tttgatttgt cagaaatggt 120
acaatgggca tttgataatg agctgacaga tgaaagcgat atggcattt 169

<210> SEQ ID NO 58
<211> LENGTH: 114
<212> TYPE: DNA
<213> ORGANISM: Human papillomavirus

<400> SEQUENCE: 58
tgatagcaat tttgatttgt cagaaatggt acaatgggca tttgataatg agctgacaga 60
tgaaagcgat atggcatttg aatatgcctt attagcagac agcaacagca atgc 114

<210> SEQ ID NO 59

<211> LENGTH: 117
<212> TYPE: DNA
<213> ORGANISM: Human papillomavirus

<400> SEQUENCE: 59
tgatagcaat tttgatttgt cagaaatggt acaatgggca tttgataatg agctgacaga 60
tgaaagcgat atggcatttg aatatgcctt attagcagac agcaacagca atgcagc 117

<210> SEQ ID NO 60
<211> LENGTH: 113
<212> TYPE: DNA
<213> ORGANISM: Human papillomavirus

<400> SEQUENCE: 60
gatagcaatt ttgatttgtc agaaatggta caatgggcat ttgataatga gctgacagat 60
gaaagcgata tggcatttga atatgcctta ttagcagaca gcaacagcaa tgc 113

<210> SEQ ID NO 61
<211> LENGTH: 116
<212> TYPE: DNA
<213> ORGANISM: Human papillomavirus

<400> SEQUENCE: 61
gatagcaatt ttgatttgtc agaaatggta caatgggcat ttgataatga gctgacagat 60
gaaagcgata tggcatttga atatgcctta ttagcagaca gcaacagcaa tgcagc 116

<210> SEQ ID NO 62
<211> LENGTH: 122
<212> TYPE: DNA
<213> ORGANISM: Human papillomavirus

<400> SEQUENCE: 62
ggaatagatg atagcaattt tgatttgtca gaaatggtac aatgggcatt tgataatgag 60
ctgacagatg aaagcgatat ggcatttgaa tatgccttat tagcagacag caacagcaat 120
gc 122

<210> SEQ ID NO 63
<211> LENGTH: 125
<212> TYPE: DNA
<213> ORGANISM: Human papillomavirus

<400> SEQUENCE: 63
ggaatagatg atagcaattt tgatttgtca gaaatggtac aatgggcatt tgataatgag 60
ctgacagatg aaagcgatat ggcatttgaa tatgccttat tagcagacag caacagcaat 120
gcagc 125

<210> SEQ ID NO 64
<211> LENGTH: 117
<212> TYPE: DNA
<213> ORGANISM: Human papillomavirus

<400> SEQUENCE: 64
ggctgatcca gaaggtacag acggggaggg cacgggttgt aacggctggt tttatgtaca 60
agctattgta gacaaaaaaa caggagatgt aatatcagat gacgaggacg aaaatgc 117

<210> SEQ ID NO 65
<211> LENGTH: 129
<212> TYPE: DNA
<213> ORGANISM: Human papillomavirus

<400> SEQUENCE: 65
ggctgatcca gaaggtacag acggggaggg cacgggttgt aacggctggt tttatgtaca 60
agctattgta gacaaaaaaa caggagatgt aatatcagat gacgaggacg aaaatgcaac 120
agacacagg 129

<210> SEQ ID NO 66
<211> LENGTH: 113
<212> TYPE: DNA
<213> ORGANISM: Human papillomavirus

<400> SEQUENCE: 66
gatccagaag gtacagacgg ggagggcacg ggttgtaacg gctggtttta tgtacaagct 60
attgtagaca aaaaaacagg agatgtaata tcagatgacg aggacgaaaa tgc 113

<210> SEQ ID NO 67
<211> LENGTH: 125
<212> TYPE: DNA
<213> ORGANISM: Human papillomavirus

<400> SEQUENCE: 67
gatccagaag gtacagacgg ggagggcacg ggttgtaacg gctggtttta tgtacaagct 60
attgtagaca aaaaaacagg agatgtaata tcagatgacg aggacgaaaa tgcaacagac 120
acagg 125

<210> SEQ ID NO 68
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 68
tggtatagaa caggaatatc aaat 24

<210> SEQ ID NO 69
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 69
gaacaggtat atccaatatt agtg 24

<210> SEQ ID NO 70
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 70
gaacaggaat gtccaatatt ag 22

<210> SEQ ID NO 71
<211> LENGTH: 26
<212> TYPE: DNA
<213> ORGANISM: Artificial
<220> FEATURE:
<223> OTHER INFORMATION: group-targeted HPV primer or probe

<400> SEQUENCE: 71
tggtatagaa caggaatatc aaatat 26

<210> SEQ ID NO 72
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 72
gtacagaaca ggaatgtcca a 21

<210> SEQ ID NO 73
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 73
ggtatcgcac aggtatatcc 20

<210> SEQ ID NO 74
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 74
tgatagcaat tttgatttgt cag 23

<210> SEQ ID NO 75
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 75
gatagcgtat ttgacctatc ag 22

<210> SEQ ID NO 76
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 76
ggaatagatg atagtgtatt tgatc 25

<210> SEQ ID NO 77
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 77
ggccgatcca gaaggtacag ac 22

<210> SEQ ID NO 78
<211> LENGTH: 21
<212> TYPE: DNA
<213> ORGANISM: Artificial
<220> FEATURE:

<223> OTHER INFORMATION: group-targeted HPV primer or probe

<400> SEQUENCE: 78
caatcgtgaa ggtacagatg g 21

<210> SEQ ID NO 79
<211> LENGTH: 18
<212> TYPE: DNA
<213> ORGANISM: Artificial
<220> FEATURE:
<223> OTHER INFORMATION: group-targeted HPV primer or probe

<400> SEQUENCE: 79
cattgctgtt gcagtctg 18

<210> SEQ ID NO 80
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 80
gcagcattac tgttacaatc 20

<210> SEQ ID NO 81
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 81
cggcgttact attactatct g 21

<210> SEQ ID NO 82
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 82
tgccatatcg ctttcatctg 20

<210> SEQ ID NO 83
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 83
aaatgctata tcactttcat ctg 23

<210> SEQ ID NO 84
<211> LENGTH: 19
<212> TYPE: DNA
<213> ORGANISM: Artificial
<220> FEATURE:
<223> OTHER INFORMATION: group-targeted HPV primer or probe

<400> SEQUENCE: 84
gcattactgt tgctgtctg 19

<210> SEQ ID NO 85

<211> LENGTH: 22
<212> TYPE: DNA
<213> ORGANISM: Artificial
<220> FEATURE:
<223> OTHER INFORMATION: group-targeted HPV primer or probe

<400> SEQUENCE: 85
gcggcattac tattacaatc tg 22

<210> SEQ ID NO 86
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 86
gcattttcat cctcatcctc tg 22

<210> SEQ ID NO 87
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 87
cctgtgtctg ttgcattttc 20

<210> SEQ ID NO 88
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 88
cagatgaaag cgatatggca tt 22

<210> SEQ ID NO 89
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 89
cagatgaaag tgatattgca tat 23

<210> SEQ ID NO 90
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 90
ctgatgaaag tgacatagca ttt 23

<210> SEQ ID NO 91
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 91
cagatgaaag tgatatggca ttt 23

<210> SEQ ID NO 92
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 92
tggaatagat gatagtgtat ttgat 25

<210> SEQ ID NO 93
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 93
gatagcaatt ttgatttgtc aga 23

<210> SEQ ID NO 94
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 94
agttgatgat agcgtgtttg ac 22

<210> SEQ ID NO 95
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 95
cgatagtaat tttgatttgt caga 24

<210> SEQ ID NO 96
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 96
aatgagttaa cagatgaaag tga 23

<210> SEQ ID NO 97
<211> LENGTH: 27
<212> TYPE: DNA
<213> ORGANISM: Artificial
<220> FEATURE:
<223> OTHER INFORMATION: group-targeted HPV primer or probe

<400> SEQUENCE: 97
gtaatggctg gttctttgta gaaacaa 27

<210> SEQ ID NO 98
<211> LENGTH: 27
<212> TYPE: DNA
<213> ORGANISM: Artificial
<220> FEATURE:

<223> OTHER INFORMATION: group-targeted HPV primer or probe

<400> SEQUENCE: 98
gtaacggctg gttttatgta caagcta 27

<210> SEQ ID NO 99
<211> LENGTH: 28
<212> TYPE: DNA
<213> ORGANISM: Artificial
<220> FEATURE:
<223> OTHER INFORMATION: group-targeted HPV primer or probe

<400> SEQUENCE: 99
gtaatggatg gttttttgta caggcaat 28

<210> SEQ ID NO 100
<211> LENGTH: 28
<212> TYPE: DNA
<213> ORGANISM: Artificial
<220> FEATURE:
<223> OTHER INFORMATION: group-targeted HPV primer or probe

<400> SEQUENCE: 100
gtaacggatg gttttttgta caagcaat 28

<210> SEQ ID NO 101
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 101
ggtgtaatgg ctggttcttt gtaga 25

<210> SEQ ID NO 102
<211> LENGTH: 34
<212> TYPE: DNA
<213> ORGANISM: Artificial
<220> FEATURE:
<223> OTHER INFORMATION: group-targeted HPV primer or probe

<400> SEQUENCE: 102
cgacgtcaga tgaaagcgat atggcattac gtcg 34

<210> SEQ ID NO 103
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 103
cgacgtcaga tgaaagtgat attgcatata cgtcg 35

<210> SEQ ID NO 104
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 104
cgacgtctga tgaaagtgac atagcattta cgtcg 35

<210> SEQ ID NO 105

<211> LENGTH: 35
<212> TYPE: DNA
<213> ORGANISM: Artificial
<220> FEATURE:
<223> OTHER INFORMATION: group-targeted HPV primer or probe

<400> SEQUENCE: 105
ccgagtcaga tgaaagtgat atggcattta ctcgg 35

<210> SEQ ID NO 106
<211> LENGTH: 37
<212> TYPE: DNA
<213> ORGANISM: Artificial
<220> FEATURE:
<223> OTHER INFORMATION: group-targeted HPV primer or probe

<400> SEQUENCE: 106
acgtcgtgga atagatgata gtgtatttga tcgacgt 37

<210> SEQ ID NO 107
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 107
cgcagtgata gcaattttga tttgtcagaa ctgcg 35

<210> SEQ ID NO 108
<211> LENGTH: 34
<212> TYPE: DNA
<213> ORGANISM: Artificial
<220> FEATURE:
<223> OTHER INFORMATION: group-targeted HPV primer or probe

<400> SEQUENCE: 108
acgtcgagtt gatgatagcg tgtttgaccg acgt 34

<210> SEQ ID NO 109
<211> LENGTH: 34
<212> TYPE: DNA
<213> ORGANISM: Artificial
<220> FEATURE:
<223> OTHER INFORMATION: group-targeted HPV primer or probe

<400> SEQUENCE: 109
ccggctagtt gatgatagcg tgtttgacag ccgg 34

<210> SEQ ID NO 110
<211> LENGTH: 36
<212> TYPE: DNA
<213> ORGANISM: Artificial
<220> FEATURE:
<223> OTHER INFORMATION: group-targeted HPV primer or probe

<400> SEQUENCE: 110
cgcagtcgat agtaattttg atttgtcaga actgcg 36

<210> SEQ ID NO 111
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 111

-continued cgcagtcaga tgaaagtgat atggcattta ctgcg 35

<210> SEQ ID NO 112
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 112
cgtcgtctga tgaaagtgac atagcattta cgacg 35

<210> SEQ ID NO 113
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 113
cgaggtcaga tgaaagtgat attgcatata cctcg 35

<210> SEQ ID NO 114
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 114
ccacgtaatg agttaacaga tgaaagtgaa cgtgg 35

<210> SEQ ID NO 115
<211> LENGTH: 39
<212> TYPE: DNA
<213> ORGANISM: Artificial
<220> FEATURE:
<223> OTHER INFORMATION: group-targeted HPV primer or probe

<400> SEQUENCE: 115
cgcgacgtaa tggctggttc tttgtagaaa caagtcgcg 39

<210> SEQ ID NO 116
<211> LENGTH: 41
<212> TYPE: DNA
<213> ORGANISM: Artificial
<220> FEATURE:
<223> OTHER INFORMATION: group-targeted HPV primer or probe

<400> SEQUENCE: 116
cgcgatcgta acggctggtt ttatgtacaa gctagatcgc g 41

<210> SEQ ID NO 117
<211> LENGTH: 42
<212> TYPE: DNA
<213> ORGANISM: Artificial
<220> FEATURE:
<223> OTHER INFORMATION: group-targeted HPV primer or probe

<400> SEQUENCE: 117
cgcgatcgta atggatggtt ttttgtacag gcaatgatcg cg 42

<210> SEQ ID NO 118
<211> LENGTH: 40
<212> TYPE: DNA
<213> ORGANISM: Artificial
<220> FEATURE:

<223> OTHER INFORMATION: group-targeted HPV primer or probe

<400> SEQUENCE: 118
cgcgctgtaa cggatggttt tttgtacaag caatagcgcg 40

<210> SEQ ID NO 119
<211> LENGTH: 37
<212> TYPE: DNA
<213> ORGANISM: Artificial
<220> FEATURE:
<223> OTHER INFORMATION: group-targeted HPV primer or probe

<400> SEQUENCE: 119
cgcgatggtg taatggctgg ttctttgtag aatcgcg 37

<210> SEQ ID NO 120
<211> LENGTH: 39
<212> TYPE: DNA
<213> ORGANISM: Artificial
<220> FEATURE:
<223> OTHER INFORMATION: group-targeted HPV primer or probe

<400> SEQUENCE: 120
cgcgatcggt gtaatggctg gttctttgta gagatcgcg 39

<210> SEQ ID NO 121
<211> LENGTH: 39
<212> TYPE: DNA
<213> ORGANISM: Artificial
<220> FEATURE:
<223> OTHER INFORMATION: group-targeted HPV primer or probe

<400> SEQUENCE: 121
ctcgctcggt gtaatggctg gttctttgta gagagcgag 39

<210> SEQ ID NO 122
<211> LENGTH: 88
<212> TYPE: DNA
<213> ORGANISM: Human papillomavirus

<400> SEQUENCE: 122
ggacgtggtc cagattaagt ttgcacgagg acgaggacaa ggaaaacgat ggagactctt 60
tgccaacgtt taaatgtgtg tcaggaca 88

<210> SEQ ID NO 123
<211> LENGTH: 191
<212> TYPE: DNA
<213> ORGANISM: Human papillomavirus

<400> SEQUENCE: 123
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa t 191

<210> SEQ ID NO 124
<211> LENGTH: 194
<212> TYPE: DNA
<213> ORGANISM: Human papillomavirus

<400> SEQUENCE: 124
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa tttt 194

<210> SEQ ID NO 125
<211> LENGTH: 192
<212> TYPE: DNA
<213> ORGANISM: Human papillomavirus

<400> SEQUENCE: 125
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa tt 192

<210> SEQ ID NO 126
<211> LENGTH: 198
<212> TYPE: DNA
<213> ORGANISM: Human papillomavirus

<400> SEQUENCE: 126
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa tttttgtc 198

<210> SEQ ID NO 127
<211> LENGTH: 196
<212> TYPE: DNA
<213> ORGANISM: Human papillomavirus

<400> SEQUENCE: 127
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa tttttg 196

<210> SEQ ID NO 128
<211> LENGTH: 190
<212> TYPE: DNA
<213> ORGANISM: Human papillomavirus

<400> SEQUENCE: 128
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat 190

<210> SEQ ID NO 129
<211> LENGTH: 193
<212> TYPE: DNA
<213> ORGANISM: Human papillomavirus

<400> SEQUENCE: 129
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat ttt 193

<210> SEQ ID NO 130
<211> LENGTH: 191
<212> TYPE: DNA
<213> ORGANISM: Human papillomavirus

<400> SEQUENCE: 130
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat t 191

<210> SEQ ID NO 131
<211> LENGTH: 197
<212> TYPE: DNA
<213> ORGANISM: Human papillomavirus

<400> SEQUENCE: 131
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat ttttgtc 197

<210> SEQ ID NO 132
<211> LENGTH: 195
<212> TYPE: DNA
<213> ORGANISM: Human papillomavirus

<400> SEQUENCE: 132
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat ttttg 195

<210> SEQ ID NO 133
<211> LENGTH: 189
<212> TYPE: DNA
<213> ORGANISM: Human papillomavirus

<400> SEQUENCE: 133
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgacca 189

<210> SEQ ID NO 134
<211> LENGTH: 193
<212> TYPE: DNA
<213> ORGANISM: Human papillomavirus

<400> SEQUENCE: 134
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa ttt 193

<210> SEQ ID NO 135
<211> LENGTH: 191
<212> TYPE: DNA
<213> ORGANISM: Human papillomavirus

<400> SEQUENCE: 135
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa t 191

<210> SEQ ID NO 136
<211> LENGTH: 188
<212> TYPE: DNA
<213> ORGANISM: Human papillomavirus

<400> SEQUENCE: 136
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgacca 188

<210> SEQ ID NO 137
<211> LENGTH: 192
<212> TYPE: DNA
<213> ORGANISM: Human papillomavirus

<400> SEQUENCE: 137
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat tt 192

<210> SEQ ID NO 138
<211> LENGTH: 190
<212> TYPE: DNA
<213> ORGANISM: Human papillomavirus

<400> SEQUENCE: 138
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat 190

<210> SEQ ID NO 139
<211> LENGTH: 182
<212> TYPE: DNA
<213> ORGANISM: Human papillomavirus

<400> SEQUENCE: 139
actacaccca tagtacattt aaaaggtgat gctaatactt taaaatgttt aagatataga 60

```
tttaaaaagc attgtacatt gtatactgca gtgtcgtcta catggcattg gacaggacat    120

aatgtaaaac ataaaagtgc aattgttaca cttacatatg atagtgaatg gcaacgtgac    180

ca                                                                    182
```

<210> SEQ ID NO 140
<211> LENGTH: 186
<212> TYPE: DNA
<213> ORGANISM: Human papillomavirus

<400> SEQUENCE: 140

```
actacaccca tagtacattt aaaaggtgat gctaatactt taaaatgttt aagatataga     60

tttaaaaagc attgtacatt gtatactgca gtgtcgtcta catggcattg gacaggacat    120

aatgtaaaac ataaaagtgc aattgttaca cttacatatg atagtgaatg gcaacgtgac    180

caattt                                                                186
```

<210> SEQ ID NO 141
<211> LENGTH: 184
<212> TYPE: DNA
<213> ORGANISM: Human papillomavirus

<400> SEQUENCE: 141

```
actacaccca tagtacattt aaaaggtgat gctaatactt taaaatgttt aagatataga     60

tttaaaaagc attgtacatt gtatactgca gtgtcgtcta catggcattg gacaggacat    120

aatgtaaaac ataaaagtgc aattgttaca cttacatatg atagtgaatg gcaacgtgac    180

caat                                                                  184
```

<210> SEQ ID NO 142
<211> LENGTH: 179
<212> TYPE: DNA
<213> ORGANISM: Human papillomavirus

<400> SEQUENCE: 142

```
acacccatag tacatttaaa aggtgatgct aatactttaa aatgtttaag atatagattt     60

aaaaagcatt gtacattgta tactgcagtg tcgtctacat ggcattggac aggacataat    120

gtaaaacata aaagtgcaat tgttacactt acatatgata gtgaatggca acgtgacca     179
```

<210> SEQ ID NO 143
<211> LENGTH: 183
<212> TYPE: DNA
<213> ORGANISM: Human papillomavirus

<400> SEQUENCE: 143

```
acacccatag tacatttaaa aggtgatgct aatactttaa aatgtttaag atatagattt     60

aaaaagcatt gtacattgta tactgcagtg tcgtctacat ggcattggac aggacataat    120

gtaaaacata aaagtgcaat tgttacactt acatatgata gtgaatggca acgtgaccaa    180

ttt                                                                   183
```

<210> SEQ ID NO 144
<211> LENGTH: 181
<212> TYPE: DNA
<213> ORGANISM: Human papillomavirus

<400> SEQUENCE: 144

```
acacccatag tacatttaaa aggtgatgct aatactttaa aatgtttaag atatagattt     60

aaaaagcatt gtacattgta tactgcagtg tcgtctacat ggcattggac aggacataat    120
```

```
gtaaaacata aaagtgcaat tgttacactt acatatgata gtgaatggca acgtgaccaa    180

t                                                                    181


<210> SEQ ID NO 145
<211> LENGTH: 180
<212> TYPE: DNA
<213> ORGANISM: Human papillomavirus

<400> SEQUENCE: 145

tacacccata gtacatttaa aaggtgatgc taatacttta aaatgtttaa gatatagatt     60

taaaaagcat tgtacattgt atactgcagt gtcgtctaca tggcattgga caggacataa    120

tgtaaaacat aaaagtgcaa ttgttacact tacatatgat agtgaatggc aacgtgacca    180


<210> SEQ ID NO 146
<211> LENGTH: 184
<212> TYPE: DNA
<213> ORGANISM: Human papillomavirus

<400> SEQUENCE: 146

tacacccata gtacatttaa aaggtgatgc taatacttta aaatgtttaa gatatagatt     60

taaaaagcat tgtacattgt atactgcagt gtcgtctaca tggcattgga caggacataa    120

tgtaaaacat aaaagtgcaa ttgttacact tacatatgat agtgaatggc aacgtgacca    180

attt                                                                 184


<210> SEQ ID NO 147
<211> LENGTH: 182
<212> TYPE: DNA
<213> ORGANISM: Human papillomavirus

<400> SEQUENCE: 147

tacacccata gtacatttaa aaggtgatgc taatacttta aaatgtttaa gatatagatt     60

taaaaagcat tgtacattgt atactgcagt gtcgtctaca tggcattgga caggacataa    120

tgtaaaacat aaaagtgcaa ttgttacact tacatatgat agtgaatggc aacgtgacca    180

at                                                                   182


<210> SEQ ID NO 148
<211> LENGTH: 163
<212> TYPE: DNA
<213> ORGANISM: Human papillomavirus

<400> SEQUENCE: 148

taaaaggtga tgctaatact ttaaaatgtt taagatatag atttaaaaag cattgtacat     60

tgtatactgc agtgtcgtct acatggcatt ggacaggaca taatgtaaaa cataaaagtg    120

caattgttac acttacatat gatagtgaat ggcaacgtga cca                      163


<210> SEQ ID NO 149
<211> LENGTH: 167
<212> TYPE: DNA
<213> ORGANISM: Human papillomavirus

<400> SEQUENCE: 149

taaaaggtga tgctaatact ttaaaatgtt taagatatag atttaaaaag cattgtacat     60

tgtatactgc agtgtcgtct acatggcatt ggacaggaca taatgtaaaa cataaaagtg    120

caattgttac acttacatat gatagtgaat ggcaacgtga ccaattt                  167


<210> SEQ ID NO 150
```

-continued

<211> LENGTH: 165
<212> TYPE: DNA
<213> ORGANISM: Human papillomavirus

<400> SEQUENCE: 150
taaaaggtga tgctaatact ttaaaatgtt taagatatag atttaaaaag cattgtacat 60
tgtatactgc agtgtcgtct acatggcatt ggacaggaca taatgtaaaa cataaaagtg 120
caattgttac acttacatat gatagtgaat ggcaacgtga ccaat 165

<210> SEQ ID NO 151
<211> LENGTH: 168
<212> TYPE: DNA
<213> ORGANISM: Human papillomavirus

<400> SEQUENCE: 151
acatttaaaa ggtgatgcta atactttaaa atgtttaaga tatagattta aaaagcattg 60
tacattgtat actgcagtgt cgtctacatg gcattggaca ggacataatg taaaacataa 120
aagtgcaatt gttacactta catatgatag tgaatggcaa cgtgacca 168

<210> SEQ ID NO 152
<211> LENGTH: 172
<212> TYPE: DNA
<213> ORGANISM: Human papillomavirus

<400> SEQUENCE: 152
acatttaaaa ggtgatgcta atactttaaa atgtttaaga tatagattta aaaagcattg 60
tacattgtat actgcagtgt cgtctacatg gcattggaca ggacataatg taaaacataa 120
aagtgcaatt gttacactta catatgatag tgaatggcaa cgtgaccaat tt 172

<210> SEQ ID NO 153
<211> LENGTH: 170
<212> TYPE: DNA
<213> ORGANISM: Human papillomavirus

<400> SEQUENCE: 153
acatttaaaa ggtgatgcta atactttaaa atgtttaaga tatagattta aaaagcattg 60
tacattgtat actgcagtgt cgtctacatg gcattggaca ggacataatg taaaacataa 120
aagtgcaatt gttacactta catatgatag tgaatggcaa cgtgaccaat 170

<210> SEQ ID NO 154
<211> LENGTH: 164
<212> TYPE: DNA
<213> ORGANISM: Human papillomavirus

<400> SEQUENCE: 154
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg acca 164

<210> SEQ ID NO 155
<211> LENGTH: 168
<212> TYPE: DNA
<213> ORGANISM: Human papillomavirus

<400> SEQUENCE: 155
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg accaattt 168

<210> SEQ ID NO 156
<211> LENGTH: 166
<212> TYPE: DNA
<213> ORGANISM: Human papillomavirus

<400> SEQUENCE: 156
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg accaat 166

<210> SEQ ID NO 157
<211> LENGTH: 215
<212> TYPE: DNA
<213> ORGANISM: Human papillomavirus

<400> SEQUENCE: 157
taaaaggtga tgctaatact ttaaaatgtt taagatatag atttaaaaag cattgtacat 60
tgtatactgc agtgtcgtct acatggcatt ggacaggaca taatgtaaaa cataaaagtg 120
caattgttac acttacatat gatagtgaat ggcaacgtga ccaatttttg tctcaagtta 180
aaataccaaa aactattaca gtgtctactg gattt 215

<210> SEQ ID NO 158
<211> LENGTH: 206
<212> TYPE: DNA
<213> ORGANISM: Human papillomavirus

<400> SEQUENCE: 158
taaaaggtga tgctaatact ttaaaatgtt taagatatag atttaaaaag cattgtacat 60
tgtatactgc agtgtcgtct acatggcatt ggacaggaca taatgtaaaa cataaaagtg 120
caattgttac acttacatat gatagtgaat ggcaacgtga ccaatttttg tctcaagtta 180
aaataccaaa aactattaca gtgtct 206

<210> SEQ ID NO 159
<211> LENGTH: 205
<212> TYPE: DNA
<213> ORGANISM: Human papillomavirus

<400> SEQUENCE: 159
taaaaggtga tgctaatact ttaaaatgtt taagatatag atttaaaaag cattgtacat 60
tgtatactgc agtgtcgtct acatggcatt ggacaggaca taatgtaaaa cataaaagtg 120
caattgttac acttacatat gatagtgaat ggcaacgtga ccaatttttg tctcaagtta 180
aaataccaaa aactattaca gtgtc 205

<210> SEQ ID NO 160
<211> LENGTH: 212
<212> TYPE: DNA
<213> ORGANISM: Human papillomavirus

<400> SEQUENCE: 160
taaaaggtga tgctaatact ttaaaatgtt taagatatag atttaaaaag cattgtacat 60
tgtatactgc agtgtcgtct acatggcatt ggacaggaca taatgtaaaa cataaaagtg 120
caattgttac acttacatat gatagtgaat ggcaacgtga ccaatttttg tctcaagtta 180
aaataccaaa aactattaca gtgtctactg ga 212

```
<210> SEQ ID NO 161
<211> LENGTH: 220
<212> TYPE: DNA
<213> ORGANISM: Human papillomavirus

<400> SEQUENCE: 161

acatttaaaa ggtgatgcta atactttaaa atgtttaaga tatagattta aaaagcattg      60

tacattgtat actgcagtgt cgtctacatg gcattggaca ggacataatg taaaacataa     120

aagtgcaatt gttacactta catatgatag tgaatggcaa cgtgaccaat ttttgtctca     180

agttaaaata ccaaaaacta ttacagtgtc tactggattt                           220

<210> SEQ ID NO 162
<211> LENGTH: 211
<212> TYPE: DNA
<213> ORGANISM: Human papillomavirus

<400> SEQUENCE: 162

acatttaaaa ggtgatgcta atactttaaa atgtttaaga tatagattta aaaagcattg      60

tacattgtat actgcagtgt cgtctacatg gcattggaca ggacataatg taaaacataa     120

aagtgcaatt gttacactta catatgatag tgaatggcaa cgtgaccaat ttttgtctca     180

agttaaaata ccaaaaacta ttacagtgtc t                                    211

<210> SEQ ID NO 163
<211> LENGTH: 210
<212> TYPE: DNA
<213> ORGANISM: Human papillomavirus

<400> SEQUENCE: 163

acatttaaaa ggtgatgcta atactttaaa atgtttaaga tatagattta aaaagcattg      60

tacattgtat actgcagtgt cgtctacatg gcattggaca ggacataatg taaaacataa     120

aagtgcaatt gttacactta catatgatag tgaatggcaa cgtgaccaat ttttgtctca     180

agttaaaata ccaaaaacta ttacagtgtc                                      210

<210> SEQ ID NO 164
<211> LENGTH: 217
<212> TYPE: DNA
<213> ORGANISM: Human papillomavirus

<400> SEQUENCE: 164

acatttaaaa ggtgatgcta atactttaaa atgtttaaga tatagattta aaaagcattg      60

tacattgtat actgcagtgt cgtctacatg gcattggaca ggacataatg taaaacataa     120

aagtgcaatt gttacactta catatgatag tgaatggcaa cgtgaccaat ttttgtctca     180

agttaaaata ccaaaaacta ttacagtgtc tactgga                              217

<210> SEQ ID NO 165
<211> LENGTH: 216
<212> TYPE: DNA
<213> ORGANISM: Human papillomavirus

<400> SEQUENCE: 165

ttaaaggtg atgctaatac tttaaaatgt ttaagatata gatttaaaaa gcattgtaca       60

ttgtatactg cagtgtcgtc tacatggcat tggacaggac ataatgtaaa acataaaagt     120

gcaattgtta cacttacata tgatagtgaa tggcaacgtg accaattttt gtctcaagtt     180

aaaataccaa aaactattac agtgtctact ggattt                               216
```

-continued

<210> SEQ ID NO 166
<211> LENGTH: 207
<212> TYPE: DNA
<213> ORGANISM: Human papillomavirus

<400> SEQUENCE: 166
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg accaattttt gtctcaagtt 180
aaaataccaa aaactattac agtgtct 207

<210> SEQ ID NO 167
<211> LENGTH: 206
<212> TYPE: DNA
<213> ORGANISM: Human papillomavirus

<400> SEQUENCE: 167
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg accaattttt gtctcaagtt 180
aaaataccaa aaactattac agtgtc 206

<210> SEQ ID NO 168
<211> LENGTH: 213
<212> TYPE: DNA
<213> ORGANISM: Human papillomavirus

<400> SEQUENCE: 168
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg accaattttt gtctcaagtt 180
aaaataccaa aaactattac agtgtctact gga 213

<210> SEQ ID NO 169
<211> LENGTH: 140
<212> TYPE: DNA
<213> ORGANISM: Human papillomavirus

<400> SEQUENCE: 169
gtcgtctaca tggcattgga caggacataa tgtaaaacat aaaagtgcaa ttgttacact 60
tacatatgat agtgaatggc aacgtgacca atttttgtct caagttaaaa taccaaaaac 120
tattacagtg tctactggat 140

<210> SEQ ID NO 170
<211> LENGTH: 133
<212> TYPE: DNA
<213> ORGANISM: Human papillomavirus

<400> SEQUENCE: 170
gtcgtctaca tggcattgga caggacataa tgtaaaacat aaaagtgcaa ttgttacact 60
tacatatgat agtgaatggc aacgtgacca atttttgtct caagttaaaa taccaaaaac 120
tattacagtg tct 133

<210> SEQ ID NO 171
<211> LENGTH: 132
<212> TYPE: DNA

<213> ORGANISM: Human papillomavirus

<400> SEQUENCE: 171
gtcgtctaca tggcattgga caggacataa tgtaaaacat aaaagtgcaa ttgttacact 60
tacatatgat agtgaatggc aacgtgacca atttttgtct caagttaaaa taccaaaaac 120
tattacagtg tc 132

<210> SEQ ID NO 172
<211> LENGTH: 142
<212> TYPE: DNA
<213> ORGANISM: Human papillomavirus

<400> SEQUENCE: 172
gtcgtctaca tggcattgga caggacataa tgtaaaacat aaaagtgcaa ttgttacact 60
tacatatgat agtgaatggc aacgtgacca atttttgtct caagttaaaa taccaaaaac 120
tattacagtg tctactggat tt 142

<210> SEQ ID NO 173
<211> LENGTH: 141
<212> TYPE: DNA
<213> ORGANISM: Human papillomavirus

<400> SEQUENCE: 173
gtcgtctaca tggcattgga caggacataa tgtaaaacat aaaagtgcaa ttgttacact 60
tacatatgat agtgaatggc aacgtgacca atttttgtct caagttaaaa taccaaaaac 120
tattacagtg tctactggat t 141

<210> SEQ ID NO 174
<211> LENGTH: 139
<212> TYPE: DNA
<213> ORGANISM: Human papillomavirus

<400> SEQUENCE: 174
gtcgtctaca tggcattgga caggacataa tgtaaaacat aaaagtgcaa ttgttacact 60
tacatatgat agtgaatggc aacgtgacca atttttgtct caagttaaaa taccaaaaac 120
tattacagtg tctactgga 139

<210> SEQ ID NO 175
<211> LENGTH: 148
<212> TYPE: DNA
<213> ORGANISM: Human papillomavirus

<400> SEQUENCE: 175
actgcagtgt cgtctacatg gcattggaca ggacataatg taaaacataa aagtgcaatt 60
gttacactta catatgatag tgaatggcaa cgtgaccaat ttttgtctca agttaaaata 120
ccaaaaacta ttacagtgtc tactggat 148

<210> SEQ ID NO 176
<211> LENGTH: 141
<212> TYPE: DNA
<213> ORGANISM: Human papillomavirus

<400> SEQUENCE: 176
actgcagtgt cgtctacatg gcattggaca ggacataatg taaaacataa aagtgcaatt 60
gttacactta catatgatag tgaatggcaa cgtgaccaat ttttgtctca agttaaaata 120
ccaaaaacta ttacagtgtc t 141

<210> SEQ ID NO 177
<211> LENGTH: 140
<212> TYPE: DNA
<213> ORGANISM: Human papillomavirus

<400> SEQUENCE: 177
actgcagtgt cgtctacatg gcattggaca ggacataatg taaaacataa aagtgcaatt 60
gttacactta catatgatag tgaatggcaa cgtgaccaat ttttgtctca agttaaaata 120
ccaaaaacta ttacagtgtc 140

<210> SEQ ID NO 178
<211> LENGTH: 150
<212> TYPE: DNA
<213> ORGANISM: Human papillomavirus

<400> SEQUENCE: 178
actgcagtgt cgtctacatg gcattggaca ggacataatg taaaacataa aagtgcaatt 60
gttacactta catatgatag tgaatggcaa cgtgaccaat ttttgtctca agttaaaata 120
ccaaaaacta ttacagtgtc tactggattt 150

<210> SEQ ID NO 179
<211> LENGTH: 149
<212> TYPE: DNA
<213> ORGANISM: Human papillomavirus

<400> SEQUENCE: 179
actgcagtgt cgtctacatg gcattggaca ggacataatg taaaacataa aagtgcaatt 60
gttacactta catatgatag tgaatggcaa cgtgaccaat ttttgtctca agttaaaata 120
ccaaaaacta ttacagtgtc tactggatt 149

<210> SEQ ID NO 180
<211> LENGTH: 147
<212> TYPE: DNA
<213> ORGANISM: Human papillomavirus

<400> SEQUENCE: 180
actgcagtgt cgtctacatg gcattggaca ggacataatg taaaacataa aagtgcaatt 60
gttacactta catatgatag tgaatggcaa cgtgaccaat ttttgtctca agttaaaata 120
ccaaaaacta ttacagtgtc tactgga 147

<210> SEQ ID NO 181
<211> LENGTH: 146
<212> TYPE: DNA
<213> ORGANISM: Human papillomavirus

<400> SEQUENCE: 181
tgcagtgtcg tctacatggc attggacagg acataatgta aaacataaaa gtgcaattgt 60
tacacttaca tatgatagtg aatggcaacg tgaccaattt ttgtctcaag ttaaaatacc 120
aaaaactatt acagtgtcta ctggat 146

<210> SEQ ID NO 182
<211> LENGTH: 139
<212> TYPE: DNA
<213> ORGANISM: Human papillomavirus

<400> SEQUENCE: 182
tgcagtgtcg tctacatggc attggacagg acataatgta aaacataaaa gtgcaattgt 60

-continued tacacttaca tatgatagtg aatggcaacg tgaccaattt ttgtctcaag ttaaaatacc 120
aaaaactatt acagtgtct 139

<210> SEQ ID NO 183
<211> LENGTH: 138
<212> TYPE: DNA
<213> ORGANISM: Human papillomavirus

<400> SEQUENCE: 183
tgcagtgtcg tctacatggc attggacagg acataatgta aaacataaaa gtgcaattgt 60
tacacttaca tatgatagtg aatggcaacg tgaccaattt ttgtctcaag ttaaaatacc 120
aaaaactatt acagtgtc 138

<210> SEQ ID NO 184
<211> LENGTH: 148
<212> TYPE: DNA
<213> ORGANISM: Human papillomavirus

<400> SEQUENCE: 184
tgcagtgtcg tctacatggc attggacagg acataatgta aaacataaaa gtgcaattgt 60
tacacttaca tatgatagtg aatggcaacg tgaccaattt ttgtctcaag ttaaaatacc 120
aaaaactatt acagtgtcta ctggattt 148

<210> SEQ ID NO 185
<211> LENGTH: 147
<212> TYPE: DNA
<213> ORGANISM: Human papillomavirus

<400> SEQUENCE: 185
tgcagtgtcg tctacatggc attggacagg acataatgta aaacataaaa gtgcaattgt 60
tacacttaca tatgatagtg aatggcaacg tgaccaattt ttgtctcaag ttaaaatacc 120
aaaaactatt acagtgtcta ctggatt 147

<210> SEQ ID NO 186
<211> LENGTH: 145
<212> TYPE: DNA
<213> ORGANISM: Human papillomavirus

<400> SEQUENCE: 186
tgcagtgtcg tctacatggc attggacagg acataatgta aaacataaaa gtgcaattgt 60
tacacttaca tatgatagtg aatggcaacg tgaccaattt ttgtctcaag ttaaaatacc 120
aaaaactatt acagtgtcta ctgga 145

<210> SEQ ID NO 187
<211> LENGTH: 143
<212> TYPE: DNA
<213> ORGANISM: Human papillomavirus

<400> SEQUENCE: 187
agtgtcgtct acatggcatt ggacaggaca taatgtaaaa cataaaagtg caattgttac 60
acttacatat gatagtgaat ggcaacgtga ccaatttttg tctcaagtta aaataccaaa 120
aactattaca gtgtctactg gat 143

<210> SEQ ID NO 188
<211> LENGTH: 136
<212> TYPE: DNA
<213> ORGANISM: Human papillomavirus

<400> SEQUENCE: 188
agtgtcgtct acatggcatt ggacaggaca taatgtaaaa cataaaagtg caattgttac 60
acttacatat gatagtgaat ggcaacgtga ccaatttttg tctcaagtta aaataccaaa 120
aactattaca gtgtct 136

<210> SEQ ID NO 189
<211> LENGTH: 135
<212> TYPE: DNA
<213> ORGANISM: Human papillomavirus

<400> SEQUENCE: 189
agtgtcgtct acatggcatt ggacaggaca taatgtaaaa cataaaagtg caattgttac 60
acttacatat gatagtgaat ggcaacgtga ccaatttttg tctcaagtta aaataccaaa 120
aactattaca gtgtc 135

<210> SEQ ID NO 190
<211> LENGTH: 145
<212> TYPE: DNA
<213> ORGANISM: Human papillomavirus

<400> SEQUENCE: 190
agtgtcgtct acatggcatt ggacaggaca taatgtaaaa cataaaagtg caattgttac 60
acttacatat gatagtgaat ggcaacgtga ccaatttttg tctcaagtta aaataccaaa 120
aactattaca gtgtctactg gattt 145

<210> SEQ ID NO 191
<211> LENGTH: 144
<212> TYPE: DNA
<213> ORGANISM: Human papillomavirus

<400> SEQUENCE: 191
agtgtcgtct acatggcatt ggacaggaca taatgtaaaa cataaaagtg caattgttac 60
acttacatat gatagtgaat ggcaacgtga ccaatttttg tctcaagtta aaataccaaa 120
aactattaca gtgtctactg gatt 144

<210> SEQ ID NO 192
<211> LENGTH: 142
<212> TYPE: DNA
<213> ORGANISM: Human papillomavirus

<400> SEQUENCE: 192
agtgtcgtct acatggcatt ggacaggaca taatgtaaaa cataaaagtg caattgttac 60
acttacatat gatagtgaat ggcaacgtga ccaatttttg tctcaagtta aaataccaaa 120
aactattaca gtgtctactg ga 142

<210> SEQ ID NO 193
<211> LENGTH: 144
<212> TYPE: DNA
<213> ORGANISM: Human papillomavirus

<400> SEQUENCE: 193
cagtgtcgtc tacatggcat tggacaggac ataatgtaaa acataaaagt gcaattgtta 60
cacttacata tgatagtgaa tggcaacgtg accaattttt gtctcaagtt aaaataccaa 120
aaactattac agtgtctact ggat 144

<210> SEQ ID NO 194

<211> LENGTH: 137
<212> TYPE: DNA
<213> ORGANISM: Human papillomavirus

<400> SEQUENCE: 194
cagtgtcgtc tacatggcat tggacaggac ataatgtaaa acataaaagt gcaattgtta 60
cacttacata tgatagtgaa tggcaacgtg accaattttt gtctcaagtt aaaataccaa 120
aaactattac agtgtct 137

<210> SEQ ID NO 195
<211> LENGTH: 136
<212> TYPE: DNA
<213> ORGANISM: Human papillomavirus

<400> SEQUENCE: 195
cagtgtcgtc tacatggcat tggacaggac ataatgtaaa acataaaagt gcaattgtta 60
cacttacata tgatagtgaa tggcaacgtg accaattttt gtctcaagtt aaaataccaa 120
aaactattac agtgtc 136

<210> SEQ ID NO 196
<211> LENGTH: 146
<212> TYPE: DNA
<213> ORGANISM: Human papillomavirus

<400> SEQUENCE: 196
cagtgtcgtc tacatggcat tggacaggac ataatgtaaa acataaaagt gcaattgtta 60
cacttacata tgatagtgaa tggcaacgtg accaattttt gtctcaagtt aaaataccaa 120
aaactattac agtgtctact ggattt 146

<210> SEQ ID NO 197
<211> LENGTH: 145
<212> TYPE: DNA
<213> ORGANISM: Human papillomavirus

<400> SEQUENCE: 197
cagtgtcgtc tacatggcat tggacaggac ataatgtaaa acataaaagt gcaattgtta 60
cacttacata tgatagtgaa tggcaacgtg accaattttt gtctcaagtt aaaataccaa 120
aaactattac agtgtctact ggatt 145

<210> SEQ ID NO 198
<211> LENGTH: 143
<212> TYPE: DNA
<213> ORGANISM: Human papillomavirus

<400> SEQUENCE: 198
cagtgtcgtc tacatggcat tggacaggac ataatgtaaa acataaaagt gcaattgtta 60
cacttacata tgatagtgaa tggcaacgtg accaattttt gtctcaagtt aaaataccaa 120
aaactattac agtgtctact gga 143

<210> SEQ ID NO 199
<211> LENGTH: 141
<212> TYPE: DNA
<213> ORGANISM: Human papillomavirus

<400> SEQUENCE: 199
tgtcgtctac atggcattgg acaggacata atgtaaaaca taaaagtgca attgttacac 60
ttacatatga tagtgaatgg caacgtgacc aatttttgtc tcaagttaaa ataccaaaaa 120
ctattacagt gtctactgga t 141

<210> SEQ ID NO 200
<211> LENGTH: 134
<212> TYPE: DNA
<213> ORGANISM: Human papillomavirus

<400> SEQUENCE: 200
tgtcgtctac atggcattgg acaggacata atgtaaaaca taaaagtgca attgttacac 60
ttacatatga tagtgaatgg caacgtgacc aatttttgtc tcaagttaaa ataccaaaaa 120
ctattacagt gtct 134

<210> SEQ ID NO 201
<211> LENGTH: 133
<212> TYPE: DNA
<213> ORGANISM: Human papillomavirus

<400> SEQUENCE: 201
tgtcgtctac atggcattgg acaggacata atgtaaaaca taaaagtgca attgttacac 60
ttacatatga tagtgaatgg caacgtgacc aatttttgtc tcaagttaaa ataccaaaaa 120
ctattacagt gtc 133

<210> SEQ ID NO 202
<211> LENGTH: 143
<212> TYPE: DNA
<213> ORGANISM: Human papillomavirus

<400> SEQUENCE: 202
tgtcgtctac atggcattgg acaggacata atgtaaaaca taaaagtgca attgttacac 60
ttacatatga tagtgaatgg caacgtgacc aatttttgtc tcaagttaaa ataccaaaaa 120
ctattacagt gtctactgga ttt 143

<210> SEQ ID NO 203
<211> LENGTH: 142
<212> TYPE: DNA
<213> ORGANISM: Human papillomavirus

<400> SEQUENCE: 203
tgtcgtctac atggcattgg acaggacata atgtaaaaca taaaagtgca attgttacac 60
ttacatatga tagtgaatgg caacgtgacc aatttttgtc tcaagttaaa ataccaaaaa 120
ctattacagt gtctactgga tt 142

<210> SEQ ID NO 204
<211> LENGTH: 140
<212> TYPE: DNA
<213> ORGANISM: Human papillomavirus

<400> SEQUENCE: 204
tgtcgtctac atggcattgg acaggacata atgtaaaaca taaaagtgca attgttacac 60
ttacatatga tagtgaatgg caacgtgacc aatttttgtc tcaagttaaa ataccaaaaa 120
ctattacagt gtctactgga 140

<210> SEQ ID NO 205
<211> LENGTH: 142
<212> TYPE: DNA
<213> ORGANISM: Human papillomavirus

<400> SEQUENCE: 205
gtgtcgtcta catggcattg gacaggacat aatgtaaaac ataaaagtgc aattgttaca 60
cttacatatg atagtgaatg gcaacgtgac caatttttgt ctcaagttaa aataccaaaa 120
actattacag tgtctactgg at 142

<210> SEQ ID NO 206
<211> LENGTH: 135
<212> TYPE: DNA
<213> ORGANISM: Human papillomavirus

<400> SEQUENCE: 206
gtgtcgtcta catggcattg gacaggacat aatgtaaaac ataaaagtgc aattgttaca 60
cttacatatg atagtgaatg gcaacgtgac caatttttgt ctcaagttaa aataccaaaa 120
actattacag tgtct 135

<210> SEQ ID NO 207
<211> LENGTH: 134
<212> TYPE: DNA
<213> ORGANISM: Human papillomavirus

<400> SEQUENCE: 207
gtgtcgtcta catggcattg gacaggacat aatgtaaaac ataaaagtgc aattgttaca 60
cttacatatg atagtgaatg gcaacgtgac caatttttgt ctcaagttaa aataccaaaa 120
actattacag tgtc 134

<210> SEQ ID NO 208
<211> LENGTH: 144
<212> TYPE: DNA
<213> ORGANISM: Human papillomavirus

<400> SEQUENCE: 208
gtgtcgtcta catggcattg gacaggacat aatgtaaaac ataaaagtgc aattgttaca 60
cttacatatg atagtgaatg gcaacgtgac caatttttgt ctcaagttaa aataccaaaa 120
actattacag tgtctactgg attt 144

<210> SEQ ID NO 209
<211> LENGTH: 143
<212> TYPE: DNA
<213> ORGANISM: Human papillomavirus

<400> SEQUENCE: 209
gtgtcgtcta catggcattg gacaggacat aatgtaaaac ataaaagtgc aattgttaca 60
cttacatatg atagtgaatg gcaacgtgac caatttttgt ctcaagttaa aataccaaaa 120
actattacag tgtctactgg att 143

<210> SEQ ID NO 210
<211> LENGTH: 141
<212> TYPE: DNA
<213> ORGANISM: Human papillomavirus

<400> SEQUENCE: 210
gtgtcgtcta catggcattg gacaggacat aatgtaaaac ataaaagtgc aattgttaca 60
cttacatatg atagtgaatg gcaacgtgac caatttttgt ctcaagttaa aataccaaaa 120
actattacag tgtctactgg a 141

<210> SEQ ID NO 211
<211> LENGTH: 23
<212> TYPE: DNA

<213> ORGANISM: Artificial
<220> FEATURE:
<223> OTHER INFORMATION: group-targeted HPV primer or probe

<400> SEQUENCE: 211
aggacgtggt ccagattaag ttt 23

<210> SEQ ID NO 212
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 212
aggacgtggt gcagattaag 20

<210> SEQ ID NO 213
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 213
aggacgtggt gcaaattaag ttt 23

<210> SEQ ID NO 214
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 214
aggacgtggt gcagattaaa ttt 23

<210> SEQ ID NO 215
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 215
aggacgtggt gcagattagg ttt 23

<210> SEQ ID NO 216
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 216
aggacgtggt gcaaattaaa ttt 23

<210> SEQ ID NO 217
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 217
aggacgtggt gcaaattagg ttt 23

<210> SEQ ID NO 218
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 218
tagtaacact acacccatag tacat 25

<210> SEQ ID NO 219
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 219
tctaacgttg cacctatcgt g 21

<210> SEQ ID NO 220
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 220
tccttctact gcacctataa taca 24

<210> SEQ ID NO 221
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 221
tagtaccact acacccatag tacat 25

<210> SEQ ID NO 222
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 222
tctaacgttg cacctatcgt gcat 24

<210> SEQ ID NO 223
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 223
tccttctact gcacctataa tacac 25

<210> SEQ ID NO 224
<211> LENGTH: 26
<212> TYPE: DNA
<213> ORGANISM: Artificial
<220> FEATURE:
<223> OTHER INFORMATION: group-targeted HPV primer or probe

<400> SEQUENCE: 224
actacaccta tagtacattt aaaagg 26

<210> SEQ ID NO 225
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 225
gcacctatag tgcatttaaa ag 22

<210> SEQ ID NO 226
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 226
tgcacctata atacacctaa aag 23

<210> SEQ ID NO 227
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 227
taaaaggtga tgctaatact ttaaa 25

<210> SEQ ID NO 228
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 228
taaaaggtga tgcaaataca ttaaa 25

<210> SEQ ID NO 229
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 229
gcatttaaaa ggtgaatcaa atag 24

<210> SEQ ID NO 230
<211> LENGTH: 26
<212> TYPE: DNA
<213> ORGANISM: Artificial
<220> FEATURE:
<223> OTHER INFORMATION: group-targeted HPV primer or probe

<400> SEQUENCE: 230
ctaaaaggtg atcctaatag tttaaa 26

<210> SEQ ID NO 231
<211> LENGTH: 20
<212> TYPE: DNA

<213> ORGANISM: Artificial
<220> FEATURE:
<223> OTHER INFORMATION: group-targeted HPV primer or probe

<400> SEQUENCE: 231
gtcgtctaca tggcattgga 20

<210> SEQ ID NO 232
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 232
caagatgctt catctacatg gag 23

<210> SEQ ID NO 233
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 233
agaagcgtca tctacatgga g 21

<210> SEQ ID NO 234
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 234
agtgtcgtct acatggcatt g 21

<210> SEQ ID NO 235
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 235
atatgtcatc tacatggcat tgg 23

<210> SEQ ID NO 236
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 236
tgtcatccac atggcattgg 20

<210> SEQ ID NO 237
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 237
atgtcatcca catggcattg 20

<210> SEQ ID NO 238
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 238
ttcatctacc tggagttgga c 21

<210> SEQ ID NO 239
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 239
tttcatctac atggagttgg ac 22

<210> SEQ ID NO 240
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 240
tgtcctgaca cacatttaaa cg 22

<210> SEQ ID NO 241
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 241
tgtcctgcac tgcatttaaa c 21

<210> SEQ ID NO 242
<211> LENGTH: 19
<212> TYPE: DNA
<213> ORGANISM: Artificial
<220> FEATURE:
<223> OTHER INFORMATION: group-targeted HPV primer or probe

<400> SEQUENCE: 242
attggtcacg ttgccattc 19

<210> SEQ ID NO 243
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 243
aaaattgttg acgttgtgtt tc 22

<210> SEQ ID NO 244
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 244
aactgttgac gttgtgtttc 20

<210> SEQ ID NO 245
<211> LENGTH: 19
<212> TYPE: DNA
<213> ORGANISM: Artificial
<220> FEATURE:
<223> OTHER INFORMATION: group-targeted HPV primer or probe

<400> SEQUENCE: 245
acatttgtcg ttgcggttc 19

<210> SEQ ID NO 246
<211> LENGTH: 26
<212> TYPE: DNA
<213> ORGANISM: Artificial
<220> FEATURE:
<223> OTHER INFORMATION: group-targeted HPV primer or probe

<400> SEQUENCE: 246
gtctctttgt gatgtactta tatatg 26

<210> SEQ ID NO 247
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 247
ccctttgata ttctgttgtg taag 24

<210> SEQ ID NO 248
<211> LENGTH: 17
<212> TYPE: DNA
<213> ORGANISM: Artificial
<220> FEATURE:
<223> OTHER INFORMATION: group-targeted HPV primer or probe

<400> SEQUENCE: 248
tggtcacgtt gccattc 17

<210> SEQ ID NO 249
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 249
aaaatcgtct ctttgtgatg t 21

<210> SEQ ID NO 250
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 250
aaacatttgt tgttgctgtt c 21

<210> SEQ ID NO 251
<211> LENGTH: 24
<212> TYPE: DNA

<213> ORGANISM: Artificial
<220> FEATURE:
<223> OTHER INFORMATION: group-targeted HPV primer or probe

<400> SEQUENCE: 251
atttatccct ttgatattct gttg 24

<210> SEQ ID NO 252
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 252
aaacagttga cgttgtgttt c 21

<210> SEQ ID NO 253
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 253
aaactgttga cgttgtgttt c 21

<210> SEQ ID NO 254
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 254
aaattgttga cgttgtgttt c 21

<210> SEQ ID NO 255
<211> LENGTH: 19
<212> TYPE: DNA
<213> ORGANISM: Artificial
<220> FEATURE:
<223> OTHER INFORMATION: group-targeted HPV primer or probe

<400> SEQUENCE: 255
acagttgtcg ttgtgtttc 19

<210> SEQ ID NO 256
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 256
aaatcctgta gacactgtaa cagt 24

<210> SEQ ID NO 257
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 257
acttatttgc acagtaggtg gt 22

<210> SEQ ID NO 258
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 258
cttacttgca cagtagttgg ta 22

<210> SEQ ID NO 259
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 259
atcctgttga cactgatact gt 22

<210> SEQ ID NO 260
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 260
tatcctgtag acactgaaac tgtg 24

<210> SEQ ID NO 261
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 261
aaatccagta gacactgtaa tagtt 25

<210> SEQ ID NO 262
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 262
atcctgtaga cactgtaaca gtt 23

<210> SEQ ID NO 263
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 263
cttacttgca cagtaggtgg ta 22

<210> SEQ ID NO 264
<211> LENGTH: 24
<212> TYPE: DNA
<213> ORGANISM: Artificial
<220> FEATURE:
<223> OTHER INFORMATION: group-targeted HPV primer or probe

```
<400> SEQUENCE: 264

tatcctgtag acactgaaac tgtg                                              24

<210> SEQ ID NO 265
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 265

accgtactta tttgcacagt g                                                 21

<210> SEQ ID NO 266
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 266

tccatcgttt tccttgtcct ct                                                22

<210> SEQ ID NO 267
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 267

tccatcgttt tctttgacct ct                                                22

<210> SEQ ID NO 268
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 268

tccatcattt tctttgacct ct                                                22

<210> SEQ ID NO 269
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 269

tctccatcat tttctttgtc ctct                                              24

<210> SEQ ID NO 270
<211> LENGTH: 22
<212> TYPE: DNA
<213> ORGANISM: Artificial
<220> FEATURE:
<223> OTHER INFORMATION: group-targeted HPV primer or probe

<400> SEQUENCE: 270

ctccatcgtt ttctttgtcc tc                                                22

<210> SEQ ID NO 271
<211> LENGTH: 24
<212> TYPE: DNA
```

<213> ORGANISM: Artificial
<220> FEATURE:
<223> OTHER INFORMATION: group-targeted HPV primer or probe

<400> SEQUENCE: 271
ctccatcatt ttctttgacc tctc 24

<210> SEQ ID NO 272
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 272
agtgtcgtct acatggcatt ggac 24

<210> SEQ ID NO 273
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 273
atatgtcatc cacctggcat tggac 25

<210> SEQ ID NO 274
<211> LENGTH: 24
<212> TYPE: DNA
<213> ORGANISM: Artificial
<220> FEATURE:
<223> OTHER INFORMATION: group-targeted HPV primer or probe

<400> SEQUENCE: 274
atatgtcatc cacctggcat tgga 24

<210> SEQ ID NO 275
<211> LENGTH: 25
<212> TYPE: DNA
<213> ORGANISM: Artificial
<220> FEATURE:
<223> OTHER INFORMATION: group-targeted HPV primer or probe

<400> SEQUENCE: 275
atgcttcatc tacatggaga tggac 25

<210> SEQ ID NO 276
<211> LENGTH: 26
<212> TYPE: DNA
<213> ORGANISM: Artificial
<220> FEATURE:
<223> OTHER INFORMATION: group-targeted HPV primer or probe

<400> SEQUENCE: 276
caagtttcat ctacatggca ttggac 26

<210> SEQ ID NO 277
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 277
gatagtgaat ggcaacgtga 20

<210> SEQ ID NO 278
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 278
ataagtacat cacaaagaga cga 23

<210> SEQ ID NO 279
<211> LENGTH: 23
<212> TYPE: DNA
<213> ORGANISM: Artificial
<220> FEATURE:
<223> OTHER INFORMATION: group-targeted HPV primer or probe

<400> SEQUENCE: 279
taactgaaca gcaacaacaa atg 23

<210> SEQ ID NO 280
<211> LENGTH: 27
<212> TYPE: DNA
<213> ORGANISM: Artificial
<220> FEATURE:
<223> OTHER INFORMATION: group-targeted HPV primer or probe

<400> SEQUENCE: 280
cacaacagaa tatcaaaggg ataaatt 27

<210> SEQ ID NO 281
<211> LENGTH: 21
<212> TYPE: DNA
<213> ORGANISM: Artificial
<220> FEATURE:
<223> OTHER INFORMATION: group-targeted HPV primer or probe

<400> SEQUENCE: 281
cgtacagtga tgaaacacaa c 21

<210> SEQ ID NO 282
<211> LENGTH: 20
<212> TYPE: DNA
<213> ORGANISM: Artificial
<220> FEATURE:
<223> OTHER INFORMATION: group-targeted HPV primer or probe

<400> SEQUENCE: 282
aacggaaaca caacgacaac 20

<210> SEQ ID NO 283
<211> LENGTH: 34
<212> TYPE: DNA
<213> ORGANISM: Artificial
<220> FEATURE:
<223> OTHER INFORMATION: group-targeted HPV primer or probe

<400> SEQUENCE: 283
cgcgattcca tcgttttcct tgtcctctat cgcg 34

<210> SEQ ID NO 284
<211> LENGTH: 32
<212> TYPE: DNA
<213> ORGANISM: Artificial
<220> FEATURE:
<223> OTHER INFORMATION: group-targeted HPV primer or probe -continued

<400> SEQUENCE: 284
cgcgatccat cgttttcctt gtcctcttcg cg 32

<210> SEQ ID NO 285
<211> LENGTH: 34
<212> TYPE: DNA
<213> ORGANISM: Artificial
<220> FEATURE:
<223> OTHER INFORMATION: group-targeted HPV primer or probe

<400> SEQUENCE: 285
cgcgattcca tcgttttctt tgacctctat cgcg 34

<210> SEQ ID NO 286
<211> LENGTH: 32
<212> TYPE: DNA
<213> ORGANISM: Artificial
<220> FEATURE:
<223> OTHER INFORMATION: group-targeted HPV primer or probe

<400> SEQUENCE: 286
cgcgatccat cgttttcttt gacctcttcg cg 32

<210> SEQ ID NO 287
<211> LENGTH: 34
<212> TYPE: DNA
<213> ORGANISM: Artificial
<220> FEATURE:
<223> OTHER INFORMATION: group-targeted HPV primer or probe

<400> SEQUENCE: 287
cgcgattcca tcattttctt tgacctctat cgcg 34

<210> SEQ ID NO 288
<211> LENGTH: 32
<212> TYPE: DNA
<213> ORGANISM: Artificial
<220> FEATURE:
<223> OTHER INFORMATION: group-targeted HPV primer or probe

<400> SEQUENCE: 288
cgcgatccat cattttcttt gacctcttcg cg 32

<210> SEQ ID NO 289
<211> LENGTH: 32
<212> TYPE: DNA
<213> ORGANISM: Artificial
<220> FEATURE:
<223> OTHER INFORMATION: group-targeted HPV primer or probe

<400> SEQUENCE: 289
cgctgtccat cattttcttt gacctctcag cg 32

<210> SEQ ID NO 290
<211> LENGTH: 34
<212> TYPE: DNA
<213> ORGANISM: Artificial
<220> FEATURE:
<223> OTHER INFORMATION: group-targeted HPV primer or probe

<400> SEQUENCE: 290
cgcgttctcc atcattttct ttgtcctcta cgcg 34

<210> SEQ ID NO 291
<211> LENGTH: 34
<212> TYPE: DNA

<213> ORGANISM: Artificial
<220> FEATURE:
<223> OTHER INFORMATION: group-targeted HPV primer or probe

<400> SEQUENCE: 291
cgccgtctcc atcattttct ttgtcctctc ggcg 34

<210> SEQ ID NO 292
<211> LENGTH: 36
<212> TYPE: DNA
<213> ORGANISM: Artificial
<220> FEATURE:
<223> OTHER INFORMATION: group-targeted HPV primer or probe

<400> SEQUENCE: 292
cgcgattctc catcattttc tttgtcctct atcgcg 36

<210> SEQ ID NO 293
<211> LENGTH: 34
<212> TYPE: DNA
<213> ORGANISM: Artificial
<220> FEATURE:
<223> OTHER INFORMATION: group-targeted HPV primer or probe

<400> SEQUENCE: 293
cgcgatctcc atcgttttct ttgtcctcat cgcg 34

<210> SEQ ID NO 294
<211> LENGTH: 34
<212> TYPE: DNA
<213> ORGANISM: Artificial
<220> FEATURE:
<223> OTHER INFORMATION: group-targeted HPV primer or probe

<400> SEQUENCE: 294
cgccgctcca tcattttctt tgacctctcc ggcg 34

<210> SEQ ID NO 295
<211> LENGTH: 36
<212> TYPE: DNA
<213> ORGANISM: Artificial
<220> FEATURE:
<223> OTHER INFORMATION: group-targeted HPV primer or probe

<400> SEQUENCE: 295
cgcgatctcc atcattttct ttgacctctc atcgcg 36

<210> SEQ ID NO 296
<211> LENGTH: 34
<212> TYPE: DNA
<213> ORGANISM: Artificial
<220> FEATURE:
<223> OTHER INFORMATION: group-targeted HPV primer or probe

<400> SEQUENCE: 296
cgcgaagtgt cgtctacatg gcattggact cgcg 34

<210> SEQ ID NO 297
<211> LENGTH: 37
<212> TYPE: DNA
<213> ORGANISM: Artificial
<220> FEATURE:
<223> OTHER INFORMATION: group-targeted HPV primer or probe

<400> SEQUENCE: 297
cgctcgatat gtcatccacc tggcattgga ccgagcg 37

<210> SEQ ID NO 298
<211> LENGTH: 37
<212> TYPE: DNA
<213> ORGANISM: Artificial
<220> FEATURE:
<223> OTHER INFORMATION: group-targeted HPV primer or probe

<400> SEQUENCE: 298
cgcatgatat gtcatccacc tggcattgga ccatgcg 37

<210> SEQ ID NO 299
<211> LENGTH: 36
<212> TYPE: DNA
<213> ORGANISM: Artificial
<220> FEATURE:
<223> OTHER INFORMATION: group-targeted HPV primer or probe

<400> SEQUENCE: 299
cgcatgatat gtcatccacc tggcattgga catgcg 36

<210> SEQ ID NO 300
<211> LENGTH: 36
<212> TYPE: DNA
<213> ORGANISM: Artificial
<220> FEATURE:
<223> OTHER INFORMATION: group-targeted HPV primer or probe

<400> SEQUENCE: 300
cgcatgatat gtcatccacc tggcattgga catgcg 36

<210> SEQ ID NO 301
<211> LENGTH: 37
<212> TYPE: DNA
<213> ORGANISM: Artificial
<220> FEATURE:
<223> OTHER INFORMATION: group-targeted HPV primer or probe

<400> SEQUENCE: 301
ccgacgatgc ttcatctaca tggagatgga ccgtcgg 37

<210> SEQ ID NO 302
<211> LENGTH: 38
<212> TYPE: DNA
<213> ORGANISM: Artificial
<220> FEATURE:
<223> OTHER INFORMATION: group-targeted HPV primer or probe

<400> SEQUENCE: 302
cgcgatcaag tttcatctac atggcattgg acatcgcg 38

<210> SEQ ID NO 303
<211> LENGTH: 38
<212> TYPE: DNA
<213> ORGANISM: Artificial
<220> FEATURE:
<223> OTHER INFORMATION: group-targeted HPV primer or probe

<400> SEQUENCE: 303
cgcgagcaag tttcatctac atggcattgg acctcgcg 38

<210> SEQ ID NO 304
<211> LENGTH: 32
<212> TYPE: DNA
<213> ORGANISM: Artificial
<220> FEATURE:
<223> OTHER INFORMATION: group-targeted HPV primer or probe

<400> SEQUENCE: 304
cagcgtgata gtgaatggca acgtgaacgc tg 32

<210> SEQ ID NO 305
<211> LENGTH: 32
<212> TYPE: DNA
<213> ORGANISM: Artificial
<220> FEATURE:
<223> OTHER INFORMATION: group-targeted HPV primer or probe

<400> SEQUENCE: 305
cggactgata gtgaatggca acgtgaagtc cg 32

<210> SEQ ID NO 306
<211> LENGTH: 32
<212> TYPE: DNA
<213> ORGANISM: Artificial
<220> FEATURE:
<223> OTHER INFORMATION: group-targeted HPV primer or probe

<400> SEQUENCE: 306
ctcgctgata gtgaatggca acgtgaagcg ag 32

<210> SEQ ID NO 307
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 307
cgagctataa gtacatcaca aagagacgaa gctcg 35

<210> SEQ ID NO 308
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 308
cgcagtataa gtacatcaca aagagacgaa ctgcg 35

<210> SEQ ID NO 309
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 309
cgcgttataa gtacatcaca aagagacgaa acgcg 35

<210> SEQ ID NO 310
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 310
cgaggttaac tgaacagcaa caacaaatga cctcg 35

<210> SEQ ID NO 311
<211> LENGTH: 35
<212> TYPE: DNA

<213> ORGANISM: Artificial
<220> FEATURE:
<223> OTHER INFORMATION: group-targeted HPV primer or probe

<400> SEQUENCE: 311
cgcgattaac tgaacagcaa caacaaatga tcgcg 35

<210> SEQ ID NO 312
<211> LENGTH: 35
<212> TYPE: DNA
<213> ORGANISM: Artificial
<220> FEATURE:
<223> OTHER INFORMATION: group-targeted HPV primer or probe

<400> SEQUENCE: 312
ccggcttaac tgaacagcaa caacaaatga gccgg 35

<210> SEQ ID NO 313
<211> LENGTH: 39
<212> TYPE: DNA
<213> ORGANISM: Artificial
<220> FEATURE:
<223> OTHER INFORMATION: group-targeted HPV primer or probe

<400> SEQUENCE: 313
cgcgatcaca acagaatatc aaagggataa attatcgcg 39

<210> SEQ ID NO 314
<211> LENGTH: 39
<212> TYPE: DNA
<213> ORGANISM: Artificial
<220> FEATURE:
<223> OTHER INFORMATION: group-targeted HPV primer or probe

<400> SEQUENCE: 314
cgcacgcaca acagaatatc aaagggataa attcgtgcg 39

<210> SEQ ID NO 315
<211> LENGTH: 39
<212> TYPE: DNA
<213> ORGANISM: Artificial
<220> FEATURE:
<223> OTHER INFORMATION: group-targeted HPV primer or probe

<400> SEQUENCE: 315
ccggctcaca acagaatatc aaagggataa attagccgg 39

<210> SEQ ID NO 316
<211> LENGTH: 33
<212> TYPE: DNA
<213> ORGANISM: Artificial
<220> FEATURE:
<223> OTHER INFORMATION: group-targeted HPV primer or probe

<400> SEQUENCE: 316
ccggctcgta cagtgatgaa acacaacagc cgg 33

<210> SEQ ID NO 317
<211> LENGTH: 32
<212> TYPE: DNA
<213> ORGANISM: Artificial
<220> FEATURE:
<223> OTHER INFORMATION: group-targeted HPV primer or probe

<400> SEQUENCE: 317
cgaggtaacg gaaacacaac gacaacacct cg 32

<210> SEQ ID NO 318
<211> LENGTH: 32
<212> TYPE: DNA
<213> ORGANISM: Artificial
<220> FEATURE:
<223> OTHER INFORMATION: group-targeted HPV primer or probe

<400> SEQUENCE: 318
cgcgttaacg gaaacacaac gacaacaacg cg 32

<210> SEQ ID NO 319
<211> LENGTH: 32
<212> TYPE: DNA
<213> ORGANISM: Artificial
<220> FEATURE:
<223> OTHER INFORMATION: group-targeted HPV primer or probe

<400> SEQUENCE: 319
cgatgcaacg gaaacacaac gacaacgcat cg 32

<210> SEQ ID NO 320
<211> LENGTH: 109
<212> TYPE: DNA
<213> ORGANISM: Human papillomavirus

<400> SEQUENCE: 320
ggcagtggaa agcagtggag acacccttcg cgttgtacag cagatgttaa tgggcgaact 60
aagcctggtt tgcccgtgtt gtgcgaacaa ctagcaacgg cgatggact 109

<210> SEQ ID NO 321
<211> LENGTH: 131
<212> TYPE: DNA
<213> ORGANISM: Human papillomavirus

<400> SEQUENCE: 321
ggcagtggaa agcagtggag acacccttcg cgttgtacag cagatgttaa tgggcgaact 60
aagcctggtt tgcccgtgtt gtgcgaacaa ctagcaacgg cgatggactg tgaaggtaca 120
gaggatgagg g 131

<210> SEQ ID NO 322
<211> LENGTH: 142
<212> TYPE: DNA
<213> ORGANISM: Human papillomavirus

<400> SEQUENCE: 322
agctccgtgt tgcaggtgtt caagtgtagt acaactggca gtggaaagca gtggagacac 60
ccttcgcgtt gtacagcaga tgttaatggg cgaactaagc ctggtttgcc cgtgttgtgc 120
gaacaactag caacggcgat gg 142

<210> SEQ ID NO 323
<211> LENGTH: 167
<212> TYPE: DNA
<213> ORGANISM: Human papillomavirus

<400> SEQUENCE: 323
agctccgtgt tgcaggtgtt caagtgtagt acaactggca gtggaaagca gtggagacac 60
ccttcgcgtt gtacagcaga tgttaatggg cgaactaagc ctggtttgcc cgtgttgtgc 120
gaacaactag caacggcgat ggactgtgaa ggtacagagg atgaggg 167

<210> SEQ ID NO 324

<211> LENGTH: 200
<212> TYPE: DNA
<213> ORGANISM: Human papillomavirus

<400> SEQUENCE: 324
atatgcgtga ccagctacca gaaagacggg ctggacaggc tacgtgttac agaattgaag 60
ctccgtgttg caggtgttca agtgtagtac aactggcagt ggaaagcagt ggagacaccc 120
ttcgcgttgt acagcagatg ttaatgggcg aactaagcct ggtttgcccg tgttgtgcga 180
acaactagca acggcgatgg 200

<210> SEQ ID NO 325
<211> LENGTH: 203
<212> TYPE: DNA
<213> ORGANISM: Human papillomavirus

<400> SEQUENCE: 325
atatgcgtga ccagctacca gaaagacggg ctggacaggc tacgtgttac agaattgaag 60
ctccgtgttg caggtgttca agtgtagtac aactggcagt ggaaagcagt ggagacaccc 120
ttcgcgttgt acagcagatg ttaatgggcg aactaagcct ggtttgcccg tgttgtgcga 180
acaactagca acggcgatgg act 203

<210> SEQ ID NO 326
<211> LENGTH: 225
<212> TYPE: DNA
<213> ORGANISM: Human papillomavirus

<400> SEQUENCE: 326
atatgcgtga ccagctacca gaaagacggg ctggacaggc tacgtgttac agaattgaag 60
ctccgtgttg caggtgttca agtgtagtac aactggcagt ggaaagcagt ggagacaccc 120
ttcgcgttgt acagcagatg ttaatgggcg aactaagcct ggtttgcccg tgttgtgcga 180
acaactagca acggcgatgg actgtgaagg tacagaggat gaggg 225

<210> SEQ ID NO 327
<211> LENGTH: 151
<212> TYPE: DNA
<213> ORGANISM: Human papillomavirus

<400> SEQUENCE: 327
atatgcgtga ccagctacca gaaagacggg ctggacaggc tacgtgttac agaattgaag 60
ctccgtgttg caggtgttca agtgtagtac aactggcagt ggaaagcagt ggagacaccc 120
ttcgcgttgt acagcagatg ttaatgggcg a 151

<210> SEQ ID NO 328
<211> LENGTH: 167
<212> TYPE: DNA
<213> ORGANISM: Human papillomavirus

<400> SEQUENCE: 328
gacaggctac gtgttacaga attgaagctc cgtgttgcag gtgttcaagt gtagtacaac 60
tggcagtgga aagcagtgga gacacccttc gcgttgtaca gcagatgtta atgggcgaac 120
taagcctggt ttgcccgtgt tgtgcgaaca actagcaacg gcgatgg 167

<210> SEQ ID NO 329
<211> LENGTH: 170
<212> TYPE: DNA
<213> ORGANISM: Human papillomavirus

<400> SEQUENCE: 329
gacaggctac gtgttacaga attgaagctc cgtgttgcag gtgttcaagt gtagtacaac 60
tggcagtgga aagcagtgga gacacccttc gcgttgtaca gcagatgtta atgggcgaac 120
taagcctggt ttgcccgtgt tgtgcgaaca actagcaacg gcgatggact 170

<210> SEQ ID NO 330
<211> LENGTH: 118
<212> TYPE: DNA
<213> ORGANISM: Human papillomavirus

<400> SEQUENCE: 330
gacaggctac gtgttacaga attgaagctc cgtgttgcag gtgttcaagt gtagtacaac 60
tggcagtgga aagcagtgga gacacccttc gcgttgtaca gcagatgtta atgggcga 118

<210> SEQ ID NO 331
<211> LENGTH: 174
<212> TYPE: DNA
<213> ORGANISM: Human papillomavirus

<400> SEQUENCE: 331
cgggctggac aggctacgtg ttacagaatt gaagctccgt gttgcaggtg ttcaagtgta 60
gtacaactgg cagtggaaag cagtggagac acccttcgcg ttgtacagca gatgttaatg 120
ggcgaactaa gcctggtttg cccgtgttgt gcgaacaact agcaacggcg atgg 174

<210> SEQ ID NO 332
<211> LENGTH: 177
<212> TYPE: DNA
<213> ORGANISM: Human papillomavirus

<400> SEQUENCE: 332
cgggctggac aggctacgtg ttacagaatt gaagctccgt gttgcaggtg ttcaagtgta 60
gtacaactgg cagtggaaag cagtggagac acccttcgcg ttgtacagca gatgttaatg 120
ggcgaactaa gcctggtttg cccgtgttgt gcgaacaact agcaacggcg atggact 177

<210> SEQ ID NO 333
<211> LENGTH: 199
<212> TYPE: DNA
<213> ORGANISM: Human papillomavirus

<400> SEQUENCE: 333
cgggctggac aggctacgtg ttacagaatt gaagctccgt gttgcaggtg ttcaagtgta 60
gtacaactgg cagtggaaag cagtggagac acccttcgcg ttgtacagca gatgttaatg 120
ggcgaactaa gcctggtttg cccgtgttgt gcgaacaact agcaacggcg atggactgtg 180
aaggtacaga ggatgaggg 199

<210> SEQ ID NO 334
<211> LENGTH: 288
<212> TYPE: DNA
<213> ORGANISM: Human papillomavirus

<400> SEQUENCE: 334
tggaccgggt catgtttggg gtgctggaga caaacatcta gagaacctag agaatctaca 60
gtataatcat gcatggtaaa gtaccaacgc tgcaagacgt tgtattagaa ctaacacctc 120
aaacagaaat tgacctacag tgcaatgagc aattggacag ctcagaggat gaggatgagg 180
atgaagtaga ccatttgcag gagcggccac agcaagctag acaagctaaa caacatacgt 240
gttacctaat acacgtacct tgttgtgagt gtaagtttgt ggtgcagt 288

<210> SEQ ID NO 335
<211> LENGTH: 303
<212> TYPE: DNA
<213> ORGANISM: Human papillomavirus

<400> SEQUENCE: 335
ctaatagcac atggttggac cgggtcatgt ttggggtgct ggagacaaac atctagagaa 60
cctagagaat ctacagtata atcatgcatg gtaaagtacc aacgctgcaa gacgttgtat 120
tagaactaac acctcaaaca gaaattgacc tacagtgcaa tgagcaattg gacagctcag 180
aggatgagga tgaggatgaa gtagaccatt tgcaggagcg gccacagcaa gctagacaag 240
ctaaacaaca tacgtgttac ctaatacacg taccttgttg tgagtgtaag tttgtggtgc 300
agt 303

<210> SEQ ID NO 336
<211> LENGTH: 191
<212> TYPE: DNA
<213> ORGANISM: Human papillomavirus

<400> SEQUENCE: 336
aaggtgctac agatgtcaaa gtccgttaac tccggaggaa aagcaattgc attgtgacag 60
aaaaagacga tttcatctaa tagcacatgg ttggaccggg tcatgtttgg ggtgctggag 120
acaaacatct agagaaccta gagaatctac agtataatca tgcatggtaa agtaccaacg 180
ctgcaagacg t 191

<210> SEQ ID NO 337
<211> LENGTH: 379
<212> TYPE: DNA
<213> ORGANISM: Human papillomavirus

<400> SEQUENCE: 337
aaggtgctac agatgtcaaa gtccgttaac tccggaggaa aagcaattgc attgtgacag 60
aaaaagacga tttcatctaa tagcacatgg ttggaccggg tcatgtttgg ggtgctggag 120
acaaacatct agagaaccta gagaatctac agtataatca tgcatggtaa agtaccaacg 180
ctgcaagacg ttgtattaga actaacacct caaacagaaa ttgacctaca gtgcaatgag 240
caattggaca gctcagagga tgaggatgag gatgaagtag accatttgca ggagcggcca 300
cagcaagcta gacaagctaa acaacatacg tgttacctaa tacacgtacc ttgttgtgag 360
tgtaagtttg tggtgcagt 379

<210> SEQ ID NO 338
<211> LENGTH: 290
<212> TYPE: DNA
<213> ORGANISM: Human papillomavirus

<400> SEQUENCE: 338
gttggaccgg gtcatgtttg gggtgctgga gacaaacatc tagagaacct agagaatcta 60
cagtataatc atgcatggta aagtaccaac gctgcaagac gttgtattag aactaacacc 120
tcaaacagaa attgacctac agtgcaatga gcaattggac agctcagagg atgaggatga 180
ggatgaagta gaccatttgc aggagcggcc acagcaagct agacaagcta aacaacatac 240
gtgttaccta atacacgtac cttgttgtga gtgtaagttt gtggtgcagt 290

<210> SEQ ID NO 339

<211> LENGTH: 161
<212> TYPE: DNA
<213> ORGANISM: Human papillomavirus

<400> SEQUENCE: 339
gaacaggaat atcaaatatt agtgaagtaa tgggagacac acctgagtgg atacaaagac 60
ttactattat acaacatgga atagatgata gcaattttga tttgtcagaa atggtacaat 120
gggcatttga taatgagctg acagatgaaa gcgatatggc a 161

<210> SEQ ID NO 340
<211> LENGTH: 164
<212> TYPE: DNA
<213> ORGANISM: Human papillomavirus

<400> SEQUENCE: 340
gaacaggaat atcaaatatt agtgaagtaa tgggagacac acctgagtgg atacaaagac 60
ttactattat acaacatgga atagatgata gcaattttga tttgtcagaa atggtacaat 120
gggcatttga taatgagctg acagatgaaa gcgatatggc attt 164

<210> SEQ ID NO 341
<211> LENGTH: 206
<212> TYPE: DNA
<213> ORGANISM: Human papillomavirus

<400> SEQUENCE: 341
tggtatagaa caggaatatc aaatattagt gaagtaatgg gagacacacc tgagtggata 60
caaagactta ctattataca acatggaata gatgatagca attttgattt gtcagaaatg 120
gtacaatggg catttgataa tgagctgaca gatgaaagcg atatggcatt tgaatatgcc 180
ttattagcag acagcaacag caatgc 206

<210> SEQ ID NO 342
<211> LENGTH: 199
<212> TYPE: DNA
<213> ORGANISM: Human papillomavirus

<400> SEQUENCE: 342
gaacaggaat atcaaatatt agtgaagtaa tgggagacac acctgagtgg atacaaagac 60
ttactattat acaacatgga atagatgata gcaattttga tttgtcagaa atggtacaat 120
gggcatttga taatgagctg acagatgaaa gcgatatggc atttgaatat gccttattag 180
cagacagcaa cagcaatgc 199

<210> SEQ ID NO 343
<211> LENGTH: 203
<212> TYPE: DNA
<213> ORGANISM: Human papillomavirus

<400> SEQUENCE: 343
ggtatagaac aggaatatca aatattagtg aagtaatggg agacacacct gagtggatac 60
aaagacttac tattatacaa catggaatag atgatagcaa ttttgatttg tcagaaatgg 120
tacaatgggc atttgataat gagctacaga tgaaagcgat atggcatttg aatatgcctt 180
attagcagac agcaacagca atg 203

<210> SEQ ID NO 344
<211> LENGTH: 207
<212> TYPE: DNA
<213> ORGANISM: Human papillomavirus

<400> SEQUENCE: 344
ggtatagaac aggaatatca aatattagtg aagtaatggg agacacacct gagtggatac 60
aaagacttac tattatacaa catggaatag atgatagcaa ttttgatttg tcagaaatgg 120
tacaatgggc atttgataat gagctgacag atgaaagcga tatggcattt gaatatgcct 180
tattagcaga cagcaacagc aatgcag 207

<210> SEQ ID NO 345
<211> LENGTH: 208
<212> TYPE: DNA
<213> ORGANISM: Human papillomavirus

<400> SEQUENCE: 345
ggtatagaac aggaatatca aatattagtg aagtaatggg agacacacct gagtggatac 60
aaagacttac tattatacaa catggaatag atgatagcaa ttttgatttg tcagaaatgg 120
tacaatgggc atttgataat gagctgacag atgaaagcga tatggcattt gaatatgcct 180
tattagcaga cagcaacagc aatgcagc 208

<210> SEQ ID NO 346
<211> LENGTH: 203
<212> TYPE: DNA
<213> ORGANISM: Human papillomavirus

<400> SEQUENCE: 346
gtatagaaca ggaatatcaa atattagtga agtaatggga gacacacctg agtggataca 60
aagacttact attatacaac atggaataga tgatagcaat tttgatttgt cagaaatggt 120
acaatgggca tttgataatg agctgacaga tgaaagcgat atggcatttg aatatgcctt 180
attagcagac agcaacagca atg 203

<210> SEQ ID NO 347
<211> LENGTH: 206
<212> TYPE: DNA
<213> ORGANISM: Human papillomavirus

<400> SEQUENCE: 347
gtatagaaca ggaatatcaa atattagtga agtaatggga gacacacctg agtggataca 60
aagacttact attatacaac atggaataga tgatagcaat tttgatttgt cagaaatggt 120
acaatgggca tttgataatg agctgacaga tgaaagcgat atggcatttg aatatgcctt 180
attagcagac agcaacagca atgcag 206

<210> SEQ ID NO 348
<211> LENGTH: 207
<212> TYPE: DNA
<213> ORGANISM: Human papillomavirus

<400> SEQUENCE: 348
gtatagaaca ggaatatcaa atattagtga agtaatggga gacacacctg agtggataca 60
aagacttact attatacaac atggaataga tgatagcaat tttgatttgt cagaaatggt 120
acaatgggca tttgataatg agctgacaga tgaaagcgat atggcatttg aatatgcctt 180
attagcagac agcaacagca atgcagc 207

<210> SEQ ID NO 349
<211> LENGTH: 206
<212> TYPE: DNA
<213> ORGANISM: Human papillomavirus

<400> SEQUENCE: 349
tggtatagaa caggaatatc aaatattagt gaagtaatgg gagacacacc tgagtggata 60
caaagactta ctattataca acatggaata gatgatagca attttgattt gtcagaaatg 120
gtacaatggg catttgataa tgagctgaca gatgaaagcg atatggcatt tgaatatgcc 180
ttattagcag acagcaacag caatgc 206

<210> SEQ ID NO 350
<211> LENGTH: 205
<212> TYPE: DNA
<213> ORGANISM: Human papillomavirus

<400> SEQUENCE: 350
ggtatagaac aggaatatca aatattagtg aagtaatggg agacacacct gagtggatac 60
aaagacttac tattatacaa catggaatag atgatagcaa ttttgatttg tcagaaatgg 120
tacaatgggc atttgataat gagctgacag atgaaagcga tatggcattt gaatatgcct 180
tattagcaga cagcaacagc aatgc 205

<210> SEQ ID NO 351
<211> LENGTH: 204
<212> TYPE: DNA
<213> ORGANISM: Human papillomavirus

<400> SEQUENCE: 351
gtatagaaca ggaatatcaa atattagtga agtaatggga gacacacctg agtggataca 60
aagacttact attatacaac atggaataga tgatagcaat tttgatttgt cagaaatggt 120
acaatgggca tttgataatg agctgacaga tgaaagcgat atggcatttg aatatgcctt 180
attagcagac agcaacagca atgc 204

<210> SEQ ID NO 352
<211> LENGTH: 207
<212> TYPE: DNA
<213> ORGANISM: Human papillomavirus

<400> SEQUENCE: 352
gtatagaaca ggaatatcaa atattagtga agtaatggga gacacacctg agtggataca 60
aagacttact attatacaac atggaataga tgatagcaat tttgatttgt cagaaatggt 120
acaatgggca tttgataatg agctgacaga tgaaagcgat atggcatttg aatatgcctt 180
attagcagac agcaacagca atgcagc 207

<210> SEQ ID NO 353
<211> LENGTH: 121
<212> TYPE: DNA
<213> ORGANISM: Human papillomavirus

<400> SEQUENCE: 353
ggaatagatg atagcaattt tgatttgtca gaaatggtac aatgggcatt tgataatgag 60
ctgacagatg aaagcgatat ggcatttgaa tatgccttat tagcagacag caacagcaat 120
g 121

<210> SEQ ID NO 354
<211> LENGTH: 124
<212> TYPE: DNA
<213> ORGANISM: Human papillomavirus

<400> SEQUENCE: 354
ggaatagatg atagcaattt tgatttgtca gaaatggtac aatgggcatt tgataatgag 60
ctgacagatg aaagcgatat ggcatttgaa tatgccttat tagcagacag caacagcaat 120
gcag 124

<210> SEQ ID NO 355
<211> LENGTH: 113
<212> TYPE: DNA
<213> ORGANISM: Human papillomavirus

<400> SEQUENCE: 355
tgatagcaat tttgatttgt cagaaatggt acaatgggca tttgataatg agctgacaga 60
tgaaagcgat atggcatttg aatatgcctt attagcagac agcaacagca atg 113

<210> SEQ ID NO 356
<211> LENGTH: 116
<212> TYPE: DNA
<213> ORGANISM: Human papillomavirus

<400> SEQUENCE: 356
tgatagcaat tttgatttgt cagaaatggt acaatgggca tttgataatg agctgacaga 60
tgaaagcgat atggcatttg aatatgcctt attagcagac agcaacagca atgcag 116

<210> SEQ ID NO 357
<211> LENGTH: 112
<212> TYPE: DNA
<213> ORGANISM: Human papillomavirus

<400> SEQUENCE: 357
gatagcaatt ttgatttgtc agaaatggta caatgggcat ttgataatga gctgacagat 60
gaaagcgata tggcatttga atatgcctta ttagcagaca gcaacagcaa tg 112

<210> SEQ ID NO 358
<211> LENGTH: 115
<212> TYPE: DNA
<213> ORGANISM: Human papillomavirus

<400> SEQUENCE: 358
gatagcaatt ttgatttgtc agaaatggta caatgggcat ttgataatga gctgacagat 60
gaaagcgata tggcatttga atatgcctta ttagcagaca gcaacagcaa tgcag 115

<210> SEQ ID NO 359
<211> LENGTH: 185
<212> TYPE: DNA
<213> ORGANISM: Human papillomavirus

<400> SEQUENCE: 359
actacaccca tagtacattt aaaaggtgat gctaatactt taaaatgttt aagatataga 60
tttaaaaagc attgtacatt gtatactgca gtgtcgtcta catggcattg gacaggacat 120
aatgtaaaac ataaaagtgc aattgttaca cttacatatg atagtgaatg gcaacgtgac 180
caatt 185

<210> SEQ ID NO 360
<211> LENGTH: 187
<212> TYPE: DNA
<213> ORGANISM: Human papillomavirus

<400> SEQUENCE: 360
actacaccca tagtacattt aaaaggtgat gctaatactt taaaatgttt aagatataga 60
tttaaaaagc attgtacatt gtatactgca gtgtcgtcta catggcattg gacaggacat 120
aatgtaaaac ataaaagtgc aattgttaca cttacatatg atagtgaatg gcaacgtgac 180
caatttt 187

<210> SEQ ID NO 361
<211> LENGTH: 189
<212> TYPE: DNA
<213> ORGANISM: Human papillomavirus

<400> SEQUENCE: 361
actacaccca tagtacattt aaaaggtgat gctaatactt taaaatgttt aagatataga 60
tttaaaaagc attgtacatt gtatactgca gtgtcgtcta catggcattg gacaggacat 120
aatgtaaaac ataaaagtgc aattgttaca cttacatatg atagtgaatg gcaacgtgac 180
caatttttg 189

<210> SEQ ID NO 362
<211> LENGTH: 191
<212> TYPE: DNA
<213> ORGANISM: Human papillomavirus

<400> SEQUENCE: 362
actacaccca tagtacattt aaaaggtgat gctaatactt taaaatgttt aagatataga 60
tttaaaaagc attgtacatt gtatactgca gtgtcgtcta catggcattg gacaggacat 120
aatgtaaaac ataaaagtgc aattgttaca cttacatatg atagtgaatg gcaacgtgac 180
caatttttgt c 191

<210> SEQ ID NO 363
<211> LENGTH: 182
<212> TYPE: DNA
<213> ORGANISM: Human papillomavirus

<400> SEQUENCE: 363
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
at 182

<210> SEQ ID NO 364
<211> LENGTH: 183
<212> TYPE: DNA
<213> ORGANISM: Human papillomavirus

<400> SEQUENCE: 364
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
att 183

<210> SEQ ID NO 365
<211> LENGTH: 185
<212> TYPE: DNA
<213> ORGANISM: Human papillomavirus

<400> SEQUENCE: 365
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
atttt 185

<210> SEQ ID NO 366
<211> LENGTH: 187
<212> TYPE: DNA
<213> ORGANISM: Human papillomavirus

<400> SEQUENCE: 366
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
atttttg 187

<210> SEQ ID NO 367
<211> LENGTH: 189
<212> TYPE: DNA
<213> ORGANISM: Human papillomavirus

<400> SEQUENCE: 367
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
atttttgtc 189

<210> SEQ ID NO 368
<211> LENGTH: 182
<212> TYPE: DNA
<213> ORGANISM: Human papillomavirus

<400> SEQUENCE: 368
acacccatag tacatttaaa aggtgatgct aatactttaa aatgtttaag atatagattt 60
aaaaagcatt gtacattgta tactgcagtg tcgtctacat ggcattggac aggacataat 120
gtaaaacata aaagtgcaat tgttacactt acatatgata gtgaatggca acgtgaccaa 180
tt 182

<210> SEQ ID NO 369
<211> LENGTH: 184
<212> TYPE: DNA
<213> ORGANISM: Human papillomavirus

<400> SEQUENCE: 369
acacccatag tacatttaaa aggtgatgct aatactttaa aatgtttaag atatagattt 60
aaaaagcatt gtacattgta tactgcagtg tcgtctacat ggcattggac aggacataat 120
gtaaaacata aaagtgcaat tgttacactt acatatgata gtgaatggca acgtgaccaa 180
tttt 184

<210> SEQ ID NO 370
<211> LENGTH: 186
<212> TYPE: DNA
<213> ORGANISM: Human papillomavirus

<400> SEQUENCE: 370
acacccatag tacatttaaa aggtgatgct aatactttaa aatgtttaag atatagattt 60
aaaaagcatt gtacattgta tactgcagtg tcgtctacat ggcattggac aggacataat 120
gtaaaacata aaagtgcaat tgttacactt acatatgata gtgaatggca acgtgaccaa 180
tttttg 186

<210> SEQ ID NO 371
<211> LENGTH: 188
<212> TYPE: DNA
<213> ORGANISM: Human papillomavirus

<400> SEQUENCE: 371
acacccatag tacatttaaa aggtgatgct aatactttaa aatgtttaag atatagattt 60
aaaaagcatt gtacattgta tactgcagtg tcgtctacat ggcattggac aggacataat 120
gtaaaacata aaagtgcaat tgttacactt acatatgata gtgaatggca acgtgaccaa 180
tttttgtc 188

<210> SEQ ID NO 372
<211> LENGTH: 231
<212> TYPE: DNA
<213> ORGANISM: Human papillomavirus

<400> SEQUENCE: 372
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa tttttgtctc aagttaaaat accaaaaact attacagtgt c 231

<210> SEQ ID NO 373
<211> LENGTH: 232
<212> TYPE: DNA
<213> ORGANISM: Human papillomavirus

<400> SEQUENCE: 373
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa tttttgtctc aagttaaaat accaaaaact attacagtgt ct 232

<210> SEQ ID NO 374
<211> LENGTH: 238
<212> TYPE: DNA
<213> ORGANISM: Human papillomavirus

<400> SEQUENCE: 374
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa tttttgtctc aagttaaaat accaaaaact attacagtgt ctactgga 238

<210> SEQ ID NO 375
<211> LENGTH: 239
<212> TYPE: DNA
<213> ORGANISM: Human papillomavirus

<400> SEQUENCE: 375
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa tttttgtctc aagttaaaat accaaaaact attacagtgt ctactggat 239

<210> SEQ ID NO 376
<211> LENGTH: 240
<212> TYPE: DNA
<213> ORGANISM: Human papillomavirus

<400> SEQUENCE: 376
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa tttttgtctc aagttaaaat accaaaaact attacagtgt ctactggatt 240

<210> SEQ ID NO 377
<211> LENGTH: 241
<212> TYPE: DNA
<213> ORGANISM: Human papillomavirus

<400> SEQUENCE: 377
tagtaacact acacccatag tacatttaaa aggtgatgct aatactttaa aatgtttaag 60
atatagattt aaaaagcatt gtacattgta tactgcagtg tcgtctacat ggcattggac 120
aggacataat gtaaaacata aaagtgcaat tgttacactt acatatgata gtgaatggca 180
acgtgaccaa tttttgtctc aagttaaaat accaaaaact attacagtgt ctactggatt 240
t 241

<210> SEQ ID NO 378
<211> LENGTH: 230
<212> TYPE: DNA
<213> ORGANISM: Human papillomavirus

<400> SEQUENCE: 378
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat ttttgtctca agttaaaata ccaaaaacta ttacagtgtc 230

<210> SEQ ID NO 379
<211> LENGTH: 231
<212> TYPE: DNA
<213> ORGANISM: Human papillomavirus

<400> SEQUENCE: 379
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat ttttgtctca agttaaaata ccaaaaacta ttacagtgtc t 231

<210> SEQ ID NO 380
<211> LENGTH: 237
<212> TYPE: DNA
<213> ORGANISM: Human papillomavirus

<400> SEQUENCE: 380
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat ttttgtctca agttaaaata ccaaaaacta ttacagtgtc tactgga 237

<210> SEQ ID NO 381
<211> LENGTH: 238
<212> TYPE: DNA
<213> ORGANISM: Human papillomavirus

<400> SEQUENCE: 381
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat ttttgtctca agttaaaata ccaaaaacta ttacagtgtc tactggat 238

<210> SEQ ID NO 382
<211> LENGTH: 239
<212> TYPE: DNA
<213> ORGANISM: Human papillomavirus

<400> SEQUENCE: 382
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat ttttgtctca agttaaaata ccaaaaacta ttacagtgtc tactggatt 239

<210> SEQ ID NO 383
<211> LENGTH: 240
<212> TYPE: DNA
<213> ORGANISM: Human papillomavirus

<400> SEQUENCE: 383
agtaacacta cacccatagt acatttaaaa ggtgatgcta atactttaaa atgtttaaga 60
tatagattta aaaagcattg tacattgtat actgcagtgt cgtctacatg gcattggaca 120
ggacataatg taaaacataa aagtgcaatt gttacactta catatgatag tgaatggcaa 180
cgtgaccaat ttttgtctca agttaaaata ccaaaaacta ttacagtgtc tactggattt 240

<210> SEQ ID NO 384
<211> LENGTH: 224
<212> TYPE: DNA
<213> ORGANISM: Human papillomavirus

<400> SEQUENCE: 384
actacaccca tagtacattt aaaaggtgat gctaatactt taaaatgttt aagatataga 60
tttaaaaagc attgtacatt gtatactgca gtgtcgtcta catggcattg gacaggacat 120
aatgtaaaac ataaaagtgc aattgttaca cttacatatg atagtgaatg gcaacgtgac 180
caatttttgt ctcaagttaa aataccaaaa actattacag tgtc 224

<210> SEQ ID NO 385
<211> LENGTH: 225
<212> TYPE: DNA
<213> ORGANISM: Human papillomavirus

<400> SEQUENCE: 385
actacaccca tagtacattt aaaaggtgat gctaatactt taaaatgttt aagatataga 60
tttaaaaagc attgtacatt gtatactgca gtgtcgtcta catggcattg gacaggacat 120
aatgtaaaac ataaaagtgc aattgttaca cttacatatg atagtgaatg gcaacgtgac 180
caatttttgt ctcaagttaa aataccaaaa actattacag tgtct 225

<210> SEQ ID NO 386
<211> LENGTH: 231
<212> TYPE: DNA
<213> ORGANISM: Human papillomavirus

<400> SEQUENCE: 386
actacaccca tagtacattt aaaaggtgat gctaatactt taaaatgttt aagatataga 60
tttaaaaagc attgtacatt gtatactgca gtgtcgtcta catggcattg gacaggacat 120
aatgtaaaac ataaaagtgc aattgttaca cttacatatg atagtgaatg gcaacgtgac 180
caatttttgt ctcaagttaa aataccaaaa actattacag tgtctactgg a 231

<210> SEQ ID NO 387
<211> LENGTH: 232
<212> TYPE: DNA
<213> ORGANISM: Human papillomavirus

<400> SEQUENCE: 387
actacaccca tagtacattt aaaaggtgat gctaatactt taaaatgttt aagatataga 60
tttaaaaagc attgtacatt gtatactgca gtgtcgtcta catggcattg gacaggacat 120
aatgtaaaac ataaaagtgc aattgttaca cttacatatg atagtgaatg gcaacgtgac 180
caatttttgt ctcaagttaa aataccaaaa actattacag tgtctactgg at 232

<210> SEQ ID NO 388
<211> LENGTH: 233
<212> TYPE: DNA
<213> ORGANISM: Human papillomavirus

<400> SEQUENCE: 388
actacaccca tagtacattt aaaaggtgat gctaatactt taaaatgttt aagatataga 60
tttaaaaagc attgtacatt gtatactgca gtgtcgtcta catggcattg gacaggacat 120
aatgtaaaac ataaaagtgc aattgttaca cttacatatg atagtgaatg gcaacgtgac 180
caatttttgt ctcaagttaa aataccaaaa actattacag tgtctactgg att 233

<210> SEQ ID NO 389
<211> LENGTH: 234
<212> TYPE: DNA
<213> ORGANISM: Human papillomavirus

<400> SEQUENCE: 389
actacaccca tagtacattt aaaaggtgat gctaatactt taaaatgttt aagatataga 60
tttaaaaagc attgtacatt gtatactgca gtgtcgtcta catggcattg gacaggacat 120
aatgtaaaac ataaaagtgc aattgttaca cttacatatg atagtgaatg gcaacgtgac 180
caatttttgt ctcaagttaa aataccaaaa actattacag tgtctactgg attt 234

<210> SEQ ID NO 390
<211> LENGTH: 222
<212> TYPE: DNA
<213> ORGANISM: Human papillomavirus

<400> SEQUENCE: 390
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
atttttgtct caagttaaaa taccaaaaac tattacagtg tc 222

<210> SEQ ID NO 391
<211> LENGTH: 223
<212> TYPE: DNA
<213> ORGANISM: Human papillomavirus

<400> SEQUENCE: 391
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
atttttgtct caagttaaaa taccaaaaac tattacagtg tct 223

<210> SEQ ID NO 392
<211> LENGTH: 229
<212> TYPE: DNA
<213> ORGANISM: Human papillomavirus

<400> SEQUENCE: 392
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
atttttgtct caagttaaaa taccaaaaac tattacagtg tctactgga 229

<210> SEQ ID NO 393
<211> LENGTH: 230
<212> TYPE: DNA
<213> ORGANISM: Human papillomavirus

<400> SEQUENCE: 393
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
atttttgtct caagttaaaa taccaaaaac tattacagtg tctactggat 230

<210> SEQ ID NO 394
<211> LENGTH: 231
<212> TYPE: DNA
<213> ORGANISM: Human papillomavirus

<400> SEQUENCE: 394
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
atttttgtct caagttaaaa taccaaaaac tattacagtg tctactggat t 231

<210> SEQ ID NO 395
<211> LENGTH: 232
<212> TYPE: DNA
<213> ORGANISM: Human papillomavirus

<400> SEQUENCE: 395
tacacccata gtacatttaa aaggtgatgc taatacttta aaatgtttaa gatatagatt 60
taaaaagcat tgtacattgt atactgcagt gtcgtctaca tggcattgga caggacataa 120
tgtaaaacat aaaagtgcaa ttgttacact tacatatgat agtgaatggc aacgtgacca 180
atttttgtct caagttaaaa taccaaaaac tattacagtg tctactggat tt 232

<210> SEQ ID NO 396
<211> LENGTH: 221
<212> TYPE: DNA
<213> ORGANISM: Human papillomavirus

<400> SEQUENCE: 396
acacccatag tacatttaaa aggtgatgct aatactttaa aatgtttaag atatagattt 60
aaaaagcatt gtacattgta tactgcagtg tcgtctacat ggcattggac aggacataat 120
gtaaaacata aaagtgcaat tgttacactt acatatgata gtgaatggca acgtgaccaa 180
tttttgtctc aagttaaaat accaaaaact attacagtgt c 221

<210> SEQ ID NO 397
<211> LENGTH: 222
<212> TYPE: DNA
<213> ORGANISM: Human papillomavirus

<400> SEQUENCE: 397
acacccatag tacatttaaa aggtgatgct aatactttaa aatgtttaag atatagattt 60
aaaaagcatt gtacattgta tactgcagtg tcgtctacat ggcattggac aggacataat 120
gtaaaacata aaagtgcaat tgttacactt acatatgata gtgaatggca acgtgaccaa 180
tttttgtctc aagttaaaat accaaaaact attacagtgt ct 222

<210> SEQ ID NO 398
<211> LENGTH: 228
<212> TYPE: DNA
<213> ORGANISM: Human papillomavirus

<400> SEQUENCE: 398
acacccatag tacatttaaa aggtgatgct aatactttaa aatgtttaag atatagattt 60
aaaaagcatt gtacattgta tactgcagtg tcgtctacat ggcattggac aggacataat 120
gtaaaacata aaagtgcaat tgttacactt acatatgata gtgaatggca acgtgaccaa 180
tttttgtctc aagttaaaat accaaaaact attacagtgt ctactgga 228

<210> SEQ ID NO 399
<211> LENGTH: 229
<212> TYPE: DNA
<213> ORGANISM: Human papillomavirus

<400> SEQUENCE: 399
acacccatag tacatttaaa aggtgatgct aatactttaa aatgtttaag atatagattt 60
aaaaagcatt gtacattgta tactgcagtg tcgtctacat ggcattggac aggacataat 120
gtaaaacata aaagtgcaat tgttacactt acatatgata gtgaatggca acgtgaccaa 180
tttttgtctc aagttaaaat accaaaaact attacagtgt ctactggat 229

<210> SEQ ID NO 400
<211> LENGTH: 230
<212> TYPE: DNA
<213> ORGANISM: Human papillomavirus

<400> SEQUENCE: 400
acacccatag tacatttaaa aggtgatgct aatactttaa aatgtttaag atatagattt 60
aaaaagcatt gtacattgta tactgcagtg tcgtctacat ggcattggac aggacataat 120
gtaaaacata aaagtgcaat tgttacactt acatatgata gtgaatggca acgtgaccaa 180
tttttgtctc aagttaaaat accaaaaact attacagtgt ctactggatt 230

<210> SEQ ID NO 401
<211> LENGTH: 231
<212> TYPE: DNA
<213> ORGANISM: Human papillomavirus

<400> SEQUENCE: 401
acacccatag tacatttaaa aggtgatgct aatactttaa aatgtttaag atatagattt 60
aaaaagcatt gtacattgta tactgcagtg tcgtctacat ggcattggac aggacataat 120
gtaaaacata aaagtgcaat tgttacactt acatatgata gtgaatggca acgtgaccaa 180
tttttgtctc aagttaaaat accaaaaact attacagtgt ctactggatt t 231

<210> SEQ ID NO 402
<211> LENGTH: 171
<212> TYPE: DNA
<213> ORGANISM: Human papillomavirus

<400> SEQUENCE: 402
acatttaaaa ggtgatgcta atactttaaa atgtttaaga tatagattta aaaagcattg 60
tacattgtat actgcagtgt cgtctacatg gcattggaca ggacataatg taaaacataa 120
aagtgcaatt gttacactta catatgatag tgaatggcaa cgtgaccaat t 171

<210> SEQ ID NO 403
<211> LENGTH: 173
<212> TYPE: DNA
<213> ORGANISM: Human papillomavirus

<400> SEQUENCE: 403
acatttaaaa ggtgatgcta atactttaaa atgtttaaga tatagattta aaaagcattg 60
tacattgtat actgcagtgt cgtctacatg gcattggaca ggacataatg taaaacataa 120
aagtgcaatt gttacactta catatgatag tgaatggcaa cgtgaccaat ttt 173

<210> SEQ ID NO 404
<211> LENGTH: 175
<212> TYPE: DNA
<213> ORGANISM: Human papillomavirus

<400> SEQUENCE: 404
acatttaaaa ggtgatgcta atactttaaa atgtttaaga tatagattta aaaagcattg 60
tacattgtat actgcagtgt cgtctacatg gcattggaca ggacataatg taaaacataa 120
aagtgcaatt gttacactta catatgatag tgaatggcaa cgtgaccaat ttttg 175

<210> SEQ ID NO 405
<211> LENGTH: 177
<212> TYPE: DNA
<213> ORGANISM: Human papillomavirus

<400> SEQUENCE: 405
acatttaaaa ggtgatgcta atactttaaa atgtttaaga tatagattta aaaagcattg 60
tacattgtat actgcagtgt cgtctacatg gcattggaca ggacataatg taaaacataa 120
aagtgcaatt gttacactta catatgatag tgaatggcaa cgtgaccaat ttttgtc 177

<210> SEQ ID NO 406
<211> LENGTH: 167
<212> TYPE: DNA
<213> ORGANISM: Human papillomavirus

<400> SEQUENCE: 406
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg accaatt 167

<210> SEQ ID NO 407
<211> LENGTH: 169
<212> TYPE: DNA
<213> ORGANISM: Human papillomavirus

<400> SEQUENCE: 407
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg accaatttt 169

<210> SEQ ID NO 408
<211> LENGTH: 171
<212> TYPE: DNA
<213> ORGANISM: Human papillomavirus

<400> SEQUENCE: 408
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg accaattttt g 171

<210> SEQ ID NO 409
<211> LENGTH: 173
<212> TYPE: DNA
<213> ORGANISM: Human papillomavirus

<400> SEQUENCE: 409
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg accaattttt gtc 173

<210> SEQ ID NO 410
<211> LENGTH: 166
<212> TYPE: DNA
<213> ORGANISM: Human papillomavirus

<400> SEQUENCE: 410
taaaaggtga tgctaatact ttaaaatgtt taagatatag atttaaaaag cattgtacat 60
tgtatactgc agtgtcgtct acatggcatt ggacaggaca taatgtaaaa cataaaagtg 120
caattgttac acttacatat gatagtgaat ggcaacgtga ccaatt 166

<210> SEQ ID NO 411
<211> LENGTH: 168
<212> TYPE: DNA
<213> ORGANISM: Human papillomavirus

<400> SEQUENCE: 411
taaaaggtga tgctaatact ttaaaatgtt taagatatag atttaaaaag cattgtacat 60

```
tgtatactgc agtgtcgtct acatggcatt ggacaggaca taatgtaaaa cataaaagtg    120

caattgttac acttacatat gatagtgaat ggcaacgtga ccaatttt                 168


<210> SEQ ID NO 412
<211> LENGTH: 170
<212> TYPE: DNA
<213> ORGANISM: Human papillomavirus

<400> SEQUENCE: 412

taaaaggtga tgctaatact ttaaaatgtt taagatatag atttaaaaag cattgtacat     60

tgtatactgc agtgtcgtct acatggcatt ggacaggaca taatgtaaaa cataaaagtg    120

caattgttac acttacatat gatagtgaat ggcaacgtga ccaatttttg               170


<210> SEQ ID NO 413
<211> LENGTH: 172
<212> TYPE: DNA
<213> ORGANISM: Human papillomavirus

<400> SEQUENCE: 413

taaaaggtga tgctaatact ttaaaatgtt taagatatag atttaaaaag cattgtacat     60

tgtatactgc agtgtcgtct acatggcatt ggacaggaca taatgtaaaa cataaaagtg    120

caattgttac acttacatat gatagtgaat ggcaacgtga ccaatttttg tc            172


<210> SEQ ID NO 414
<211> LENGTH: 218
<212> TYPE: DNA
<213> ORGANISM: Human papillomavirus

<400> SEQUENCE: 414

acatttaaaa ggtgatgcta atactttaaa atgtttaaga tatagattta aaaagcattg     60

tacattgtat actgcagtgt cgtctacatg gcattggaca ggacataatg taaaacataa    120

aagtgcaatt gttacactta catatgatag tgaatggcaa cgtgaccaat ttttgtctca    180

agttaaaata ccaaaaacta ttacagtgtc tactggat                            218


<210> SEQ ID NO 415
<211> LENGTH: 219
<212> TYPE: DNA
<213> ORGANISM: Human papillomavirus

<400> SEQUENCE: 415

acatttaaaa ggtgatgcta atactttaaa atgtttaaga tatagattta aaaagcattg     60

tacattgtat actgcagtgt cgtctacatg gcattggaca ggacataatg taaaacataa    120

aagtgcaatt gttacactta catatgatag tgaatggcaa cgtgaccaat ttttgtctca    180

agttaaaata ccaaaaacta ttacagtgtc tactggatt                           219


<210> SEQ ID NO 416
<211> LENGTH: 214
<212> TYPE: DNA
<213> ORGANISM: Human papillomavirus

<400> SEQUENCE: 416

ttaaaaggtg atgctaatac tttaaaatgt ttaagatata gatttaaaaa gcattgtaca     60

ttgtatactg cagtgtcgtc tacatggcat tggacaggac ataatgtaaa acataaaagt    120

gcaattgtta cacttacata tgatagtgaa tggcaacgtg accaattttt gtctcaagtt    180

aaaataccaa aaactattac agtgtctact ggat                                214
```

<210> SEQ ID NO 417
<211> LENGTH: 215
<212> TYPE: DNA
<213> ORGANISM: Human papillomavirus

<400> SEQUENCE: 417
ttaaaaggtg atgctaatac tttaaaatgt ttaagatata gatttaaaaa gcattgtaca 60
ttgtatactg cagtgtcgtc tacatggcat tggacaggac ataatgtaaa acataaaagt 120
gcaattgtta cacttacata tgatagtgaa tggcaacgtg accaattttt gtctcaagtt 180
aaaataccaa aaactattac agtgtctact ggatt 215

<210> SEQ ID NO 418
<211> LENGTH: 213
<212> TYPE: DNA
<213> ORGANISM: Human papillomavirus

<400> SEQUENCE: 418
taaaaggtga tgctaatact ttaaaatgtt taagatatag atttaaaaag cattgtacat 60
tgtatactgc agtgtcgtct acatggcatt ggacaggaca taatgtaaaa cataaaagtg 120
caattgttac acttacatat gatagtgaat ggcaacgtga ccaatttttg tctcaagtta 180
aaataccaaa aactattaca gtgtctactg gat 213

<210> SEQ ID NO 419
<211> LENGTH: 214
<212> TYPE: DNA
<213> ORGANISM: Human papillomavirus

<400> SEQUENCE: 419
taaaaggtga tgctaatact ttaaaatgtt taagatatag atttaaaaag cattgtacat 60
tgtatactgc agtgtcgtct acatggcatt ggacaggaca taatgtaaaa cataaaagtg 120
caattgttac acttacatat gatagtgaat ggcaacgtga ccaatttttg tctcaagtta 180
aaataccaaa aactattaca gtgtctactg gatt 214

<210> SEQ ID NO 420
<211> LENGTH: 7844
<212> TYPE: DNA
<213> ORGANISM: Human papillomavirus

<400> SEQUENCE: 420
gaaagtttca atcatacttt tatatattgg gagtgaccga aaagggttta agaccgaaaa 60
cggtacatat aaaaggcagc ttattctgtg tggacatatc catggagcca caattcaaca 120
atccacagga acgtccacga agcctgcacc acttgagtga ggtattagaa atacctttaa 180
ttgatcttag attatcatgt gtatattgca aaaaagaact aacacgtgct gaggtatata 240
attttgcatg cactgaatta aaattagtgt atagggatga ttttccttat gcagtgtgca 300
gagtatgttt attgttttat agtaaagtta gaaaatatag gtattatgac tattcagtgt 360
atggagctac actagaaagt ataactaaaa aacagttatg tgatttatta ataaggtgct 420
acagatgtca aagtccgtta actccggagg aaaagcaatt gcattgtgac agaaaaagac 480
gatttcatct aatagcacat ggttggaccg ggtcatgttt ggggtgctgg agacaaacat 540
ctagagaacc tagagaatct acagtataat catgcatggt aaagtaccaa cgctgcaaga 600
cgttgtatta gaactaacac ctcaaacaga aattgaccta cagtgcaatg agcaattgga 660
cagctcagag gatgaggatg aggatgaagt agaccatttg caggagcggc cacagcaagc 720

-continued

```
tagacaagct aaacaacata cgtgttacct aatacacgta ccttgttgtg agtgtaagtt    780
tgtggtgcag ttggacattc agagtaccaa agaggacctg cgtgttgtac aacagctgct    840
tatgggtgcg ttaacagtaa cgtgcccact ctgcgcatca agtaactaac tgcaatggcg    900
tcacctgaag gtacagatgg ggaggggaag ggatgttgtg gatggtttga agtagaggca    960
attgtagaaa aaaaaacagg agataaaata tcagatgatg aaagtgacga ggaggatgaa   1020
atagatacag atttagatgg atttatagac gattcatata tacaaaatat acaggcagac   1080
gcagaaacag tcaacaattg ttgcaagtac aaacagcaca tgcagataaa cagacgttgc   1140
aaaaactaaa acgaaagtat atagctagtc cattaaggga tattagtaat cagcaaactg   1200
tgtgccggga aggagtaaaa cggaggctta ttttatcaga cctacaagac agcgggtatg   1260
gcaatacatt ggaaactctg gaaacaccag aacaggtaga tgaagaggta cagggacgtg   1320
ggtgcgggaa tacacaaaat ggaggctcac aaaacagtac ctatagtaac aatagtgagg   1380
actctgtaat acatatggat attgatagaa acaatgaaac gccaacacaa caattgcagg   1440
acttgtttaa aagtagcaat ttacaaggta aattatatta taaatttaaa gaagtgtatg   1500
gtattccatt ttcagaattg gtgcgtacgt ttaaaagtga tagtacatgt tgcaatgatt   1560
ggatatgtgc tatatttggt gttaatgaaa cattagccga ggcactaaaa actataataa   1620
aaccacactg tatgtattat catatgcaat gtttaacatg tacatggggg gttatagtaa   1680
tgatgctaat tagatataca tgtggcaaaa acagaaaaac aattgcaaaa gcattaagct   1740
caatattaaa tgtaccacag gagcaaatgt taattcaacc accaaaaata cgaagtcctg   1800
ctgtagcttt atatttttat aaaacagcaa tgtcaaatat tagtgatgtg tatggagaca   1860
caccagaatg gatacaaaga caaacacaat tgcaacacag tttacaggat agtcaatttg   1920
aattatctaa aatggtgcag tgggcatttg ataatgaagt aacagatgat agccaaattg   1980
cgtttcaata tgcacaatta gcagatgtag acagcaatgc acaagccttt ttaaaaagca   2040
atatgcaggc aaaatatgta aaggattgtg gaataatgtg tagacattat aaaagggcac   2100
aacagcaaca aatgaatatg tgccagtgga taaagcacat atgtagtaaa acagatgaag   2160
ggggtgattg gaaacccatt gtacaatttt taagatatca aggggtcgat ttcatttcat   2220
ttctaagtta ctttaaatta tttctacaag gaacacctaa acataactgt ttggtacttt   2280
gtggaccgcc aaatacaggt aaatcatgct ttgctatgag tcttataaag tttttttcaag   2340
ggtctgtcat ttcatttgtg aattcacaaa gccacttttg gttgcagcca ttagacaatg   2400
ctaaacttgg gttgttggat gatgcaacag aaatatgttg gaaatatata gacgattatt   2460
taaggaattt ggtagatgga aatcctataa gtttagatag aaaacataaa caattagtac   2520
aaataaaatg tccaccatta ctaattacaa ccaatataaa tcctatgcta gatgctaaat   2580
tacgatattt acacagtaga atgttagtgt ttcagtttca aaatccattt ccattagata   2640
ataatggtaa tcctgtatat gaattaagta atgtaaactg gaaatgtttc tttacaagga   2700
cgtggtccag attaaatttg gataacgacg aggacaaaga aaacaatgga gacgctttcc   2760
caacgtttaa atgcgtgcca gaacaaaata ctagactgtt ttgaaaaaag atagtagatg   2820
tattgcagat catatagaat attggaaagc tgtgcgacat gaaaatgtgc tatactataa   2880
agcaagagaa aatgacatta ctgtactaaa ccaccagatg gtgccttgtt tacaagtatg   2940
taaagcaaaa gcatgtagtg caatagaagt gcaaatagca ctggaatcat taagtacaac   3000
aatatataac aatgaagagt ggacattaag agacacatgc gaggaactat ggcttactga   3060
acctaaaaaa tgctttaaaa aagaaggaca acatatagaa gtatggtttg atggtagtaa   3120
```

-continued

```
aaacaattgt atgcaatatg tagcctggaa atatatatat tacaatggag attgtgggtg   3180
gcaaaaagtg tgttctgggg tagactatag aggtatatat tatgtacatg atggccacaa   3240
aacatactac acagactttg aacaagaggc caaaaaattt gggtgtaaaa acatatggga   3300
agtacatatg gaaaatgaga gtatttattg tcctgactct gtgtctagta cctgtagata   3360
caacgtatcc cctgttgaaa ctgttaacga atacaacacc cacaagacca ccaccaccac   3420
ctccacgtcc gtgggcaacc aagacgccgc agtatcccac agaccaggaa aacgacccag   3480
actacgggaa tcagaatttg actcctccag agagtcccac gcaaagtgtg tcacaacaca   3540
cacacacatc agcgacacag acaataccga cagtagaagt agaagtatca acaacaacaa   3600
ccaccctggt gataagacta cgcctgtagt acatttaaaa ggtgaaccta acagattaaa   3660
atgttgtaga tatcgatttc aaaaatataa aacattgttt gtggatgtaa catcaacata   3720
tcattggaca agtacagaca ataaaaatta tagcataatt acaattatat ataaggatga   3780
aacacaacga aacagctttt taagtcatgt aaaaattcca gtagtgtaca ggttagtttg   3840
ggacaaatga gttttccata aagtgctgta tatattgtat atacatttgt gttattgtaa   3900
cacacaaata cgtgaagtgt acctgccata cattgctgct acgcatatat attgcaacca   3960
ttgatttttg tgttattggt gtgtttgcgc tttgcttttg tgtttgtttg cttgtgtgtc   4020
atgttgtccc gcttttgcta tctgcctctg tgttttccag ttgtatatta ttaataatat   4080
tgttttggtt tgttatagcc acatcctttt ttaatacatt tataatattt ttgatatttt   4140
tttactgtcc tgtgctgtgt atatatttac atgctttgtg gataataaat aatatgtaaa   4200
tgtagtagta ctgttactac tatggttgcc caccgtgcca cacgacgcaa acgcgcatct   4260
gcaacacaac tatataaaac atgtaagttg tctggtacat gtccagagga tgttgttaat   4320
aaaatagagc aaaaaacatg ggctgataaa atattgcaat ggggaagttt atttacatat   4380
tttggaggcc ttggcattgg tacaggaact gggtctgggg gtcgtgcagg ctatgttcca   4440
ttggggtcta ggccttccac aatagttgat gtaactccgg cgcgaccacc tattgttgtg   4500
gaatccgtag ggcctacaga cccttccatt gttacattag ttgaggagtc cagtgttata   4560
gaatctggtg cagggattcc taattttact gggtctgggg gatttgaaat tacatcctca   4620
tcaacaacta cacctgccgt gttggatatt acaccaacct ctagtactgt acatgtcagt   4680
agtacccata taaccaatcc gttatttatt gatcccccctg ttattgaggc cccacaaaca   4740
ggcgaggtgt ctggcaatat tttaattagc acacccacat ctggtataca tagctatgaa   4800
gaaataccta tgcaaacatt tgctgttcac ggttctggta cagaacctat tagtagtact   4860
cctattccag gctttaggcg tattgcagct cctagattat atagaaaagc atttcagcag   4920
gttaaggtaa ctgaccctgc atttcttgat agacctgcaa cattagtatc tgctgataat   4980
ccactttttg aaggtactga cacatcttta gctttttctc cgtcgggtgt ggctcctgac   5040
cctgatttta tgaatatagt agcattacat aggcctgcat ttactacacg taggggtggt   5100
gtacgtttta gtaggcttgg cagaaaggct actatacaaa cacgtagagg cacacaaata   5160
ggtgcccgtg tgcattatta ttatgatata agtcctattg cacaggctga ggaaattgaa   5220
atgcagccat tattgtctgc aaataattca tttgatggcc tatatgatat ttatgcaaat   5280
atagatgatg aagcacctgg tttgtctagc cagtcagttg ctacaccttc tgcacactta   5340
cctataaagc cttccacatt gtcttttgct agtaacacca ctaatgtaac tgcccccttta   5400
ggtaatgtgt gggaaacacc attttattca ggtcctgaca tagtgttgcc tacaggcccc   5460
agtacgtggc cctttgttcc tcagtctcct tatgatgtta cccatgatgt atatatacag   5520
```

-continued

```
ggatcctcct ttgcattatg gcctgtgtat ttttttagac gtaggcgccg taaacgtatt   5580
ccctattttt ttgcagatgg cgacgtggcg gcctagtgaa aataaggtgt atctacctcc   5640
aacacctgtt tcaaaggttg tggcaacgga ttcctatgta aaacgcacta gtatatttta   5700
tcatgcaggc agttcacgat tgcttgccgt aggacatccc tattactctg tgactaagga   5760
caataccaaa acaaacattc ccaaagttag tgcatatcaa tatagggtat ttagggtacg   5820
gttgcccgac cctaataagt ttgggcttcc agatactaat atttataatc cggaccagga   5880
acggttagtg tgggcatgtg taggtttgga ggtaggccgc ggacagcctt taggtgctgg   5940
gctaagtggc catccattgt ttaataggct ggatgatact gaaagttcca atttagcaaa   6000
taataatgtt atagaagata gtagggacaa tatatcagtt gatggcaagc aaacacagtt   6060
gtgtattgtt ggatgtactc ccgctatggg tgaacattgg actaaaggtg ctgtgtgtaa   6120
gtccacacaa gttaccacag gggactgccc gcctcttgca ttaattaata cacctataga   6180
ggatggggac atgatagaca caggatttgg cgctatggac tttaaggtgt tgcaggaatc   6240
taaggctgag gtacctttag acattgtaca atccacctgt aaatatcctg actatttaaa   6300
aatgtctgca gatgcctatg gtgattctat gtggttttac ttacgcaggg aacaattatt   6360
tgccagacat tattttaata gggctggtaa agttggggaa acaatacctg cagagttata   6420
tttaaagggt agcaatggta gagaaccccc tccgagttct gtatatgttg ctacgcctag   6480
tgggtctatg attacgtctg aggcacagtt atttaataaa ccttattggt tgcaacgtgc   6540
ccaaggccat aataatggca tttgctgggg taatcaatta tttgttactg tagtagatac   6600
tactagaagt actaacatga ctattagtac tgctacagaa cagttaagta aatatgatgc   6660
acgaaaaatt aatcagtacc ttagacatgt ggaggaatat gaattacaat ttgtttttca   6720
attatgcaaa attactttgt ctgcagaggt tatggcatat ttacataata tgaatgctaa   6780
cctactggag gactggaata ttgggttatc ccgcgccagtg gccaccagcc tagaagataa   6840
atatagatat gttagaagca cagctataac atgtcaacgg gaacagccac caacagaaaa   6900
acaggaccca ttagctaaat ataaattttg ggatgttaac ttacaggaca gtttttctac   6960
agacctggat caatttccac tgggtagaaa atttttaatg caactgggca ctaggtcaaa   7020
gcctgctgta gctacctcta aaaagcgatc tgctcctacc tccacctcta caccagcaaa   7080
acgtaaaagg cggtagtgtg ttgttgtgtg tttgtgtaac tgtgtttgtg tgttgtatat   7140
atggtatgtt tgtgtatgtg ctttatttta tactttgtat gtgtatgttg tgtttgtgta   7200
aatgtttgtg tgaaatgttt gtgtgtgtat tcattgtatg tatgactgta tatatgtgta   7260
atgtttgtgt gtctgtaata aacatgaatg agtgctttta cgcgtggttg cataaactaa   7320
ggtgtgtcat tattgtggct tttgttttgt aagttattgt gtacagtgta ctatgtgtat   7380
tgtgcataca tatatatacc ataacatact ccattttgtt gtttttccgc cattttgtac   7440
atgcaaccga attcggttgc atggcctagt gccattattt aaactaaaag gaattcggtt   7500
gcatggccta gtgccattat ttaaaccaaa aggccctttt cagcagaaca gttaatcctt   7560
tggcatattg ccgtttcctg tgttttatac ttgaattatg tacagtaccg caccctgtat   7620
tactcacagg tactatgact gccaactatg cttttatctg catactttag tgctgttggg   7680
cacacatttt tatacatgtg tctgcaactt tggtgttttg gcttgcagaa tacactatgt   7740
aggccaagta tctgtcagta tctgttttgc aaacatgtaa catacaatta ctcatttttt   7800
aaaaccgttt acggtcgtgc aaaaacaggt ttcttttaat tgtt                     7844
```

<210> SEQ ID NO 421

<211> LENGTH: 7808
<212> TYPE: DNA
<213> ORGANISM: Human papillomavirus

<400> SEQUENCE: 421
aacaattatc ttgtaaaaac tagggtgtaa ccgaaaaggg ttatgaccga aaacggtgca 60
tataaaagtg cagtggtaaa agtatagaag aacaccatgt tcgaagacaa gagggaaaga 120
ccacgaacgc tgcatgaatt atgtgaagct ttgaacgttt ctatgcacaa tatacaggta 180
gtgtgtgtgt attgtaaaaa ggaattatgt agagcagatg tatataatgt agcatttact 240
gaaattaaga ttgtatatag ggataataat ccatatgcag tatgcaaaca atgtttactg 300
ttttattcaa aaattagaga gtatagacgt tatagcaggt ctgtgtatgg tactacatta 360
gaggcaatta ctaaaaaaag cttatatgat ttatcgataa ggtgtcatag atgtcaaaga 420
ccacttgggc ctgaagaaaa gcaaaaattg gtggacgaaa aaaaaaggtt ccatgaaata 480
gcgggacgtt ggacggggca atgcgctaat tgctggcaac gtacacgaca acgtaacgaa 540
acccaagtgt aataaagcca tgcgtggtaa tgtaccacaa ttaaaagatg tagtattgca 600
tttaacacca cagactgaaa ttgacttgca atgctacgag caatttgaca gctcagagga 660
ggaggatgaa gtagataata tgcgtgacca gctaccagaa agacgggctg gacaggctac 720
gtgttacaga attgaagctc cgtgttgcag gtgttcaagt gtagtacaac tggcagtgga 780
aagcagtgga gacacccttc gcgttgtaca gcagatgtta atgggcgaac taagcctggt 840
ttgcccgtgt tgtgcgaaca actagcaacg gcgatggact gtgaaggtac agaggatgag 900
ggggcggggt gtaatgggtg gttttttgtt gaagcaatag tagaaaaaaa aacaggagat 960
aatgtttcgg atgatgagga tgaaaatgca gatgatacag gatctgattt aataaacttt 1020
atagatagtg aaactagtat ttgcagtcag gcggaacagg agacagcacg ggcgttgttt 1080
caggcccaag aattacaggc aaacaaagag gctgtgcatc agttaaaacg aaagtttcta 1140
gtcagcccgc gaagcagccc attaggagac attacaaatc aaaacaacac acacagccat 1200
agtcaggcaa acgagtcaca agttaaaagg agattactgg acagttatcc ggacagcgga 1260
tatggcaata cacaagtgga aactgtggaa gcaacgttgc aggtagatgg gcaacatggc 1320
ggttcacaga acagtgtgtg tagtagcggg gggggcagtg ttatggatgt ggaaacaaca 1380
gaaagctgtg caaatgtaga actaaacagt atatgtgaag tattaaaaag cagtaatgca 1440
aaagcaacgt taatggcaaa atttaaagag ttgtatggta ttagttataa tgagttggta 1500
cgggtgttta aaagtgataa aacatgttgt atagattggg tttgtgcatt gtttggcgtt 1560
tccccaatgg tagcagaaaa tttaaaaaca ctaattaagc cattttgcat gtactaccat 1620
atacaatgtt tatcatgtga ttggggcacc attgtattaa tgctaattag gttttcatgt 1680
gcaaaaaaca gaacaacaat tgctaagtgt ttaagtacat tagtaaatat cccacaatca 1740
caaatgttta tagaaccacc aaaattacgt agtacacctg tggcattata tttttataga 1800
acaggcatat caaacattag caatacatat ggagagacac ctgaatggat tacacgacaa 1860
acgcaactac aacatagttt tgaggatagt acctttgaat tatcacaaat ggtgcaatgg 1920
gcatttgacc atgaagtatt agatgatagt gaaatagcat ttcattatgc acaattagca 1980
gatatagata gtaatgctgc agcgtttttta aagagtaatt gccaagcaaa atatgtaaaa 2040
gattgtggga ccatggcacg gcattacaaa cgagcacaaa gaaaatcatt atctatgtca 2100
gcctggataa ggtatagatg tgatagagca aaggatggag gcaactggag agaaattgct 2160
aaatttttaa gatatcaagg tgtaaacttt atgtccttta ttcaaatgtt taaacagttt 2220

-continued

```
ttaaaaggaa caccaaaaca caattgcata gtcatatatg gcccaccaaa cacaggcaag   2280
tcattatttg caatgagcct aatgaagttt atgcaagggt ccattatttc atatgtaaac   2340
tctggtagtc atttttggtt acagccacta gaggatgcta aaatagcatt gttagatgat   2400
gctacgtatg ggtgttggac atatattgat cagtatttaa gaaacttttt agatggtaat   2460
ccatgtagta tagatagaaa acataggagt ttaatacaat tagtatgtcc accattacta   2520
ataacgtcaa acataaatcc acaagaggat gcaaacctaa tgtatttaca tacaagggta   2580
acagtattaa agtttttaaa tacatttcca tttgataaca atgggaatgc tgtgtataca   2640
ttgaatgatg aaaattggaa aaattttttt tccaccacat ggtccagatt agatttggag   2700
gaggaagagg acaaagaaaa tggagaccct atgccaccgt ttaaatgtgt gccaggagaa   2760
aatactagac tgttatgaac tggacagtga taaattagta gatcaaatta actattggac   2820
attgttacga tatgaagctg ctatgtttta tgcagcacgg gaaagaaact tacgaacaat   2880
caatcaccag gtagtaccag caacaacagt atcaaaacaa aaggcctgtc aagcaattga   2940
aatgcacatg gccttacaat cgcttaacaa atcagactat aacatggaac catggacaat   3000
gcgggagaca tgttatgaac tatggtgtgt ggctcccaag caatgtttca aaaagggggg   3060
cataactgta acagttatat ttgatggaaa taaggacaat gcaatggact atacaagctg   3120
gaaatttata tatatatatg ataatgataa gtgggtaaag acaaatggaa atgtggacta   3180
tacgggtata tattacactg taaattcaaa aaaagaatat tatgtacagt ttaaagatga   3240
agccaaaata tatggggcac aacagtggga ggtctatatg tatggtactg taataacatg   3300
tcctgaatat gtatctagta cctgcagcga cgcgttatcc actactacaa ctgttgaaca   3360
actatcaaac accccaacga ccaatcccct taccacctgc gtgggcgcca aagaagccca   3420
gacacaacag cgaaaacgac agcgacttac tgagcccgac tcctccacaa tctccccact   3480
gtccgtggac aatacaaaca accaaataca ctgtggaagt ggaagcacta acactggagg   3540
gcaccaaagt gcaactcaga ctgcgtttat agtgcattta aaaggtgata caaattgttt   3600
aaaatgtttt agatacagat ttacaaaaca caaagggtta tataaaaacg tatcctcaac   3660
ctggcattgg accagtaata ctaaaacagg cattgttacc attgtgtttg acagtgcaca   3720
tcaacgggaa acatttataa aaaccattaa agtaccccca agtgtaacac tgtcattggg   3780
aattatgaca ctgtaactag tgtaatatat gtattgtaca tatatactgt cacaagccaa   3840
tatgtgctgc taattgtata gacatattgt aaccattgca gtgtttatta ttttgctatt   3900
tgtgctttgc ttgtgtgtgt gtcttgtgtt gtgttgtttg ttgccgctac tgctgtccca   3960
atacgtgttt gcagctgcct tattattaat tttatgtttt tggtttgttg ttgcaacatc   4020
ccaattaact acatttttg tatatttgat tttttttac ttaccttgtt tacttttaca   4080
tctatataca tttttacttt tgcaataaac ttgttatatt tttgtgatta aatatggtgg   4140
ctacacgtgc acggcgtcgg aagcgagcat ctgtaacaca attatattct acatgcaaag   4200
ctgctggtac atgtcctcct gatgttgtga ataaggttga aggtactaca ttggccgata   4260
aaatattaca gtggagtggg ttgggtatat ttttgggtgg cctaggtatt ggtactgggt   4320
ctggatctgg ggggcgtact ggatatatcc ctttaggtgg tgggggtcgc ccaggcgtgg   4380
tggatattgc tcctgcaagg ccacctatta taattgacct atggcaccat actgaacctt   4440
ctatagtaaa tttggttgag gactctagta ttattcagtc tgggtctcct atacctacct   4500
ttactggtac cgatggcttt gaaattactt catcttccac aacaacccct gctgtgttgg   4560
acatcacccc atctgctggt actgtacatg tttctagtac taacattgaa aatcctttat   4620
```

-continued

```
atattgaacc tccatccatt gaggctccac aatctggaga agtgtcagat atatatttac   4680
tagtacacta ctctggtact catgggtatg aagaaatacc tatggaagtg tttgcatcca   4740
atgtcagtac tggtactgaa cctattagca gcacacctac tccaggggtt agtcgcatag   4800
ctgctccccg cttgtatagt aagtcctaca cacaggttaa agttacaaat cctgatttta   4860
ttagtaagcc atccacattt gttacattta ataatcctgc ttttgagcct attgacacat   4920
ccataacttt tgaggaacct gatgctgttg cacctgatcc tgattttctg gatattatta   4980
cactgcaccg ccctgccctt acatctcgta gaggcacagt acgctttagt aggttaggtc   5040
aaaaggccac catgcgcact cgtagtggca aacaaattgg tgctcgtgta cattattatc   5100
atgatattag tagaattgca ccagctgatg aacttgaaat gcagccttta ctttcacctt   5160
ctaataatta tagttatgac atttatgctg atttagatga agctgaaaca ggttttatac   5220
agcccacaca caccacacct atgtcacact cctctttgtc taggcagttg ccctccttat   5280
cttcatctat gtcttcatct tatgcaaatg ttactattcc attttcaact acatattctg   5340
ttcctattca tacagggcct gatgtggtat tgcccacatc tcctacagta tggccttatg   5400
ttccccacac ttccattgac accaagcatt ctattgttat actaggtggg gattactatt   5460
tgtggcccta tacacattta ctacgcaaac gccgtaaacg tataccctat ttttttacag   5520
atggcattgt ggcgcactaa tgacagcaag gtgtatttgc cacctgcacc tgtgtctcga   5580
attgtgaata cagaagaata tatcacacgc accggcatat attactatgc aggcagttcc   5640
agactaataa cattaggaca tccctatttt ccaataccta aaacctcaac gcgtgctgct   5700
attcctaaag tatctgcatt tcaatacagg gtatttaggg tacagttacc agatcctaac   5760
aagtttggac tcccggatcc aaatttatat aatccagaca cagataggtt ggtgtggggt   5820
tgtgtgggcg ttgaggtggg cagaggacag ccccttggtg ttggccttag tggtcatccc   5880
ttatttaata aatatgatga cacagaaaat tcacgcatag caaatggcaa tgcacaacaa   5940
gatgttagag ataacacatc tgttgacaac aaacagactc agttatgtat aataggctgt   6000
gctccaccta ttggggaaca ctggggtatt ggcactacat gcaaaaacac acctgtacct   6060
ccaggagact gccccccct ggaacttgta tcctctgtca ttcaggatgg cgatatgatt   6120
gatacagggt ttggagctat ggatttcgct gccctacagg ccaccaaatc agacgtccct   6180
ttggatattt cacagtctgt ttgtaaatat cctgattatt taaaaatgtc tgcagacaca   6240
tatggtaatt ccatgttttt tcatttacgc agggagcaaa tctttgctag gcactattat   6300
aataaacttg taggtgttgg ggaagacatt cctaacgatt attatattaa gggtagtggt   6360
aatggccgtg accctataga aagttatata tactctgcta ctcccagtgg gtctatgata   6420
acatctgatt ctcaaatttt taataagcct tattggctcc accgtgcgca gggtcacaat   6480
aatggcattt gctggaacaa tcagcttttt attacctgtg ttgatactac cagaagtaca   6540
aatttaacta ttagcactgc cactgctgcg gtttccccaa catttactcc aagtaacttt   6600
aagcaatata ttaggcatgg ggaagagtat gaattgcaat ttatttttca attatgtaaa   6660
attactttaa ctacagaggt aatggcttat ttacacacaa tggatcctac cattcttgaa   6720
cagtggaatt ttggattaac attacctccg tctgctagtt tggaggatgc atataggttt   6780
gttagaaatg cagctactag ctgtcaaaag gacacccctc cacaggctaa gccagatcct   6840
ttggccaaat ataaattttg ggatgttgat ttaaaggaac gattttcttt agatttagac   6900
caatttgcat tgggtcgcaa gtttttgttg caggttggcg tacaacgcaa gcccagacca   6960
ggccttaaac gcccggcctc atcggcatcc tcttcctctt cctcttcagc caaacgtaaa   7020
```

-continued cgtgttaaaa agtaatgtat gttagttttt gtatgcttgt gcacactgtt gtatgcctgt 7080
atgtatatgt ttgtgtatgt actgtatgtg tttttgtgtg tgtgtgtgtt gttgttcctg 7140
tatgtatgag ttatgtatgt ttattattaa taaactatgt ggtgtgtgtg tgtgtgtttt 7200
tgcatgactg catttgtatg acatgtacgg gtgtatgtgg gtattacatt atccccgtag 7260
gtcaagggtg gtgtttcggt ggcgtcccta ttgccctacc catttttttgc agcacaacag 7320 tttatatttg tgctatttag ttatactttg tagcttccat tttgttacag ctgcagccat 7380
tttgagtgca accgatttcg gttcgtgtac ttttagtata tttgccaagt tttaaaccac 7440
aactgccagt tgtttttggc ataaaccatc atttttttat gacatagtgc atacatccgc 7500
ccgcccacgc cttgtacttg gcgcgcctta ccggcgctag tcatacaacc tattagtcat 7560
ttgtacttta acaattgttg gcacactgtt ttccgcccta taataattta actgcttata 7620
ggcatgtatt ttttggcata ttttatctta ctaattgcat agttggcagg tcaaatacta 7680
tgtttttagt gccaagtttc tatcctactt ataaaccatc ttactcatat gcaggtgtgc 7740
tacacaaatg tgttacctaa ccgatttgtg ttctgcctat gcttgcaaca ttttttctta 7800
taacattt 7808

<210> SEQ ID NO 422
<211> LENGTH: 7904
<212> TYPE: DNA
<213> ORGANISM: Human papillomavirus

<400> SEQUENCE: 422
actacaataa ttcatgtata aaactaaggg cgtaaccgaa atcggttgaa ccgaaaccgg 60
ttagtataaa agcagacatt ttatgcacca aaagagaact gcaatgtttc aggacccaca 120
ggagcgaccc agaaagttac cacagttatg cacagagctg caaacaacta tacatgatat 180
aatattagaa tgtgtgtact gcaagcaaca gttactgcga cgtgaggtat atgactttgc 240
ttttcgggat ttatgcatag tatatagaga tgggaatcca tatgctgtat gtgataaatg 300
tttaaagttt tattctaaaa ttagtgagta tagacattat tgttatagtt tgtatggaac 360
aacattagaa cagcaataca acaaaccgtt gtgtgatttg ttaattaggt gtattaactg 420
tcaaaagcca ctgtgtcctg aagaaaagca aagacatctg gacaaaaagc aaagattcca 480
taatataagg ggtcggtgga ccggtcgatg tatgtcttgt tgcagatcat caagaacacg 540
tagagaaacc cagctgtaat catgcatgga gatacaccta cattgcatga atatatgtta 600
gatttgcaac cagagacaac tgatctctac tgttatgagc aattaaatga cagctcagag 660
gaggaggatg aaatagatgg tccagctgga caagcagaac cggacagagc ccattacaat 720
attgtaacct tttgttgcaa gtgtgactct acgcttcggt tgtgcgtaca aagcacacac 780
gtagacattc gtactttgga agacctgtta atgggcacac taggaattgt gtgccccatc 840
tgttctcaga aaccataatc taccatggct gatcctgcag gtaccaatgg ggaagagggt 900
acgggatgta atggatggtt ttatgtagag gctgtagtgg aaaaaaaaac aggggatgct 960
atatcagatg acgagaacga aaatgacagt gatacaggtg aagatttggt agattttata 1020
gtaaatgata atgattattt aacacaggca gaaacagaga cagcacatgc gttgtttact 1080
gcacaggaag caaaacaaca tagagatgca gtacaggttc taaaacgaaa gtatttggta 1140
gtccacttag tgatattagt ggatgtgtag acaataaatat tagtcctaga ttaaaagcta 1200
tatgtataga aaaacaaagt agagctgcaa aaaggagatt atttgaaagc gaagacagcg 1260
ggtatggcaa tactgaagtg gaaactcagc agatgttaca ggtagaaggg cgccatgaga 1320

-continued

```
ctgaaacacc atgtagtcag tatagtggtg gaagtggggg tggttgcagt cagtacagta   1380
gtggaagtgg gggagagggt gttagtgaaa gacacactat atgccaaaca ccacttacaa   1440
atattttaaa tgtactaaaa actagtaatg caaaggcagc aatgttagca aaatttaaag   1500
agttatacgg ggtgagtttt tcagaattag taagaccatt taaaagtaat aaatcaacgt   1560
gttgcgattg gtgtattgct gcatttggac ttacacccag tatagctgac agtataaaaa   1620
cactattaca acaatattgt ttatatttac acattcaaag tttagcatgt tcatggggaa   1680
tggttgtgtt actattagta agatataaat gtggaaaaaa tagagaaaca attgaaaaat   1740
tgctgtctaa actattatgt gtgtctccaa tgtgtatgat gatagagcct ccaaaattgc   1800
gtagtacagc agcagcatta tattggtata aaacaggtat atcaaatatt agtgaagtgt   1860
atggagacac gccagaatgg atacaaagac aaacagtatt acaacatagt tttaatgatt   1920
gtacatttga attatcacag atggtacaat gggcctacga taatgacata gtagacgata   1980
gtgaaattgc atataaatat gcacaattgg cagacactaa tagtaatgca agtgcctttc   2040
taaaaagtaa ttcacaggca aaaattgtaa aggattgtgc aacaatgtgt agacattata   2100
aacgagcaga aaaaaaacaa atgagtatga gtcaatggat aaaatataga tgtgataggg   2160
tagatgatgg aggtgattgg aagcaaattg ttatgttttt aaggtatcaa ggtgtagagt   2220
ttatgtcatt tttaactgca ttaaaaagat tttgcaagg cataccctaaa aaaaattgca   2280
tattactata tggtgcagct aacacaggta aatcattatt tggtatgagt ttaatgaaat   2340
ttctgcaagg gtctgtaata tgttttgtaa attctaaaag ccatttttgg ttacaaccat   2400
tagcagatgc caaaataggt atgttagatg atgctacagt gccctgttgg aactacatag   2460
atgacaattt aagaaatgca ttggatggaa atttagtttc tatggatgta aagcatagac   2520
cattggtaca actaaaatgc cctccattat taattacatc taacattaat gctggtacag   2580
attctaggtg gccttattta cataatagat tggtggtgtt tacatttcct aatgagtttc   2640
catttgacga aaacggaaat ccagtgtatg agcttaatga taagaactgg aaatcctttt   2700
tctcaaggac gtggtccaga ttaagtttgc acgaggacga ggacaaggaa aacgatggag   2760
actctttgcc aacgtttaaa tgtgtgtcag gacaaaatac taacacatta tgaaaatgat   2820
agtacagacc tacgtgacca tatagactat tggaaacaca tgcgcctaga atgtgctatt   2880
tattacaagg ccagagaaat gggatttaaa catattaacc accaagtggt gccaacactg   2940
gctgtatcaa agaataaagc attacaagca attgaactgc aactaacgtt agaaacaata   3000
tataactcac aatatagtaa tgaaaagtgg acattacaag acgttagcct tgaagtgtat   3060
ttaactgcac caacaggatg tataaaaaaa catggatata cagtggaagt gcagtttgat   3120
ggagacatat gcaatacaat gcattataca aactggacac atatatatat ttgtgaagaa   3180
gcatcagtaa ctgtggtaga gggtcaagtt gactattatg gtttatatta tgttcatgaa   3240
ggaatacgaa catattttgt gcagtttaaa gatgatgcag aaaaatatag taaaaataaa   3300
gtatgggaag ttcatgcggg tggtcaggta atattatgtc ctacatctgt gtttagcagc   3360
aacgaagtat cctctcctga aattattagg cagcacttgg ccaaccaccc cgccgcgacc   3420
cataccaaag ccgtcgcctt gggcaccgaa gaaacacaga cgactatcca gcgaccaaga   3480
tcagagccag acaccggaaa cccctgccac accactaagt tgttgcacag agactcagtg   3540
gacagtgctc caatcctcac tgcatttaac agctcacaca aaggacggat taactgtaat   3600
agtaacacta cacccatagt acatttaaaa ggtgatgcta atactttaaa atgtttaaga   3660
tatagattta aaaagcattg tacattgtat actgcagtgt cgtctacatg gcattggaca   3720
```

-continued

```
ggacataatg taaaacataa aagtgcaatt gttacactta catatgatag tgaatggcaa   3780
cgtgaccaat ttttgtctca agttaaaata ccaaaaacta ttacagtgtc tactggattt   3840
atgtctatat gacaaatctt gatactgcat ccacaacatt actggcgtgc tttttgcttt   3900
gctttgtgtg cttttgtgtg tctgcctatt aatacgtccg ctgcttttgt ctgtgtctac   3960
atacacatca ttaataatat tggtattact attgtggata acagcagcct ctgcgtttag   4020
gtgttttatt gtatatatta tatttgttta tataccatta tttttaatac atacacatgc   4080
acgcttttta attacataat gtatatgtac ataatgtaat tgttacatat aattgttgta   4140
taccataact tactattttt tctttttat tttcatatat aatttttttt tttgtttgtt   4200
tgtttgtttt ttaataaact gttattactt aacaatgcga cacaaacgtt ctgcaaaacg   4260
cacaaaacgt gcatcggcta cccaacttta taaaacatgc aaacaggcag gtacatgtcc   4320
acctgacatt atacctaagg ttgaaggcaa aactattgct gaacaaatat tacaatatgg   4380
aagtatgggt gtattttttg gtgggttagg aattggaaca gggtcgggta caggcggacg   4440
cactgggtat attccattgg gaacaaggcc tcccacagct acagatacac ttgctcctgt   4500
aagaccccct ttaacagtag atcctgtggg cccttctgat ccttctatag tttctttagt   4560
ggaagaaact agttttattg atgctggtgc accaacatct gtaccttcca ttcccccaga   4620
tgtatcagga tttagtatta ctacttcaac tgataccaca cctgctatat tagatattaa   4680
taatactgtt actactgtta ctacacataa taatcccact ttcactgacc catctgtatt   4740
gcagcctcca acacctgcag aaactggagg gcattttaca ctttcatcat ccactattag   4800
tacacataat tatgaagaaa ttcctatgga tacatttatt gttagcacaa accctaacac   4860
agtaactagt agcacaccca taccagggtc tcgcccagtg gcacgcctag gattatatag   4920
tcgcacaaca caacaggtta aagttgtaga ccctgctttt gtaaccactc ccactaaact   4980
tattacatat gataatcctg catatgaagg tatagatgtg gataatacat tatatttttc   5040
tagtaatgat aatagtatta atatagctcc agatcctgac tttttggata tagttgcttt   5100
acataggcca gcattaacct ctaggcgtac tggcattagg tacagtagaa ttggtaataa   5160
acaaacacta cgtactcgta gtggaaaatc tataggtgct aaggtacatt attattatga   5220
tttaagtact attgatcctg cagaagaaat agaattacaa actataacac cttctacata   5280
tactaccact tcacatgcag cctcacctac ttctattaat aatggattat atgatattta   5340
tgcagatgac tttattacag atacttctac aaccccggta ccatctgtac cctctacatc   5400
tttatcaggt tatattcctg caaatacaac aattcctttt ggtggtgcat acaatattcc   5460
tttagtatca ggtcctgata tacccattaa tataactgac caagctcctt cattaattcc   5520
tatagttcca gggtctccac aatatacaat tattgctgat gcaggtgact tttatttaca   5580
tcctagttat tacatgttac gaaaacgacg taaacgttta ccatattttt tttcagatgt   5640
ctctttggct gcctagtgag gccactgtct acttgcctcc tgtcccagta tctaaggttg   5700
taagcacgga tgaatatgtt gcacgcacaa acatatatta tcatgcagga acatccagac   5760
tacttgcagt tggacatccc tattttccta ttaaaaaacc taacaataac aaaatattag   5820
ttcctaaagt atcaggatta caatacaggg tatttagaat acatttacct gaccccaata   5880
agtttggttt tcctgacacc tcattttata atccagatac acagcggctg gtttgggcct   5940
gtgtaggtgt tgaggtaggt cgtggtcagc cattaggtgt gggcattagt ggccatcctt   6000
tattaaataa attggatgac acagaaaatg ctagtgctta tgcagcaaat gcaggtgtgg   6060
ataatagaga atgtatatct atggattaca aacaaacaca attgtgttta attggttgca   6120
```

aaccacctat aggggaacac tggggcaaag gatccccatg taccaatgtt gcagtaaatc 6180
caggtgattg tccaccatta gagttaataa acacagttat tcaggatggt gatatggttc 6240
atactggctt tggtgctatg gactttacta cattacaggc taacaaaagt gaagttccac 6300
tggatatttg tacatctatt tgcaaatatc cagattatat taaaatggtg tcagaaccat 6360
atggcgacag cttatttttt tatttacgaa gggaacaaat gtttgttaga catttattta 6420
atagggctgg tactgttggt gaaaatgtac cagacgattt atacattaaa ggctctgggt 6480
ctactgcaaa tttagccagt tcaaattatt ttcctacacc tagtggttct atggttacct 6540
ctgatgccca aatattcaat aaaccttatt ggttacaacg agcacagggc cacaataatg 6600
gcatttgttg gggtaaccaa ctatttgtta ctgttgttga tactacacgc agtacaaata 6660
tgtcattatg tgctgccata tctacttcag aaactacata taaaaatact aactttaagg 6720
agtacctacg acatggggag gaatatgatt tacagtttat ttttcaactg tgcaaaataa 6780
ccttaactgc agacgttatg acatacatac attctatgaa ttccactatt ttggaggact 6840
ggaattttgg tctacaacct cccccaggag gcacactaga agatacttat aggtttgtaa 6900
cccaggcaat tgcttgtcaa aaacatacac ctccagcacc taaagaagat gatcccctta 6960
aaaaatacac tttttgggaa gtaaatttaa aggaaaagtt ttctgcagac ctagatcagt 7020
ttcctttagg acgcaaattt ttactacaag caggattgaa ggccaaacca aaatttacat 7080
taggaaaacg aaaagctaca cccaccacct catctacctc tacaactgct aaacgcaaaa 7140
aacgtaagct gtaagtattg tatgtatgtt gaattagtgt tgtttgttgt gtatatgttt 7200
gtatgtgctt gtatgtgctt gtaaatatta agttgtatgt gtgtttgtat gtatggtata 7260
ataaacacgt gtgtatgtgt ttttaaatgc ttgtgtaact attgtgtcat gcaacataaa 7320
taaacttatt gtttcaacac ctactaattg tgttgtggtt attcattgta tataaactat 7380
atttgctaca tcctgttttt gttttatata tactatattt tgtagcgcca ggcccatttt 7440
gtagcttcaa ccgaattcgg ttgcatgctt tttggcacaa aatgtgtttt tttaaatagt 7500
tctatgtcag caactatggt ttaaacttgt acgtttcctg cttgccatgc gtgccaaatc 7560
cctgttttcc tgacctgcac tgcttgccaa ccattccatt gttttttaca ctgcactatg 7620
tgcaactact gaatcactat gtacattgtg tcatataaaa taaatcacta tgcgccaacg 7680
ccttacatac cgctgttagg cacatatttt tggcttgttt taactaacct aattgcatat 7740
ttggcataag gtttaaactt ctaaggccaa ctaaatgtca ccctagttca tacatgaact 7800
gtgtaaaggt tagtcataca ttgttcattt gtaaaactgc acatgggtgt gtgcaaaccg 7860
attttgggtt acacatttac aagcaactta tataataata ctaa 7904

<210> SEQ ID NO 423
<211> LENGTH: 7857
<212> TYPE: DNA
<213> ORGANISM: Human papillomavirus

<400> SEQUENCE: 423
attaatactt ttaacaattg tagtatataa aaaagggagt aaccgaaaac ggtcgggacc 60
gaaaacggtg tatataaaag atgtgagaaa cacaccacaa tactatggcg cgctttgagg 120
atccaacacg gcgaccctac aagctacctg atctgtgcac ggaactgaac acttcactgc 180
aagacataga aataacctgt gtatattgca agacagtatt ggaacttaca gaggtatttg 240
aatttgcatt taaagattta tttgtggtgt atagagacag tataccccat gctgcatgcc 300
ataaatgtat agatttttat tctagaatta gagaattaag acattattca gactctgtgt 360

-continued atggagacac attggaaaaa ctaactaaca ctgggttata caatttatta ataaggtgcc 420
tgcggtgcca gaaaccgttg aatccagcag aaaaacttag acaccttaat gaaaaacgac 480
gatttcacaa catagctggg cactatagag gccagtgcca ttcgtgctgc aaccgagcac 540
gacaggaacg actccaacga cgcagagaaa cacaagtata atattaagta tgcatggacc 600
taaggcaaca ttgcaagaca ttgtattgca tttagagccc caaaatgaaa ttccggttga 660
ccttctatgt cacgagcaat taagcgactc agaggaagaa aacgatgaaa tagatggagt 720
taatcatcaa catttaccag cccgacgagc cgaaccacaa cgtcacacaa tgttgtgtat 780
gtgttgtaag tgtgaagcca gaattgagct agtagtagaa agctcagcag acgaccttcg 840
agcattccag cagctgtttc tgaacaccct gtcctttgtg tgtccgtggt gtgcatccca 900
gcagtaagca acaatggctg atccagaagg tacagacggg gagggcacgg gttgtaacgg 960
ctggttttat gtacaagcta ttgtagacaa aaaaacagga gatgtaatat cagatgacga 1020
ggacgaaaat gcaacagaca cagggtcgga tatggtagat tttattgata cacaaggaac 1080
attttgtgaa caggcagagc tagagacagc acaggcattg ttccatgcgc aggaggtcca 1140
caatgatgca caagtgttgc atgttttaaa acgaaagttt gcaggaggca gcacagaaaa 1200
cagtccatta ggggagcggc tggaggtgga tacagagtta agtccacggt tacaagaaat 1260
atctttaaat agtgggcaga aaaaggcaaa aaggcggctg tttacaatat cagatagtgg 1320
ctatggctgt tctgaagtgg aagcaacaca gattcaggta actacaaatg gcgaacatgg 1380
cggcaatgta tgtagtggcg gcagtacgga ggctatagac aacgggggca cagagggcaa 1440
caacagcagt gtagacggta caagtgacaa tagcaatata gaaaatgtaa atccacaatg 1500
taccatagca caattaaaag acttgttaaa agtaaacaat aaacaaggag ctatgttagc 1560
agtatttaaa gacacatatg ggctatcatt tacagattta gttagaaatt ttaaaagtga 1620
taaaaccacg tgtacagatt gggttacagc tatatttgga gtaaacccaa caatagcaga 1680
aggatttaaa acactaatac agccatttat attatatgcc catattcaat gtctagactg 1740
taaatgggga gtattaatat tagccctgtt gcgttacaaa tgtggtaaga gtagactaac 1800
agttgctaaa ggtttaagta cgttgttaca cgtacctgaa acttgtatgt taattcaacc 1860
accaaaattg cgaagtagtg ttgcagcact atattggtat agaacaggaa tatcaaatat 1920
tagtgaagta atgggagaca cacctgagtg gatacaaaga cttactatta tacaacatgg 1980
aatagatgat agcaattttg atttgtcaga aatggtacaa tgggcatttg ataatgagct 2040
gacagatgaa agcgatatgg catttgaata tgccttatta gcagacagca acagcaatgc 2100
agctgccttt ttaaaaagca attgccaagc taaatattta aaagattgtg ccacaatgtg 2160
caaacattat aggcgagccc aaaaacgaca aatgaatatg tcacagtgga tacgatttag 2220
atgttcaaaa atagatgaag gggagattg gagaccaata gtgcaattcc tgcgatacca 2280
acaaatagag tttataacat ttttaggagc cttaaaatca tttttaaaag gaacccccaa 2340
aaaaaattgt ttagtatttt gtggaccagc aaatacagga aaatcatatt ttggaatgag 2400
ttttatacac tttatacaag gagcagtaat atcatttgtg aattccacta gtcatttttg 2460
gttggaaccg ttaacagata ctaaggtggc catgttagat gatgcaacga ccacgtgttg 2520
gacatacttt gatacctata tgagaaatgc gttagatggc aatccaataa gtattgatag 2580
aaagcacaaa ccattaatac aactaaaatg tcctccaata ctactaacca caaatataca 2640
tccagcaaag gataatagat ggccatattt agaaagtaga ataacagtat ttgaatttcc 2700
aaatgcattt ccatttgata aaaatggcaa tccagtatat gaaataaatg acaaaaattg 2760
gaaatgtttt tttgaaagga catggtccag attagatttg cacgaggaag aggaagatgc 2820
agacaccgaa ggaaaccctt tcggaacgtt taagttgcgt gcaggacaaa atcatagacc 2880
actatgaaaa tgacagtaaa gacatagaca gccaaataca gtattggcaa ctaatacgtt 2940
gggaaaatgc aatattcttt gcagcaaggg aacatggcat acagacatta aaccaccagg 3000
tggtgccagc ctataacatt tcaaaaagta aagcacataa agctattgaa ctgcaaatgg 3060
ccctacaagg ccttgcacaa agtcgataca aaaccgagga ttggacactg caagacacat 3120
gcgaggaact atggaataca gaacctactc actgctttaa aaaaggtggc caaacagtac 3180
aagtatattt tgatggcaac aaagacaatt gtatgaccta tgtagcatgg gacagtgtgt 3240
attatatgac tgatgcagga acatgggaca aaaccgctac ctgtgtaagt cacaggggat 3300
tgtattatgt aaaggaaggg tacaacacgt tttatataga atttaaaagt gaatgtgaaa 3360
aatatgggaa cacaggtacg tgggaagtac attttgggaa taatgtaatt gattgtaatg 3420
actctatgtg cagtaccagt gacgacacgg tatccgctac tcagcttgtt aaacagctac 3480
agcacacccc ctcaccgtat tccagcaccg tgtccgtggg caccgcaaag acctacggcc 3540
agacgtcggc tgctacacga cctggacact gtggactcgc ggagaagcag cattgtggac 3600
ctgtcaaccc acttctcggt gcagctacac ctacaggcaa caacaaaaga cggaaactct 3660
gtagtggtaa cactacgcct ataatacatt taaaaggtga cagaaacagt ttaaaatgtt 3720
tacggtacag attgcgaaaa catagcgacc actatagaga tatatcatcc acctggcatt 3780
ggacaggtgc aggcaatgaa aaaacaggaa tactgactgt aacataccat agtgaaacac 3840
aaagaacaaa atttttaaat actgttgcaa ttccagatag tgtacaaata ttggtgggat 3900
acatgacaat gtaatacata tgctgtagta ccaatatgtt atcacttatt tttttatttt 3960
gcttttgtgt atgcatgtat gtgtgctgcc atgtcccgct tttgccatct gtctgtatgt 4020
gtgcgtatgc atgggtattg gtatttgtgt atattgtggt aataacgtcc cctgccacag 4080
cattcacagt atatgtattt tgttttttat tgcccatgtt actattgcat atacatgcta 4140
tattgtcttt acagtaattg tataggttgt tttatacagt gtattgtaca ttgtatattt 4200
tgttttatac cttttatgct ttttgtattt ttgtaataaa agtatggtat cccaccgtgc 4260
cgcacgacgc aaacgggctt cggtaactga cttatataaa acatgtaaac aatctggtac 4320
atgtccacct gatgttgttc ctaaggtgga gggcaccacg ttagcagata aaatattgca 4380
atggtcaagc cttggtatat ttttgggtgg acttggcata ggtactggca gtggtacagg 4440
gggtcgtaca gggtacattc cattgggtgg gcgttccaat acagtggtgg atgttggtcc 4500
tacacgtccc ccagtggtta ttgaacctgt gggccccaca gacccatcta ttgttacatt 4560
aatagaggac tccagtgtgg ttacatcagg tgcacctagg cctacgttta ctggcacgtc 4620
tgggtttgat ataacatctg cgggtacaac tacacctgcg gttttggata tcacaccttc 4680
gtctacctct gtgtctattt ccacaaccaa ttttaccaat cctgcatttt ctgatccgtc 4740
cattattgaa gttccacaaa ctggggaggt ggcaggtaat gtatttgttg gtacccctac 4800
atctggaaca catgggtatg aggaaatacc tttacaaaca tttgcttctt ctggtacggg 4860
ggaggaaccc attagtagta ccccattgcc tactgtgcgg cgtgtagcag gtccccgcct 4920
ttacagtagg gcctaccaac aagtgtcagt ggctaaccct gagtttctta cacgtccatc 4980
ctctttaatt acatatgaca acccggcctt tgagcctgtg gacactacat taacatttga 5040
tcctcgtagt gatgttcctg attcagattt tatggatatt atccgtctac ataggcctgc 5100
tttaacatcc aggcgtggga ctgttcgctt tagtagatta ggtcaacggg caactatgtt 5160

-continued

```
tacccgcagc ggtacacaaa taggtgctag ggttcacttt tatcatgata taagtcctat   5220
tgcaccttcc ccagaatata ttgaactgca gcctttagta tctgccacgg aggacaatga   5280
cttgtttgat atatatgcag atgacatgga ccctgcagtg cctgtaccat cgcgttctac   5340
tacctccttt gcattttta aatattcgcc cactatatct tctgcctctt cctatagtaa   5400
tgtaacggtc cctttaacct cctcttggga tgtgcctgta tacacgggtc ctgatattac   5460
attaccatct actacctctg tatggcccat tgtatcaccc acggcccctg cctctacaca   5520
gtatattggt atacatggta cacattatta tttgtggcca ttatattatt ttattcctaa   5580
gaaacgtaaa cgtgttccct attttttgc agatggcttt gtggcggcct agtgacaata   5640
ccgtatatct tccacctcct tctgtggcaa gagttgtaaa taccgatgat tatgtgactc   5700
ccacaagcat attttatcat gctggcagct ctagattatt aactgttggt aatccatatt   5760
ttagggttcc tgcaggtggt ggcaataagc aggatattcc taaggtttct gcataccaat   5820
atagagtatt tagggtgcag ttacctgacc caaataaatt tggtttacct gatactagta   5880
tttataatcc tgaaacacaa cgtttagtgt gggcctgtgc tggagtggaa attggccgtg   5940
gtcagccttt aggtgttggc cttagtgggc atccatttta taataaatta gatgacactg   6000
aaagttccca tgccgccacg tctaatgttt ctgaggacgt tagggacaat gtgtctgtag   6060
attataagca gacacagtta tgtattttgg gctgtgcccc tgctattggg gaacactggg   6120
ctaaaggcac tgcttgtaaa tcgcgtcctt tatcacaggg cgattgcccc cctttagaac   6180
ttaaaaacac agttttggaa gatggtgata tggtagatac tggatatggt gccatggact   6240
ttagtacatt gcaagatact aaatgtgagg taccattgga tatttgtcag tctatttgta   6300
aatatcctga ttatttacaa atgtctgcag atccttatgg ggattccatg tttttttgct   6360
tacggcgtga gcagcttttt gctaggcatt tttggaatag agcaggtact atgggtgaca   6420
ctgtgcctca atccttatat attaaaggca caggtatgcc tgcttcacct ggcagctgtg   6480
tgtattctcc ctctccaagt ggctctattg ttacctctga ctcccagttg tttaataaac   6540
catattggtt acataaggca cagggtcata acaatggtgt ttgctggcat aatcaattat   6600
ttgttactgt ggtagatacc actcccagta ccaatttaac aatatgtgct tctacacagt   6660
ctcctgtacc tgggcaatat gatgctacca aatttaagca gtatagcaga catgttgagg   6720
aatatgattt gcagtttatt tttcagttgt gtactattac tttaactgca gatgttatgt   6780
cctatattca tagtatgaat agcagtattt tagaggattg gaactttggt gttccccccc   6840
ccccaactac tagtttggtg gatacatatc gttttgtaca atctgttgct attacctgtc   6900
aaaaggatgc tgcaccggct gaaaataagg atccctatga taagttaaag ttttggaatg   6960
tggatttaaa ggaaaagttt tctttagact tagatcaata tccccttgga cgtaaatttt   7020
tggttcaggc tggattgcgt cgcaagccca ccataggccc tcgcaaacgt tctgctccat   7080
ctgccactac gtcttctaaa cctgccaagc gtgtgcgtgt acgtgccagg aagtaatatg   7140
tgtgtgtgta tatatatata catctattgt tgtgtttgta tgtcctgtgt ttgtgtttgt   7200
tgtatgattg cattgtatgg tatgtatggt tgttgttgta tgttgtatgt tactatattt   7260
gttggtatgt ggcattaaat aaaatatgtt ttgtggttct gtgtgttatg tggttgcgcc   7320
ctagtgagta acaactgtat ttgtgtttgt ggtatgggtg ttgcttgttg ggctatatat   7380
tgtcctgtat ttcaagttat aaaactgcac accttacagc atccatttta tcctacaatc   7440
ctccattttg ctgtgcaacc gatttcggtt gcctttggct tatgtctgtg gttttctgca   7500
caatacagta cgctggcact attgcaaact ttaatctttt gggcactgct cctacatatt   7560
```

```
ttgaacaatt ggcgcgcctc tttggcgcat ataaggcgca cctggtatta gtcattttcc   7620

tgtccaggtg cgctacaaca attgcttgca taactatatc cactccctaa gtaataaaac   7680

tgcttttagg cacatatttt agtttgtttt tacttaagct aattgcatac ttggcttgta   7740

caactacttt catgtccaac attctgtcta cccttaacat gaactataat atgactaagc   7800

tgtgcataca tagtttatgc aaccgaaata ggttgggcag cacatactat acttttc      7857


<210> SEQ ID NO 424
<211> LENGTH: 155
<212> TYPE: PRT
<213> ORGANISM: Human papilloma virus

<400> SEQUENCE: 424

Met Glu Pro Gln Phe Asn Asn Pro Gln Glu Arg Pro Arg Ser Leu His
1               5                   10                  15

His Leu Ser Glu Val Leu Glu Ile Pro Leu Ile Asp Leu Arg Leu Ser
            20                  25                  30

Cys Val Tyr Cys Lys Lys Glu Leu Thr Arg Ala Glu Val Tyr Asn Phe
        35                  40                  45

Ala Cys Thr Glu Leu Lys Leu Val Tyr Arg Asp Asp Phe Pro Tyr Ala
    50                  55                  60

Val Cys Arg Val Cys Leu Leu Phe Tyr Ser Lys Val Arg Lys Tyr Arg
65                  70                  75                  80

Tyr Tyr Asp Tyr Ser Val Tyr Gly Ala Thr Leu Glu Ser Ile Thr Lys
                85                  90                  95

Lys Gln Leu Cys Asp Leu Leu Ile Arg Cys Tyr Arg Cys Gln Ser Pro
            100                 105                 110

Leu Thr Pro Glu Glu Lys Gln Leu His Cys Asp Arg Lys Arg Arg Phe
        115                 120                 125

His Leu Ile Ala His Gly Trp Thr Gly Ser Cys Leu Gly Cys Trp Arg
    130                 135                 140

Gln Thr Ser Arg Glu Pro Arg Glu Ser Thr Val
145                 150                 155


<210> SEQ ID NO 425
<211> LENGTH: 105
<212> TYPE: PRT
<213> ORGANISM: Human papilloma virus

<400> SEQUENCE: 425

Met His Gly Lys Val Pro Thr Leu Gln Asp Val Val Leu Glu Leu Thr
1               5                   10                  15

Pro Gln Thr Glu Ile Asp Leu Gln Cys Asn Glu Gln Leu Asp Ser Ser
            20                  25                  30

Glu Asp Glu Asp Glu Asp Glu Val Asp His Leu Gln Glu Arg Pro Gln
        35                  40                  45

Gln Ala Arg Gln Ala Lys Gln His Thr Cys Tyr Leu Ile His Val Pro
    50                  55                  60

Cys Cys Glu Cys Lys Phe Val Val Gln Leu Asp Ile Gln Ser Thr Lys
65                  70                  75                  80

Glu Asp Leu Arg Val Val Gln Gln Leu Leu Met Gly Ala Leu Thr Val
                85                  90                  95

Thr Cys Pro Leu Cys Ala Ser Ser Asn
            100                 105


<210> SEQ ID NO 426
<211> LENGTH: 636
```

<212> TYPE: PRT
<213> ORGANISM: Human papilloma virus

<400> SEQUENCE: 426

```
Met Ala Ser Pro Glu Gly Thr Asp Gly Glu Gly Lys Gly Cys Cys Gly
1               5                   10                  15

Trp Phe Glu Val Glu Ala Ile Val Glu Lys Lys Thr Gly Asp Lys Ile
            20                  25                  30

Ser Asp Asp Glu Ser Asp Glu Glu Asp Glu Ile Asp Thr Asp Leu Asp
        35                  40                  45

Gly Phe Ile Asp Asp Ser Tyr Ile Gln Asn Ile Gln Ala Asp Ala Glu
    50                  55                  60

Thr Ser Gln Gln Leu Leu Gln Val Gln Thr Ala His Ala Asp Lys Gln
65                  70                  75                  80

Thr Leu Gln Lys Leu Lys Arg Lys Tyr Ile Ala Ser Pro Leu Arg Asp
                85                  90                  95

Ile Ser Asn Gln Gln Thr Val Cys Arg Glu Gly Val Lys Arg Arg Leu
            100                 105                 110

Ile Leu Ser Asp Leu Gln Asp Ser Gly Tyr Gly Asn Thr Leu Glu Thr
        115                 120                 125

Leu Glu Thr Pro Glu Gln Val Asp Glu Glu Val Gln Gly Arg Gly Cys
    130                 135                 140

Gly Asn Thr Gln Asn Gly Gly Ser Gln Asn Ser Thr Tyr Ser Asn Asn
145                 150                 155                 160

Ser Glu Asp Ser Val Ile His Met Asp Ile Asp Arg Asn Asn Glu Thr
                165                 170                 175

Pro Thr Gln Gln Leu Gln Asp Leu Phe Lys Ser Ser Asn Leu Gln Gly
            180                 185                 190

Lys Leu Tyr Tyr Lys Phe Lys Glu Val Tyr Gly Ile Pro Phe Ser Glu
        195                 200                 205

Leu Val Arg Thr Phe Lys Ser Asp Ser Thr Cys Cys Asn Asp Trp Ile
    210                 215                 220

Cys Ala Ile Phe Gly Val Asn Glu Thr Leu Ala Glu Ala Leu Lys Thr
225                 230                 235                 240

Ile Ile Lys Pro His Cys Met Tyr Tyr His Met Gln Cys Leu Thr Cys
                245                 250                 255

Thr Trp Gly Val Ile Val Met Met Leu Ile Arg Tyr Thr Cys Gly Lys
            260                 265                 270

Asn Arg Lys Thr Ile Ala Lys Ala Leu Ser Ser Ile Leu Asn Val Pro
        275                 280                 285

Gln Glu Gln Met Leu Ile Gln Pro Pro Lys Ile Arg Ser Pro Ala Val
    290                 295                 300

Ala Leu Tyr Phe Tyr Lys Thr Ala Met Ser Asn Ile Ser Asp Val Tyr
305                 310                 315                 320

Gly Asp Thr Pro Glu Trp Ile Gln Arg Gln Thr Gln Leu Gln His Ser
                325                 330                 335

Leu Gln Asp Ser Gln Phe Glu Leu Ser Lys Met Val Gln Trp Ala Phe
            340                 345                 350

Asp Asn Glu Val Thr Asp Asp Ser Gln Ile Ala Phe Gln Tyr Ala Gln
        355                 360                 365

Leu Ala Asp Val Asp Ser Asn Ala Gln Ala Phe Leu Lys Ser Asn Met
    370                 375                 380

Gln Ala Lys Tyr Val Lys Asp Cys Gly Ile Met Cys Arg His Tyr Lys
385                 390                 395                 400
```

```
Arg Ala Gln Gln Gln Gln Met Asn Met Cys Gln Trp Ile Lys His Ile
                405                 410                 415

Cys Ser Lys Thr Asp Glu Gly Gly Asp Trp Lys Pro Ile Val Gln Phe
            420                 425                 430

Leu Arg Tyr Gln Gly Val Asp Phe Ile Ser Phe Leu Ser Tyr Phe Lys
        435                 440                 445

Leu Phe Leu Gln Gly Thr Pro Lys His Asn Cys Leu Val Leu Cys Gly
    450                 455                 460

Pro Pro Asn Thr Gly Lys Ser Cys Phe Ala Met Ser Leu Ile Lys Phe
465                 470                 475                 480

Phe Gln Gly Ser Val Ile Ser Phe Val Asn Ser Gln Ser His Phe Trp
                485                 490                 495

Leu Gln Pro Leu Asp Asn Ala Lys Leu Gly Leu Leu Asp Asp Ala Thr
            500                 505                 510

Glu Ile Cys Trp Lys Tyr Ile Asp Asp Tyr Leu Arg Asn Leu Val Asp
        515                 520                 525

Gly Asn Pro Ile Ser Leu Asp Arg Lys His Lys Gln Leu Val Gln Ile
    530                 535                 540

Lys Cys Pro Pro Leu Leu Ile Thr Thr Asn Ile Asn Pro Met Leu Asp
545                 550                 555                 560

Ala Lys Leu Arg Tyr Leu His Ser Arg Met Leu Val Phe Gln Phe Gln
                565                 570                 575

Asn Pro Phe Pro Leu Asp Asn Asn Gly Asn Pro Val Tyr Glu Leu Ser
            580                 585                 590

Asn Val Asn Trp Lys Cys Phe Phe Thr Arg Thr Trp Ser Arg Leu Asn
        595                 600                 605

Leu Asp Asn Asp Glu Asp Lys Glu Asn Asn Gly Asp Ala Phe Pro Thr
    610                 615                 620

Phe Lys Cys Val Pro Glu Gln Asn Thr Arg Leu Phe
625                 630                 635


<210> SEQ ID NO 427
<211> LENGTH: 310
<212> TYPE: PRT
<213> ORGANISM: Human papilloma virus

<400> SEQUENCE: 427

Met Val Pro Cys Leu Gln Val Cys Lys Ala Lys Ala Cys Ser Ala Ile
1               5                   10                  15

Glu Val Gln Ile Ala Leu Glu Ser Leu Ser Thr Thr Ile Tyr Asn Asn
            20                  25                  30

Glu Glu Trp Thr Leu Arg Asp Thr Cys Glu Glu Leu Trp Leu Thr Glu
        35                  40                  45

Pro Lys Lys Cys Phe Lys Lys Glu Gly Gln His Ile Glu Val Trp Phe
    50                  55                  60

Asp Gly Ser Lys Asn Asn Cys Met Gln Tyr Val Ala Trp Lys Tyr Ile
65                  70                  75                  80

Tyr Tyr Asn Gly Asp Cys Gly Trp Gln Lys Val Cys Ser Gly Val Asp
                85                  90                  95

Tyr Arg Gly Ile Tyr Tyr Val His Asp Gly His Lys Thr Tyr Tyr Thr
            100                 105                 110

Asp Phe Glu Gln Glu Ala Lys Lys Phe Gly Cys Lys Asn Ile Trp Glu
        115                 120                 125

Val His Met Glu Asn Glu Ser Ile Tyr Cys Pro Asp Ser Val Ser Ser
    130                 135                 140
```

Thr Cys Arg Tyr Asn Val Ser Pro Val Glu Thr Val Asn Glu Tyr Asn
145 150 155 160

Thr His Lys Thr Thr Thr Thr Thr Ser Thr Ser Val Gly Asn Gln Asp
165 170 175

Ala Ala Val Ser His Arg Pro Gly Lys Arg Pro Arg Leu Arg Glu Ser
180 185 190

Glu Phe Asp Ser Ser Arg Glu Ser His Ala Lys Cys Val Thr Thr His
195 200 205

Thr His Ile Ser Asp Thr Asp Asn Thr Asp Ser Arg Ser Arg Ser Ile
210 215 220

Asn Asn Asn Asn His Pro Gly Asp Lys Thr Thr Pro Val Val His Leu
225 230 235 240

Lys Gly Glu Pro Asn Arg Leu Lys Cys Cys Arg Tyr Arg Phe Gln Lys
245 250 255

Tyr Lys Thr Leu Phe Val Asp Val Thr Ser Thr Tyr His Trp Thr Ser
260 265 270

Thr Asp Asn Lys Asn Tyr Ser Ile Ile Thr Ile Ile Tyr Lys Asp Glu
275 280 285

Thr Gln Arg Asn Ser Phe Leu Ser His Val Lys Ile Pro Val Val Tyr
290 295 300

Arg Leu Val Trp Asp Lys
305 310

<210> SEQ ID NO 428
<211> LENGTH: 464
<212> TYPE: PRT
<213> ORGANISM: Human papilloma virus

<400> SEQUENCE: 428

Met Val Ala His Arg Ala Thr Arg Arg Lys Arg Ala Ser Ala Thr Gln
1 5 10 15

Leu Tyr Lys Thr Cys Lys Leu Ser Gly Thr Cys Pro Glu Asp Val Val
20 25 30

Asn Lys Ile Glu Gln Lys Thr Trp Ala Asp Lys Ile Leu Gln Trp Gly
35 40 45

Ser Leu Phe Thr Tyr Phe Gly Gly Leu Gly Ile Gly Thr Gly Thr Gly
50 55 60

Ser Gly Gly Arg Ala Gly Tyr Val Pro Leu Gly Ser Arg Pro Ser Thr
65 70 75 80

Ile Val Asp Val Thr Pro Ala Arg Pro Pro Ile Val Val Glu Ser Val
85 90 95

Gly Pro Thr Asp Pro Ser Ile Val Thr Leu Val Glu Glu Ser Ser Val
100 105 110

Ile Glu Ser Gly Ala Gly Ile Pro Asn Phe Thr Gly Ser Gly Gly Phe
115 120 125

Glu Ile Thr Ser Ser Ser Thr Thr Thr Pro Ala Val Leu Asp Ile Thr
130 135 140

Pro Thr Ser Ser Thr Val His Val Ser Ser Thr His Ile Thr Asn Pro
145 150 155 160

Leu Phe Ile Asp Pro Pro Val Ile Glu Ala Pro Gln Thr Gly Glu Val
165 170 175

Ser Gly Asn Ile Leu Ile Ser Thr Pro Thr Ser Gly Ile His Ser Tyr
180 185 190

Glu Glu Ile Pro Met Gln Thr Phe Ala Val His Gly Ser Gly Thr Glu
195 200 205

```
Pro Ile Ser Ser Thr Pro Ile Pro Gly Phe Arg Arg Ile Ala Ala Pro
    210                 215                 220

Arg Leu Tyr Arg Lys Ala Phe Gln Gln Val Lys Val Thr Asp Pro Ala
225                 230                 235                 240

Phe Leu Asp Arg Pro Ala Thr Leu Val Ser Ala Asp Asn Pro Leu Phe
                245                 250                 255

Glu Gly Thr Asp Thr Ser Leu Ala Phe Ser Pro Ser Gly Val Ala Pro
            260                 265                 270

Asp Pro Asp Phe Met Asn Ile Val Ala Leu His Arg Pro Ala Phe Thr
        275                 280                 285

Thr Arg Arg Gly Gly Val Arg Phe Ser Arg Leu Gly Arg Lys Ala Thr
    290                 295                 300

Ile Gln Thr Arg Arg Gly Thr Gln Ile Gly Ala Arg Val His Tyr Tyr
305                 310                 315                 320

Tyr Asp Ile Ser Pro Ile Ala Gln Ala Glu Glu Ile Glu Met Gln Pro
                325                 330                 335

Leu Leu Ser Ala Asn Asn Ser Phe Asp Gly Leu Tyr Asp Ile Tyr Ala
            340                 345                 350

Asn Ile Asp Asp Glu Ala Pro Gly Leu Ser Ser Gln Ser Val Ala Thr
        355                 360                 365

Pro Ser Ala His Leu Pro Ile Lys Pro Ser Thr Leu Ser Phe Ala Ser
    370                 375                 380

Asn Thr Thr Asn Val Thr Ala Pro Leu Gly Asn Val Trp Glu Thr Pro
385                 390                 395                 400

Phe Tyr Ser Gly Pro Asp Ile Val Leu Pro Thr Gly Pro Ser Thr Trp
                405                 410                 415

Pro Phe Val Pro Gln Ser Pro Tyr Asp Val Thr His Asp Val Tyr Ile
            420                 425                 430

Gln Gly Ser Ser Phe Ala Leu Trp Pro Val Tyr Phe Phe Arg Arg Arg
        435                 440                 445

Arg Arg Lys Arg Ile Pro Tyr Phe Phe Ala Asp Gly Asp Val Ala Ala
    450                 455                 460


<210> SEQ ID NO 429
<211> LENGTH: 534
<212> TYPE: PRT
<213> ORGANISM: Human papilloma virus

<400> SEQUENCE: 429

Met Met Leu Pro Met Met Tyr Ile Tyr Arg Asp Pro Pro Leu His Tyr
1               5                   10                  15

Gly Leu Cys Ile Phe Leu Asp Val Gly Ala Val Asn Val Phe Pro Ile
            20                  25                  30

Phe Leu Gln Met Ala Thr Trp Arg Pro Ser Glu Asn Lys Val Tyr Leu
        35                  40                  45

Pro Pro Thr Pro Val Ser Lys Val Val Ala Thr Asp Ser Tyr Val Lys
    50                  55                  60

Arg Thr Ser Ile Phe Tyr His Ala Gly Ser Ser Arg Leu Leu Ala Val
65                  70                  75                  80

Gly His Pro Tyr Tyr Ser Val Thr Lys Asp Asn Thr Lys Thr Asn Ile
                85                  90                  95

Pro Lys Val Ser Ala Tyr Gln Tyr Arg Val Phe Arg Val Arg Leu Pro
            100                 105                 110

Asp Pro Asn Lys Phe Gly Leu Pro Asp Thr Asn Ile Tyr Asn Pro Asp
        115                 120                 125
```

-continued

```
Gln Glu Arg Leu Val Trp Ala Cys Val Gly Leu Glu Val Gly Arg Gly
    130                 135                 140

Gln Pro Leu Gly Ala Gly Leu Ser Gly His Pro Leu Phe Asn Arg Leu
145                 150                 155                 160

Asp Asp Thr Glu Ser Ser Asn Leu Ala Asn Asn Asn Val Ile Glu Asp
                165                 170                 175

Ser Arg Asp Asn Ile Ser Val Asp Gly Lys Gln Thr Gln Leu Cys Ile
            180                 185                 190

Val Gly Cys Thr Pro Ala Met Gly Glu His Trp Thr Lys Gly Ala Val
        195                 200                 205

Cys Lys Ser Thr Gln Val Thr Thr Gly Asp Cys Pro Pro Leu Ala Leu
    210                 215                 220

Ile Asn Thr Pro Ile Glu Asp Gly Asp Met Ile Asp Thr Gly Phe Gly
225                 230                 235                 240

Ala Met Asp Phe Lys Val Leu Gln Glu Ser Lys Ala Glu Val Pro Leu
                245                 250                 255

Asp Ile Val Gln Ser Thr Cys Lys Tyr Pro Asp Tyr Leu Lys Met Ser
            260                 265                 270

Ala Asp Ala Tyr Gly Asp Ser Met Trp Phe Tyr Leu Arg Arg Glu Gln
        275                 280                 285

Leu Phe Ala Arg His Tyr Phe Asn Arg Ala Gly Lys Val Gly Glu Thr
    290                 295                 300

Ile Pro Ala Glu Leu Tyr Leu Lys Gly Ser Asn Gly Arg Glu Pro Pro
305                 310                 315                 320

Pro Ser Ser Val Tyr Val Ala Thr Pro Ser Gly Ser Met Ile Thr Ser
                325                 330                 335

Glu Ala Gln Leu Phe Asn Lys Pro Tyr Trp Leu Gln Arg Ala Gln Gly
            340                 345                 350

His Asn Asn Gly Ile Cys Trp Gly Asn Gln Leu Phe Val Thr Val Val
        355                 360                 365

Asp Thr Thr Arg Ser Thr Asn Met Thr Ile Ser Thr Ala Thr Glu Gln
    370                 375                 380

Leu Ser Lys Tyr Asp Ala Arg Lys Ile Asn Gln Tyr Leu Arg His Val
385                 390                 395                 400

Glu Glu Tyr Glu Leu Gln Phe Val Phe Gln Leu Cys Lys Ile Thr Leu
                405                 410                 415

Ser Ala Glu Val Met Ala Tyr Leu His Asn Met Asn Ala Asn Leu Leu
            420                 425                 430

Glu Asp Trp Asn Ile Gly Leu Ser Pro Pro Val Ala Thr Ser Leu Glu
        435                 440                 445

Asp Lys Tyr Arg Tyr Val Arg Ser Thr Ala Ile Thr Cys Gln Arg Glu
    450                 455                 460

Gln Pro Pro Thr Glu Lys Gln Asp Pro Leu Ala Lys Tyr Lys Phe Trp
465                 470                 475                 480

Asp Val Asn Leu Gln Asp Ser Phe Ser Thr Asp Leu Asp Gln Phe Pro
                485                 490                 495

Leu Gly Arg Lys Phe Leu Met Gln Leu Gly Thr Arg Ser Lys Pro Ala
            500                 505                 510

Val Ala Thr Ser Lys Lys Arg Ser Ala Pro Thr Ser Thr Ser Thr Pro
        515                 520                 525

Ala Lys Arg Lys Arg Arg
    530
```

<210> SEQ ID NO 430

<211> LENGTH: 151
<212> TYPE: PRT
<213> ORGANISM: Human papilloma virus

<400> SEQUENCE: 430

Met Phe Glu Asp Lys Arg Glu Arg Pro Arg Thr Leu His Glu Leu Cys
1 5 10 15

Glu Ala Leu Asn Val Ser Met His Asn Ile Gln Val Val Cys Val Tyr
20 25 30

Cys Lys Lys Glu Leu Cys Arg Ala Asp Val Tyr Asn Val Ala Phe Thr
35 40 45

Glu Ile Lys Ile Val Tyr Arg Asp Asn Asn Pro Tyr Ala Val Cys Lys
50 55 60

Gln Cys Leu Leu Phe Tyr Ser Lys Ile Arg Glu Tyr Arg Arg Tyr Ser
65 70 75 80

Arg Ser Val Tyr Gly Thr Thr Leu Glu Ala Ile Thr Lys Lys Ser Leu
85 90 95

Tyr Asp Leu Ser Ile Arg Cys His Arg Cys Gln Arg Pro Leu Gly Pro
100 105 110

Glu Glu Lys Gln Lys Leu Val Asp Glu Lys Lys Arg Phe His Glu Ile
115 120 125

Ala Gly Arg Trp Thr Gly Gln Cys Ala Asn Cys Trp Gln Arg Thr Arg
130 135 140

Gln Arg Asn Glu Thr Gln Val
145 150

<210> SEQ ID NO 431
<211> LENGTH: 101
<212> TYPE: PRT
<213> ORGANISM: Human papilloma virus

<400> SEQUENCE: 431

Met Arg Gly Asn Val Pro Gln Leu Lys Asp Val Val Leu His Leu Thr
1 5 10 15

Pro Gln Thr Glu Ile Asp Leu Gln Cys Tyr Glu Gln Phe Asp Ser Ser
20 25 30

Glu Glu Glu Asp Glu Val Asp Asn Met Arg Asp Gln Leu Pro Glu Arg
35 40 45

Arg Ala Gly Gln Ala Thr Cys Tyr Arg Ile Glu Ala Pro Cys Cys Arg
50 55 60

Cys Ser Ser Val Val Gln Leu Ala Val Glu Ser Ser Gly Asp Thr Leu
65 70 75 80

Arg Val Val Gln Gln Met Leu Met Gly Glu Leu Ser Leu Val Cys Pro
85 90 95

Cys Cys Ala Asn Asn
100

<210> SEQ ID NO 432
<211> LENGTH: 634
<212> TYPE: PRT
<213> ORGANISM: Human papilloma virus

<400> SEQUENCE: 432

Met Asp Cys Glu Gly Thr Glu Asp Glu Gly Ala Gly Cys Asn Gly Trp
1 5 10 15

Phe Phe Val Glu Ala Ile Val Glu Lys Lys Thr Gly Asp Asn Val Ser
20 25 30

Asp Asp Glu Asp Glu Asn Ala Asp Asp Thr Gly Ser Asp Leu Ile Asn

```
        35                  40                  45

Phe Ile Asp Ser Glu Thr Ser Ile Cys Ser Gln Ala Glu Gln Glu Thr
    50                  55                  60

Ala Arg Ala Leu Phe Gln Ala Gln Glu Leu Gln Ala Asn Lys Glu Ala
65                  70                  75                  80

Val His Gln Leu Lys Arg Lys Phe Leu Val Ser Pro Arg Ser Ser Pro
                85                  90                  95

Leu Gly Asp Ile Thr Asn Gln Asn Asn Thr His Ser His Ser Gln Ala
            100                 105                 110

Asn Glu Ser Gln Val Lys Arg Arg Leu Leu Asp Ser Tyr Pro Asp Ser
        115                 120                 125

Gly Tyr Gly Asn Thr Gln Val Glu Thr Val Glu Ala Thr Leu Gln Val
    130                 135                 140

Asp Gly Gln His Gly Gly Ser Gln Asn Ser Val Cys Ser Ser Gly Gly
145                 150                 155                 160

Gly Ser Val Met Asp Val Glu Thr Thr Glu Ser Cys Ala Asn Val Glu
                165                 170                 175

Leu Asn Ser Ile Cys Glu Val Leu Lys Ser Ser Asn Ala Lys Ala Thr
            180                 185                 190

Leu Met Ala Lys Phe Lys Glu Leu Tyr Gly Ile Ser Tyr Asn Glu Leu
        195                 200                 205

Val Arg Val Phe Lys Ser Asp Lys Thr Cys Cys Ile Asp Trp Val Cys
    210                 215                 220

Ala Leu Phe Gly Val Ser Pro Met Val Ala Glu Asn Leu Lys Thr Leu
225                 230                 235                 240

Ile Lys Pro Phe Cys Met Tyr Tyr His Ile Gln Cys Leu Ser Cys Asp
                245                 250                 255

Trp Gly Thr Ile Val Leu Met Leu Ile Arg Phe Ser Cys Ala Lys Asn
            260                 265                 270

Arg Thr Thr Ile Ala Lys Cys Leu Ser Thr Leu Val Asn Ile Pro Gln
        275                 280                 285

Ser Gln Met Phe Ile Glu Pro Pro Lys Leu Arg Ser Thr Pro Val Ala
    290                 295                 300

Leu Tyr Phe Tyr Arg Thr Gly Ile Ser Asn Ile Ser Asn Thr Tyr Gly
305                 310                 315                 320

Glu Thr Pro Glu Trp Ile Thr Arg Gln Thr Gln Leu Gln His Ser Phe
                325                 330                 335

Glu Asp Ser Thr Phe Glu Leu Ser Gln Met Val Gln Trp Ala Phe Asp
            340                 345                 350

His Glu Val Leu Asp Asp Ser Glu Ile Ala Phe His Tyr Ala Gln Leu
        355                 360                 365

Ala Asp Ile Asp Ser Asn Ala Ala Ala Phe Leu Lys Ser Asn Cys Gln
    370                 375                 380

Ala Lys Tyr Val Lys Asp Cys Gly Thr Met Ala Arg His Tyr Lys Arg
385                 390                 395                 400

Ala Gln Arg Lys Ser Leu Ser Met Ser Ala Trp Ile Arg Tyr Arg Cys
                405                 410                 415

Asp Arg Ala Lys Asp Gly Gly Asn Trp Arg Glu Ile Ala Lys Phe Leu
            420                 425                 430

Arg Tyr Gln Gly Val Asn Phe Met Ser Phe Ile Gln Met Phe Lys Gln
        435                 440                 445

Phe Leu Lys Gly Thr Pro Lys His Asn Cys Ile Val Ile Tyr Gly Pro
    450                 455                 460
```

```
Pro Asn Thr Gly Lys Ser Leu Phe Ala Met Ser Leu Met Lys Phe Met
465                 470                 475                 480

Gln Gly Ser Ile Ile Ser Tyr Val Asn Ser Gly Ser His Phe Trp Leu
                485                 490                 495

Gln Pro Leu Glu Asp Ala Lys Ile Ala Leu Leu Asp Asp Ala Thr Tyr
            500                 505                 510

Gly Cys Trp Thr Tyr Ile Asp Gln Tyr Leu Arg Asn Phe Leu Asp Gly
        515                 520                 525

Asn Pro Cys Ser Ile Asp Arg Lys His Arg Ser Leu Ile Gln Leu Val
    530                 535                 540

Cys Pro Pro Leu Leu Ile Thr Ser Asn Ile Asn Pro Gln Glu Asp Ala
545                 550                 555                 560

Asn Leu Met Tyr Leu His Thr Arg Val Thr Val Leu Lys Phe Leu Asn
                565                 570                 575

Thr Phe Pro Phe Asp Asn Asn Gly Asn Ala Val Tyr Thr Leu Asn Asp
            580                 585                 590

Glu Asn Trp Lys Asn Phe Phe Ser Thr Thr Trp Ser Arg Leu Asp Leu
        595                 600                 605

Glu Glu Glu Glu Asp Lys Glu Asn Gly Asp Pro Met Pro Pro Phe Lys
    610                 615                 620

Cys Val Pro Gly Glu Asn Thr Arg Leu Leu
625                 630


<210> SEQ ID NO 433
<211> LENGTH: 358
<212> TYPE: PRT
<213> ORGANISM: Human papilloma virus

<400> SEQUENCE: 433

Met Glu Thr Leu Cys His Arg Leu Asn Val Cys Gln Glu Lys Ile Leu
1               5                   10                  15

Asp Cys Tyr Glu Leu Asp Ser Asp Lys Leu Val Asp Gln Ile Asn Tyr
            20                  25                  30

Trp Thr Leu Leu Arg Tyr Glu Ala Ala Met Phe Tyr Ala Ala Arg Glu
        35                  40                  45

Arg Asn Leu Arg Thr Ile Asn His Gln Val Val Pro Ala Thr Thr Val
    50                  55                  60

Ser Lys Gln Lys Ala Cys Gln Ala Ile Glu Met His Met Ala Leu Gln
65                  70                  75                  80

Ser Leu Asn Lys Ser Asp Tyr Asn Met Glu Pro Trp Thr Met Arg Glu
                85                  90                  95

Thr Cys Tyr Glu Leu Trp Cys Val Ala Pro Lys Gln Cys Phe Lys Lys
            100                 105                 110

Gly Gly Ile Thr Val Thr Val Ile Phe Asp Gly Asn Lys Asp Asn Ala
        115                 120                 125

Met Asp Tyr Thr Ser Trp Lys Phe Ile Tyr Ile Tyr Asp Asn Asp Lys
    130                 135                 140

Trp Val Lys Thr Asn Gly Asn Val Asp Tyr Thr Gly Ile Tyr Tyr Thr
145                 150                 155                 160

Val Asn Ser Lys Lys Glu Tyr Tyr Val Gln Phe Lys Asp Glu Ala Lys
                165                 170                 175

Ile Tyr Gly Ala Gln Gln Trp Glu Val Tyr Met Tyr Gly Thr Val Ile
            180                 185                 190

Thr Cys Pro Glu Tyr Val Ser Ser Thr Cys Ser Asp Ala Leu Ser Thr
        195                 200                 205
```

```
Thr Thr Thr Val Glu Gln Leu Ser Asn Thr Pro Thr Thr Asn Pro Leu
    210                 215                 220

Thr Thr Cys Val Gly Ala Lys Glu Ala Gln Thr Gln Gln Arg Lys Arg
225                 230                 235                 240

Gln Arg Leu Thr Glu Pro Asp Ser Ser Thr Ile Ser Pro Leu Ser Val
                245                 250                 255

Asp Asn Thr Asn Asn Gln Ile His Cys Gly Ser Gly Ser Thr Asn Thr
            260                 265                 270

Gly Gly His Gln Ser Ala Thr Gln Thr Ala Phe Ile Val His Leu Lys
        275                 280                 285

Gly Asp Thr Asn Cys Leu Lys Cys Phe Arg Tyr Arg Phe Thr Lys His
    290                 295                 300

Lys Gly Leu Tyr Lys Asn Val Ser Ser Thr Trp His Trp Thr Ser Asn
305                 310                 315                 320

Thr Lys Thr Gly Ile Val Thr Ile Val Phe Asp Ser Ala His Gln Arg
                325                 330                 335

Glu Thr Phe Ile Lys Thr Ile Lys Val Pro Pro Ser Val Thr Leu Ser
            340                 345                 350

Leu Gly Ile Met Thr Leu
        355


<210> SEQ ID NO 434
<211> LENGTH: 87
<212> TYPE: PRT
<213> ORGANISM: Human papilloma virus

<400> SEQUENCE: 434

Met Tyr Leu Val Pro Ala Ala Thr Arg Tyr Pro Leu Leu Gln Leu Leu
1               5                   10                  15

Asn Asn Tyr Gln Thr Pro Gln Arg Pro Ile Pro Leu Pro Pro Ala Trp
            20                  25                  30

Ala Pro Lys Lys Pro Arg His Asn Ser Glu Asn Asp Ser Asp Leu Leu
        35                  40                  45

Ser Pro Thr Pro Pro Gln Ser Pro His Cys Pro Trp Thr Ile Gln Thr
    50                  55                  60

Thr Lys Tyr Thr Val Glu Val Glu Ala Leu Thr Leu Glu Gly Thr Lys
65                  70                  75                  80

Val Gln Leu Arg Leu Arg Leu
                85


<210> SEQ ID NO 435
<211> LENGTH: 468
<212> TYPE: PRT
<213> ORGANISM: Human papilloma virus

<400> SEQUENCE: 435

Met Val Ala Thr Arg Ala Arg Arg Arg Lys Arg Ala Ser Val Thr Gln
1               5                   10                  15

Leu Tyr Ser Thr Cys Lys Ala Ala Gly Thr Cys Pro Pro Asp Val Val
            20                  25                  30

Asn Lys Val Glu Gly Thr Thr Leu Ala Asp Lys Ile Leu Gln Trp Ser
        35                  40                  45

Gly Leu Gly Ile Phe Leu Gly Gly Leu Gly Ile Gly Thr Gly Ser Gly
    50                  55                  60

Ser Gly Gly Arg Thr Gly Tyr Ile Pro Leu Gly Gly Gly Gly Arg Pro
65                  70                  75                  80

Gly Val Val Asp Ile Ala Pro Ala Arg Pro Pro Ile Ile Ile Asp Leu
```

-continued

```
                85                  90                  95

Trp His His Thr Glu Pro Ser Ile Val Asn Leu Val Glu Asp Ser Ser
            100                 105                 110

Ile Ile Gln Ser Gly Ser Pro Ile Pro Thr Phe Thr Gly Thr Asp Gly
        115                 120                 125

Phe Glu Ile Thr Ser Ser Ser Thr Thr Thr Pro Ala Val Leu Asp Ile
    130                 135                 140

Thr Pro Ser Ala Gly Thr Val His Val Ser Ser Thr Asn Ile Glu Asn
145                 150                 155                 160

Pro Leu Tyr Ile Glu Pro Pro Ser Ile Glu Ala Pro Gln Ser Gly Glu
                165                 170                 175

Val Ser Asp Ile Tyr Leu Leu Val His Tyr Ser Gly Thr His Gly Tyr
            180                 185                 190

Glu Glu Ile Pro Met Glu Val Phe Ala Ser Asn Val Ser Thr Gly Thr
        195                 200                 205

Glu Pro Ile Ser Ser Thr Pro Thr Pro Gly Val Ser Arg Ile Ala Ala
    210                 215                 220

Pro Arg Leu Tyr Ser Lys Ser Tyr Thr Gln Val Lys Val Thr Asn Pro
225                 230                 235                 240

Asp Phe Ile Ser Lys Pro Ser Thr Phe Val Thr Phe Asn Asn Pro Ala
                245                 250                 255

Phe Glu Pro Ile Asp Thr Ser Ile Thr Phe Glu Glu Pro Asp Ala Val
            260                 265                 270

Ala Pro Asp Pro Asp Phe Leu Asp Ile Ile Thr Leu His Arg Pro Ala
        275                 280                 285

Leu Thr Ser Arg Arg Gly Thr Val Arg Phe Ser Arg Leu Gly Gln Lys
    290                 295                 300

Ala Thr Met Arg Thr Arg Ser Gly Lys Gln Ile Gly Ala Arg Val His
305                 310                 315                 320

Tyr Tyr His Asp Ile Ser Arg Ile Ala Pro Ala Asp Glu Leu Glu Met
                325                 330                 335

Gln Pro Leu Leu Ser Pro Ser Asn Asn Tyr Ser Tyr Asp Ile Tyr Ala
            340                 345                 350

Asp Leu Asp Glu Ala Glu Thr Gly Phe Ile Gln Pro Thr His Thr Thr
        355                 360                 365

Pro Met Ser His Ser Ser Leu Ser Arg Gln Leu Pro Ser Leu Ser Ser
    370                 375                 380

Ser Met Ser Ser Ser Tyr Ala Asn Val Thr Ile Pro Phe Ser Thr Thr
385                 390                 395                 400

Tyr Ser Val Pro Ile His Thr Gly Pro Asp Val Val Leu Pro Thr Ser
                405                 410                 415

Pro Thr Val Trp Pro Tyr Val Pro His Thr Ser Ile Asp Thr Lys His
            420                 425                 430

Ser Ile Val Ile Leu Gly Gly Asp Tyr Tyr Leu Trp Pro Tyr Thr His
        435                 440                 445

Leu Leu Arg Lys Arg Arg Lys Arg Ile Pro Tyr Phe Phe Thr Asp Gly
    450                 455                 460

Ile Val Ala His
465
```

<210> SEQ ID NO 436
<211> LENGTH: 504
<212> TYPE: PRT
<213> ORGANISM: Human papilloma virus

<400> SEQUENCE: 436

Met Ala Leu Trp Arg Thr Asn Asp Ser Lys Val Tyr Leu Pro Pro Ala
1               5                   10                  15

Pro Val Ser Arg Ile Val Asn Thr Glu Glu Tyr Ile Thr Arg Thr Gly
            20                  25                  30

Ile Tyr Tyr Tyr Ala Gly Ser Ser Arg Leu Ile Thr Leu Gly His Pro
        35                  40                  45

Tyr Phe Pro Ile Pro Lys Thr Ser Thr Arg Ala Ala Ile Pro Lys Val
    50                  55                  60

Ser Ala Phe Gln Tyr Arg Val Phe Arg Val Gln Leu Pro Asp Pro Asn
65                  70                  75                  80

Lys Phe Gly Leu Pro Asp Pro Asn Leu Tyr Asn Pro Asp Thr Asp Arg
                85                  90                  95

Leu Val Trp Gly Cys Val Gly Val Glu Val Gly Arg Gly Gln Pro Leu
            100                 105                 110

Gly Val Gly Leu Ser Gly His Pro Leu Phe Asn Lys Tyr Asp Asp Thr
        115                 120                 125

Glu Asn Ser Arg Ile Ala Asn Gly Asn Ala Gln Gln Asp Val Arg Asp
    130                 135                 140

Asn Thr Ser Val Asp Asn Lys Gln Thr Gln Leu Cys Ile Ile Gly Cys
145                 150                 155                 160

Ala Pro Pro Ile Gly Glu His Trp Gly Ile Gly Thr Thr Cys Lys Asn
                165                 170                 175

Thr Pro Val Pro Pro Gly Asp Cys Pro Pro Leu Glu Leu Val Ser Ser
            180                 185                 190

Val Ile Gln Asp Gly Asp Met Ile Asp Thr Gly Phe Gly Ala Met Asp
        195                 200                 205

Phe Ala Ala Leu Gln Ala Thr Lys Ser Asp Val Pro Leu Asp Ile Ser
    210                 215                 220

Gln Ser Val Cys Lys Tyr Pro Asp Tyr Leu Lys Met Ser Ala Asp Thr
225                 230                 235                 240

Tyr Gly Asn Ser Met Phe Phe His Leu Arg Arg Glu Gln Ile Phe Ala
                245                 250                 255

Arg His Tyr Tyr Asn Lys Leu Val Gly Val Gly Glu Asp Ile Pro Asn
            260                 265                 270

Asp Tyr Tyr Ile Lys Gly Ser Gly Asn Gly Arg Asp Pro Ile Glu Ser
        275                 280                 285

Tyr Ile Tyr Ser Ala Thr Pro Ser Gly Ser Met Ile Thr Ser Asp Ser
    290                 295                 300

Gln Ile Phe Asn Lys Pro Tyr Trp Leu His Arg Ala Gln Gly His Asn
305                 310                 315                 320

Asn Gly Ile Cys Trp Asn Asn Gln Leu Phe Ile Thr Cys Val Asp Thr
                325                 330                 335

Thr Arg Ser Thr Asn Leu Thr Ile Ser Thr Ala Thr Ala Ala Val Ser
            340                 345                 350

Pro Thr Phe Thr Pro Ser Asn Phe Lys Gln Tyr Ile Arg His Gly Glu
        355                 360                 365

Glu Tyr Glu Leu Gln Phe Ile Phe Gln Leu Cys Lys Ile Thr Leu Thr
    370                 375                 380

Thr Glu Val Met Ala Tyr Leu His Thr Met Asp Pro Thr Ile Leu Glu
385                 390                 395                 400

Gln Trp Asn Phe Gly Leu Thr Leu Pro Pro Ser Ala Ser Leu Glu Asp
                405                 410                 415

Ala Tyr Arg Phe Val Arg Asn Ala Ala Thr Ser Cys Gln Lys Asp Thr
420 425 430

Pro Pro Gln Ala Lys Pro Asp Pro Leu Ala Lys Tyr Lys Phe Trp Asp
435 440 445

Val Asp Leu Lys Glu Arg Phe Ser Leu Asp Leu Asp Gln Phe Ala Leu
450 455 460

Gly Arg Lys Phe Leu Leu Gln Val Gly Val Gln Arg Lys Pro Arg Pro
465 470 475 480

Gly Leu Lys Arg Pro Ala Ser Ser Ala Ser Ser Ser Ser Ser Ser Ser
485 490 495

Ala Lys Arg Lys Arg Val Lys Lys
500

<210> SEQ ID NO 437
<211> LENGTH: 158
<212> TYPE: PRT
<213> ORGANISM: Human papilloma virus

<400> SEQUENCE: 437

Met His Gln Lys Arg Thr Ala Met Phe Gln Asp Pro Gln Glu Arg Pro
1 5 10 15

Arg Lys Leu Pro Gln Leu Cys Thr Glu Leu Gln Thr Thr Ile His Asp
20 25 30

Ile Ile Leu Glu Cys Val Tyr Cys Lys Gln Gln Leu Leu Arg Arg Glu
35 40 45

Val Tyr Asp Phe Ala Phe Arg Asp Leu Cys Ile Val Tyr Arg Asp Gly
50 55 60

Asn Pro Tyr Ala Val Cys Asp Lys Cys Leu Lys Phe Tyr Ser Lys Ile
65 70 75 80

Ser Glu Tyr Arg His Tyr Cys Tyr Ser Leu Tyr Gly Thr Thr Leu Glu
85 90 95

Gln Gln Tyr Asn Lys Pro Leu Cys Asp Leu Leu Ile Arg Cys Ile Asn
100 105 110

Cys Gln Lys Pro Leu Cys Pro Glu Glu Lys Gln Arg His Leu Asp Lys
115 120 125

Lys Gln Arg Phe His Asn Ile Arg Gly Arg Trp Thr Gly Arg Cys Met
130 135 140

Ser Cys Cys Arg Ser Ser Arg Thr Arg Arg Glu Thr Gln Leu
145 150 155

<210> SEQ ID NO 438
<211> LENGTH: 98
<212> TYPE: PRT
<213> ORGANISM: Human papilloma virus

<400> SEQUENCE: 438

Met His Gly Asp Thr Pro Thr Leu His Glu Tyr Met Leu Asp Leu Gln
1 5 10 15

Pro Glu Thr Thr Asp Leu Tyr Cys Tyr Glu Gln Leu Asn Asp Ser Ser
20 25 30

Glu Glu Glu Asp Glu Ile Asp Gly Pro Ala Gly Gln Ala Glu Pro Asp
35 40 45

Arg Ala His Tyr Asn Ile Val Thr Phe Cys Cys Lys Cys Asp Ser Thr
50 55 60

Leu Arg Leu Cys Val Gln Ser Thr His Val Asp Ile Arg Thr Leu Glu
65 70 75 80

Asp Leu Leu Met Gly Thr Leu Gly Ile Val Cys Pro Ile Cys Ser Gln

```
                85                  90                  95

Lys Pro


<210> SEQ ID NO 439
<211> LENGTH: 649
<212> TYPE: PRT
<213> ORGANISM: Human papilloma virus

<400> SEQUENCE: 439

Met Ala Asp Pro Ala Gly Thr Asn Gly Glu Glu Gly Thr Gly Cys Asn
1               5                   10                  15

Gly Trp Phe Tyr Val Glu Ala Val Val Glu Lys Lys Thr Gly Asp Ala
            20                  25                  30

Ile Ser Asp Asp Glu Asn Glu Asn Asp Ser Asp Thr Gly Glu Asp Leu
        35                  40                  45

Val Asp Phe Ile Val Asn Asp Asn Asp Tyr Leu Thr Gln Ala Glu Thr
    50                  55                  60

Glu Thr Ala His Ala Leu Phe Thr Ala Gln Glu Ala Lys Gln His Arg
65                  70                  75                  80

Asp Ala Val Gln Val Leu Lys Arg Lys Tyr Leu Val Ser Pro Leu Ser
                85                  90                  95

Asp Ile Ser Gly Cys Val Asp Asn Asn Ile Ser Pro Arg Leu Lys Ala
            100                 105                 110

Ile Cys Ile Glu Lys Gln Ser Arg Ala Ala Lys Arg Arg Leu Phe Glu
        115                 120                 125

Ser Glu Asp Ser Gly Tyr Gly Asn Thr Glu Val Glu Thr Gln Gln Met
    130                 135                 140

Leu Gln Val Glu Gly Arg His Glu Thr Glu Thr Pro Cys Ser Gln Tyr
145                 150                 155                 160

Ser Gly Gly Ser Gly Gly Gly Cys Ser Gln Tyr Ser Ser Gly Ser Gly
                165                 170                 175

Gly Glu Gly Val Ser Glu Arg His Thr Ile Cys Gln Thr Pro Leu Thr
            180                 185                 190

Asn Ile Leu Asn Val Leu Lys Thr Ser Asn Ala Lys Ala Ala Met Leu
        195                 200                 205

Ala Lys Phe Lys Glu Leu Tyr Gly Val Ser Phe Ser Glu Leu Val Arg
    210                 215                 220

Pro Phe Lys Ser Asn Lys Ser Thr Cys Cys Asp Trp Cys Ile Ala Ala
225                 230                 235                 240

Phe Gly Leu Thr Pro Ser Ile Ala Asp Ser Ile Lys Thr Leu Leu Gln
                245                 250                 255

Gln Tyr Cys Leu Tyr Leu His Ile Gln Ser Leu Ala Cys Ser Trp Gly
            260                 265                 270

Met Val Val Leu Leu Leu Val Arg Tyr Lys Cys Gly Lys Asn Arg Glu
        275                 280                 285

Thr Ile Glu Lys Leu Leu Ser Lys Leu Leu Cys Val Ser Pro Met Cys
    290                 295                 300

Met Met Ile Glu Pro Pro Lys Leu Arg Ser Thr Ala Ala Ala Leu Tyr
305                 310                 315                 320

Trp Tyr Lys Thr Gly Ile Ser Asn Ile Ser Glu Val Tyr Gly Asp Thr
                325                 330                 335

Pro Glu Trp Ile Gln Arg Gln Thr Val Leu Gln His Ser Phe Asn Asp
            340                 345                 350

Cys Thr Phe Glu Leu Ser Gln Met Val Gln Trp Ala Tyr Asp Asn Asp
        355                 360                 365
```

```
Ile Val Asp Asp Ser Glu Ile Ala Tyr Lys Tyr Ala Gln Leu Ala Asp
    370                 375                 380

Thr Asn Ser Asn Ala Ser Ala Phe Leu Lys Ser Asn Ser Gln Ala Lys
385                 390                 395                 400

Ile Val Lys Asp Cys Ala Thr Met Cys Arg His Tyr Lys Arg Ala Glu
                405                 410                 415

Lys Lys Gln Met Ser Met Ser Gln Trp Ile Lys Tyr Arg Cys Asp Arg
            420                 425                 430

Val Asp Asp Gly Gly Asp Trp Lys Gln Ile Val Met Phe Leu Arg Tyr
        435                 440                 445

Gln Gly Val Glu Phe Met Ser Phe Leu Thr Ala Leu Lys Arg Phe Leu
    450                 455                 460

Gln Gly Ile Pro Lys Lys Asn Cys Ile Leu Leu Tyr Gly Ala Ala Asn
465                 470                 475                 480

Thr Gly Lys Ser Leu Phe Gly Met Ser Leu Met Lys Phe Leu Gln Gly
                485                 490                 495

Ser Val Ile Cys Phe Val Asn Ser Lys Ser His Phe Trp Leu Gln Pro
            500                 505                 510

Leu Ala Asp Ala Lys Ile Gly Met Leu Asp Asp Ala Thr Val Pro Cys
        515                 520                 525

Trp Asn Tyr Ile Asp Asp Asn Leu Arg Asn Ala Leu Asp Gly Asn Leu
    530                 535                 540

Val Ser Met Asp Val Lys His Arg Pro Leu Val Gln Leu Lys Cys Pro
545                 550                 555                 560

Pro Leu Leu Ile Thr Ser Asn Ile Asn Ala Gly Thr Asp Ser Arg Trp
                565                 570                 575

Pro Tyr Leu His Asn Arg Leu Val Val Phe Thr Phe Pro Asn Glu Phe
            580                 585                 590

Pro Phe Asp Glu Asn Gly Asn Pro Val Tyr Glu Leu Asn Asp Lys Asn
        595                 600                 605

Trp Lys Ser Phe Phe Ser Arg Thr Trp Ser Arg Leu Ser Leu His Glu
    610                 615                 620

Asp Glu Asp Lys Glu Asn Asp Gly Asp Ser Leu Pro Thr Phe Lys Cys
625                 630                 635                 640

Val Ser Gly Gln Asn Thr Asn Thr Leu
                645
```

<210> SEQ ID NO 440
<211> LENGTH: 365
<212> TYPE: PRT
<213> ORGANISM: Human papilloma virus

<400> SEQUENCE: 440

```
Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95
```

```
Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
        275                 280                 285

Val His Leu Lys Gly Asp Ala Asn Thr Leu Lys Cys Leu Arg Tyr Arg
    290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile
            340                 345                 350

Pro Lys Thr Ile Thr Val Ser Thr Gly Phe Met Ser Ile
        355                 360                 365
```

```
<210> SEQ ID NO 441
<211> LENGTH: 95
<212> TYPE: PRT
<213> ORGANISM: Human papilloma virus

<400> SEQUENCE: 441

Tyr Tyr Val Leu His Leu Cys Leu Ala Ala Thr Lys Tyr Pro Leu Leu
1               5                   10                  15

Lys Leu Leu Gly Ser Thr Trp Pro Thr Thr Pro Pro Arg Pro Ile Pro
            20                  25                  30

Lys Pro Ser Pro Trp Ala Pro Lys Lys His Arg Arg Leu Ser Ser Asp
        35                  40                  45

Gln Asp Gln Ser Gln Thr Pro Glu Thr Pro Ala Thr Pro Leu Ser Cys
    50                  55                  60

Cys Thr Glu Thr Gln Trp Thr Val Leu Gln Ser Ser Leu His Leu Thr
65                  70                  75                  80

Ala His Thr Lys Asp Gly Leu Thr Val Ile Val Thr Leu His Pro
                85                  90                  95

<210> SEQ ID NO 442
```

```
<211> LENGTH: 78
<212> TYPE: PRT
<213> ORGANISM: Human papilloma virus

<400> SEQUENCE: 442

Tyr Cys Ile His Asn Ile Thr Gly Val Leu Phe Ala Leu Leu Cys Val
1               5                   10                  15

Leu Leu Cys Val Cys Leu Leu Ile Arg Pro Leu Leu Leu Ser Val Ser
            20                  25                  30

Thr Tyr Thr Ser Leu Ile Ile Leu Val Leu Leu Leu Trp Ile Thr Ala
        35                  40                  45

Ala Ser Ala Phe Arg Cys Phe Ile Val Tyr Ile Ile Phe Val Tyr Ile
    50                  55                  60

Pro Leu Phe Leu Ile His Thr His Ala Arg Phe Leu Ile Thr
65                  70                  75


<210> SEQ ID NO 443
<211> LENGTH: 473
<212> TYPE: PRT
<213> ORGANISM: Human papilloma virus

<400> SEQUENCE: 443

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270
```

Asn Ser Ile Asn Ile Ala Pro Asp Pro Asp Phe Leu Asp Ile Val Ala
275 280 285

Leu His Arg Pro Ala Leu Thr Ser Arg Arg Thr Gly Ile Arg Tyr Ser
290 295 300

Arg Ile Gly Asn Lys Gln Thr Leu Arg Thr Arg Ser Gly Lys Ser Ile
305 310 315 320

Gly Ala Lys Val His Tyr Tyr Tyr Asp Leu Ser Thr Ile Asp Pro Ala
325 330 335

Glu Glu Ile Glu Leu Gln Thr Ile Thr Pro Ser Thr Tyr Thr Thr Thr
340 345 350

Ser His Ala Ala Ser Pro Thr Ser Ile Asn Asn Gly Leu Tyr Asp Ile
355 360 365

Tyr Ala Asp Asp Phe Ile Thr Asp Thr Ser Thr Thr Pro Val Pro Ser
370 375 380

Val Pro Ser Thr Ser Leu Ser Gly Tyr Ile Pro Ala Asn Thr Thr Ile
385 390 395 400

Pro Phe Gly Gly Ala Tyr Asn Ile Pro Leu Val Ser Gly Pro Asp Ile
405 410 415

Pro Ile Asn Ile Thr Asp Gln Ala Pro Ser Leu Ile Pro Ile Val Pro
420 425 430

Gly Ser Pro Gln Tyr Thr Ile Ile Ala Asp Ala Gly Asp Phe Tyr Leu
435 440 445

His Pro Ser Tyr Tyr Met Leu Arg Lys Arg Arg Lys Arg Leu Pro Tyr
450 455 460

Phe Phe Ser Asp Val Ser Leu Ala Ala
465 470

<210> SEQ ID NO 444
<211> LENGTH: 531
<212> TYPE: PRT
<213> ORGANISM: Human papilloma virus

<400> SEQUENCE: 444

Met Gln Val Thr Phe Ile Tyr Ile Leu Val Ile Thr Cys Tyr Glu Asn
1 5 10 15

Asp Val Asn Val Tyr His Ile Phe Phe Gln Met Ser Leu Trp Leu Pro
20 25 30

Ser Glu Ala Thr Val Tyr Leu Pro Pro Val Pro Val Ser Lys Val Val
35 40 45

Ser Thr Asp Glu Tyr Val Ala Arg Thr Asn Ile Tyr Tyr His Ala Gly
50 55 60

Thr Ser Arg Leu Leu Ala Val Gly His Pro Tyr Phe Pro Ile Lys Lys
65 70 75 80

Pro Asn Asn Asn Lys Ile Leu Val Pro Lys Val Ser Gly Leu Gln Tyr
85 90 95

Arg Val Phe Arg Ile His Leu Pro Asp Pro Asn Lys Phe Gly Phe Pro
100 105 110

Asp Thr Ser Phe Tyr Asn Pro Asp Thr Gln Arg Leu Val Trp Ala Cys
115 120 125

Val Gly Val Glu Val Gly Arg Gly Gln Pro Leu Gly Val Gly Ile Ser
130 135 140

Gly His Pro Leu Leu Asn Lys Leu Asp Asp Thr Glu Asn Ala Ser Ala
145 150 155 160

Tyr Ala Ala Asn Ala Gly Val Asp Asn Arg Glu Cys Ile Ser Met Asp
165 170 175

Tyr Lys Gln Thr Gln Leu Cys Leu Ile Gly Cys Lys Pro Pro Ile Gly
180 185 190

Glu His Trp Gly Lys Gly Ser Pro Cys Thr Asn Val Ala Val Asn Pro
195 200 205

Gly Asp Cys Pro Pro Leu Glu Leu Ile Asn Thr Val Ile Gln Asp Gly
210 215 220

Asp Met Val His Thr Gly Phe Gly Ala Met Asp Phe Thr Thr Leu Gln
225 230 235 240

Ala Asn Lys Ser Glu Val Pro Leu Asp Ile Cys Thr Ser Ile Cys Lys
245 250 255

Tyr Pro Asp Tyr Ile Lys Met Val Ser Glu Pro Tyr Gly Asp Ser Leu
260 265 270

Phe Phe Tyr Leu Arg Arg Glu Gln Met Phe Val Arg His Leu Phe Asn
275 280 285

Arg Ala Gly Thr Val Gly Glu Asn Val Pro Asp Asp Leu Tyr Ile Lys
290 295 300

Gly Ser Gly Ser Thr Ala Asn Leu Ala Ser Ser Asn Tyr Phe Pro Thr
305 310 315 320

Pro Ser Gly Ser Met Val Thr Ser Asp Ala Gln Ile Phe Asn Lys Pro
325 330 335

Tyr Trp Leu Gln Arg Ala Gln Gly His Asn Asn Gly Ile Cys Trp Gly
340 345 350

Asn Gln Leu Phe Val Thr Val Val Asp Thr Thr Arg Ser Thr Asn Met
355 360 365

Ser Leu Cys Ala Ala Ile Ser Thr Ser Glu Thr Thr Tyr Lys Asn Thr
370 375 380

Asn Phe Lys Glu Tyr Leu Arg His Gly Glu Glu Tyr Asp Leu Gln Phe
385 390 395 400

Ile Phe Gln Leu Cys Lys Ile Thr Leu Thr Ala Asp Val Met Thr Tyr
405 410 415

Ile His Ser Met Asn Ser Thr Ile Leu Glu Asp Trp Asn Phe Gly Leu
420 425 430

Gln Pro Pro Pro Gly Gly Thr Leu Glu Asp Thr Tyr Arg Phe Val Thr
435 440 445

Gln Ala Ile Ala Cys Gln Lys His Thr Pro Pro Ala Pro Lys Glu Asp
450 455 460

Asp Pro Leu Lys Lys Tyr Thr Phe Trp Glu Val Asn Leu Lys Glu Lys
465 470 475 480

Phe Ser Ala Asp Leu Asp Gln Phe Pro Leu Gly Arg Lys Phe Leu Leu
485 490 495

Gln Ala Gly Leu Lys Ala Lys Pro Lys Phe Thr Leu Gly Lys Arg Lys
500 505 510

Ala Thr Pro Thr Thr Ser Ser Thr Ser Thr Thr Ala Lys Arg Lys Lys
515 520 525

Arg Lys Leu
530

<210> SEQ ID NO 445
<211> LENGTH: 158
<212> TYPE: PRT
<213> ORGANISM: Human papilloma virus

<400> SEQUENCE: 445

Met Ala Arg Phe Glu Asp Pro Thr Arg Arg Pro Tyr Lys Leu Pro Asp
1 5 10 15

```
Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Phe Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Arg Glu Thr Gln Val
145                 150                 155


<210> SEQ ID NO 446
<211> LENGTH: 105
<212> TYPE: PRT
<213> ORGANISM: Human papilloma virus

<400> SEQUENCE: 446

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105


<210> SEQ ID NO 447
<211> LENGTH: 657
<212> TYPE: PRT
<213> ORGANISM: Human papilloma virus

<400> SEQUENCE: 447

Met Ala Asp Pro Glu Gly Thr Asp Gly Glu Gly Thr Gly Cys Asn Gly
1               5                   10                  15

Trp Phe Tyr Val Gln Ala Ile Val Asp Lys Lys Thr Gly Asp Val Ile
            20                  25                  30

Ser Asp Asp Glu Asp Glu Asn Ala Thr Asp Thr Gly Ser Asp Met Val
        35                  40                  45

Asp Phe Ile Asp Thr Gln Gly Thr Phe Cys Glu Gln Ala Glu Leu Glu
    50                  55                  60

Thr Ala Gln Ala Leu Phe His Ala Gln Glu Val His Asn Asp Ala Gln
65                  70                  75                  80

Val Leu His Val Leu Lys Arg Lys Phe Ala Gly Gly Ser Thr Glu Asn
```

```
                85                  90                  95

Ser Pro Leu Gly Glu Arg Leu Glu Val Asp Thr Glu Leu Ser Pro Arg
            100                 105                 110

Leu Gln Glu Ile Ser Leu Asn Ser Gly Gln Lys Lys Ala Lys Arg Arg
        115                 120                 125

Leu Phe Thr Ile Ser Asp Ser Gly Tyr Gly Cys Ser Glu Val Glu Ala
    130                 135                 140

Thr Gln Ile Gln Val Thr Thr Asn Gly Glu His Gly Gly Asn Val Cys
145                 150                 155                 160

Ser Gly Gly Ser Thr Glu Ala Ile Asp Asn Gly Gly Thr Glu Gly Asn
                165                 170                 175

Asn Ser Ser Val Asp Gly Thr Ser Asp Asn Ser Asn Ile Glu Asn Val
            180                 185                 190

Asn Pro Gln Cys Thr Ile Ala Gln Leu Lys Asp Leu Leu Lys Val Asn
        195                 200                 205

Asn Lys Gln Gly Ala Met Leu Ala Val Phe Lys Asp Thr Tyr Gly Leu
    210                 215                 220

Ser Phe Thr Asp Leu Val Arg Asn Phe Lys Ser Asp Lys Thr Thr Cys
225                 230                 235                 240

Thr Asp Trp Val Thr Ala Ile Phe Gly Val Asn Pro Thr Ile Ala Glu
                245                 250                 255

Gly Phe Lys Thr Leu Ile Gln Pro Phe Ile Leu Tyr Ala His Ile Gln
            260                 265                 270

Cys Leu Asp Cys Lys Trp Gly Val Leu Ile Leu Ala Leu Leu Arg Tyr
        275                 280                 285

Lys Cys Gly Lys Ser Arg Leu Thr Val Ala Lys Gly Leu Ser Thr Leu
    290                 295                 300

Leu His Val Pro Glu Thr Cys Met Leu Ile Gln Pro Pro Lys Leu Arg
305                 310                 315                 320

Ser Ser Val Ala Ala Leu Tyr Trp Tyr Arg Thr Gly Ile Ser Asn Ile
                325                 330                 335

Ser Glu Val Met Gly Asp Thr Pro Glu Trp Ile Gln Arg Leu Thr Ile
            340                 345                 350

Ile Gln His Gly Ile Asp Asp Ser Asn Phe Asp Leu Ser Glu Met Val
        355                 360                 365

Gln Trp Ala Phe Asp Asn Glu Leu Thr Asp Glu Ser Asp Met Ala Phe
    370                 375                 380

Glu Tyr Ala Leu Leu Ala Asp Ser Asn Ser Asn Ala Ala Ala Phe Leu
385                 390                 395                 400

Lys Ser Asn Cys Gln Ala Lys Tyr Leu Lys Asp Cys Ala Thr Met Cys
                405                 410                 415

Lys His Tyr Arg Arg Ala Gln Lys Arg Gln Met Asn Met Ser Gln Trp
            420                 425                 430

Ile Arg Phe Arg Cys Ser Lys Ile Asp Glu Gly Gly Asp Trp Arg Pro
        435                 440                 445

Ile Val Gln Phe Leu Arg Tyr Gln Gln Ile Glu Phe Ile Thr Phe Leu
    450                 455                 460

Gly Ala Leu Lys Ser Phe Leu Lys Gly Thr Pro Lys Lys Asn Cys Leu
465                 470                 475                 480

Val Phe Cys Gly Pro Ala Asn Thr Gly Lys Ser Tyr Phe Gly Met Ser
                485                 490                 495

Phe Ile His Phe Ile Gln Gly Ala Val Ile Ser Phe Val Asn Ser Thr
            500                 505                 510
```

Ser His Phe Trp Leu Glu Pro Leu Thr Asp Thr Lys Val Ala Met Leu
        515                 520                 525

Asp Asp Ala Thr Thr Thr Cys Trp Thr Tyr Phe Asp Thr Tyr Met Arg
    530                 535                 540

Asn Ala Leu Asp Gly Asn Pro Ile Ser Ile Asp Arg Lys His Lys Pro
545                 550                 555                 560

Leu Ile Gln Leu Lys Cys Pro Pro Ile Leu Leu Thr Thr Asn Ile His
                565                 570                 575

Pro Ala Lys Asp Asn Arg Trp Pro Tyr Leu Glu Ser Arg Ile Thr Val
            580                 585                 590

Phe Glu Phe Pro Asn Ala Phe Pro Phe Asp Lys Asn Gly Asn Pro Val
        595                 600                 605

Tyr Glu Ile Asn Asp Lys Asn Trp Lys Cys Phe Phe Glu Arg Thr Trp
    610                 615                 620

Ser Arg Leu Asp Leu His Glu Glu Glu Glu Asp Ala Asp Thr Glu Gly
625                 630                 635                 640

Asn Pro Phe Gly Thr Phe Lys Leu Arg Ala Gly Gln Asn His Arg Pro
                645                 650                 655

Leu

<210> SEQ ID NO 448
<211> LENGTH: 365
<212> TYPE: PRT
<213> ORGANISM: Human papilloma virus

<400> SEQUENCE: 448

Met Gln Thr Pro Lys Glu Thr Leu Ser Glu Arg Leu Ser Cys Val Gln
1               5                   10                  15

Asp Lys Ile Ile Asp His Tyr Glu Asn Asp Ser Lys Asp Ile Asp Ser
            20                  25                  30

Gln Ile Gln Tyr Trp Gln Leu Ile Arg Trp Glu Asn Ala Ile Phe Phe
        35                  40                  45

Ala Ala Arg Glu His Gly Ile Gln Thr Leu Asn His Gln Val Val Pro
    50                  55                  60

Ala Tyr Asn Ile Ser Lys Ser Lys Ala His Lys Ala Ile Glu Leu Gln
65                  70                  75                  80

Met Ala Leu Gln Gly Leu Ala Gln Ser Arg Tyr Lys Thr Glu Asp Trp
                85                  90                  95

Thr Leu Gln Asp Thr Cys Glu Glu Leu Trp Asn Thr Glu Pro Thr His
            100                 105                 110

Cys Phe Lys Lys Gly Gly Gln Thr Val Gln Val Tyr Phe Asp Gly Asn
        115                 120                 125

Lys Asp Asn Cys Met Thr Tyr Val Ala Trp Asp Ser Val Tyr Tyr Met
    130                 135                 140

Thr Asp Ala Gly Thr Trp Asp Lys Thr Ala Thr Cys Val Ser His Arg
145                 150                 155                 160

Gly Leu Tyr Tyr Val Lys Glu Gly Tyr Asn Thr Phe Tyr Ile Glu Phe
                165                 170                 175

Lys Ser Glu Cys Glu Lys Tyr Gly Asn Thr Gly Thr Trp Glu Val His
            180                 185                 190

Phe Gly Asn Asn Val Ile Asp Cys Asn Asp Ser Met Cys Ser Thr Ser
        195                 200                 205

Asp Asp Thr Val Ser Ala Thr Gln Leu Val Lys Gln Leu Gln His Thr
    210                 215                 220

Pro Ser Pro Tyr Ser Ser Thr Val Ser Val Gly Thr Ala Lys Thr Tyr 225 230 235 240

Gly Gln Thr Ser Ala Ala Thr Arg Pro Gly His Cys Gly Leu Ala Glu
245 250 255

Lys Gln His Cys Gly Pro Val Asn Pro Leu Leu Gly Ala Ala Thr Pro
260 265 270

Thr Gly Asn Asn Lys Arg Arg Lys Leu Cys Ser Gly Asn Thr Thr Pro
275 280 285

Ile Ile His Leu Lys Gly Asp Arg Asn Ser Leu Lys Cys Leu Arg Tyr
290 295 300

Arg Leu Arg Lys His Ser Asp His Tyr Arg Asp Ile Ser Ser Thr Trp
305 310 315 320

His Trp Thr Gly Ala Gly Asn Glu Lys Thr Gly Ile Leu Thr Val Thr
325 330 335

Tyr His Ser Glu Thr Gln Arg Thr Lys Phe Leu Asn Thr Val Ala Ile
340 345 350

Pro Asp Ser Val Gln Ile Leu Val Gly Tyr Met Thr Met
355 360 365

<210> SEQ ID NO 449
<211> LENGTH: 88
<212> TYPE: PRT
<213> ORGANISM: Human papilloma virus

<400> SEQUENCE: 449

Met Thr Leu Cys Ala Val Pro Val Thr Thr Arg Tyr Pro Leu Leu Ser
1 5 10 15

Leu Leu Asn Ser Tyr Ser Thr Pro Pro His Arg Ile Pro Ala Pro Cys
20 25 30

Pro Trp Ala Pro Gln Arg Pro Thr Ala Arg Arg Arg Leu Leu His Asp
35 40 45

Leu Asp Thr Val Asp Ser Arg Arg Ser Ser Ile Val Asp Leu Ser Thr
50 55 60

His Phe Ser Val Gln Leu His Leu Gln Ala Thr Thr Lys Asp Gly Asn
65 70 75 80

Ser Val Val Val Thr Leu Arg Leu
85

<210> SEQ ID NO 450
<211> LENGTH: 73
<212> TYPE: PRT
<213> ORGANISM: Human papilloma virus

<400> SEQUENCE: 450

Met Leu Ser Leu Ile Phe Leu Phe Cys Phe Cys Val Cys Met Tyr Val
1 5 10 15

Cys Cys His Val Pro Leu Leu Pro Ser Val Cys Met Cys Ala Tyr Ala
20 25 30

Trp Val Leu Val Phe Val Tyr Ile Val Val Ile Thr Ser Pro Ala Thr
35 40 45

Ala Phe Thr Val Tyr Val Phe Cys Phe Leu Leu Pro Met Leu Leu Leu
50 55 60

His Ile His Ala Ile Leu Ser Leu Gln
65 70

<210> SEQ ID NO 451
<211> LENGTH: 462
<212> TYPE: PRT
<213> ORGANISM: Human papilloma virus

<400> SEQUENCE: 451

```
Met Val Ser His Arg Ala Ala Arg Arg Lys Arg Ala Ser Val Thr Asp
1               5                   10                  15

Leu Tyr Lys Thr Cys Lys Gln Ser Gly Thr Cys Pro Pro Asp Val Val
            20                  25                  30

Pro Lys Val Glu Gly Thr Thr Leu Ala Asp Lys Ile Leu Gln Trp Ser
        35                  40                  45

Ser Leu Gly Ile Phe Leu Gly Gly Leu Gly Ile Gly Thr Gly Ser Gly
    50                  55                  60

Thr Gly Gly Arg Thr Gly Tyr Ile Pro Leu Gly Gly Arg Ser Asn Thr
65                  70                  75                  80

Val Val Asp Val Gly Pro Thr Arg Pro Pro Val Val Ile Glu Pro Val
                85                  90                  95

Gly Pro Thr Asp Pro Ser Ile Val Thr Leu Ile Glu Asp Ser Ser Val
            100                 105                 110

Val Thr Ser Gly Ala Pro Arg Pro Thr Phe Thr Gly Thr Ser Gly Phe
        115                 120                 125

Asp Ile Thr Ser Ala Gly Thr Thr Thr Pro Ala Val Leu Asp Ile Thr
    130                 135                 140

Pro Ser Ser Thr Ser Val Ser Ile Ser Thr Thr Asn Phe Thr Asn Pro
145                 150                 155                 160

Ala Phe Ser Asp Pro Ser Ile Ile Glu Val Pro Gln Thr Gly Glu Val
                165                 170                 175

Ala Gly Asn Val Phe Val Gly Thr Pro Thr Ser Gly Thr His Gly Tyr
            180                 185                 190

Glu Glu Ile Pro Leu Gln Thr Phe Ala Ser Ser Gly Thr Gly Glu Glu
        195                 200                 205

Pro Ile Ser Ser Thr Pro Leu Pro Thr Val Arg Arg Val Ala Gly Pro
    210                 215                 220

Arg Leu Tyr Ser Arg Ala Tyr Gln Gln Val Ser Val Ala Asn Pro Glu
225                 230                 235                 240

Phe Leu Thr Arg Pro Ser Ser Leu Ile Thr Tyr Asp Asn Pro Ala Phe
                245                 250                 255

Glu Pro Val Asp Thr Thr Leu Thr Phe Asp Pro Arg Ser Asp Val Pro
            260                 265                 270

Asp Ser Asp Phe Met Asp Ile Ile Arg Leu His Arg Pro Ala Leu Thr
        275                 280                 285

Ser Arg Arg Gly Thr Val Arg Phe Ser Arg Leu Gly Gln Arg Ala Thr
    290                 295                 300

Met Phe Thr Arg Ser Gly Thr Gln Ile Gly Ala Arg Val His Phe Tyr
305                 310                 315                 320

His Asp Ile Ser Pro Ile Ala Pro Ser Pro Glu Tyr Ile Glu Leu Gln
                325                 330                 335

Pro Leu Val Ser Ala Thr Glu Asp Asn Asp Leu Phe Asp Ile Tyr Ala
            340                 345                 350

Asp Asp Met Asp Pro Ala Val Pro Val Pro Ser Arg Ser Thr Thr Ser
        355                 360                 365

Phe Ala Phe Phe Lys Tyr Ser Pro Thr Ile Ser Ser Ala Ser Ser Tyr
    370                 375                 380

Ser Asn Val Thr Val Pro Leu Thr Ser Ser Trp Asp Val Pro Val Tyr
385                 390                 395                 400

Thr Gly Pro Asp Ile Thr Leu Pro Ser Thr Thr Ser Val Trp Pro Ile
                405                 410                 415
```

```
Val Ser Pro Thr Ala Pro Ala Ser Thr Gln Tyr Ile Gly Ile His Gly
            420                 425                 430

Thr His Tyr Tyr Leu Trp Pro Leu Tyr Tyr Phe Ile Pro Lys Lys Arg
        435                 440                 445

Lys Arg Val Pro Tyr Phe Phe Ala Asp Gly Phe Val Ala Ala
    450                 455                 460


<210> SEQ ID NO 452
<211> LENGTH: 568
<212> TYPE: PRT
<213> ORGANISM: Human papilloma virus

<400> SEQUENCE: 452

Met Cys Leu Tyr Thr Arg Val Leu Ile Leu His Tyr His Leu Leu Pro
1               5                   10                  15

Leu Tyr Gly Pro Leu Tyr His Pro Arg Pro Leu Pro Leu His Ser Ile
            20                  25                  30

Leu Val Tyr Met Val His Ile Ile Ile Cys Gly His Tyr Ile Ile Leu
        35                  40                  45

Phe Leu Arg Asn Val Asn Val Phe Pro Ile Phe Leu Gln Met Ala Leu
    50                  55                  60

Trp Arg Pro Ser Asp Asn Thr Val Tyr Leu Pro Pro Pro Ser Val Ala
65                  70                  75                  80

Arg Val Val Asn Thr Asp Asp Tyr Val Thr Pro Thr Ser Ile Phe Tyr
                85                  90                  95

His Ala Gly Ser Ser Arg Leu Leu Thr Val Gly Asn Pro Tyr Phe Arg
            100                 105                 110

Val Pro Ala Gly Gly Gly Asn Lys Gln Asp Ile Pro Lys Val Ser Ala
        115                 120                 125

Tyr Gln Tyr Arg Val Phe Arg Val Gln Leu Pro Asp Pro Asn Lys Phe
    130                 135                 140

Gly Leu Pro Asp Thr Ser Ile Tyr Asn Pro Glu Thr Gln Arg Leu Val
145                 150                 155                 160

Trp Ala Cys Ala Gly Val Glu Ile Gly Arg Gly Gln Pro Leu Gly Val
                165                 170                 175

Gly Leu Ser Gly His Pro Phe Tyr Asn Lys Leu Asp Asp Thr Glu Ser
            180                 185                 190

Ser His Ala Ala Thr Ser Asn Val Ser Glu Asp Val Arg Asp Asn Val
        195                 200                 205

Ser Val Asp Tyr Lys Gln Thr Gln Leu Cys Ile Leu Gly Cys Ala Pro
    210                 215                 220

Ala Ile Gly Glu His Trp Ala Lys Gly Thr Ala Cys Lys Ser Arg Pro
225                 230                 235                 240

Leu Ser Gln Gly Asp Cys Pro Pro Leu Glu Leu Lys Asn Thr Val Leu
                245                 250                 255

Glu Asp Gly Asp Met Val Asp Thr Gly Tyr Gly Ala Met Asp Phe Ser
            260                 265                 270

Thr Leu Gln Asp Thr Lys Cys Glu Val Pro Leu Asp Ile Cys Gln Ser
        275                 280                 285

Ile Cys Lys Tyr Pro Asp Tyr Leu Gln Met Ser Ala Asp Pro Tyr Gly
    290                 295                 300

Asp Ser Met Phe Phe Cys Leu Arg Arg Glu Gln Leu Phe Ala Arg His
305                 310                 315                 320

Phe Trp Asn Arg Ala Gly Thr Met Gly Asp Thr Val Pro Gln Ser Leu
                325                 330                 335
```

-continued

```
Tyr Ile Lys Gly Thr Gly Met Pro Ala Ser Pro Gly Ser Cys Val Tyr
            340                 345                 350

Ser Pro Ser Pro Ser Gly Ser Ile Val Thr Ser Asp Ser Gln Leu Phe
        355                 360                 365

Asn Lys Pro Tyr Trp Leu His Lys Ala Gln Gly His Asn Asn Gly Val
    370                 375                 380

Cys Trp His Asn Gln Leu Phe Val Thr Val Val Asp Thr Thr Pro Ser
385                 390                 395                 400

Thr Asn Leu Thr Ile Cys Ala Ser Thr Gln Ser Pro Val Pro Gly Gln
                405                 410                 415

Tyr Asp Ala Thr Lys Phe Lys Gln Tyr Ser Arg His Val Glu Glu Tyr
            420                 425                 430

Asp Leu Gln Phe Ile Phe Gln Leu Cys Thr Ile Thr Leu Thr Ala Asp
        435                 440                 445

Val Met Ser Tyr Ile His Ser Met Asn Ser Ser Ile Leu Glu Asp Trp
    450                 455                 460

Asn Phe Gly Val Pro Pro Pro Pro Thr Thr Ser Leu Val Asp Thr Tyr
465                 470                 475                 480

Arg Phe Val Gln Ser Val Ala Ile Thr Cys Gln Lys Asp Ala Ala Pro
                485                 490                 495

Ala Glu Asn Lys Asp Pro Tyr Asp Lys Leu Lys Phe Trp Asn Val Asp
            500                 505                 510

Leu Lys Glu Lys Phe Ser Leu Asp Leu Asp Gln Tyr Pro Leu Gly Arg
        515                 520                 525

Lys Phe Leu Val Gln Ala Gly Leu Arg Arg Lys Pro Thr Ile Gly Pro
    530                 535                 540

Arg Lys Arg Ser Ala Pro Ser Ala Thr Thr Ser Ser Lys Pro Ala Lys
545                 550                 555                 560

Arg Val Arg Val Arg Ala Arg Lys
                565
```